United States Patent
Blackburn et al.

(10) Patent No.: US 7,459,448 B2
(45) Date of Patent: Dec. 2, 2008

(54) LACTAM COMPOUNDS USEFUL AS PROTEIN KINASE INHIBITORS

(75) Inventors: Christopher Blackburn, Natick, MA (US); Christopher F. Claiborne, Cambridge, MA (US); Courtney A. Cullis, Bedford, MA (US); Natalie A. Dales, Arlington, MA (US); Michael Patane, Reading, MA (US); Matthew Stirling, Boston, MA (US); Omar Stradella, Waltham, MA (US); Gabriel S. Weatherhead, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/242,413

(22) Filed: Oct. 3, 2005

(65) Prior Publication Data

US 2006/0100194 A1 May 11, 2006

Related U.S. Application Data

(60) Provisional application No. 60/615,761, filed on Oct. 4, 2004.

(51) Int. Cl.
*C07D 487/04* (2006.01)
*A61K 31/55* (2006.01)

(52) U.S. Cl. .................. 514/212.06; 540/521
(58) Field of Classification Search ............ 540/521; 514/212.06
See application file for complete search history.

(56) References Cited

U.S. PATENT DOCUMENTS 5,854,236 A 12/1998 Albright et al.
6,686,352 B2 2/2004 Masciadri et al.
2003/0083327 A1 5/2003 Davies et al.
2003/0181439 A1 9/2003 Meijer et al.

FOREIGN PATENT DOCUMENTS

WO WO 02/094834 A1 11/2002
WO WO 2004/076424 A1 9/2004
WO WO 2005/037843 A1 4/2005
WO WO 2005/111039 A2 11/2005

OTHER PUBLICATIONS

Chetoni, Fabio, et al., "Synthesis of Novel 1-Aryl[1]benzoxepino[5,4-c]pyrazole and [1]Benzoxepino [5,4-d]pyrimidine Derivatives," *Journal of Heterocyclic Chemistry*, vol. 30 (Dec. 1993) pp. 1653-1658.

Chen, Wen-Yean, et al., "Synthesis of 7-Phenylpyrimido [5,4-d][1]benzazepin-2-ones (1)," *Journal of Heterocyclic Chemistry*, vol. 20 (May-Jun. 1983) pp. 663-666.

Kunick, Conrad, et al., "Evaluation and Comparison of 3D-QSAR CoMSIA Models for CDK1, CDK5, and GSK-3 Inhibition by Paullones," *Journal of Medicinal Chemistry*, vol. 47, No. 1 (2004) pp. 22-36.

Link, Andreas, et al., "*d*-Fused [1]Benzazepines with Selective in Vitro Antitumor Activity: Synthesis and Structure-Activity Relationships," *Journal of Medicinal Chemistry*. vol. 41, No. 8 (1998) pp. 1299-1305.

Leost, Maryse, et al., "Paullones Are Potent Inhibitors of Glycogen Synthase Kinase-3β and Cyclin-Dependent Kinase 5/p25," *Journal of Biochemistry*, vol. 267 (2000), pp. 5983-5994.

Proctor, George R., et al., "Azabenzocycloheptenones. Part 19. Formation of Some Heterocyclic Annelated Compounds from 1,2,3,4-Tetrahydro-1-benzazepine Derivatives," *Journal of the Chemical Society.Perkin Transactions I* (1978) pp. 862-870.

International Search Report issued in PCT Application No. PCT/US2005/035458, which corresponds to U.S. Appl. No. 11/242,413.

*Primary Examiner*—Bruck Kifle

(57) ABSTRACT

The present invention provides novel compounds useful as inhibitors of protein kinases. The invention also provides pharmaceutical compositions comprising the compounds of the invention and methods of using the compositions in the treatment of various diseases.

22 Claims, No Drawings

LACTAM COMPOUNDS USEFUL AS PROTEIN KINASE INHIBITORS

PRIORITY CLAIM

This application priority from U.S. Provisional Patent Application Ser. No. 60/615,761, filed Oct. 4, 2004, the contents of which are hereby incorporated by reference in their entirety.

BACKGROUND OF THE INVENTION

1. Field of the Invention

The present invention relates to inhibitors of protein kinases. The invention also provides pharmaceutical compositions comprising the compounds of the invention and methods of using the compositions in the treatment of various diseases.

2. Background of the Invention

Protein kinases constitute a large family of structurally related enzymes that effect the transfer of a phosphate group from a nucleoside triphosphate to a protein acceptor. A vast array of cellular functions, including DNA replication, cell cycle progression, energy metabolism, and cell growth and differentiation, are regulated by reversible protein phosphorylation events mediated by protein kinases. Additionally, protein kinase activity has been implicated in a number of disease states. Accordingly, protein kinase targets have attracted substantial drug discovery efforts in recent years, with several protein kinase inhibitors achieving regulatory approval (reviewed in Fischer, *Curr. Med. Chem.*, 11:1563 (2004); Dancey and Sausville, *Nature Rev. Drug Disc.*, 2:296 (2003)).

Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B, Aurora C) regulate mitotic progression through modulation of centrosome separation, spindle dynamics, spindle assembly checkpoint, chromosome alignment, and cytokinesis (Dutertre et al., *Oncogene,* 21: 6175 (2002); Berdnik et al., *Curr. Biol.,* 12: 640 (2002)). Overexpression and/or amplification of Aurora kinases have been linked to oncogenesis in several tumor types including those of colon and breast (Warner et al., *Mol. Cancer Ther.,* 2: 589 (2003); Bischoff et al., *EMBO,* 17: 3062 (1998); Sen et al., *Cancer Res.,* 94: 1320 (2002)). Moreover, Aurora kinase inhibition in tumor cells results in mitotic arrest and apoptosis, suggesting that these kinases are important targets for cancer therapy (Ditchfield, *J. Cell Biol.,* 161: 267 (2003); Harrington et al., *Nature Med.*, 1 (2004)). Given the central role of mitosis in the progression of virtually all malignancies, inhibitors of the Aurora kinases are expected to have application across a broad range of human tumors.

PLK is a serine/threonine protein kinase that plays a key role in cell cycle control. PLK controls entry and progression through mitosis at multiple stages by regulating centrosome maturation, activation of initiating factors, degradation of inhibitory components, chromosome condensation, and exit from mitosis (reviewed in Barr et al., *Nature Reviews Mol Cell Biol.*, 5; 429 (2004)). PLK has been reported to be overexpressed in numerous cancers such as melanoma, ovarian, colorectal, lung and squamous cell carcinoma of the head and neck. Increased levels of expression are additionally correlated with poor prognosis and survival. (Kneisel et al., *J. Cutan Pathol* 29: 354 (2002); Takai et al. *Cancer Lett* 164: 41 (2001); Takahashi et al *Cancer Sci.;* 94(2):148 (2003); Wolf et al. *Oncogene* 14: 543 (1997); Knecht et al. *Cancer Res.* 59 (1999)). Overexpression of the kinase transforms cells, rendering them oncogenic such that they acquire the ability to form tumors in mice (Smith et al., *Biochem. Biophys. Res. Commun.* 234; 397 (1997)). PLK protein levels are also elevated in tumor relative to normal cell lines in culture. Downregulation of PLK protein expression by RNA interference in tumor cell lines results in a reduction of cell proliferation, mitotic arrest at prometaphase and the rapid progression into apoptosis (Spankuch-Schmitt et al. *J. Natl. Cancer Inst.* 94(24):1863 (2002); Spankuch-Schmitt et al. *Oncogene* 21(20):3162 (2002)). This effect was not observed in normal cell lines. Moreover downregulation of PLK by short hairpin expression in mice with human xenografts reduced tumor growth to 18% (Spankuch B et al. (2004) *J. Natl. Cancer Inst.* 96(11):862-72). The key role of PLK in mitotic progression, its overexpression in a wide range of malignancies and the anti-proliferative effect observed upon its inhibition demonstrate its feasibility as a therapeutic target.

Anti-mitotic drugs that bind to tubulin (taxanes and vinca alkaloids) are currently utilized as chemotherapeutic drugs. Tubulin regulates cellular processes outside of mitosis therefore these drugs offer no selectivity towards cancer cells and are toxic to normal cells. Small molecule inhibitors that target the mitotic process specifically by targeting kinases that are overexpressed and active only in rapidly proliferating mitotic cells, such as PLK and Aurora kinase, may be clinically effective against tumors and not constrained by dose-limiting toxicities.

Cell cycle checkpoints are regulatory pathways that control the order and timing of cell cycle transitions. They ensure that critical events such as DNA replication and chromosome segregation are completed in high fidelity. The regulation of these cell cycle checkpoints is a critical determinant of the manner in which tumor cells respond to many chemotherapies and radiation. Many effective cancer therapies work by causing DNA damage; however, resistance to these agents remains a significant limitation in the treatment of cancer. One important mechanism leading to drug resistance is the activation of a checkpoint pathway that arrests the cell cycle to provide time for repair and induces the transcription of genes that facilitate repair. Cell cycle progression is prevented, and immediate cell death of the damaged cell is avoided. By abrogating such checkpoint arrests at, for example, the G2 checkpoint, it may be possible to synergistically augment the tumor cell death induced by DNA damage and to circumvent resistance. (Shyjan et al., U.S. Pat. No. 6,723,498 (2004)). Human Chk-1 plays a role in regulating cell cycle arrest by phosphorylating the phosphatase cdc25 on Serine 216, thereby preventing the activation of cdc2/cyclin B and the initiation of mitosis. (Sanchez et al., Science, 277: 1497 (1997)). Therefore, inhibition of Chk-1 should enhance the effect of DNA damaging agents by initiating mitosis before DNA repair is complete, thereby promoting tumor cell death.

Accordingly, there is a need to develop inhibitors of protein kinases, including Chk-1, Aurora, and PLK. Such inhibitors are useful for treating various diseases or conditions associated with protein kinase activity, and are especially needed in view of the inadequate treatments currently available for many of these disorders.

DESCRIPTION OF THE INVENTION

The present invention provides compounds that are effective inhibitors of protein kinases, including Chk-1, Aurora kinase, and PLK. These compounds are useful for inhibiting kinase activity in vitro and in vivo, and are especially useful for the treatment of various cell proliferative diseases.

The compounds of the invention are represented by formula (I):

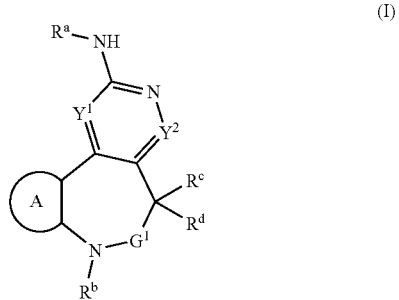

or a pharmaceutically acceptable salt thereof;

wherein:

Ring A is an optionally substituted 5- or 6-membered aryl or heteroaryl ring;

$G^1$ is C=O, C=S, or S(=O)$_2$;

$Y^1$ is N or CH and $Y^2$ is N or $CR^e$, provided that at least one of $Y^1$ and $Y^2$ is N;

$R^a$ is hydrogen, —C(O)$R^{5a}$, —C(O)N($R^{4a}$)$_2$, —CO$_2R^{6a}$, —SO$_2R^{6a}$, —SO$_2$N($R^{4a}$)$_2$, an optionally substituted $C_{1-10}$ aliphatic, or an optionally substituted aryl, heteroaryl, or heterocyclyl ring;

$R^b$ is hydrogen or an optionally substituted aliphatic, aryl, heteroaryl, or heterocyclyl group;

$R^c$ is hydrogen, fluoro, —OR$^5$, —N(R$^4$)$_2$, or an optionally substituted $C_{1-4}$ aliphatic;

$R^d$ is hydrogen, fluoro, $C_{1-4}$ aliphatic, or $C_{1-4}$ fluoroaliphatic; or $R^c$ and $R^d$, taken together with the carbon atom to which they are attached, form an optionally substituted 3- to 6-membered carbocyclic ring;

$R^e$ is hydrogen, halo, —NO$_2$, —CN, —C(R$^5$)=C(R$^5$)$_2$, —C≡C—R$^5$, —C(R$^5$)=C(R$^5$)(R$^{10}$), —C≡C—R$^{10}$, —OR$^5$, —N(R$^4$)$_2$, —NR$^4$C(O)R$^5$, —NR$^4$C(O)N(R$^4$)$_2$, —NR$^4$CO$_2R^6$, —CO$_2R^5$, —C(O)R$^5$, —C(O)N(R$^4$)$_2$, —N(R$^4$)SO$_2R^6$, —N(R$^4$)SO$_2$N(R$^4$)$_2$, or an optionally substituted $C_{1-4}$ aliphatic;

each $R^3$ independently is selected from the group consisting of $C_{1-3}$ aliphatic, -fluoro, —OH, and —O(C$_{1-3}$ alkyl), or two substituents $R^3$ on the same carbon atom, taken together with the carbon atom to which they are attached, form a 3- to 6-membered carbocyclic ring;

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 3- to -membered heterocyclyl ring having, in addition to the nitrogen atom, 0-2 ring heteroatoms selected from N, O, and S;

each $R^{4a}$ independently is hydrogen or an optionally substituted aliphatic, aryl, heteroaryl, or heterocyclyl group; or two $R^{4a}$ on the same nitrogen atom, taken together with the nitrogen atom, form an optionally substituted 4- to 8-membered heterocyclyl ring having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^{5a}$ independently is hydrogen or an optionally substituted aliphatic, aryl, heteroaryl, or heterocyclyl group;

each $R^6$ independently is an optionally substituted aliphatic or aryl group;

each $R^{6a}$ independently is an optionally substituted aliphatic or aryl group; and $R^{10}$ is —CO$_2R^5$ or —C(O)N(R$^4$)$_2$.

Compounds of this invention include those described generally above, and are further illustrated by the classes, subclasses, and species disclosed herein. Terms used herein shall be accorded the following defined meanings, unless otherwise indicated.

The term "aliphatic" or "aliphatic group", as used herein, means a substituted or unsubstituted straight-chain, branched or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, alkynyl groups and hybrids thereof, such as (cylcoalkyl)alkyl, (cycloalkenyl)alkyl or (cycloalkyl)alkenyl. In various embodiments, the aliphatic group has 1 to 12, 1 to 8, 1 to 6, 1 to 4, or 1 to 3 carbons.

The terms "alkyl", "alkenyl", and "alkynyl", used alone or as part of a larger moiety, refer to a straight and branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring. The term "cycloaliphatic" may be used interchangeably with the terms "carbocycle", "carbocyclyl", "carbocyclo", or "carbocyclic".

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$ aryl($C_{1-3}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, for an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro.

The term "linker group" or "linker" means an organic moiety that connects two parts of a compound. Linkers typically comprise an atom such as oxygen or sulfur, a unit such as —NH—, —CH$_2$—, —C(O)—, —C(O)NH—, or a chain of atoms, such as an alkylene chain. The molecular mass of a linker is typically in the range of about 14 to 200, preferably in the range of 14 to 96 with a length of up to about six atoms. In some embodiments, the linker is a $C_{1-16}$ alkylene chain.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include $-C(R^*)=C(R^*)-$, $-C\equiv C-$, $-O-$, $-S-$, $-S(O)-$, $-S(O)_2-$, $-S(O)_2N(R^+)-$, $-N(R^*)-$, $-N(R^+)CO-$, $-N(R^+)C(O)N(R^+)-$, $-N(R^+)CO_2-$, $-C(O)N(R^+)-$, $-C(O)-$, $-C(O)-C(O)-$, $-CO_2-$, $-OC(O)-$, $-OC(O)O-$, $-OC(O)N(R^+)-$, $-C(NR^+)=N-$, $-C(OR^*)=N-$, $-N(R^+)-N(R^+)-$, or $-N(R^+)S(O)_2-$. Each $R^+$, independently, is hydrogen or an optionally substituted aliphatic, aryl, heteroaryl, or heterocyclyl group, or two $R^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each $R^*$ independently is hydrogen or an optionally substituted aliphatic, aryl, heteroaryl, or heterocyclyl group.

Examples of $C_{3-6}$ alkylene chains that have been "interrupted" with $-O-$ include $-CH_2OCH_2-$, $-CH_2O(CH_2)_2-$, $-CH_2O(CH_2)_3-$, $-CH_2O(CH)_4-$, $-(CH_2)_2OCH_2-$, $-(CH_2)_2O(CH_2)_2-$, $-(CH_2)_2O(CH_2)_3-$, $-(CH_2)_3O(CH_2)-$, $-(CH_2)_3O(CH_2)_2-$, and $-(CH_2)_4O(CH_2)-$. Other examples of alkylene chains that are "interrupted" with functional groups include $-CH_2ZCH_2-$, $-CH_2Z(CH_2)_2-$, $-CH_2Z(CH_2)_3-$, $-CH_2Z(CH_2)_4-$, $-(CH_2)_2ZCH_2-$, $-(CH_2)_2Z(CH_2)_2-$, $-(CH_2)_2Z(CH_2)_3-$, $-(CH_2)_3Z(CH_2)-$, $-(CH_2)_3Z(CH_2)_2-$, and $-(CH_2)_4Z(CH_2)-$, wherein Z is one of the "interrupting" functional groups listed above.

One of ordinary skill in the art will recognize that when an alkylene chain having an interruption is attached to a functional group, certain combinations are not sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably from about −20° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

As used herein, the term "independently selected" means that the same or different values may be selected for multiple instances of a given variable in a single compound. By way of example, in a compound of formula (I), if Ring A is substituted with two substituents $-R^{2h}$, each substituent is selected from the group of defined values for $R^{2h}$, and the two values selected may be the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, $-NO_2$, $-CN$, $-R^*$, $-C(R^*)=C(R^*)_2$, $-C\equiv C-R^*$, $-OR^*$, $-SR^\circ$, $-S(O)R^\circ$, $-SO_2R^\circ$, $-SO_3R^*$, $-SO_2N(R^+)_2$, $-N(R^+)_2$, $-NR^+C(O)R^*$, $-NR^+C(O)N(R^+)_2$, $-NR^+CO_2R^\circ$, $-O-CO_2R^*$, $-OC(O)N(R^+)_2$, $-O-C(O)R^*$, $-CO_2R^*$, $-C(O)-C(O)R^*$, $-C(O)R^*$, $-C(O)N(R^+)_2$, $-C(O)N(R^+)C(=NR^+)-N(R^+)_2$, $-N(R^+)C(=NR^+)-N(R^+)-C(O)R^*$, $-C(=NR^+)-N(R^+)_2$, $-C(=NR^+)-OR^*$, $-N(R^+)-N(R^+)_2$, $-N(R^+)C(=NR^+)-N(R^+)_2$, $-NR^+SO_2R-$, $-NR^+SO_2N(R^+)_2$, $-P(O)(R^*)_2$, $-P(O)(OR^*)_2$, $-P(O)-OR^*$, and $-P(O)(NR^+)-N(R^+)_2$, wherein $R^\circ$ is an optionally substituted aliphatic or aryl group, and $R^+$ and $R^*$ are as defined above, or two adjacent substituents, taken together with their intervening atoms, form a 5-6 membered unsaturated or partially unsaturated ring having 0-3 ring atoms selected from the group consisting of N, O, and S.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: $=O$, $=S$, $=C(R^*)_2$, $=N-N(R^*)_2$, $=N-OR^*$, $=N-NHC(O)R^*$, $=N-NHCO_2R^\circ$, $=N-NHSO_2R^\circ$, or $=N-R^*$, where each $R^*$ and $R^\circ$ is as defined above.

Suitable substituents on the nitrogen atom of a non-aromatic heterocyclic ring include $-R^*$, $-N(R^*)_2$, $-C(O)R^*$, $-CO_2R^*$, $-C(O)-C(O)R^*$, $-C(O)CH_2C(O)R^*$, $-SO_2R^*$, $-SO_2N(R^*)_2$, $-C(=S)N(R^*)_2$, $-C(=NH)-N(R^*)_2$, and $-NR^*SO_2R^*$; wherein each $R^*$ is as defined above.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. When a mixture is enriched in one enantiomer relative to its optical isomer, the mixture preferably contains an enantiomeric excess of at least 50%, 75%, 90%, 95%, 99%, or 99.5%. Similarly, when a mixture is enriched in one diastereomer relative to other diastereomer(s), the mixture preferably contains a diastereomeric excess of at least 50%, 75%, 90%, 95%, 99%, or 99.5%.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

Also included within the scope of the invention are solvates of the compounds disclosed herein. As used herein, the term "solvate" means a physical association of a compound of this invention with one or more solvent molecules. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Representative solvates include hydrates, ethanolates, and methanolates.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

The present invention provides compounds of formula (I), as described above, and pharmaceutically acceptable salts thereof. In formula (I), $Y^1$ is N or CH and $Y^2$ is N or $CR^e$, provided that at least one of $Y^1$ and $Y^2$ is N. The variable $R^e$ is hydrogen, halo, $-NO_2$, $-CN$, $-C(R^5)=C(R^5)_2$, $-C\equiv C-R^5$, $-C(R^5)=C(R^5)(R^{10})$, $-C\equiv C-R^{10}$, $-OR^5$, $-N(R^4)_2$, $-NR^4C(O)R^5$, $-NR^4C(O)N(R^4)_2$, $-NR^4CO_2R^6$, $-CO_2R^5$, $-C(O)R^5$, $-C(O)N(R^4)_2$, $-N(R^4)SO_2R^6$, $-N(R^4)SO_2N(R^4)_2$, or an optionally substituted $C_{1-4}$ aliphatic.

One embodiment of the invention relates to a compound of formula (I), wherein $Y^2$ is $CR^e$ and $R^e$ is hydrogen, halo, $C_{1-4}$ aliphatic, $C_{1-4}$ fluoroaliphatic, $-R^{2e}$, $-T^3-R^{1e}$, $-T^3-R^{2e}$, $-V^2-T^3-R^{1e}$, or $-V^2-T^3-R^{2e}$. The variables $V^2$, $T^3$, $R^{1e}$, $R^{2e}$ have the values described below.

$V^2$ is $-C(R^5)=C(R^5)-$ or $-C\equiv C-$.

$T^3$ is a $C_{1-4}$ alkylene chain optionally substituted with one or two $R^3$. In some embodiments, $T^3$ is a $C_{1-3}$ alkylene chain.

$R^{1e}$ is an optionally substituted aryl, heteroaryl, heterocyclyl, or cycloaliphatic ring.

$R^{2e}$ is $-NO_2$, $-CN$, $-C(R^5)=C(R^5)_2$, $-C(R^5)=C(R^5)(R^{10})$, $-C\equiv C-R^5$, $-C\equiv C-R^{10}$, $-OR^5$, $-N(R^4)_2$, $-NR^4C(O)R^5$, $-NR^4C(O)N(R^4)_2$, $-NR^4CO_2R^6$, $-CO_2R^5$, $-C(O)R^5$, $-C(O)N(R^4)_2$, $-N(R^4)SO_2R^6$, or $-N(R^4)SO_2N(R^4)_2$. In some embodiments, $R^{2e}$, is $-OR^5$, $-N(R^4)_2$, $-CN$, $-CO_2R^5$, $-C(O)N(R^4)_2$, $-C(R^5)=C(R^5)_2$, $-C(R^5)=C(R^5)(R^{10})$, $-C\equiv C-R^5$, or $-C\equiv C-R^{10}$.

In particular embodiments of the present invention, the compound of formula (I) is characterized by one or more, and preferably all, of the following features (a)-(e):

(a) $Y^1$ is N;
(b) $Y^2$ is $CR^e$, where $R^e$ is selected from the group consisting of hydrogen, $C_{1-4}$ aliphatic, $C_{1-4}$ fluoroaliphatic, -halo, $-OR^5$, $-N(R^4)_2$, $-CN$, $-CO_2R^5$, $-C(O)N(R^4)_2$, $-C(R^5)=C(R^5)_2$, $-C(R^5)=C(R^5)(R^{10})$, $-C\equiv C-R^5$, and $-C\equiv C-R^{10}$;
(c) $G^1$ is C=O;
(d) $R^c$ is selected from the group consisting of hydrogen, fluoro, $-OR^5$, $-N(R^4)_2$, and $C_{1-4}$ aliphatic optionally substituted with one or two groups independently selected from $C_{1-3}$ aliphatic, fluoro, $-OR^5$, $-N(R^4)_2$, $-CO_2R^5$, $-C(O)N(R^4)_2$, and optionally substituted 5- or 6-membered aryl or heteroaryl; and
(e) $R^d$ is hydrogen.

Some embodiments of the invention relate to a compound of formula (I), wherein $Y^1$ is N, $Y^2$ is $CR^e$, $G^1$ is C=O, $R^c$ is hydrogen or $C_{1-4}$ aliphatic, and $R^d$ is hydrogen. In a particular embodiment, $Y^1$ is N, $Y^2$ is CH, $G^1$ is C=O, and each of $R^c$ and $R^d$ is hydrogen.

Ring A is a substituted or unsubstituted 5- or 6-membered aryl or heteroaryl ring. Nonlimiting examples of Ring A include furano, thieno, pyrrolo, oxazolo, thiazolo, imidazolo, pyrazolo, isoxazolo, isothiazolo, oxadiazolo, triazolo, thiadiazolo, benzo, pyridino, pyridazino, pyrimidino, pyrazino, and triazino, any of which groups may be substituted or unsubstituted. Particular values for Ring A include substituted or unsubstituted rings selected from the group consisting of furano, thieno, benzo, pyridino, pyridazino, pyrimidino, and pyrazino.

In some embodiments, Ring A is substituted with 0-2 $R^h$ and 0-2 $R^{8h}$, or is substituted with 0-1 $R^h$ and 0-2 $R^{8h}$. Each $R^h$ independently is selected from the group consisting of $C_{1-6}$ aliphatic, $C_{1-6}$ fluoroaliphatic, halo, $-R^{1h}$, $-R^{2h}$, $-T^4-R^{2h}$, $-T^4-R^{1h}$, $-V^3-T^4-R^{1h}$, and $-V^3-T^4-R^{2h}$, or two adjacent $R^h$, taken together with the intervening ring atoms, form an optionally substituted fused 5- to 6-membered aromatic or 4- to 8-membered non-aromatic ring having 0-3 ring heteroatoms selected from the group consisting of O, N, and S. Each $R^{8h}$ independently is selected from the group consisting of $C_{1-4}$ aliphatic, $C_{1-4}$ fluoroaliphatic, -halo, and $-O(C_{1-4}$ aliphatic).

The variables $R^{1h}$, $R^{2h}$, $T^4$, and $V^3$ have the values described below.

Each $R^{1h}$ independently is an optionally substituted aryl, heteroaryl, heterocyclyl, or cycloaliphatic ring. In some embodiments, $R^{1h}$ is an optionally substituted 5- or 6-membered aryl, heteroaryl, heterocyclyl, or cycloaliphatic ring.

Each $R^{2h}$ independently is $-NO_2$, $-CN$, $-C(R^5)=C(R^5)_2$, $-C\equiv C-R^5$, $-C(R^5)=C(R^5)(R^{10})$, $-C\equiv C-R^{10}$, $-OR^5$, $-SR^6$, $-S(O)R^6$, $-SO_2R^6$, $SO_3R^5$, $-SO_2N(R^4)_2$, $-N(R^4)_2$, $-NR^4C(O)R^5$, $-NR^4C(O)N(R^4)_2$, $-NR^4CO_2R^6$, $-O-CO_2R^5$, $-OC(O)N(R^4)_2$, $-O-C(O)R^5$, $-CO_2R^5$, $-C(O)-C(O)R^5$, $-C(O)R^5$, $-C(O)N(R^4)_2$, $-C(O)N(R^4)C(=NR^4)-N(R^4)_2$, $-N(R^4)C(=NR^4)-N(R^4)-C(O)$, $-C(=NR^4)-N(R^4)_2$, $-C(=NR^4)-OR^5$, $-C(R^6)=N-OR^5$, $-N(R^4)C(=NR^4)-N(R^4)_2$, $-N(R^4)SO_2R^6$, $-N(R^4)SO_2N(R^4)_2$, $-P(O)(R^5)_2$, or $-P(O)(OR^5)_2$. In some embodiments, $R^{2h}$ is $-C(R^5)=C(R^5)_2$, $-C\equiv C-R^5$, $-OR^5$, $-N(R^4)_2$, $-NR^4C(O)R^5$, $-NR^4C(O)N(R^4)_2$, $-NR^4CO_2R^6$, $-OC(O)N(R^4)_2$, $-C(O)R^5$, $-C(O)N(R^4)_2-N(R^4)SO_2R^6$, or $-N(R^4)SO_2N(R^4)_2$. In certain embodiments, $R^{2h}$ is $-N(R^4)_2$, $-C(O)R^5$, or $-C(O)N(R^4)_2$.

$V^3$ is $-C(R^5)=C(R^5)-$, $-C\equiv C-$, $-O-$, $-S-$, $-S(O)-$, $-S(O)_2-$, $-SO_2N(R^4)-$, $-N(R^4)-$, $-N(R^4)C(O)-$, $-NR^4C(O)N(R^4)-$, $-N(R^4)CO_2-$, $-C(O)N(R^4)-$, $-C(O)-C(O)-$, $-CO_2-$, $-OC(O)-$, $-OC(O)O-$, $-OC(O)N(R^4)-$, $-C(NR^4)=N-$, $-C(OR^5)=N-$, $-N(R^4)SO_2-$, $-N(R^4)SO_2N(R^4)-$, $-P(O)(R^5)-$, $-P(O)(OR^5)-O-$, $-P(O)-O-$, or $-P(O)(NR^5)-N(R^5)-$. In some embodiments, $-V^3$ is $-C(R^5)=C(R^5)-$, $-C\equiv C-$, $-O-$, $-N(R^4)-$, $-N(R^4)C(O)-$, $-NR^4C(O)N(R^4)-$, $-N(R^4)CO_2-$, $-OC(O)N(R^4)-$, $-C(O)-$, $-C(O)N(R^4)-$, $-N(R^4)SO_2-$, or $-N(R^4)SO_2N(R^4)-$. In certain embodiments, $-V^3$ is $-C(R^5)=C(R^5)-$, $-C\equiv C-$, or $-C(O)N(R^4)-$.

$T^4$ is a $C_{1-6}$ alkylene chain optionally substituted with one or two independently selected $R^{3a}$, or $R^{3b}$, wherein the alkylene chain optionally is interrupted by —C($R^5$)=C($R^5$)—, —C≡C—, —O—, —S—, —S(O)—, —S(O)$_2$—, —SO$_2$N($R^4$)—, —N($R^4$)—, —N($R^4$)C(O)—, —NR$^4$C(O)N($R^4$)—, —N($R^4$)CO$_2$—, —C(O)N($R^4$)—, —C(O)—, —C(O)—C(O)—, —CO$_2$—, —OC(O)—, —OC(O)O—, —OC(O)N($R^4$)—, —N($R^4$)SO$_2$—, or —SO$_2$N($R^4$)—, and wherein $T^4$ or a portion thereof optionally forms part of a 3-7 membered ring. In some embodiments, $T^4$ is a $C_{1-4}$ or $C_{2-4}$ alkylene chain, optionally substituted with one or two independently selected $R^{3a}$ or $R^{3b}$.

Each $R^{3a}$ independently is selected from the group consisting of —F, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$ alkyl). In some embodiments, $R^3$, is —F, —OH, —O($C_{1-3}$ alkyl), or —N($R^4$)$_2$, where each $R^4$ independently is hydrogen, $C_{1-4}$ alkyl, or $C_{6-10}$ar($C_{1-6}$)alkyl, the aryl portion of which is optionally substituted, or —N($R^4$)$_2$ is an optionally substituted pyrrolidinyl, imidazolyl, pyrazolyl, piperidinyl, morpholinyl, or piperazinyl ring.

Each $R^{3b}$ independently is a $C_{1-3}$ aliphatic optionally substituted with $R^{3a}$ or $R^7$, or two substituents $R^{3b}$ on the same carbon atom, taken together with the carbon atom to which they are attached, form a 3- to 6-membered carbocyclic ring. Each $R^7$ independently is an optionally substituted aryl or heteroaryl ring.

In some embodiments, Ring A is an optionally substituted pyridino, thieno, or furano ring, wherein Ring A is substituted with 0, 1, or 2 $R^h$ and 0, 1, or 2 $R^{8h}$, where $R^h$ and $R^{8h}$ have the values described above. In some such embodiments, two adjacent substituents on Ring A are taken together to form an optionally substituted fused 5- to -6-membered aromatic or 4- to 8-membered non-aromatic ring having 0-3 ring heteroatoms selected from the group consisting of O, N, and S. In certain such embodiments, two adjacent substituents on Ring A are taken together to form a fused benzene ring.

In some other embodiments, Ring A is an optionally substituted phenyl ring, and the invention relates to a compound of formula (II):

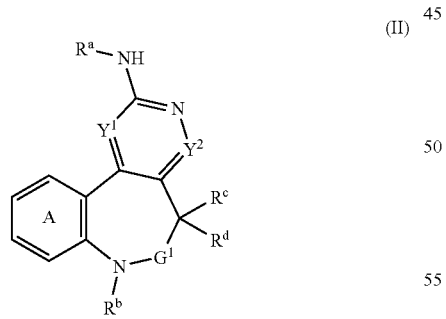

(II)

or a pharmaceutically acceptable salt thereof;

wherein Ring A is substituted with 0, 1, or 2 $R^h$ and 0, 1, or 2 $R^{8h}$. The variables $R^a$, $R^b$, $R^c$, $R^d$, $R^h$, $R^{8h}$, $G^1$, $Y^1$, and $Y^2$ have the values described above for formula (I).

In certain embodiments, the compound of formula (II) is represented by one of formulae (II-A)-(II-F):

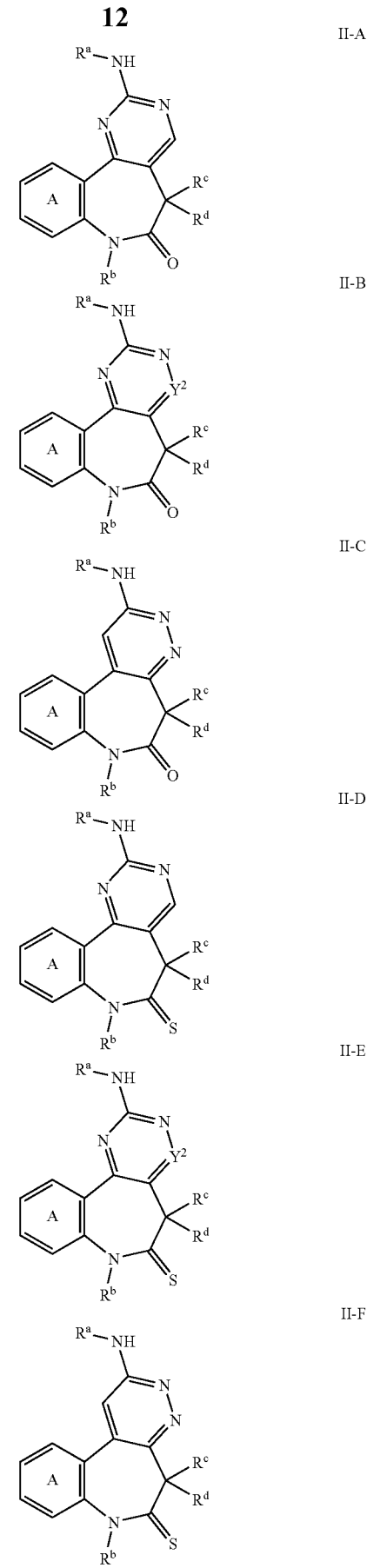

with 0-2 substituents independently selected from the group consisting of $C_{1-4}$ aliphatic, $C_{1-4}$ fluoroaliphatic, -halo, and —O($C_{1-4}$ aliphatic), or two adjacent substituents on Ring A, taken together with the intervening ring atoms, form a fused dioxolane or dioxane ring.

In some embodiments, Ring A in formula (II) has the formula A-i, A-ii, or A-iii:

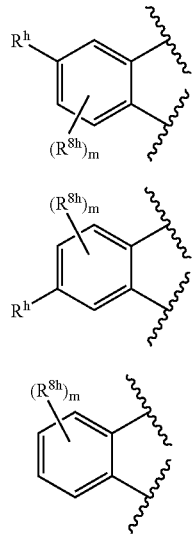

A-i

A-ii

A-iii $R^h$ and $R^{8h}$ are as described above for formula (I), and m is 0, 1, or 2, preferably 0 or 1.

In some embodiments, $R^h$ in formula A-i or A-ii is selected from —CN, —$CO_2R^5$, —C(O)N($R^4$)$_2$, —N($R^4$)$_2$, or —$OR^5$. In a particular embodiment, $R^h$ is —C(O)N($R^4$)$_2$ or —N($R^4$)$_2$, wherein one $R^4$ is hydrogen or $C_{1-4}$ alkyl, and the other $R^4$ is hydrogen, $C_{1-4}$ alkyl, or a phenyl, cyclohexyl, piperidinyl, piperazinyl, or pyrrolidinyl ring, any of which groups optionally is substituted with one or two substituents independently selected from the group consisting of -halo, $C_{1-4}$ aliphatic, $C_{1-4}$ fluoroaliphatic, —OH, —O($C_{1-4}$ alkyl), —$NH_2$, —NH($C_{1-4}$ alkyl), and —N($C_{1-4}$ alkyl)$_2$, or two adjacent substituents on a phenyl ring optionally are taken together to form a fused furan, dihydrofuran, oxazole, pyrrole, dioxolane, or dioxane ring. In another particular embodiment, $R^h$ is —C(O)N($R^4$)$_2$ or —N($R^4$)$_2$, wherein the two $R^4$ are taken together with the nitrogen to which they are attached to form a piperidinyl, piperazinyl, or pyrrolidinyl ring optionally substituted with one or two substituents independently selected from the group consisting of -fluoro, $C_{1-4}$ aliphatic, $C_{1-4}$ fluoroaliphatic, —OH, —O($C_{1-4}$ alkyl), —$NH_2$, —NH($C_{1-4}$ alkyl), and —N($C_{1-4}$ alkyl)$_2$.

In other embodiments, $R^h$ in formula A-i or A-ii is -$T^4$-$R^{2h}$, -$V^3$-$T^4$-$R^{2h}$, or -Cy-$T^4$-$R^{2h}$, where Cy is a 5- or 6-membered arylene or heteroarylene. In some such embodiments, $T^4$ is a $C_{1-4}$ alkylene chain; $V^3$ is —C≡C—, —C($R^5$)=C($R^5$)—, —N($R^4$)—, or —C(O)N($R^4$)—; Cy is phenylene or thienylene; and $R^{2h}$ is —$OR^5$, —N($R^4$)$_2$, or —C(O)N($R^4$)$_2$. In a particular embodiment, $R^{2h}$ is —N($R^4$)$_2$, wherein one $R^4$ is hydrogen or $C_{1-4}$ alkyl, and the other $R^4$ is hydrogen, $C_{1-4}$ alkyl, optionally substituted $C_{6-10}$ aryl, or optionally substituted $C_{6-10}$ ar($C_{1-4}$)alkyl. In another particular embodiment, $R^{2h}$ is —N($R^4$)$_2$, wherein the two $R^4$, taken together with the nitrogen to which they are attached, form a piperidinyl, piperazinyl, or pyrrolidinyl ring optionally substituted with one or two substituents independently selected from the group consisting of -fluoro, $C_{1-4}$ alkyl, $C_{1-4}$ fluoroalkyl, —OH, —O($C_{1-4}$ alkyl), —$NH_2$, —NH($C_{1-4}$ alkyl), and —N($C_{1-4}$ alkyl)$_2$.

The variable $R^a$ is hydrogen, —C(O)$R^{5a}$, —C(O)N($R^{4a}$)$_2$, —$CO_2R^{6a}$, —$SO_2R^{6a}$, —$SO_2$N($R^{4a}$)$_2$, an optionally substituted $C_{1-10}$ aliphatic, or an optionally substituted aryl, heteroaryl, or heterocyclyl ring. One embodiment of the invention relates to a compound of formula (I), wherein $R^a$ is hydrogen, $C_{1-6}$ aliphatic, or a substituted $C_{1-6}$ aliphatic having the formula -$T^{11}$-$R^{1a}$, -$T^{11}$-$R^{21a}$, or -$T^{12}$-$R^{22a}$. In another embodiment, $R^a$ is -$V^1$-$T^{11}$-$R^{1a}$, -$V^1$-$T^{11}$-$R^{21a}$, or -$V^1$-$T^{11}$-$R^{22a}$. In another embodiment, $R^a$ is —$R^{1a}$ or -$T^{11}$-$R^{1a}$. The variables $V^1$, $T^{11}$, $T^{12}$, $R^{1a}$, $R^{21a}$, and $R^{22a}$ have the values described below.

$V^1$ is —C(O)—, —C(O)N($R^{4a}$)—, —C(O)O—, —$SO_2$—, or —$SO_2$N($R^{4a}$)—. In certain embodiments, -$V^1$ is —C(O)—.

$T^{11}$ is a $C_{1-6}$ alkylene chain optionally substituted with one or two independently selected $R^{3a}$ or $R^{3b}$, wherein the alkylene chain optionally is interrupted by —C($R^5$)=C($R^5$)— or —C≡C—. The variables $R^{3a}$ and $R^{3b}$ have the values and preferred values described above in connection with Ring A. In certain embodiments, $T^{11}$ is a $C_{1-3}$ alkylene chain optionally substituted with one or two independently selected $R^{3a}$ or $R^{3b}$.

$T^{12}$ is a $C_{2-6}$ alkylene chain optionally substituted with one or two independently selected $R^3$, or $R^{3b}$, wherein the alkylene chain optionally is interrupted by —C($R^5$)=C($R^5$)— or —C≡C—. In certain embodiments, $T^{12}$ is a $C_{2-3}$ alkylene chain optionally substituted with one or two independently selected $R^{3a}$ or $R^{3b}$.

$R^{21a}$ is C($R^{5a}$)=C($R^{5a}$)$_2$, —C≡C$R^{5a}$, —S(O)$R^{6a}$, —$SO_2R^{6a}$, —$SO_3R^{6a}$, —$SO_2$N($R^{4a}$)$_2$, —$CO_2R^{5a}$, —C(O)—C(O)$R^{5a}$, —C(O)$R^{5a}$, —C(O)N($R^{4a}$)$_2$, —C(O)N($R^{4a}$)C(=N$R^{4a}$)—N($R^{4a}$)$_2$, —C(=N$R^{4a}$)N($R^{4a}$)$_2$, —C(=N$R^{4a}$)—$OR^{5a}$, —C($R^{6a}$)=N—$OR^{5a}$, —P(O)($R^{5a}$)$_2$, or —P(O)($OR^{5a}$)$_2$. In certain embodiments, $R^{21a}$ is —$CO_2R^{5a}$, —C(O)N($R^{4a}$)$_2$, —$SO_2$N($R^{4a}$)$_2$, —C(O)N($R^{4a}$)C(=N$R^{4a}$)—N($R^{4a}$)$_2$, or —C(=N$R^{4a}$)—N($R^{4a}$)$_2$.

$R^{22a}$ is —$NO_2$, —CN, —$OR^{5a}$, —$SR^{6a}$, —N($R^{4a}$)$_2$, —$NR^{4a}$C(O)$R^{5a}$, —$NR^{4a}$C(O)N($R^{4a}$)$_2$, —$NR^{4a}CO_2R^{6a}$, O—$CO_2R^{5a}$, —OC(O)N($R^{4a}$)$_2$, —O—C(O)$R^{5a}$, —N($R^{4a}$)C(=N$R^{4a}$)—N($R^{4a}$)$_2$, —N($R^{4a}$)C(=N$R^{4a}$)—N($R^{4a}$)—C(O)$R^5$, —N($R^{4a}$)$SO_2R^{6a}$, or N($R^{4a}$)$SO_2$N($R^{4a}$)$_2$. In certain embodiments, $R^{22a}$ is —$OR^{5a}$, —N($R^{4a}$)$_2$, —$NR^{4a}$C(O)$R^{5a}$, $NR^{4a}$C(O)N($R^{4a}$)$_2$, N($R^4$)C(=N$R^{4a}$)—N($R^{4a}$)$_2$ N($R^{4a}$)C(=N$R^{4a}$)—N($R^{4a}$)—C(O)$R^5$, or —N($R^{4a}$)$SO_2R^{6a}$.

$R^{1a}$ is an optionally substituted aryl, heteroaryl, heterocyclyl, or cycloaliphatic ring. In some embodiments, $R^{1a}$ is a 5- or 6-membered aryl or heteroaryl ring that is substituted with 0, 1, or 2 independently selected $R^j$ and 0, 1, or 2 independently selected $R^{8j}$. Each $R^j$ independently is selected from the group consisting of $C_{1-6}$ aliphatic, $C_{1-6}$ fluoroaliphatic, halo, —$R^{1j}$, —$R^{2j}$, -$T^5$-$R^{2j}$, -$T^5$-$R^{1j}$, -$V^4$-$T^5$-$R^{1j}$, and -$V^4$-$T^5$-$R^{2j}$; or two adjacent $R^j$, taken together with the intervening ring atoms, form an optionally substituted fused 5- to 6-membered aromatic or 4- to 8-membered non-aromatic ring having 0-3 ring heteroatoms selected from the group consisting of O, N, and S. Each $R^{8j}$ independently is selected from the group consisting of $C_{1-4}$ aliphatic, $C_{1-4}$ fluoroaliphatic, -halo, —$CO_2H$, —$CO_2$($C_{1-4}$ aliphatic), —OH, and —O($C_{1-4}$ aliphatic). In some embodiments, two adjacent $R^j$, taken together with the intervening ring atoms, form an optionally substituted fused furan, dihydrofuran, oxazole, pyrrole, dioxolane, or dioxane ring.

The variables $R^{1j}$, $R^{2j}$, $T^5$, and $V^4$ have the values described below:

Each $R^{1j}$ independently is an optionally substituted aryl, heteroaryl, heterocyclyl, or cycloaliphatic ring. In some embodiments, $R^{1j}$ is an optionally substituted 5- to 6-membered aryl, heteroaryl, heterocyclyl, or cycloaliphatic ring.

Each $R^{2j}$ independently is —$NO_2$, —CN, —$C(R^5)$=$C$ $(R^5)_2$, —C≡C—$R^5$, —$C(R^5)$=$C(R^5)(R^{10})$, —C≡C—$R^{10}$, —$OR^5$, —$SR^6$, —$S(O)R^6$, —$SO_2R^6$, —$SO_3R^5$, —$SO_2N$ $(R^4)_2$, —$N(R^4)_2$, —$NR^4C(O)R^5$, —$NR^4C(O)N(R^4)_2$, —$NR^4CO_2R^6$, —O—$CO_2R^5$, —OC(O)$N(R^4)_2$, —O—C(O) $R^5$, —O—$CO_2R^5$, —C(O)—$C(O)R^5$, —$C(O)R^5$, —C(O)N $(R^4)_2$, —$C(O)N(R^4)C(=NR^4)$—$N(R^4)_2$, —$N(R^4)C$ $(=NR^4)$—$N(R^4)$—$C(O)$, —$C(=NR^4)$—$N(R^4)_2$, —$C(=NR^4)$—$OR^5$, —$N(R^4)C(=NR^4)$—$N(R^4)_2$, —$N(R^4)$ $SO_2R^6$, —$N(R^4)SO_2N(R^4)_2$, —$P(O)(R^5)_2$, or —$P(O)(OR^5)_2$. In some embodiments, $R^{2j}$ is —$C(R^5)$=$C(R^5)_2$, —C≡C— $R^5$, —$OR^5$, —$N(R^4)_2$, —$NR^4C(O)R^5$, —$NR^4C(O)N(R^4)_2$, —$NR^4CO_2R^6$, —OC(O)$N(R^4)_2$, —$C(O)R^5$, —C(O)$N(R^4)_2$, —$N(R^4)SO_2R^6$, or —$N(R^4)SO_2N(R^4)_2$.

$V^4$ is —$(R^5)$=$C(R^5)$—, —C≡C—, —O—, —S—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —OC $(O)O$—, —OC(O)$N(R^4)$—, —$C(NR^4)$=N—, —$C(OR^5)$ =N—, —$N(R^4)SO_2$—, —$N(R^4)SO_2N(R^4)$—, —P(O) $(R^5)$—, —$P(O)(OR^5)$—O—, —P(O)—O—, or —P(O) $(NR^5)$—$N(R^5)$—. In some embodiments, -$V^4$ is —$C(R^5)$=C $(R^5)$—, —C≡C—, —O—, —$N(R^4)$—, —$N(R^4)C(O)$—, —$NR^4C(O)N(R^4)$—, —$N(R^4)CO_2$—, —OC(O)$N(R^4)$—, —C(O)—, —$C(O)N(R^4)$—, —$N(R^4)SO_2$—, or —$N(R^4)$ $SO_2N(R^4)$—. In certain embodiments, -$V^4$ is —$C(R^5)$=C $(R^5)$—, —C≡C—, or —$C(O)N(R^4)$—.

$T^5$ is a $C_{1-6}$ alkylene chain optionally substituted with one or two independently selected $R^{3a}$ or $R^{3b}$, wherein the alkylene chain optionally is interrupted by —$C(R^5)$=$C(R^5)$—, —C≡C—, —O—, —S—, —S(O)—, —$S(O)_2$—, —$SO_2N$ $(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C (O)—, —$CO_2$—, —OC(O)—, —OC(O)O—, —OC(O)N $(R^4)$—, —$N(R^4)SO_2$—, or —$SO_2N(R^4)$—, and wherein $T^5$ or a portion thereof optionally forms part of a 3-7 membered ring. In some embodiments, $T^5$ is a $C_{1-4}$, or $C_{2-4}$ alkylene chain, optionally substituted with one or two independently selected $R^{3a}$, or $R^{3b}$. The variables $R^{3a}$ and $R^{3b}$ have the values and preferred values described above in connection with Ring A.

In some embodiments, $R^a$ is an optionally substituted 5- or 6-membered aryl or heteroaryl ring. In some such embodiments, $R^a$ is selected from the group consisting of imidazolyl, pyrazolyl, oxazolyl, isoxazolyl, oxadiazolyl, thiazolyl, thiadiazolyl, triazolyl, pyridyl, pyrimidinyl, pyridazinyl, pyrazinyl, and triazinyl.

In certain other embodiments, Ring B is an optionally substituted phenyl ring, and the invention relates to a compound of formula (III):

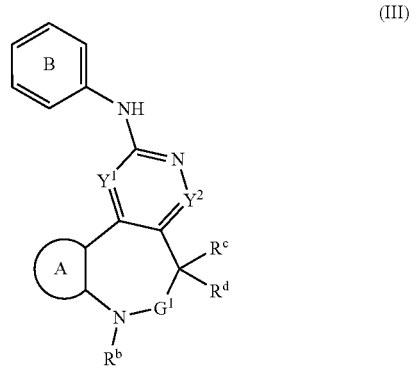

(III)

or a pharmaceutically acceptable salt thereof;
wherein Ring B is substituted with 0, 1, or 2 $R^j$ and 0, 1, or 2 $R^{8j}$. Ring A, and the variables $R^b$, $R^c$, $R^d$, $R^j$, $R^{8j}$, $G^1$, $Y^1$, and $Y^2$ have the values described above for formula (I). In some such embodiments, Ring B is substituted with 0-2 $R^{8j}$ and one $R^j$.

In some embodiments, $R^j$ is an optionally substituted aryl, heteroaryl, or heterocyclyl ring. In certain such embodiments, $R^j$ is selected from the group consisting of imidazolyl, pyrrolyl, pyrazolyl, oxazolyl, thienyl, phenyl, pyridyl, pyrimidinyl, piperazinyl, piperidinyl, or morpholinyl.

In other embodiments, $R^j$ is selected from the group consisting of —$CO_2R^5$, —$C(O)N(R^4)_2$, —$SO_2N(R^4)_2$, —$C(=NR^4)$—$N(R^4)_2$, —$N(R^4)C(=NR^4)$—$(N(R^4)_2$, —$C(O)N(R^4)C(=NR^4)$—$N(R^4)_2$, and —$N(R^4)C(=NR^4)$—$N(R^4)$—$C(O)R^5$. In certain such embodiments, $R^j$ is —$CO_2H$.

In some other embodiments, $R^j$ has the formula -$T^5$-$R^{2j}$ or -$V^4$-$T^5$-$R^{2j}$, wherein $V^4$ is —C≡C— or —$C(R^5)$=$C(R^5)$—, and $R^{2j}$ is —$OR^5$ or —$N(R^4)_2$.

In still other embodiments, $R^j$ has the formula -$V^4$-$T^5$-$R^{2j}$ or -$V^4$-$T^5$-$R^{1j}$, wherein $V^4$ is —$C(O)N(R^4)$— or —$SO_2N$ $(R^4)$— and $T^5$ is a $C_{2-4}$ alkylene chain, optionally substituted with —F or $C_{1-4}$ aliphatic. The variables $R^{1j}$ and $R^{2j}$ have the values described above for formula (I). In certain embodiments, $R^{1j}$ is an optionally substituted 3- to 6-membered heterocyclyl or an optionally substituted 5- to 6-membered heteroaryl. A particular value for $R^{2j}$ is —$N(R^4)_2$, where each $R^4$ independently is hydrogen or $C_{1-4}$ aliphatic, or —$N(R^4)_2$ is an optionally substituted 3- to 6-membered heterocyclyl or an optionally substituted 5- to 6-membered heteroaryl, having, in addition to the nitrogen, 0-2 ring heteroatoms selected from N, O, and S.

In some embodiments, Ring B is substituted with one or two substituents independently selected from the group consisting of $C_{1-4}$ aliphatic, $C_{1-4}$ fluoroaliphatic, -halo, —$OR^5$, or —$N(R^4)_2$, or two adjacent $R^j$, taken together with the intervening ring atoms, form an optionally substituted fused benzene, pyridine, furan, dihydrofuran, oxazole, thiazole, oxadiazole, thiadiazole, pyrrole, pyrazole, dioxolane, or dioxane ring.

In yet other embodiments, Ring B is substituted with 0-2 substituents independently selected from the group consisting of $C_{1-4}$ aliphatic, $C_{1-4}$ fluoroaliphatic, -halo, and —$O(C_{1-4}$ aliphatic), or two adjacent substituents, taken together with the intervening ring atoms, form a fused dioxolane or dioxane ring.

In some embodiments, Ring B has the formula B-i, B-ii, or B-iii:

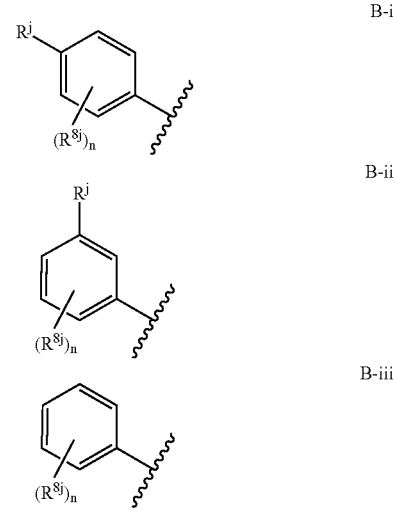

B-i

B-ii

B-iii wherein n is 0, 1, or 2, preferably 0 or 1. $R^j$ and $R^{8j}$ have the values and preferred values described above described above for formulae (I) and (III).

The variable $R^b$ is hydrogen or an optionally substituted aliphatic, aryl, heteroaryl, or heterocyclyl group. In some embodiments, the invention relates to a compound of formula (I), wherein $R^b$ is hydrogen or $C_{1-6}$ aliphatic. In certain such embodiments, $R^b$ is hydrogen or methyl.

In some other embodiments, the invention relates to a compound of formula (I), wherein $R^b$ is an optionally substituted $C_{1-6}$ aliphatic. In some such embodiments, $R^b$ has the formula -$T^{21}$-$R^{1b}$-$T^{21}$-$R^{21b}$, or -$T^{22}$-$R^{22b}$. The variable $R^{1b}$, $R^{21b}$, $R^{22b}$ $T^{21}$, and $T^{22}$ have the values described below:

$R^{1b}$ is an optionally substituted aryl, heteroaryl, heterocyclyl, or cycloaliphatic ring. In some embodiments, $R^{1b}$ is an optionally substituted pyrrolyl, imidazolyl, pyrazolyl, triazolyl, phenyl, pyridyl, pyrimidinyl, pyrazinyl, pyrrolidinyl, piperidinyl, piperazinyl, or morpholinyl ring.

$R^{21b}$ is —C($R^5$)=C($R^5$)$_2$, —C≡C—$R^5$, —C($R^5$)=C($R^5$)($R^{10}$), —C≡C—$R^{10}$, —S(O)$R^6$, —SO$_2R^6$, —SO$_3R^5$, —SO$_2$N($R^4$)$_2$, —CO$_2R^5$, —C(O)—C(O)$R^5$, —C(O)$R^5$, —C(O)N($R^4$)$_2$, —C(O)N($R^4$)C(=N$R^4$)—N($R^4$)$_2$, —C(=N$R^4$)—N($R^4$)$_2$, —C(=N$R^4$)—O$R^5$, —C($R^6$)=N—O$R^5$, —P(O)($R^5$)$_2$, or —P(O)(O$R^5$)$_2$. In some embodiments, $R^{21b}$ is —CO$_2R^5$ or —C(O)N($R^4$)$_2$. In certain such embodiments, $R^5$ is hydrogen, $C_{1-4}$ alkyl, or $C_{6-10}$ar($C_{1-4}$)alkyl, and each $R^4$ independently is hydrogen, $C_{1-4}$ alkyl, or $C_{6-10}$ar($C_{1-4}$)alkyl, or two $R^4$, taken together with the nitrogen atom to which they are attached, form an optionally substituted 5- to 6-membered heterocyclyl ring having, in addition to the nitrogen atom, 0-2 ring heteroatoms selected from N, O, and S.

$R^{22b}$ is —NO$_2$, —CN, —O$R^5$, —S$R^6$, —N($R^4$)$_2$, —N$R^4$C(O)$R^5$, —N$R^4$C(O)N($R^4$)$_2$, —N$R^4$CO$_2R^6$, —O—CO$_2R^5$, —OC(O)N($R^4$)$_2$, —O—C(O)$R^5$, —N($R^4$)C(=N$R^4$)—N($R^4$)$_2$, —N($R^4$)C(=N$R^4$)—N($R^4$)—C(O)$R^5$, —N($R^4$)SO$_2R^6$, or —N($R^4$)SO$_2$N($R^4$)$_2$. In some embodiments, $R^2$ is —O$R^5$ or —N($R^4$)$_2$. In certain such embodiments, $R^5$ is hydrogen, $C_{1-4}$ alkyl, or $C_{6-10}$ar($C_{1-4}$)alkyl, and each $R^4$ independently is hydrogen, $C_{1-4}$ alkyl, or $C_{6-10}$ar($C_{1-4}$)alkyl, or two $R^4$, taken together with the nitrogen atom to which they are attached, form an optionally substituted 5- to 6-membered heterocyclyl ring having, in addition to the nitrogen atom, 0-2 ring heteroatoms selected from N, O, and S.

$T^{21}$ is a $C_{1-6}$ alkylene chain optionally substituted with one or two $R^3$, wherein the alkylene chain optionally is interrupted by —C($R^5$)=C($R^5$)— or —C≡C—. In some embodiments, $T^{21}$ is a $C_{1-4}$ alkylene chain. $T^{22}$ is a $C_{2-6}$alkylene chain optionally substituted with one or two $R^3$, wherein the alkylene chain optionally is interrupted by —C($R^5$)=C($R^5$)— or —C≡C—. In some embodiments, $T^{22}$ is a $C_{2-4}$ alkylene chain.

In other embodiments, the invention relates to a compound of formula (I), wherein $R^b$ is an optionally substituted aryl, heteroaryl, or heterocyclyl ring. In some such embodiments, $R^b$ is a 5- or 6-membered aryl or heteroaryl ring that is substituted with 0-2 independently selected $R^k$ and 0-2 independently selected $R^{8k}$. Each $R^k$ independently is selected from the group consisting of $C_{1-6}$ aliphatic, $C_{1-6}$ fluoroaliphatic, -halo, $R^{1k}$, —$R^{2k}$, -$T^6$-$R^{2k}$, -$T^6$-$R^{1k}$, -$V^5$-$T^6$-$R^{1k}$, and -$V^5$-$T^6$-$R^{2k}$; or two adjacent $R^k$, taken together with the intervening ring atoms, form an optionally substituted fused 4- to 8-membered aromatic or non-aromatic ring having 0-3 ring heteroatoms selected from the group consisting of O, N, and S. Each $R^{8k}$ independently is selected from the group consisting of $C_{1-4}$ aliphatic, $C_{1-4}$ fluoroaliphatic, -halo, and —O($C_{1-4}$ aliphatic).

The variables $R^{1k}$, $R^{2k}$, $T^6$, and $V^5$ have the values described below:

Each $R^{1k}$ independently is an optionally substituted aryl, heteroaryl, heterocyclyl, or cycloaliphatic ring. In some embodiments, $R^{1k}$ is an optionally substituted 5- or 6-membered aryl, heteroaryl, heterocyclyl, or cycloaliphatic ring.

Each $R^{2k}$ independently is —NO$_2$, —CN, —C($R^5$)=C($R^5$)$_2$, —C≡C—$R^5$, —C($R^5$)=C($R^5$)($R^{10}$), —C≡C—$R^{10}$, —O$R^5$, —S$R^6$, —S(O)$R^6$, —SO$_2R^6$, —SO$_3R^5$, —SO$_2$N($R^4$)$_2$, —N($R^4$)$_2$, —N$R^4$C(O)$R^5$, —N$R^4$C(O)N($R^4$)$_2$, —N$R^4$CO$_2R^6$, —O—CO$_2R^5$, —OC(O)N($R^4$)$_2$, —O—C(O)$R^5$, —CO$_2R^5$, —C(O)—C(O)$R^5$, —C(O)$R^5$, —C(O)N($R^4$)$_2$, —C(O)N($R^4$)C(=N$R^4$)—N($R^4$)$_2$, —N($R^4$)C(=N$R^4$)—N($R^4$)—C(O), —C(=N$R^4$)—N($R^4$)$_2$, —C(=N$R^4$)—O$R^5$, —N($R^4$)C(=N$R^4$)—N($R^4$), —N($R^4$)SO$_2R^6$, —N($R^4$)SO$_2$N($R^4$)$_2$, —P(O)($R^5$)$_2$, or —P(O)(O$R^5$)$_2$.

$V^5$ is —C($R^5$)=C($R^5$)—, —C≡C—, —O—, —S—, —S(O)—, —S(O)$_2$—, —SO$_2$N($R^4$)—, —N($R^4$)—, —N($R^4$)C(O)—, —N$R^4$C(O)N($R^4$)—, —N($R^4$)CO$_2$—, —C(O)N($R^4$)—, —C(O)—, —C(O)—C(O)—, —CO$_2$—, —OC(O)—, —OC(O)O—, —OC(O)N($R^4$)—, —C(N$R^4$)=N—, —C(O$R^5$)=N—, —N($R^4$)SO$_2$—, —N($R^4$)SO$_2$N($R^4$)—, —P(O)($R^5$)—, —P(O)(O$R^5$)—O—, —P(O)—O—, or —P(O)(N$R^5$)—N($R^5$)—. In some embodiments, -$V^5$- is —C($R^5$)=C($R^5$)—, —C≡C—, —O—, —N($R^4$)—, —N($R^4$)C(O)—, —N$R^4$C(O)N($R^4$)—, —N($R^4$)CO$_2$—, —OC(O)N($R^4$)—, —C(O)—, —C(O)N($R^4$)—, —N($R^4$)SO$_2$—, or —N($R^4$)SO$_2$N($R^4$)—. In certain embodiments, -$V^5$- is —C($R^5$)=C($R^5$)—, —C≡C—, or —C(O)N($R^4$)—.

$T^6$ is a $C_{1-6}$ alkylene chain optionally substituted with one or two independently selected $R^{3a}$ or $R^{3b}$, wherein the alkylene chain optionally is interrupted by —C($R^5$)=C($R^5$)—, —C≡C—, —O—, —S—, —S(O)—, —S(O)$_2$—, —SO$_2$N($R^4$)—, —N($R^4$)—, —N($R^4$)C(O)—, —N$R^4$C(O)N($R^4$)—, —N($R^4$)CO$_2$—, —C(O)N($R^4$)—, —C(O)—, —C(O)—C(O)—, —CO$_2$—, —OC(O)—, —OC(O)O—, —OC(O)N($R^4$)—, —N($R^4$)SO$_2$—, or —SO$_2$N($R^4$)—, and wherein $T^6$ or a portion thereof optionally forms part of a 3-7 membered ring. The variables $R^{3a}$ and $R^{3b}$ have the values and preferred values described above in connection with Ring A.

In a particular embodiment, $R^b$ is an optionally substituted phenyl ring, and the invention relates to a compound of formula (IV):

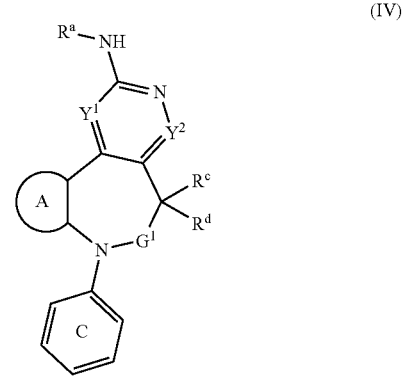

(IV)

or a pharmaceutically acceptable salt thereof;

wherein Ring C is substituted with 0, 1, or 2 $R^k$ and 0, 1, or 2 $R^{8k}$. Ring A, and the variables $R^a$, $R^c$, $R^d$, $R^k$, $R^{8k}$, $G^1$, $Y^1$, and $Y^2$ have the values described above for formula (I).

In some such embodiments, Ring C is substituted with 0-2 $R^{8k}$ and one $R^k$. In some embodiments, Ring C is substituted with 1 or 2 $R^{8k}$. In some embodiments, Ring C is substituted with 0-2 substituents independently selected from the group consisting of $C_{1-4}$ aliphatic, $C_{1-4}$ fluoroaliphatic, -halo, and —O($C_{1-4}$ aliphatic).

In certain embodiments, Ring C has the formula v or vi:

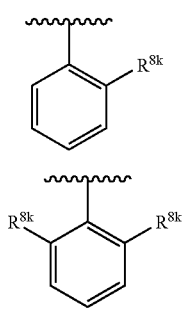

wherein each $R^{8k}$ independently is selected from the group consisting of $C_{1-4}$ aliphatic, $C_{1-4}$ fluoroaliphatic, -halo, and —O($C_{1-4}$ aliphatic).

In some embodiments, the invention relates to a subgenus of the compounds of formula (I) represented by formula (V):

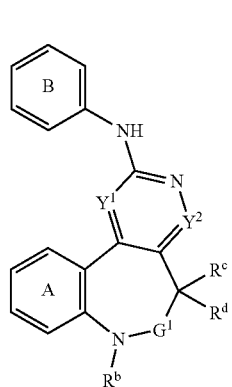

or a pharmaceutically acceptable salt thereof;

wherein Ring A is substituted with 0-2 $R^h$ and 0-2 $R^{8h}$, and Ring B is substituted with 0-2 $R^j$ and 0-2 $R^{8j}$. The variables $G^1, Y^1, Y^2, R^b, R^c, R^d, R^h, R^j, R^{8h}$, and $R^{8j}$ have the values and preferred values described above for formulae (I)-(III).

In some embodiments, the invention relates to a compound of any one of formulae (II)-(V), characterized by one or more, and preferably all, of the following features (a)-(e):

(a) $Y^1$ is N;
(b) $Y^2$ is $CR^e$, where $R^e$ is selected from the group consisting of hydrogen, $C_{1-4}$ aliphatic, $C_{1-4}$ fluoroaliphatic, -halo, —$OR^5$, —$N(R^4)_2$, —CN, —$CO_2R^5$, —C(O)N$(R^4)_2$, —$C(R^5)$=C$(R^5)_2$, —$C(R^5)$=$C(R^5)(R^{10})$, —C≡C—$R^5$, and —C≡C—$R^{10}$;
(c) $G^1$ is C=O;
(d) $R^c$ is selected from the group consisting of hydrogen, fluoro, —$OR^5$, —$N(R^4)_2$, and $C_{1-4}$ aliphatic optionally substituted with one or two groups independently selected from $C_{1-4}$ aliphatic, fluoro, —$OR^5$, —$N(R^4)_2$, —$CO_2R^5$, —C(O)N$(R^4)_2$, and optionally substituted 5- or 6-membered aryl or heteroaryl; and
(e) $R^d$ is hydrogen.

In some embodiments, the invention relates to a compound of any one of formulae (I)-(V) wherein $G^1$ is C=O, $Y^1$ is N, $Y^2$ is CH, and each of $R^c$ and $R^d$ is hydrogen.

In some embodiments, the invention relates to a subgenus of the compounds of formula (I) represented by formula (VI) or (VIa):

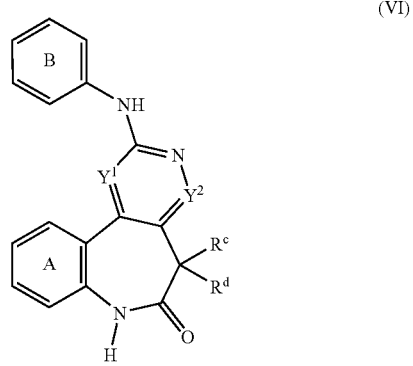

or a pharmaceutically acceptable salt thereof;

wherein Ring A is substituted with 0-2 $R^h$ and 0-2 $R^{8h}$, and Ring B is substituted with 0-2 $R^j$ and 0-2 $R^{8j}$. The variables $G^1, Y^1, Y^2, R^b, R^c, R^d, R^h, R^j, R^{8h}$, and $R^{8j}$ have the values and preferred values described above for formulae (I)-(III).

In some embodiments, the invention relates to a subgenus of the compounds of formula (I) represented by formula (VII) or (VIIa):

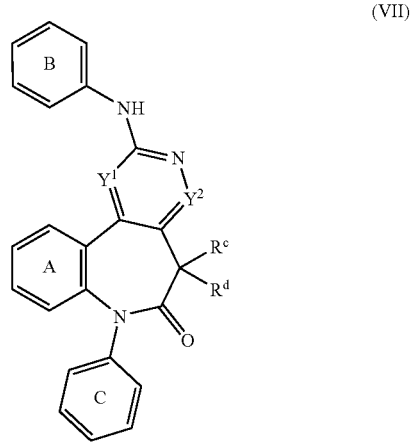

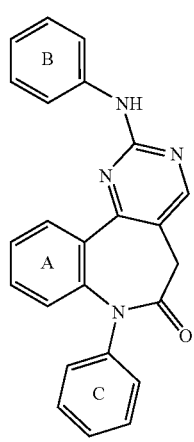

(VIIa)

or a pharmaceutically acceptable salt thereof;

wherein Ring A is substituted with 0-2 $R^h$ and 0-2 $R^{8h}$, Ring B is substituted with 0-2 $R^j$, and 0-2 $R^{8j}$, and Ring C is substituted with 0-2 $R^k$ and 0-2 $R^{8k}$. The variables $G^1, Y^1, Y^2$, $R^b, R^c, R^d, R^h, R^j, R^k, R^{8h}, R^{8j}$, and $R^{8k}$ have the values and preferred values described above for formulae (I)-(IV).

Subgenus definitions for Rings A, B, and C described for any one of formulae (I)-(VI), or exemplified in any specific compound(s) disclosed herein, apply also to the other formulae. Compounds embodying any combination of the preferred values for the variables described herein are considered to be within the scope of the present invention.

Specific examples of compounds of formula (I) are shown below in Table 1.

TABLE 1

Protein Kinase Inhibitors

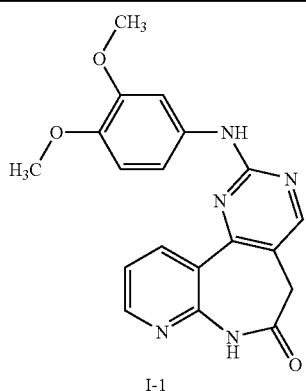

I-1

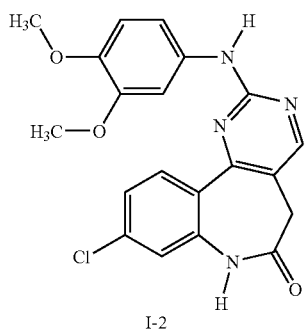

I-2

TABLE 1-continued

Protein Kinase Inhibitors

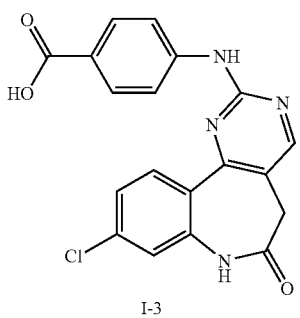

I-3

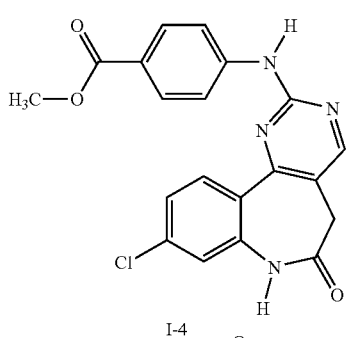

I-4

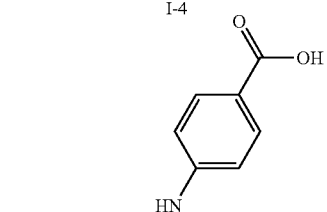

I-5

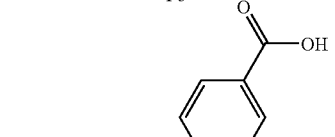

I-6

TABLE 1-continued
Protein Kinase Inhibitors
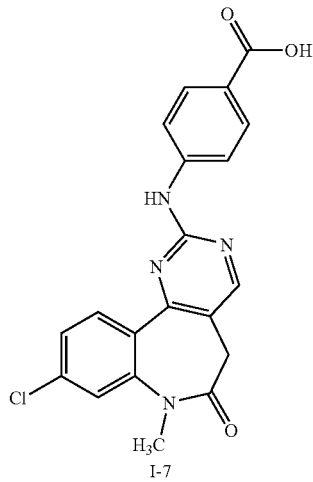
I-7
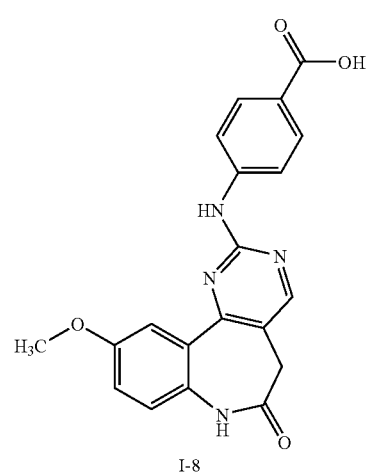
I-8
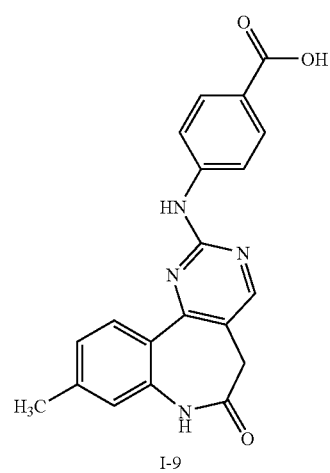
I-9
TABLE 1-continued
Protein Kinase Inhibitors
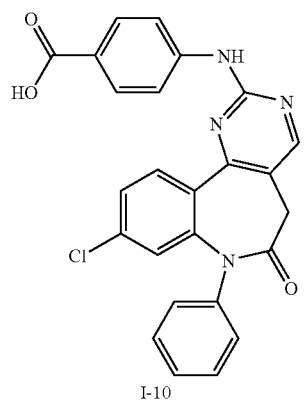
I-10
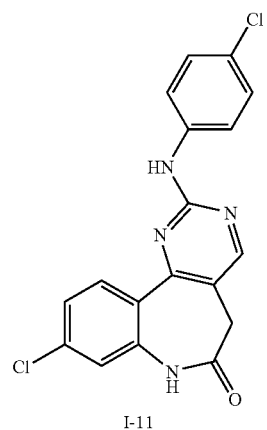
I-11
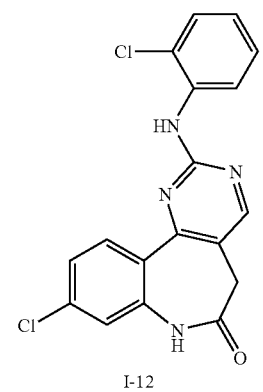
I-12

TABLE 1-continued
Protein Kinase Inhibitors
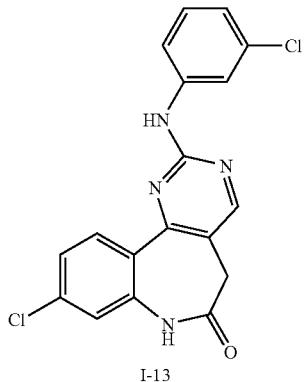
I-13
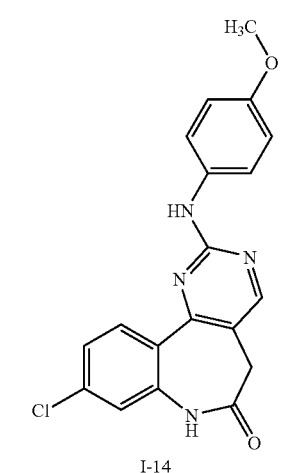
I-14
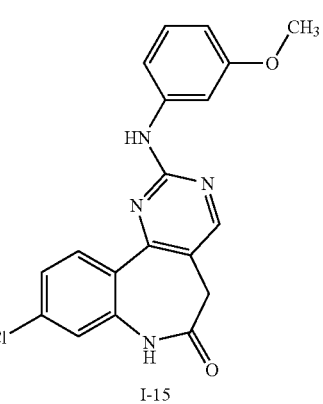
I-15
TABLE 1-continued
Protein Kinase Inhibitors
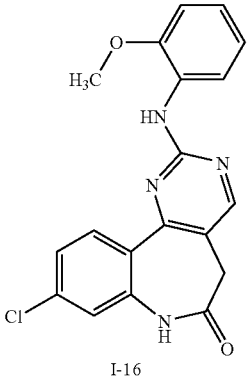
I-16
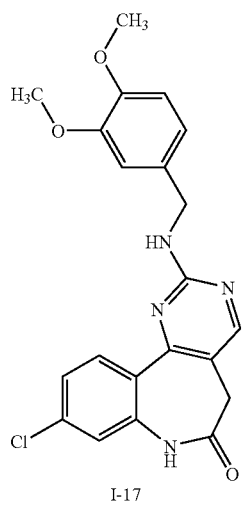
I-17
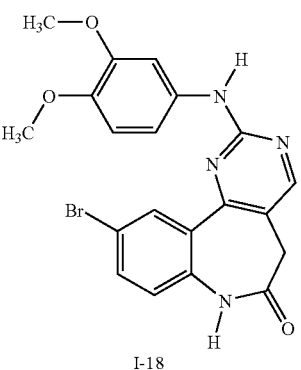
I-18

TABLE 1-continued
Protein Kinase Inhibitors
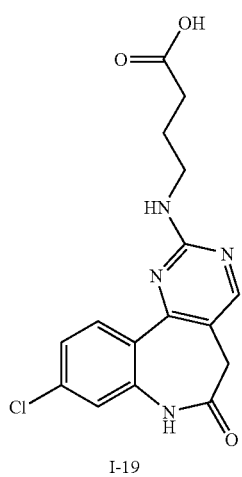
I-19
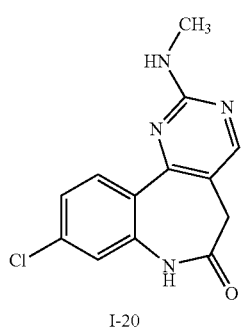
I-20
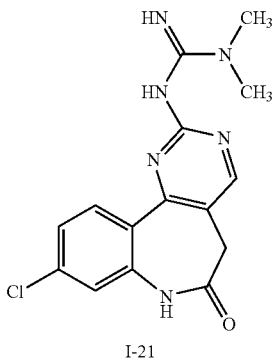
I-21
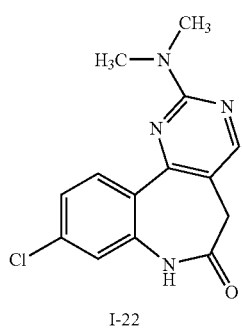
I-22
TABLE 1-continued
Protein Kinase Inhibitors
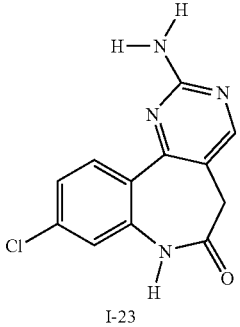
I-23
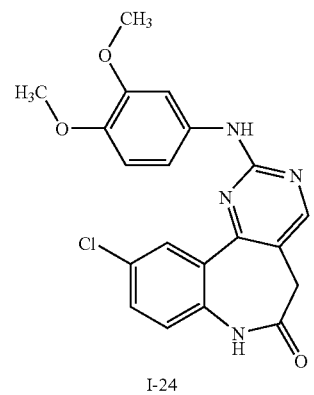
I-24
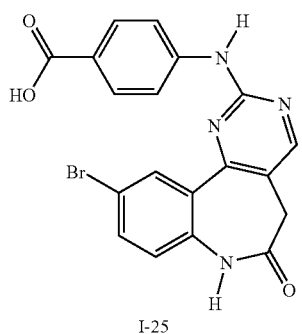
I-25
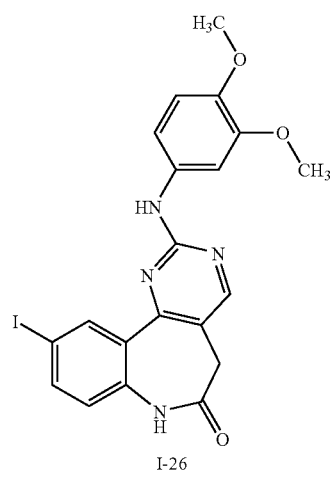
I-26

TABLE 1-continued

Protein Kinase Inhibitors

I-27

I-28

I-29

I-30

I-31

I-32

I-33

I-34

TABLE 1-continued
Protein Kinase Inhibitors
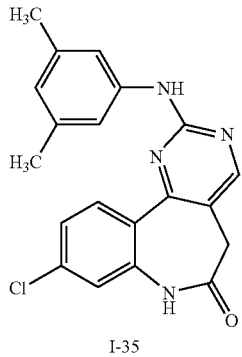
I-35
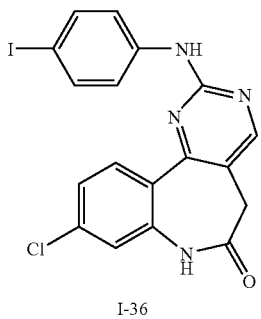
I-36
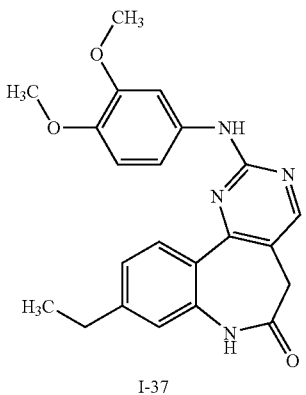
I-37
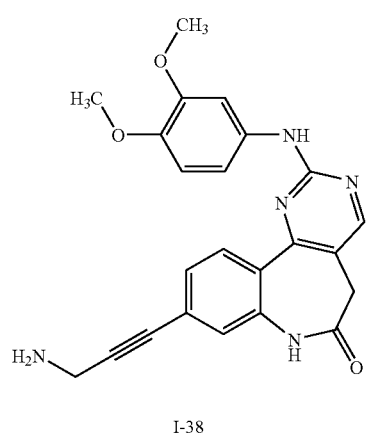
I-38
TABLE 1-continued
Protein Kinase Inhibitors
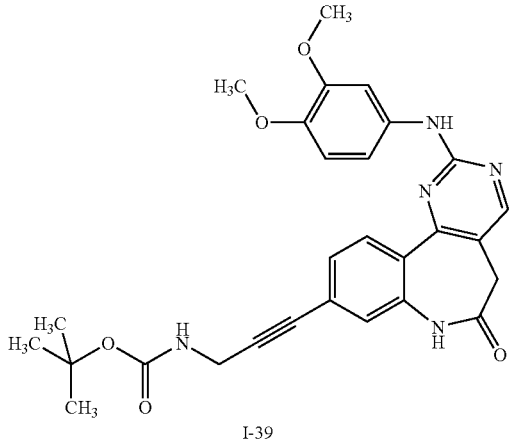
I-39
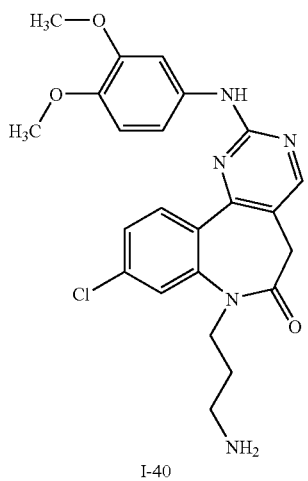
I-40
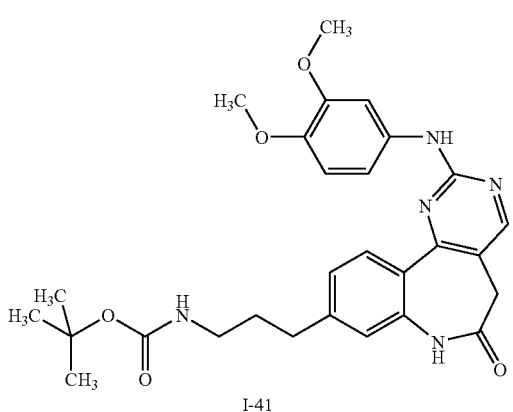
I-41

TABLE 1-continued
Protein Kinase Inhibitors
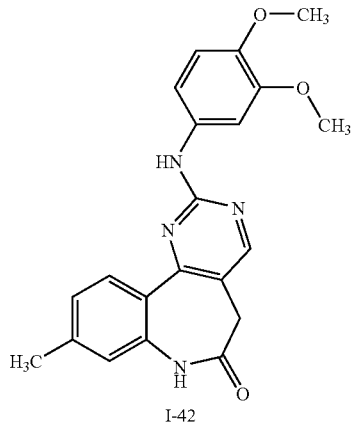
I-42
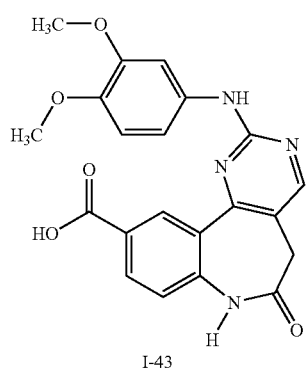
I-43
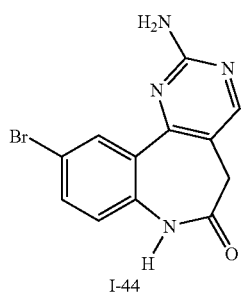
I-44
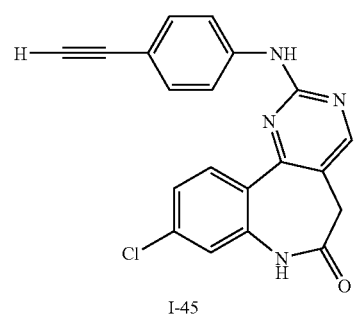
I-45
TABLE 1-continued
Protein Kinase Inhibitors
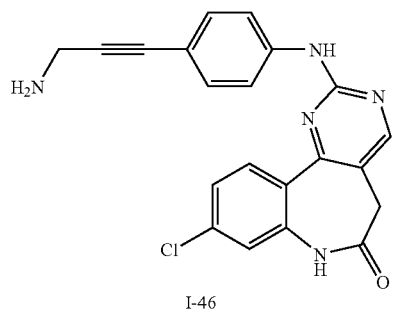
I-46
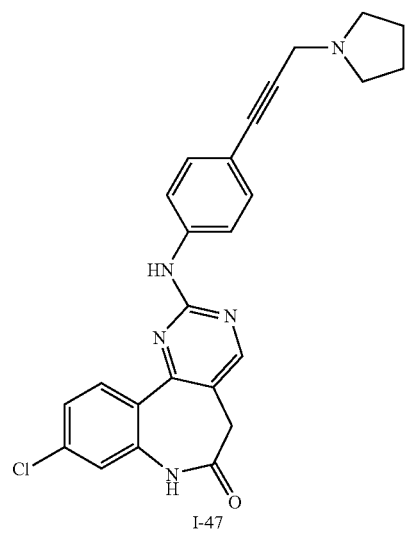
I-47
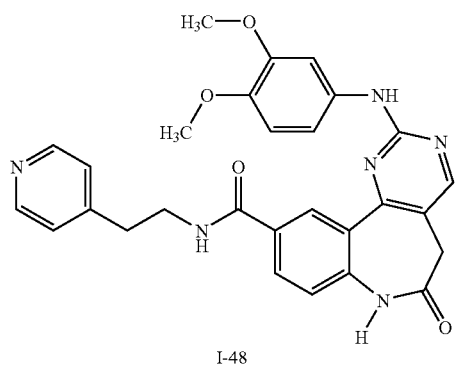
I-48

TABLE 1-continued

Protein Kinase Inhibitors

I-49

I-50

I-51

I-52

I-53

I-54

I-55

TABLE 1-continued
Protein Kinase Inhibitors
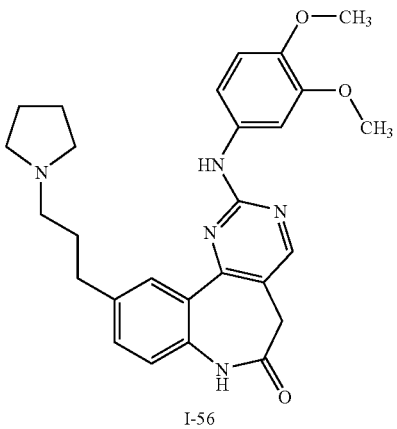
I-56
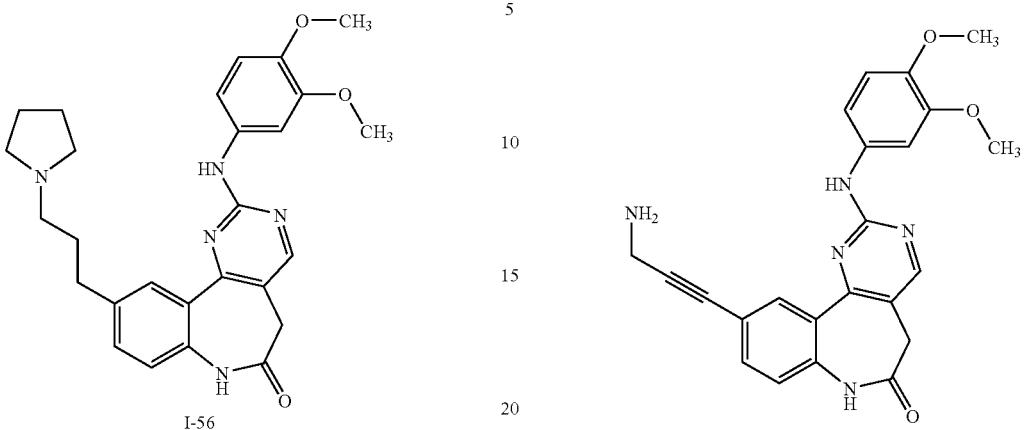
I-59
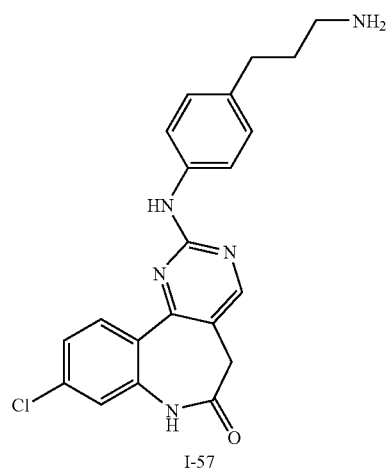
I-57
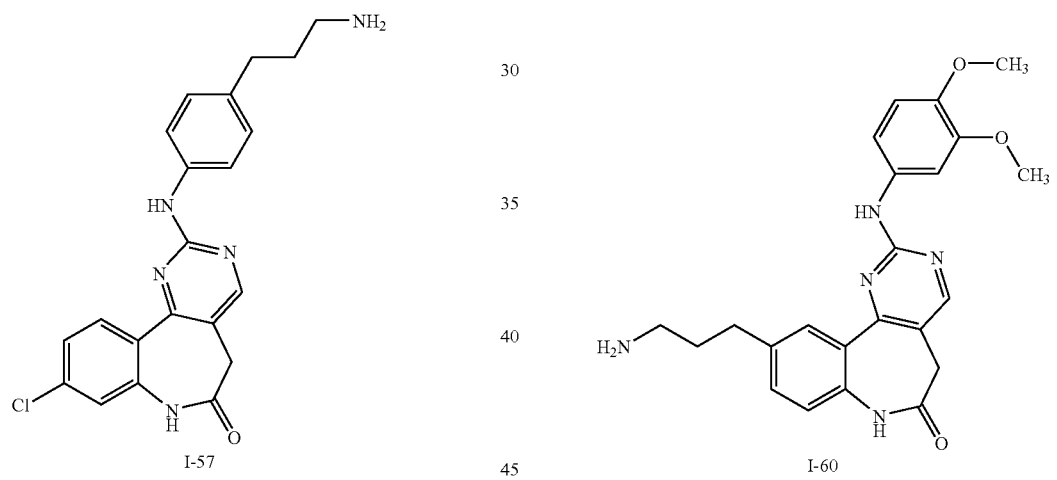
I-60
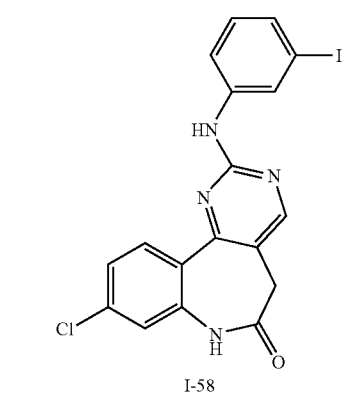
I-58
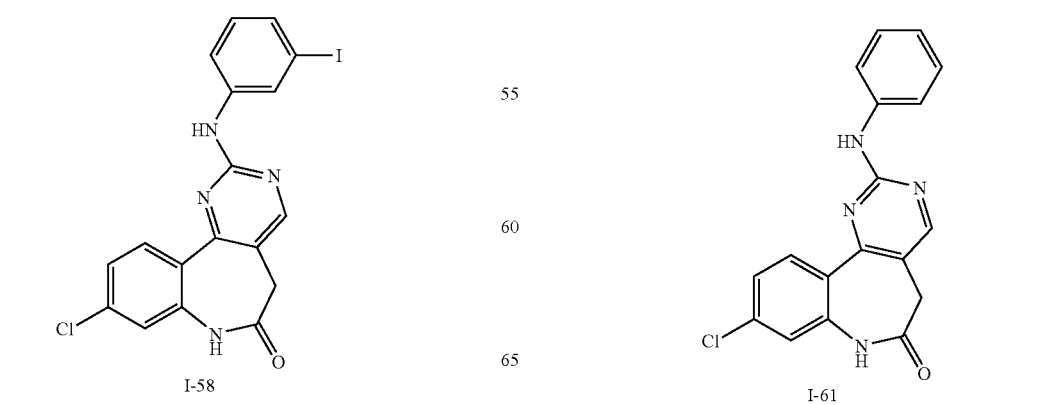
I-61

TABLE 1-continued
Protein Kinase Inhibitors
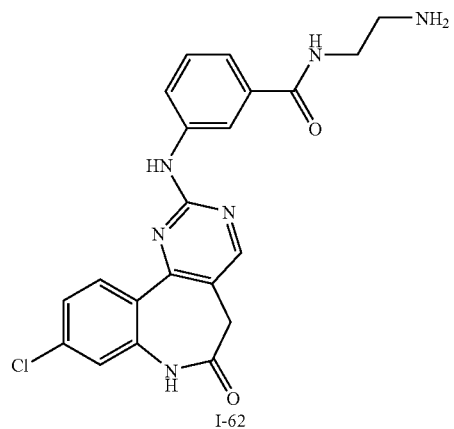
I-62
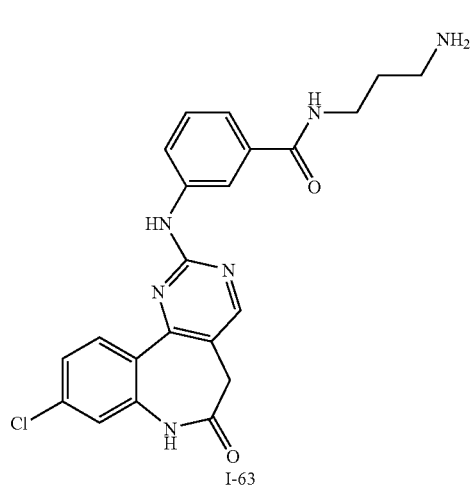
I-63
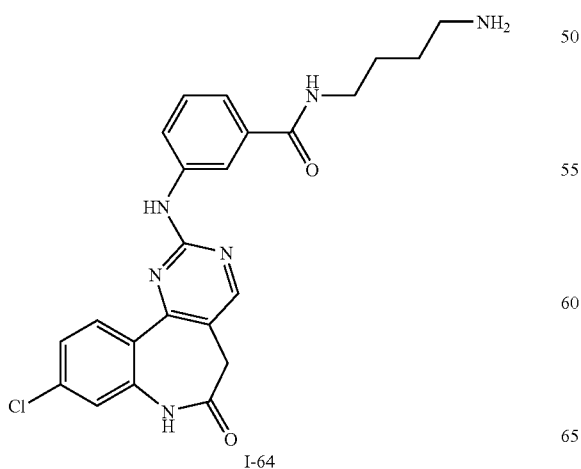
I-64
TABLE 1-continued
Protein Kinase Inhibitors
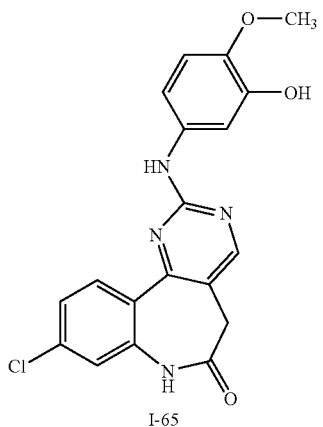
I-65
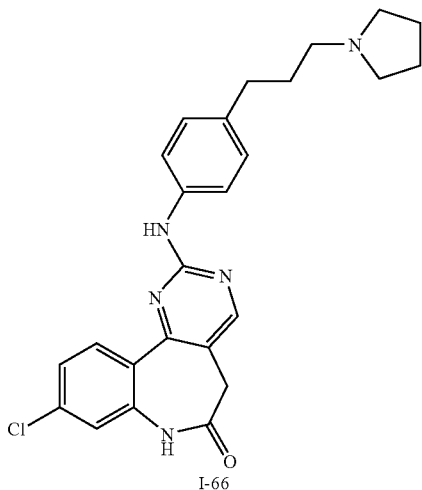
I-66
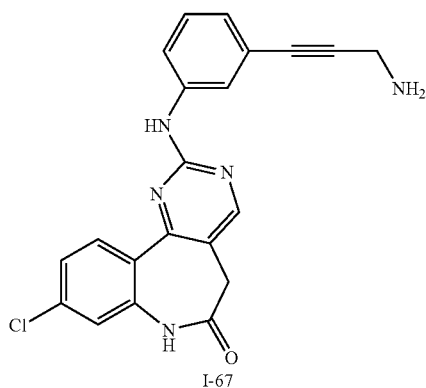
I-67

TABLE 1-continued
Protein Kinase Inhibitors
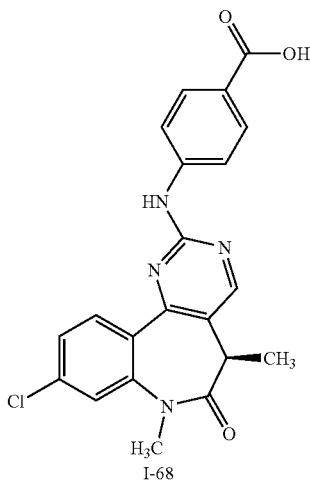
I-68
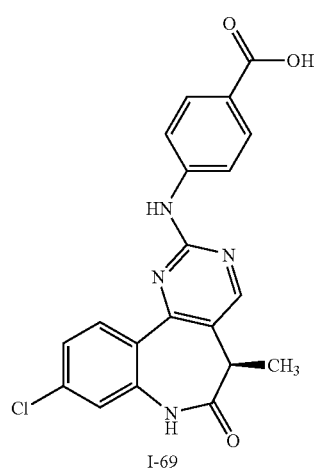
I-69
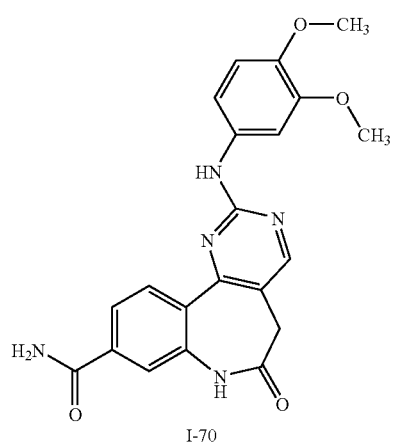
I-70
TABLE 1-continued
Protein Kinase Inhibitors
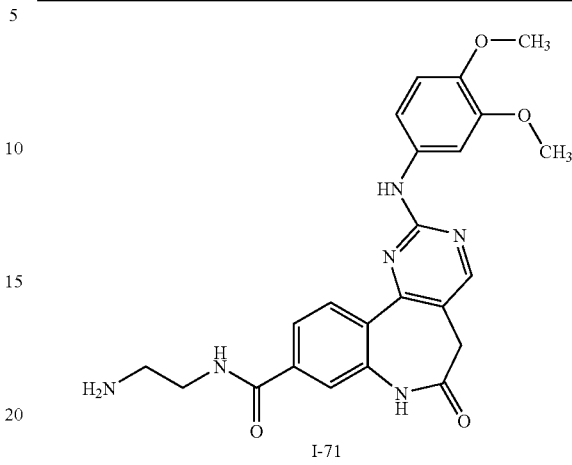
I-71
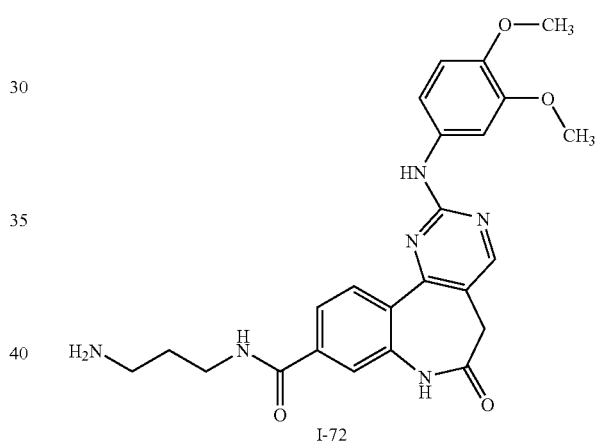
I-72
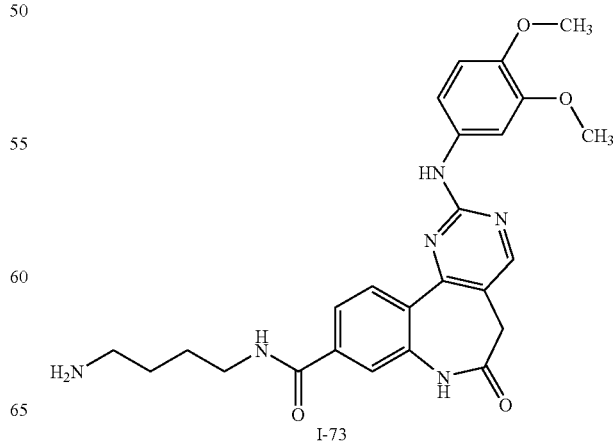
I-73

TABLE 1-continued

Protein Kinase Inhibitors

I-74

I-75

I-76

I-77

I-78

I-79

I-80

I-81

TABLE 1-continued
Protein Kinase Inhibitors
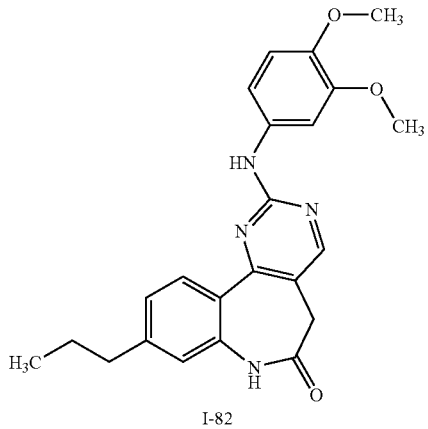
I-82
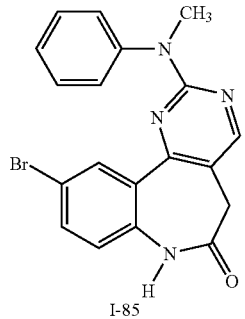
I-85
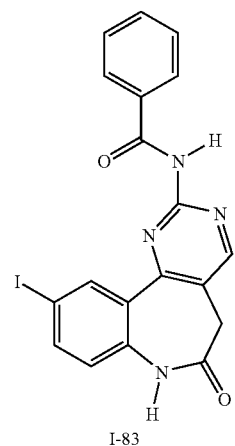
I-83
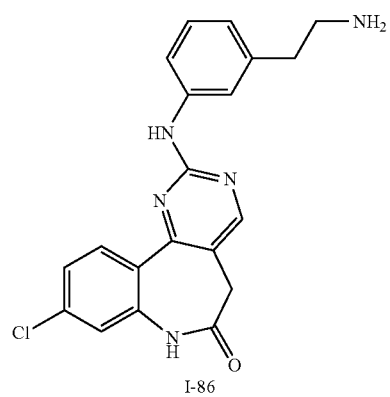
I-86
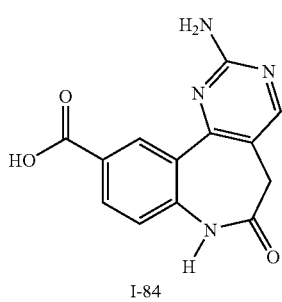
I-84
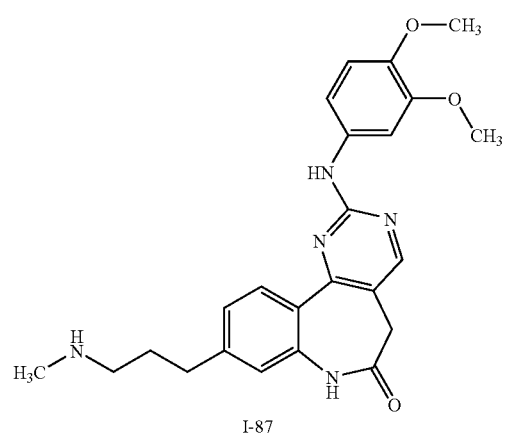
I-87

TABLE 1-continued
Protein Kinase Inhibitors
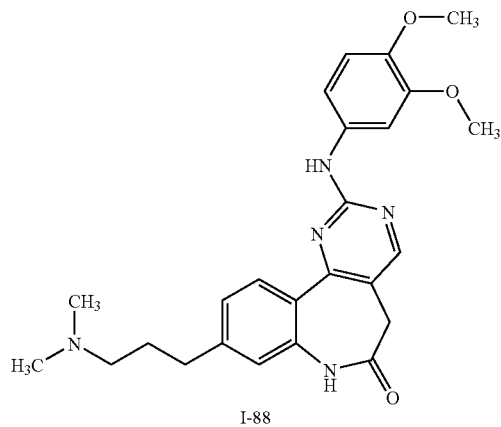
I-88
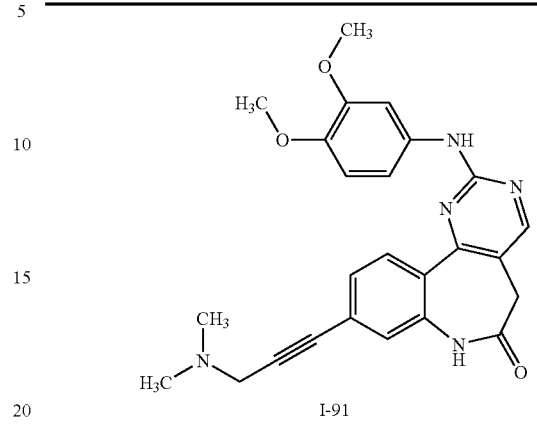
I-91
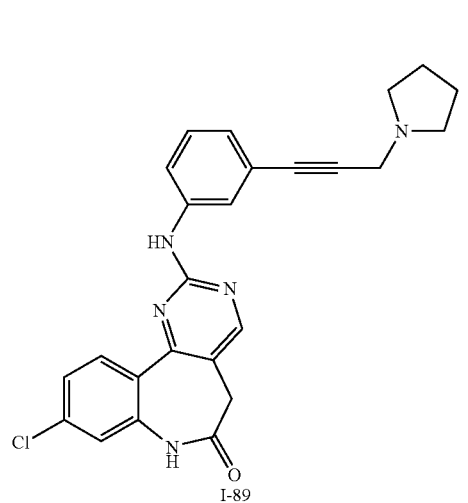
I-89
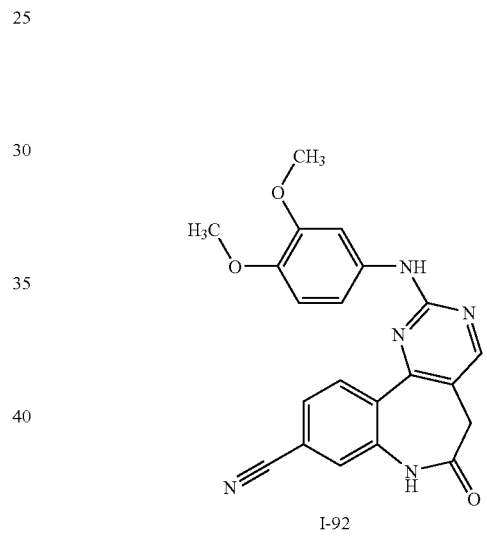
I-92
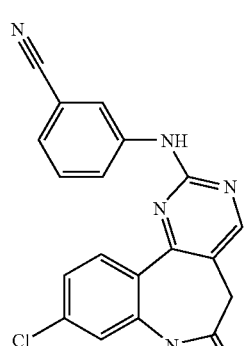
I-90
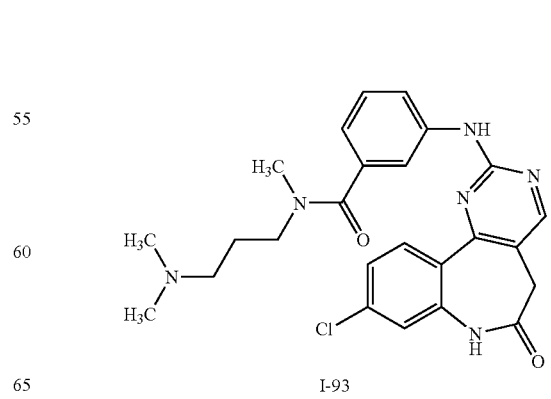
I-93

TABLE 1-continued
Protein Kinase Inhibitors
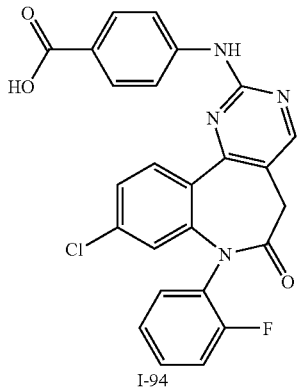
I-94
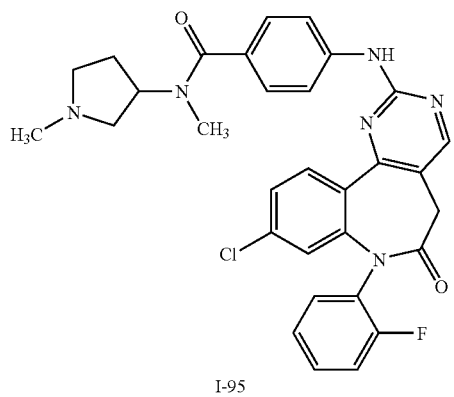
I-95
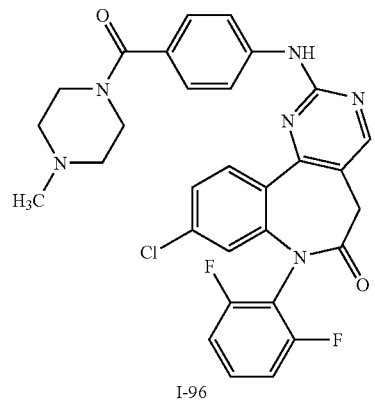
I-96
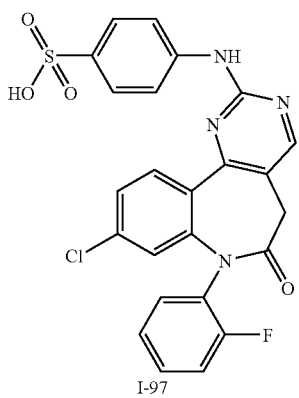
I-97
TABLE 1-continued
Protein Kinase Inhibitors
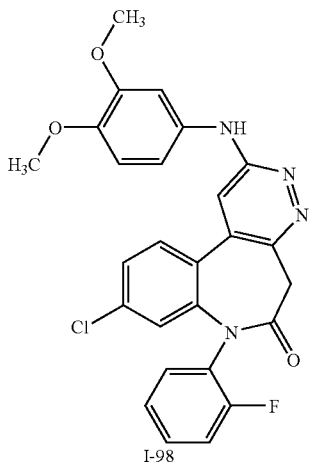
I-98
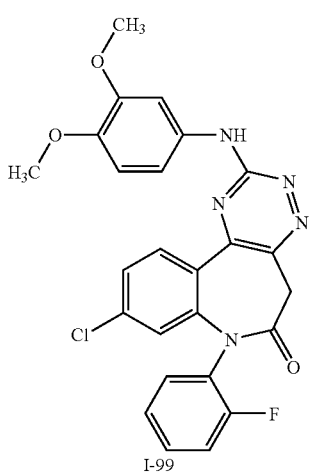
I-99
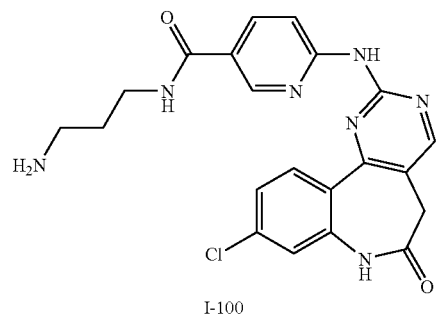
I-100
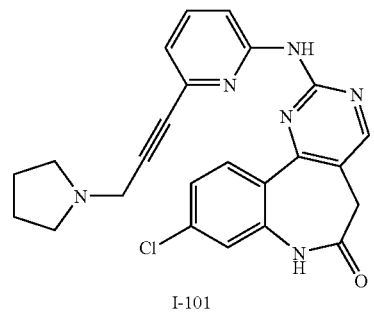
I-101

TABLE 1-continued
Protein Kinase Inhibitors
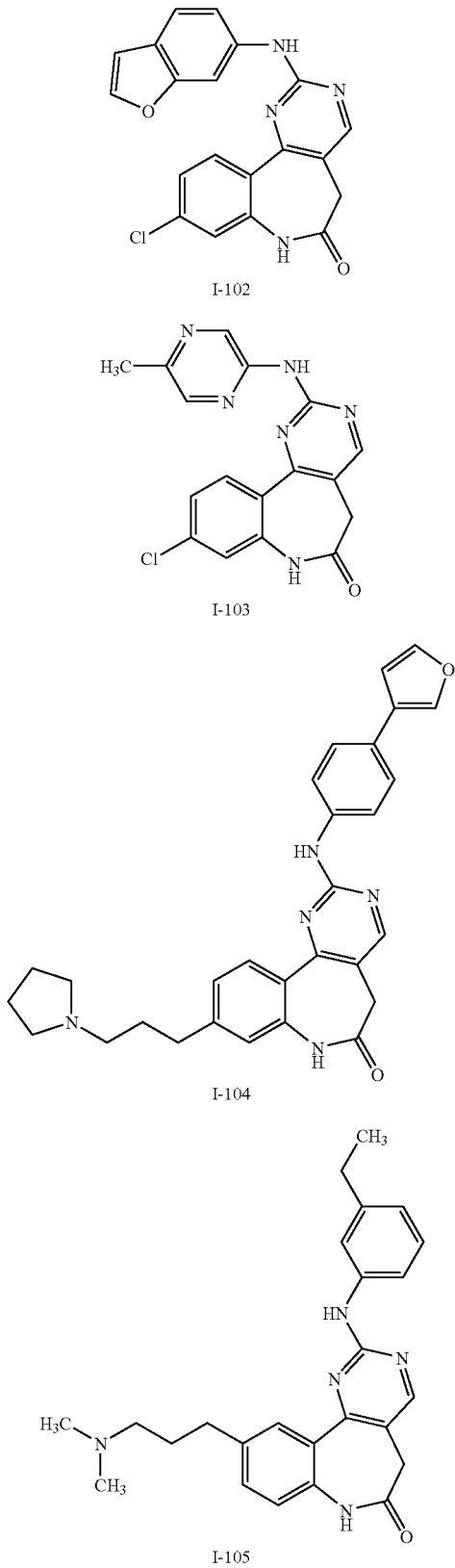
I-102
I-103
I-104
I-105
I-106
I-107
I-108

TABLE 1-continued
Protein Kinase Inhibitors
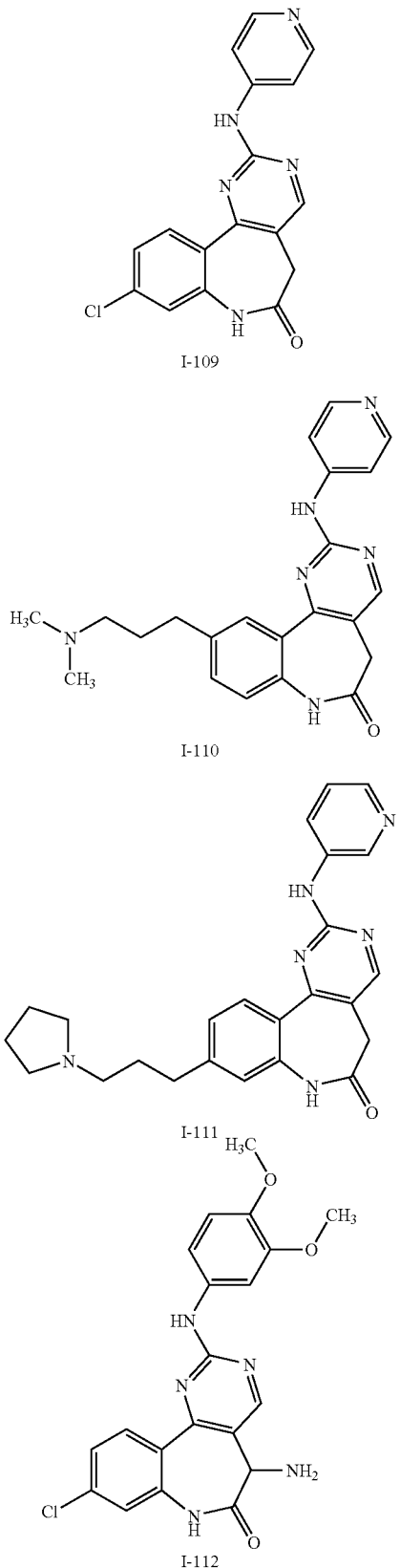
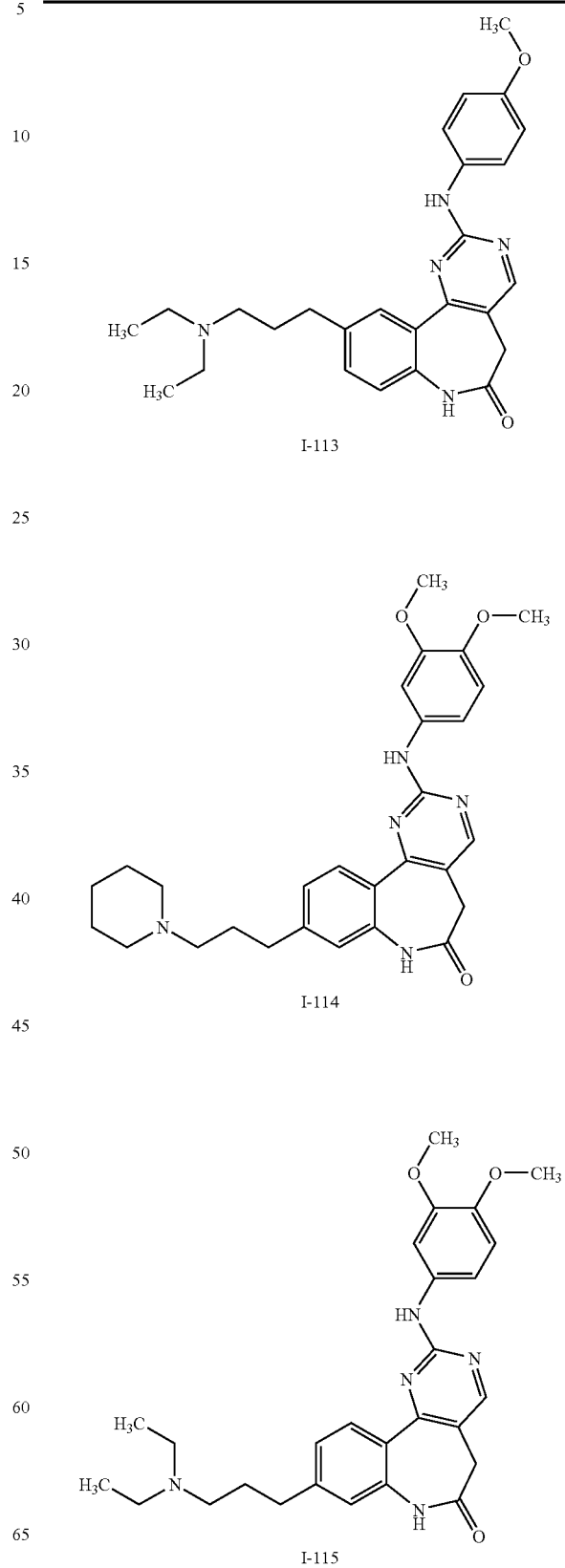

TABLE 1-continued
Protein Kinase Inhibitors
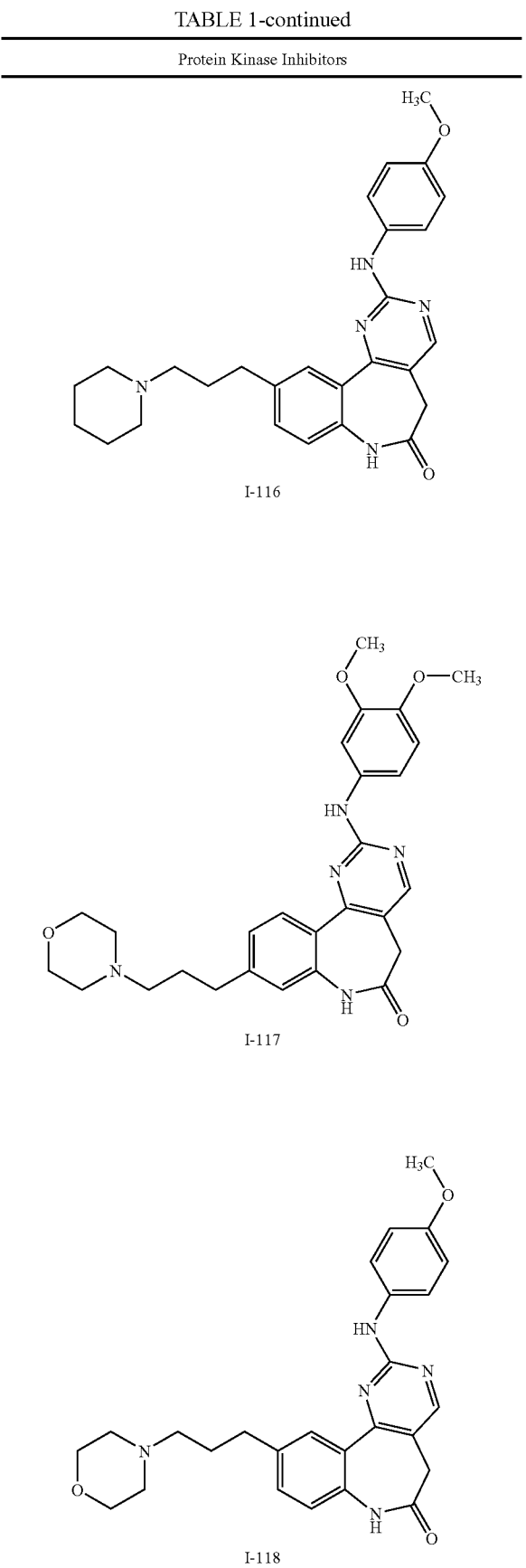
I-116
I-117
I-118
TABLE 1-continued
Protein Kinase Inhibitors
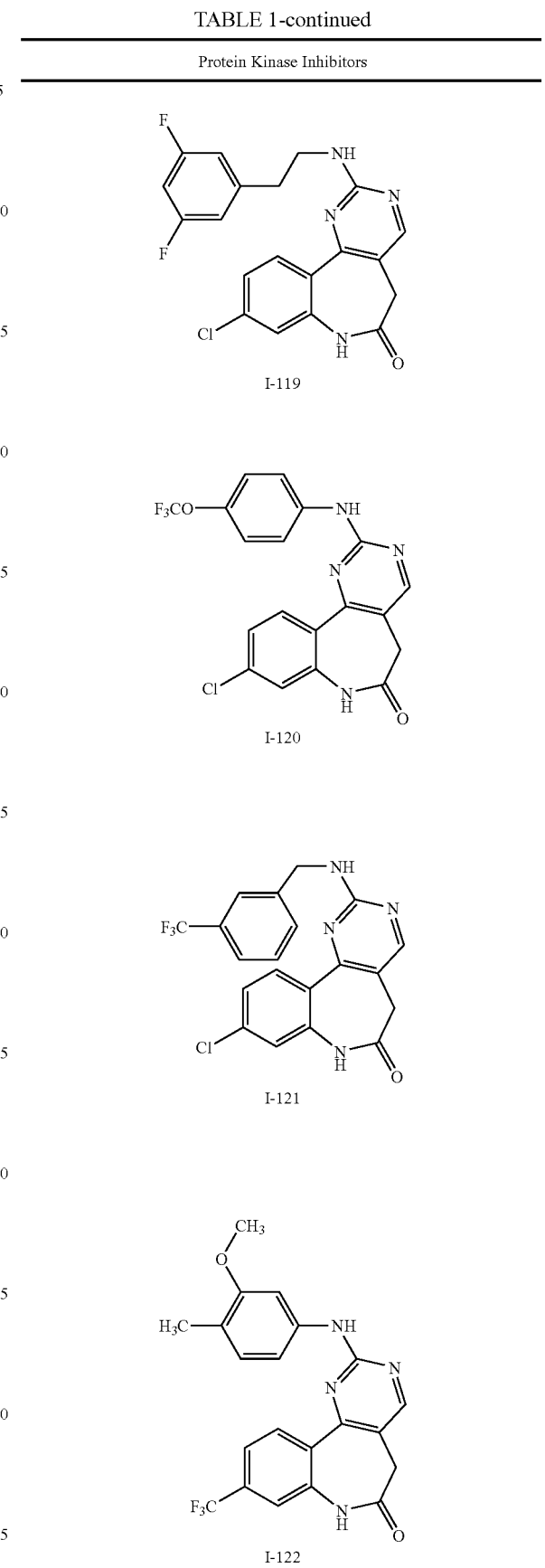
I-119
I-120
I-121
I-122

TABLE 1-continued
Protein Kinase Inhibitors
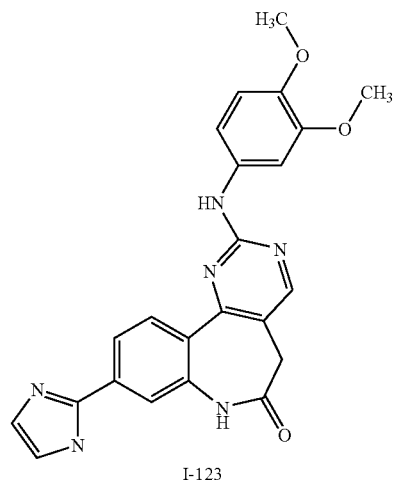
I-123
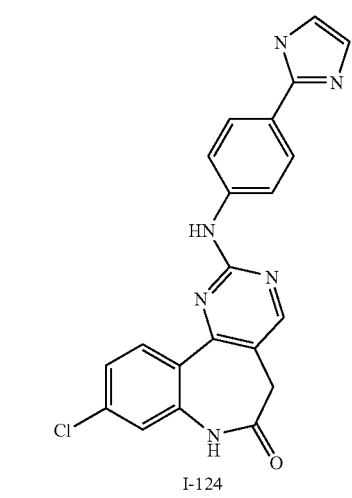
I-124
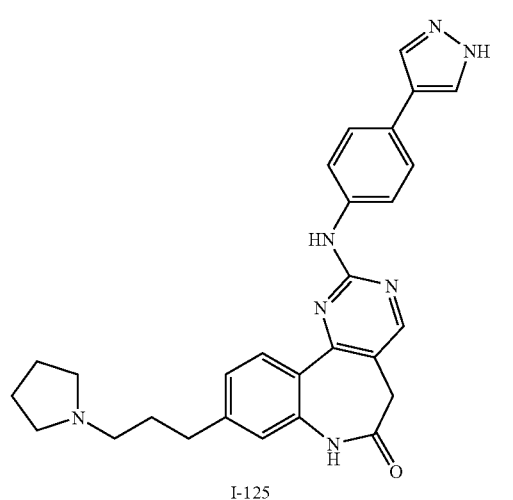
I-125
TABLE 1-continued
Protein Kinase Inhibitors
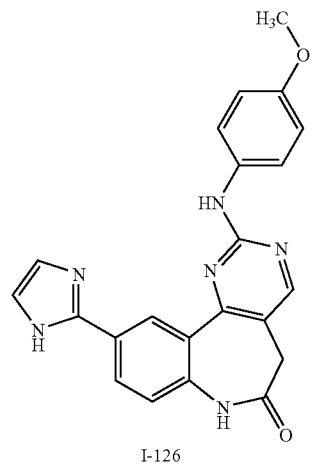
I-126
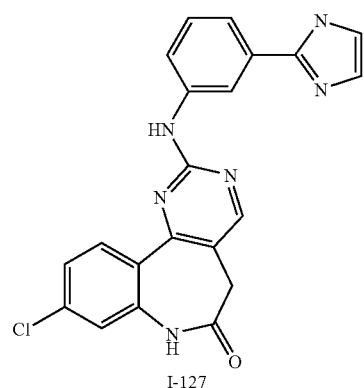
I-127
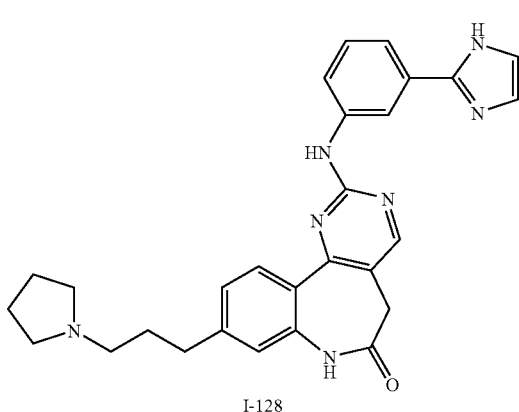
I-128

TABLE 1-continued

Protein Kinase Inhibitors

I-129

I-130

I-131

I-132

I-133

I-134

TABLE 1-continued
Protein Kinase Inhibitors
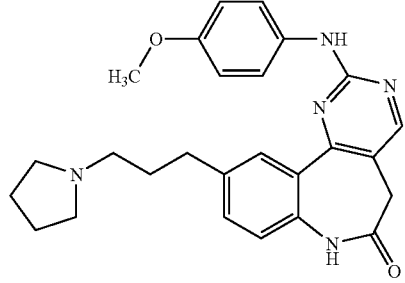
I-135
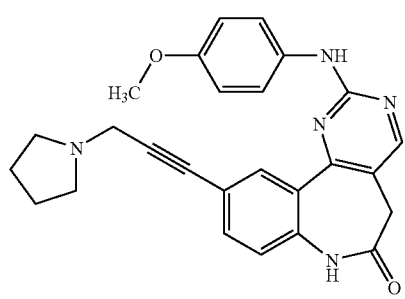
I-136
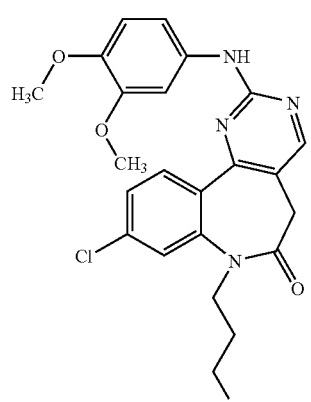
I-137
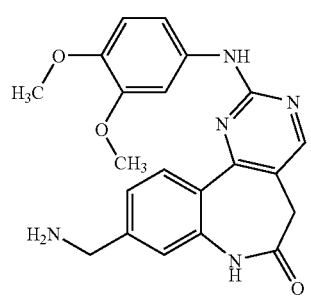
I-138
TABLE 1-continued
Protein Kinase Inhibitors
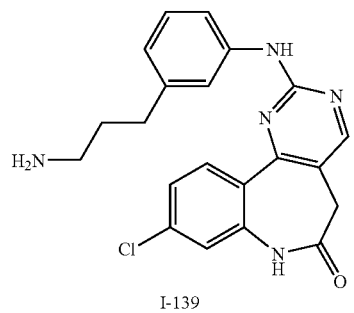
I-139
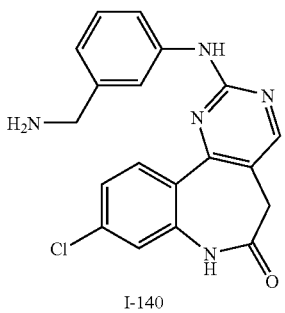
I-140
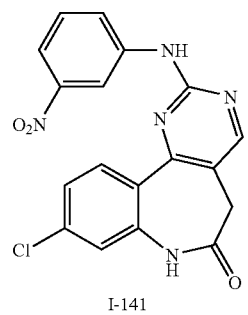
I-141
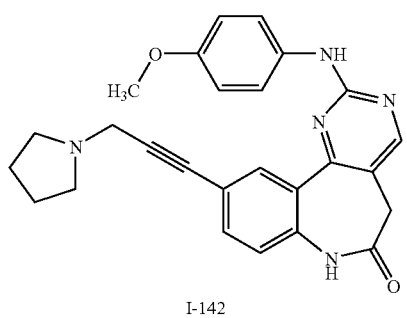
I-142

TABLE 1-continued
Protein Kinase Inhibitors
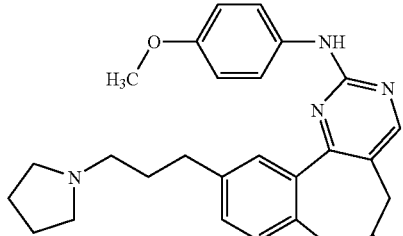
I-143
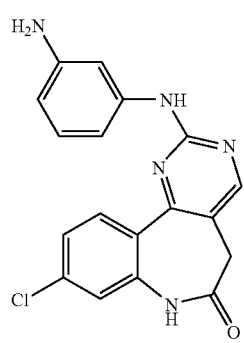
I-144
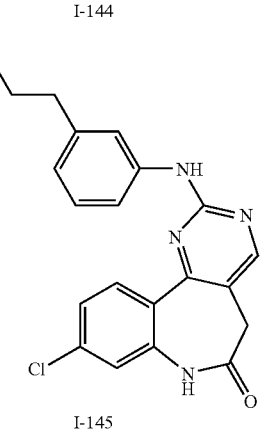
I-145
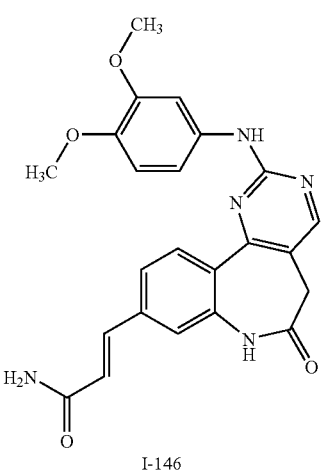
I-146
TABLE 1-continued
Protein Kinase Inhibitors
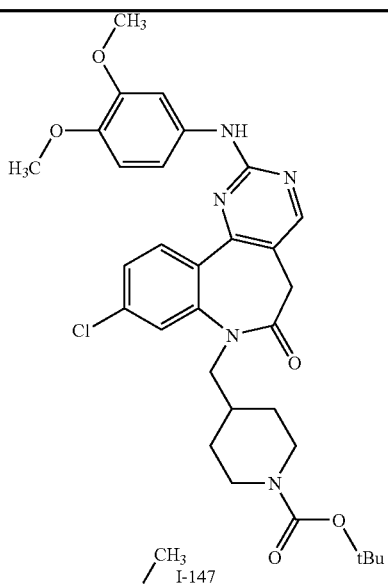
I-147
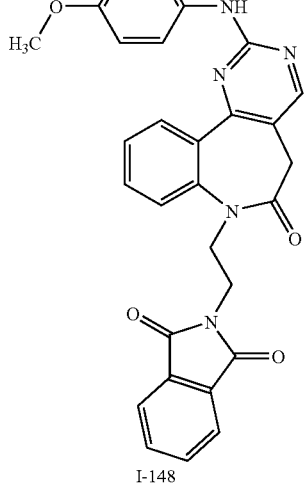
I-148
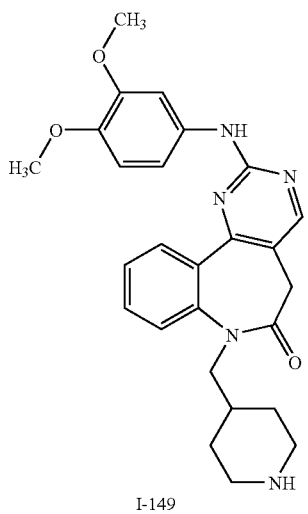
I-149

TABLE 1-continued

Protein Kinase Inhibitors

I-150

I-151

I-152

I-153

I-154

I-155

I-156

TABLE 1-continued
Protein Kinase Inhibitors
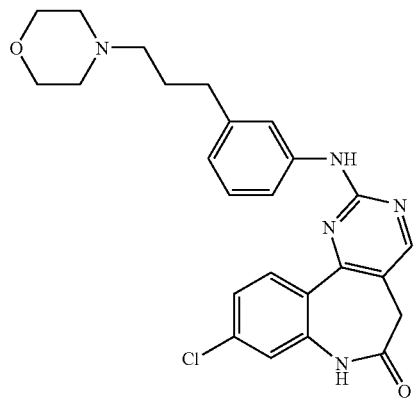
I-157
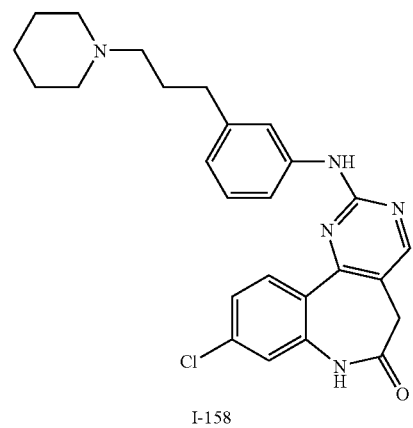
I-158
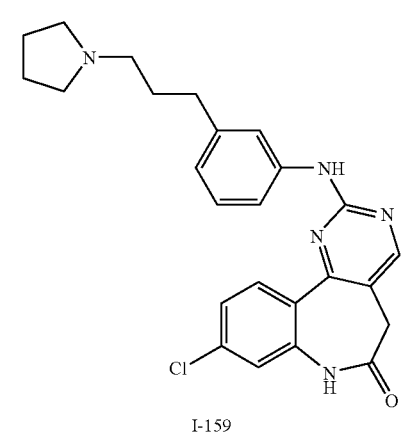
I-159
TABLE 1-continued
Protein Kinase Inhibitors
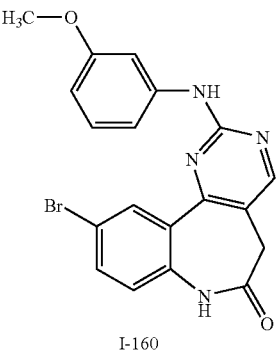
I-160
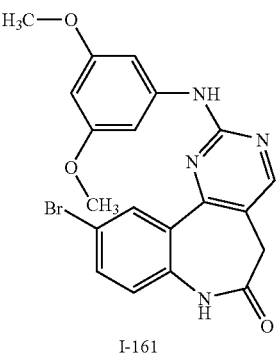
I-161
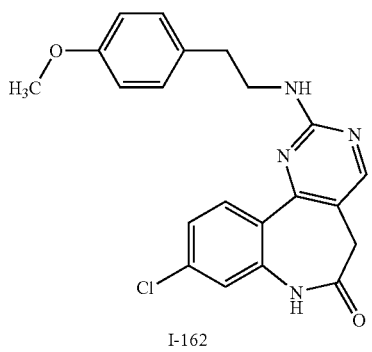
I-162

TABLE 1-continued
Protein Kinase Inhibitors
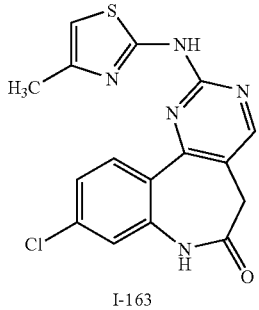
I-163
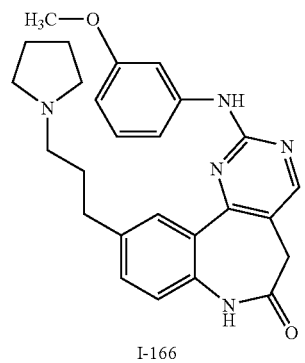
I-166
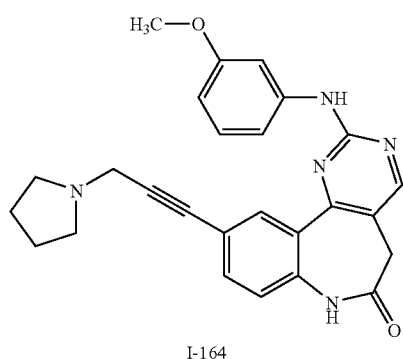
I-164
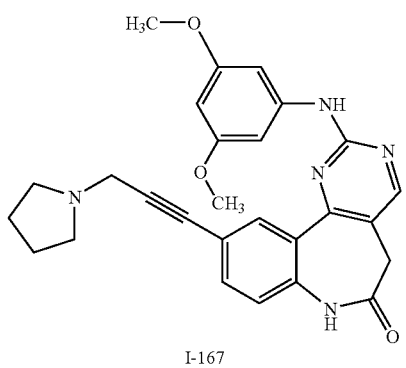
I-167
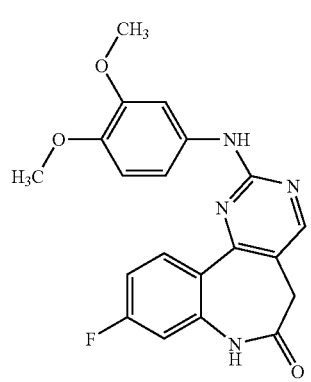
I-165
I-168

TABLE 1-continued
Protein Kinase Inhibitors
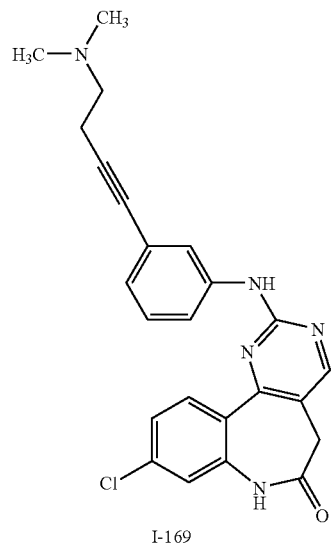
I-169
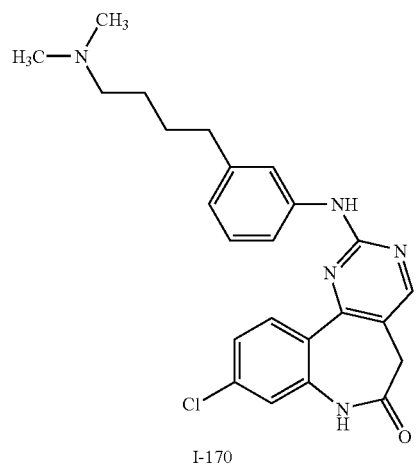
I-170
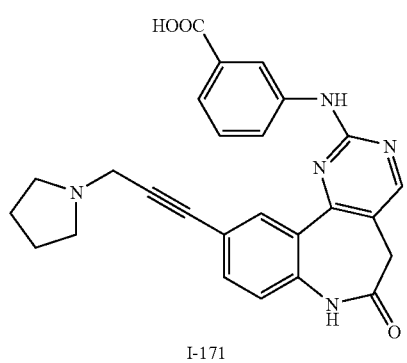
I-171
TABLE 1-continued
Protein Kinase Inhibitors
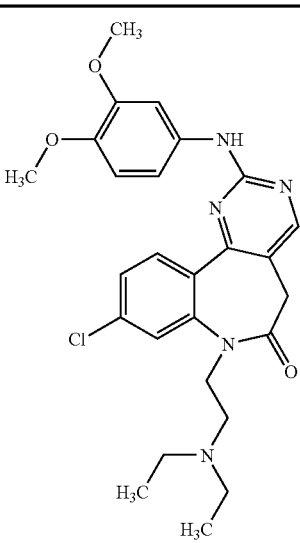
I-172
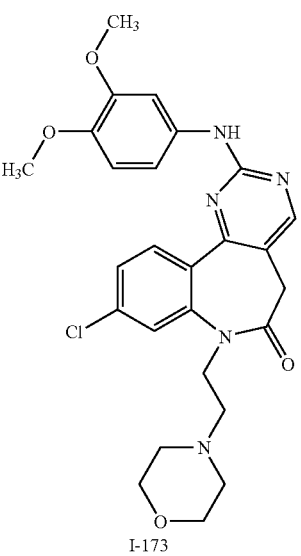
I-173

TABLE 1-continued

Protein Kinase Inhibitors

I-174

I-175

I-176

I-177

I-178

I-179

I-180

TABLE 1-continued
Protein Kinase Inhibitors
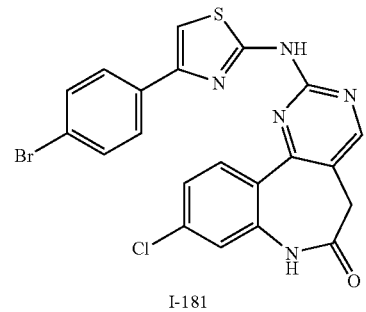
I-181
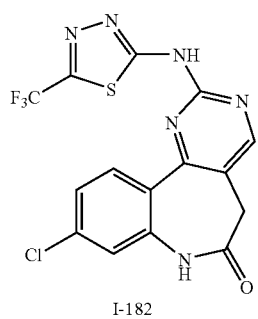
I-182
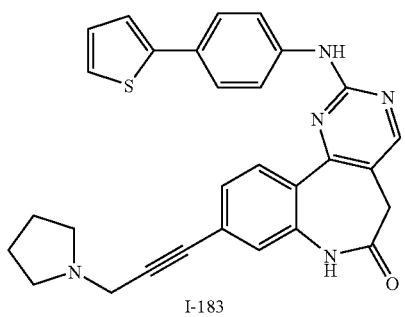
I-183
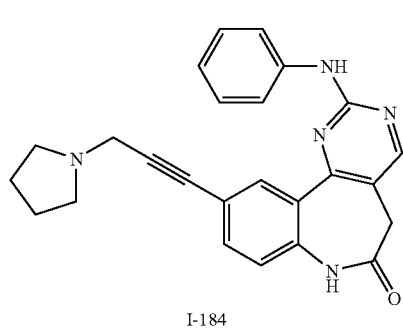
I-184
TABLE 1-continued
Protein Kinase Inhibitors
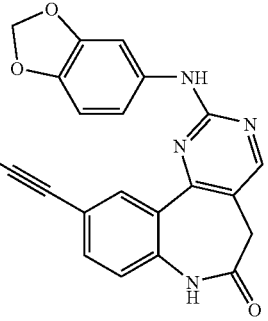
I-185
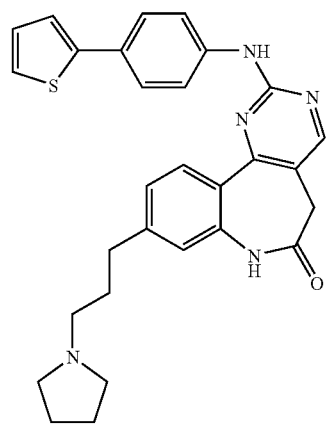
I-186
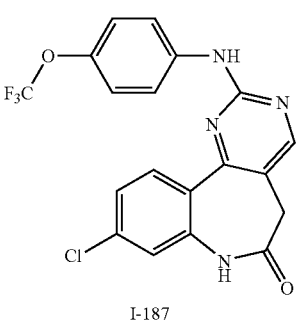
I-187

TABLE 1-continued
Protein Kinase Inhibitors
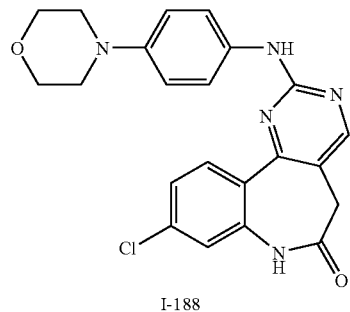
I-188
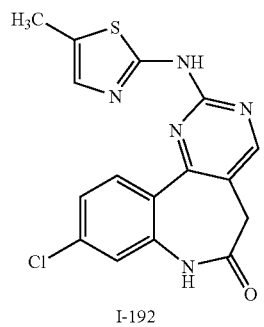
I-192
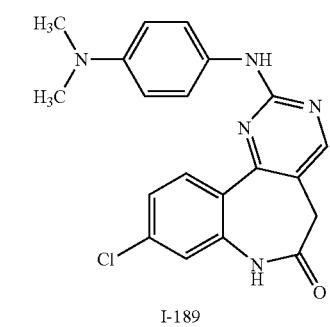
I-189
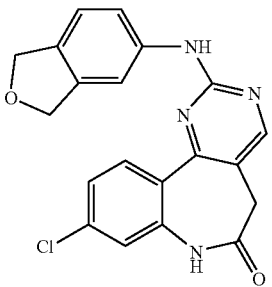
I-193
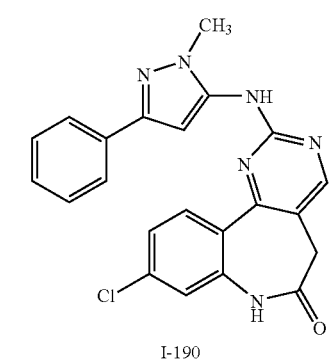
I-190
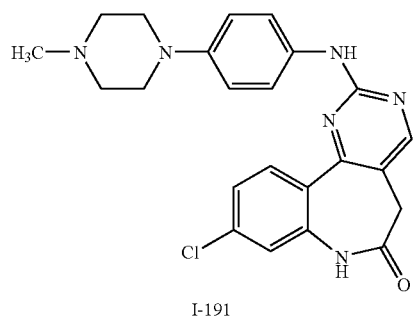
I-191
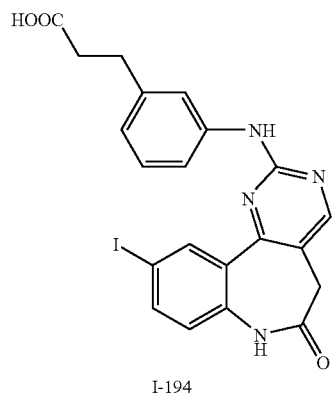
I-194

TABLE 1-continued

Protein Kinase Inhibitors

I-195

I-196

I-197

I-198

I-199

I-200

I-201

I-202

TABLE 1-continued
Protein Kinase Inhibitors
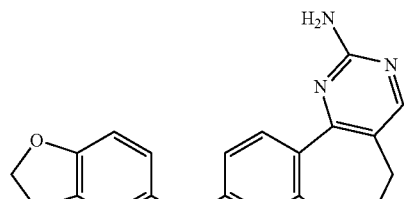
I-203
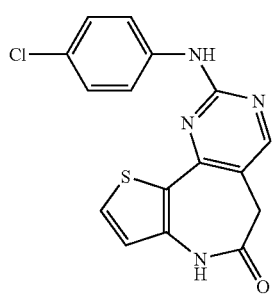
I-204
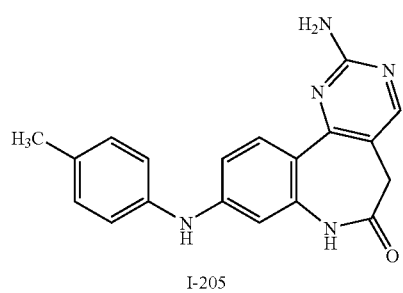
I-205
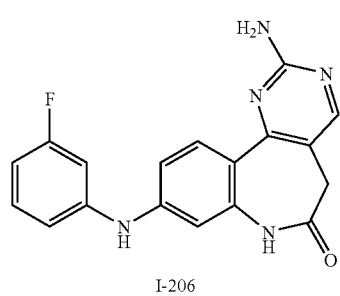
I-206
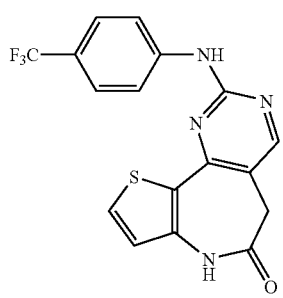
I-207
TABLE 1-continued
Protein Kinase Inhibitors
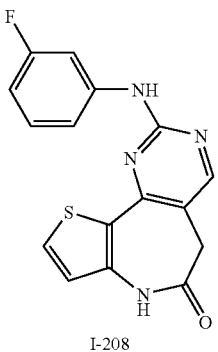
I-208
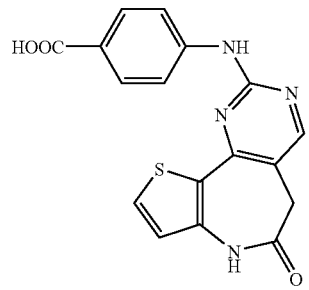
I-209
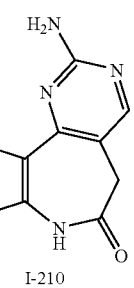
I-210
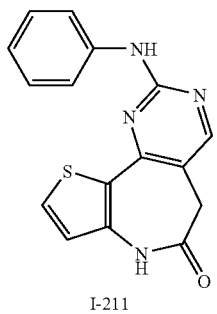
I-211
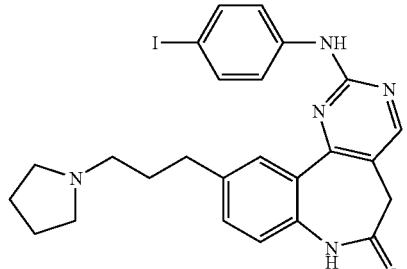
I-212

TABLE 1-continued
Protein Kinase Inhibitors
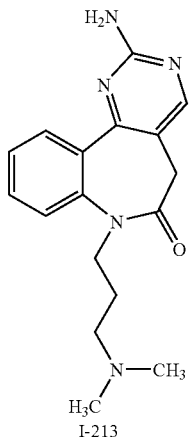
I-213
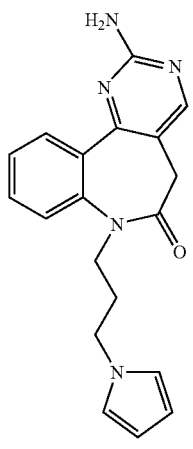
I-216
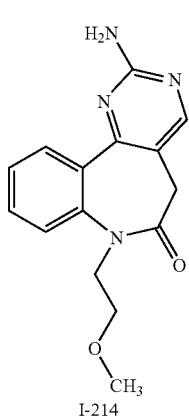
I-214
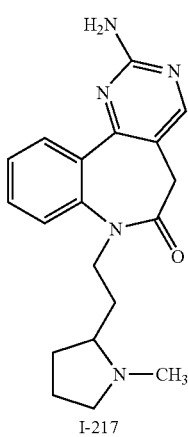
I-217
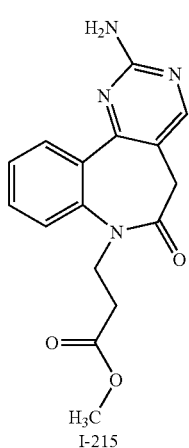
I-215
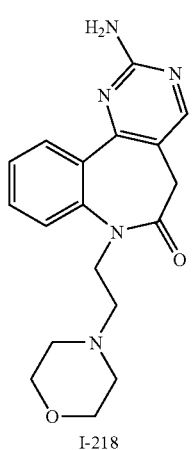
I-218

TABLE 1-continued
Protein Kinase Inhibitors
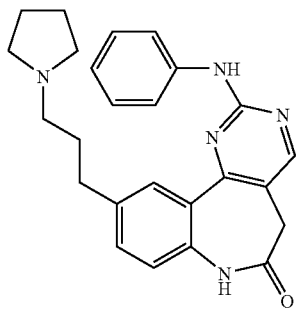
I-219
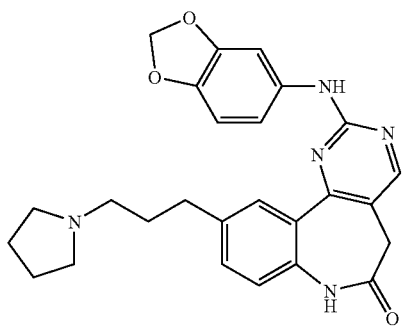
I-220
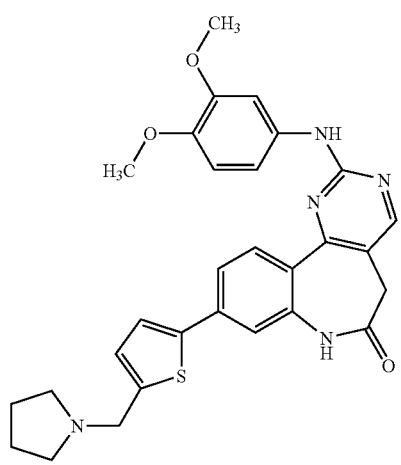
I-221
TABLE 1-continued
Protein Kinase Inhibitors
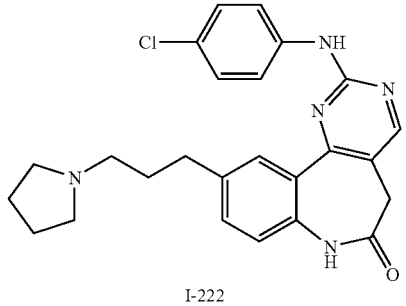
I-222
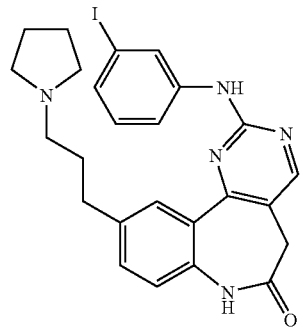
I-223
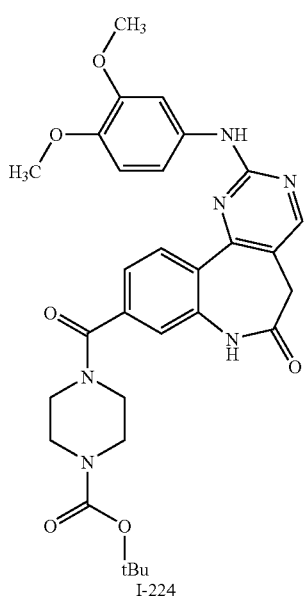
I-224

TABLE 1-continued
Protein Kinase Inhibitors
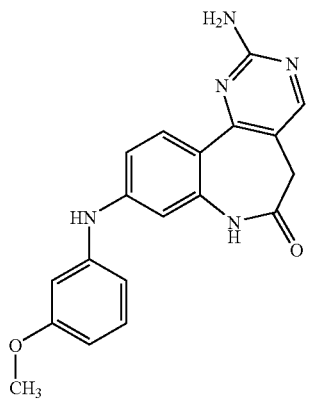
I-225
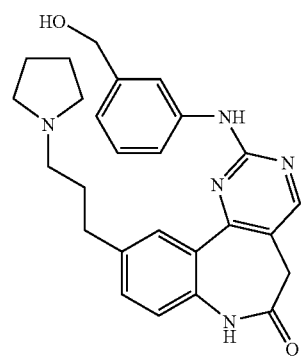
I-226
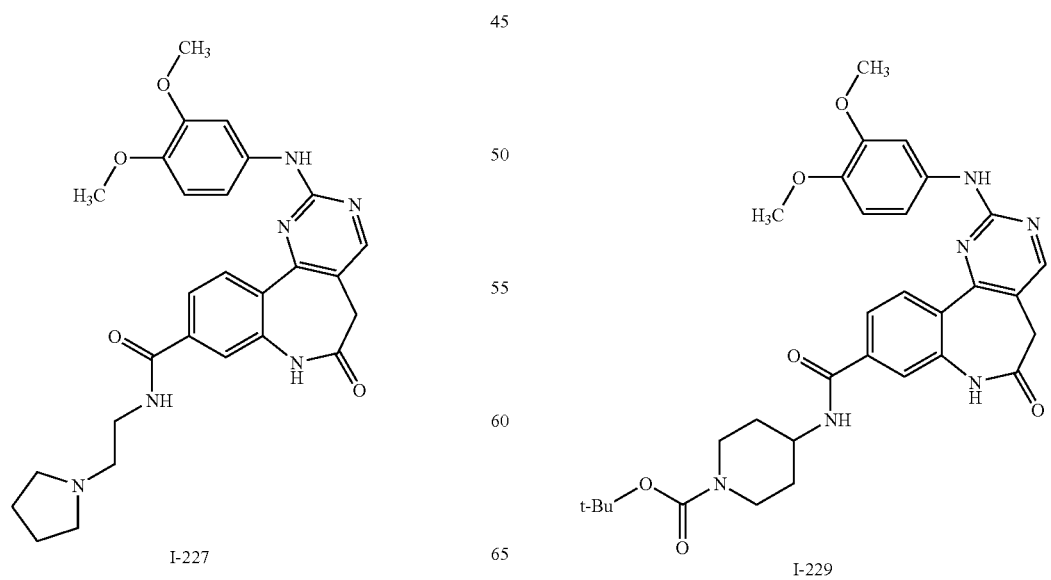
I-227
TABLE 1-continued
Protein Kinase Inhibitors
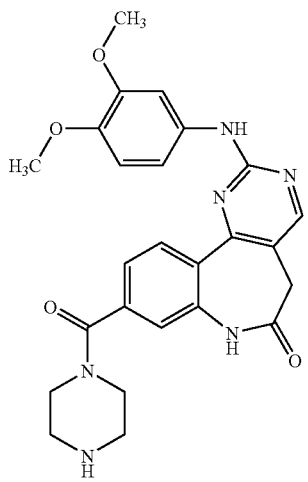
I-228
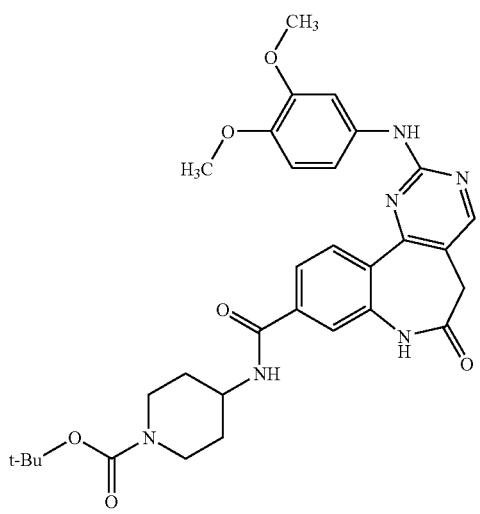
I-229

TABLE 1-continued
Protein Kinase Inhibitors
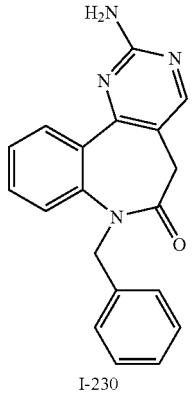
I-230
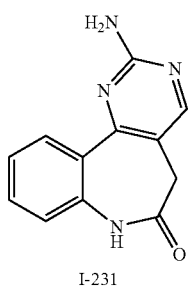
I-231
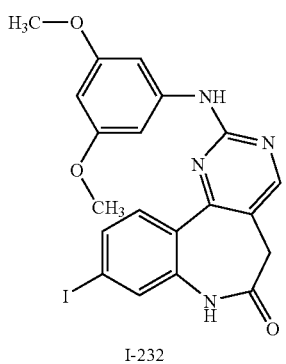
I-232
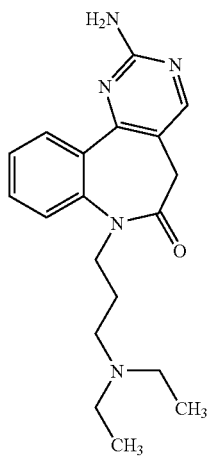
I-233
TABLE 1-continued
Protein Kinase Inhibitors
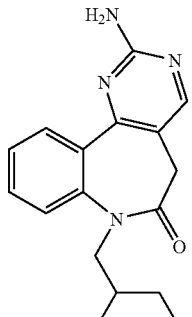
I-234
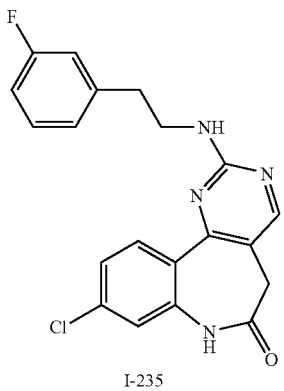
I-235
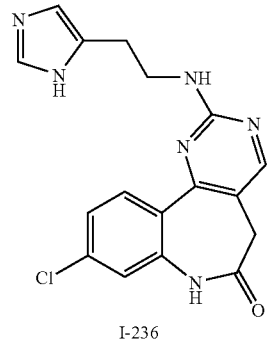
I-236
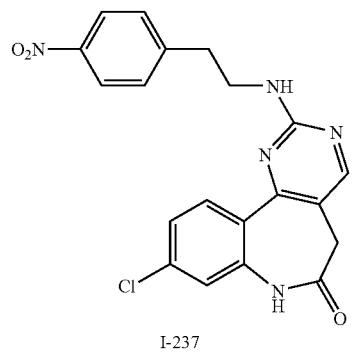
I-237

TABLE 1-continued
Protein Kinase Inhibitors
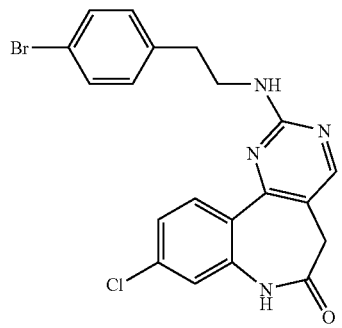
I-238
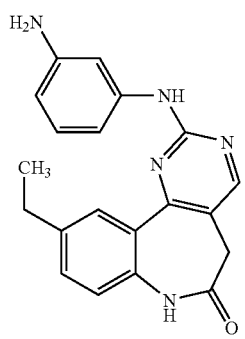
I-239
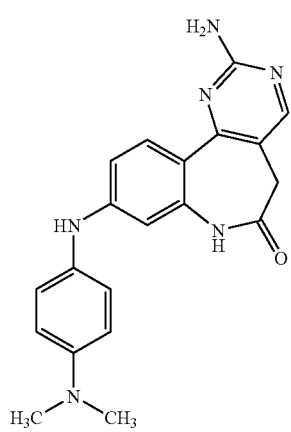
I-240
TABLE 1-continued
Protein Kinase Inhibitors
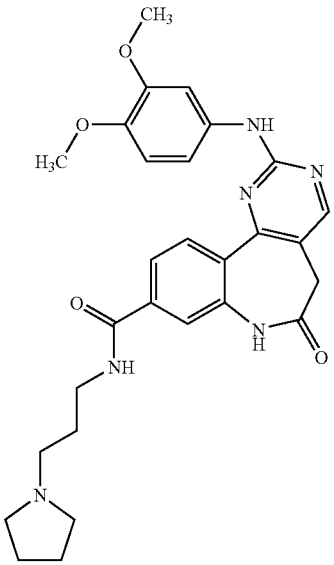
I-241
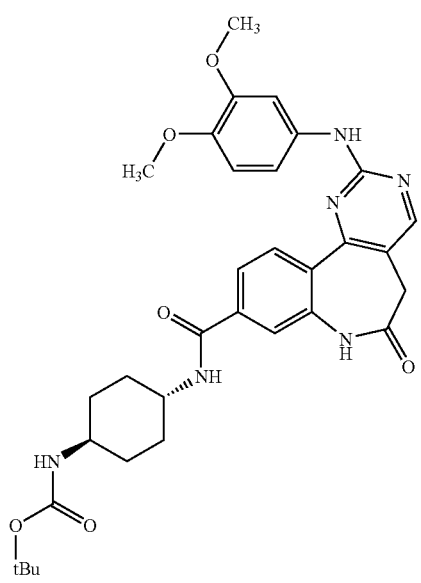
I-242

TABLE 1-continued
Protein Kinase Inhibitors
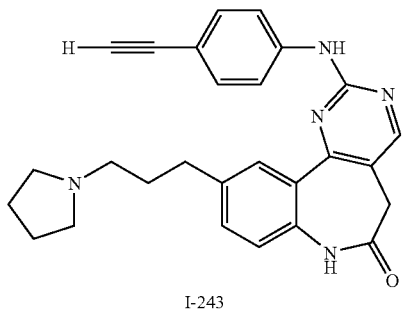
I-243
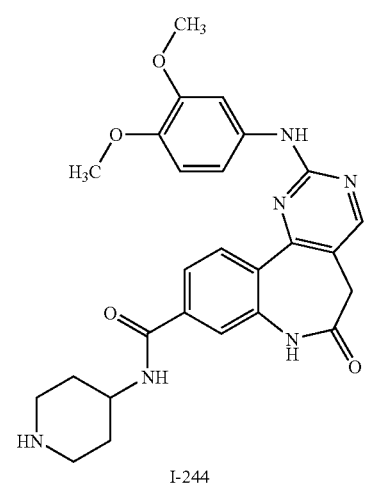
I-244
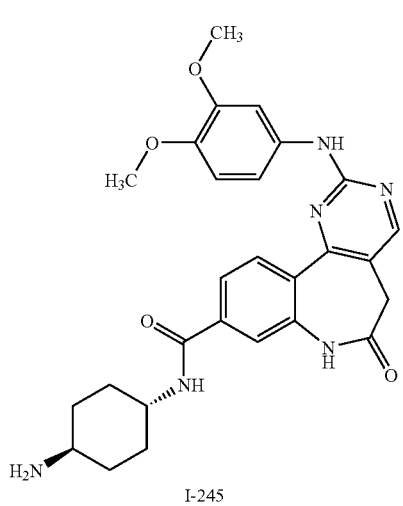
I-245
TABLE 1-continued
Protein Kinase Inhibitors
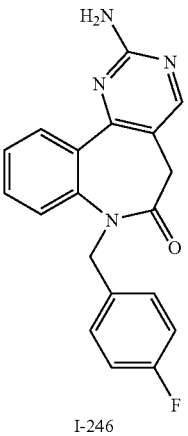
I-246
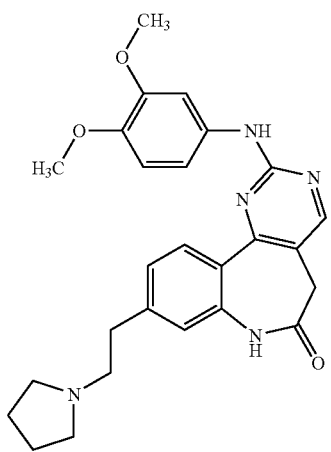
I-247
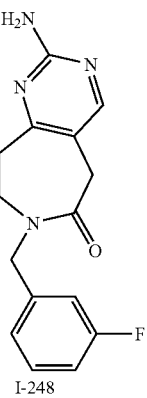
I-248

TABLE 1-continued
Protein Kinase Inhibitors
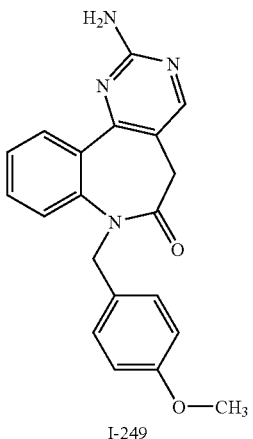
I-249
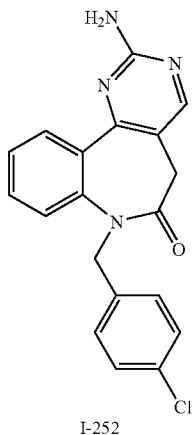
I-252
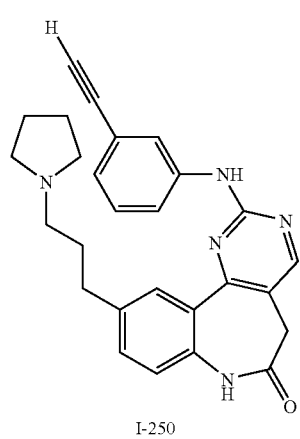
I-250
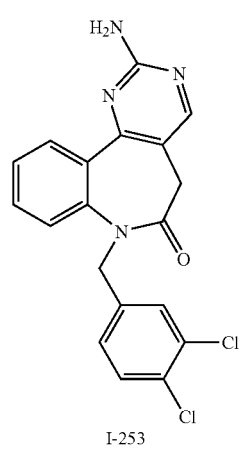
I-253
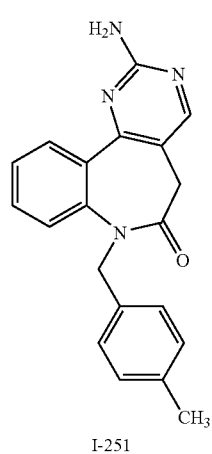
I-251
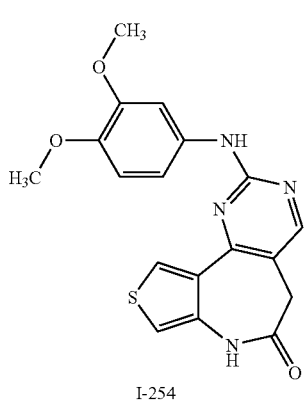
I-254

TABLE 1-continued
Protein Kinase Inhibitors
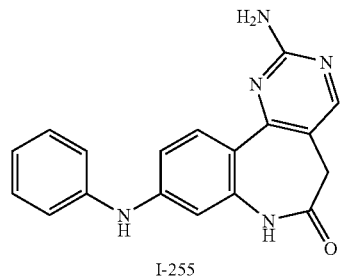
I-255
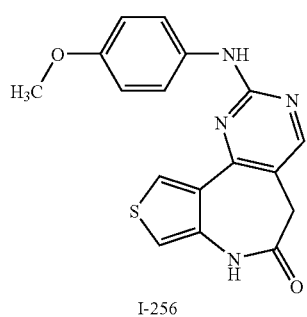
I-256
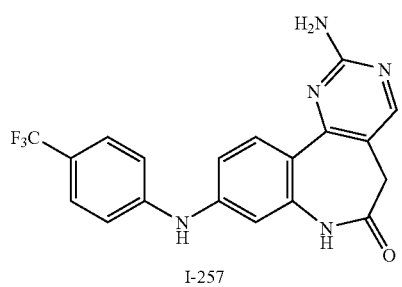
I-257
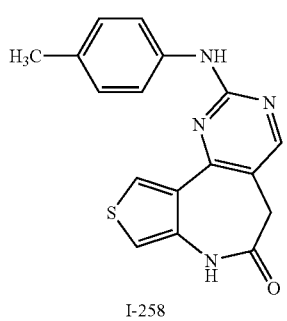
I-258
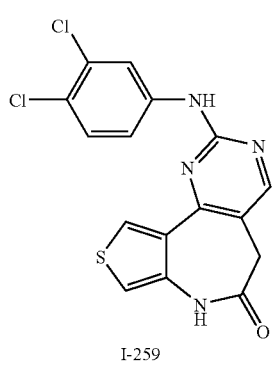
I-259
TABLE 1-continued
Protein Kinase Inhibitors
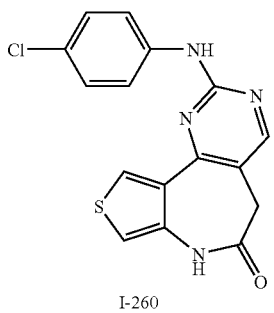
I-260
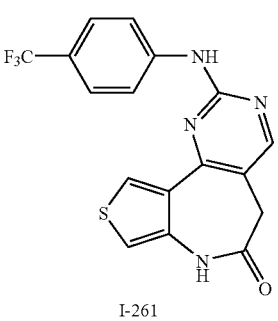
I-261
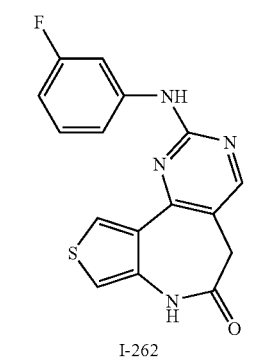
I-262
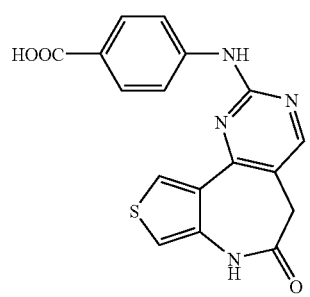
I-263
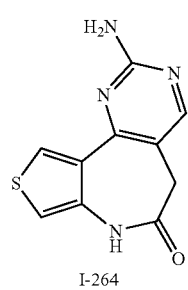
I-264

TABLE 1-continued
Protein Kinase Inhibitors
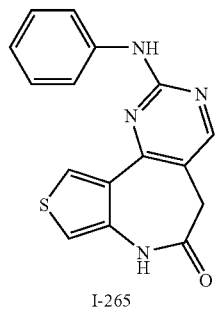
I-265
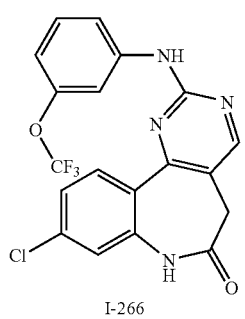
I-266
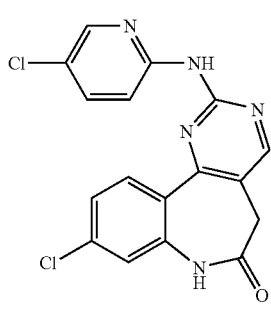
I-267
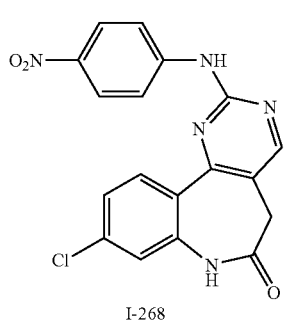
I-268
TABLE 1-continued
Protein Kinase Inhibitors
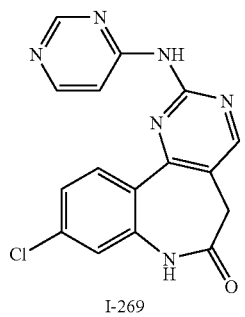
I-269
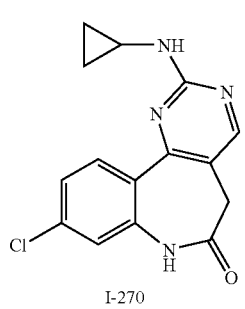
I-270
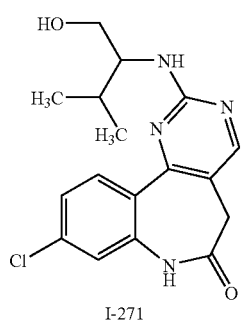
I-271
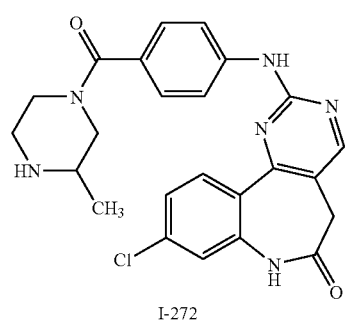
I-272

TABLE 1-continued
Protein Kinase Inhibitors
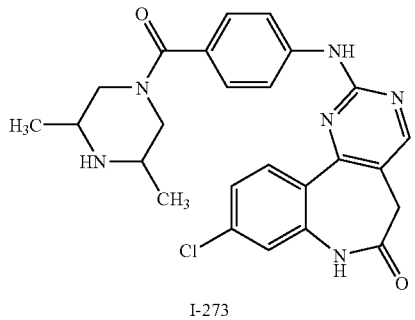
I-273
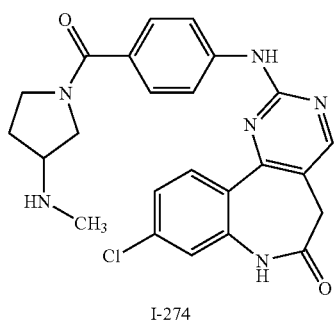
I-274
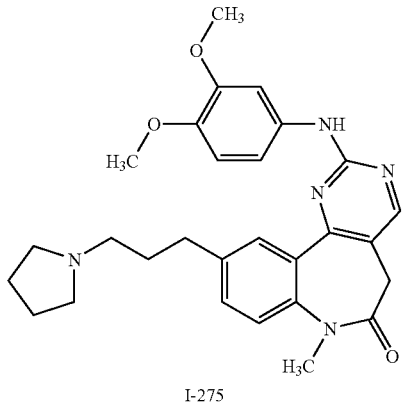
I-275
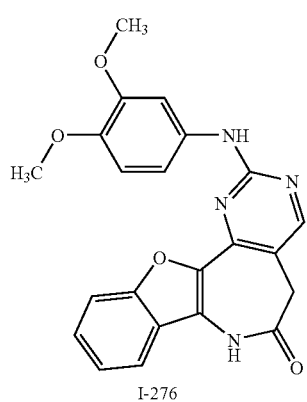
I-276
TABLE 1-continued
Protein Kinase Inhibitors
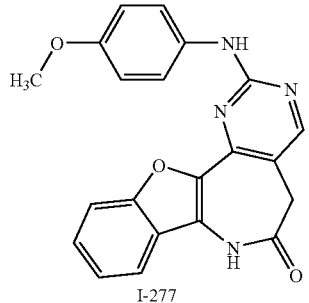
I-277
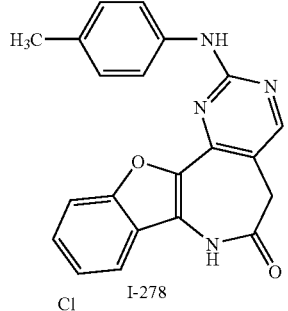
I-278
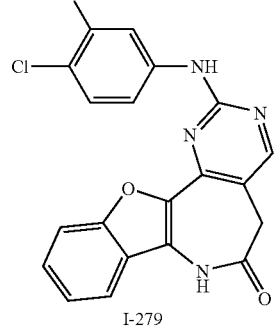
I-279
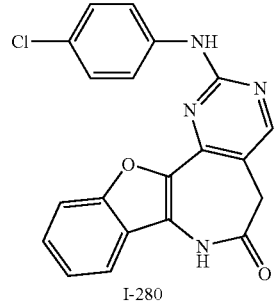
I-280
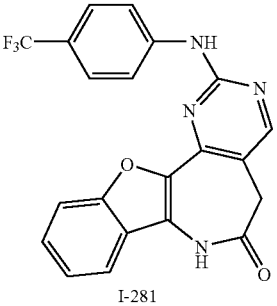
I-281

TABLE 1-continued
Protein Kinase Inhibitors
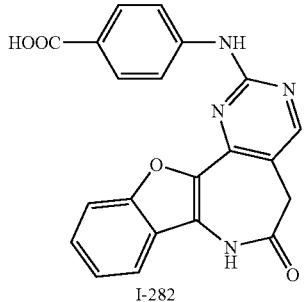
I-282
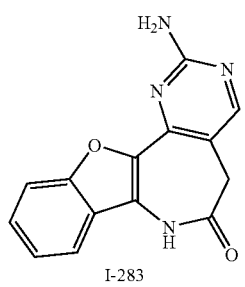
I-283
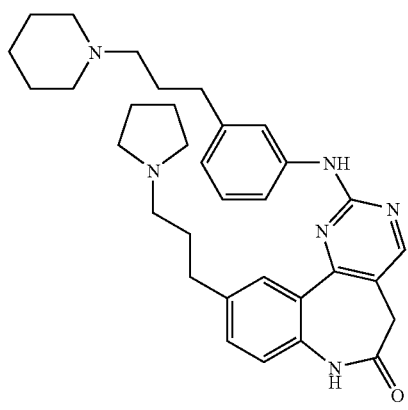
I-284
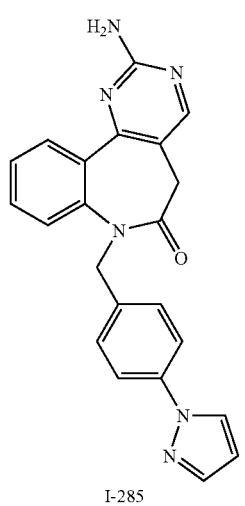
I-285
TABLE 1-continued
Protein Kinase Inhibitors
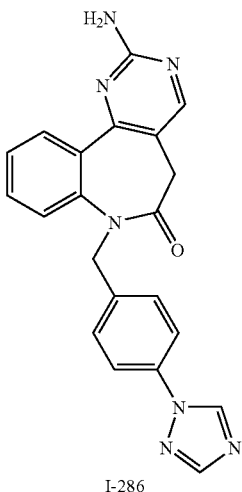
I-286
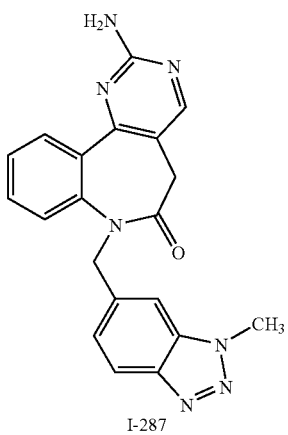
I-287
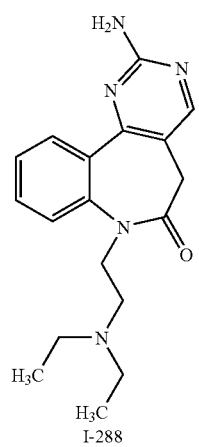
I-288

TABLE 1-continued
Protein Kinase Inhibitors
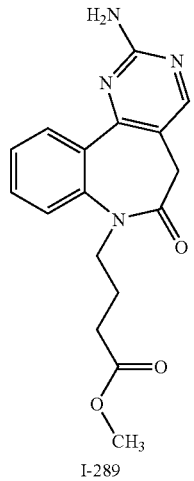
I-289
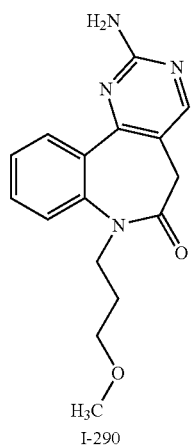
I-290
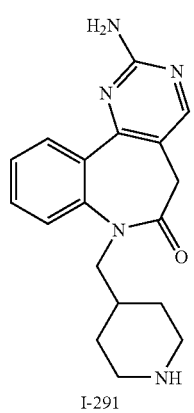
I-291
TABLE 1-continued
Protein Kinase Inhibitors
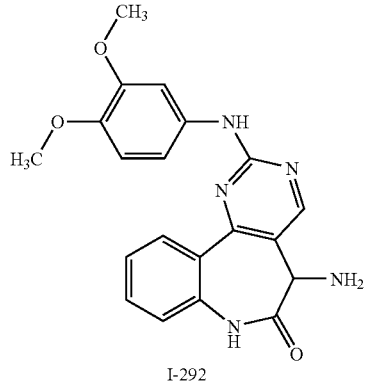
I-292
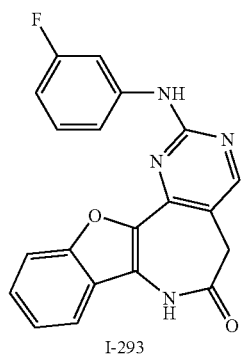
I-293
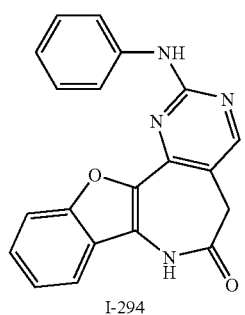
I-294

TABLE 1-continued
Protein Kinase Inhibitors
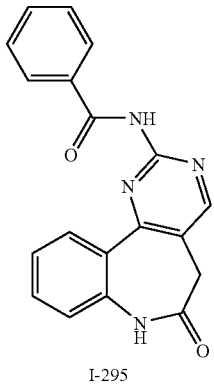
I-295
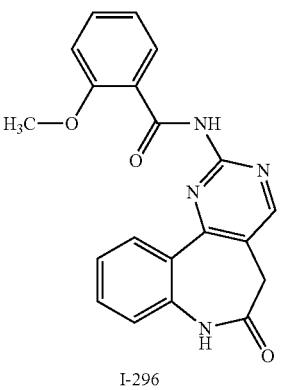
I-296
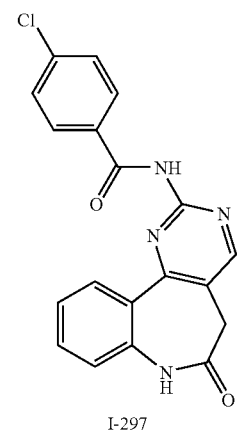
I-297
TABLE 1-continued
Protein Kinase Inhibitors
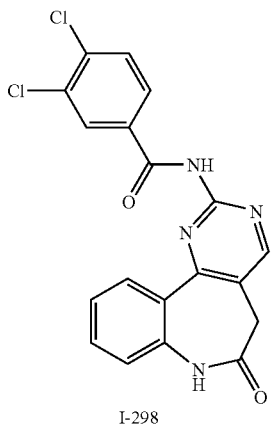
I-298
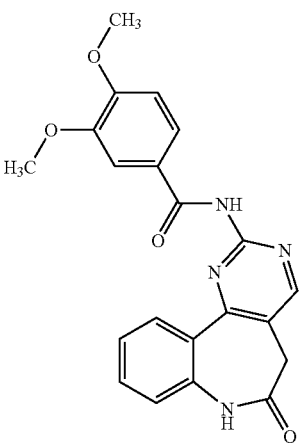
I-299
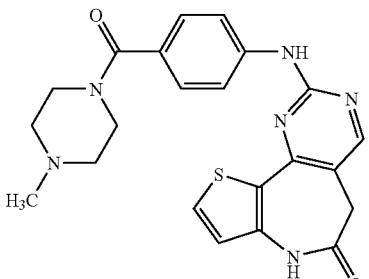
I-300

TABLE 1-continued

Protein Kinase Inhibitors

I-301

I-302

I-303

I-304

I-305

I-306

I-307

TABLE 1-continued
Protein Kinase Inhibitors
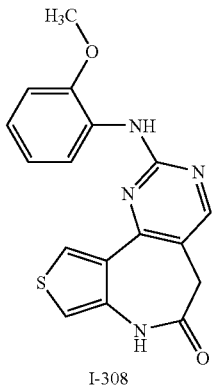
I-308
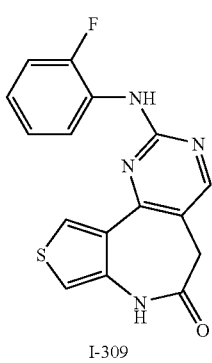
I-309
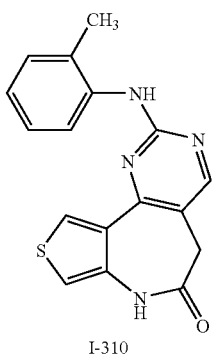
I-310
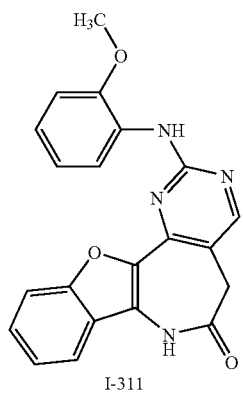
I-311
TABLE 1-continued
Protein Kinase Inhibitors
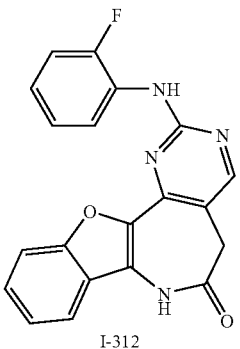
I-312
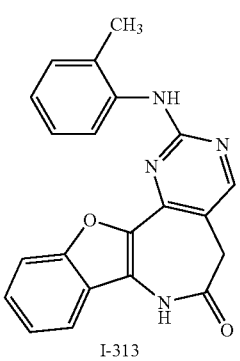
I-313
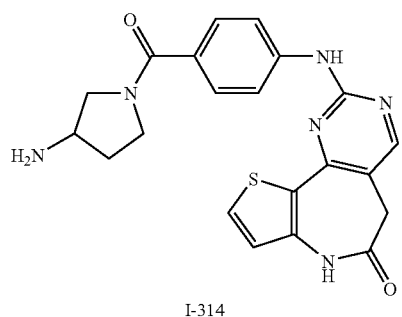
I-314
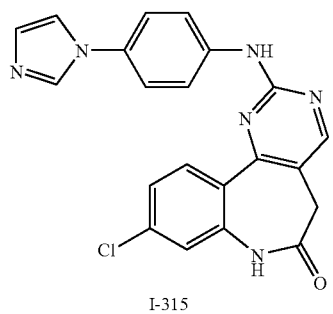
I-315

TABLE 1-continued
Protein Kinase Inhibitors
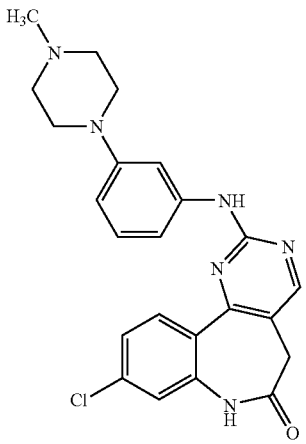
I-316
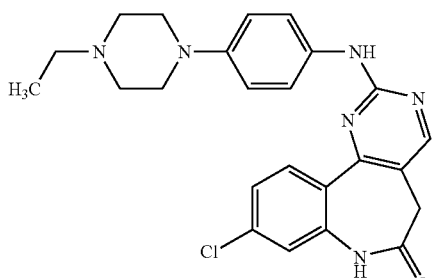
I-317
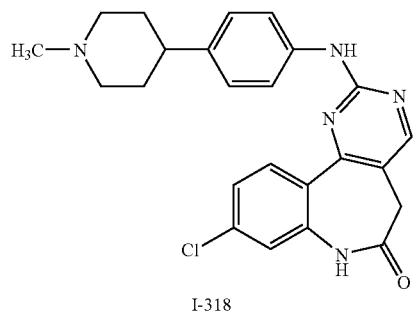
I-318
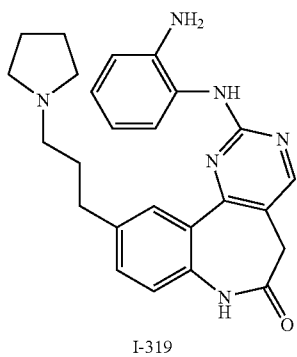
I-319
TABLE 1-continued
Protein Kinase Inhibitors
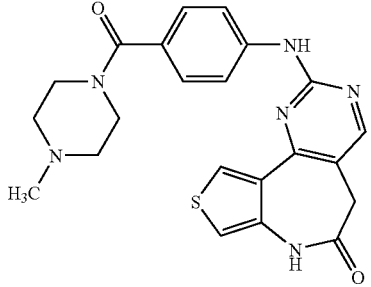
I-320
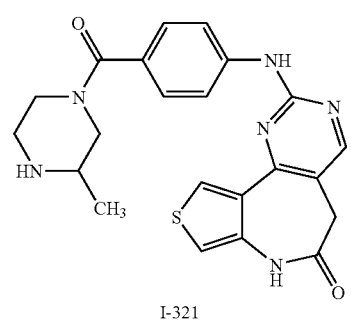
I-321
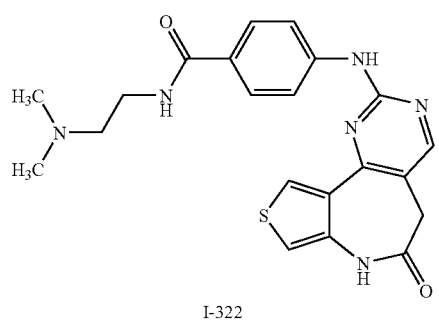
I-322
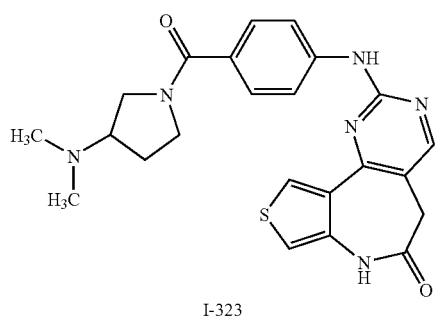
I-323

TABLE 1-continued
Protein Kinase Inhibitors
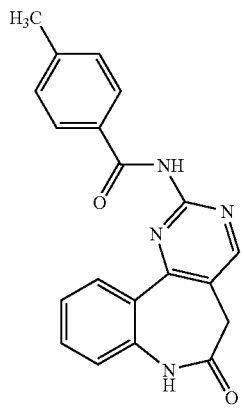
I-324
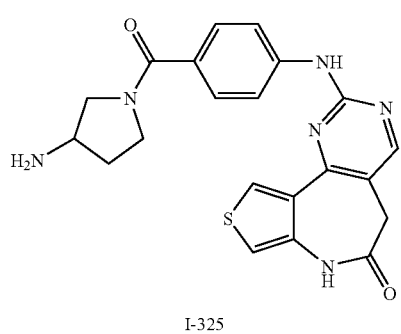
I-325
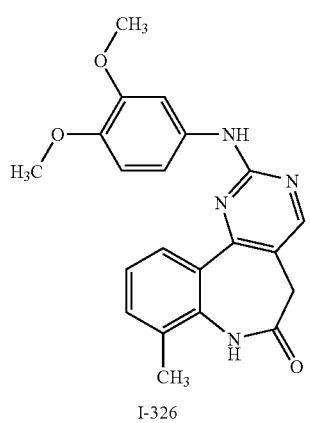
I-326
TABLE 1-continued
Protein Kinase Inhibitors
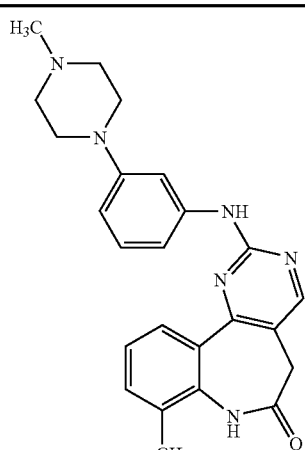
I-327
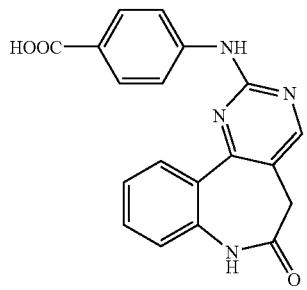
I-328
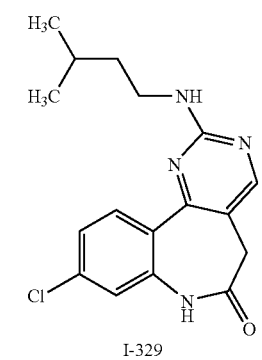
I-329

US 7,459,448 B2
117                                              118
TABLE 1-continued
Protein Kinase Inhibitors
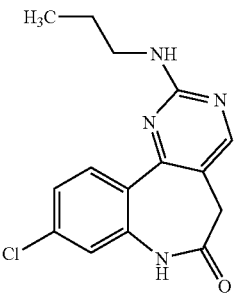
I-330
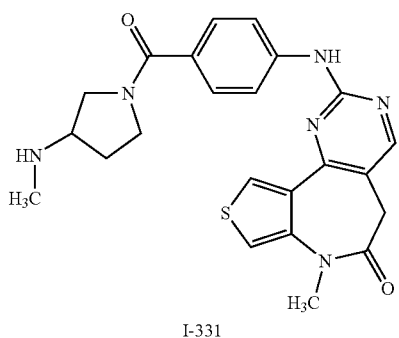
I-331
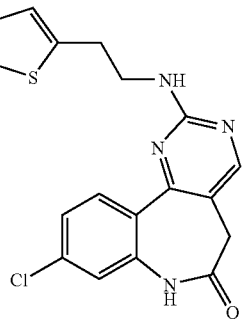
I-332
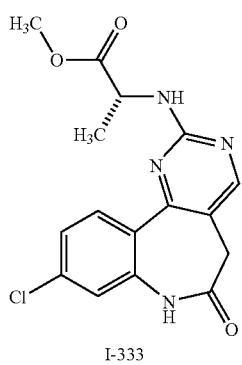
I-333
TABLE 1-continued
Protein Kinase Inhibitors
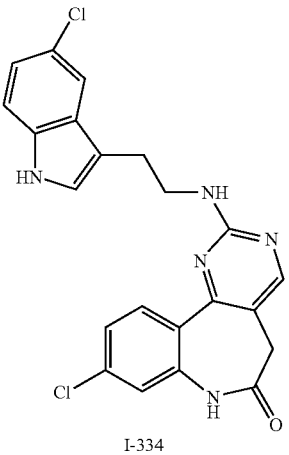
I-334
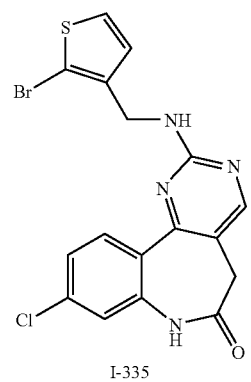
I-335
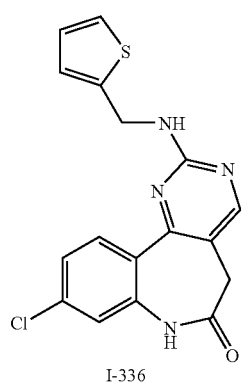
I-336

TABLE 1-continued
Protein Kinase Inhibitors
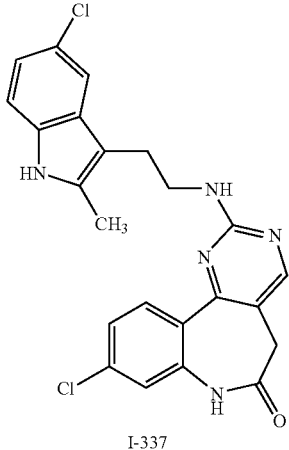
I-337
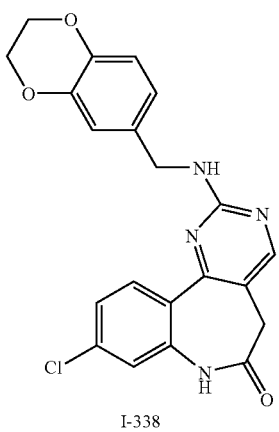
I-338
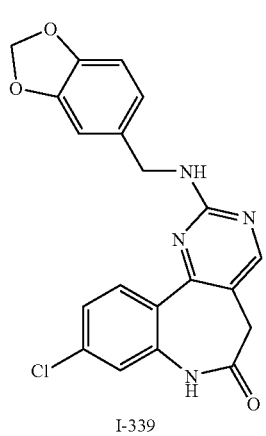
I-339
TABLE 1-continued
Protein Kinase Inhibitors
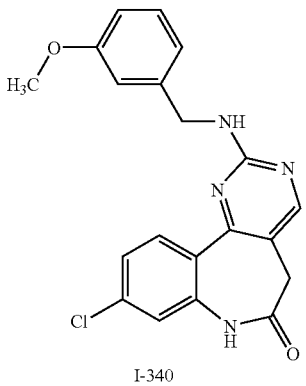
I-340
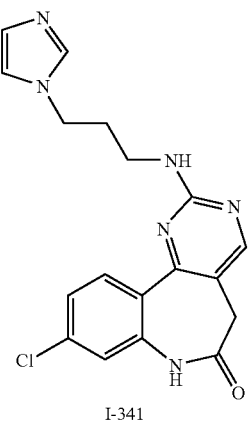
I-341
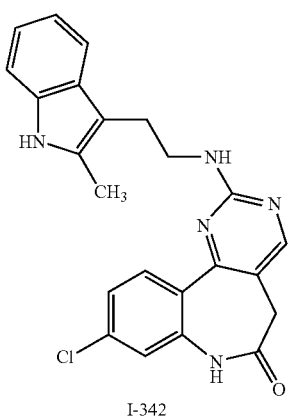
I-342

TABLE 1-continued
Protein Kinase Inhibitors
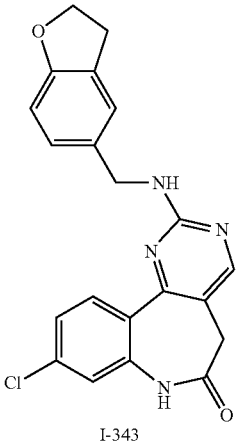
I-343
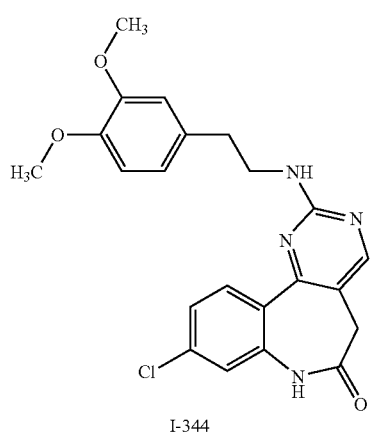
I-344
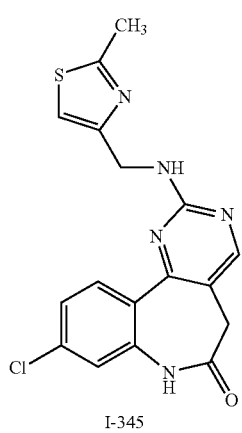
I-345
TABLE 1-continued
Protein Kinase Inhibitors
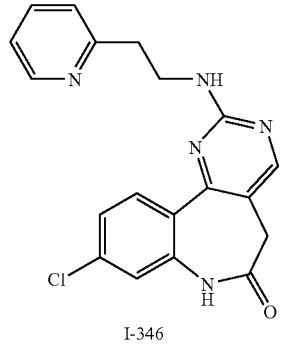
I-346
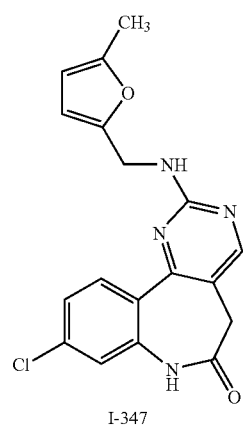
I-347
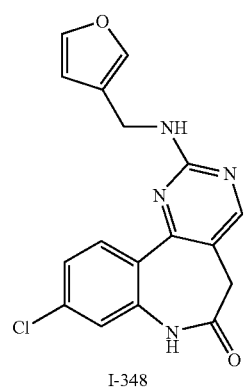
I-348

TABLE 1-continued
Protein Kinase Inhibitors
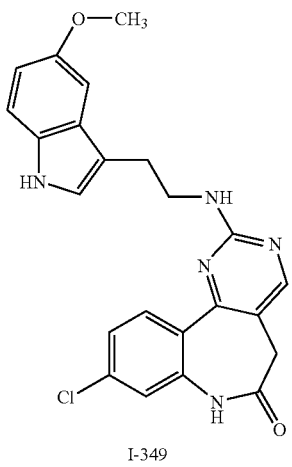
I-349
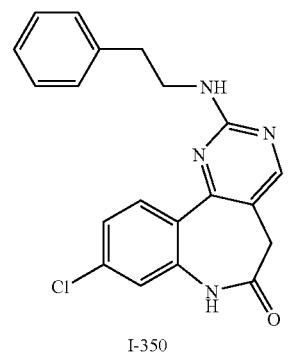
I-350
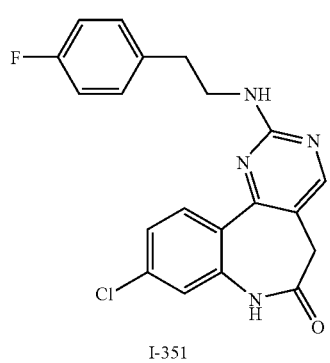
I-351
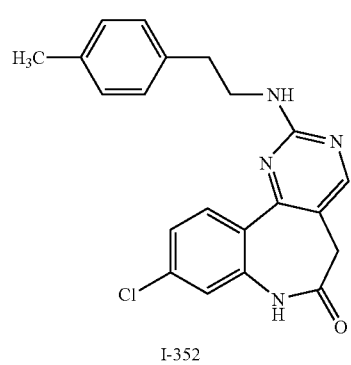
I-352
TABLE 1-continued
Protein Kinase Inhibitors
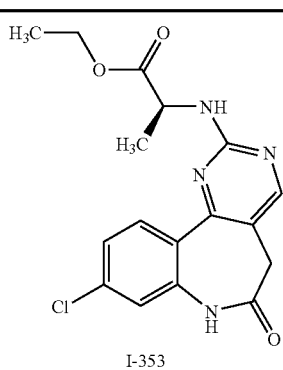
I-353
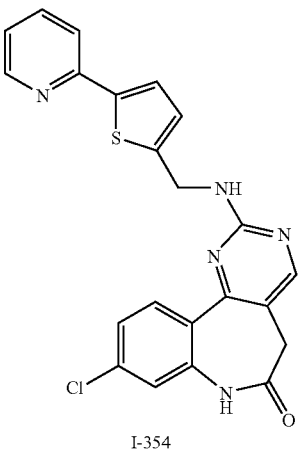
I-354
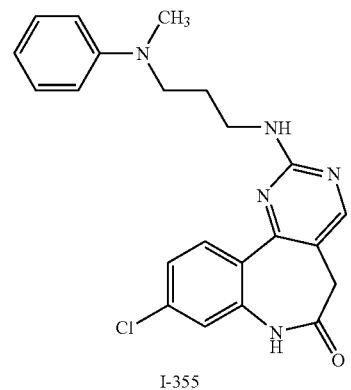
I-355
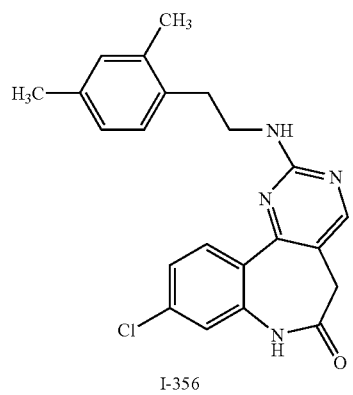
I-356

TABLE 1-continued

Protein Kinase Inhibitors

I-357

I-358

I-359

I-360

I-361

I-362

I-363

I-364

TABLE 1-continued
Protein Kinase Inhibitors
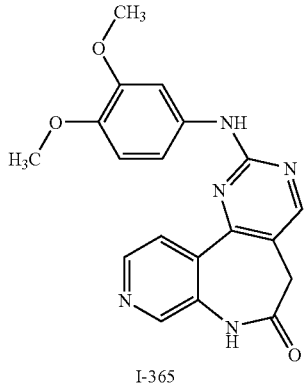
I-365
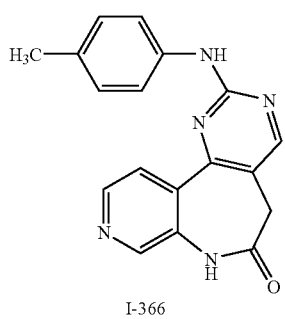
I-366
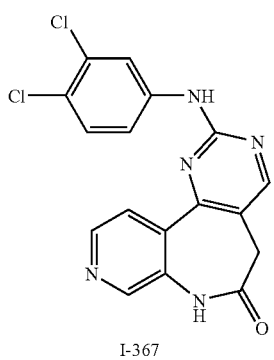
I-367
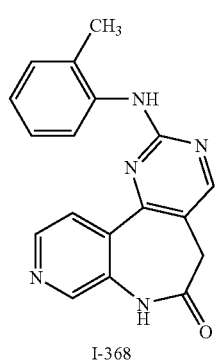
I-368
TABLE 1-continued
Protein Kinase Inhibitors
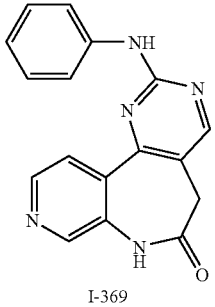
I-369
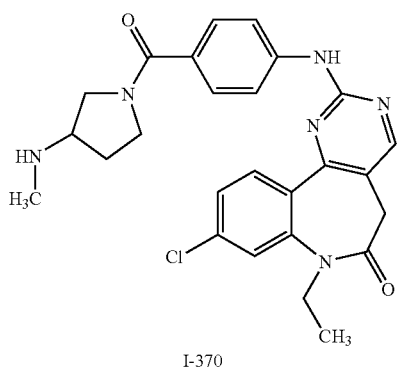
I-370
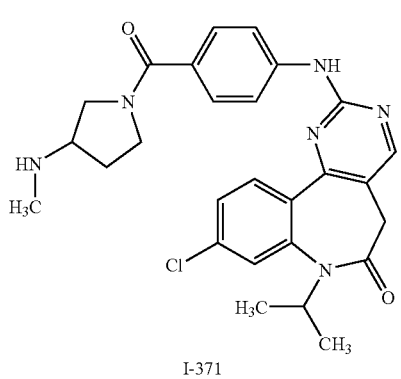
I-371
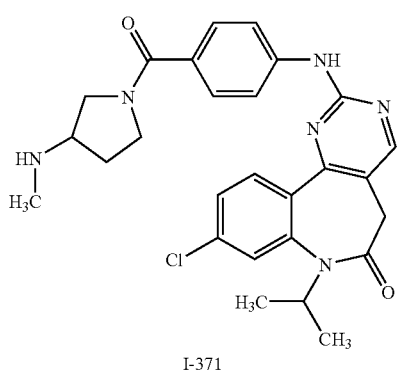
I-371

TABLE 1-continued
Protein Kinase Inhibitors
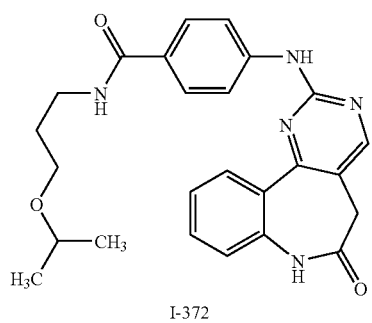
I-372
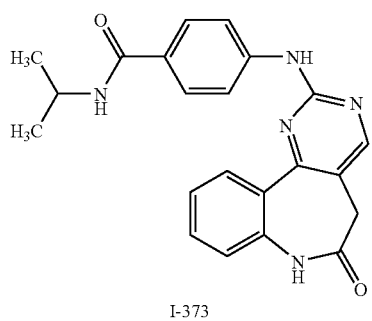
I-373
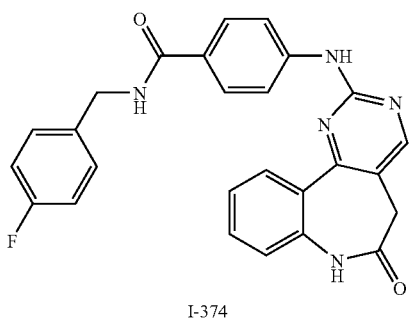
I-374
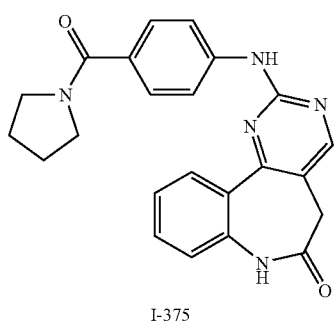
I-375
TABLE 1-continued
Protein Kinase Inhibitors
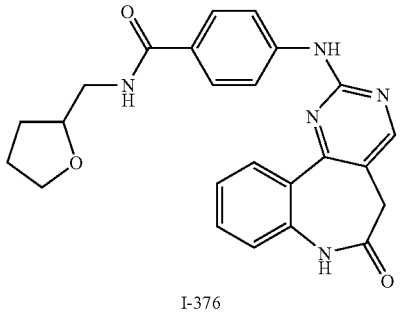
I-376
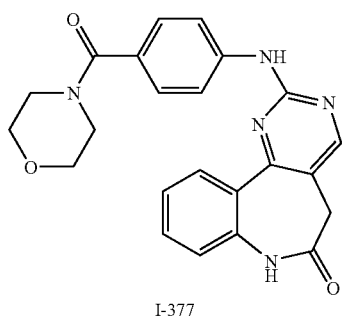
I-377
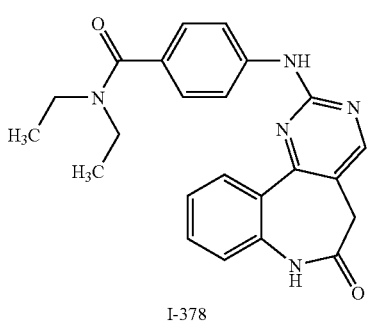
I-378
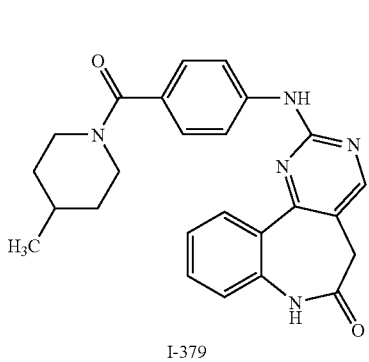
I-379

TABLE 1-continued
Protein Kinase Inhibitors
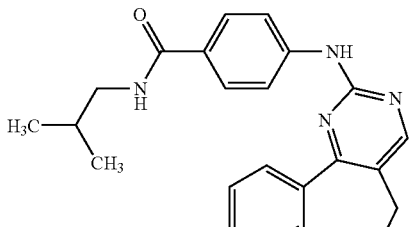
I-380
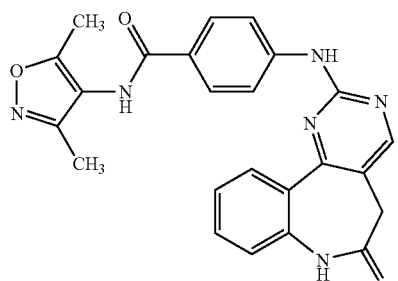
I-381
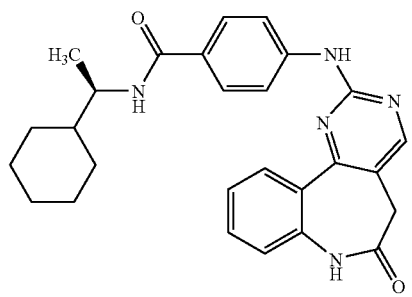
I-382
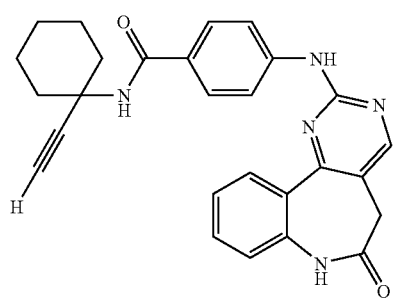
I-383
TABLE 1-continued
Protein Kinase Inhibitors
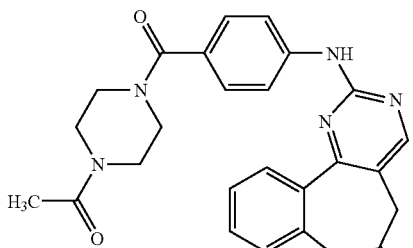
I-384
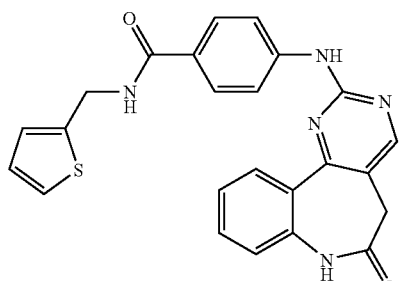
I-385
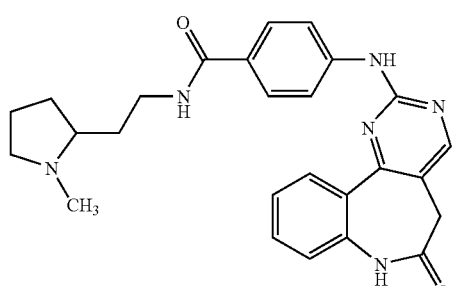
I-386
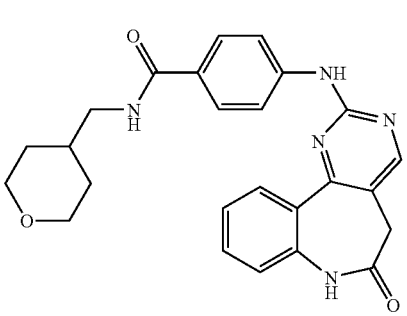
I-387

TABLE 1-continued
Protein Kinase Inhibitors
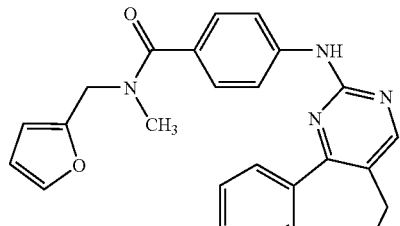
I-388
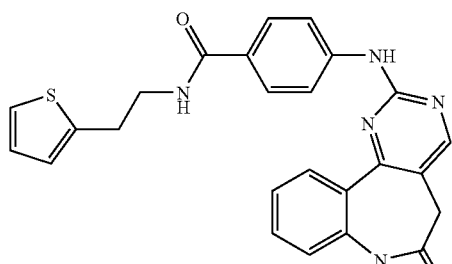
I-389
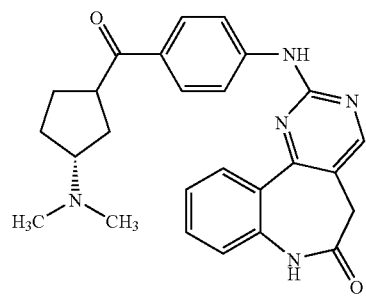
I-390
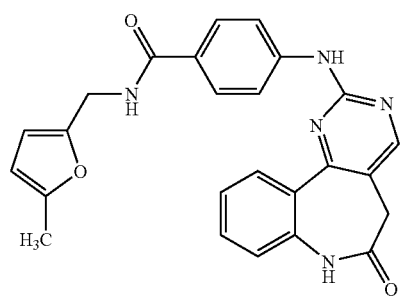
I-391
TABLE 1-continued
Protein Kinase Inhibitors
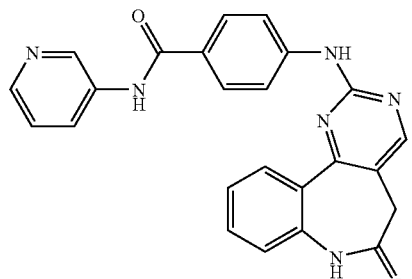
I-392
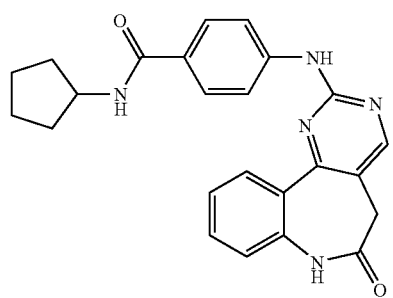
I-393
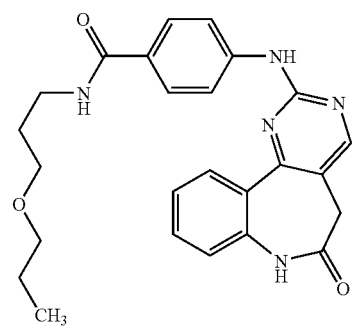
I-394
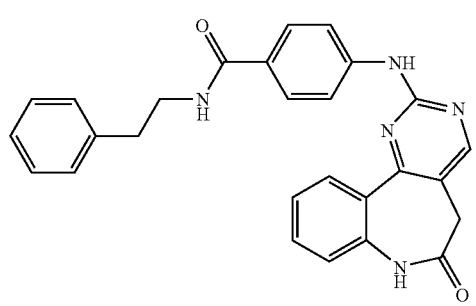
I-395

TABLE 1-continued
Protein Kinase Inhibitors
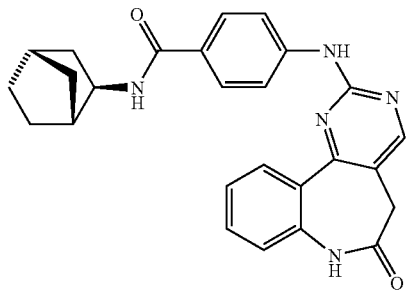
I-396
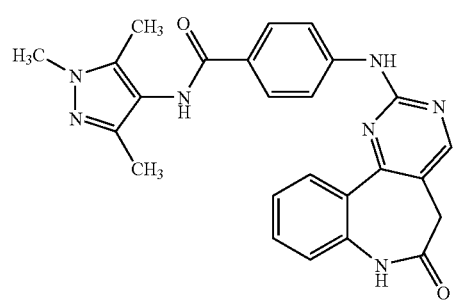
I-397
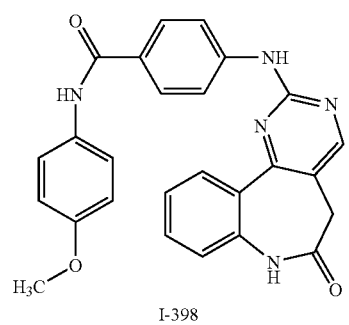
I-398
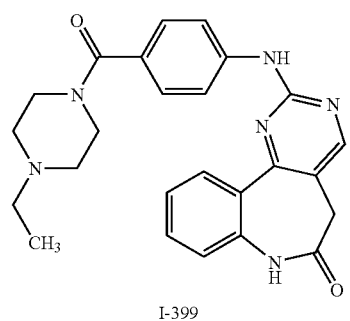
I-399
TABLE 1-continued
Protein Kinase Inhibitors
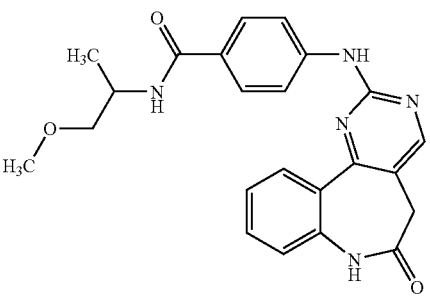
I-400
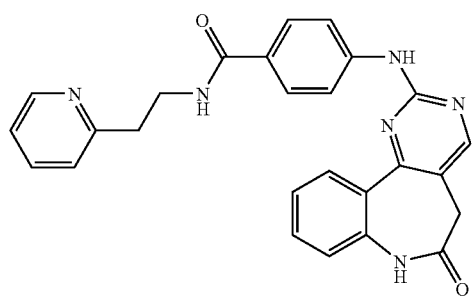
I-401
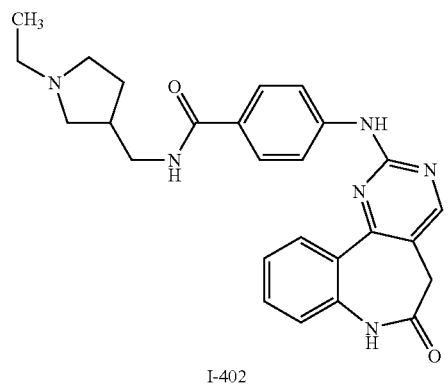
I-402
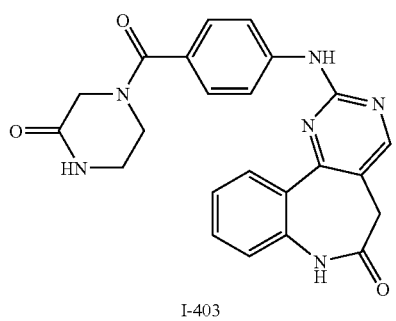
I-403

TABLE 1-continued
Protein Kinase Inhibitors
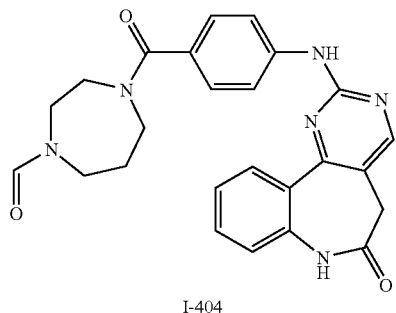
I-404
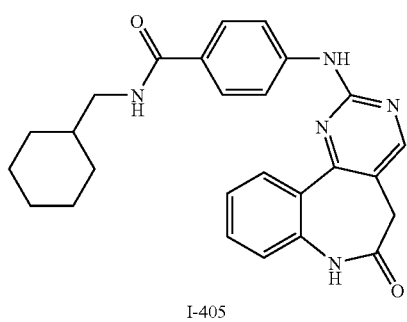
I-405
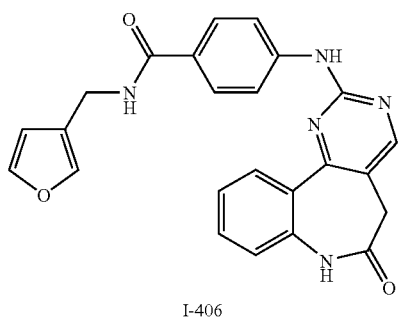
I-406
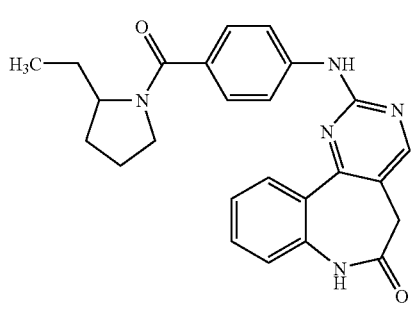
I-407
TABLE 1-continued
Protein Kinase Inhibitors
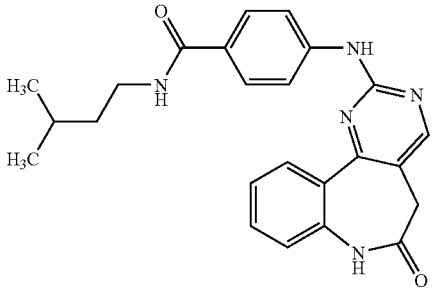
I-408
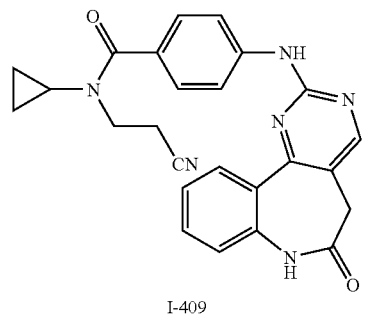
I-409
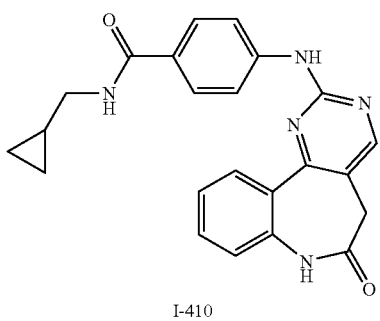
I-410
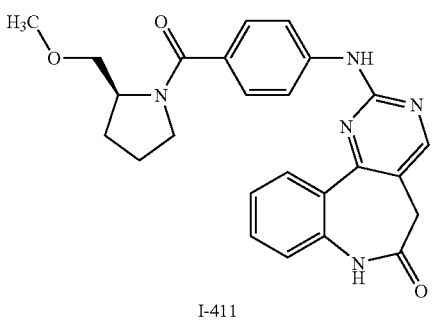
I-411

TABLE 1-continued

Protein Kinase Inhibitors

I-412

I-413

I-414

I-415

I-416

I-417

I-418

I-419

TABLE 1-continued
Protein Kinase Inhibitors
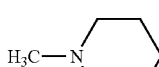

TABLE 1-continued
Protein Kinase Inhibitors
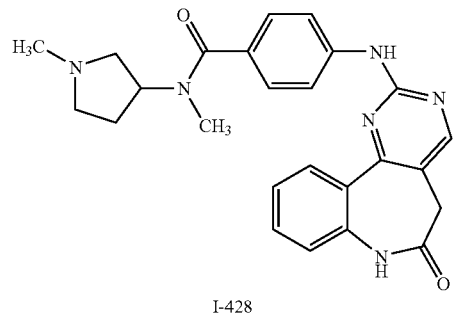
I-428
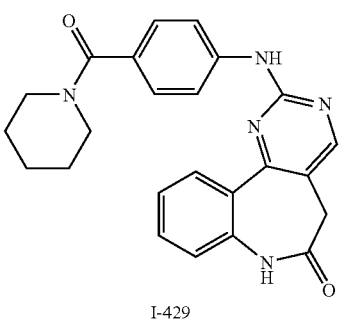
I-429
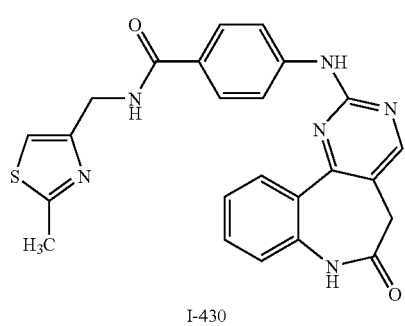
I-430
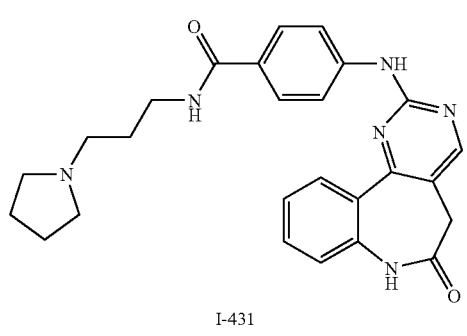
I-431
TABLE 1-continued
Protein Kinase Inhibitors
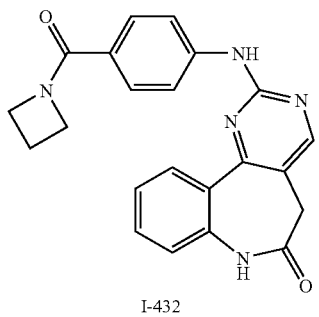
I-432
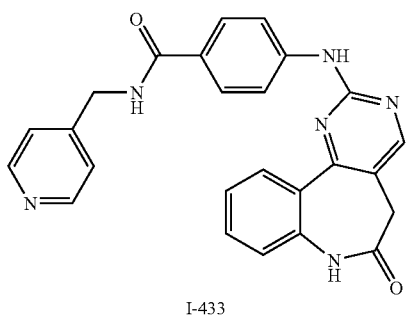
I-433
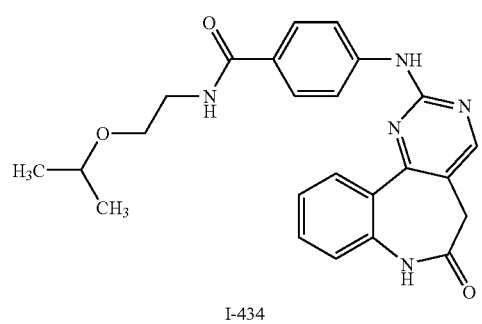
I-434
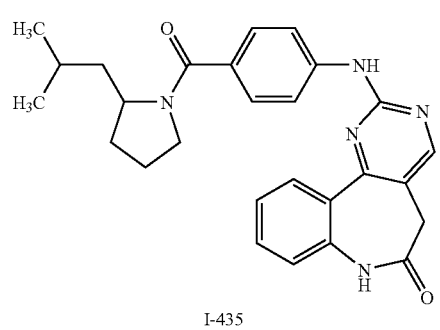
I-435

TABLE 1-continued
Protein Kinase Inhibitors
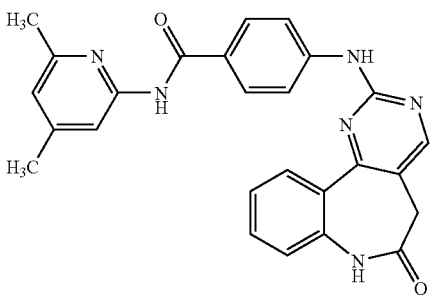
I-436
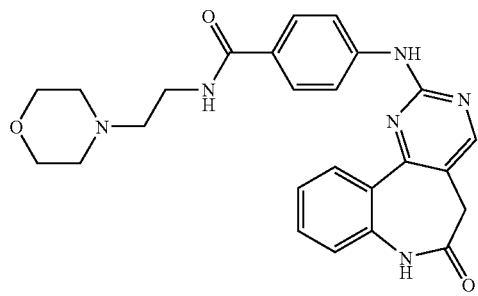
I-437
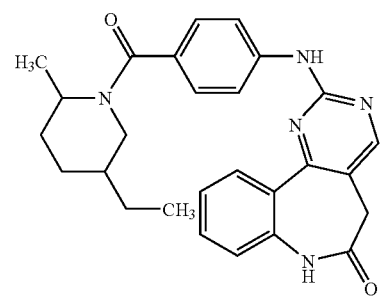
I-438
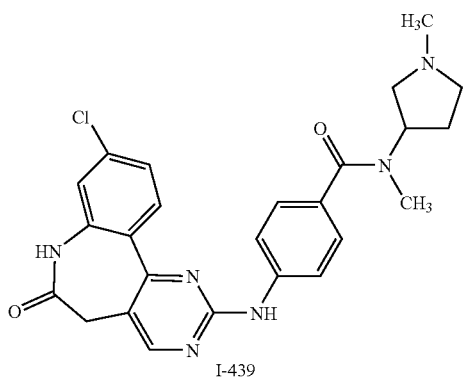
I-439
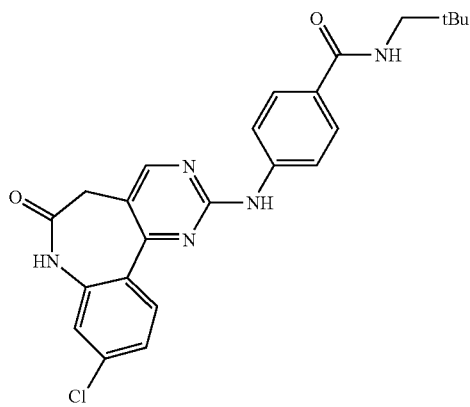
I-440
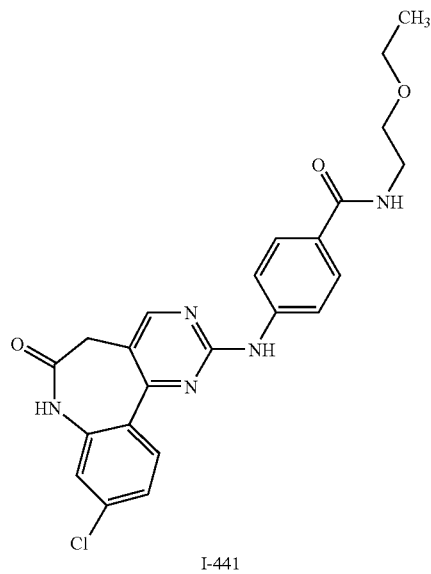
I-441

TABLE 1-continued
Protein Kinase Inhibitors
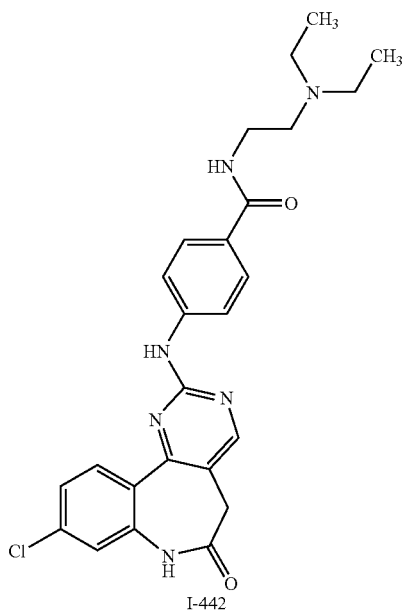
I-442
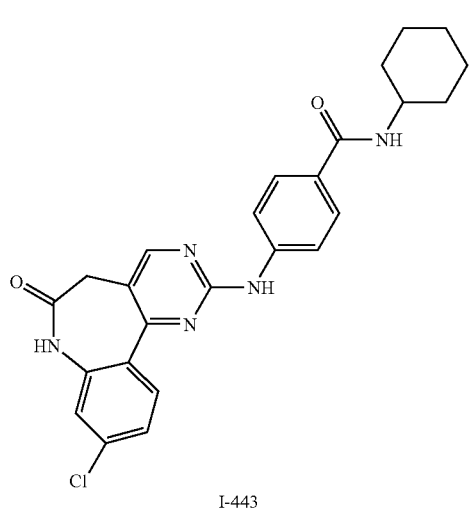
I-443
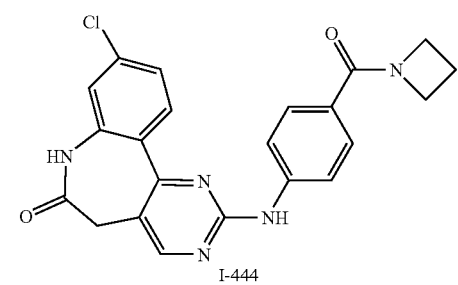
I-444
TABLE 1-continued
Protein Kinase Inhibitors
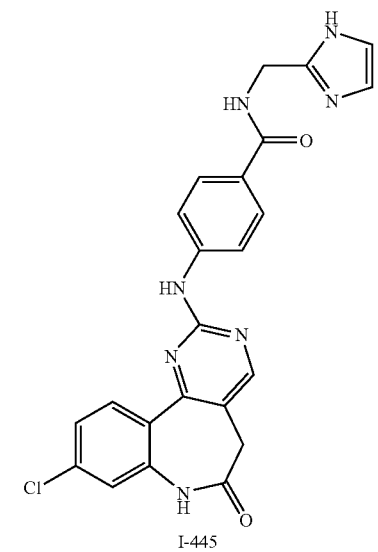
I-445
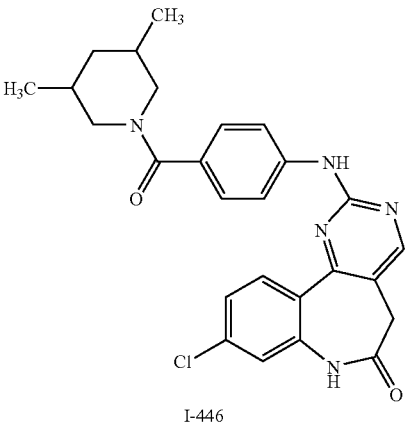
I-446
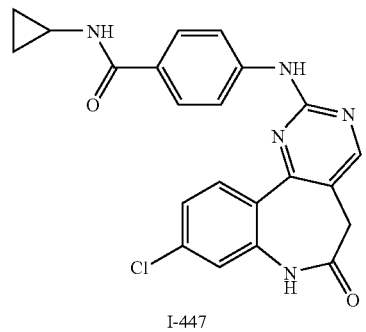
I-447

TABLE 1-continued
Protein Kinase Inhibitors
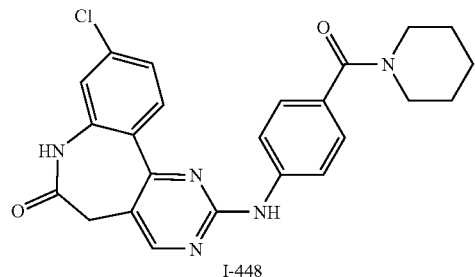
I-448
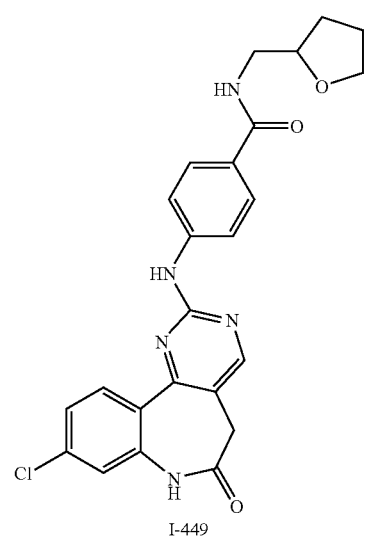
I-449
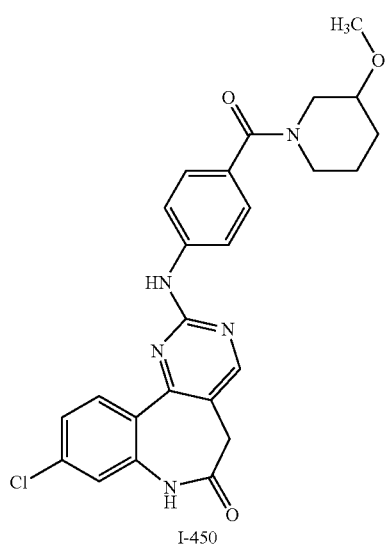
I-450
TABLE 1-continued
Protein Kinase Inhibitors
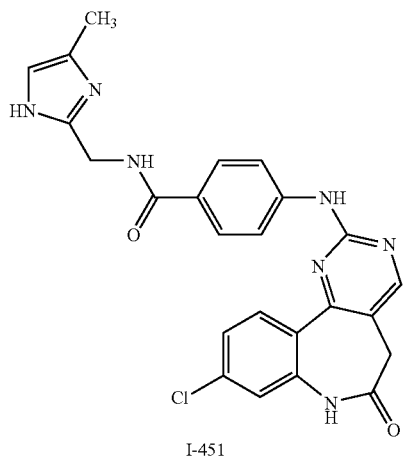
I-451
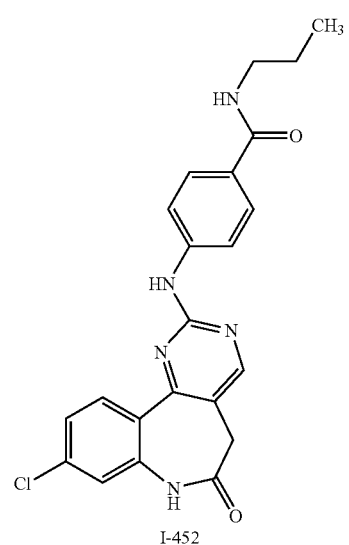
I-452

TABLE 1-continued
Protein Kinase Inhibitors
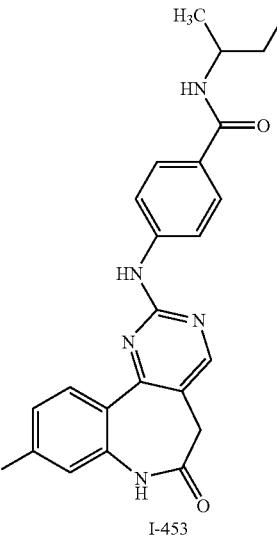
I-453
I-454
I-455
I-456
I-457

TABLE 1-continued
Protein Kinase Inhibitors
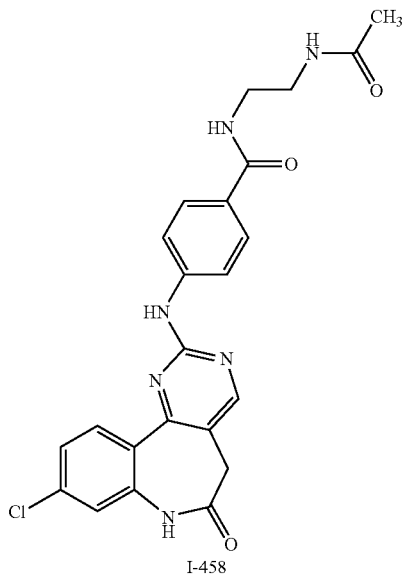
I-458
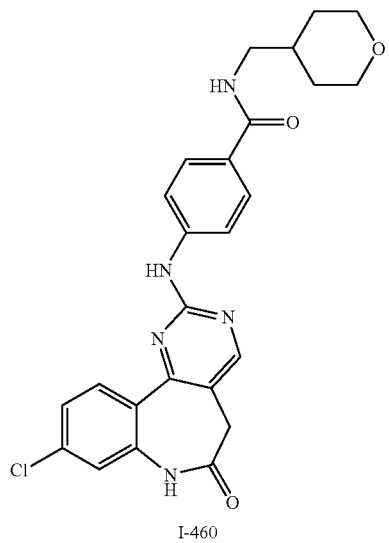
I-460
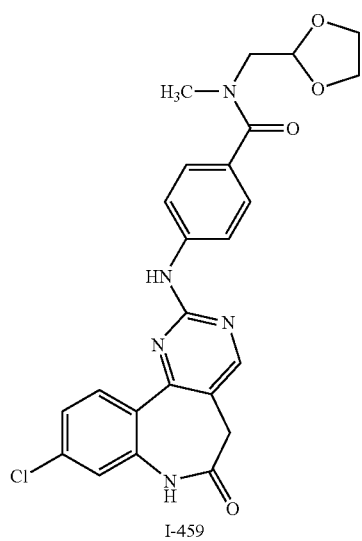
I-459
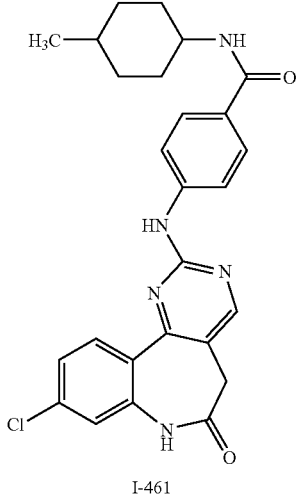
I-461

TABLE 1-continued

Protein Kinase Inhibitors

I-462

I-463

I-464

I-465

I-466

I-467

TABLE 1-continued
Protein Kinase Inhibitors
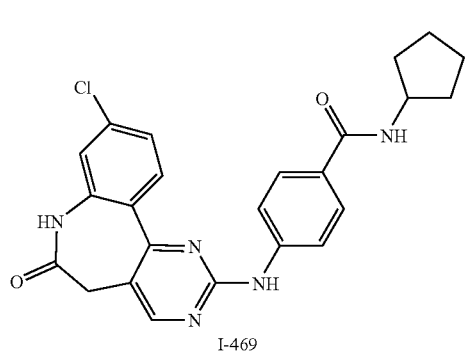
I-468
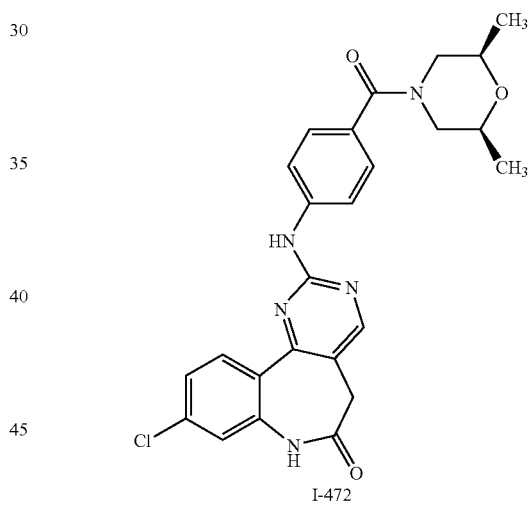
I-471
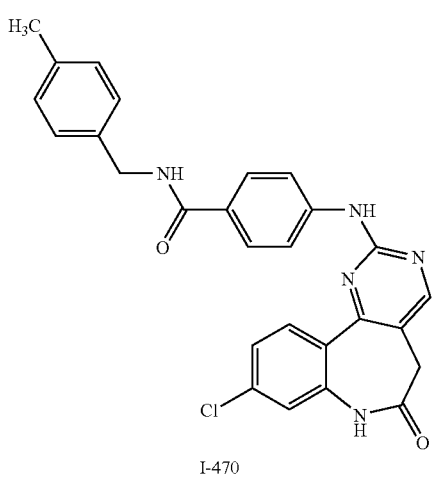
I-469
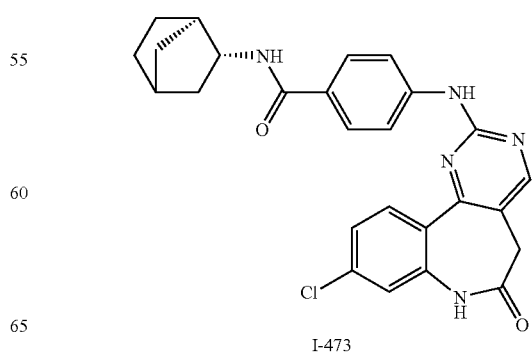
I-472
I-470
I-473

TABLE 1-continued
Protein Kinase Inhibitors
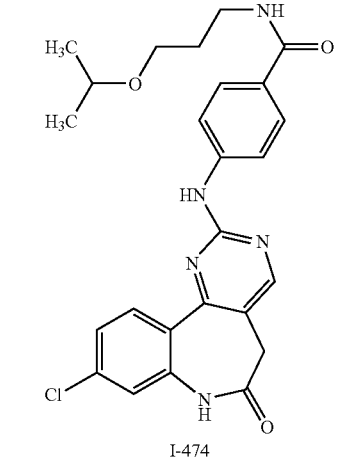
I-474
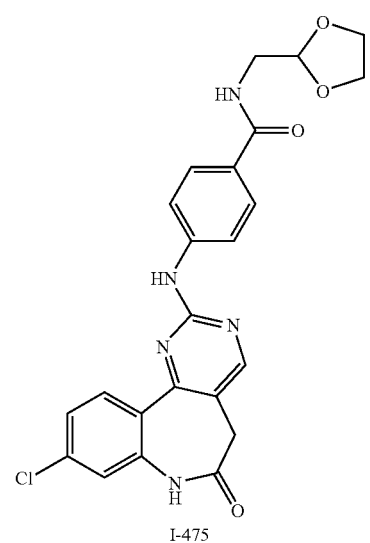
I-475
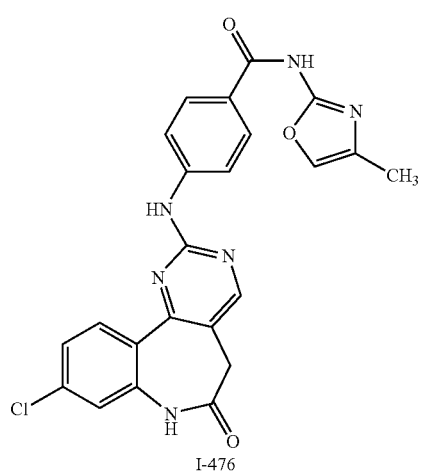
I-476
TABLE 1-continued
Protein Kinase Inhibitors
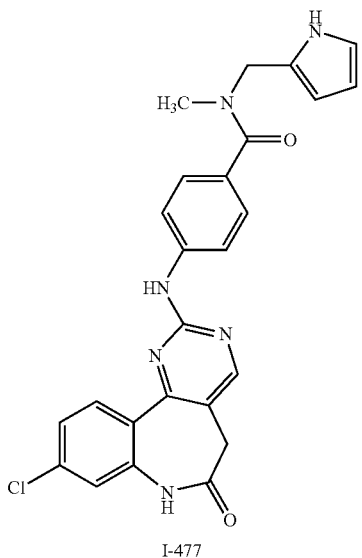
I-477
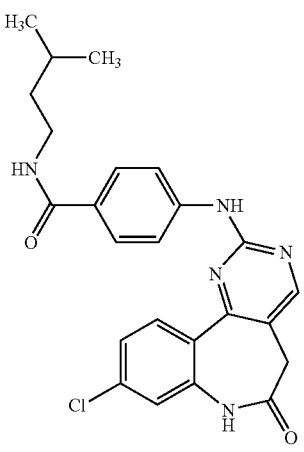
I-478
I-479

TABLE 1-continued
Protein Kinase Inhibitors
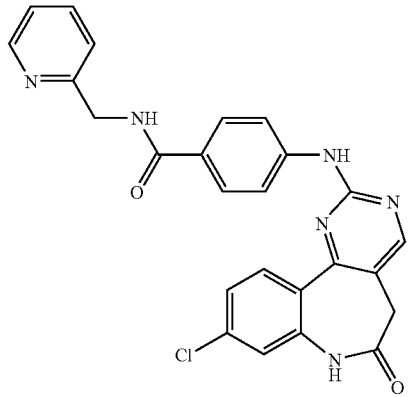
I-480
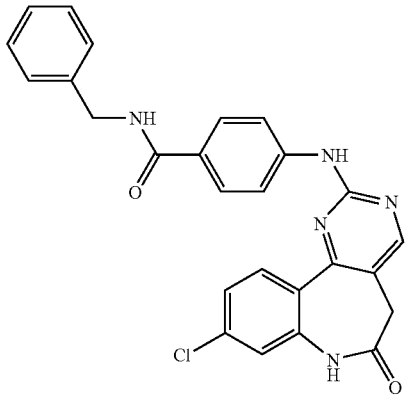
I-483
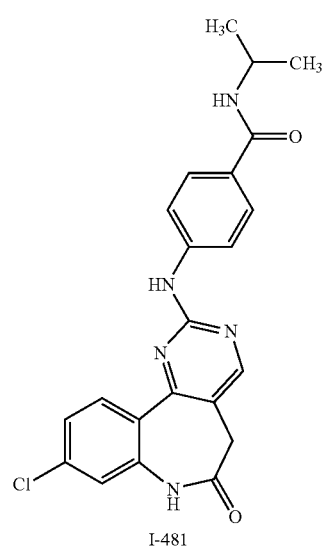
I-481
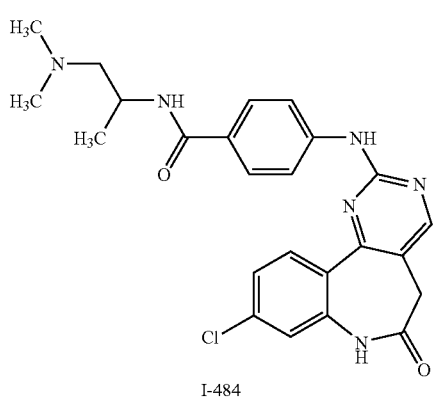
I-484
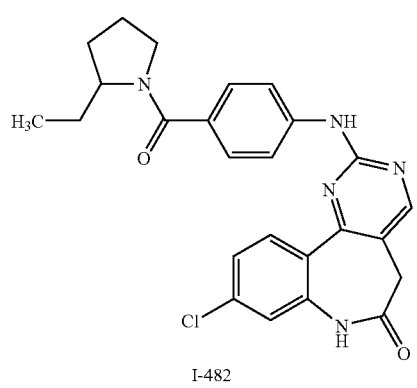
I-482
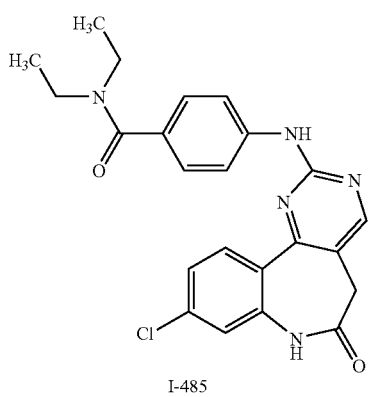
I-485

TABLE 1-continued
Protein Kinase Inhibitors
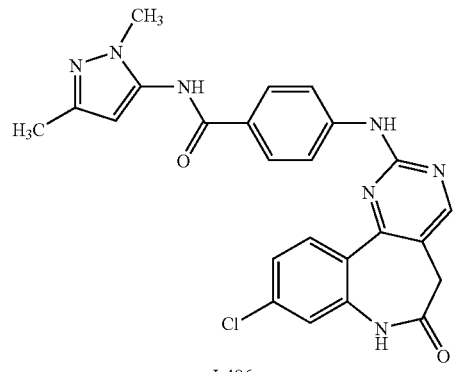
I-486
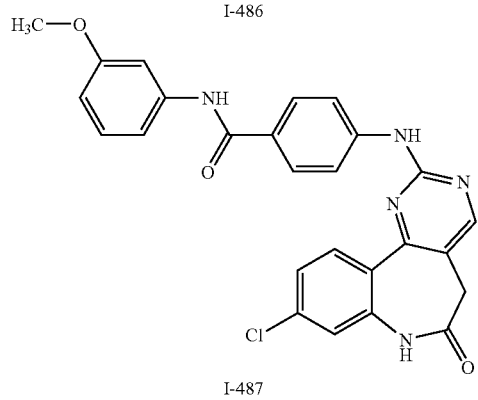
I-487
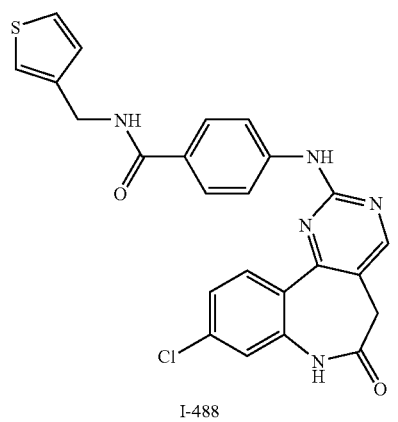
I-488
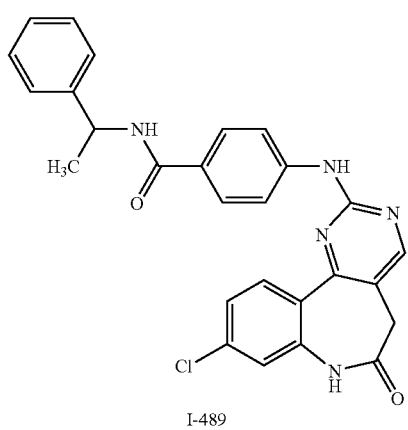
I-489
TABLE 1-continued
Protein Kinase Inhibitors
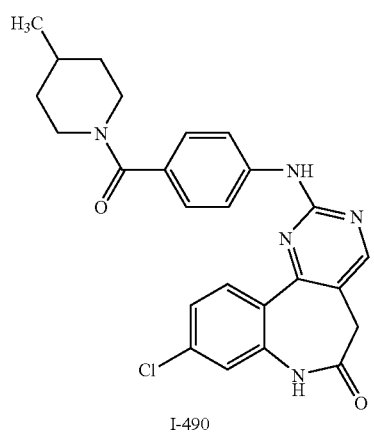
I-490
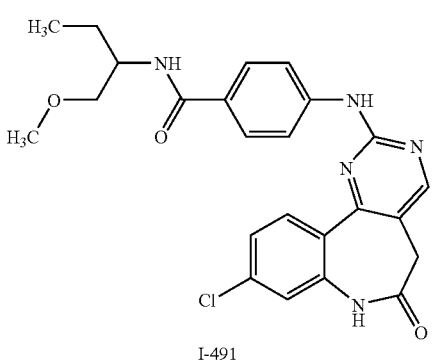
I-491
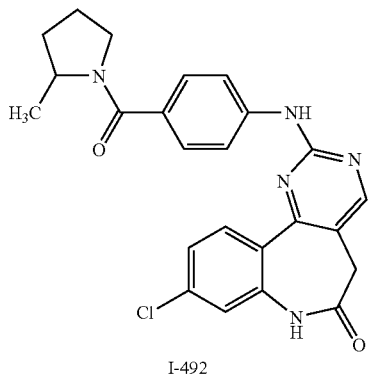
I-492
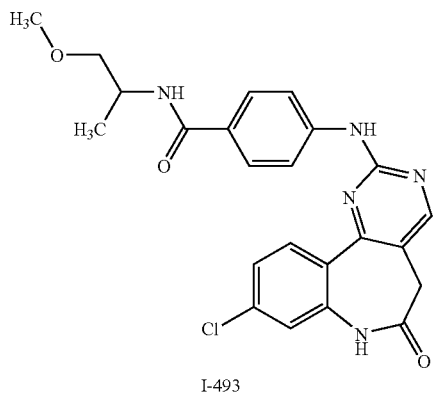
I-493

TABLE 1-continued
Protein Kinase Inhibitors
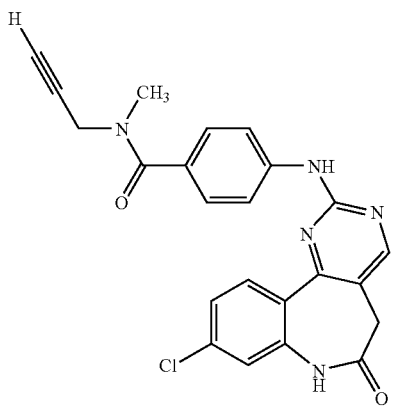
I-494
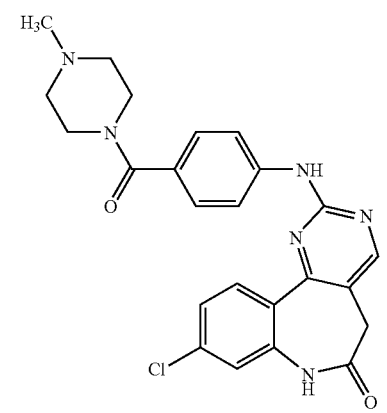
I-495
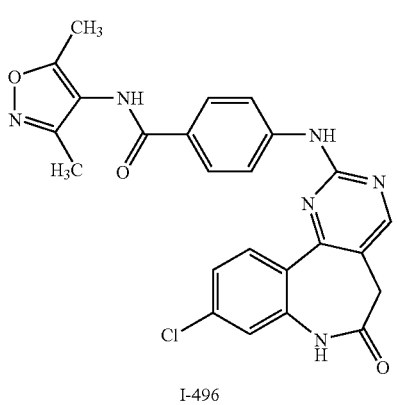
I-496
TABLE 1-continued
Protein Kinase Inhibitors
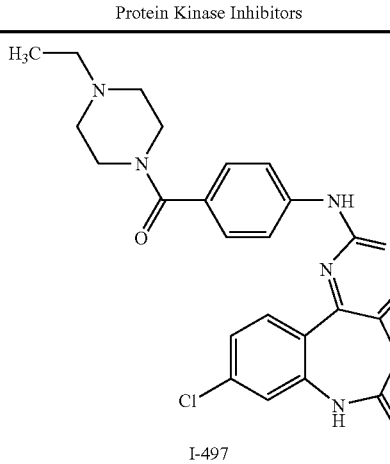
I-497
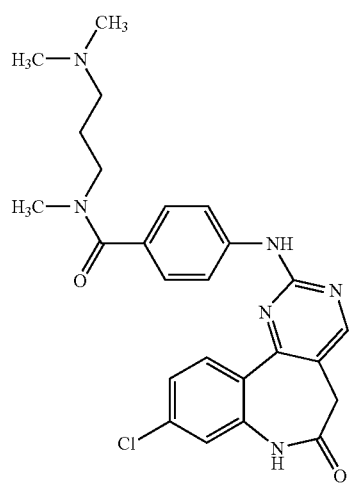
I-498
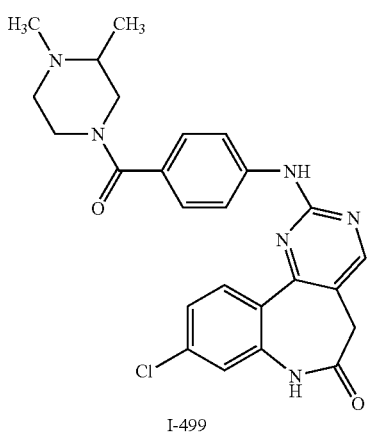
I-499

TABLE 1-continued

Protein Kinase Inhibitors

I-500

I-501

I-502

I-503

I-504

I-505

I-506

TABLE 1-continued
Protein Kinase Inhibitors
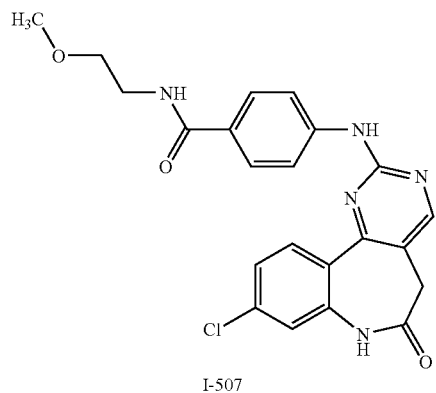
I-507
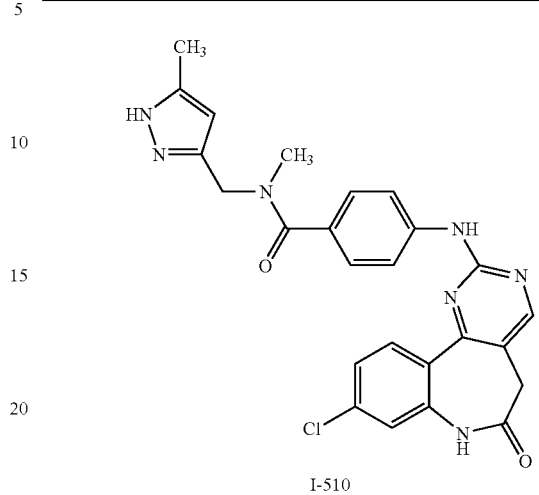
I-510
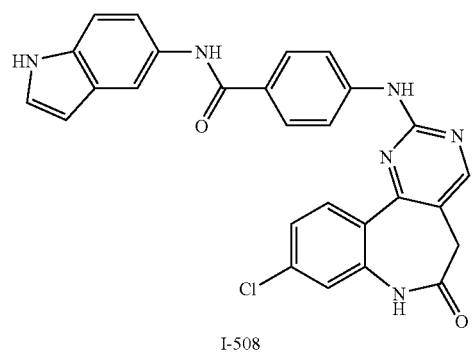
I-508
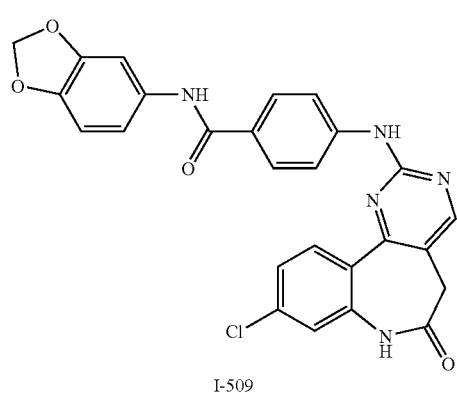
I-509
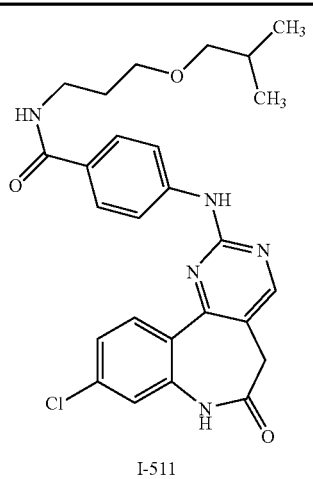
I-511

-continued
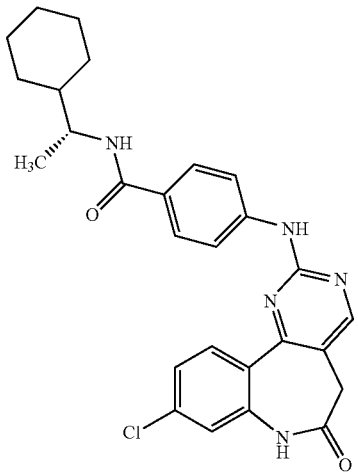
I-512
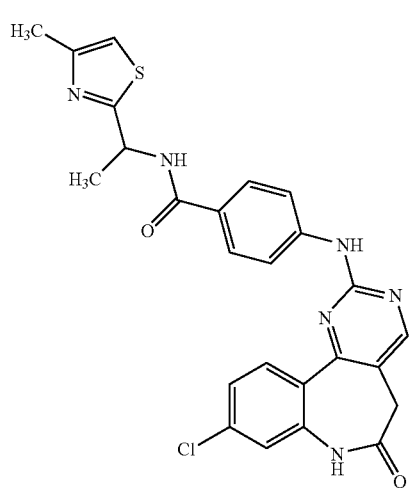
I-513
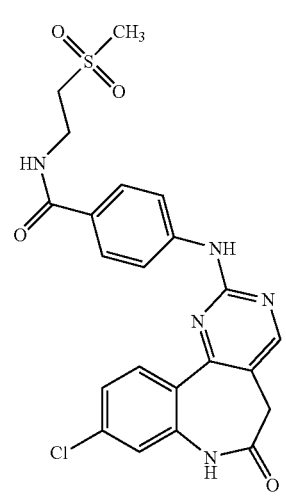
I-514
-continued
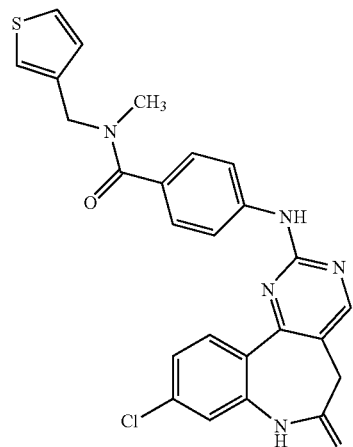
I-515
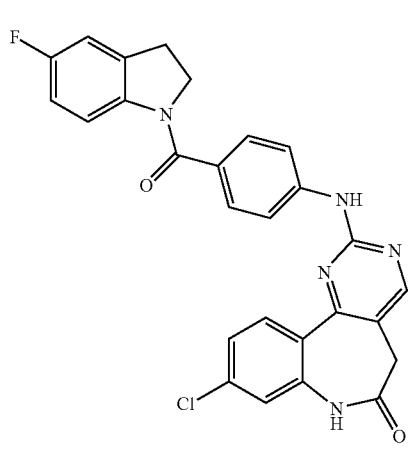
I-516
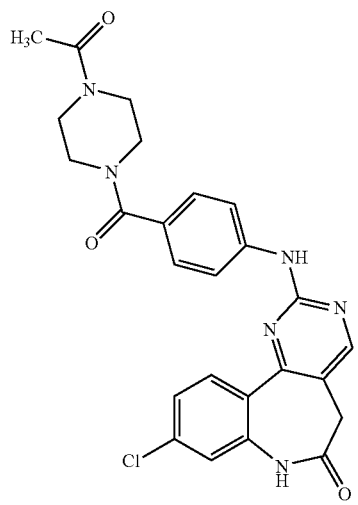
I-517

-continued
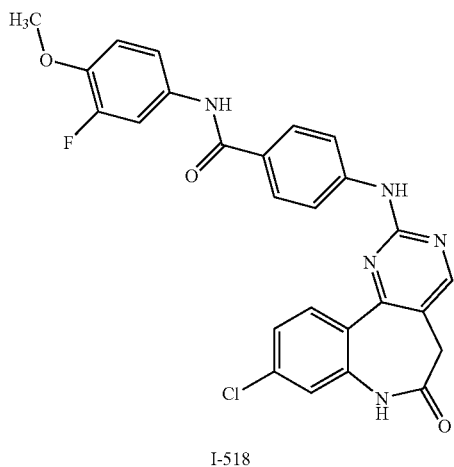
I-518
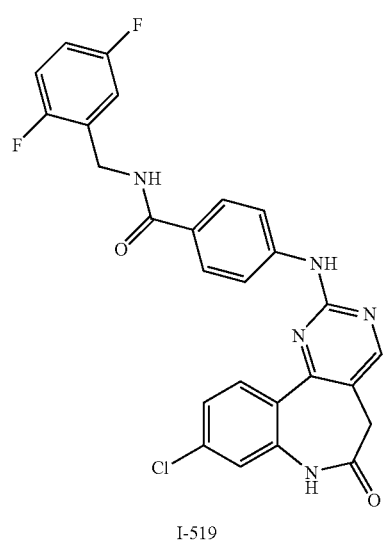
I-519
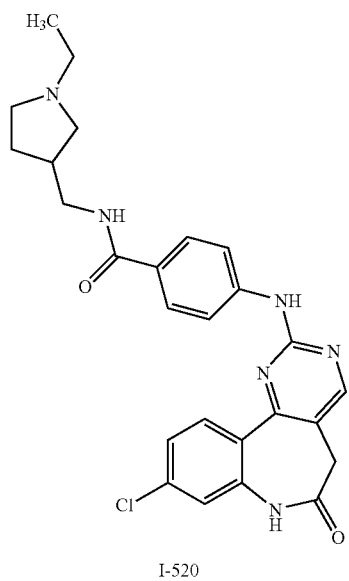
I-520
-continued
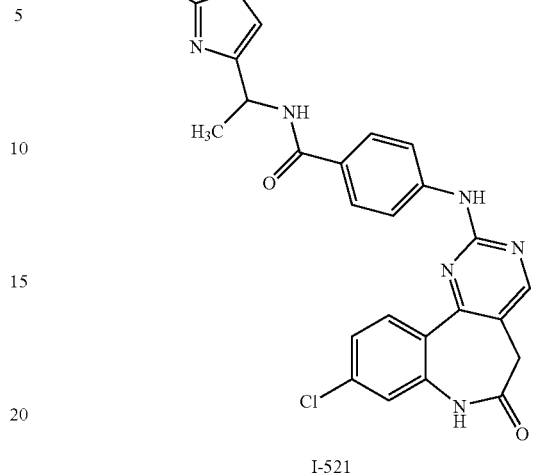
I-521
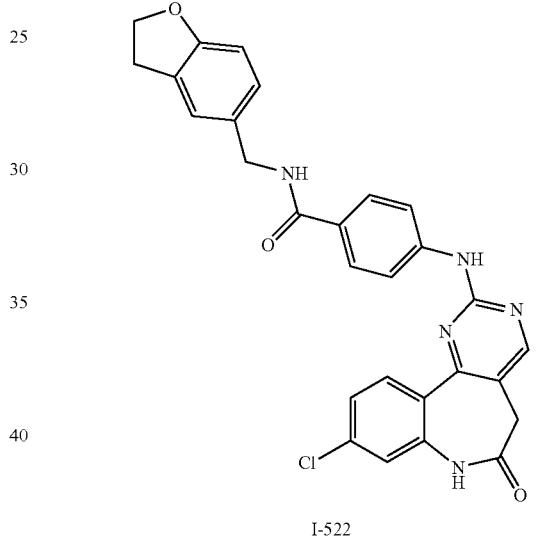
I-522
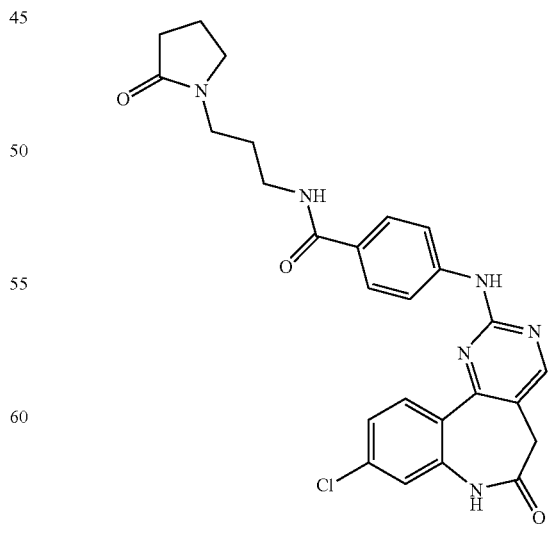
I-523

-continued
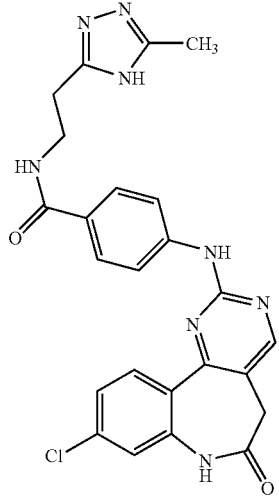
I-524
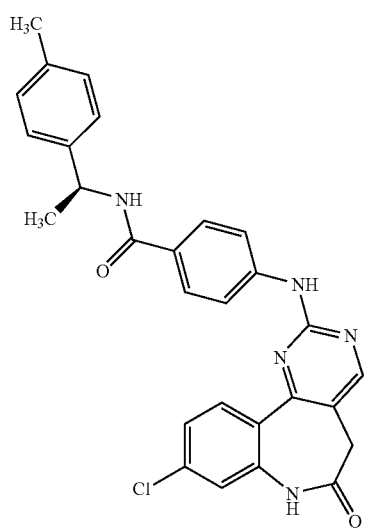
I-525
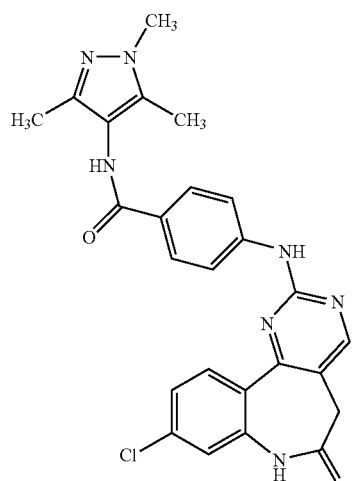
I-526
-continued
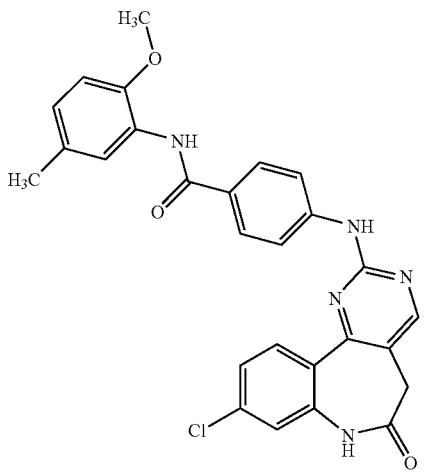
I-527
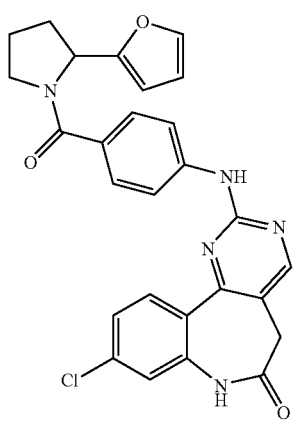
I-528
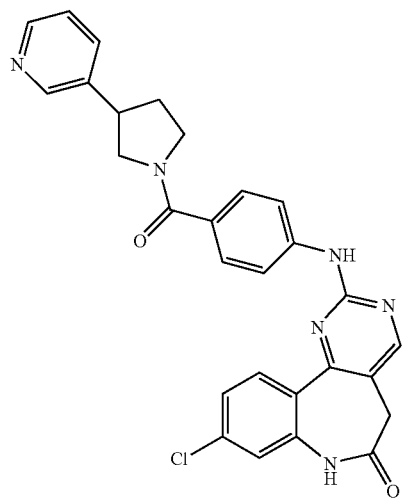
I-529

-continued
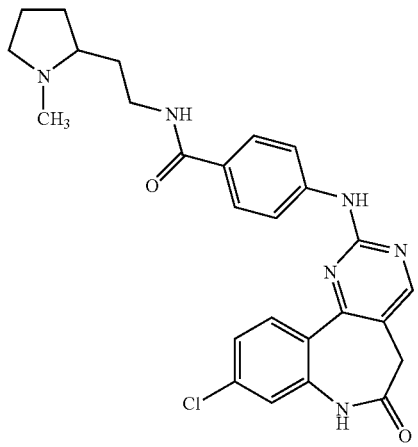
I-530
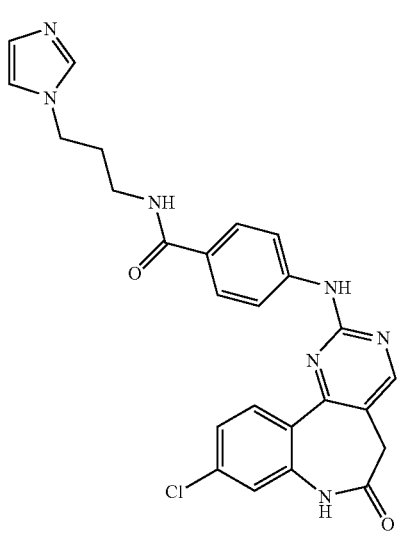
I-531
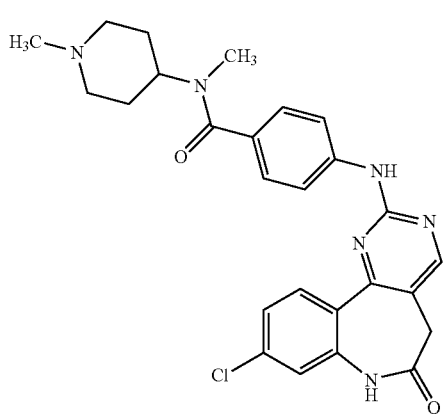
I-532
-continued
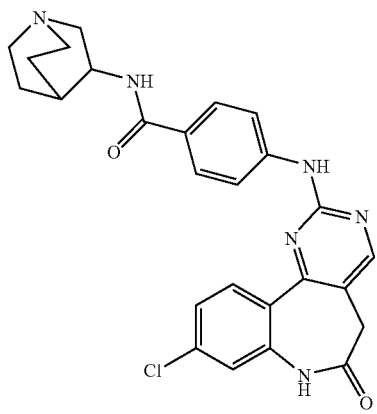
I-533
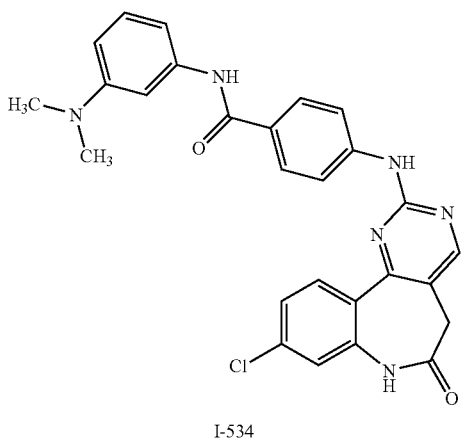
I-534
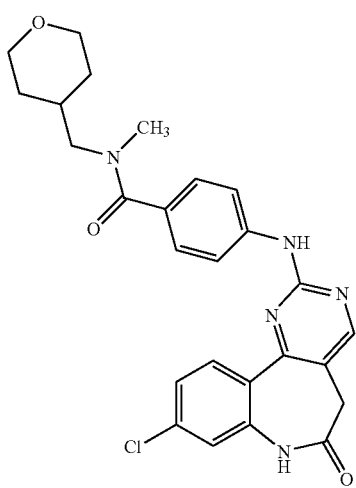
I-535

-continued
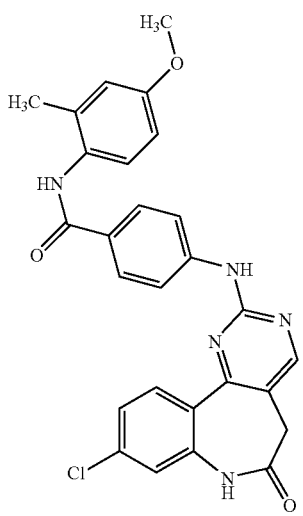
I-536
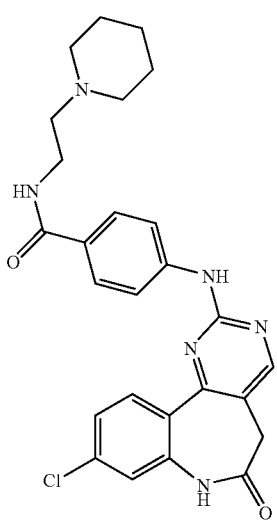
I-537
-continued
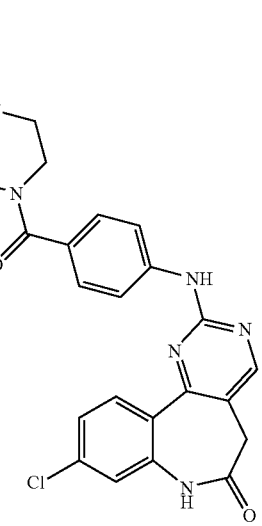
I-538
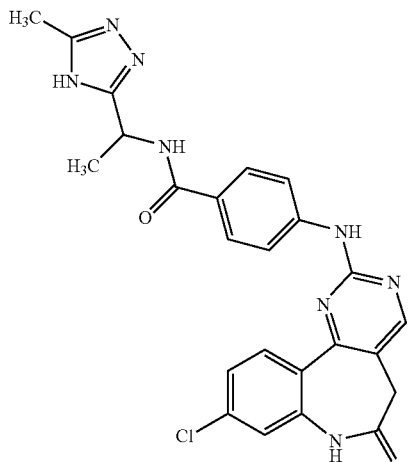
I-539

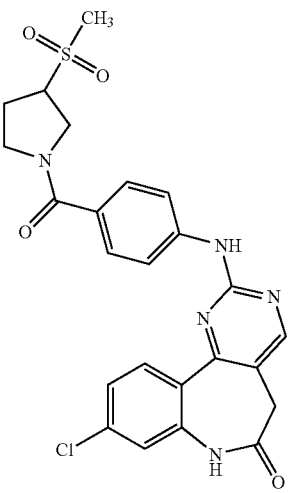
I-540
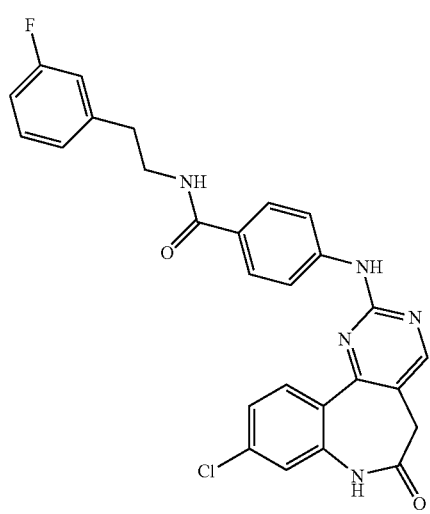
I-541
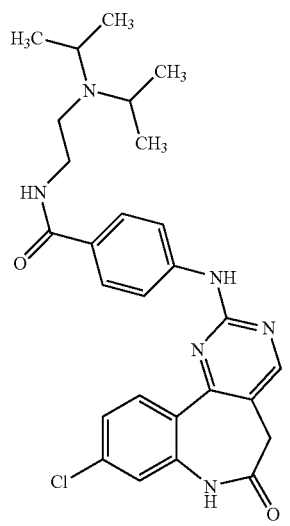
I-542
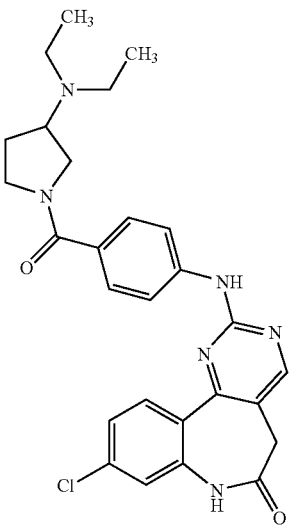
I-543
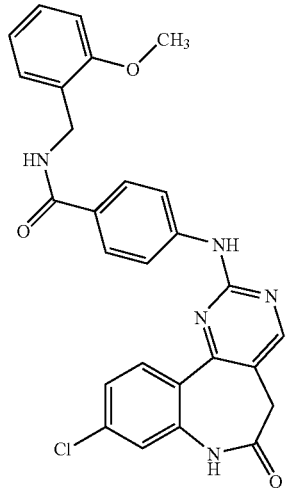
I-544

-continued
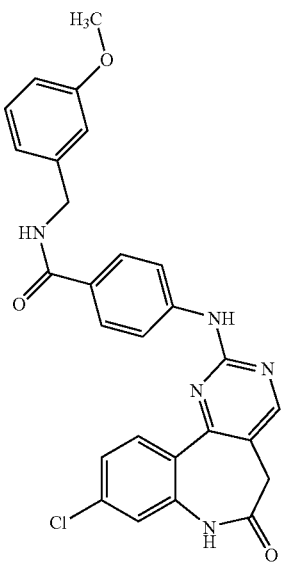
I-545
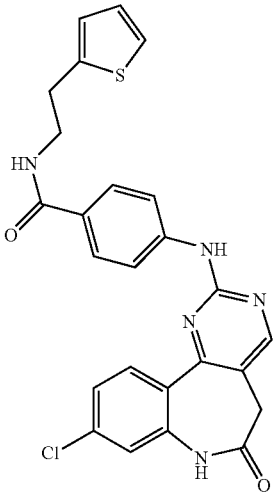
I-547
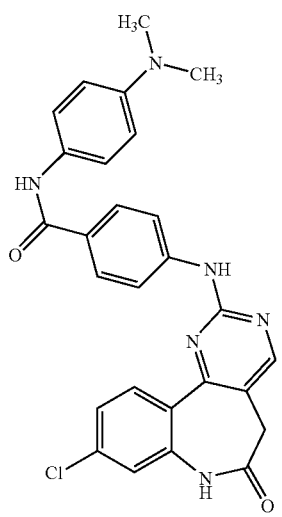
I-546
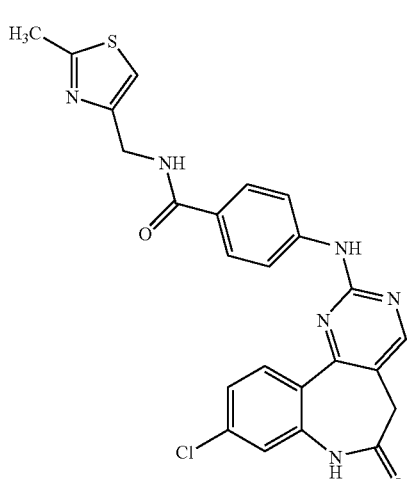
I-548

-continued
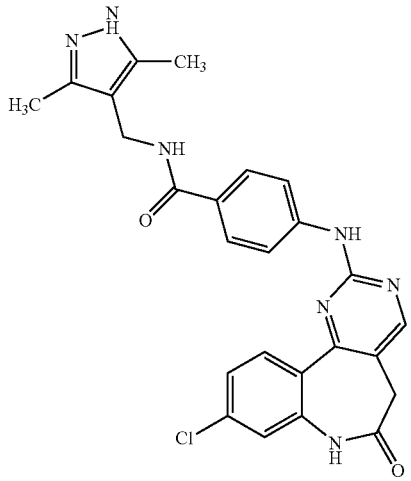
I-549
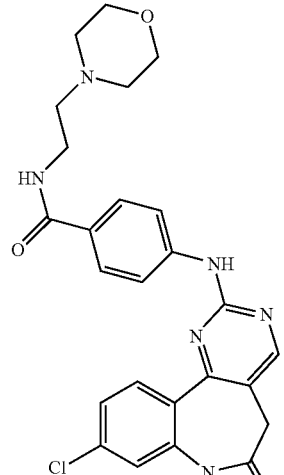
I-551
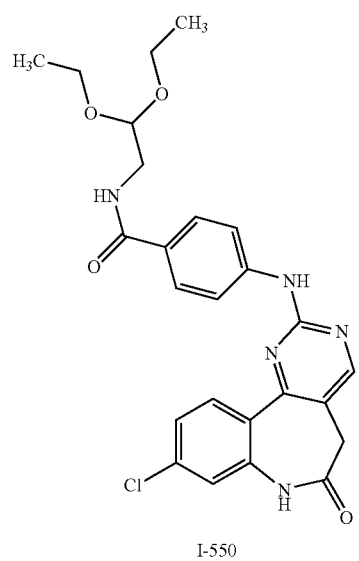
I-550
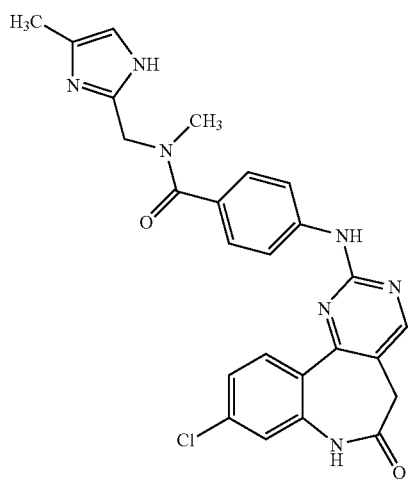
I-552

-continued
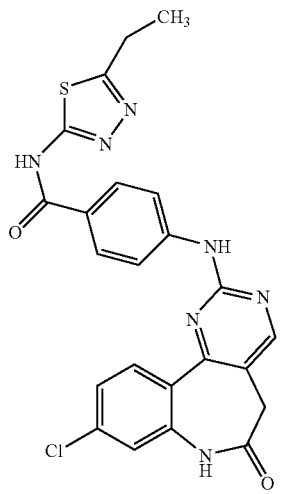
I-553
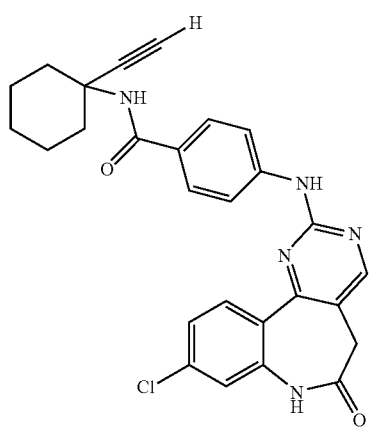
I-554
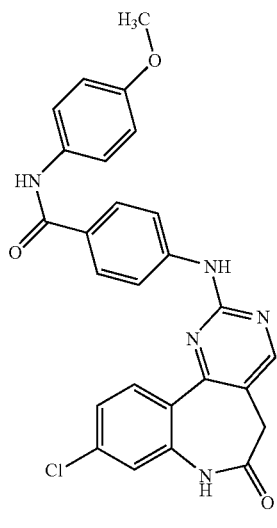
I-555
-continued
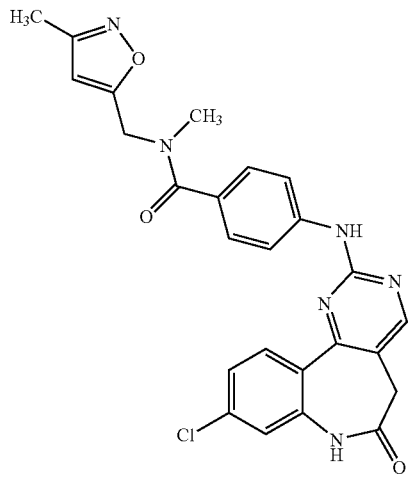
I-556
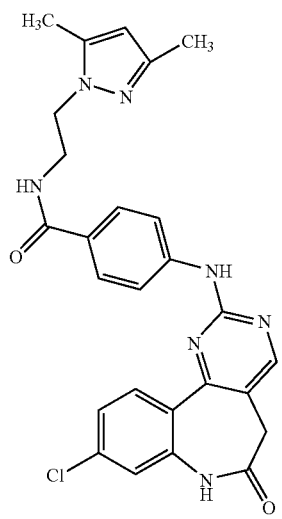
I-557
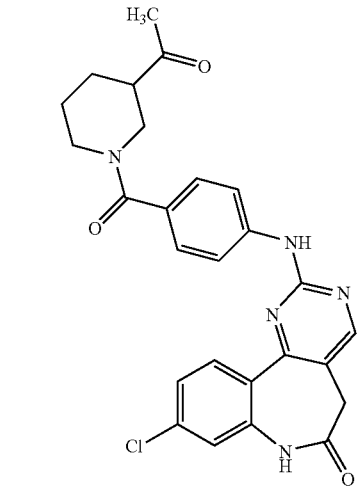
I-558

-continued
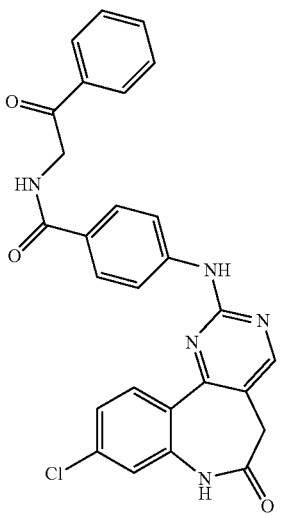
I-559
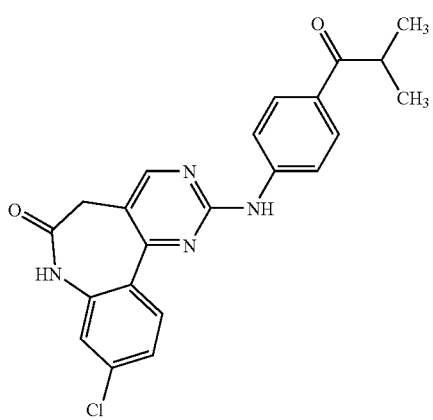
I-560
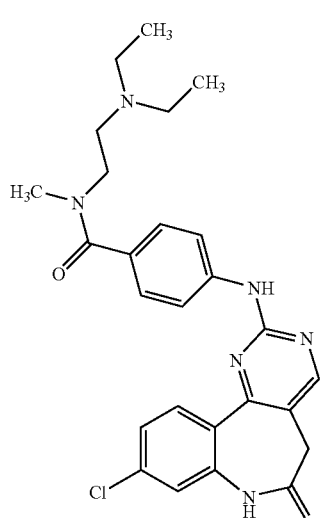
I-561
-continued
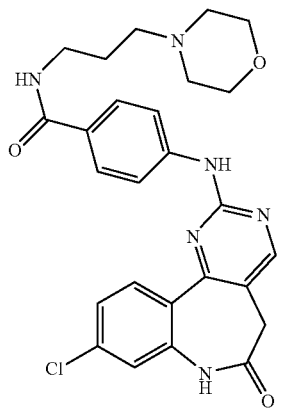
I-562
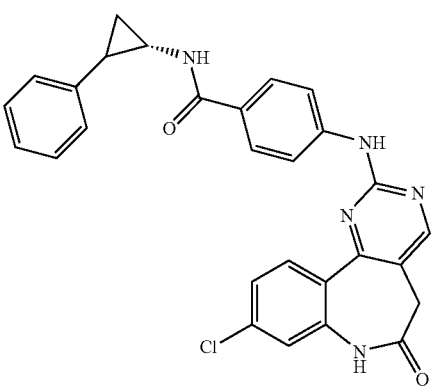
I-563
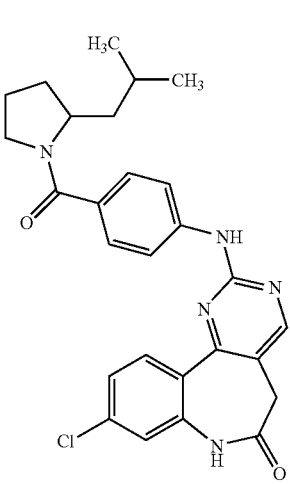
I-564

-continued
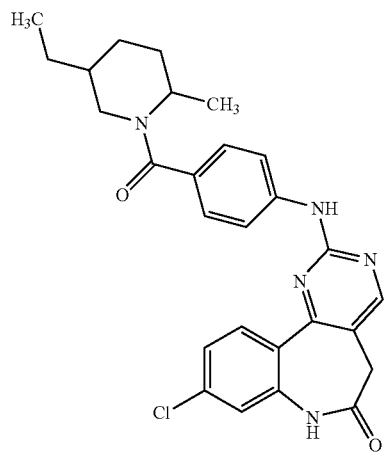
I-565
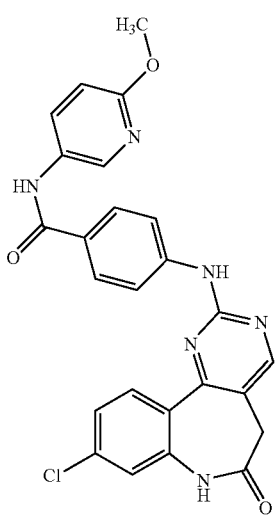
I-566
-continued
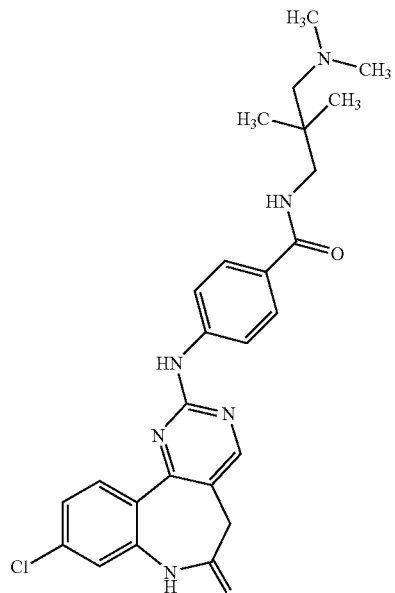
I-567
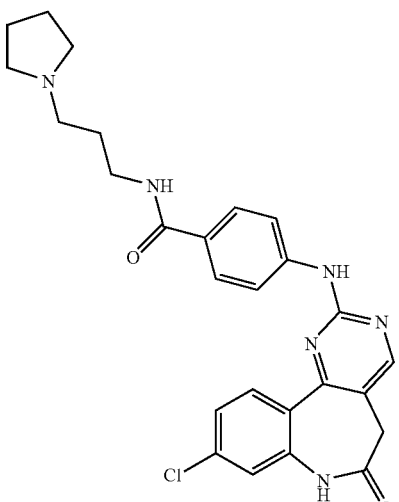
I-568

-continued
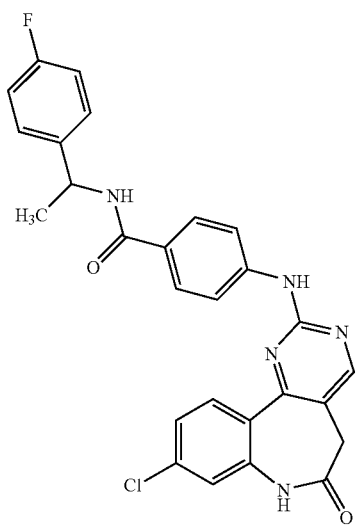
I-569
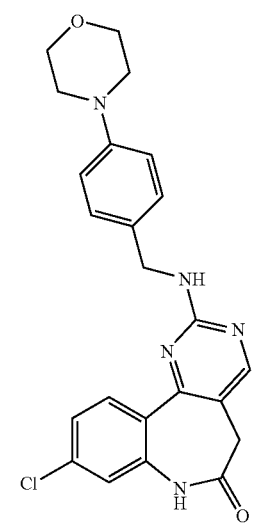
I-570
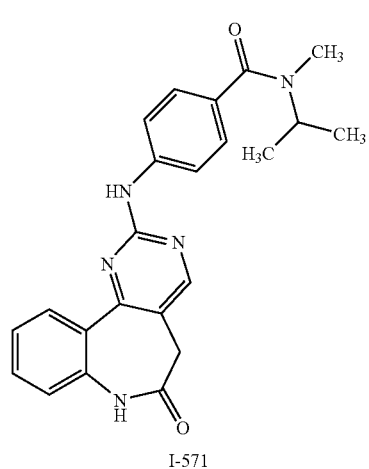
I-571
-continued
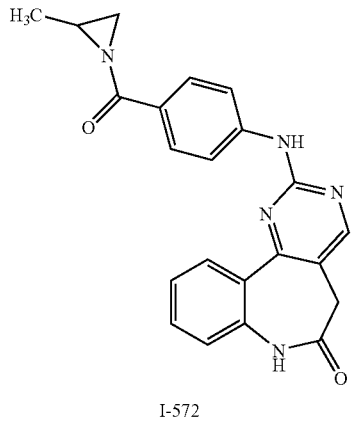
I-572
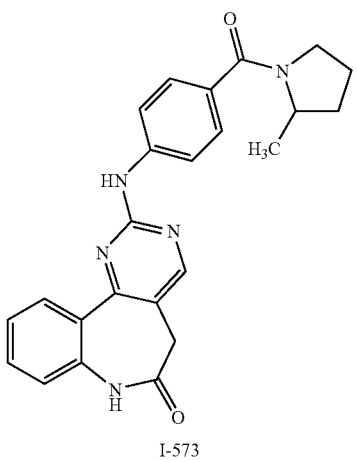
I-573
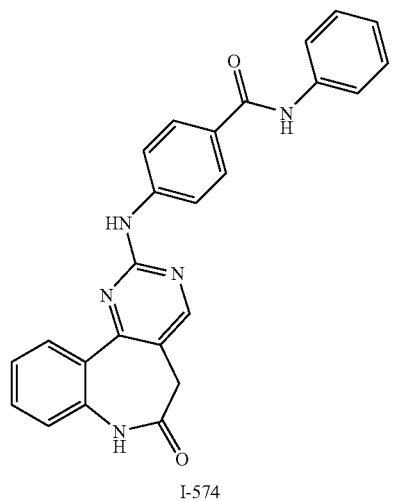
I-574

-continued
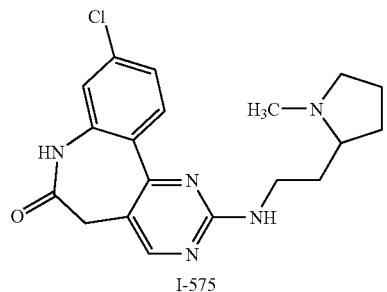
I-575
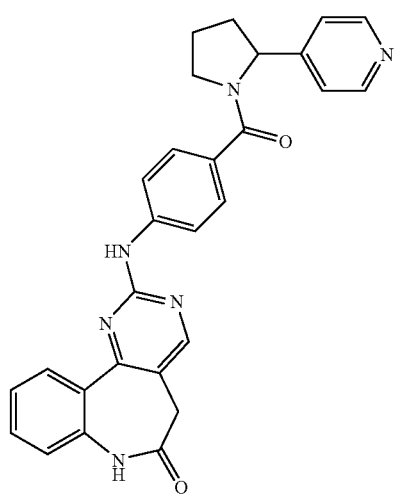
I-576
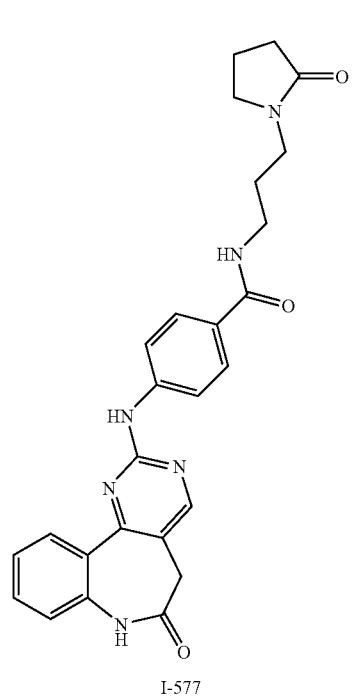
I-577
-continued
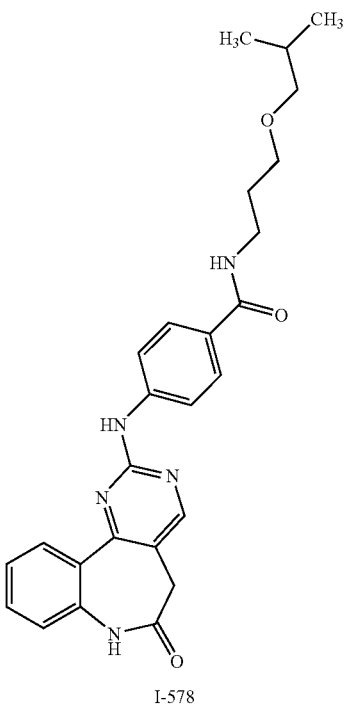
I-578
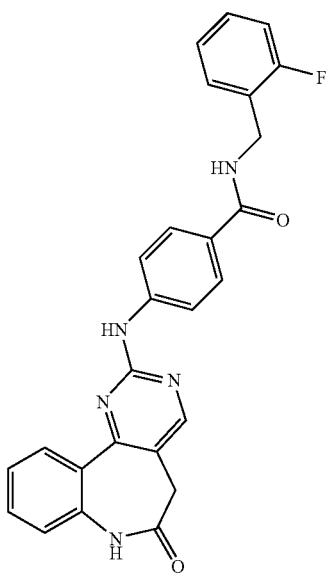
I-579

-continued
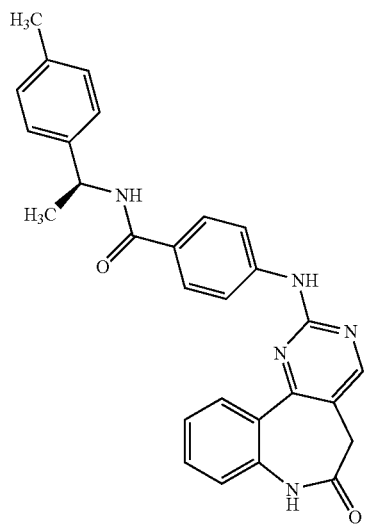
I-580
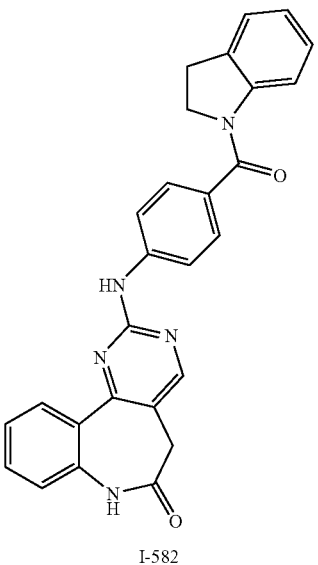
I-582
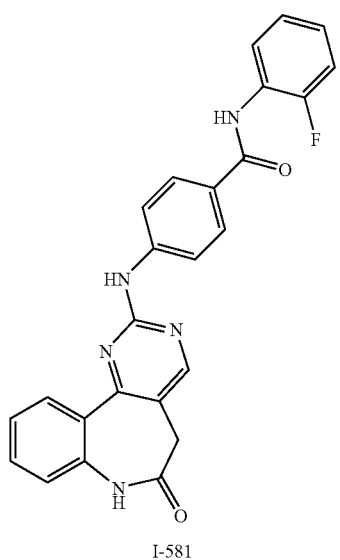
I-581
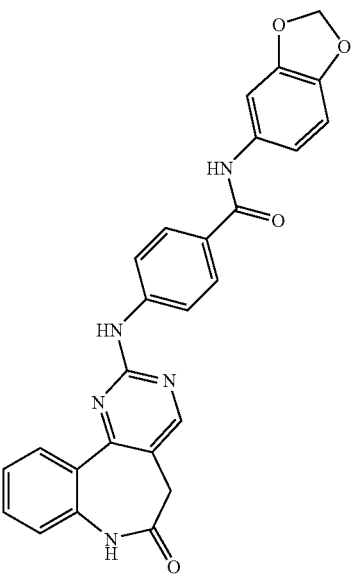
I-583

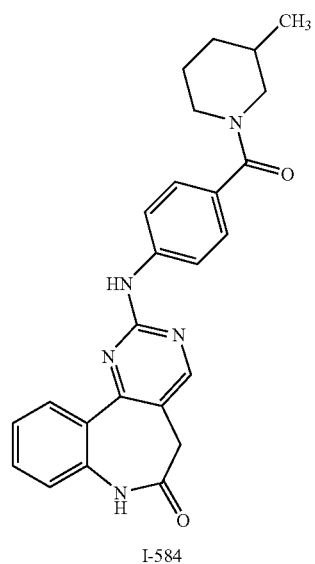
I-584
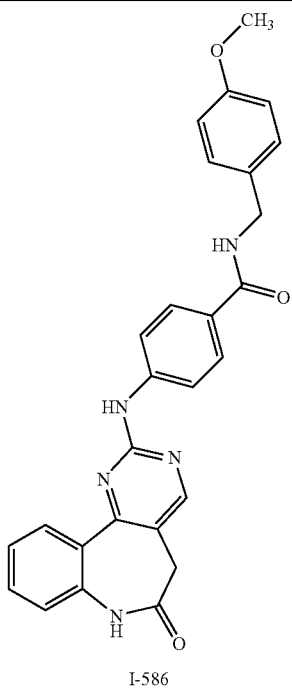
I-586
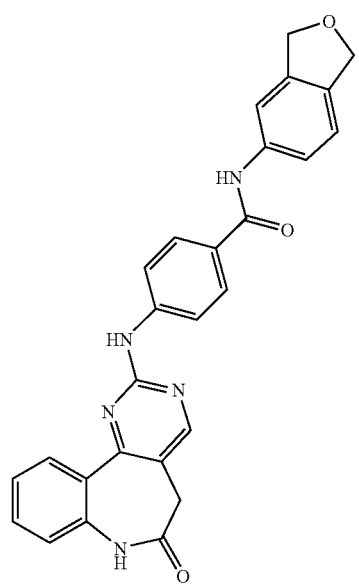
I-585
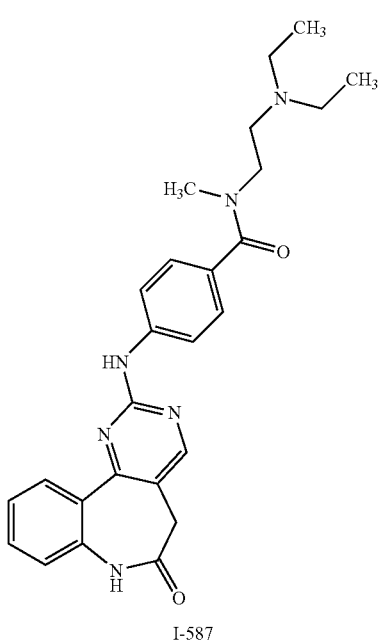
I-587

-continued
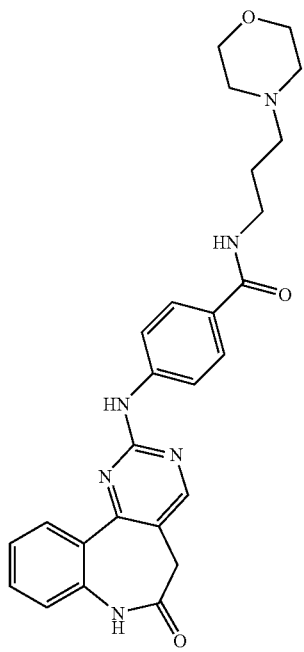
I-588
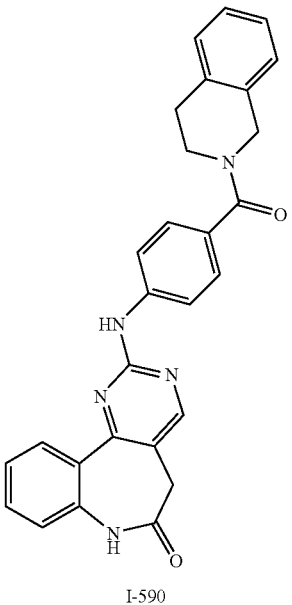
I-590
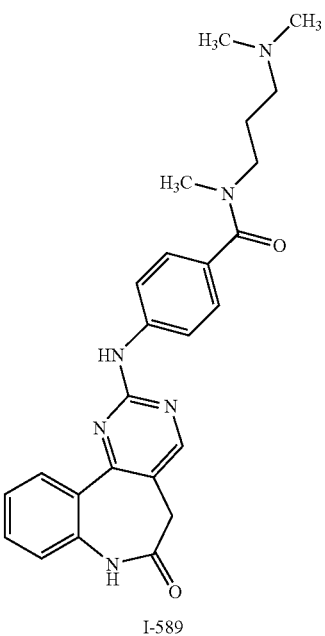
I-589
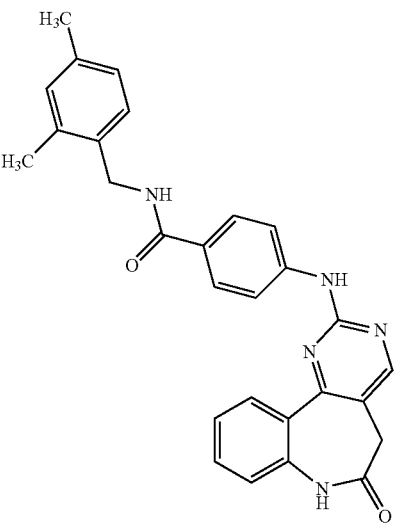
I-591

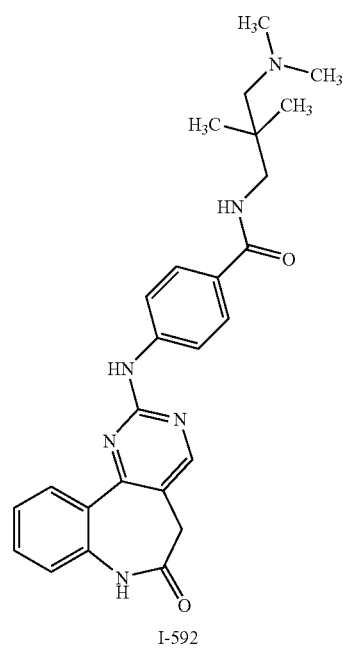
I-592
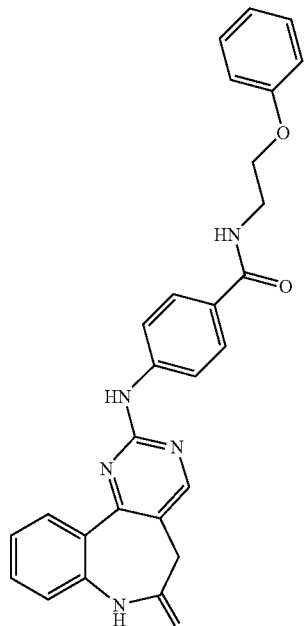
I-594
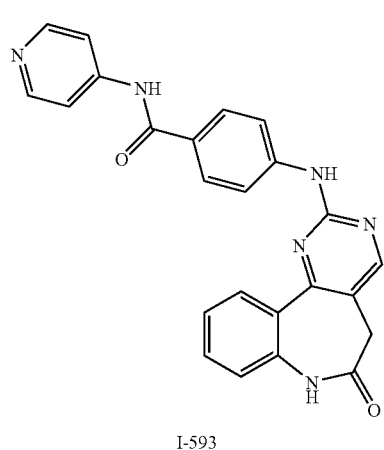
I-593
I-595

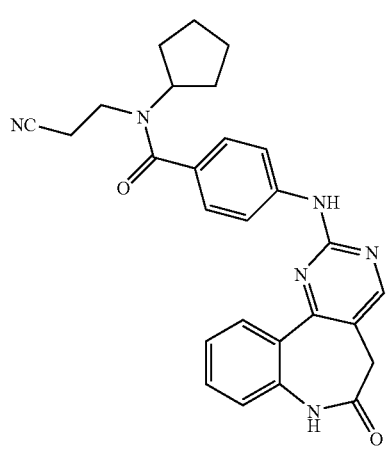
I-596
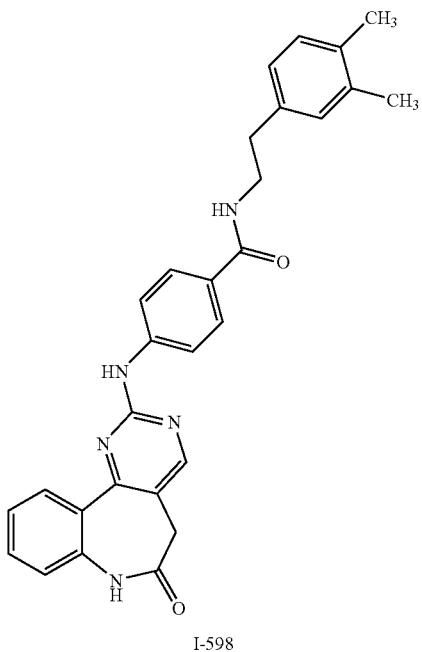
I-598
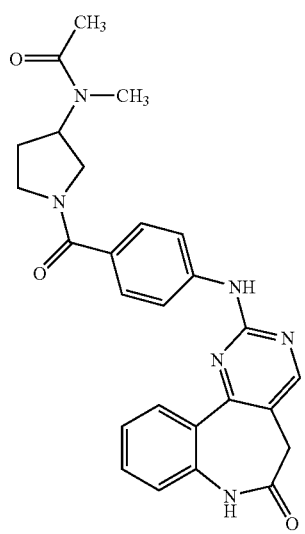
I-597
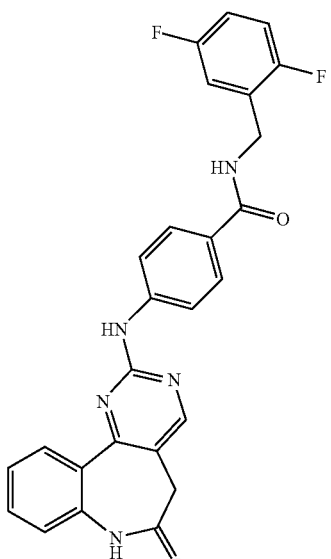
I-599

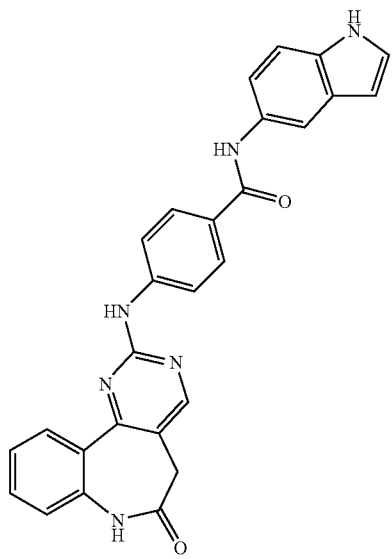
I-600
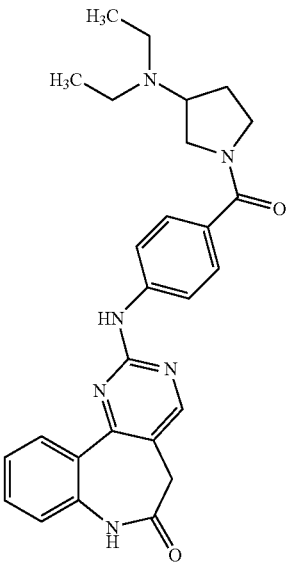
I-602
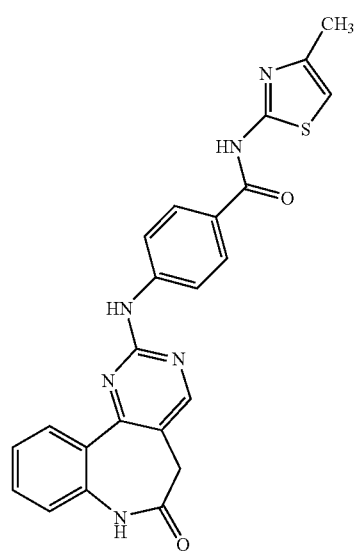
I-601
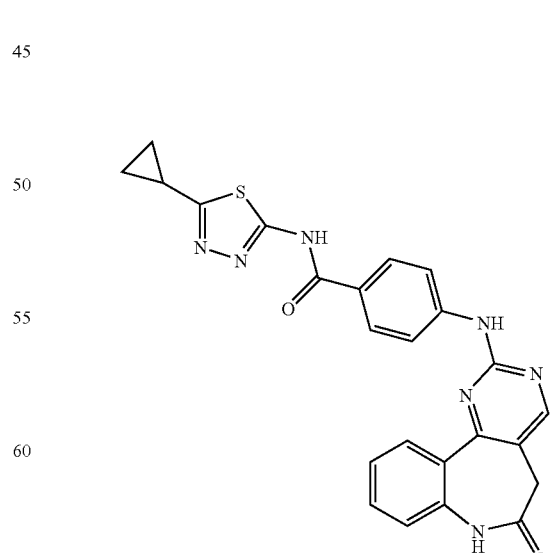
I-603

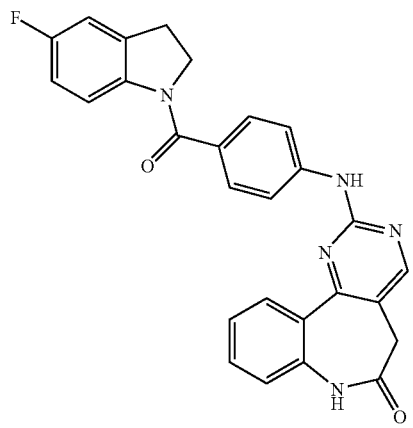
I-604
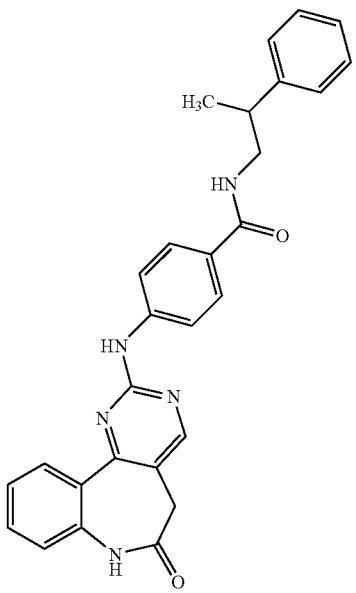
I-606
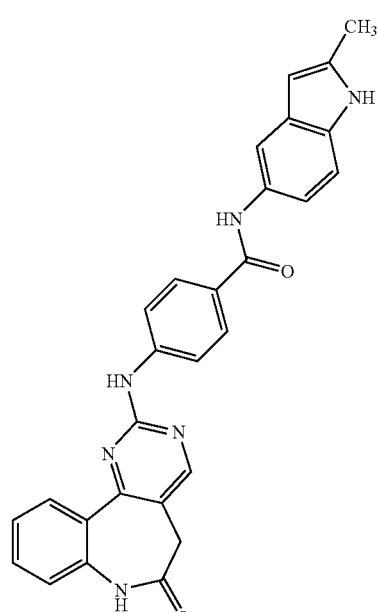
I-605
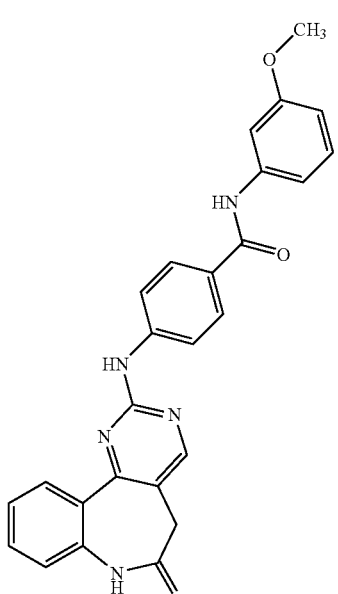
I-607

-continued
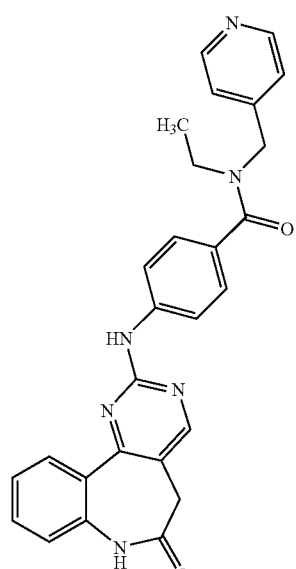
I-608
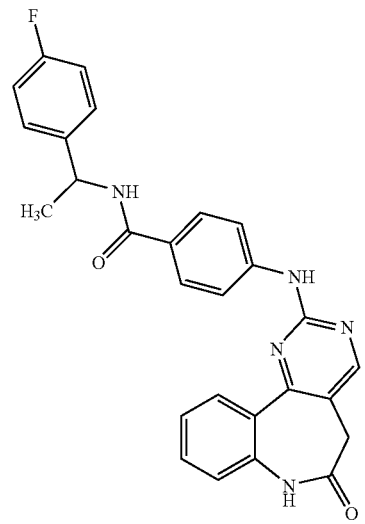
I-610
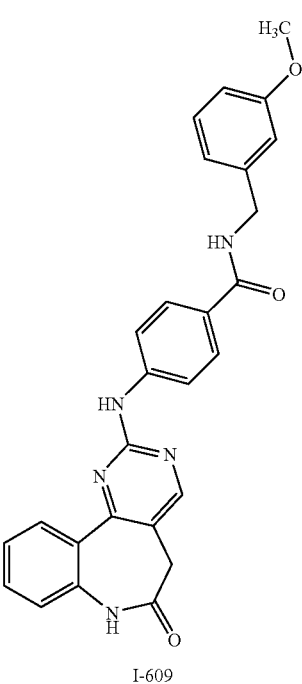
I-609
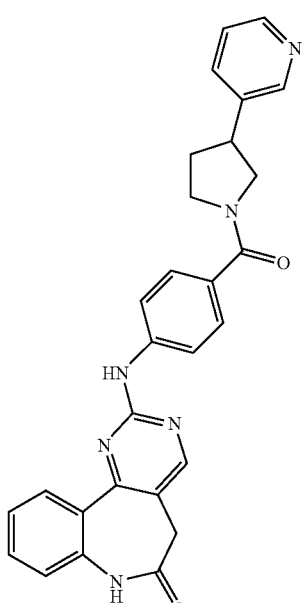
I-611

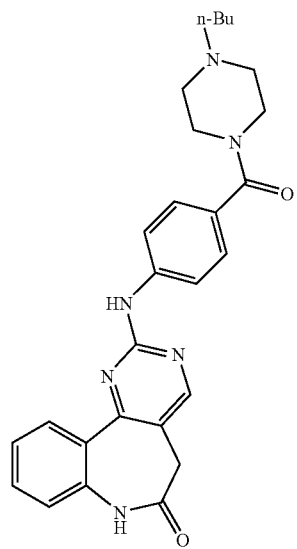
I-612
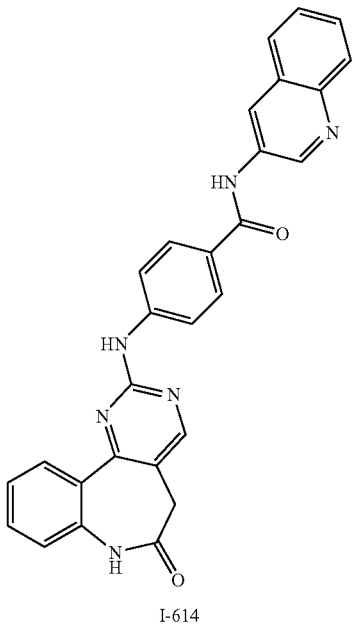
I-614
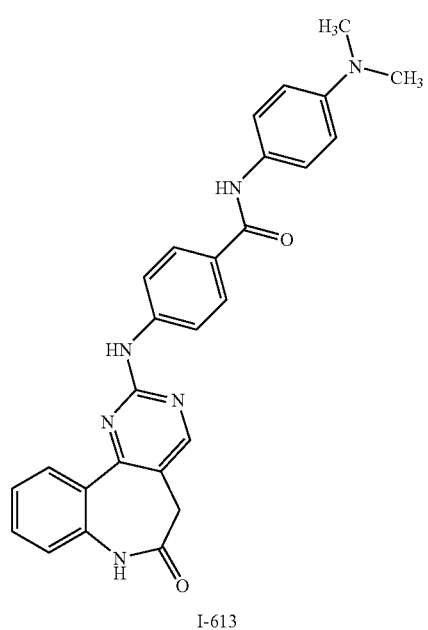
I-613
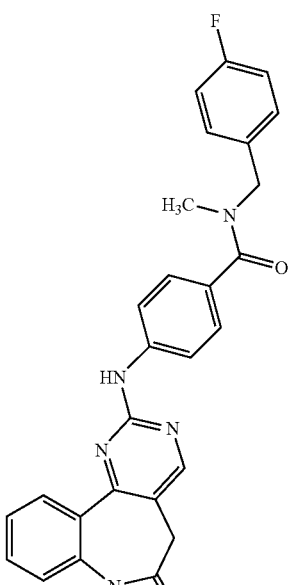
I-615

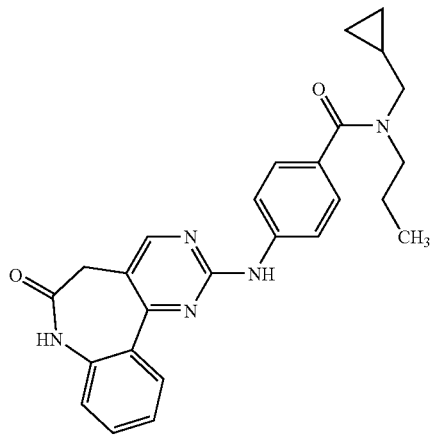
I-616
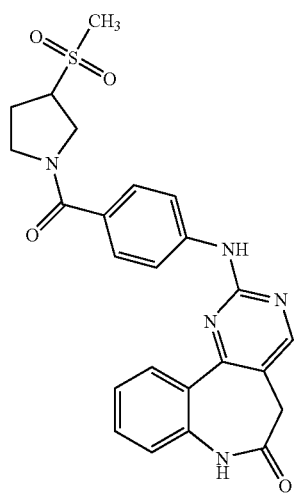
I-617
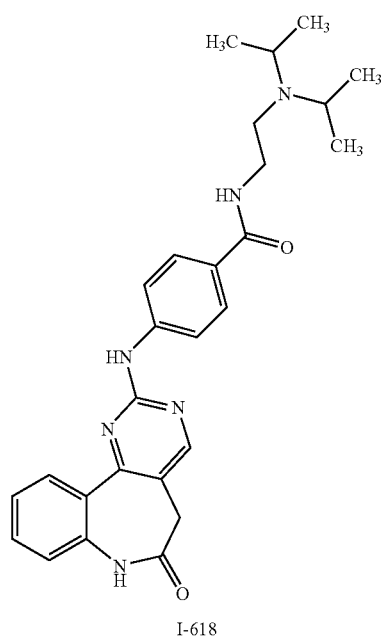
I-618
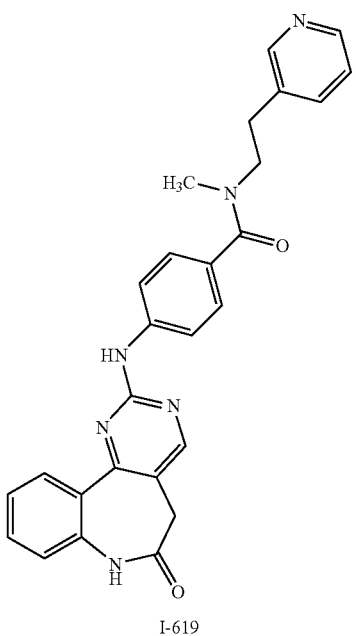
I-619
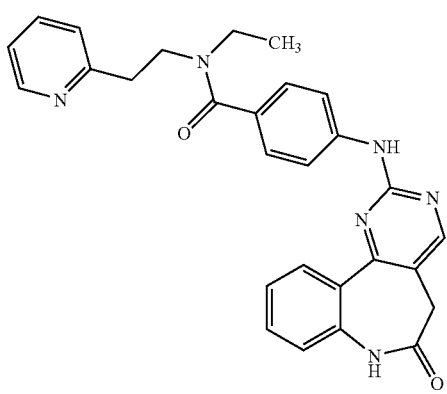
I-620

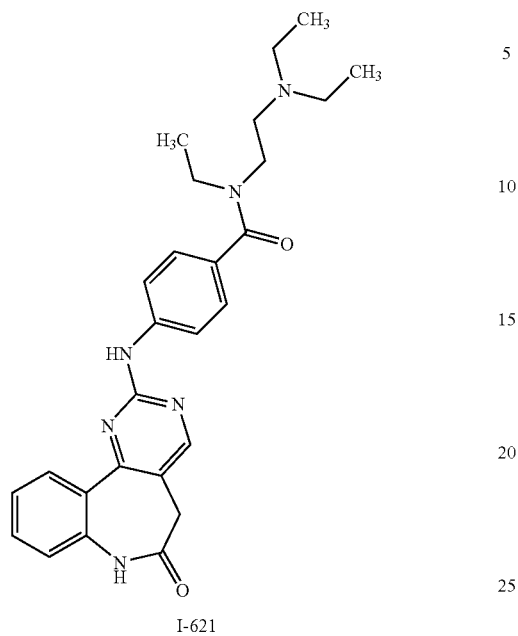
I-621
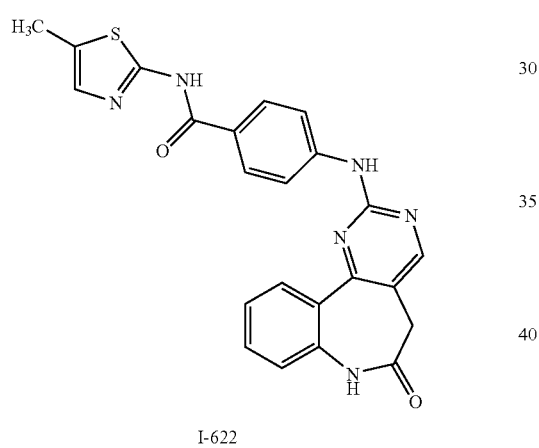
I-622
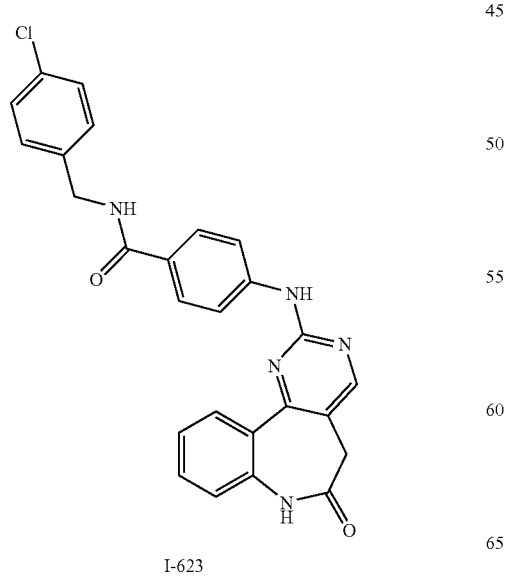
I-623
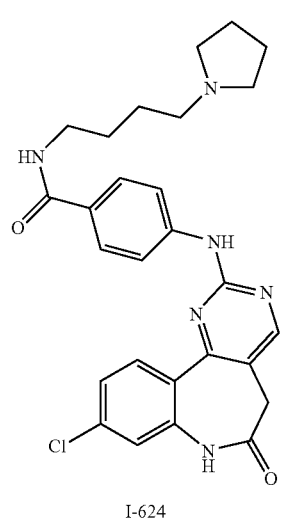
I-624
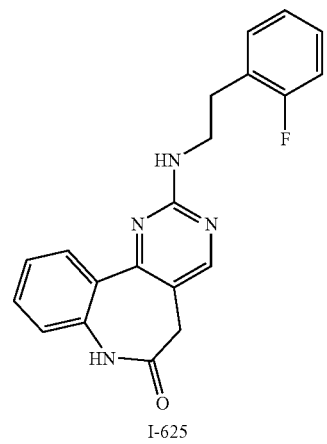
I-625
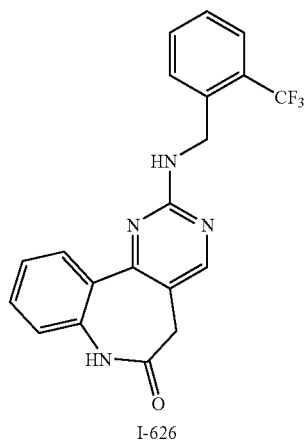
I-626

-continued
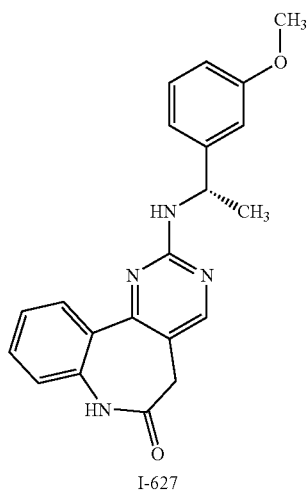
I-627
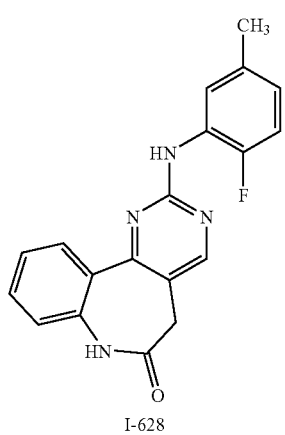
I-628
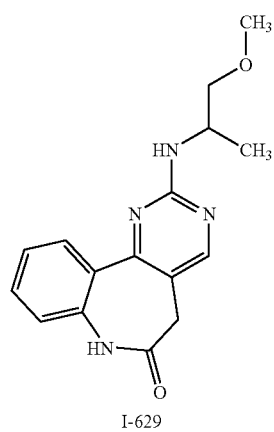
I-629
-continued
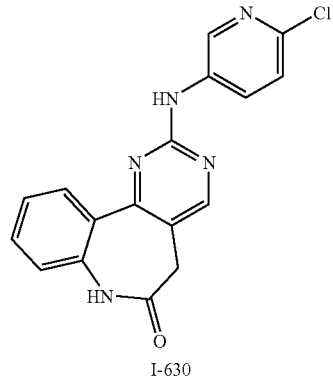
I-630
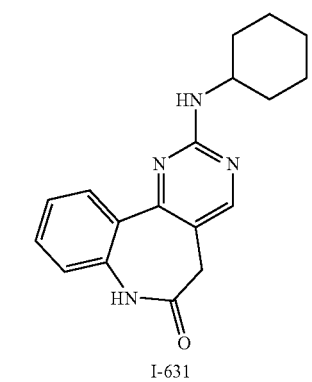
I-631
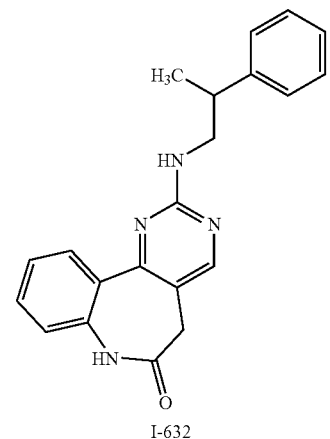
I-632

221
-continued
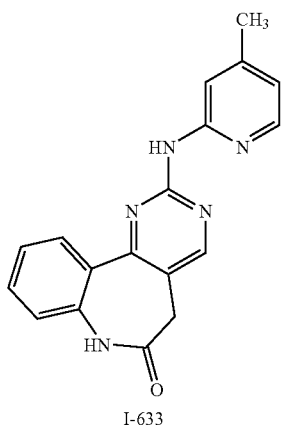
I-633
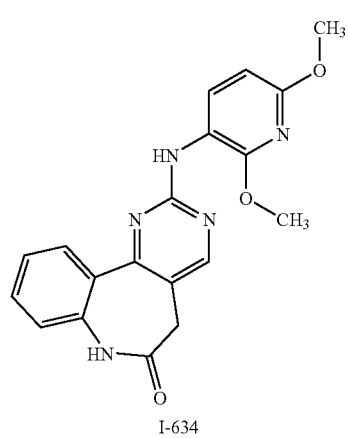
I-634
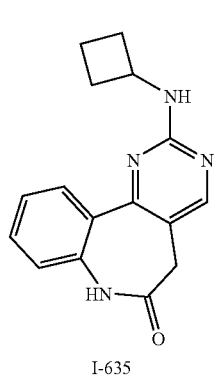
I-635
222
-continued
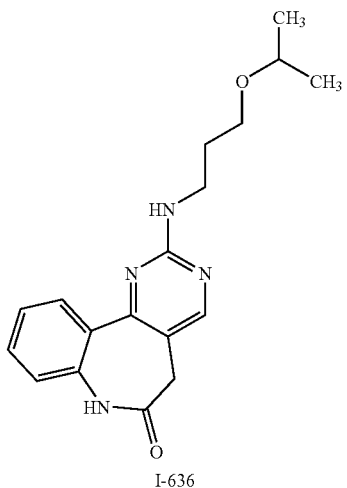
I-636
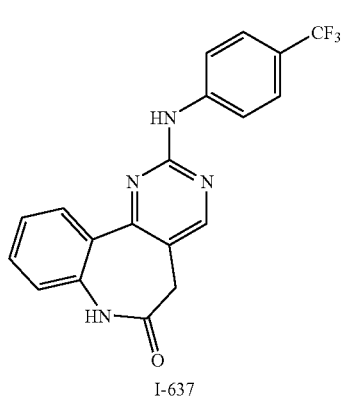
I-637
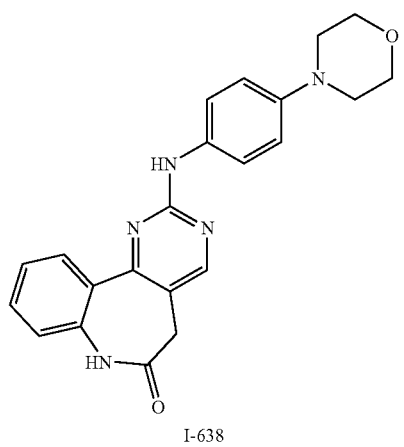
I-638

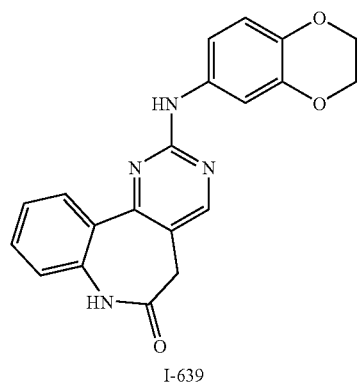
I-639
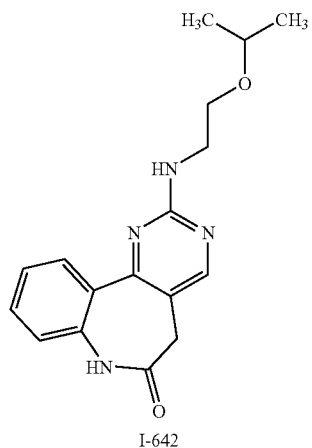
I-642
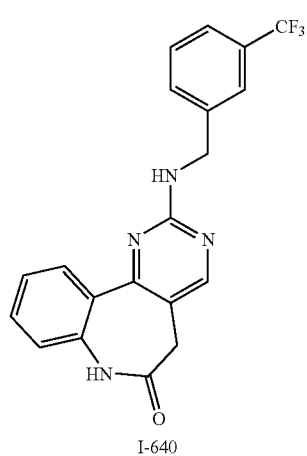
I-640
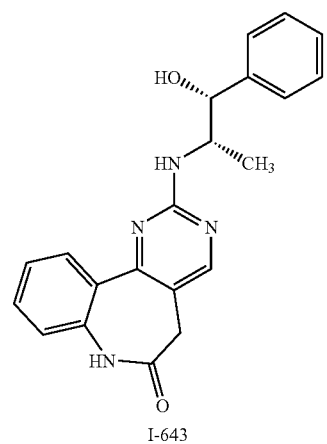
I-643
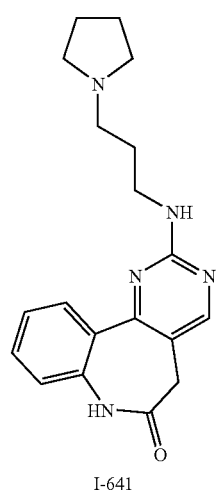
I-641
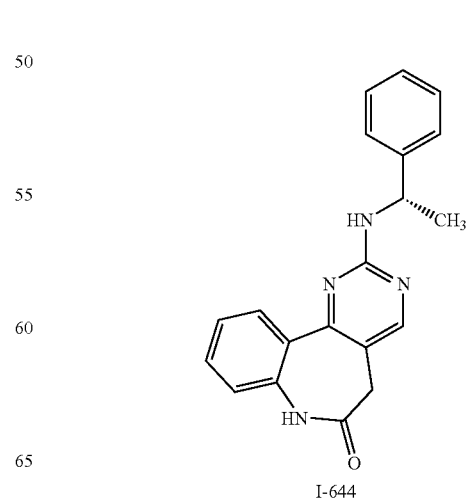
I-644

225
-continued
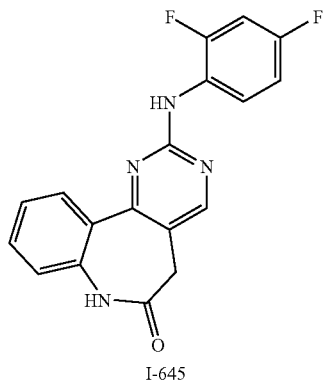
I-645
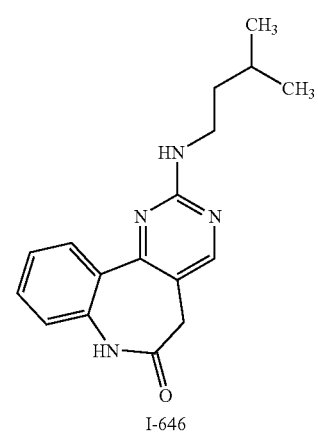
I-646
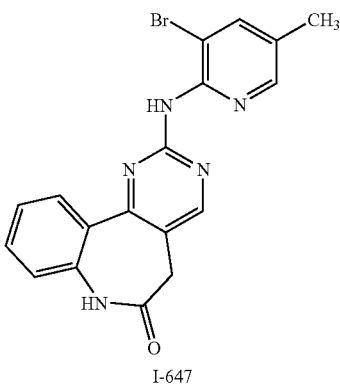
I-647
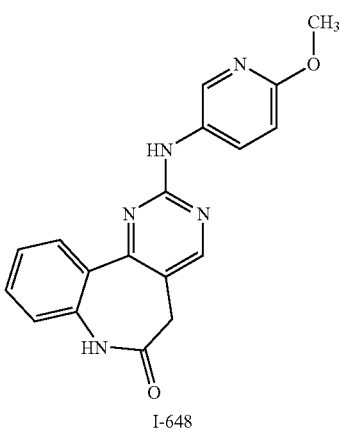
I-648
226
-continued
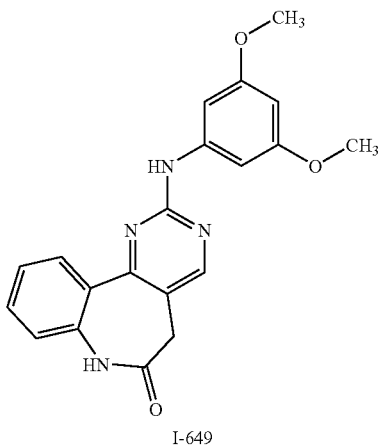
I-649
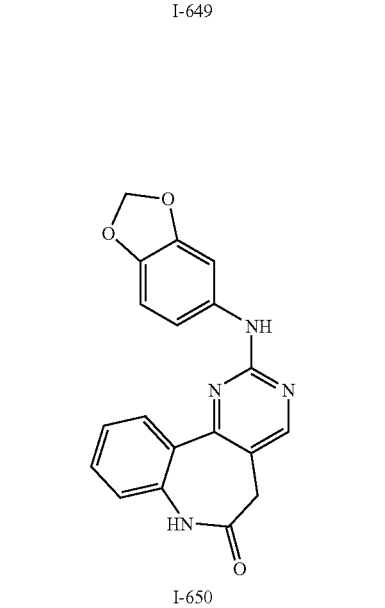
I-650
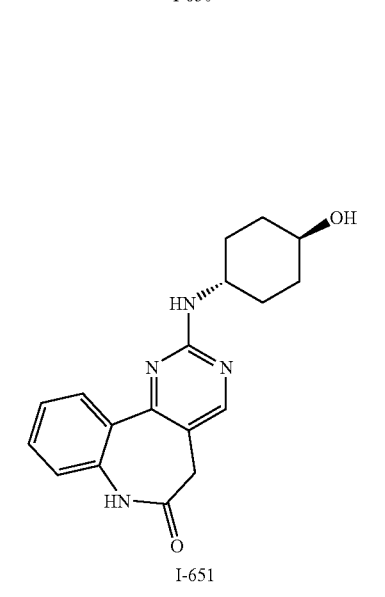
I-651

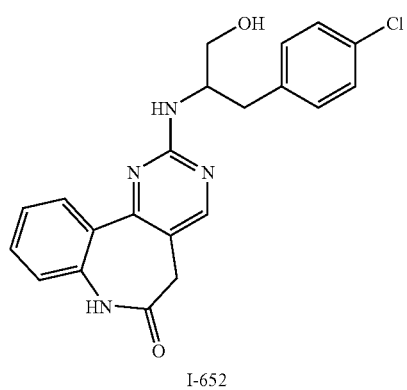
I-652
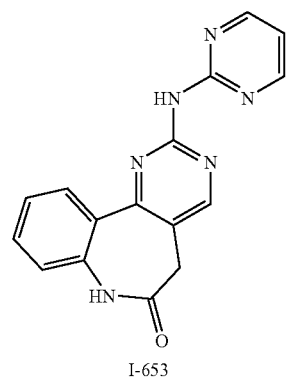
I-653
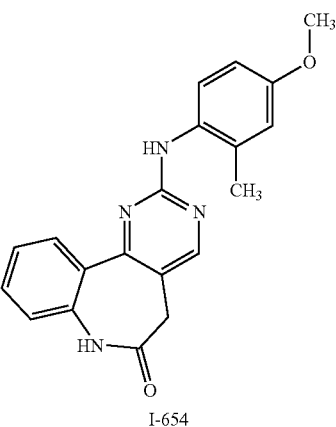
I-654
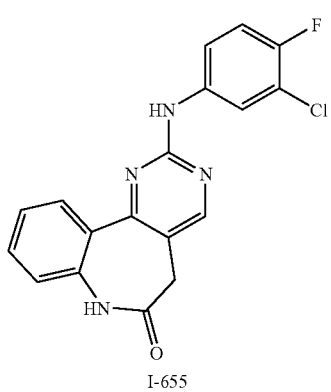
I-655
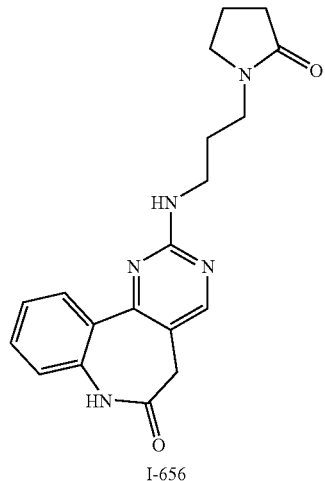
I-656
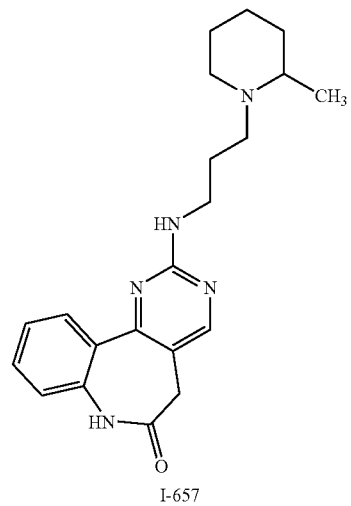
I-657
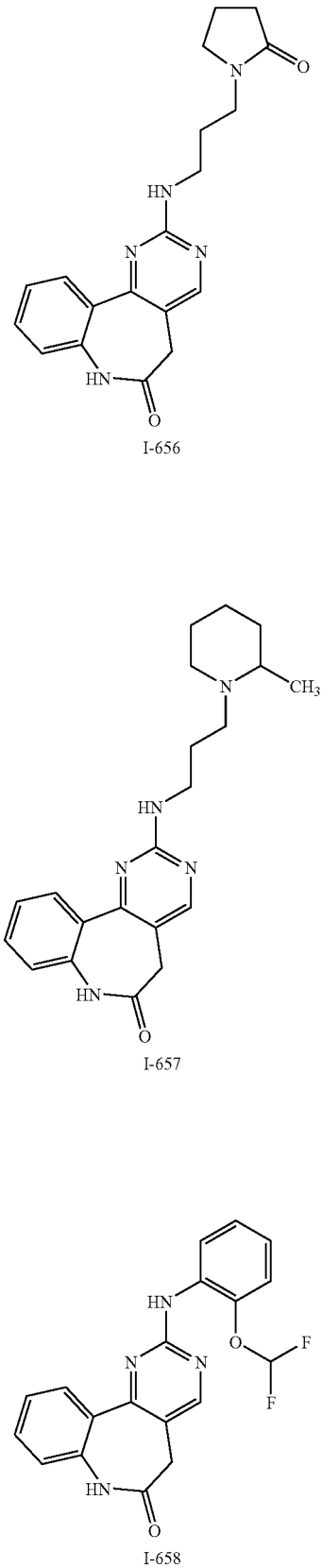
I-658

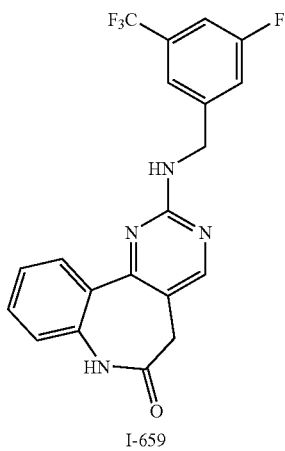
I-659
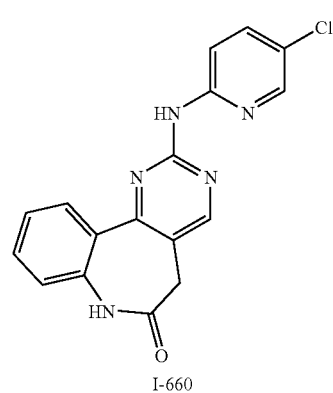
I-660
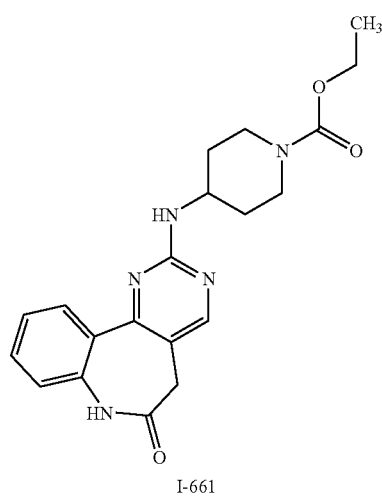
I-661
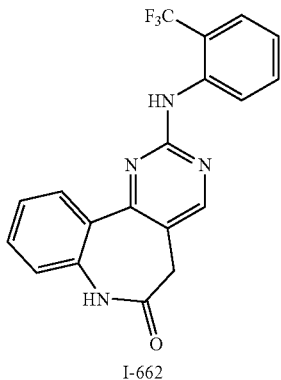
I-662
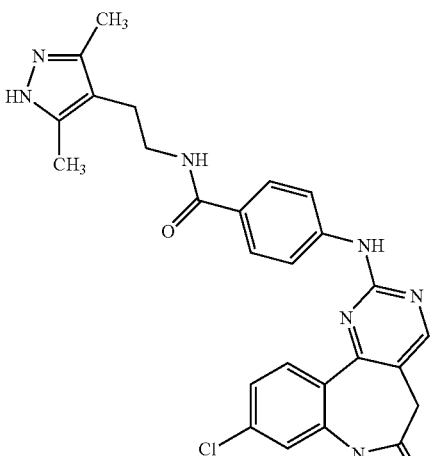
I-663
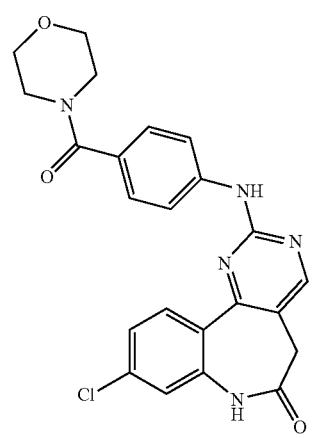
I-664

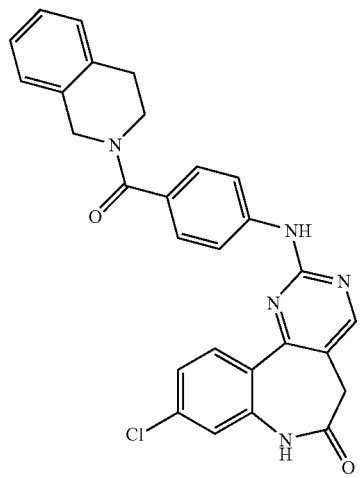
I-665
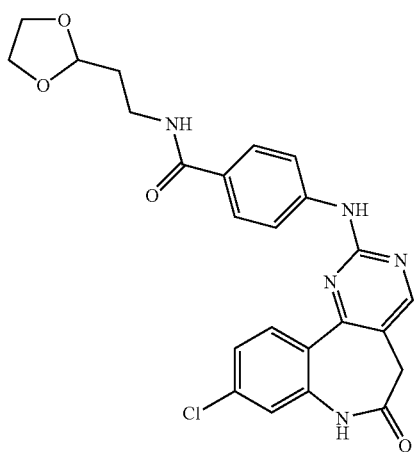
I-666
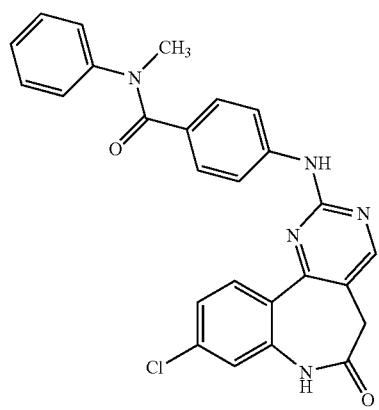
I-667
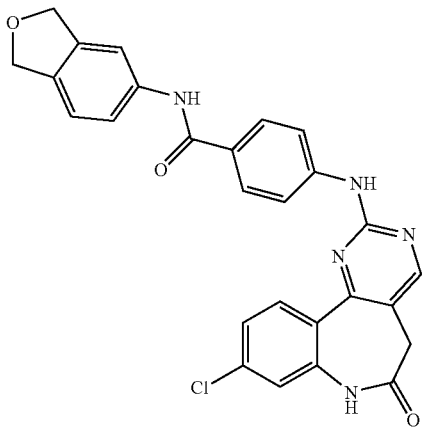
I-668
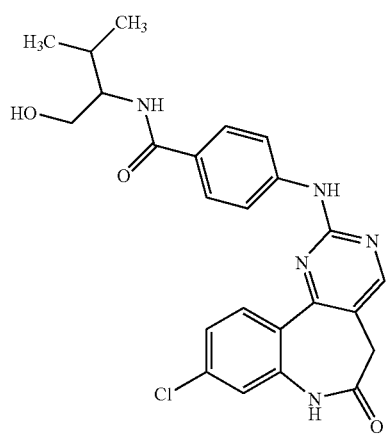
I-669
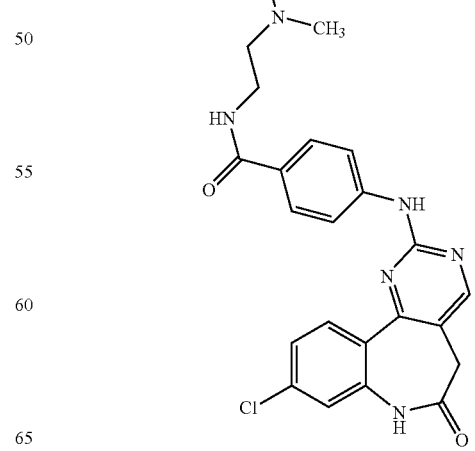
I-670

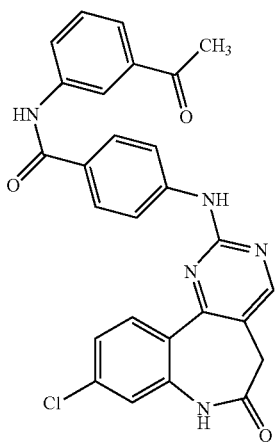
I-671
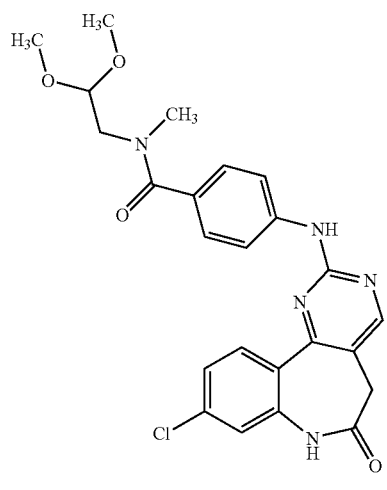
I-672
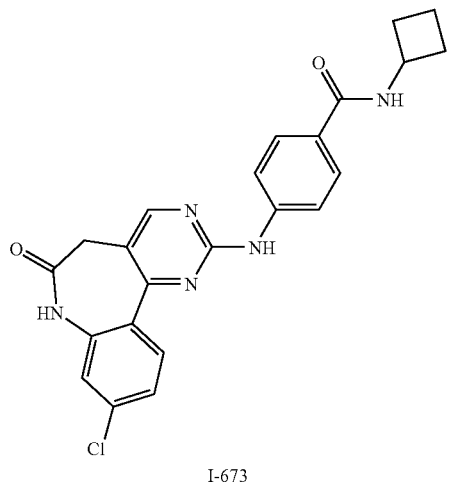
I-673
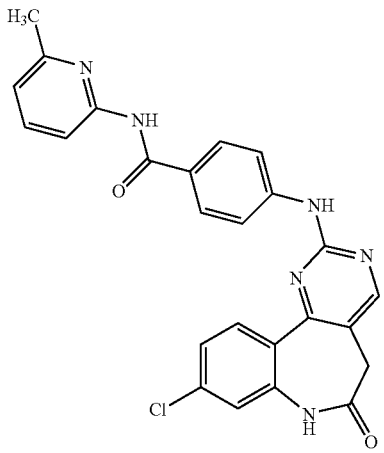
I-674
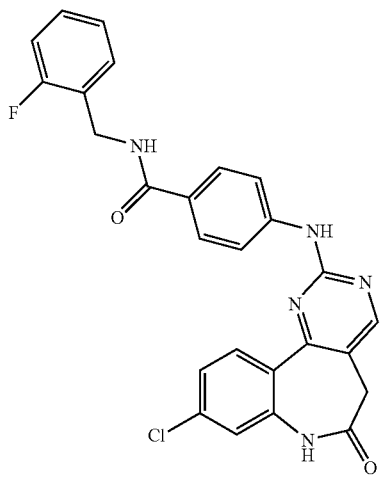
I-675
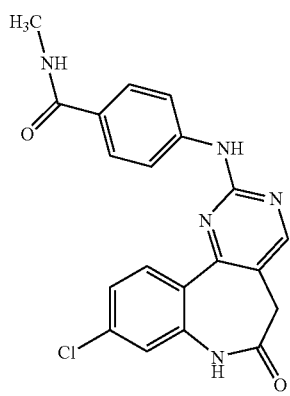
I-676

I-677

I-678

I-679

I-680

I-681

I-682

-continued
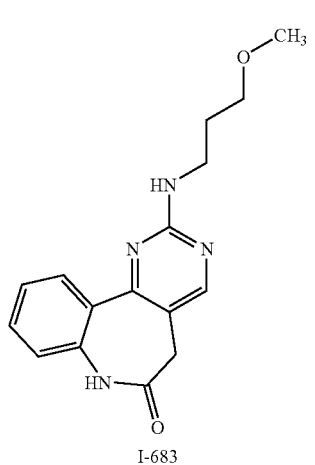
I-683
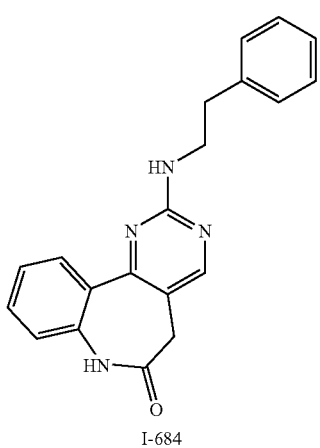
I-684
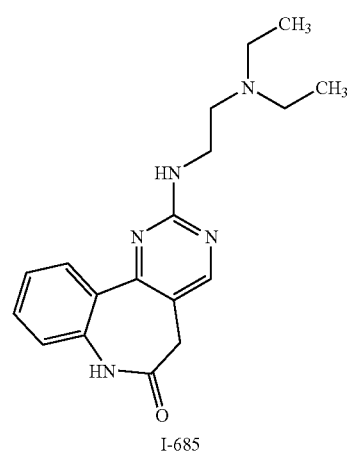
I-685
-continued
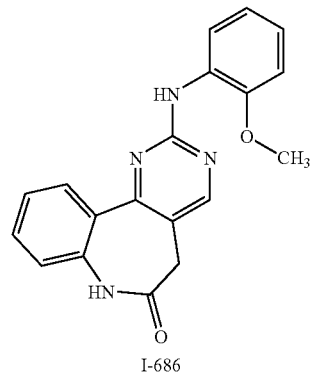
I-686
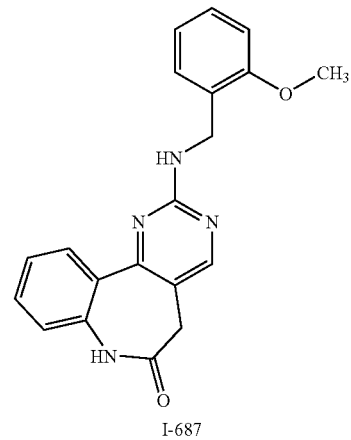
I-687
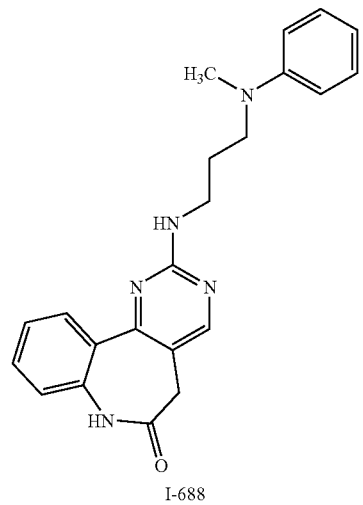
I-688

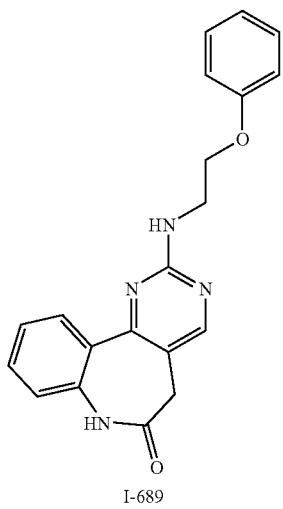
I-689
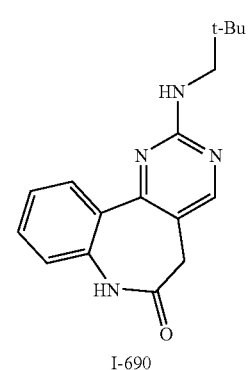
I-690
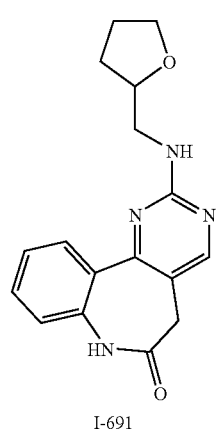
I-691
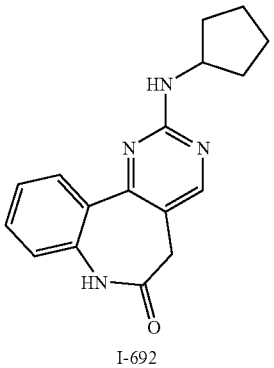
I-692
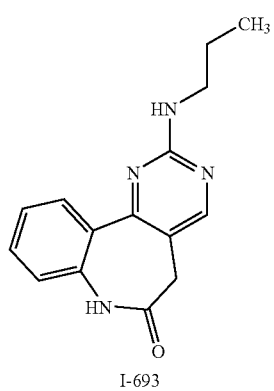
I-693
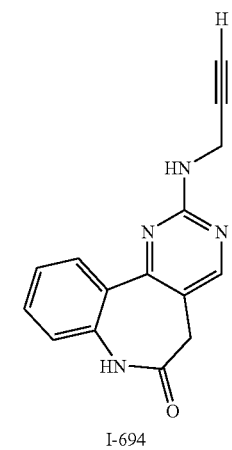
I-694

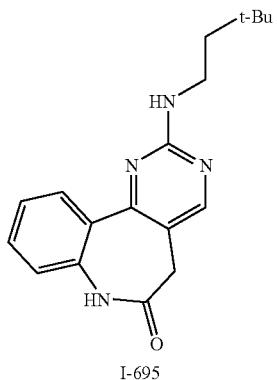
I-695
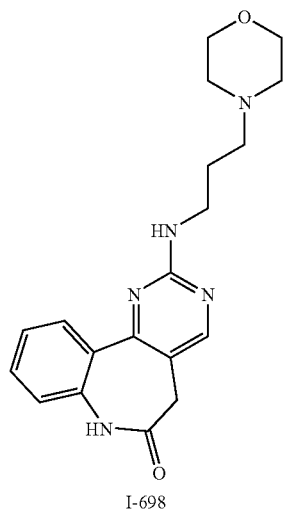
I-698
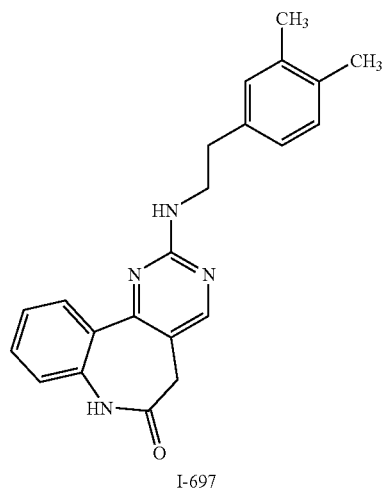
I-696
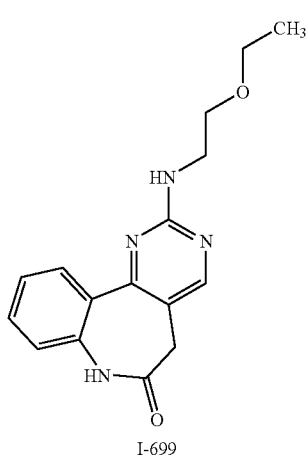
I-699
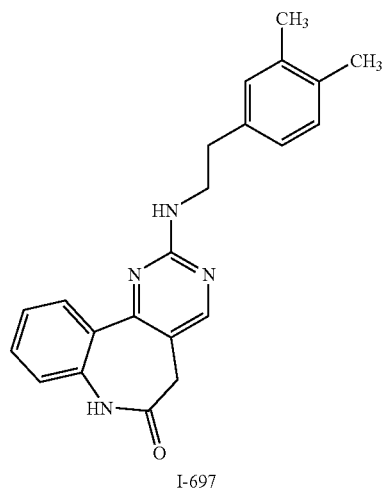
I-697
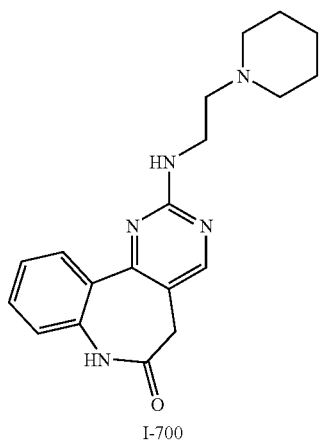
I-700

-continued
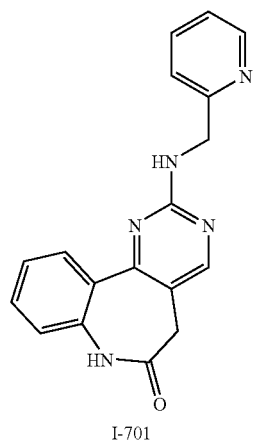
I-701
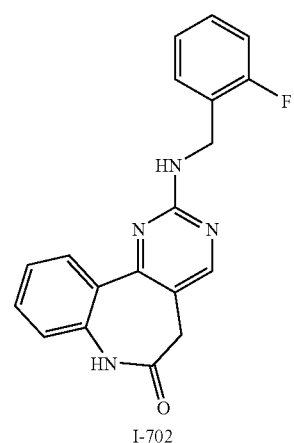
I-702
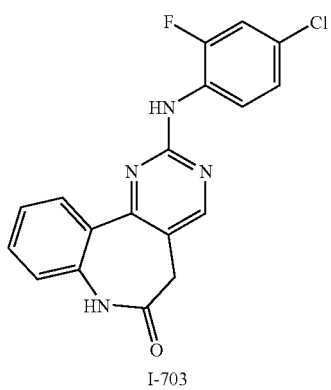
I-703
-continued
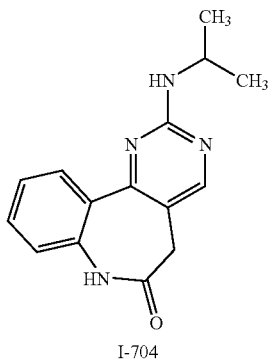
I-704
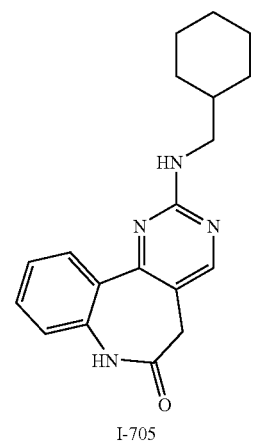
I-705
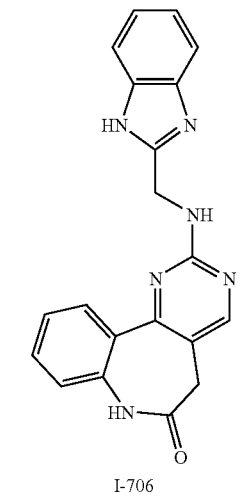
I-706

-continued
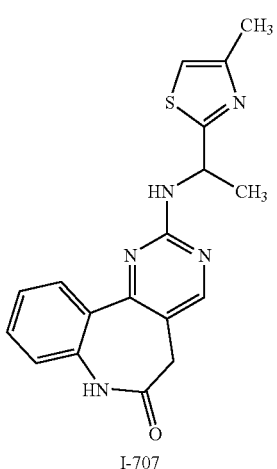
I-707
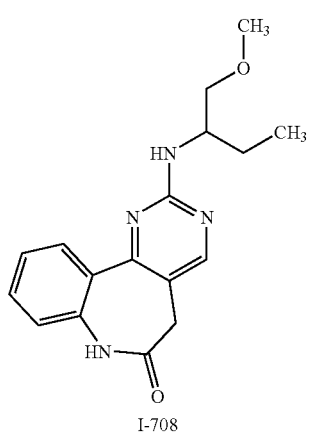
I-708
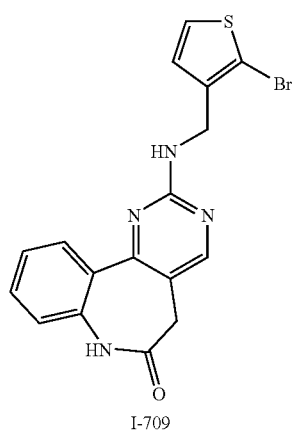
I-709
-continued
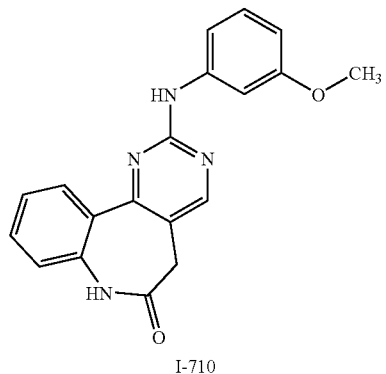
I-710
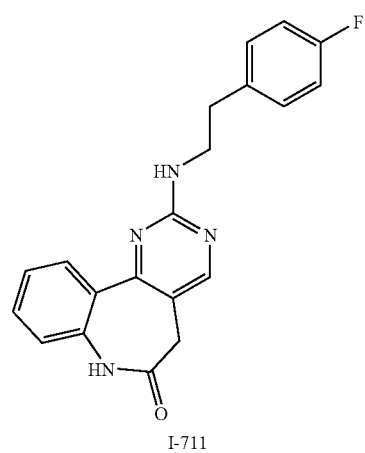
I-711
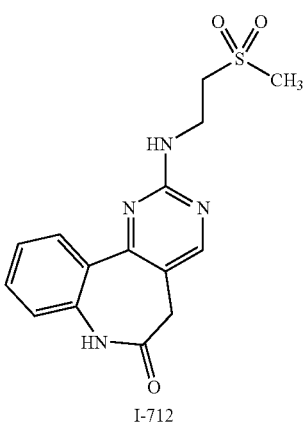
I-712

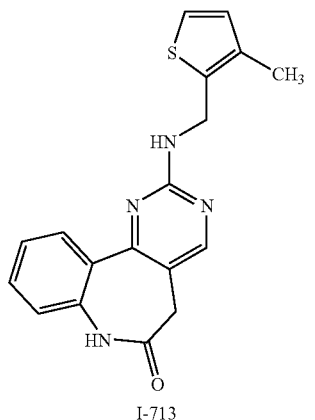
I-713
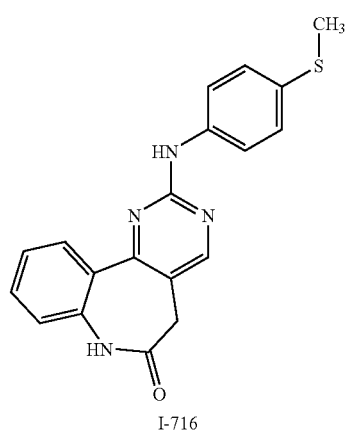
I-716
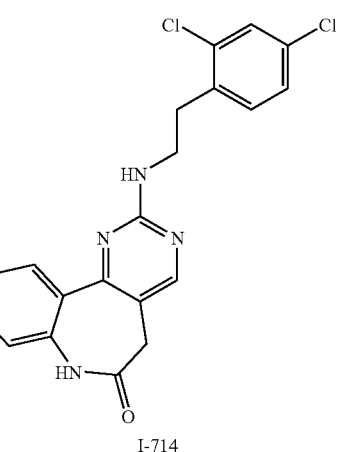
I-714
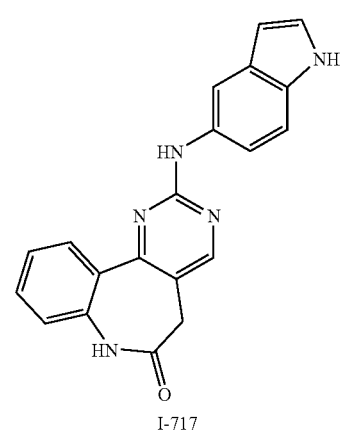
I-717
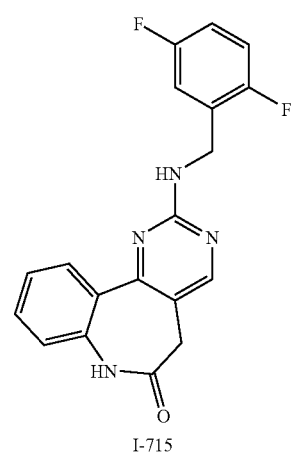
I-715
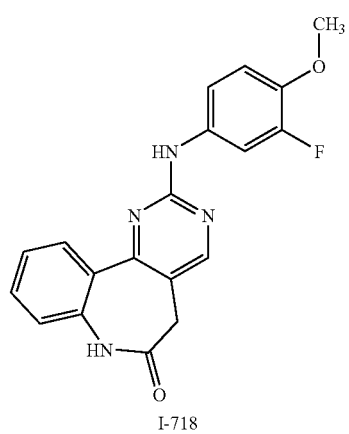
I-718

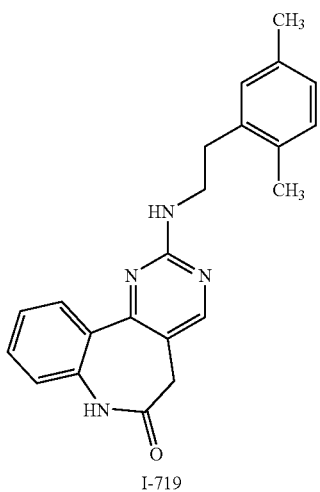
I-719
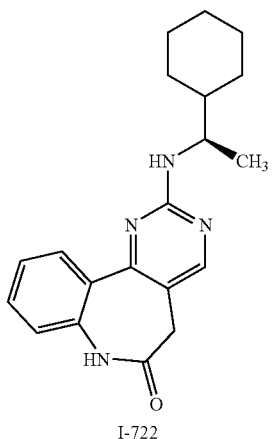
I-722
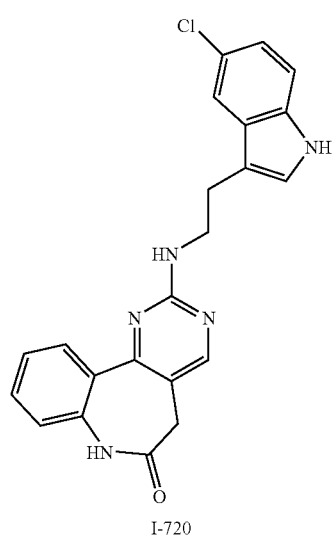
I-720
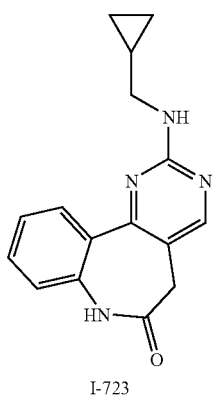
I-723
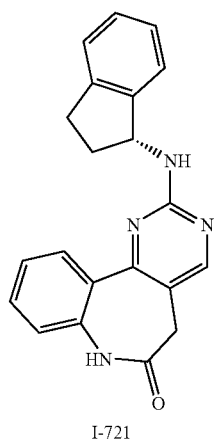
I-721
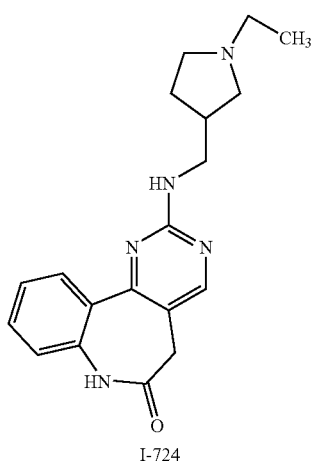
I-724

251
-continued
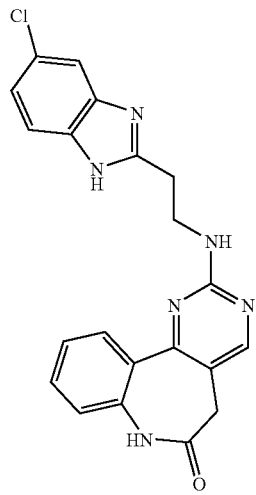
I-725
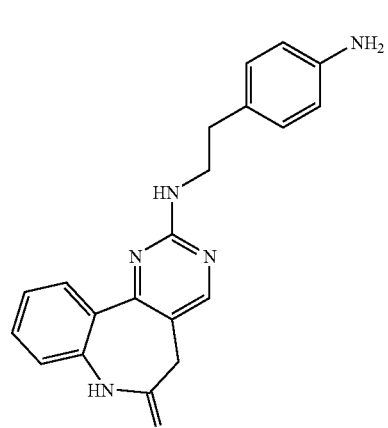
I-726
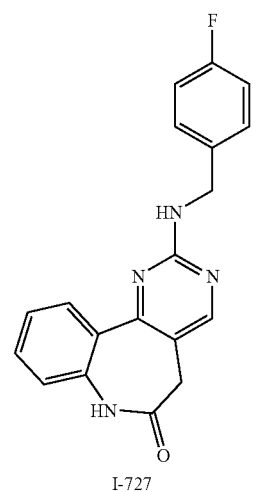
I-727
252
-continued
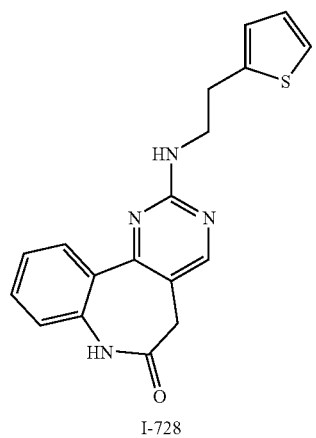
I-728
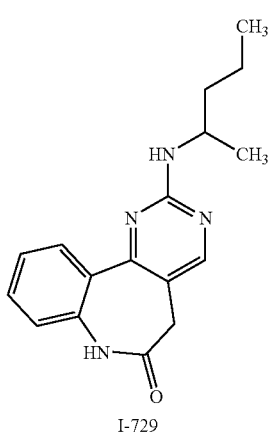
I-729
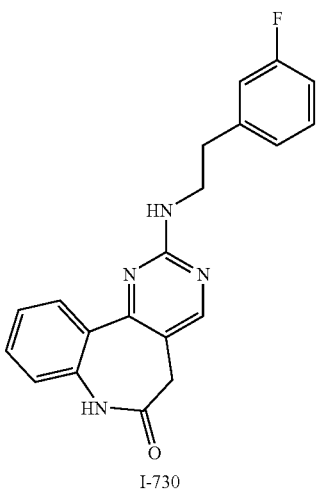
I-730

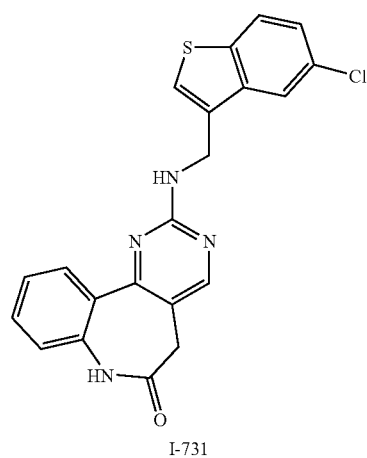
I-731
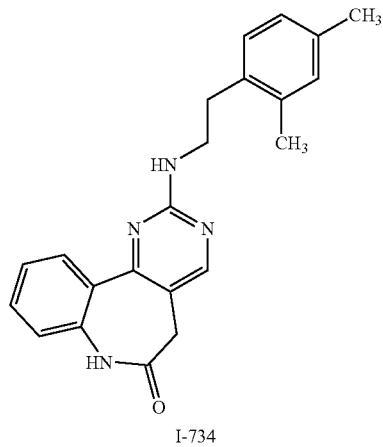
I-734
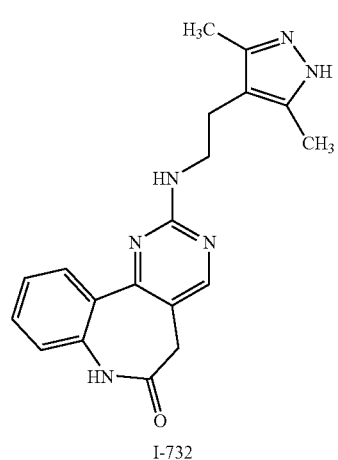
I-732
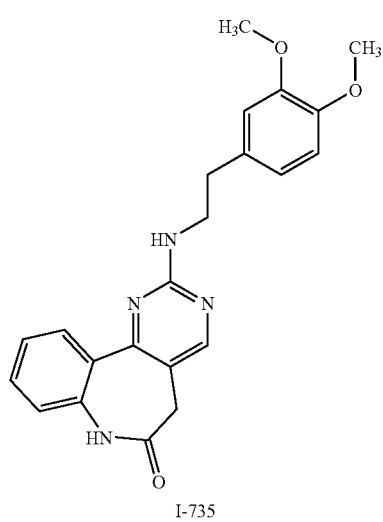
I-735
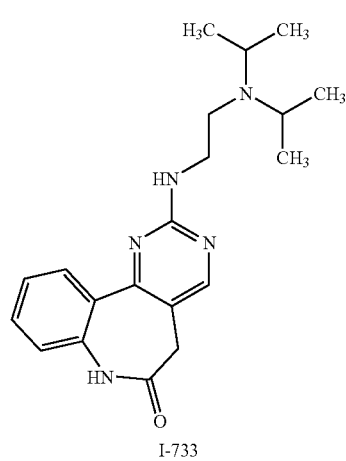
I-733
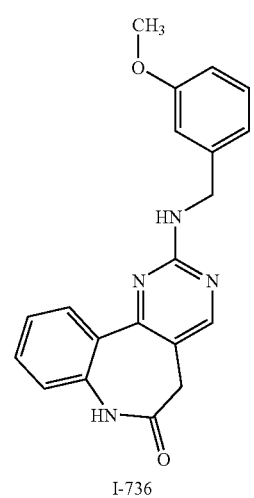
I-736

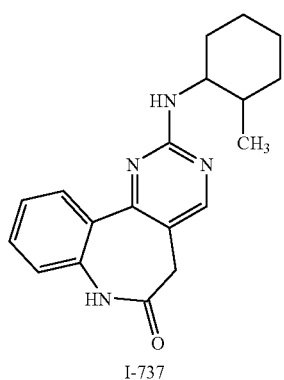
I-737
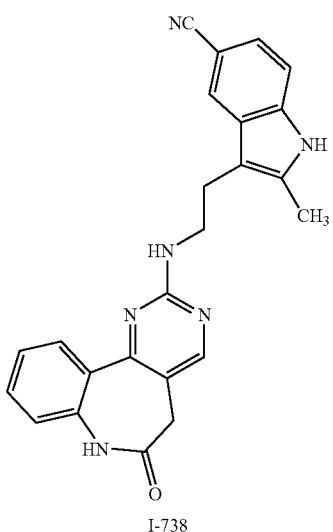
I-738
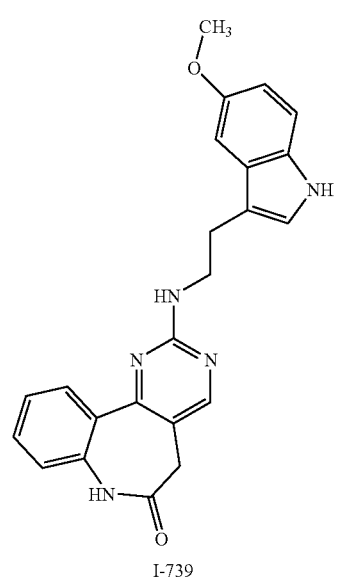
I-739
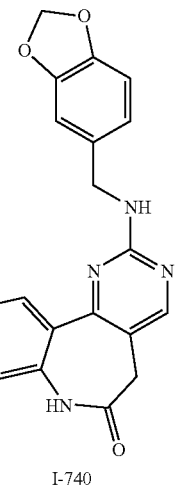
I-740
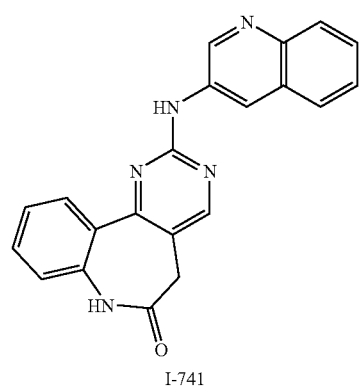
I-741
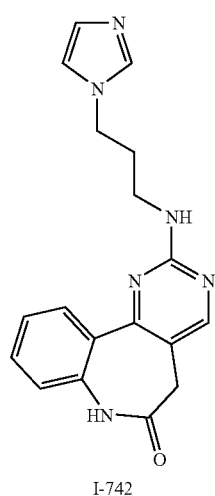
I-742

-continued
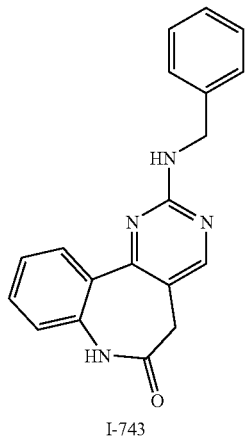
I-743
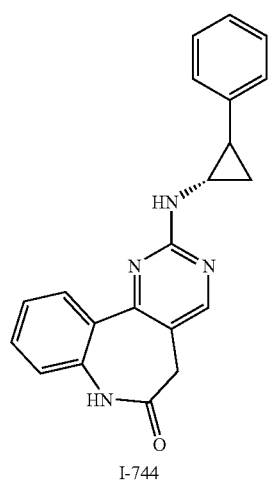
I-744
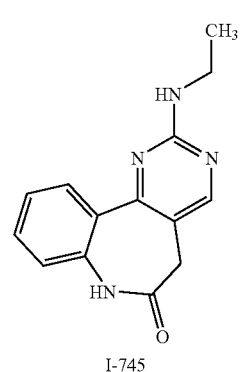
I-745
-continued
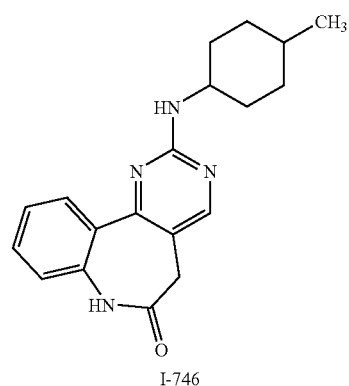
I-746
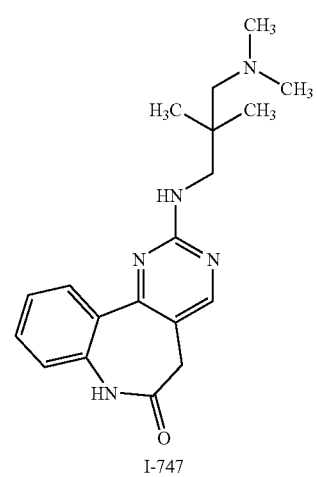
I-747
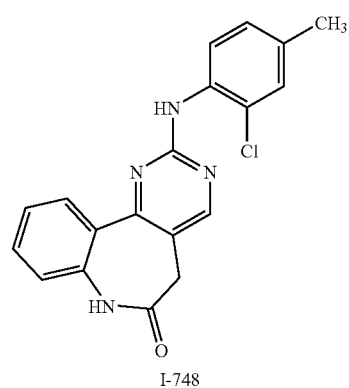
I-748

-continued
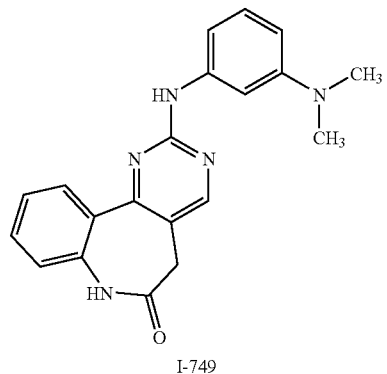
I-749
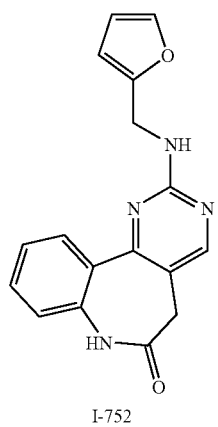
I-752
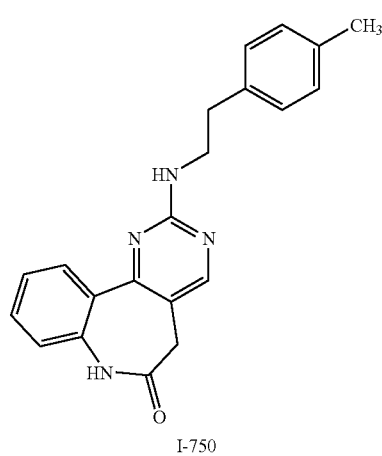
I-750
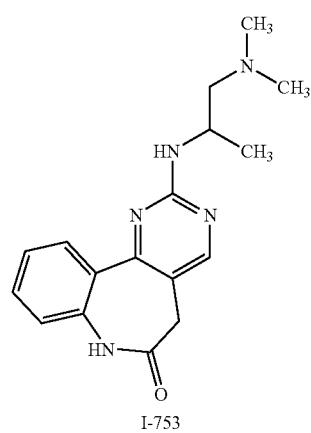
I-753
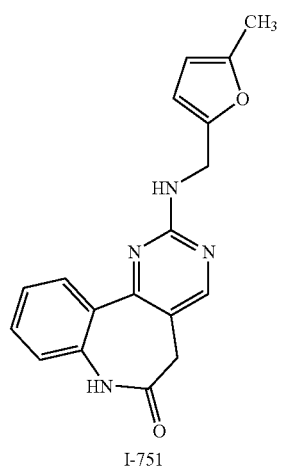
I-751
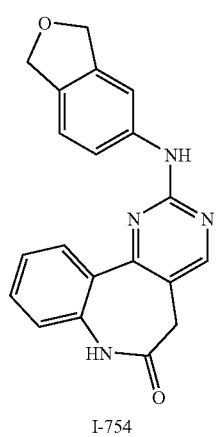
I-754

-continued
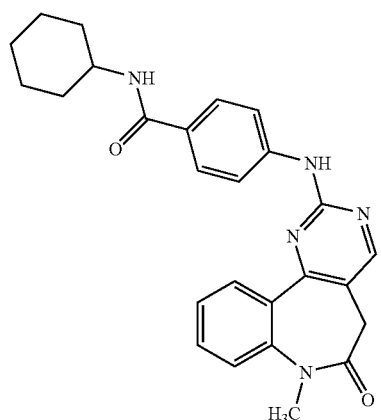
I-755
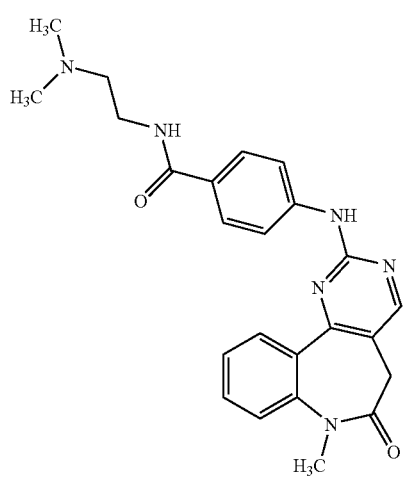
I-756
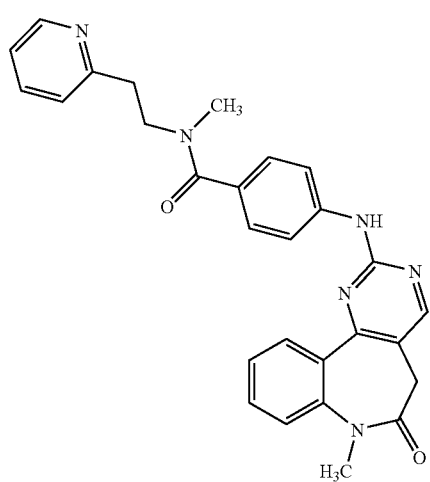
I-757
-continued
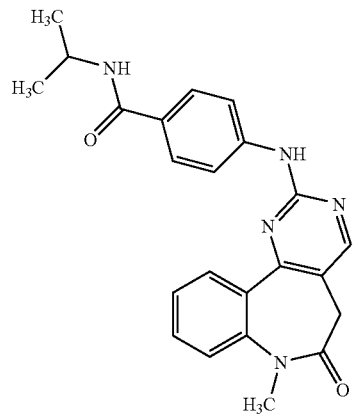
I-758
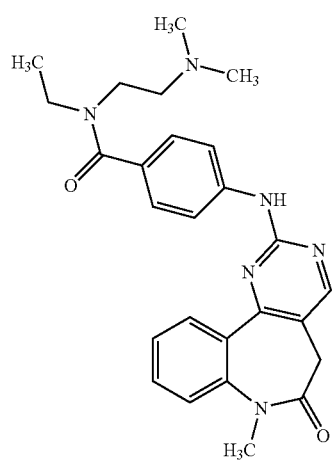
I-759
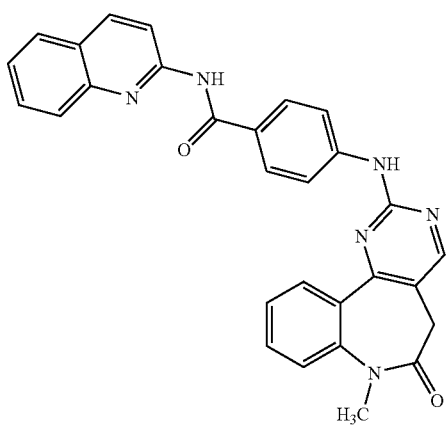
I-760

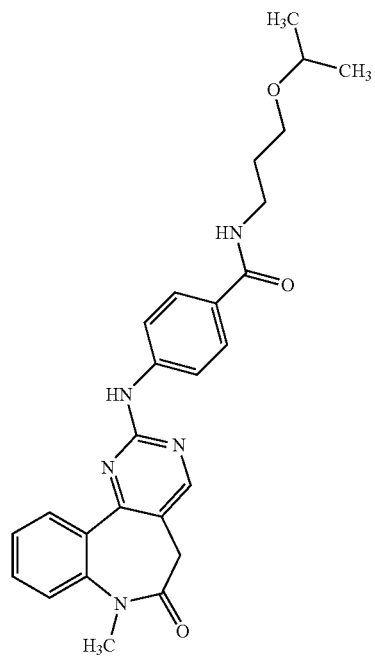
I-761
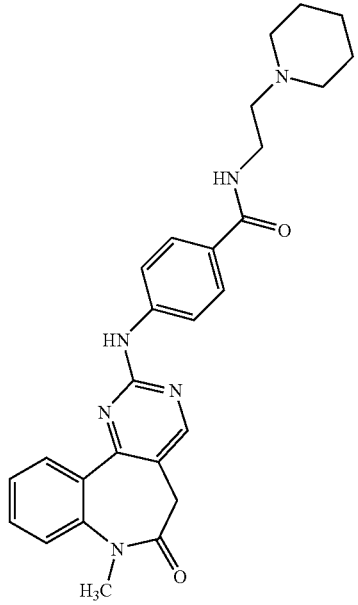
I-763
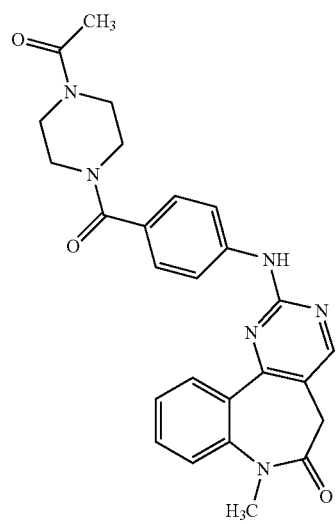
I-762
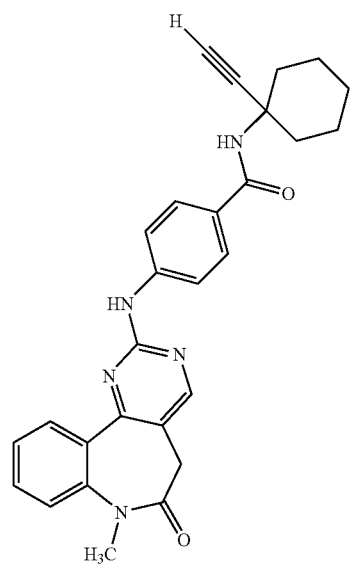
I-764

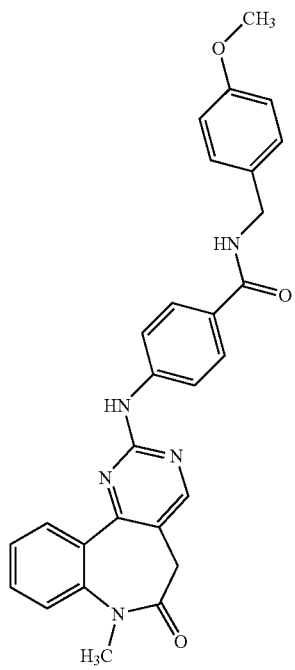
I-765
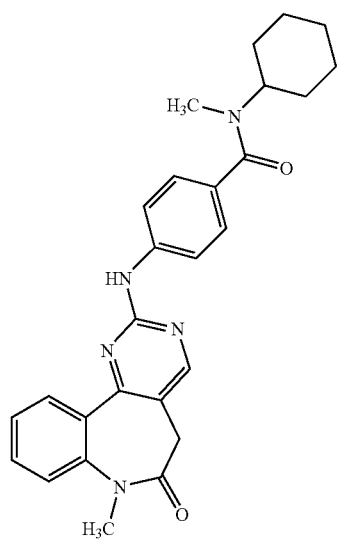
I-767
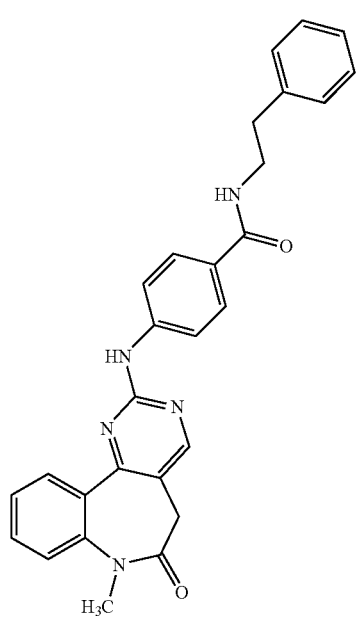
I-766
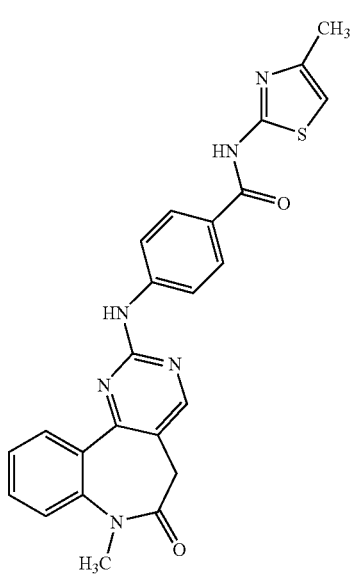
I-768

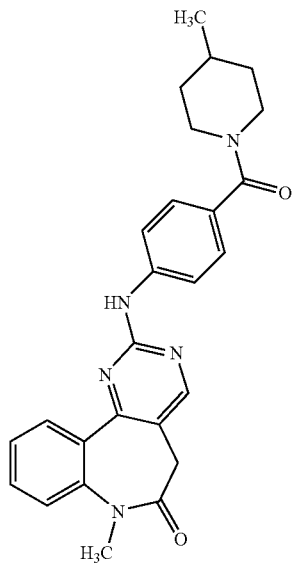
I-769
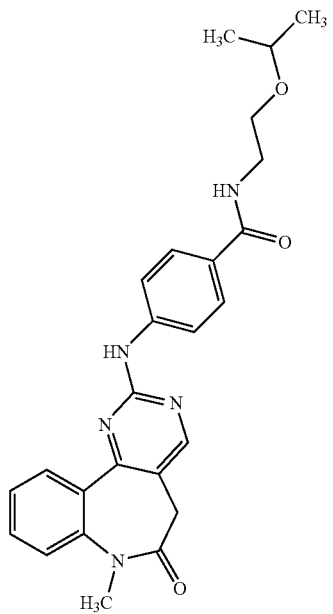
I-771
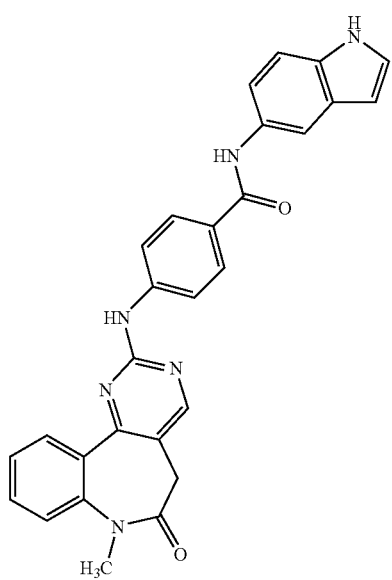
I-770
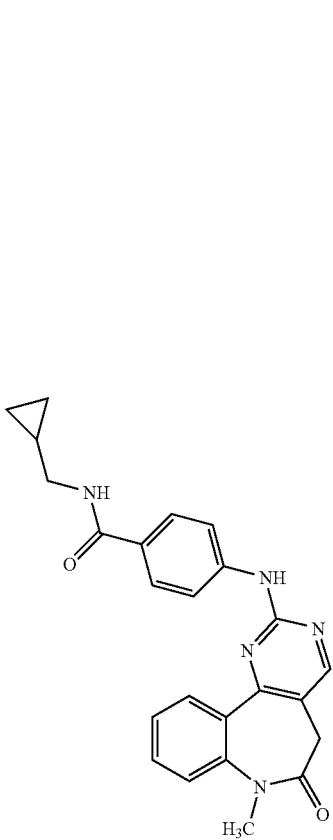
I-772

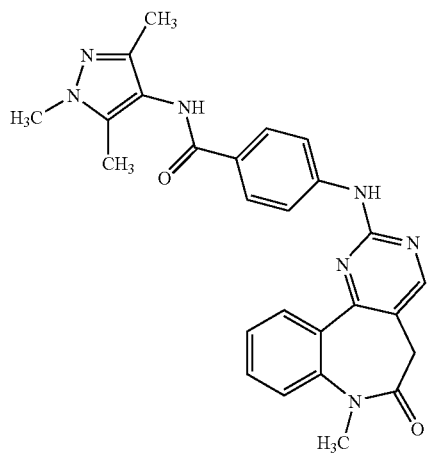
I-773
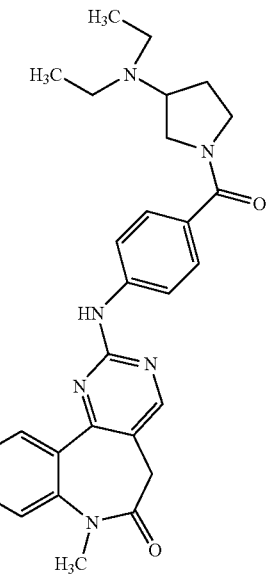
I-775
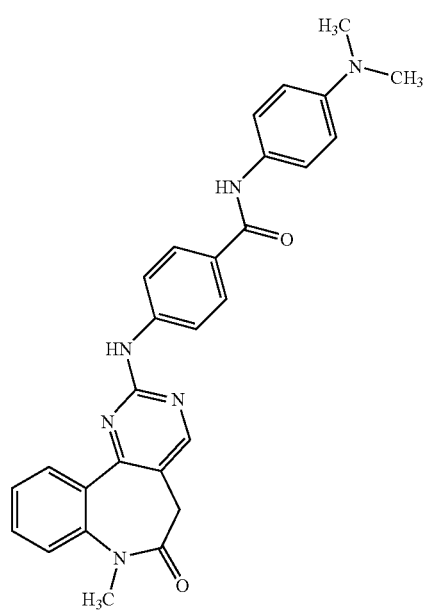
I-774
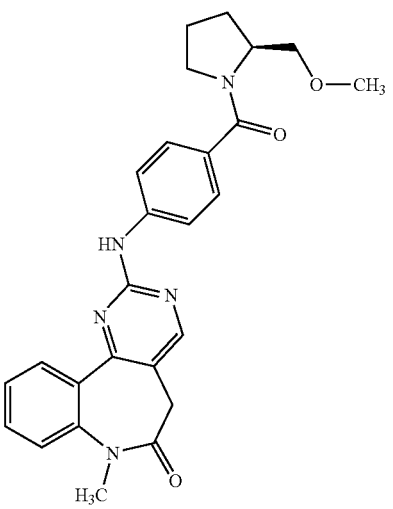
I-776

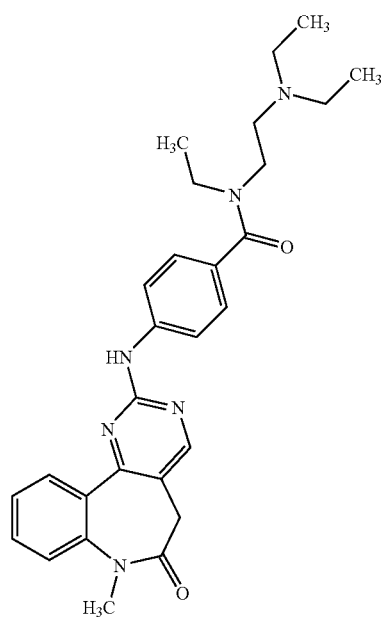
I-777
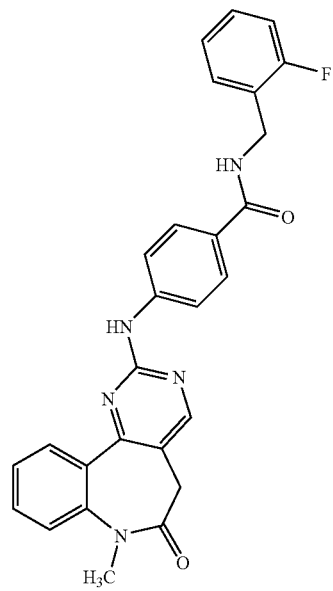
I-779
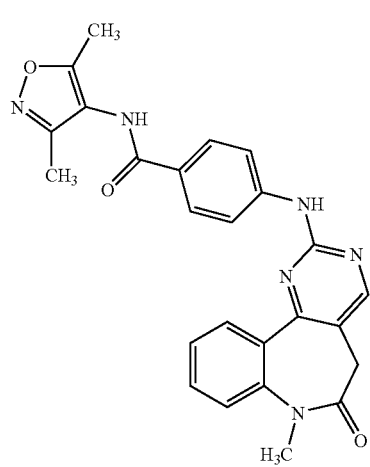
I-778
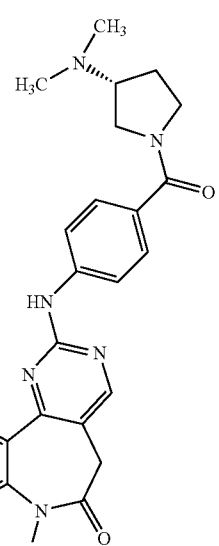
I-780

-continued
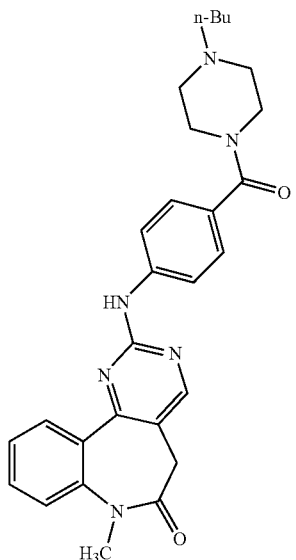
I-781
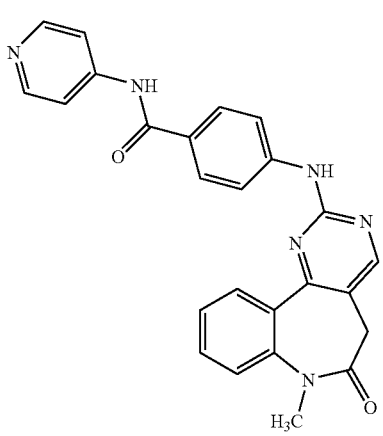
I-783
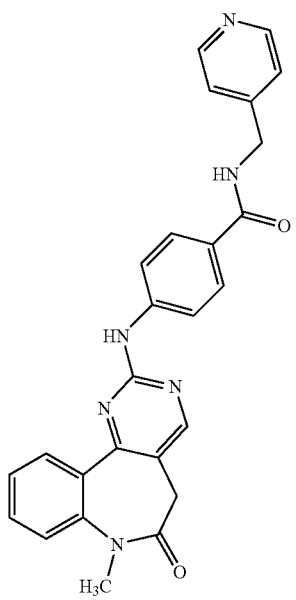
I-782
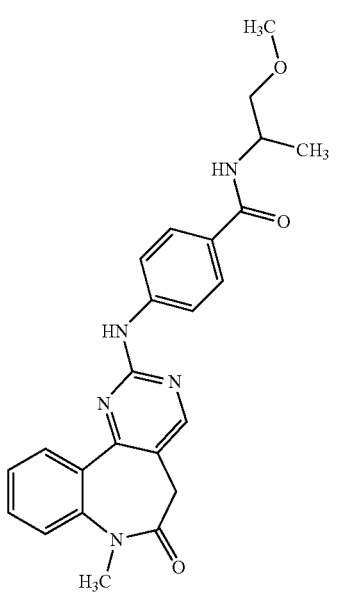
I-784

275
-continued
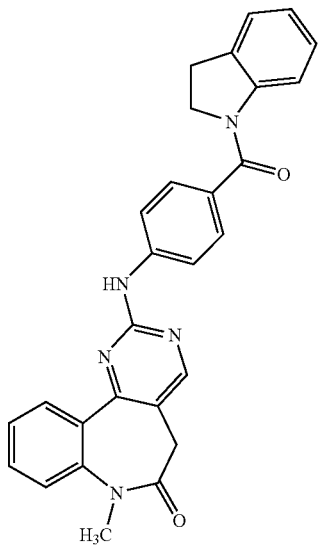
I-785
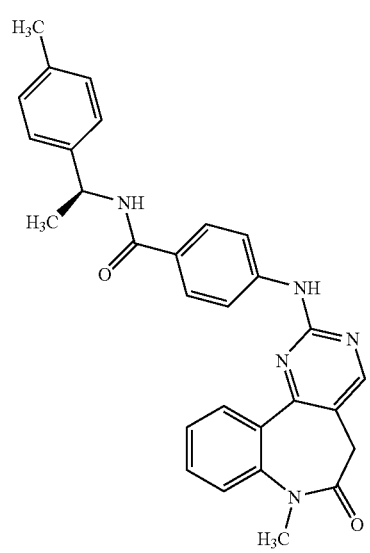
I-786
276
-continued
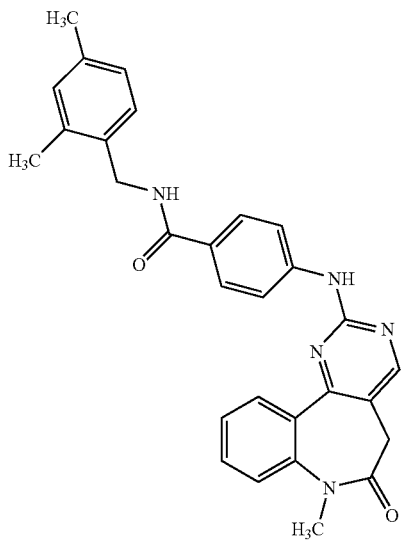
I-787
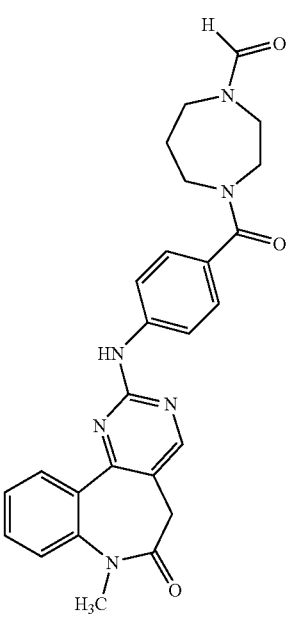
I-788

-continued
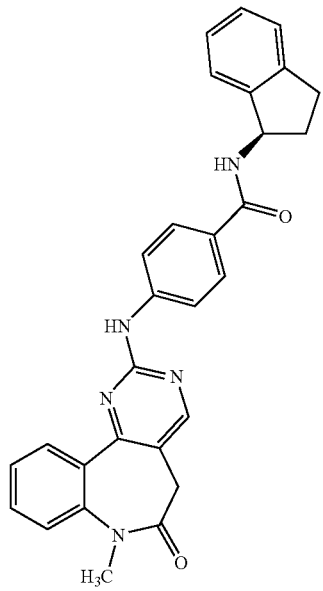
I-789
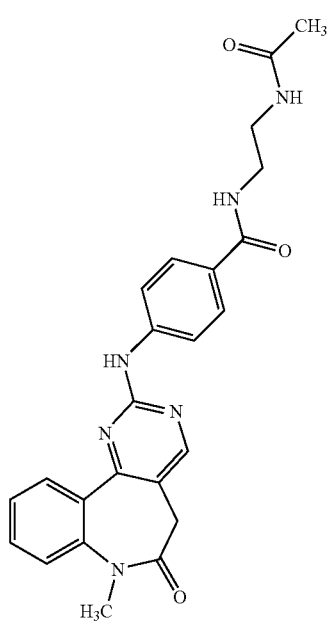
I-791
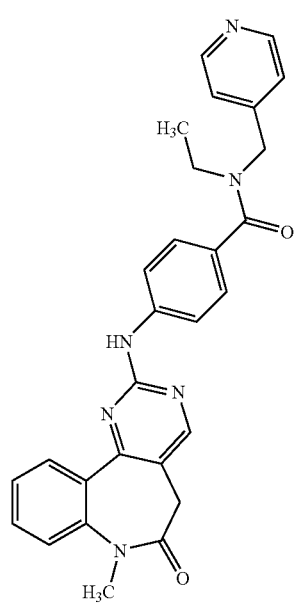
I-790
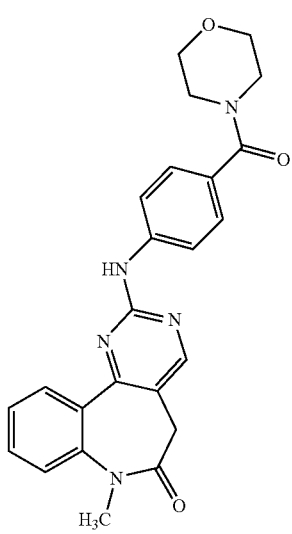
I-792

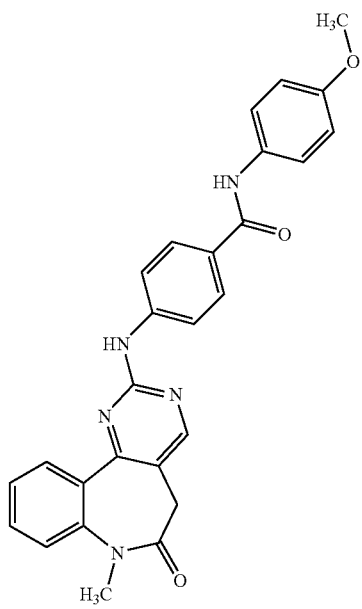
I-793
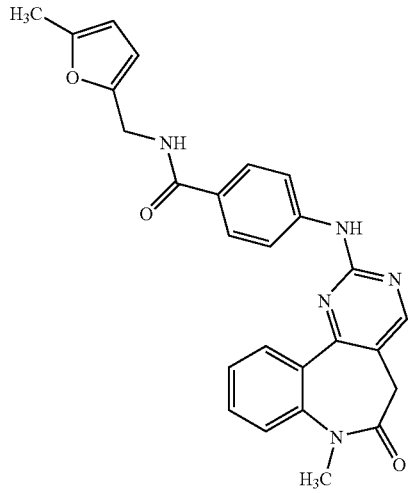
I-795
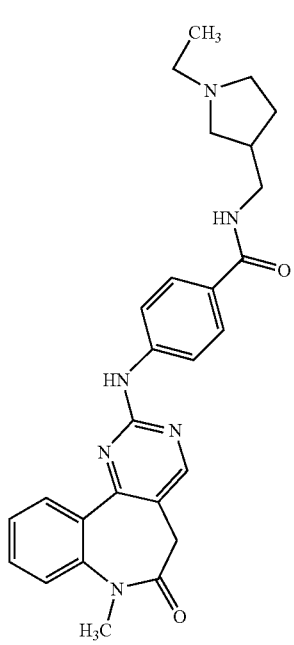
I-794
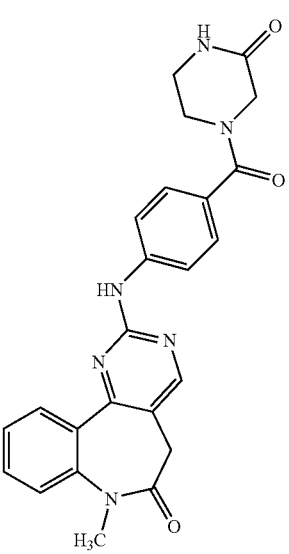
I-796

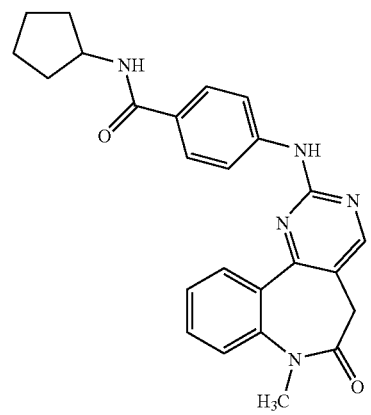
I-797
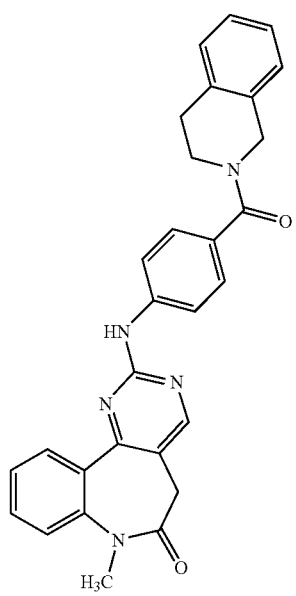
I-800
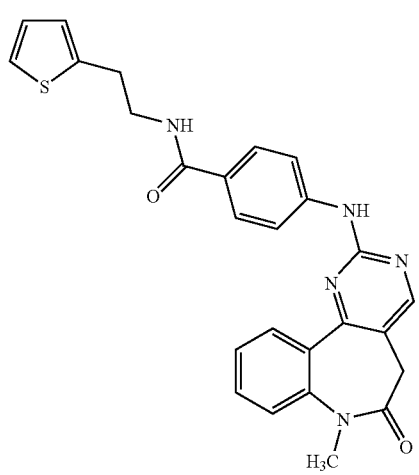
I-798
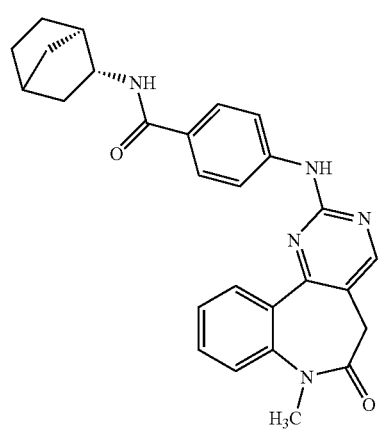
I-799
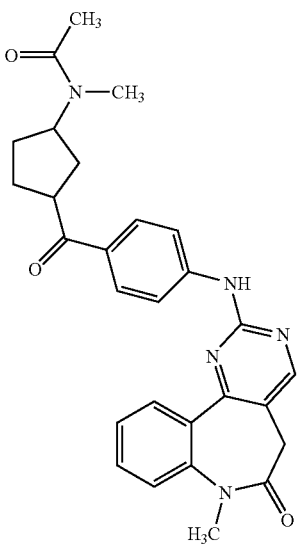
I-801

-continued
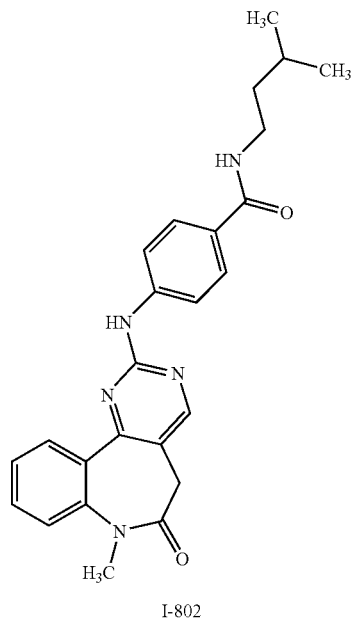
I-802
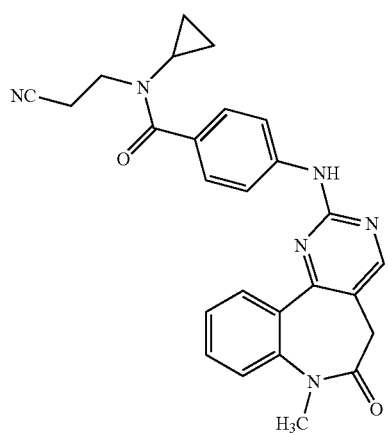
I-803
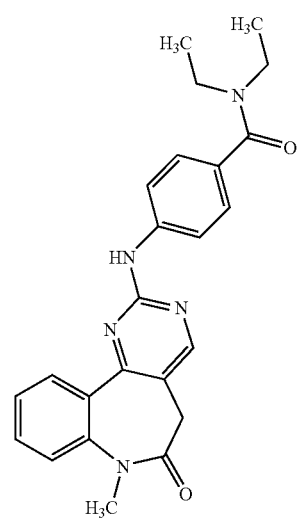
I-804
-continued
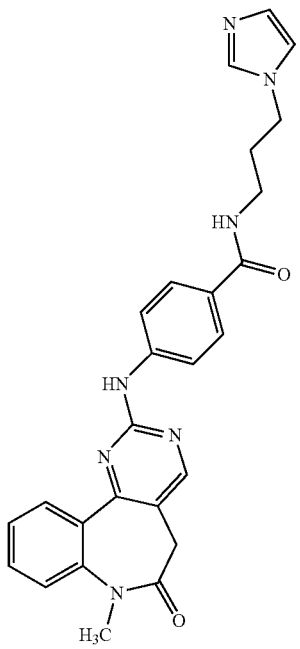
I-805
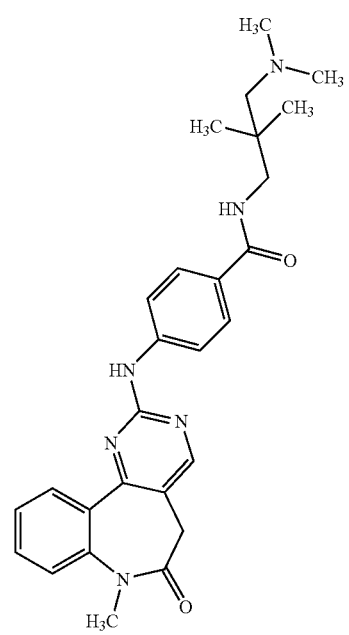
I-806

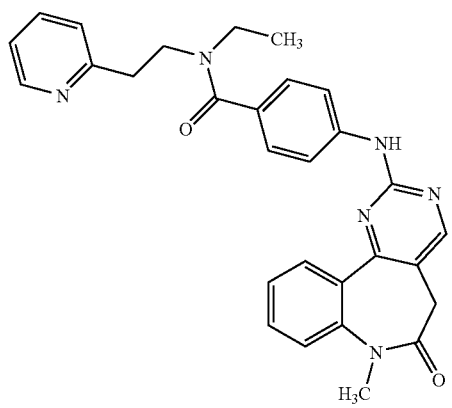
I-807
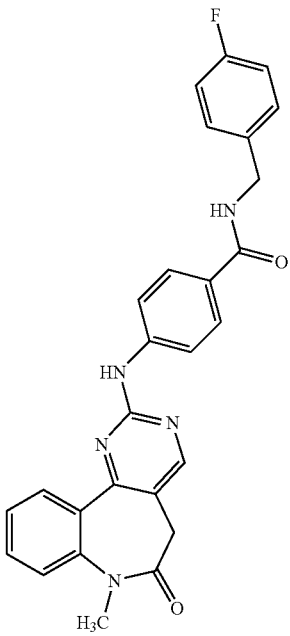
I-809
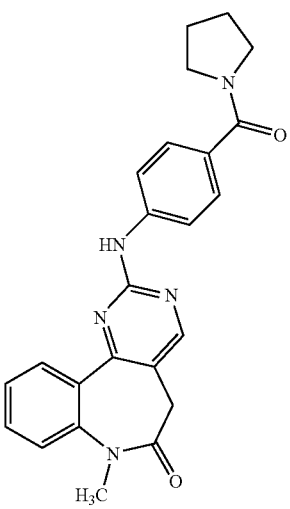
I-808
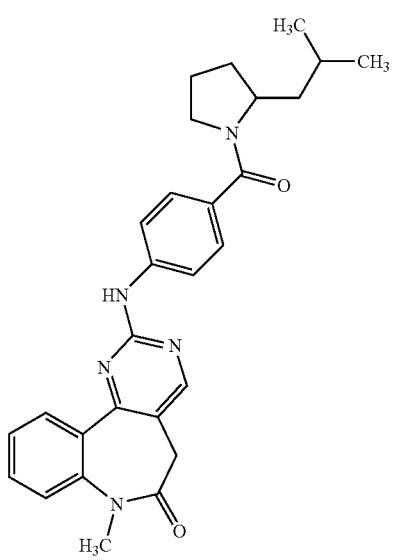
I-810

-continued
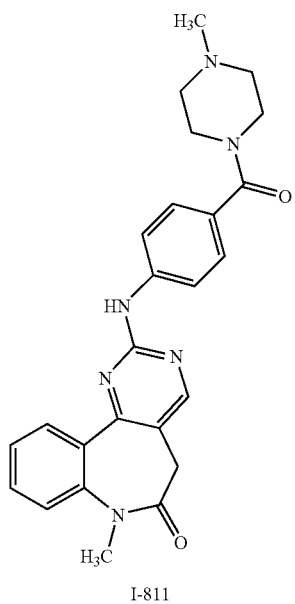
I-811
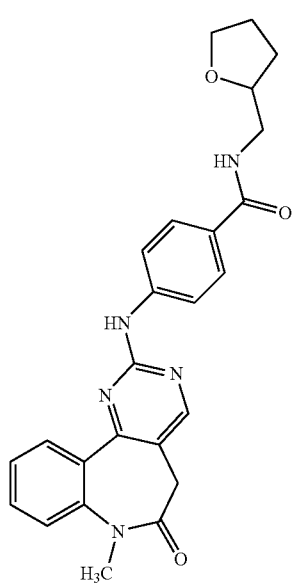
I-812
-continued
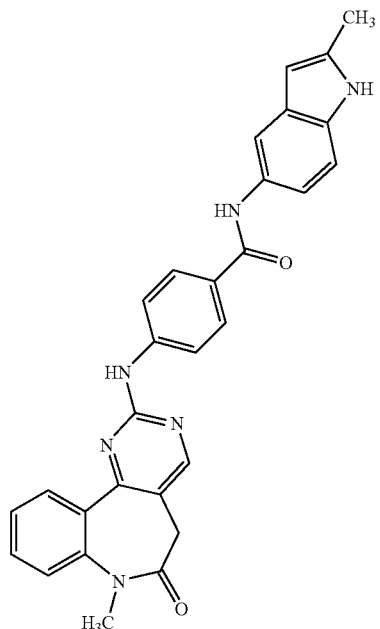
I-813
I-814

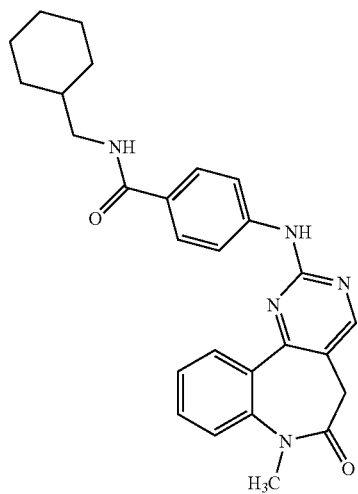
I-815
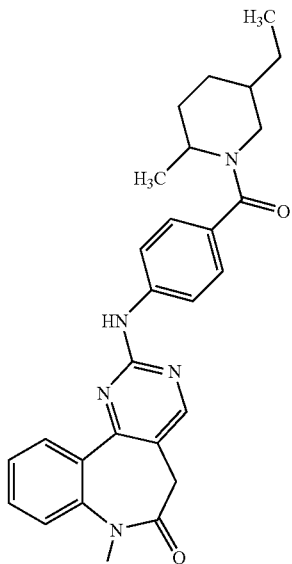
I-817
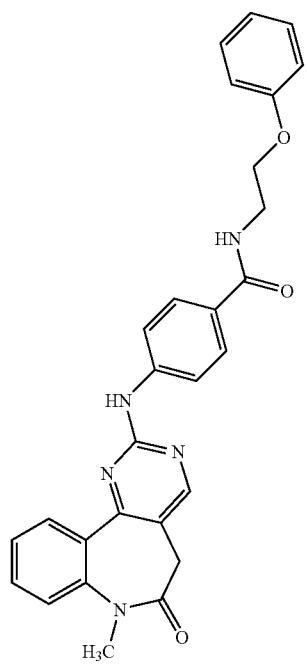
I-816
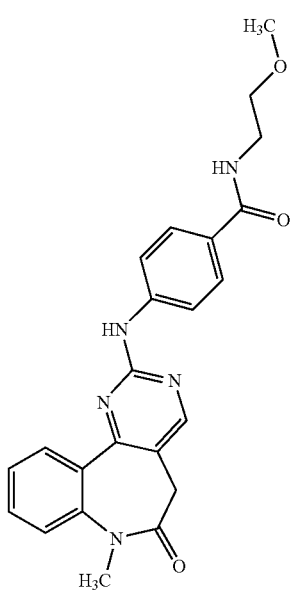
I-818

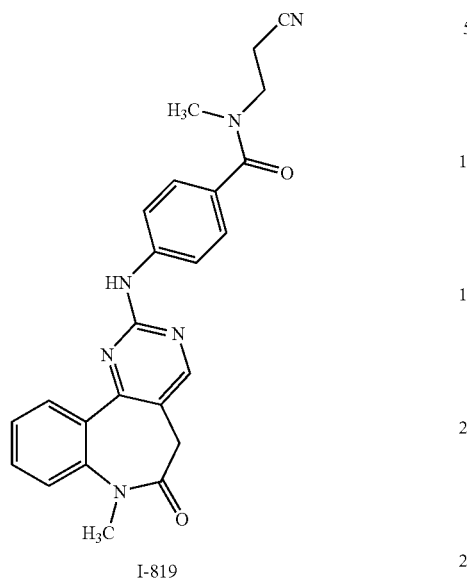
I-819
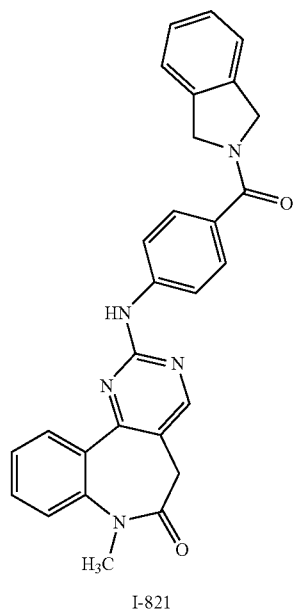
I-821
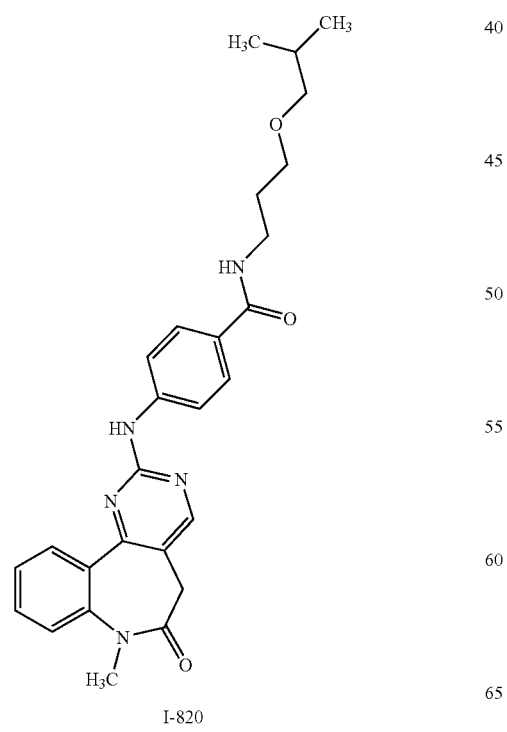
I-820
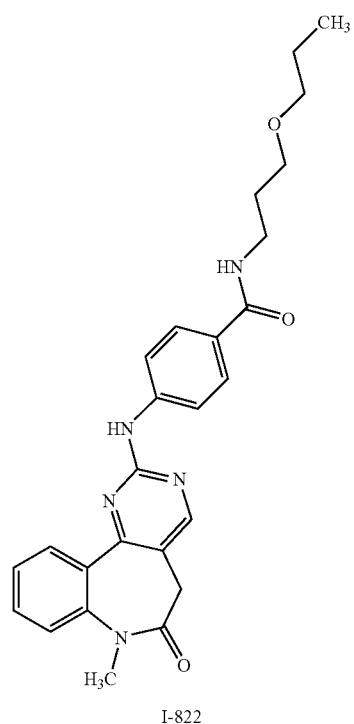
I-822

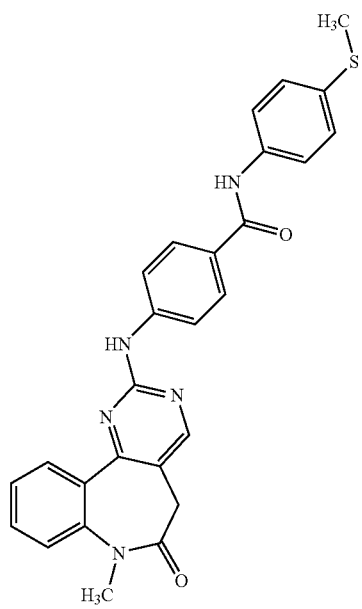
I-823
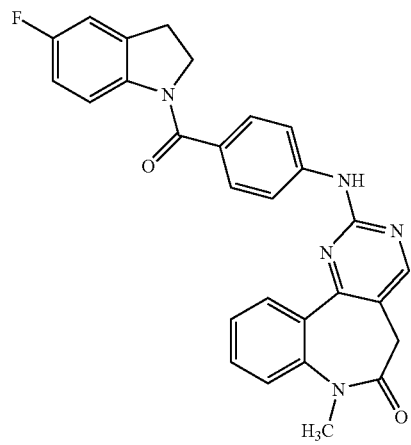
I-825
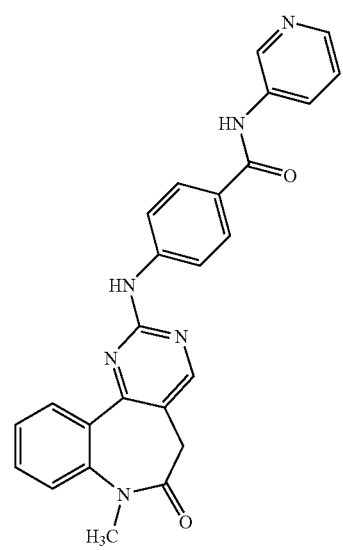
I-824
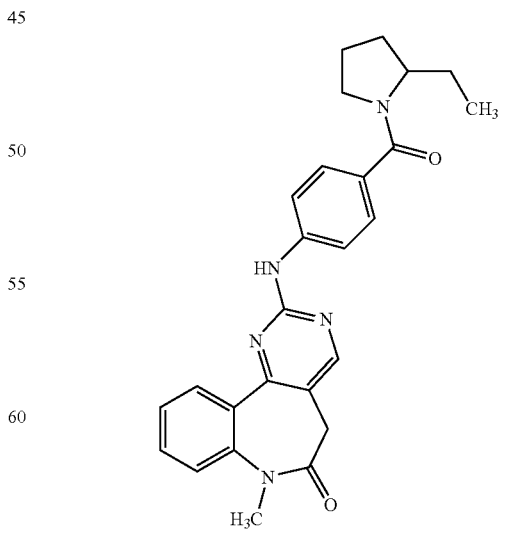
I-826

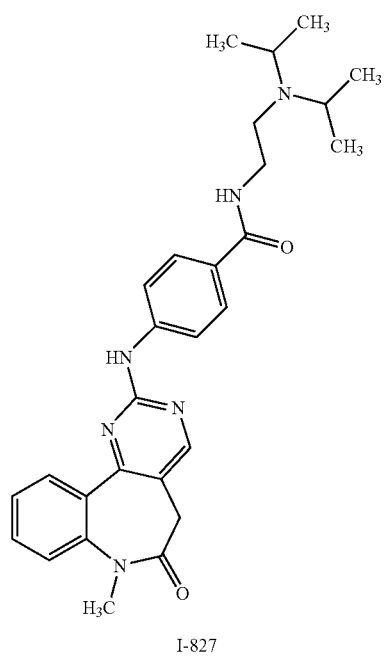
I-827
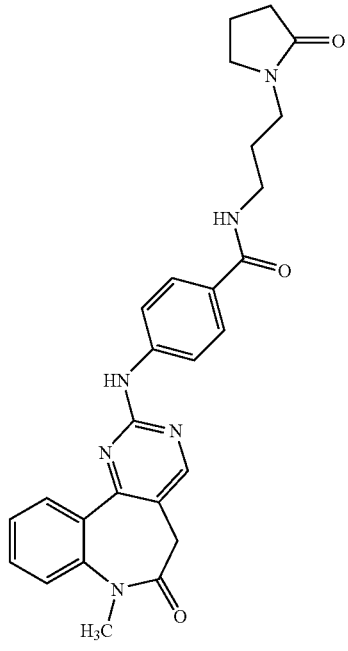
I-829
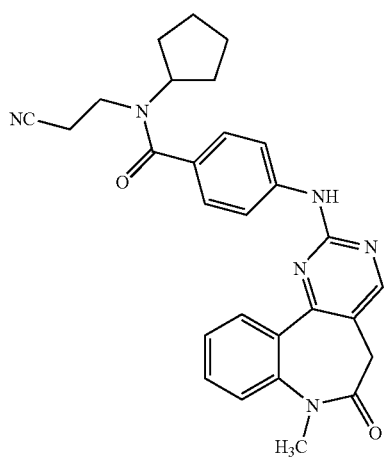
I-828
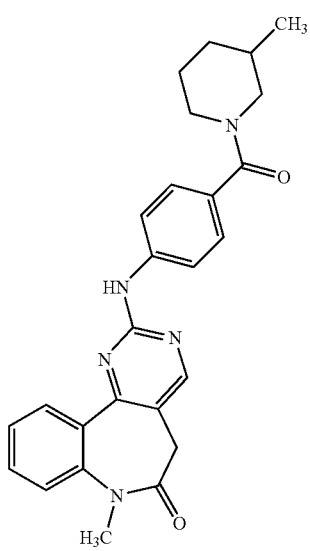
I-830

297
-continued
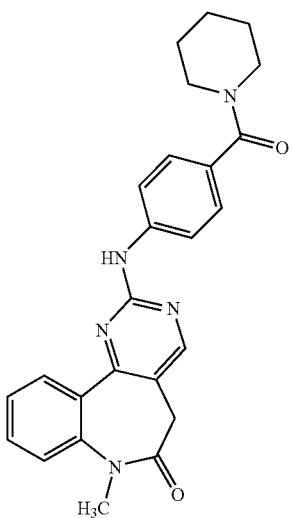
I-831
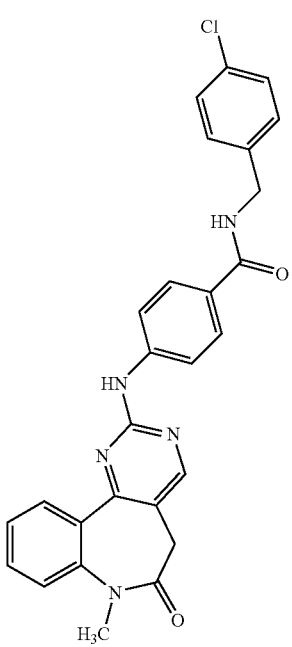
I-832
298
-continued
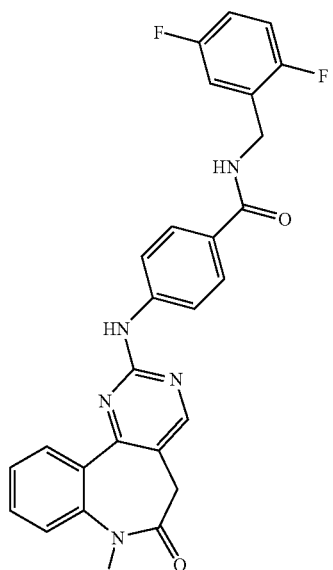
I-833
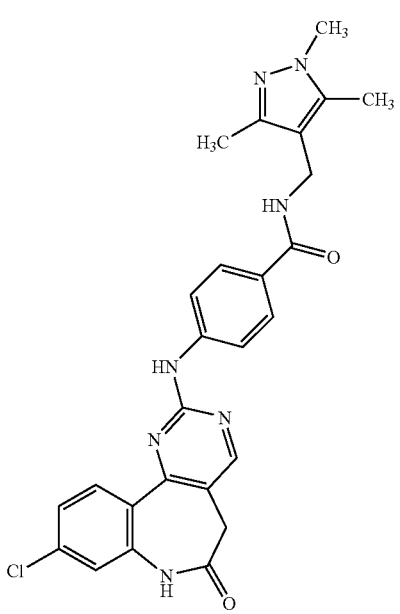
I-834

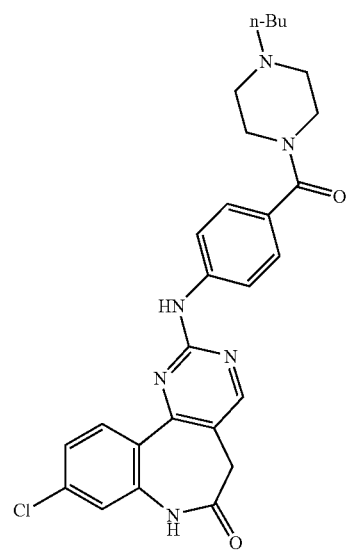
I-835
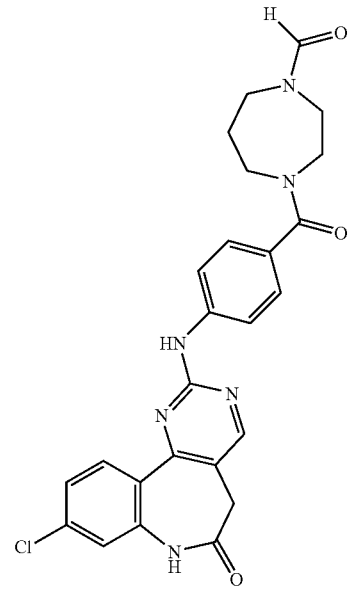
I-837
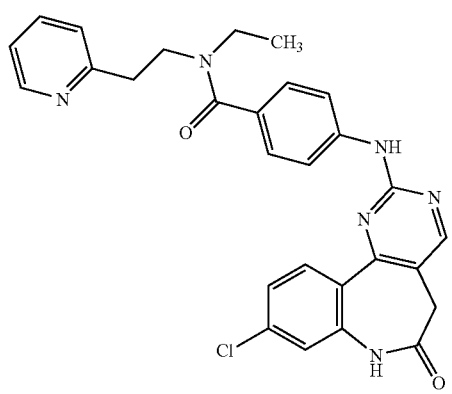
I-836
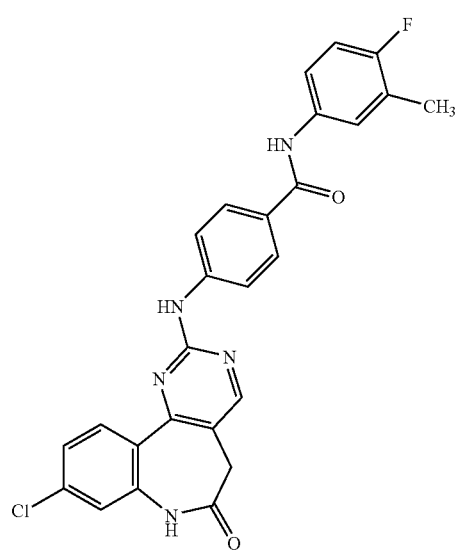
I-838

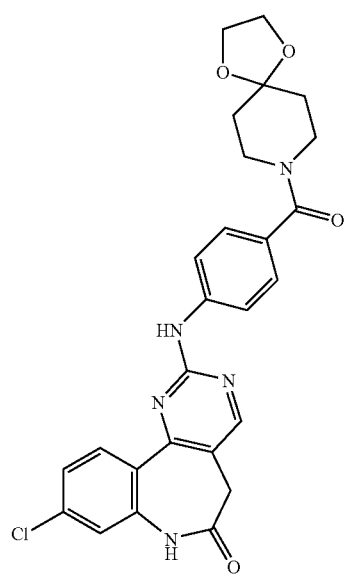
I-839
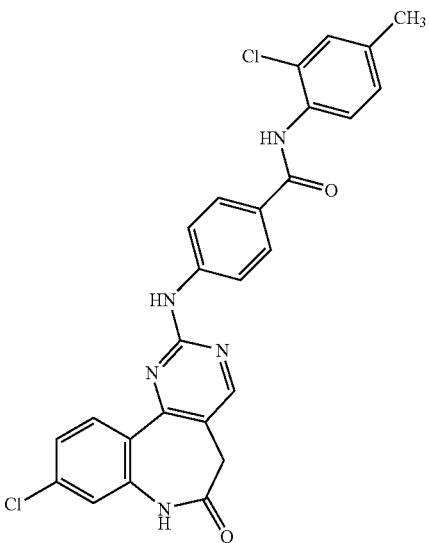
I-841
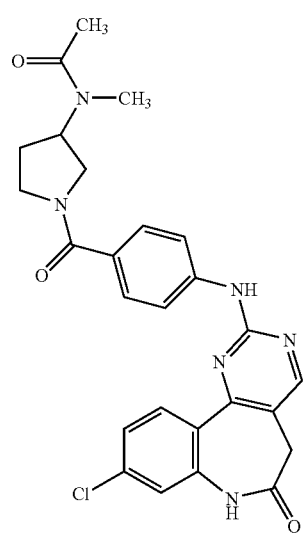
I-840
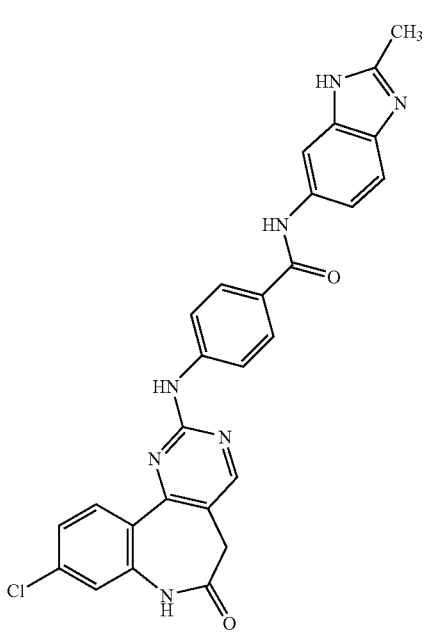
I-842

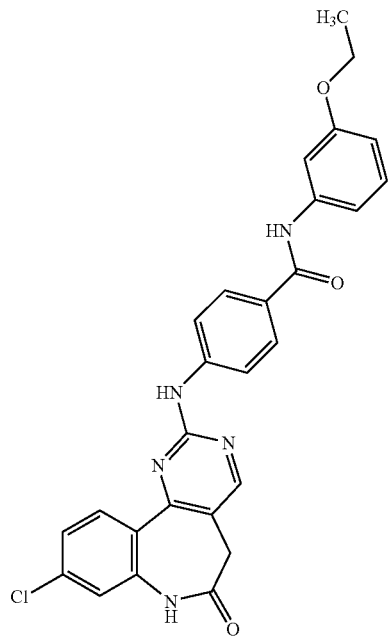
I-843
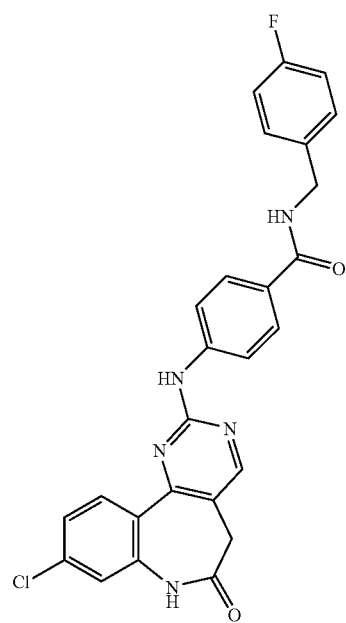
I-845
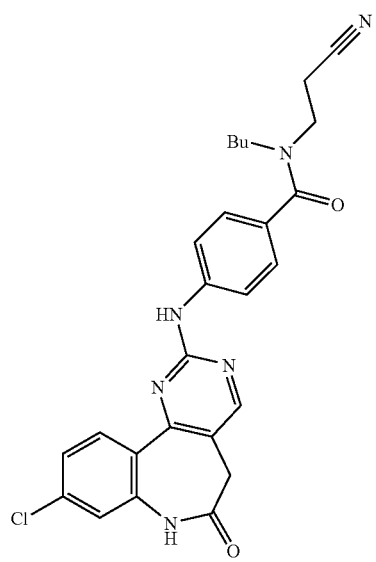
I-844
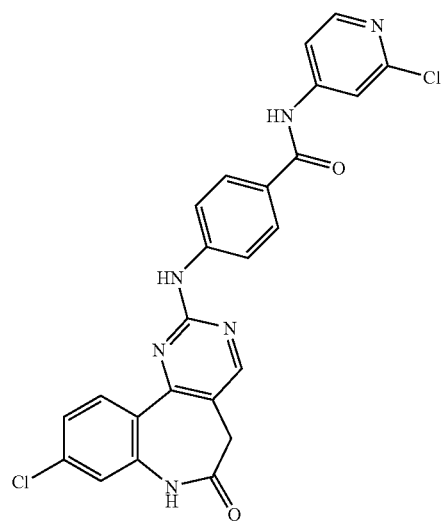
I-846

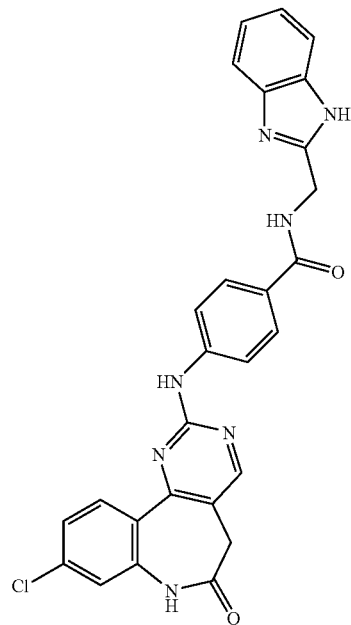
I-847
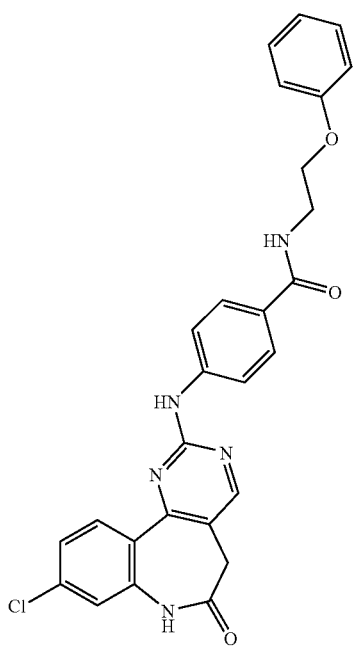
I-849
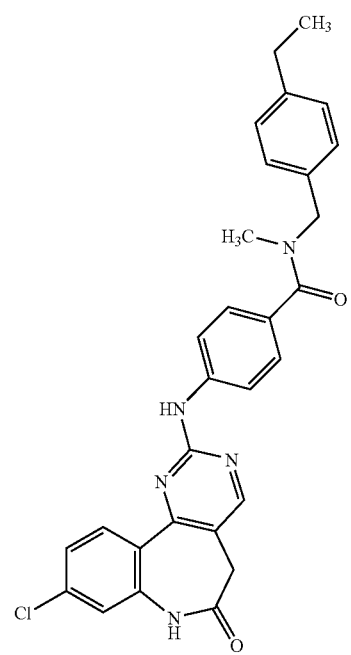
I-848
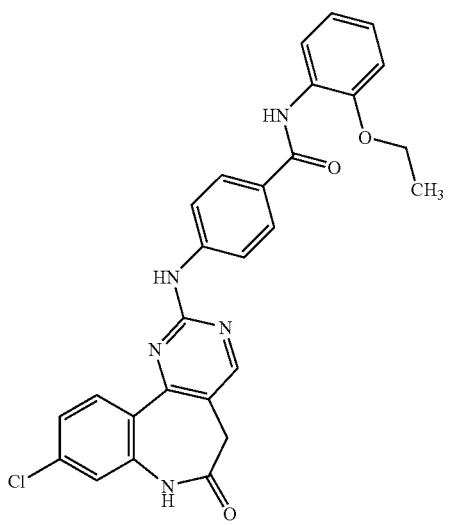
I-850

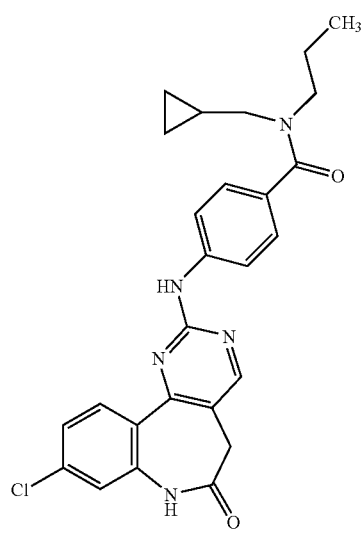
I-851
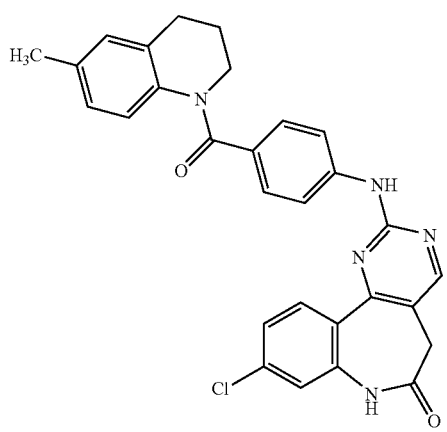
I-853
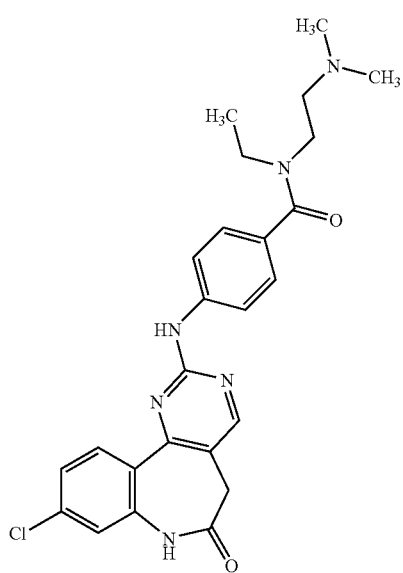
I-852
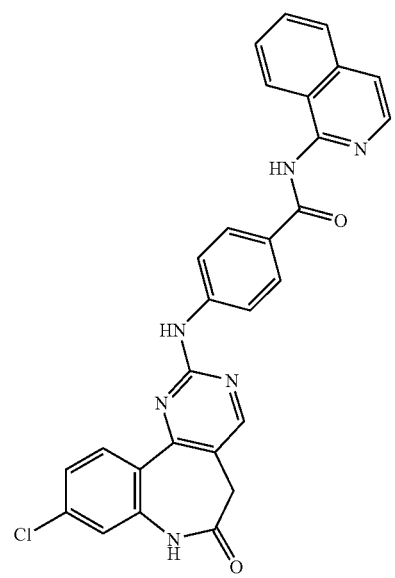
I-854

-continued
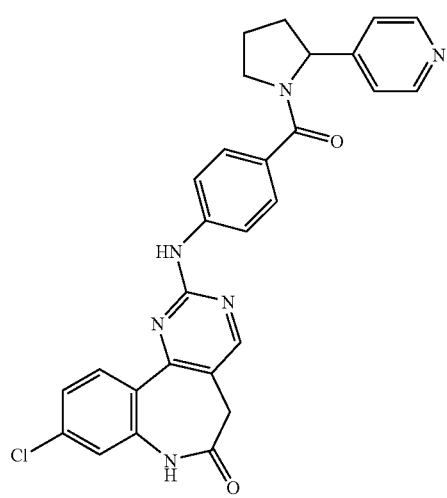
I-855
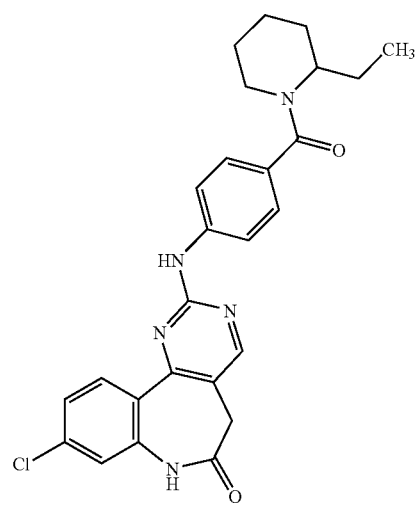
I-856
-continued
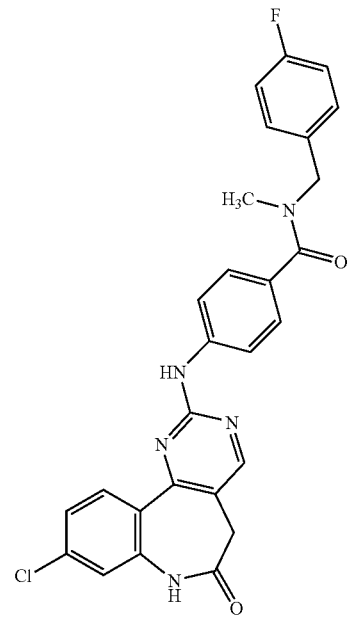
I-857
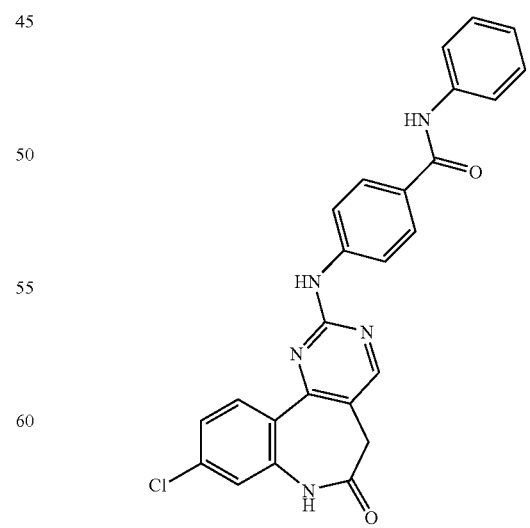
I-858

-continued
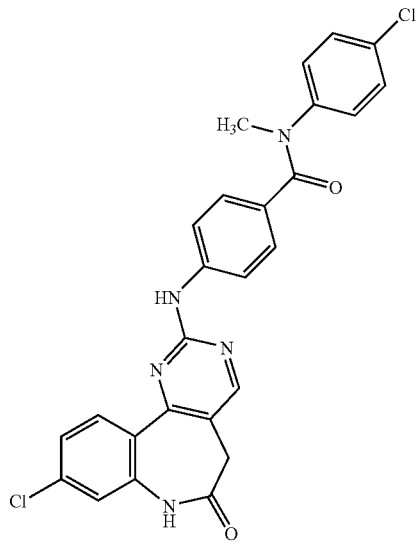
I-859
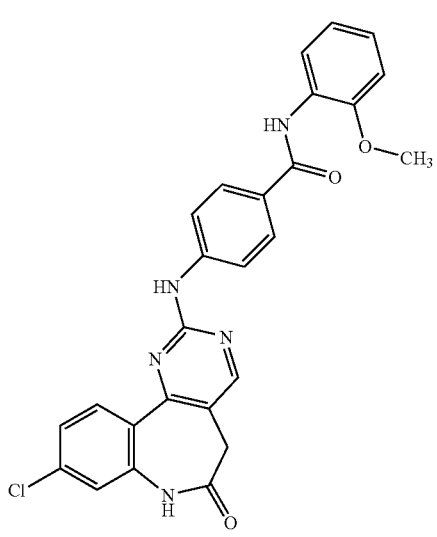
I-861
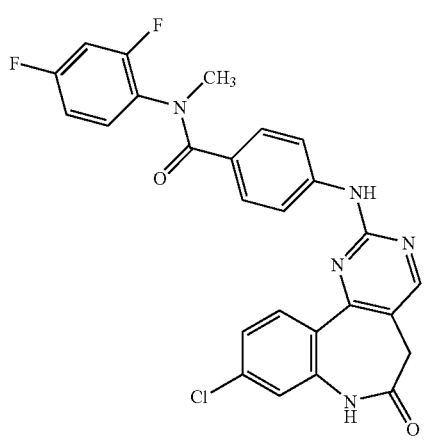
I-860
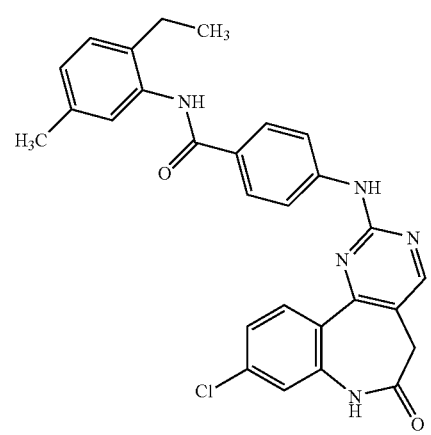
I-862

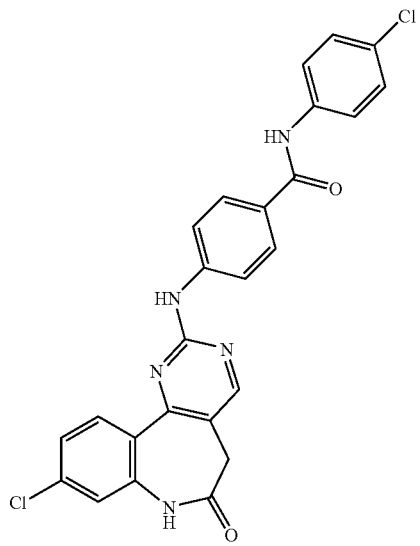
I-863
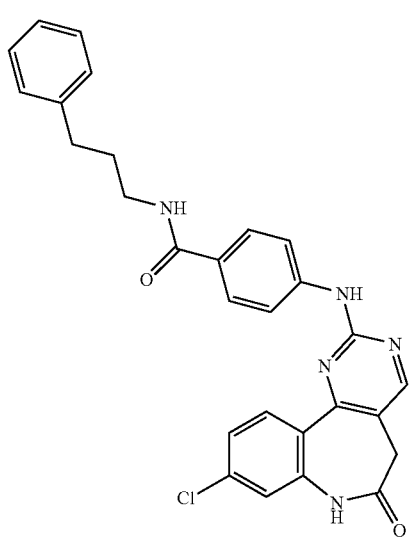
I-865
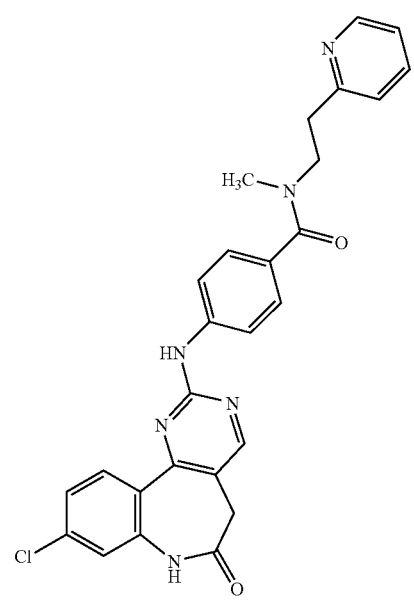
I-864
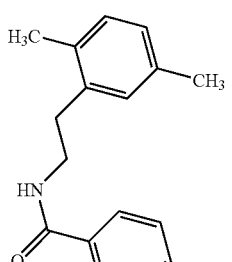
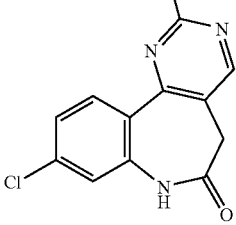
I-866

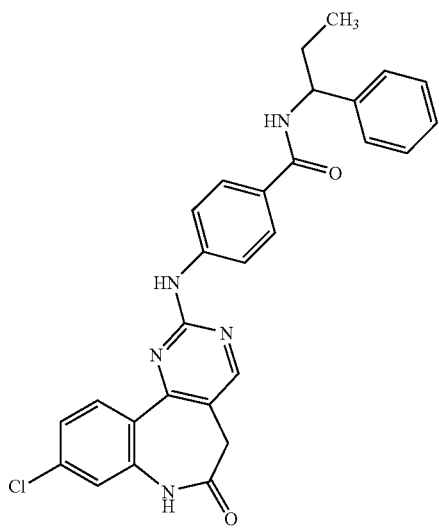
I-867
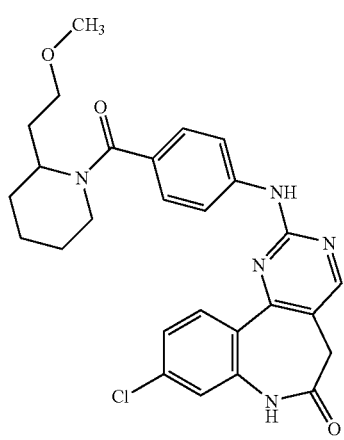
I-868
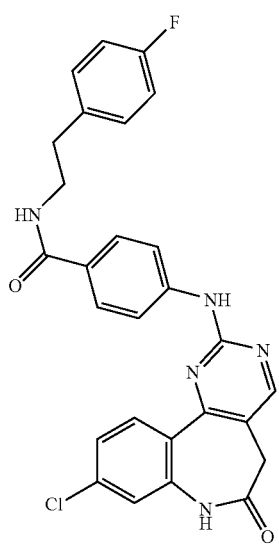
I-869
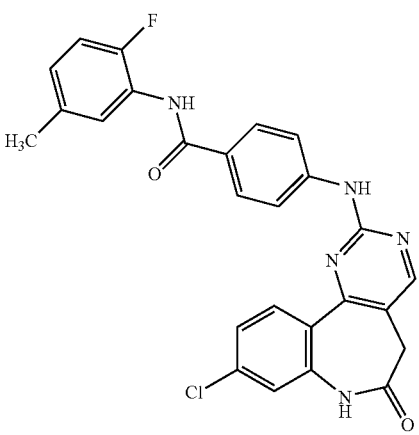
I-870
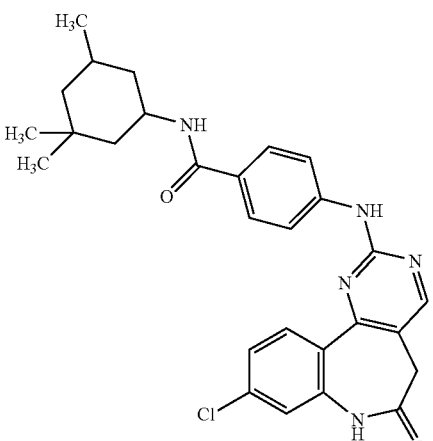
I-871
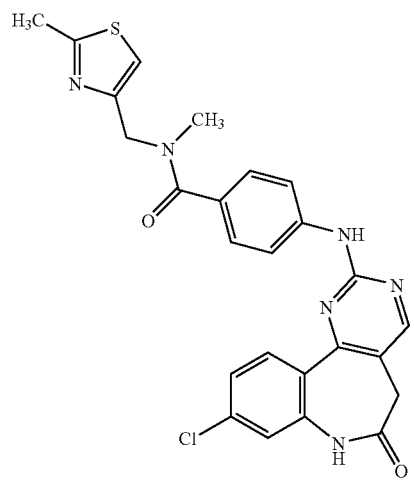
I-872

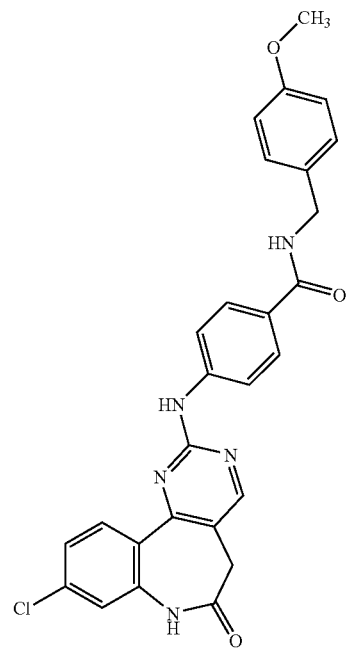
I-873
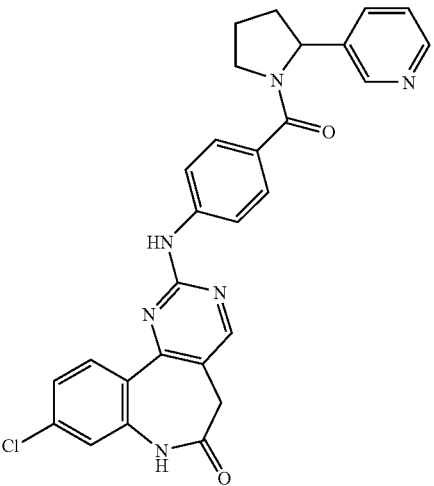
I-875
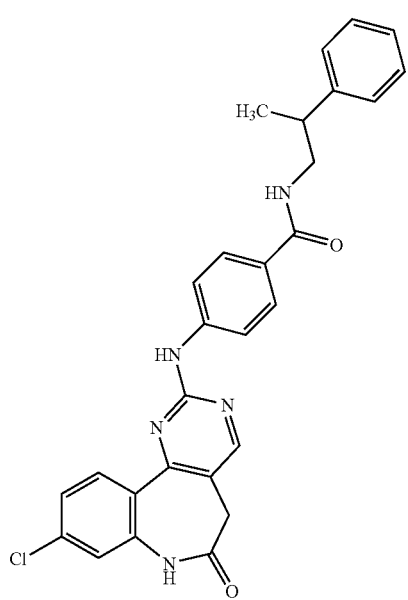
I-874

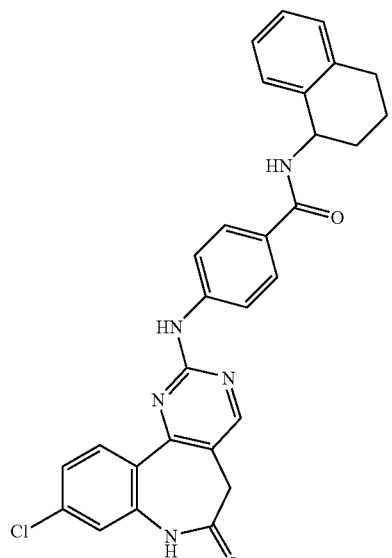
I-877
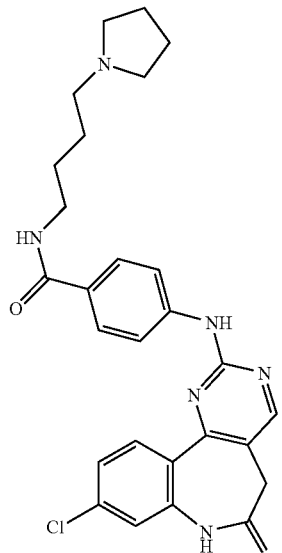
I-879
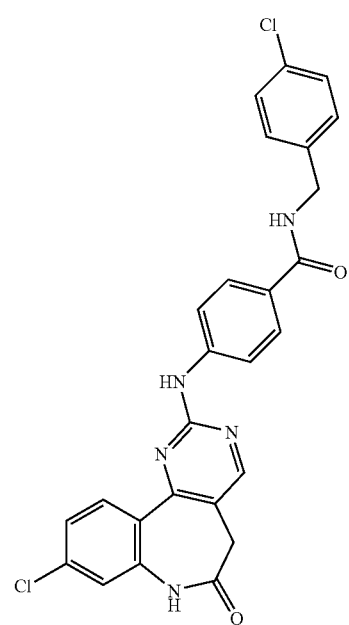
I-878
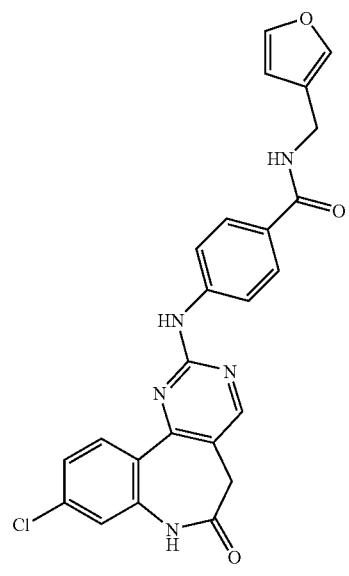
I-880

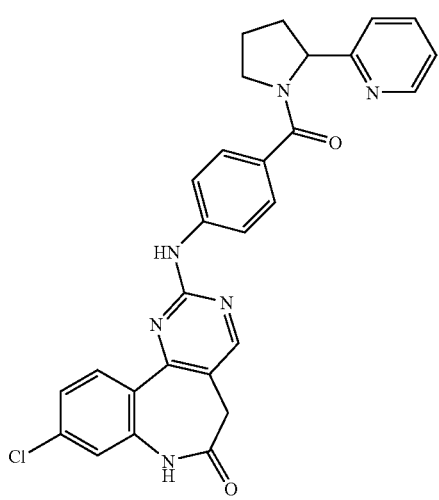
I-881
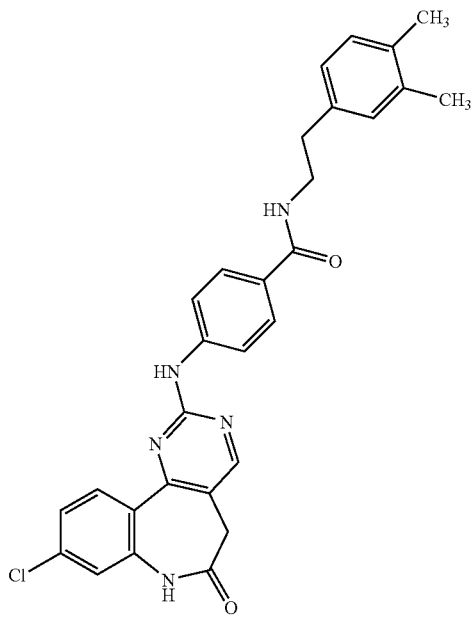
I-883
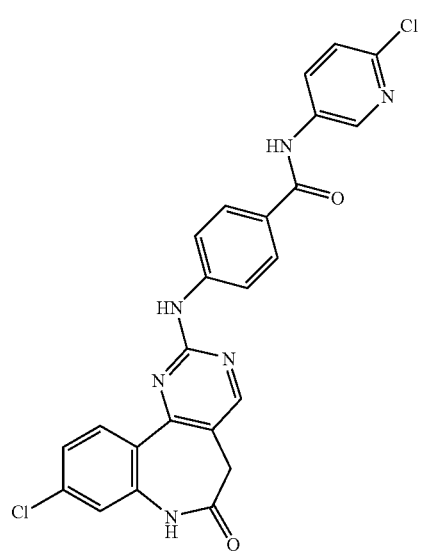
I-882
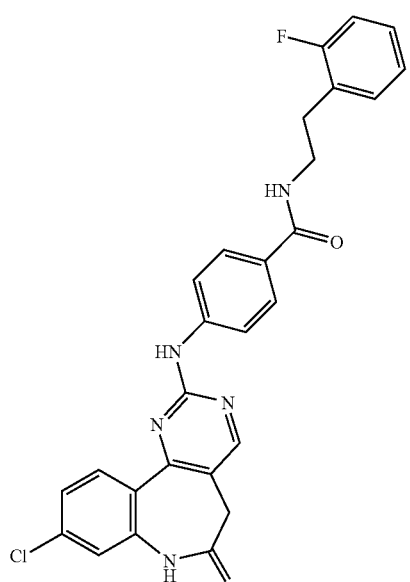
I-884

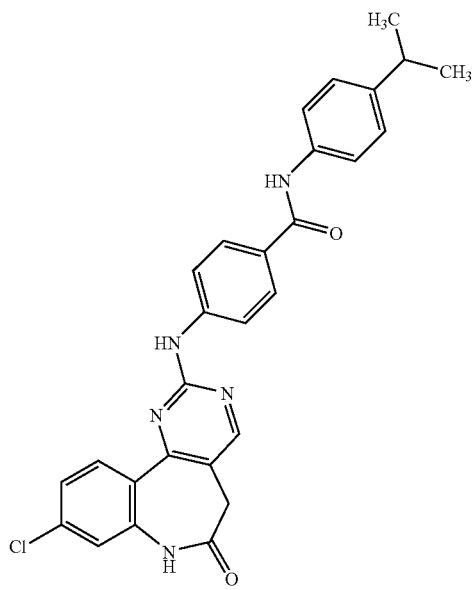
I-885
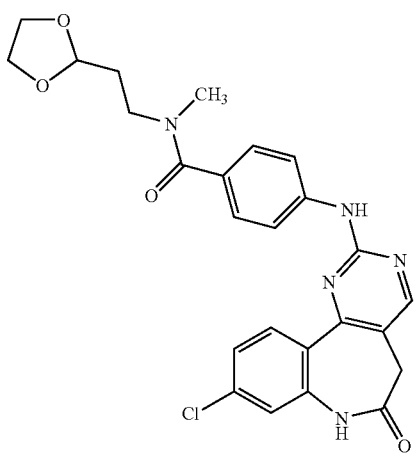
I-887
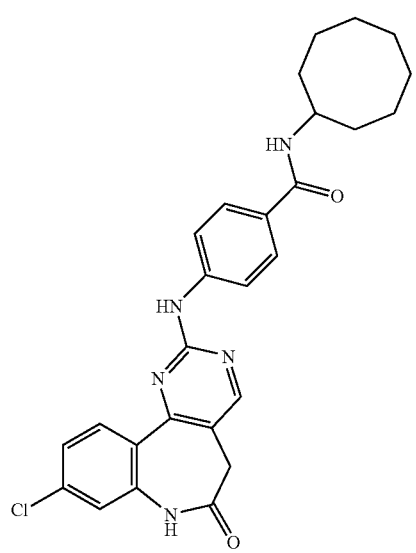
I-886
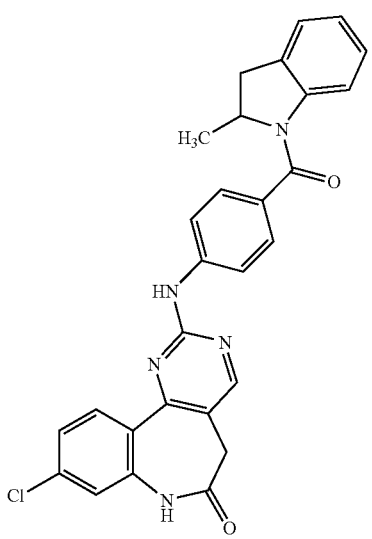
I-888

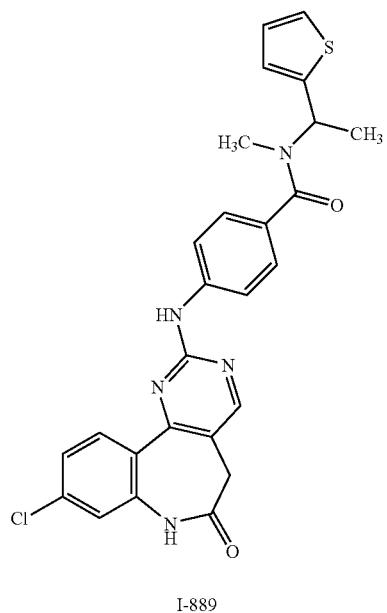
I-889
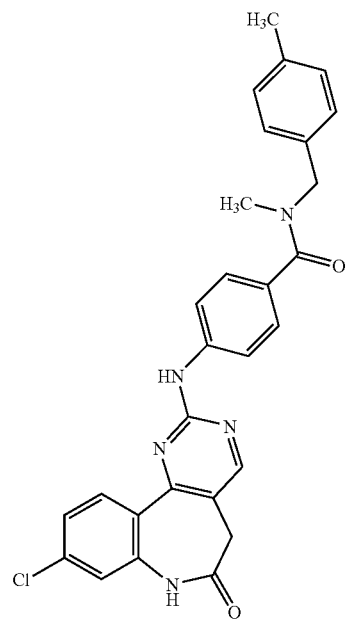
I-891
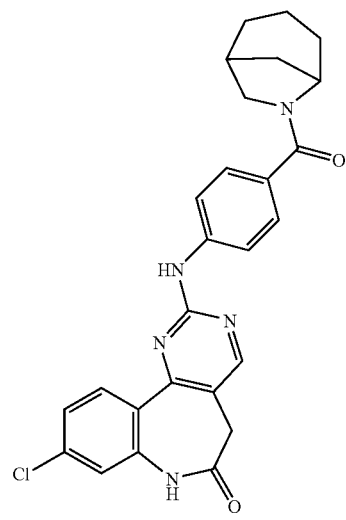
I-892
I-890

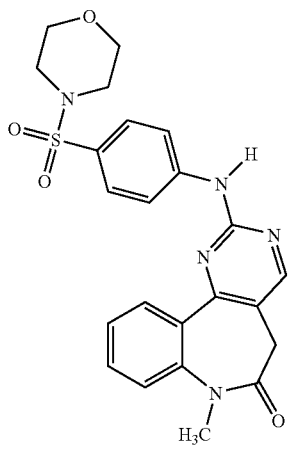
I-893
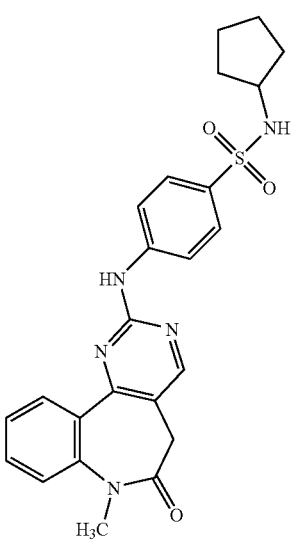
I-894
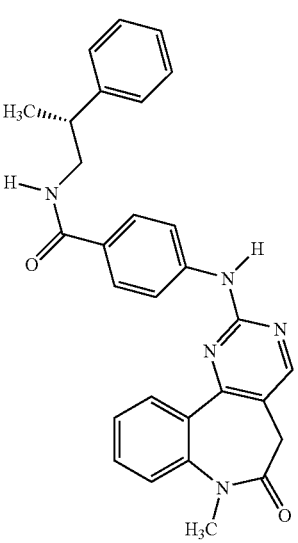
I-895
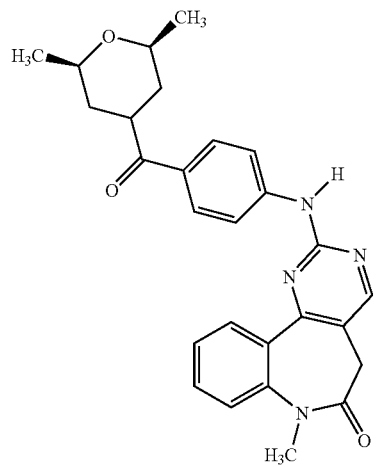
I-896
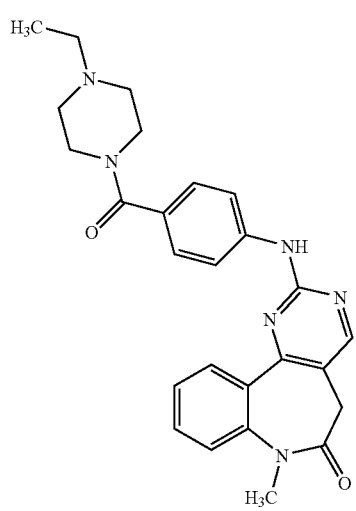
I-897
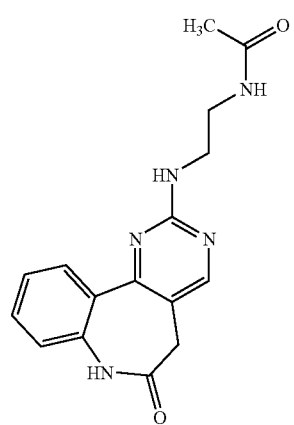
I-898

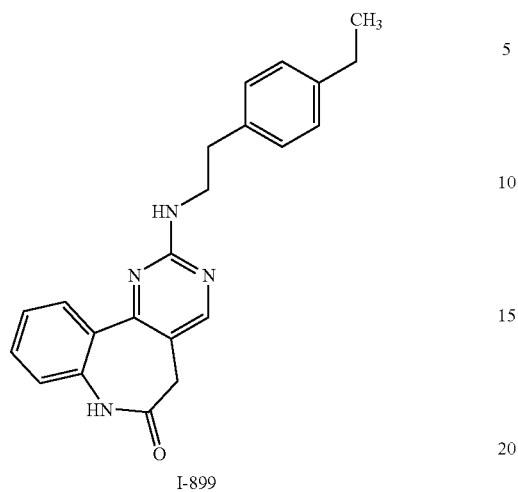
I-899
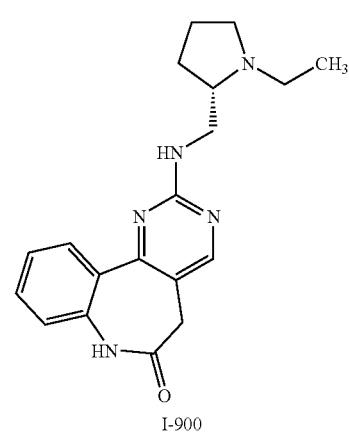
I-900
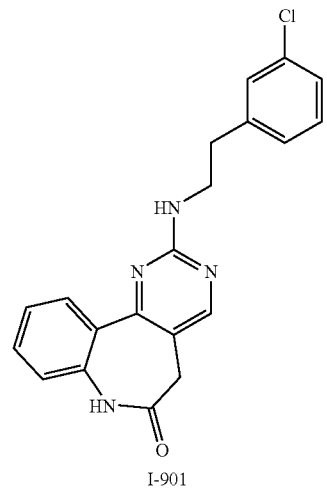
I-901
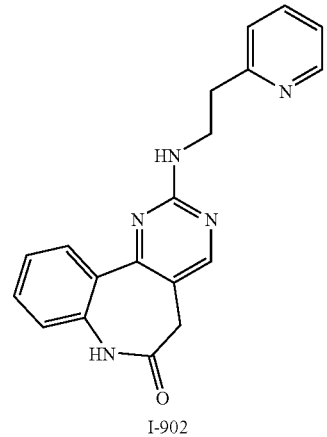
I-902
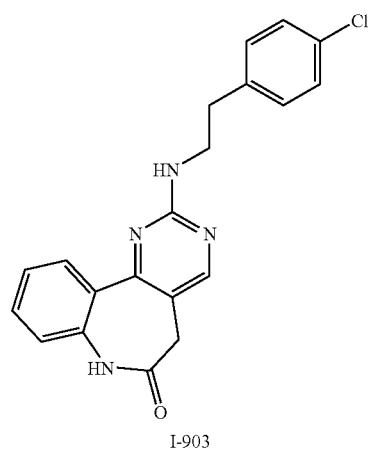
I-903
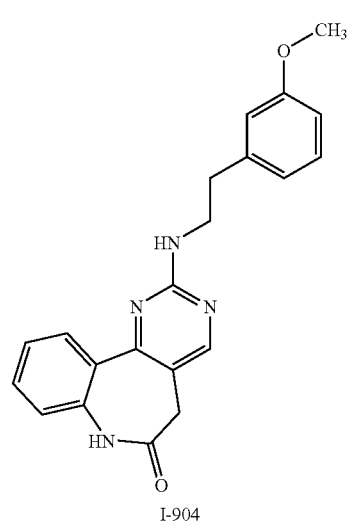
I-904

-continued
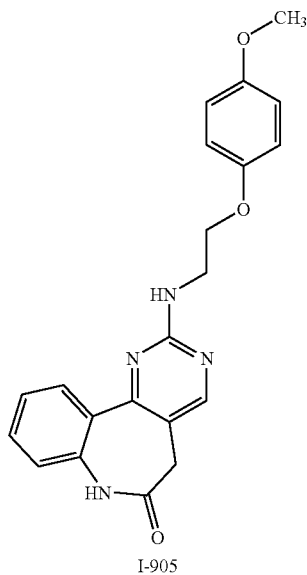
I-905
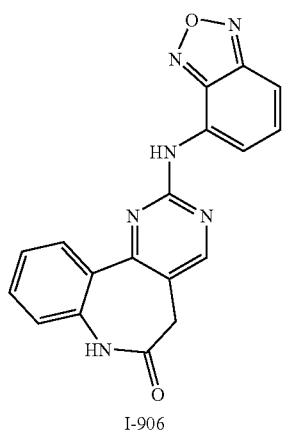
I-906
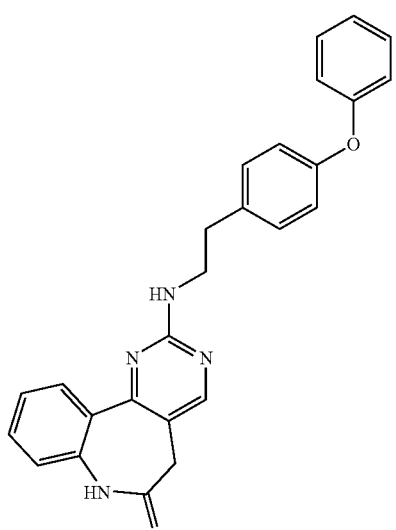
I-907
-continued
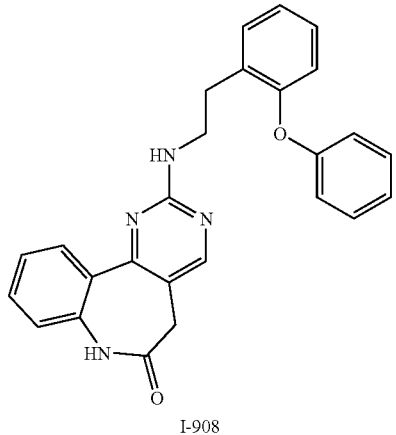
I-908
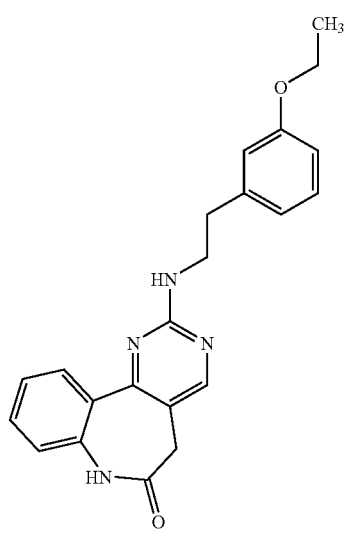
I-909
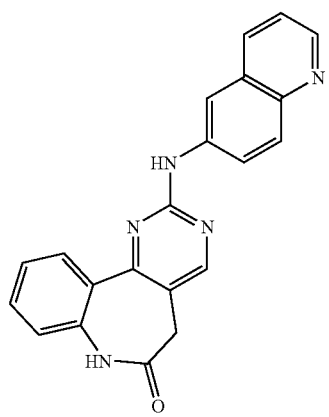
I-910

-continued
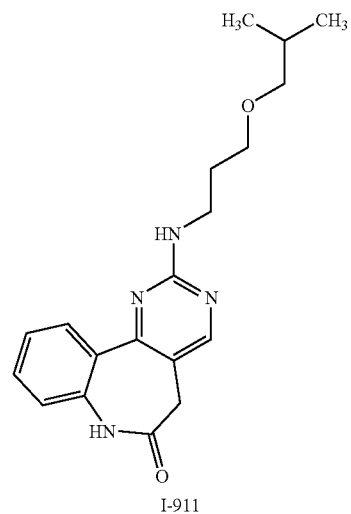
I-911
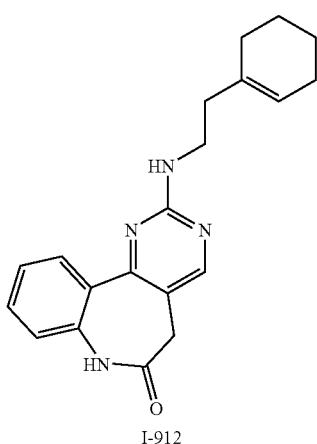
I-912
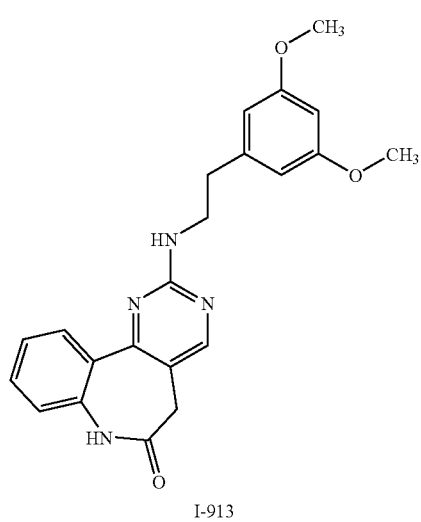
I-913
-continued
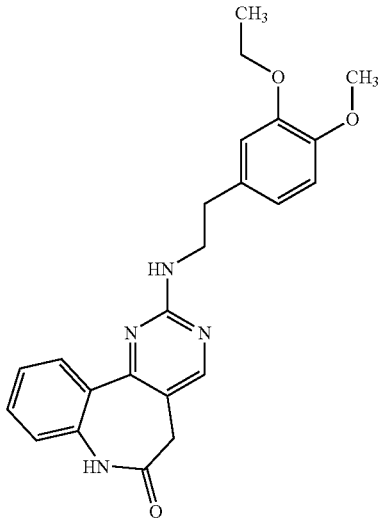
I-914
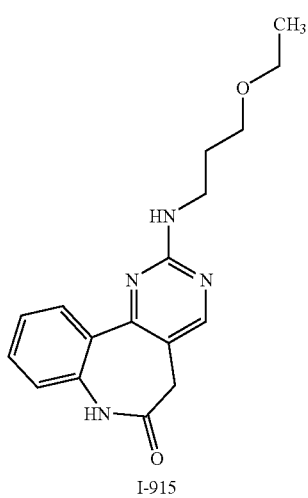
I-915
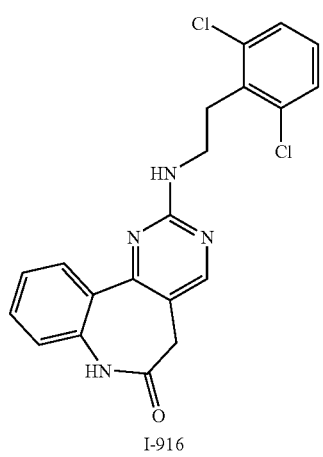
I-916

-continued
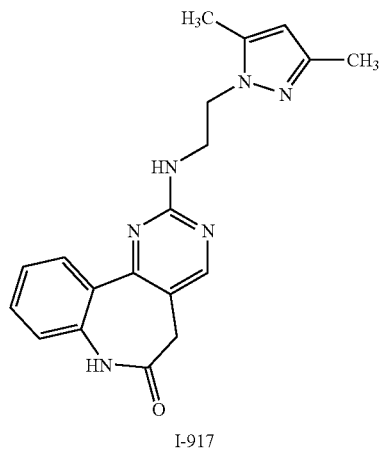
I-917
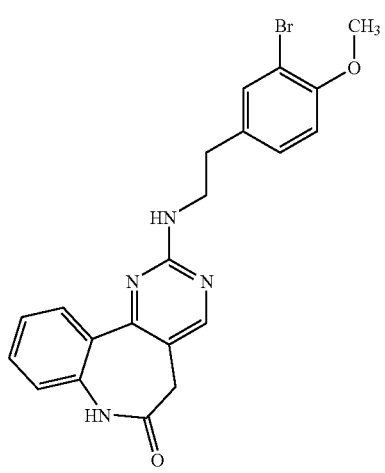
I-918
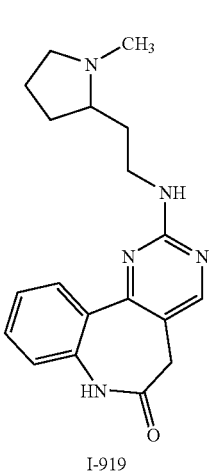
I-919
-continued
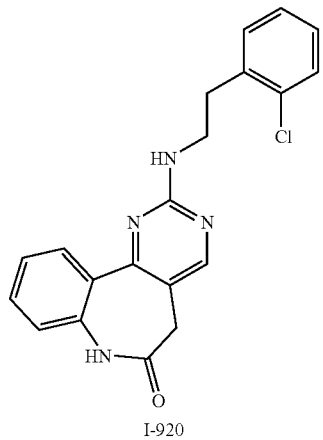
I-920
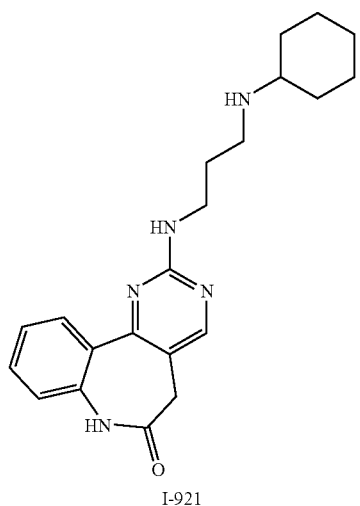
I-921
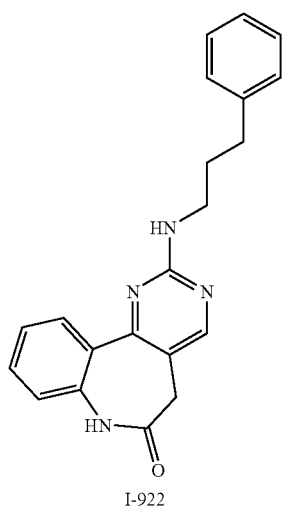
I-922

-continued
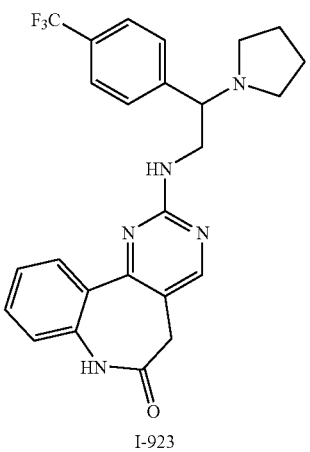
I-923
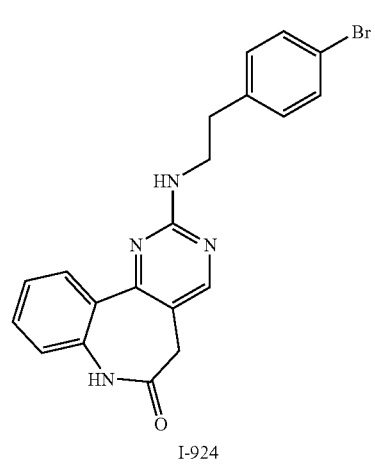
I-924
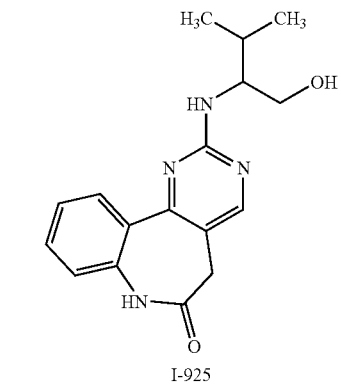
I-925
-continued
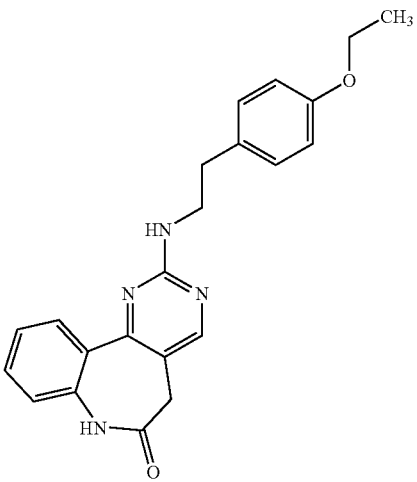
I-926
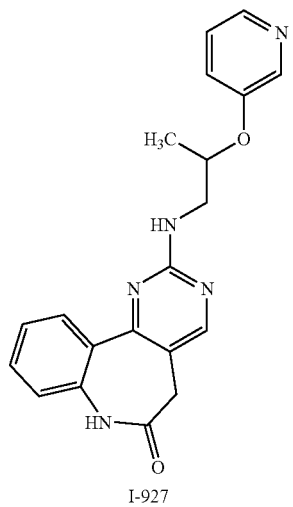
I-927
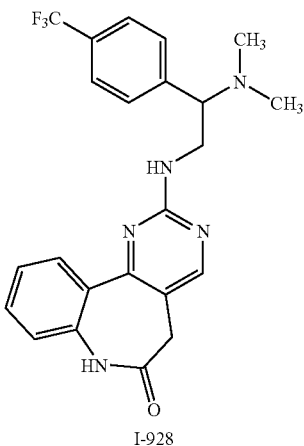
I-928

| 339 | 340 |
|---|---|
| -continued | -continued |
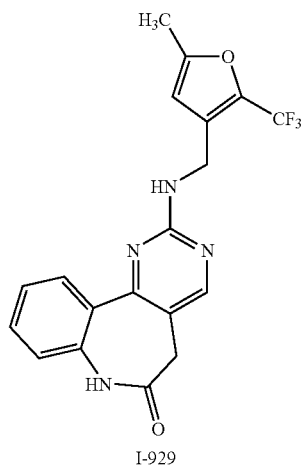
I-929
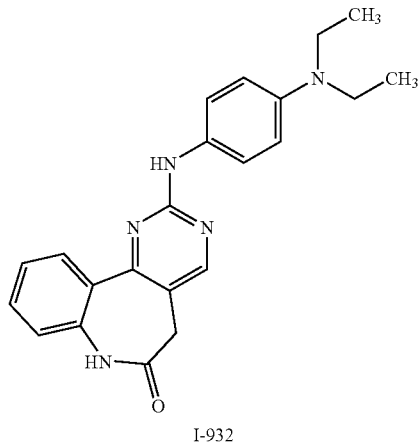
I-932
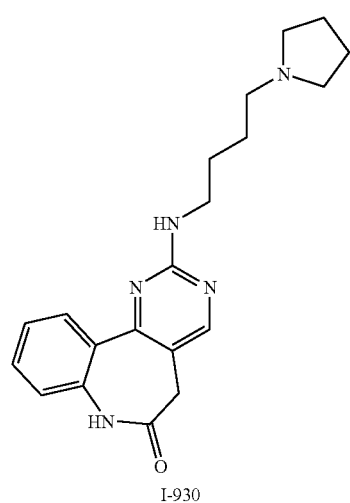
I-930
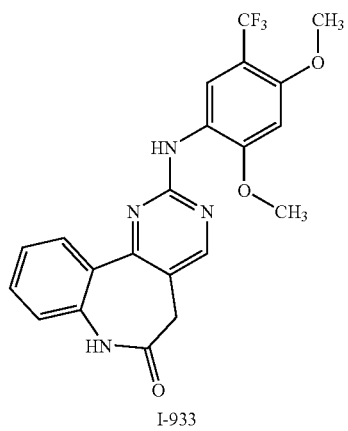
I-933
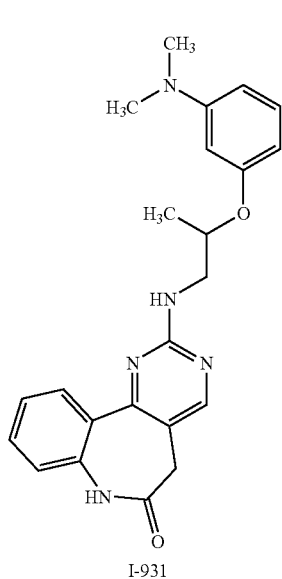
I-931
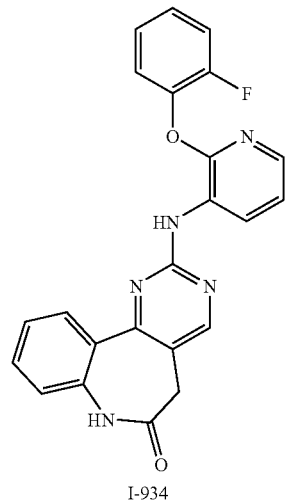
I-934

341
-continued
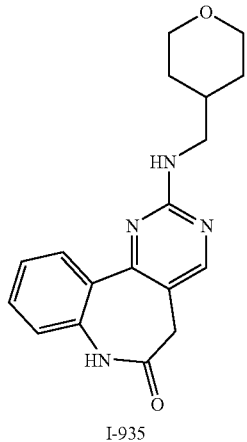
I-935
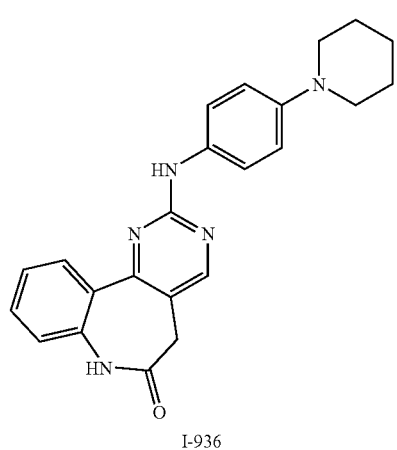
I-936
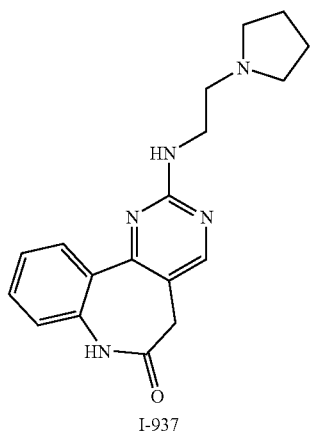
I-937
342
-continued
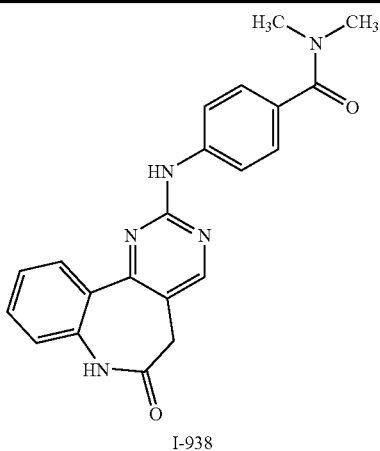
I-938
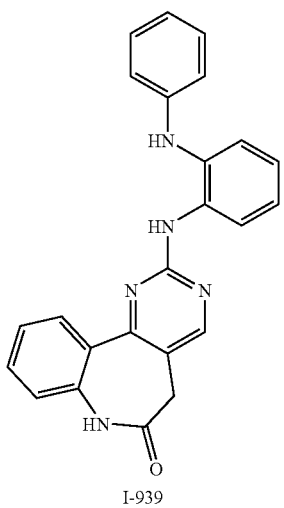
I-939
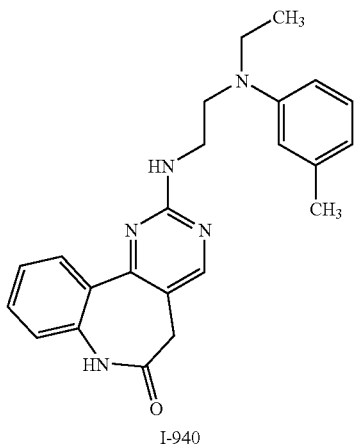
I-940

-continued
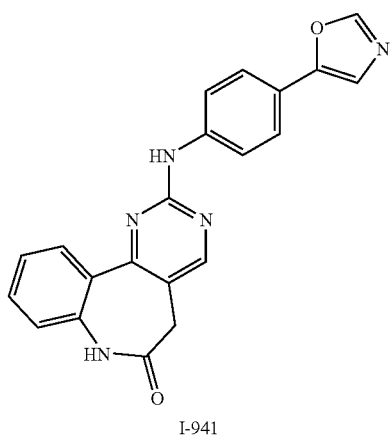
I-941
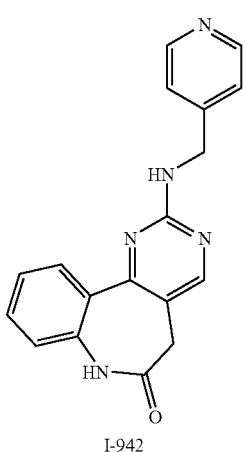
I-942
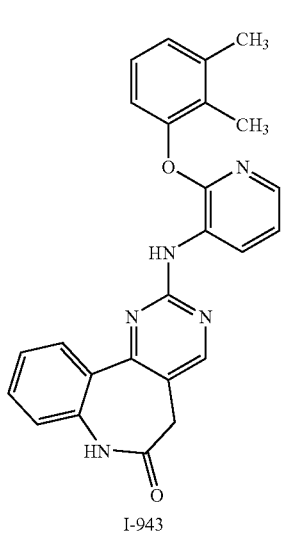
I-943
-continued
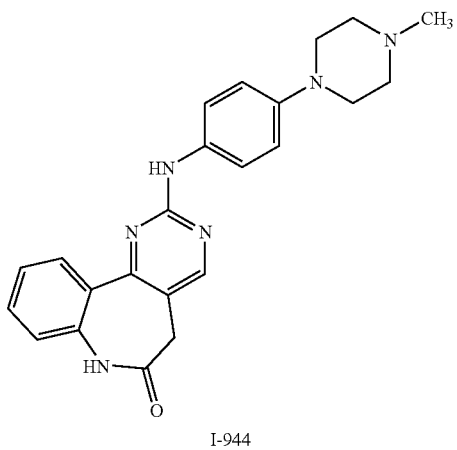
I-944
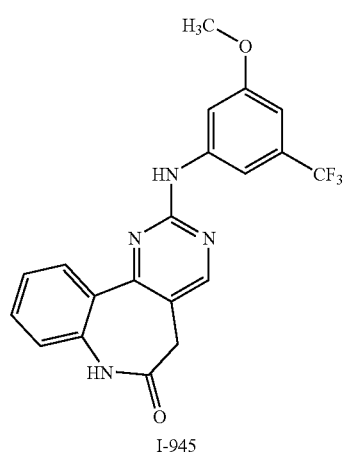
I-945
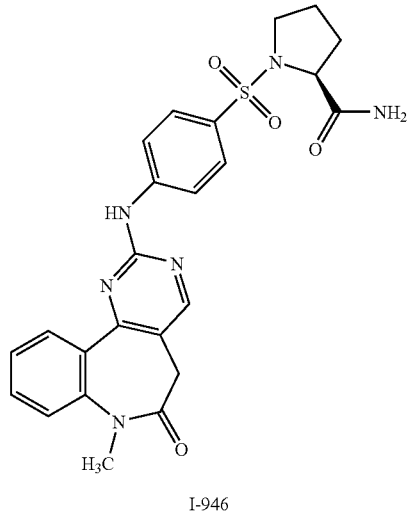
I-946

-continued
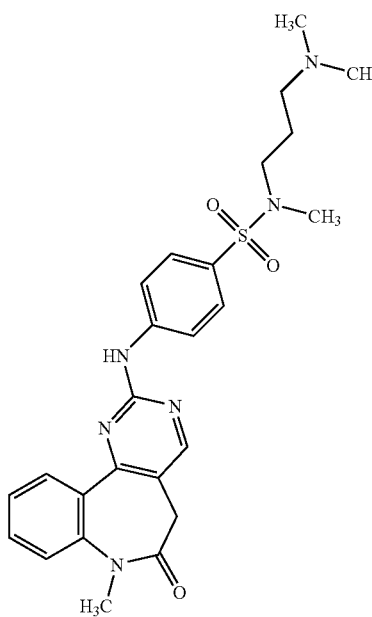
I-947
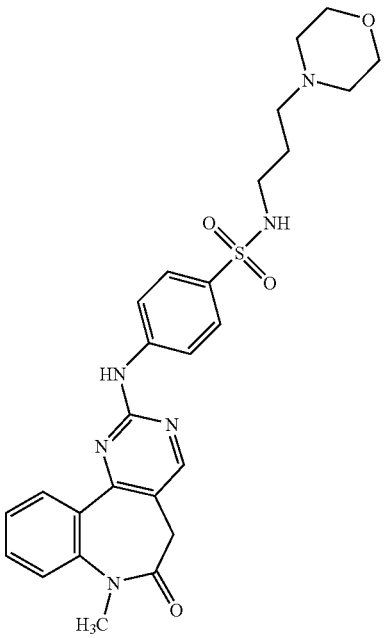
I-949
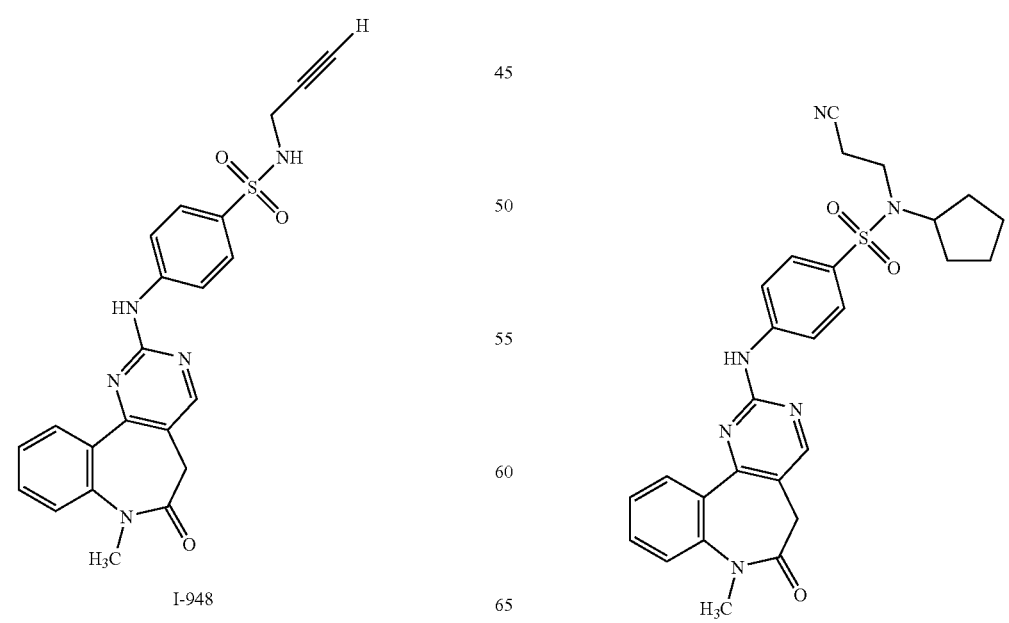
I-948
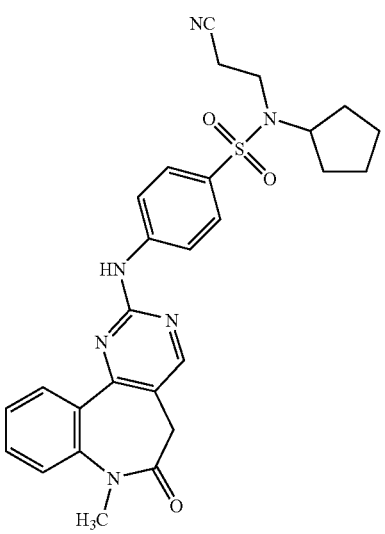
I-950

-continued
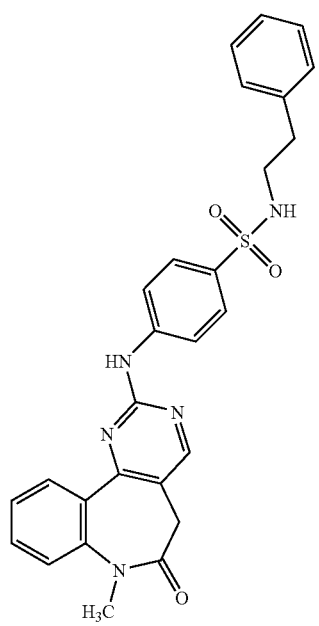
I-951
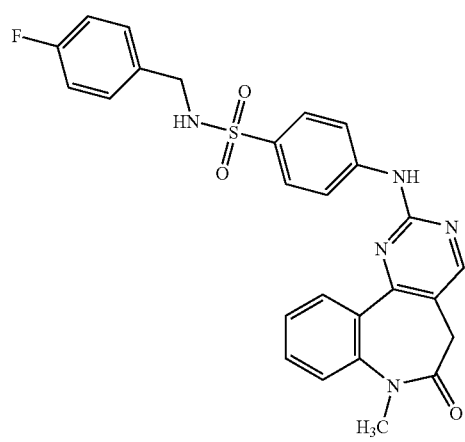
I-952
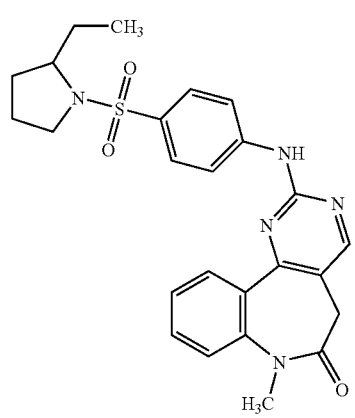
I-953
-continued
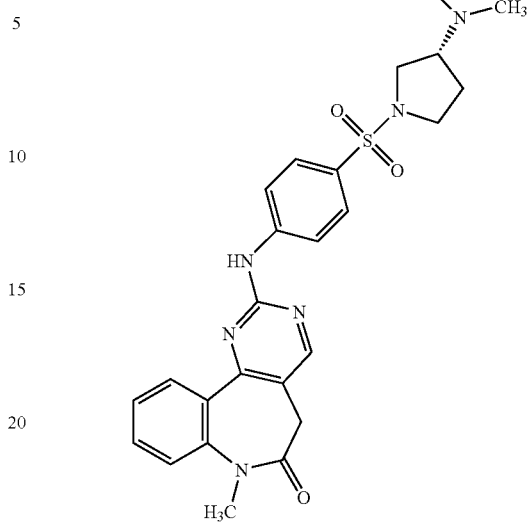
I-954
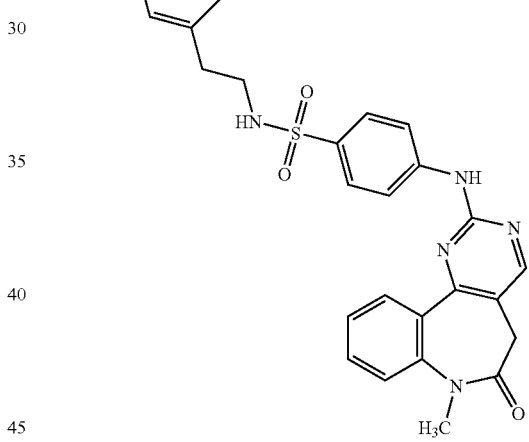
I-955
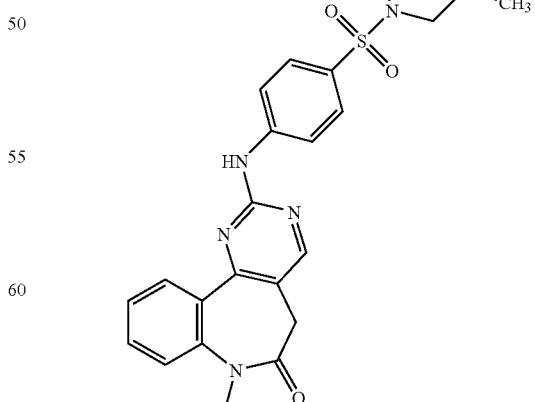
I-956

| 349 | 350 |
|---|---|
| -continued | -continued |
| 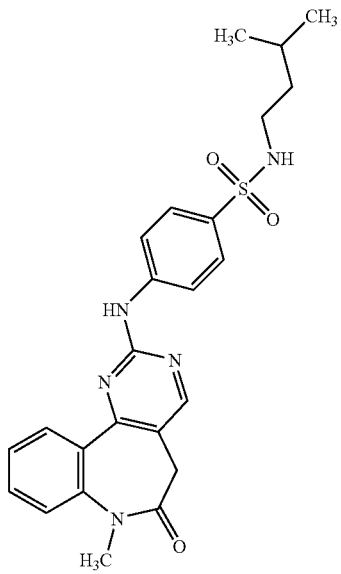<br>I-957 | 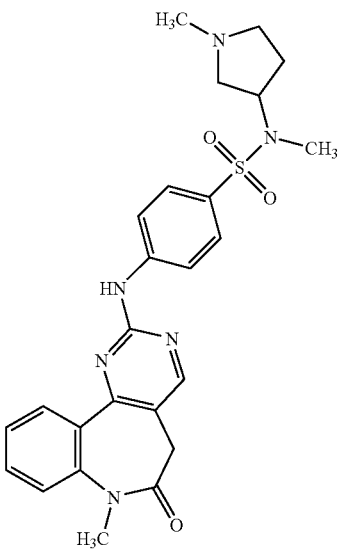<br>I-959 |
| 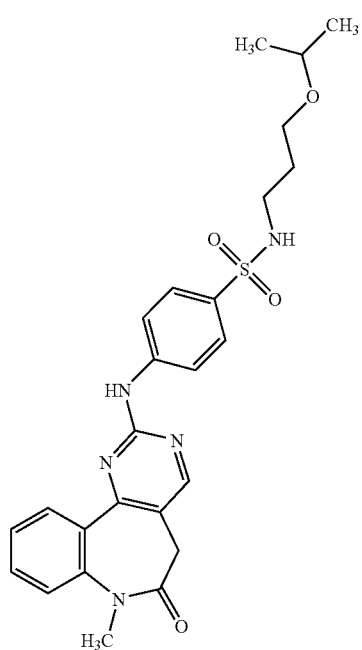<br>I-958 | 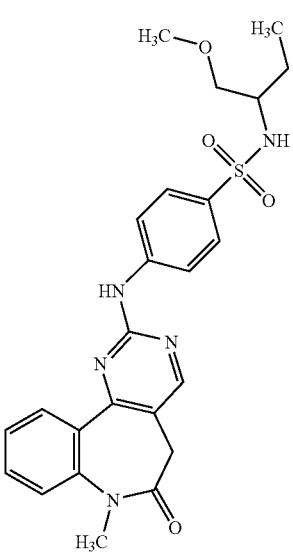<br>I-960 |

-continued
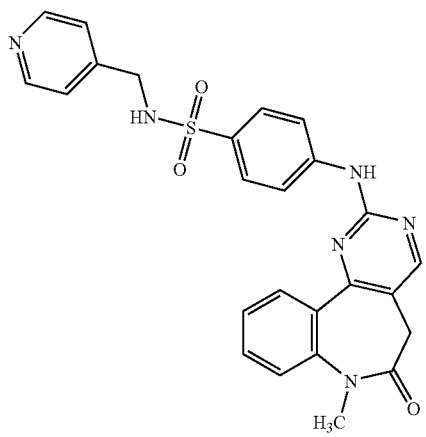
I-961
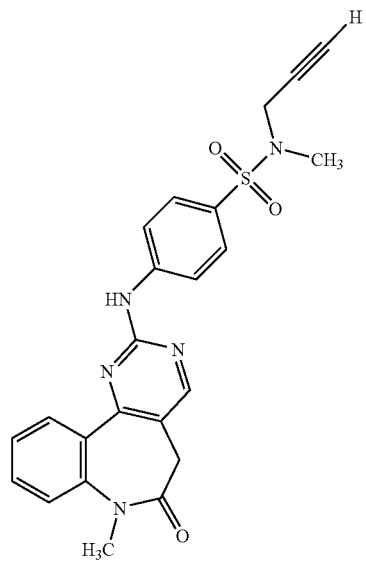
I-963
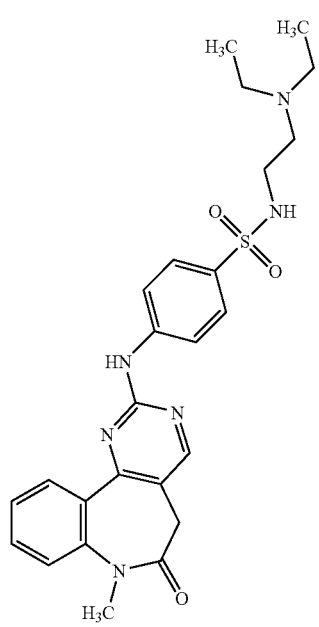
I-962
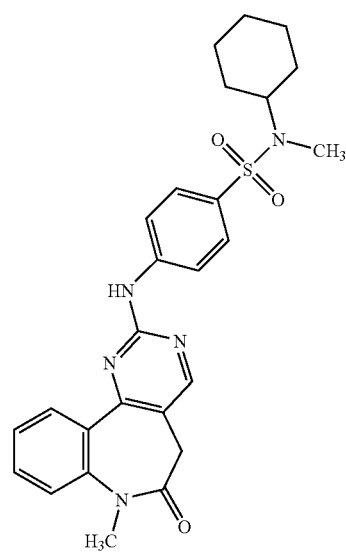
I-964

-continued
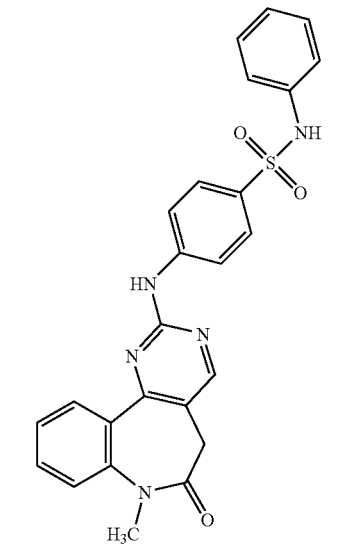
I-965
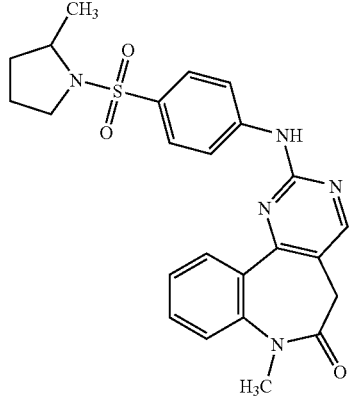
I-966
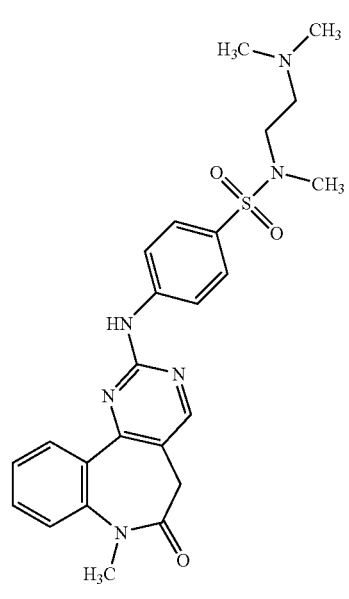
I-967
-continued
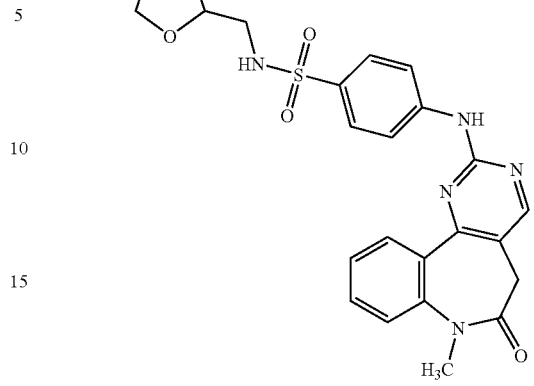
I-968
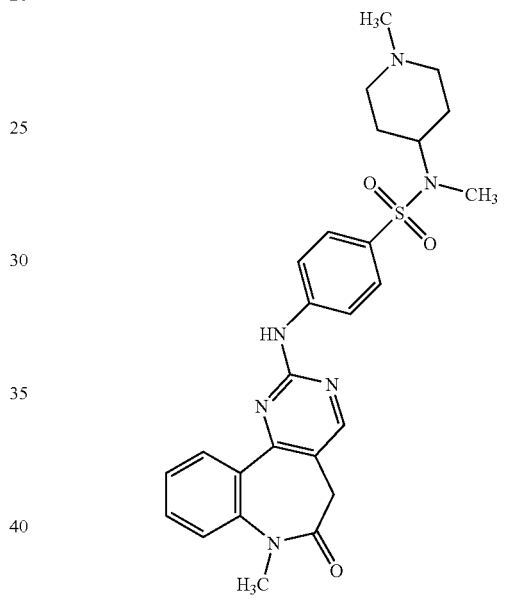
I-969
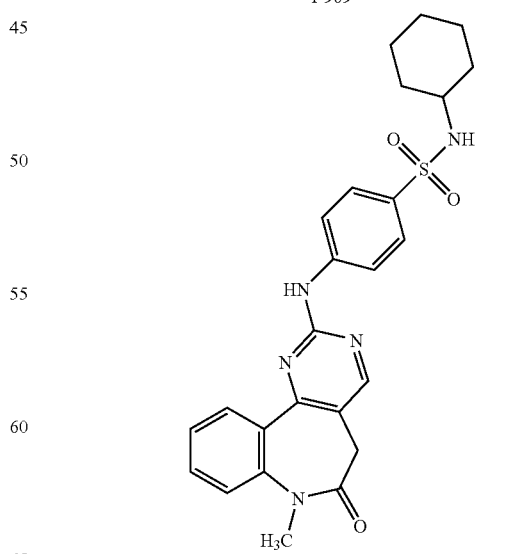
I-970

-continued
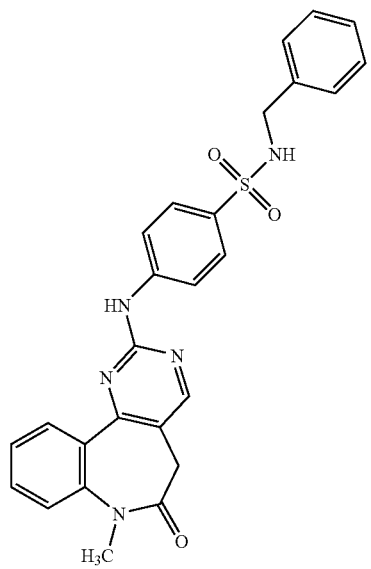
I-971
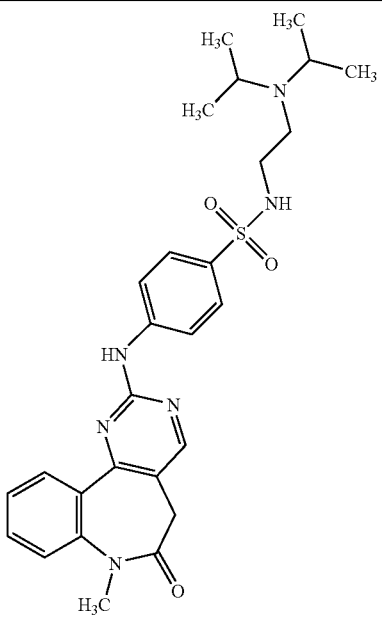
I-973
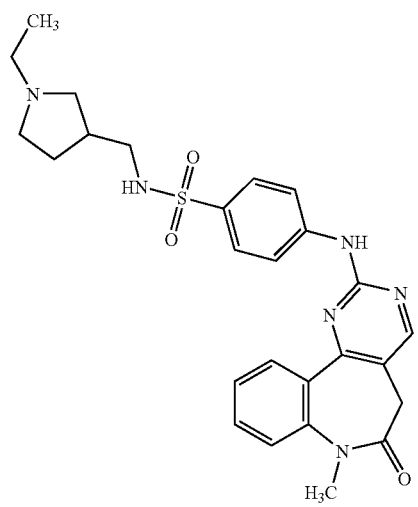
I-972
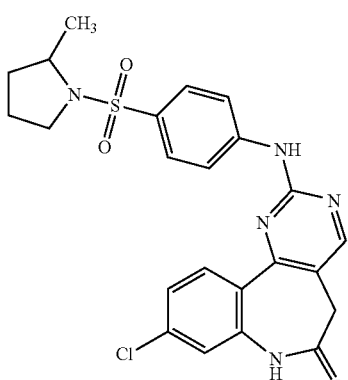
I-974

-continued
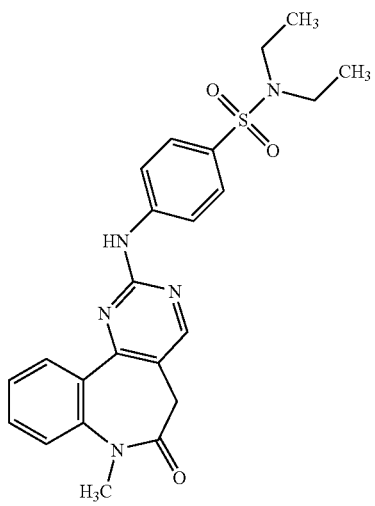
I-975
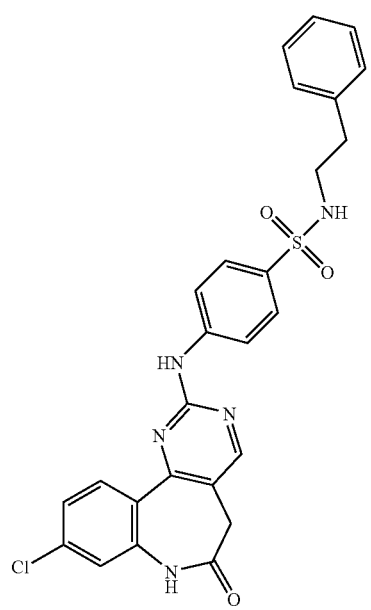
I-976
-continued
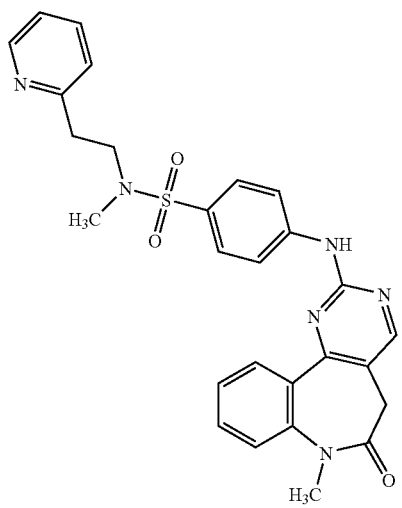
I-977
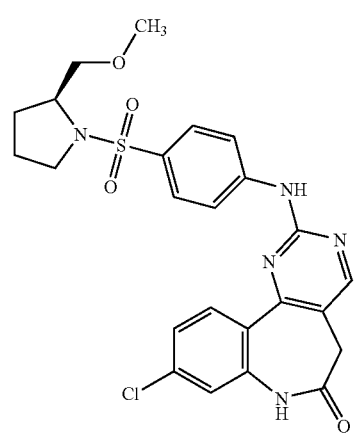
I-978

-continued
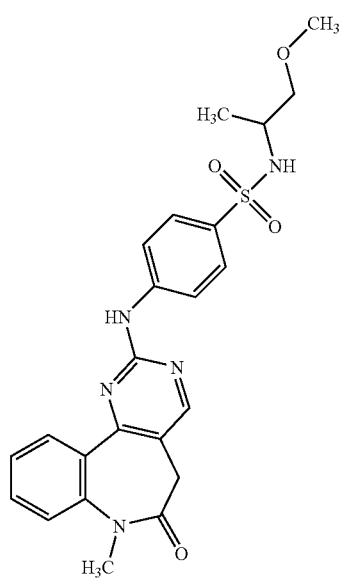
I-979
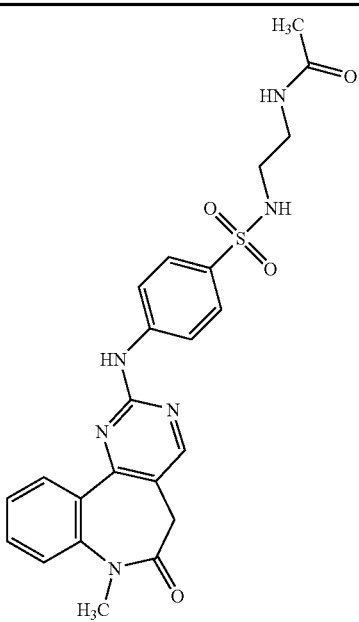
I-981
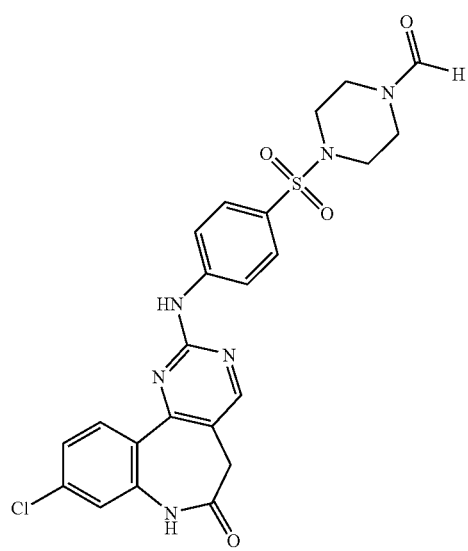
I-980
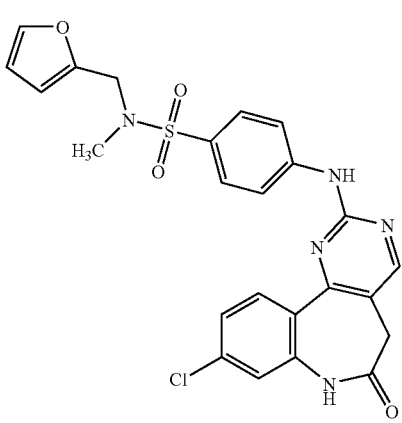
I-982

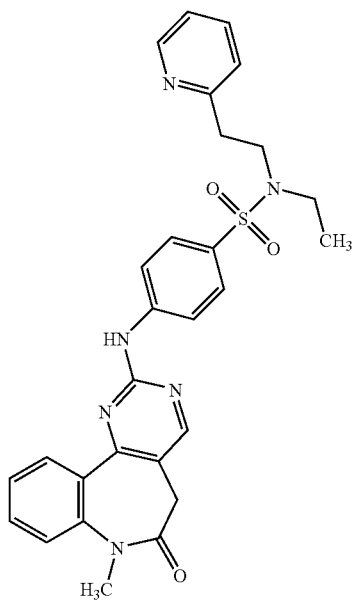
I-983
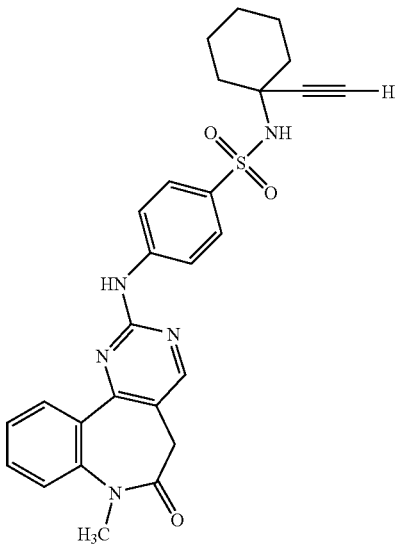
I-985
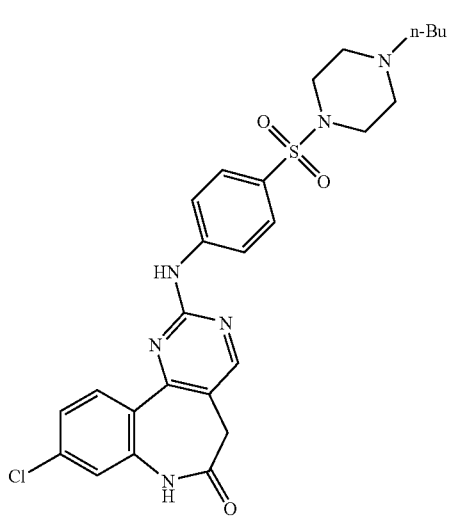
I-984
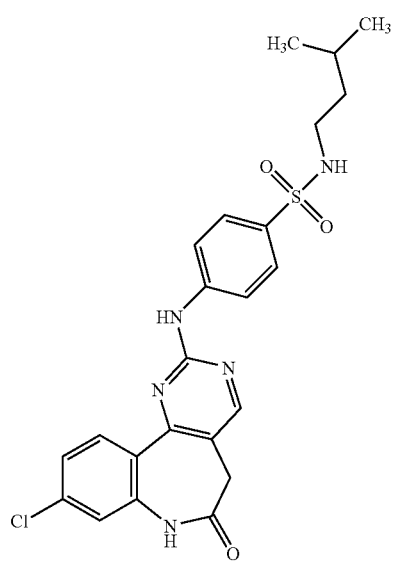
I-986

363
-continued
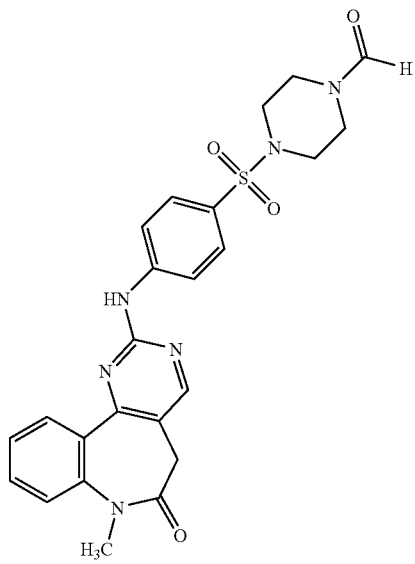
I-987
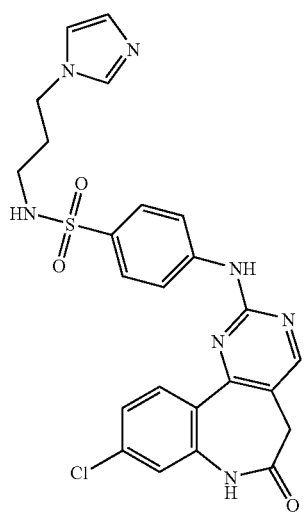
I-988
364
-continued
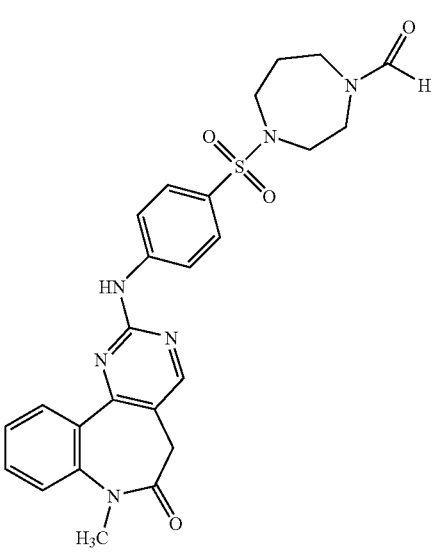
I-989
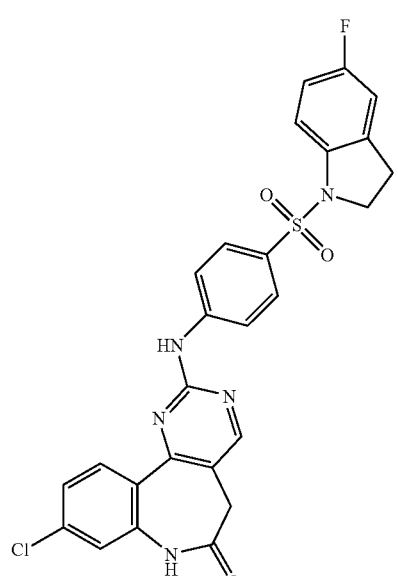
I-990

-continued
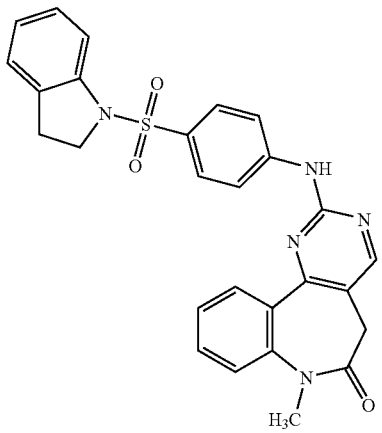
I-991
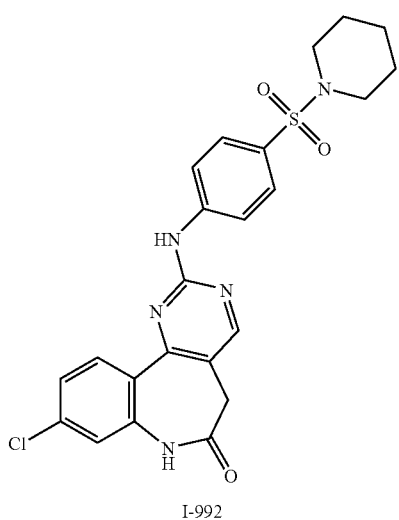
I-992
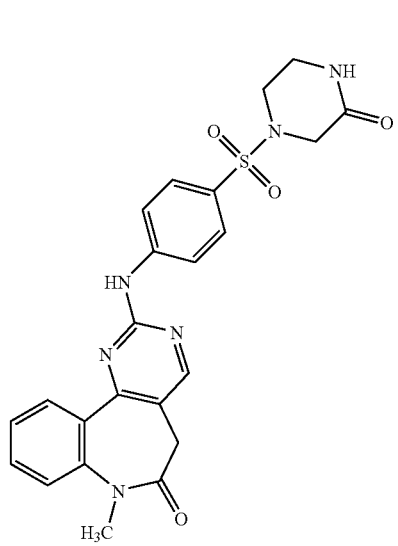
I-993
-continued
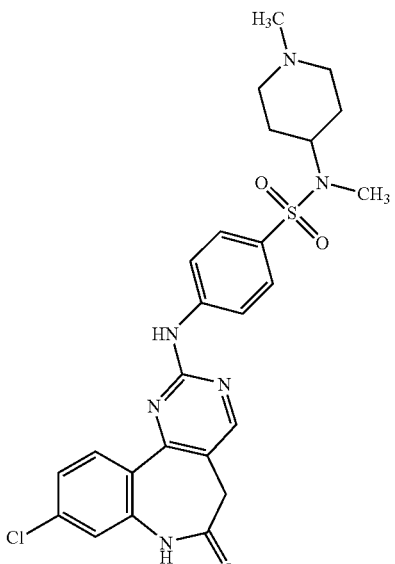
I-994
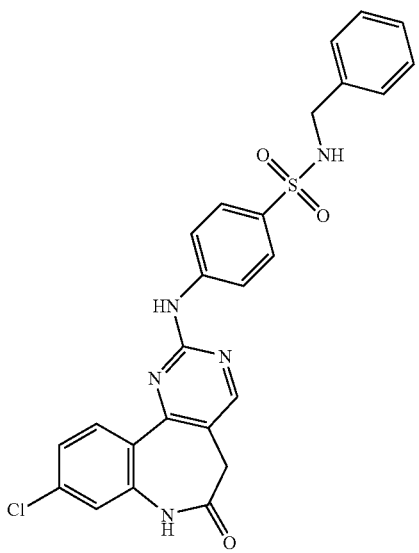
I-995

-continued
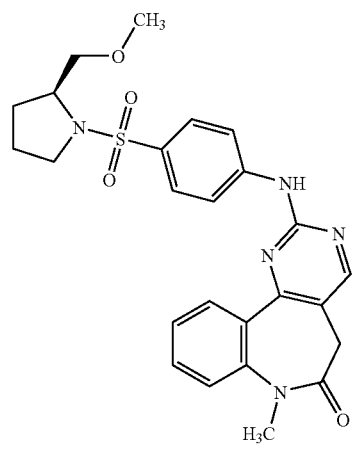
I-996
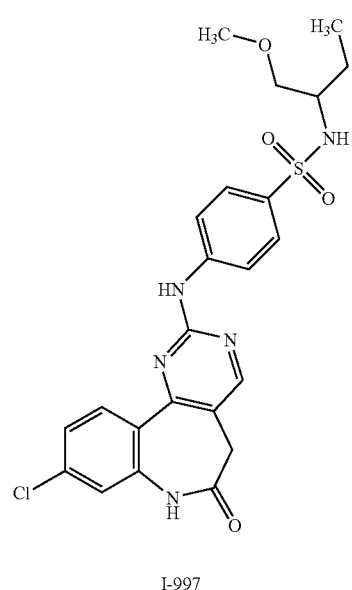
I-997
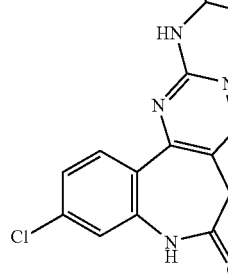
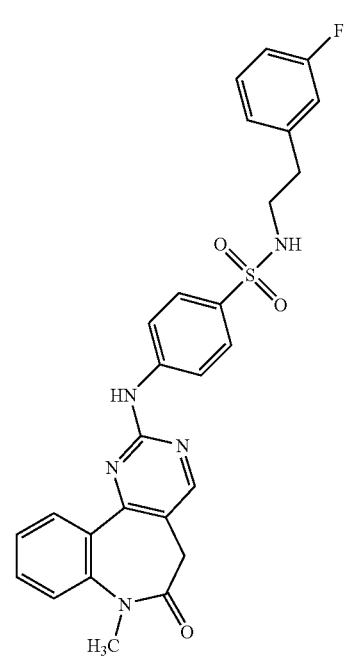
I-998
-continued
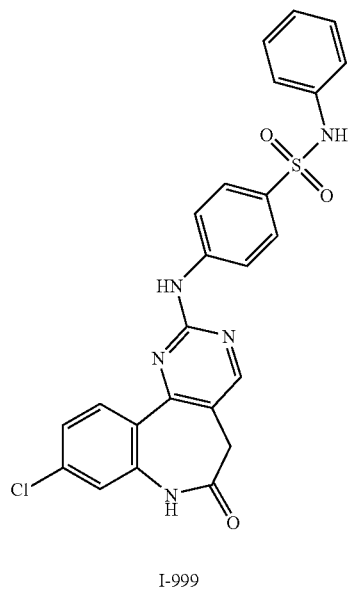
I-999
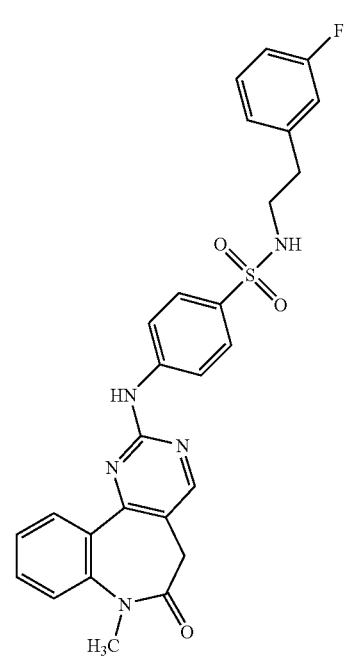
I-1000

-continued
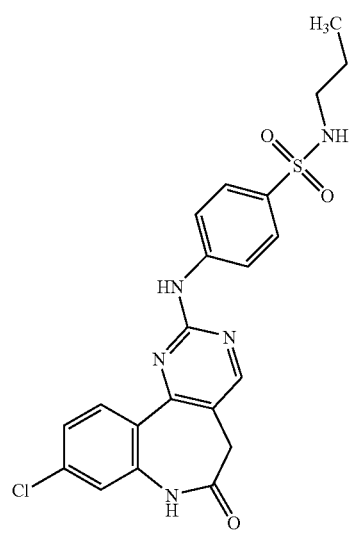
I-1001
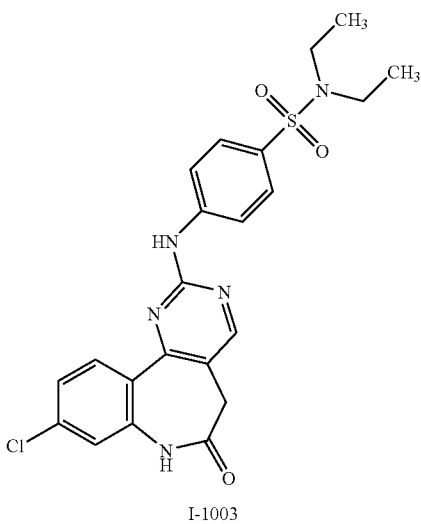
I-1003
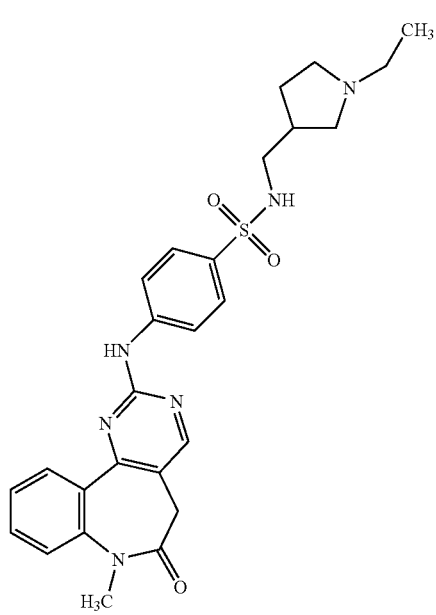
I-1002
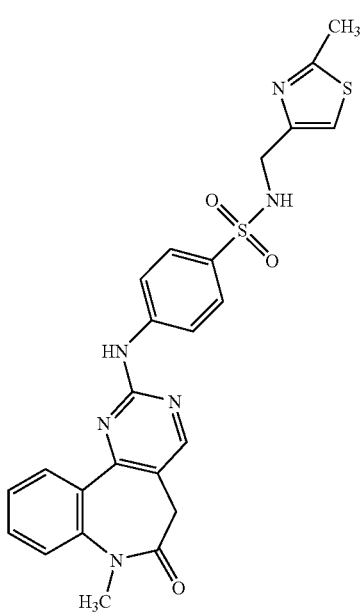
I-1004

-continued
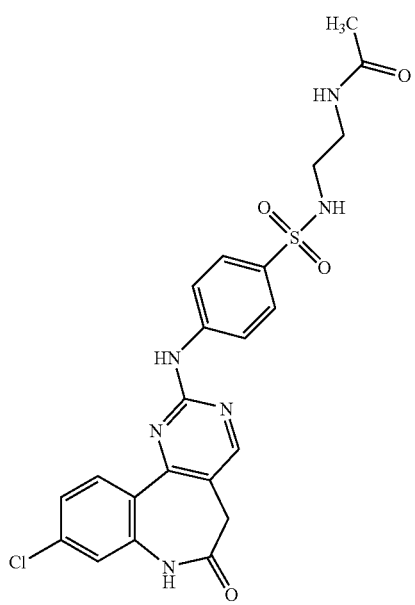
I-1005
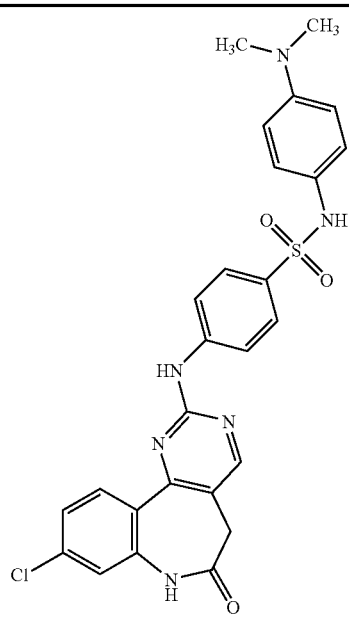
I-1007
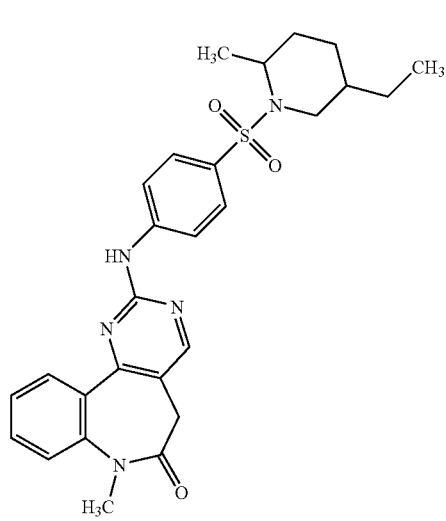
I-1006
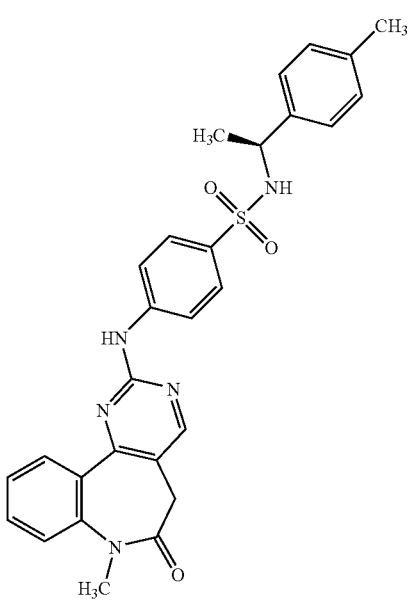
I-1008

-continued
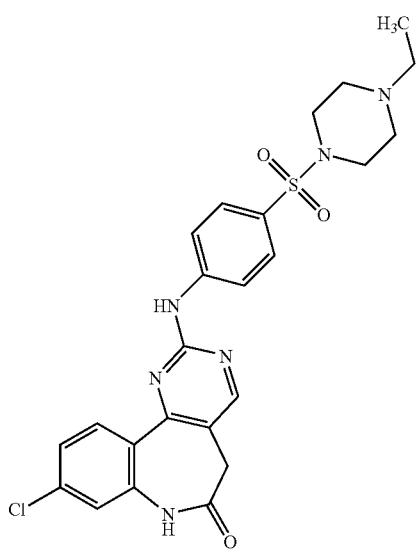
I-1009
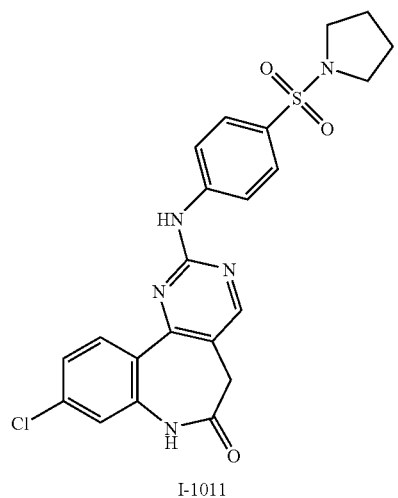
I-1011
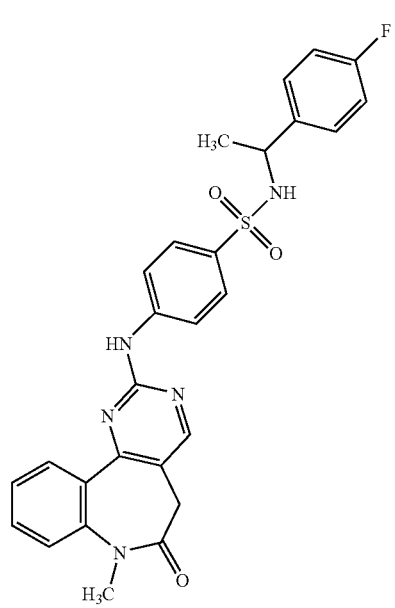
I-1010
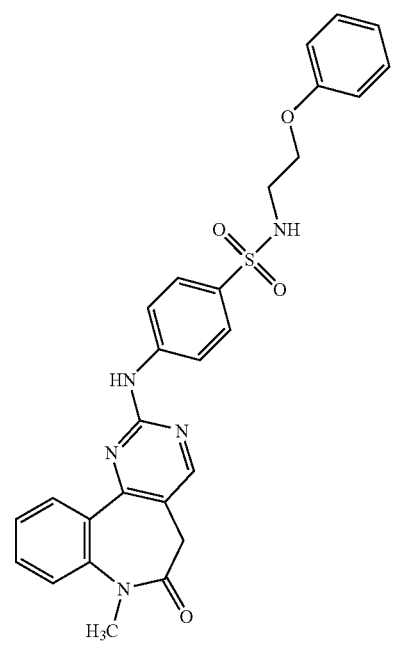
I-1012

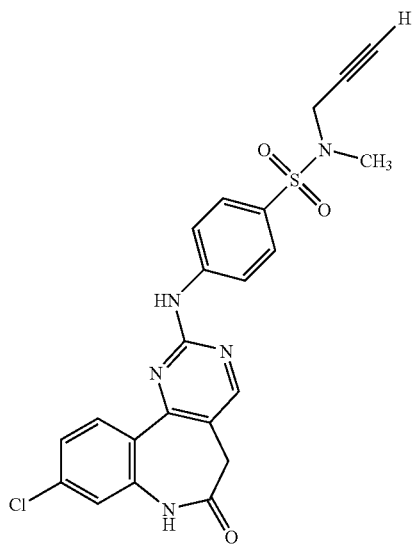
I-1013
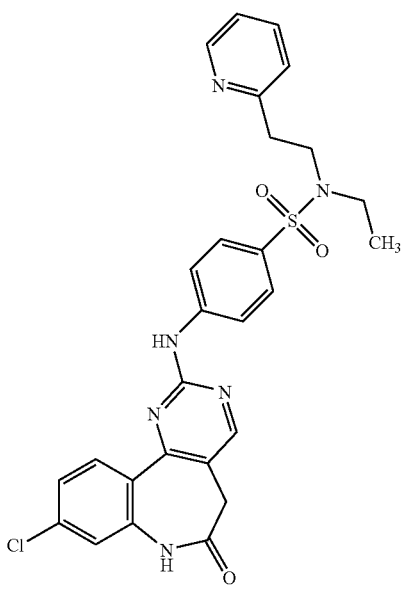
I-1015
I-1014
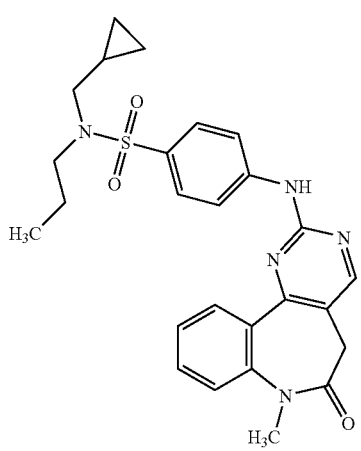
I-1016

-continued
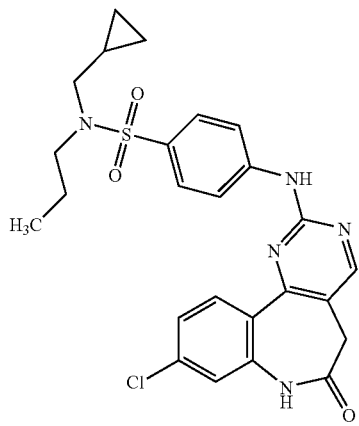
I-1017
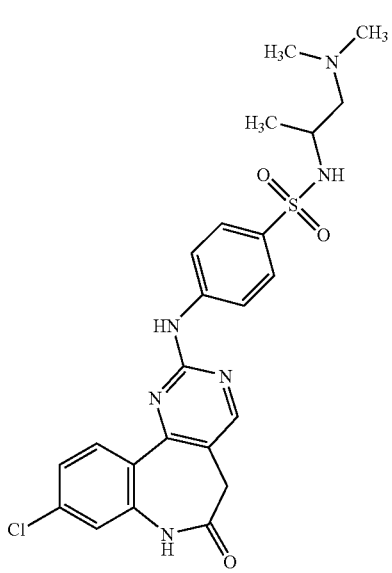
I-1019
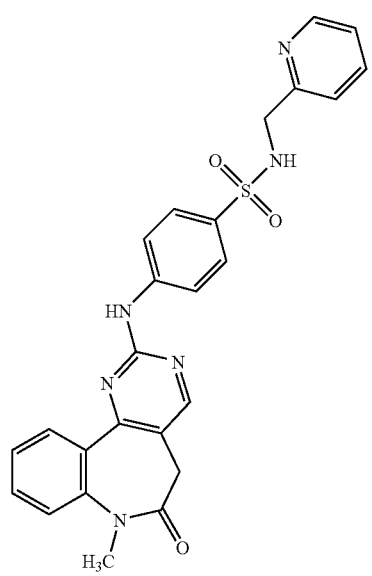
I-1018
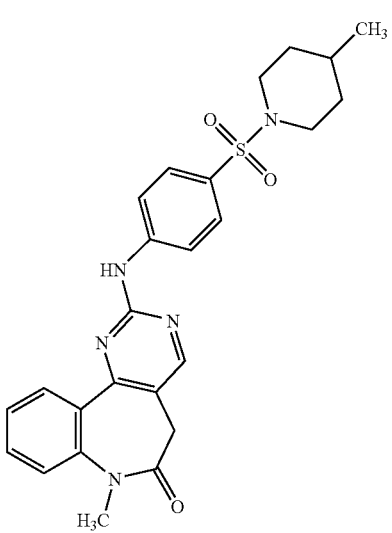
I-1020

-continued
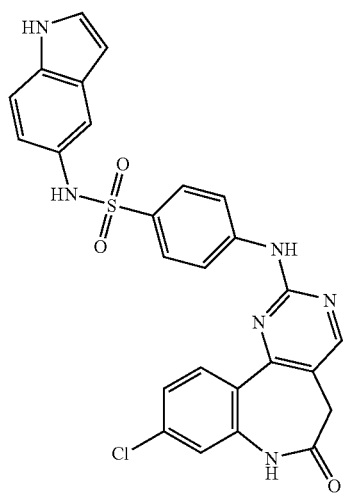
I-1021
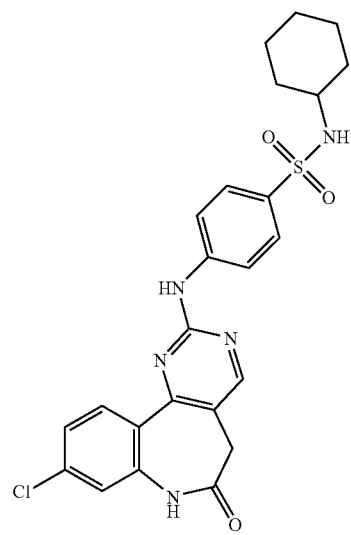
I-1023
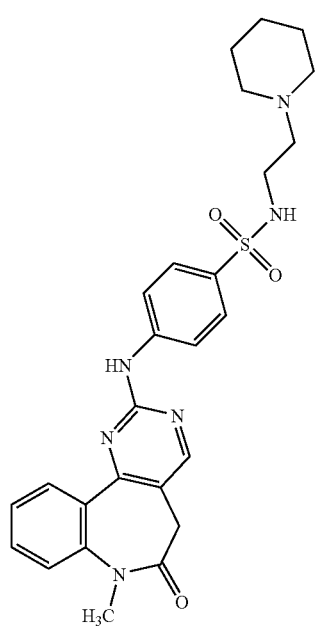
I-1022
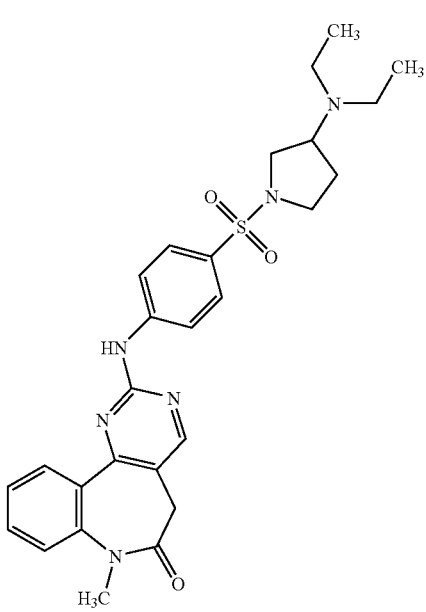
I-1024

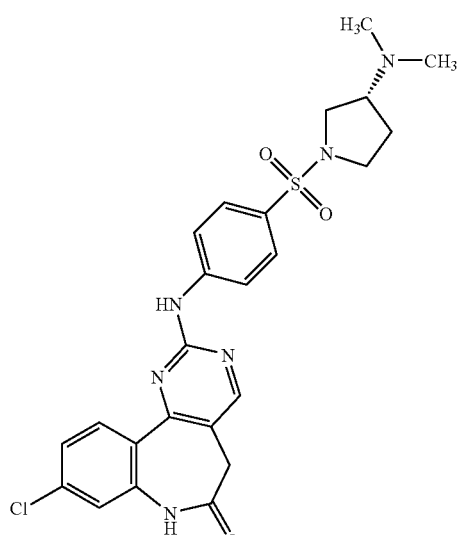
I-1025
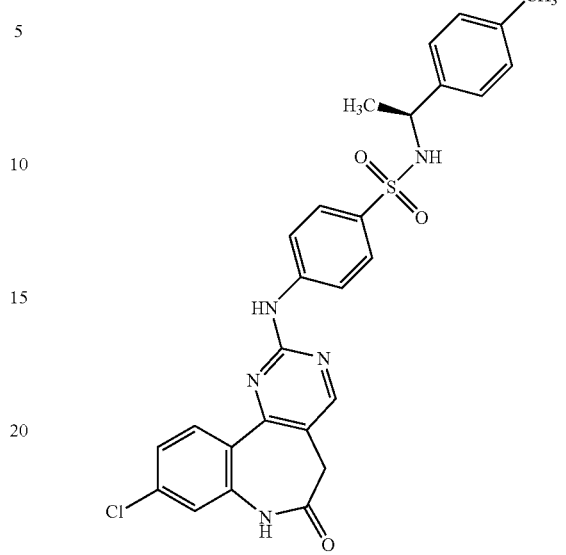
I-1027
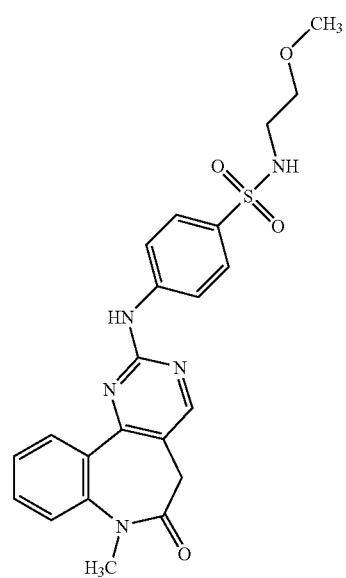
I-1026
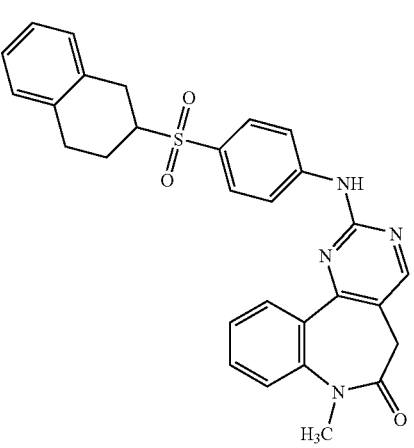
I-1028

-continued
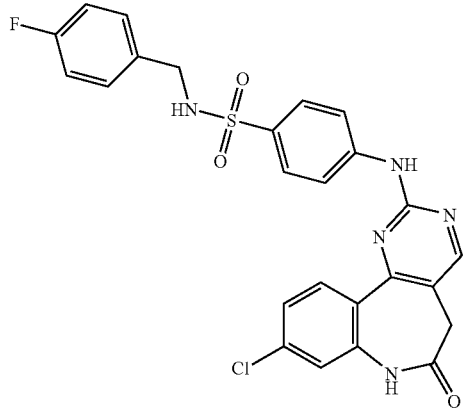
I-1029
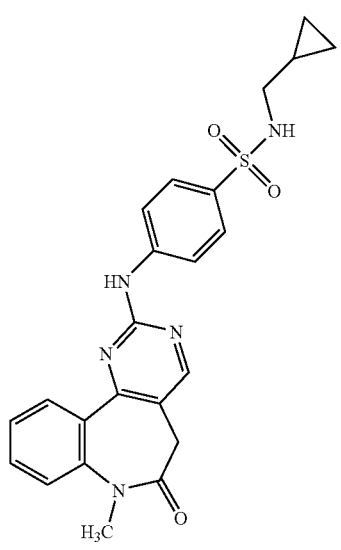
I-1030
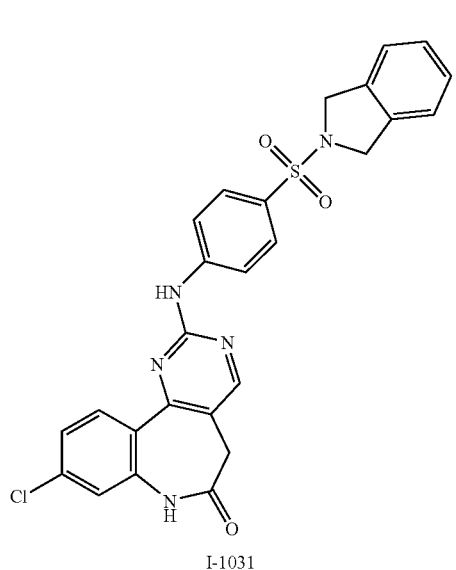
I-1031
-continued
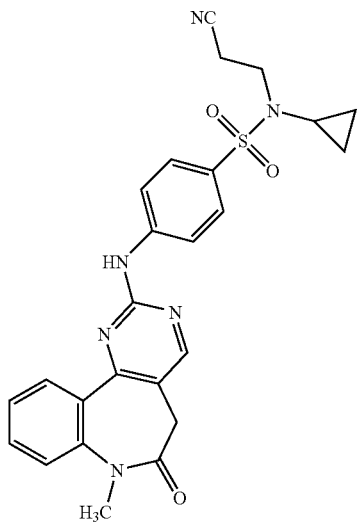
I-1032
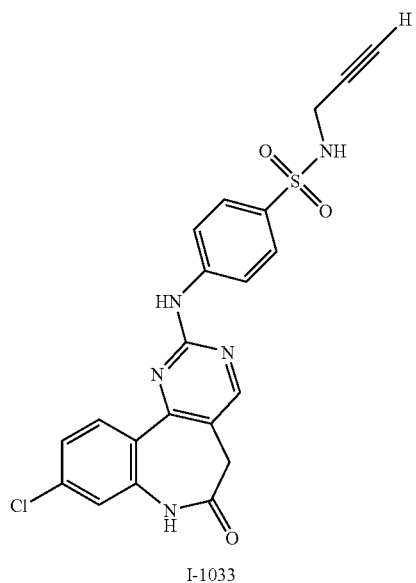
I-1033

-continued
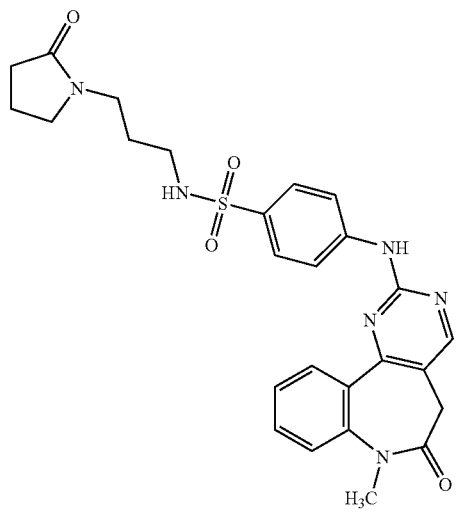
I-1034
-continued
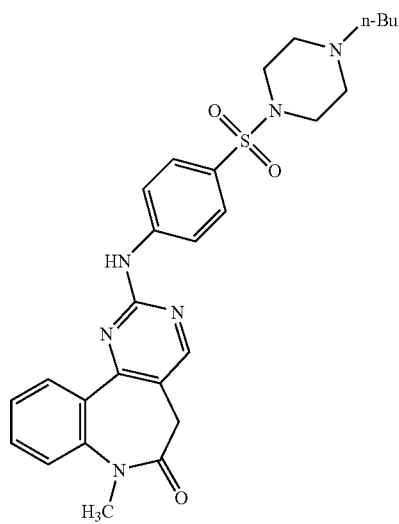
I-1036
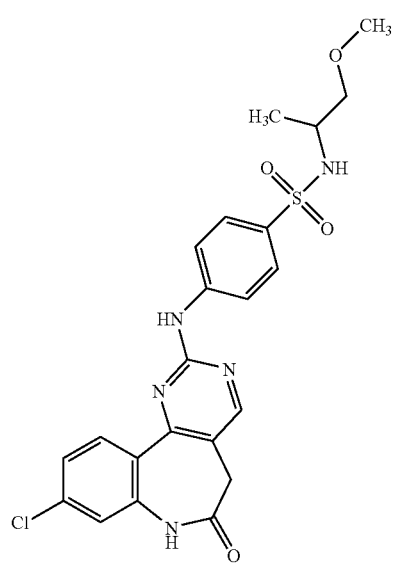
I-1035
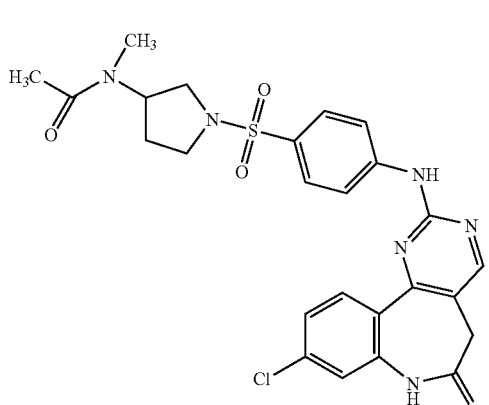
I-1037

387 388
-continued
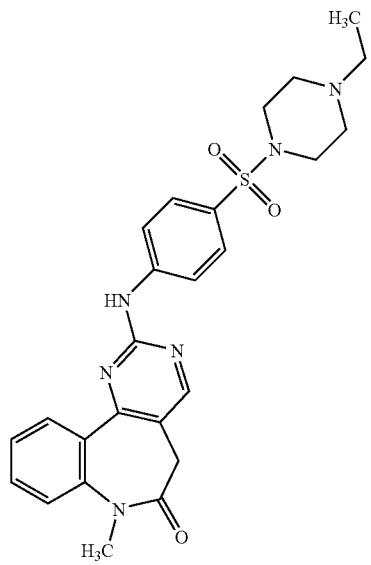
I-1038
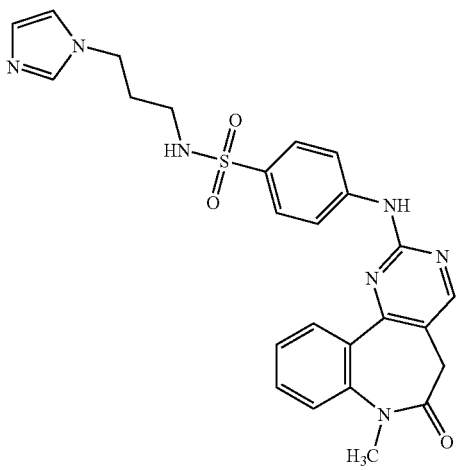
I-1040
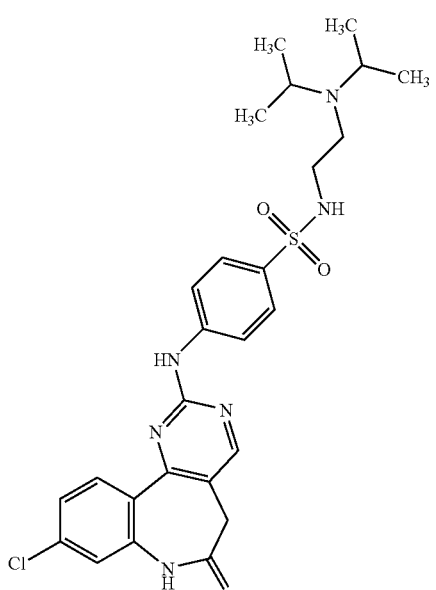
I-1039
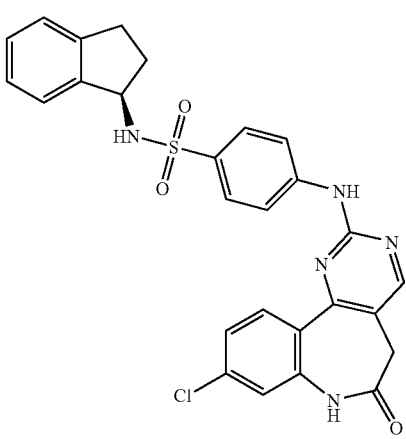
I-1041

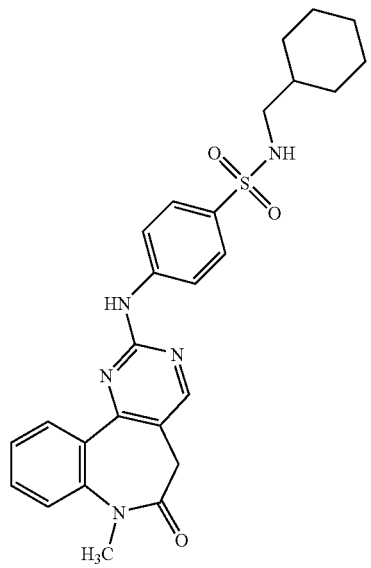
I-1042
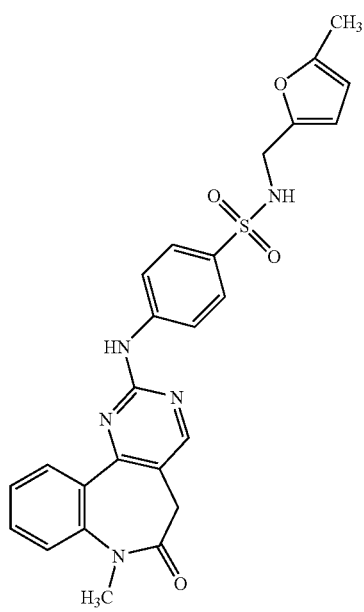
I-1044
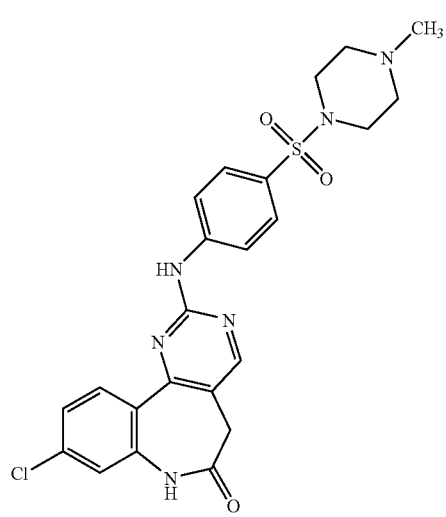
I-1043
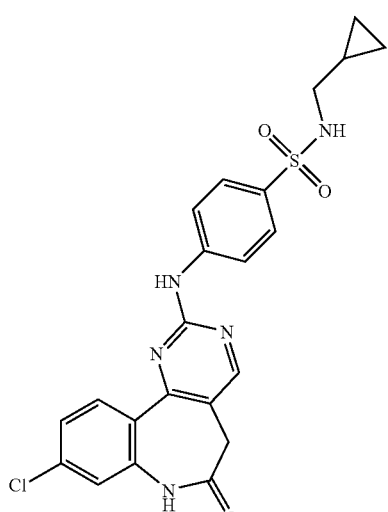
I-1045

391 -continued
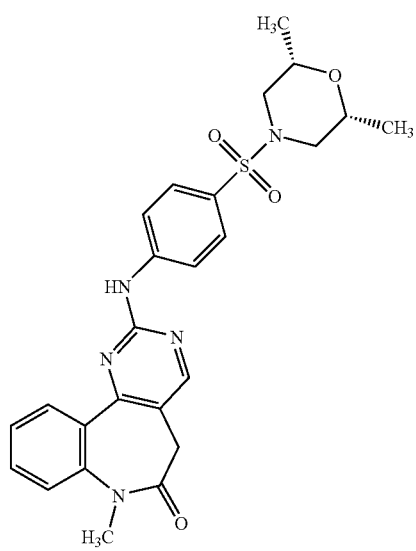
I-1046
I-1047
392 -continued
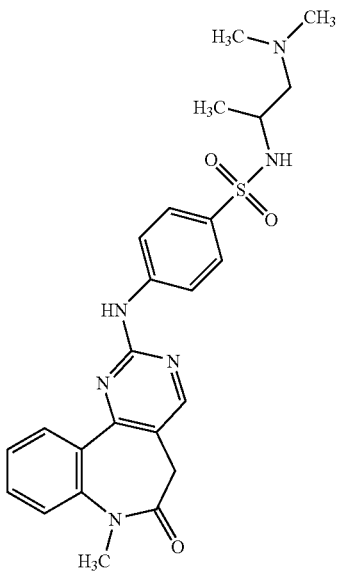
I-1048
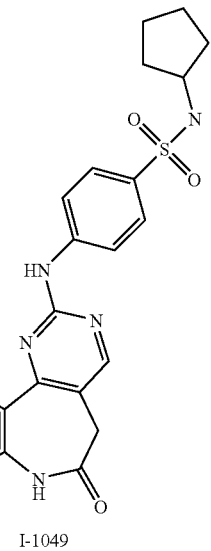
I-1049

-continued
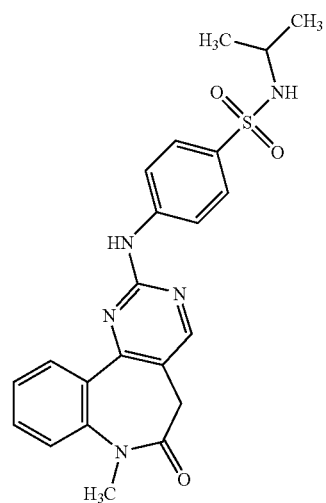
I-1050
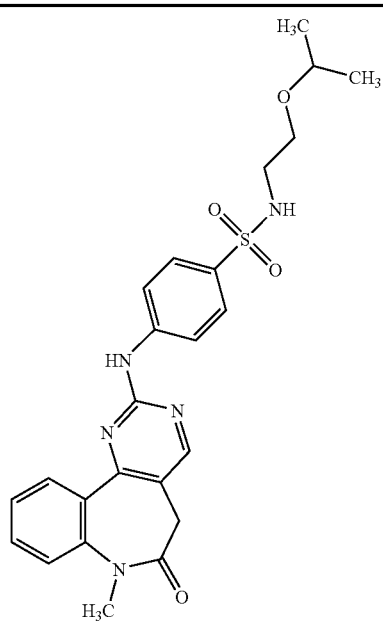
I-1052
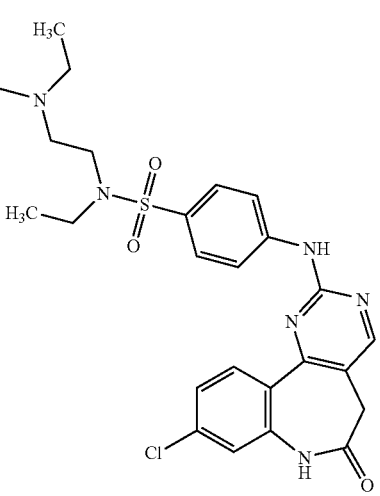
I-1051
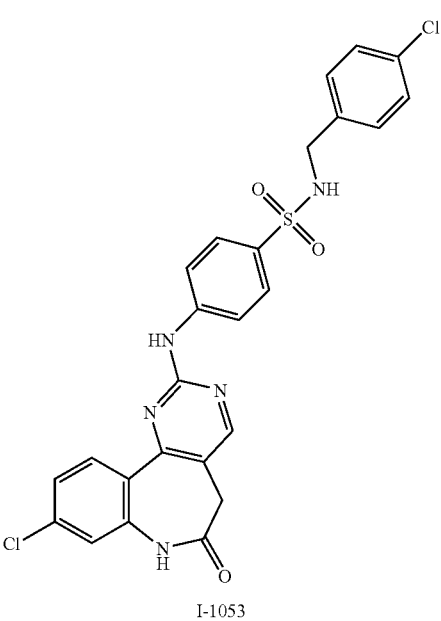
I-1053

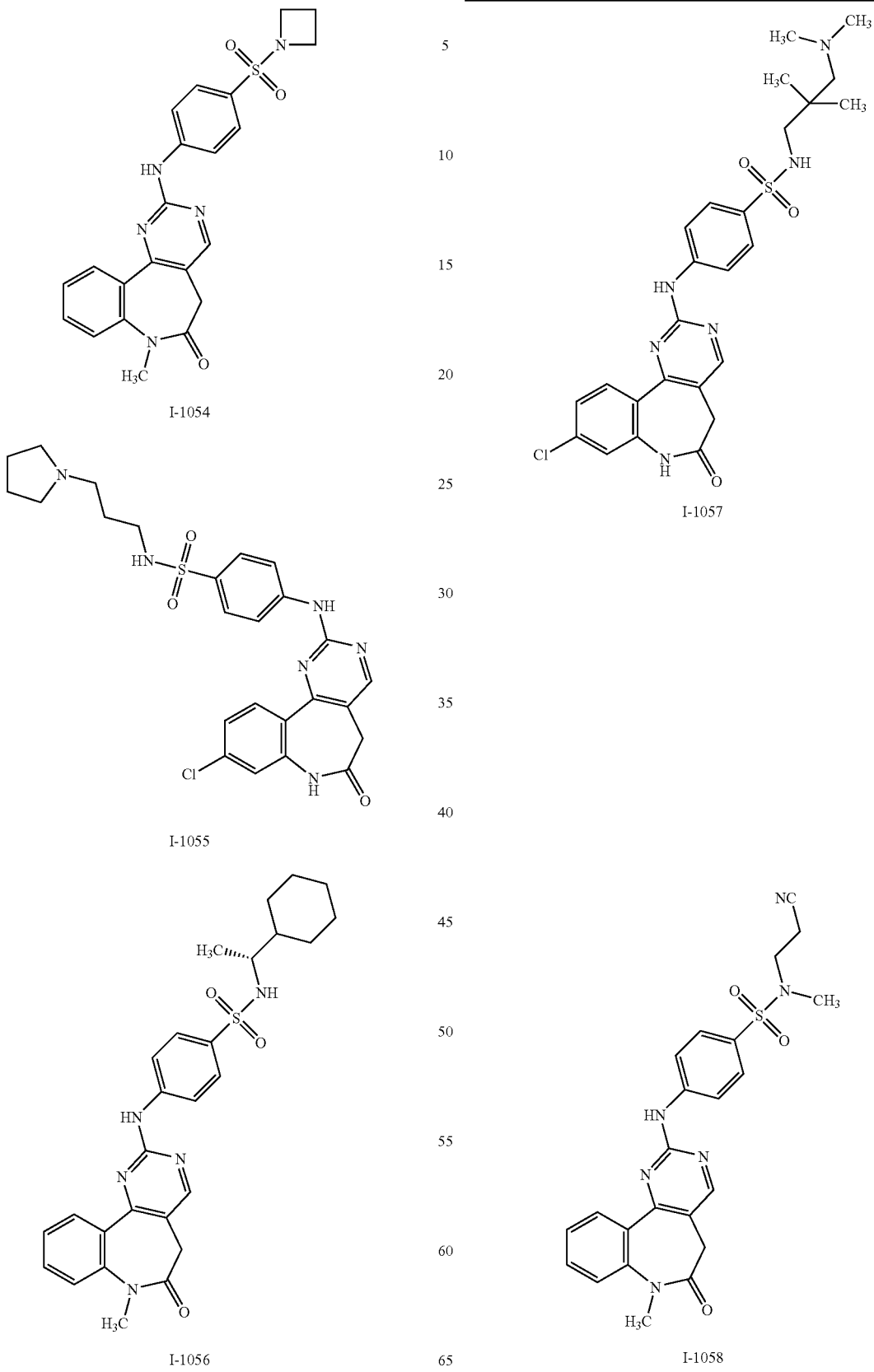

-continued
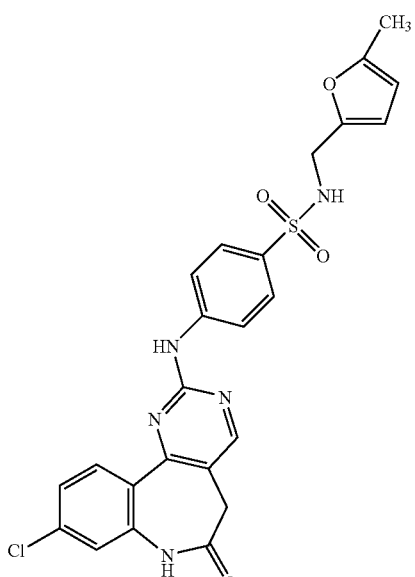
I-1059
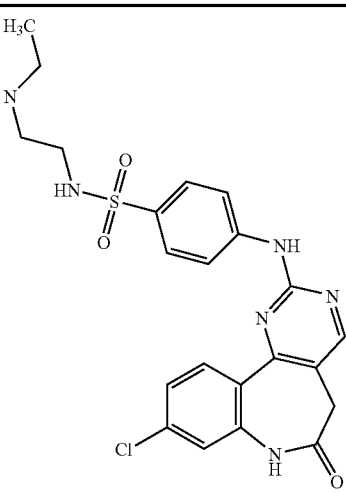
I-1061
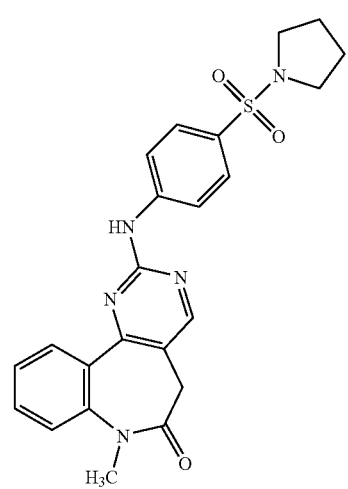
I-1060
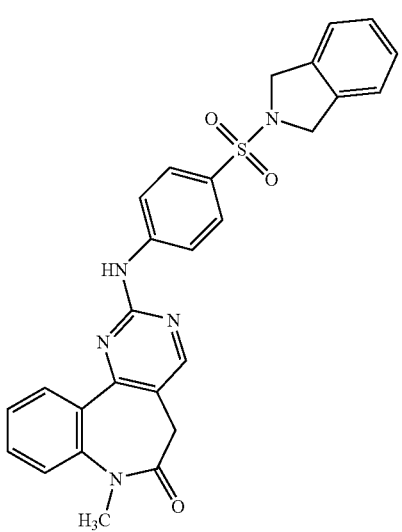
I-1062

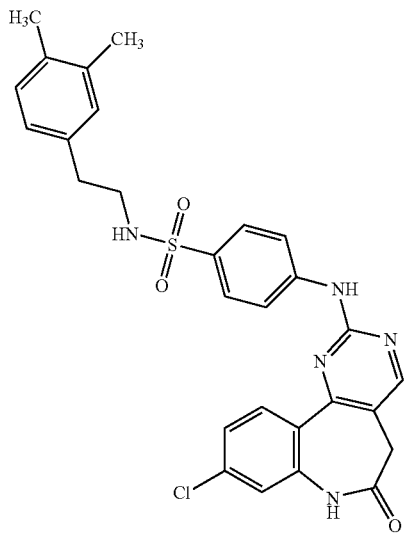
I-1063
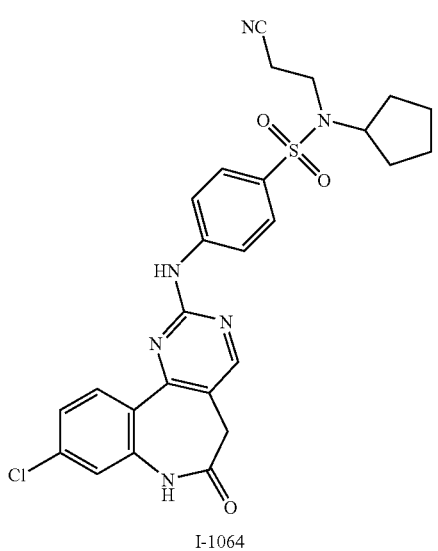
I-1064
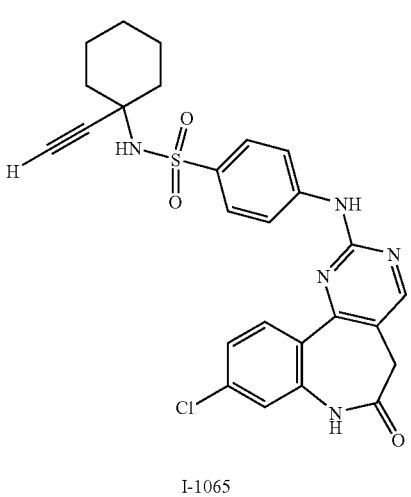
I-1065
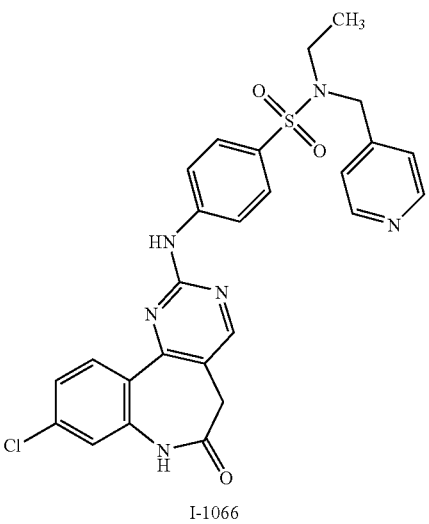
I-1066
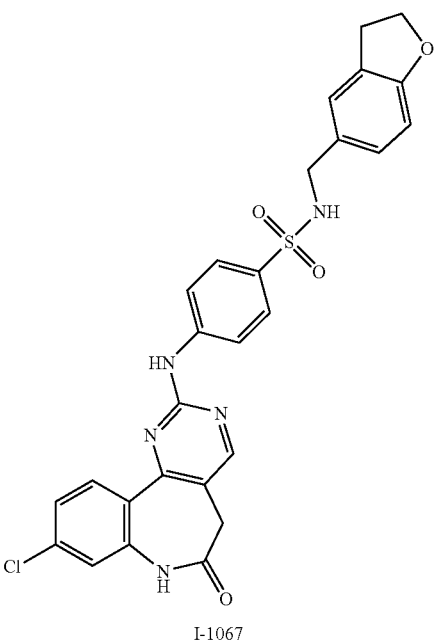
I-1067

-continued
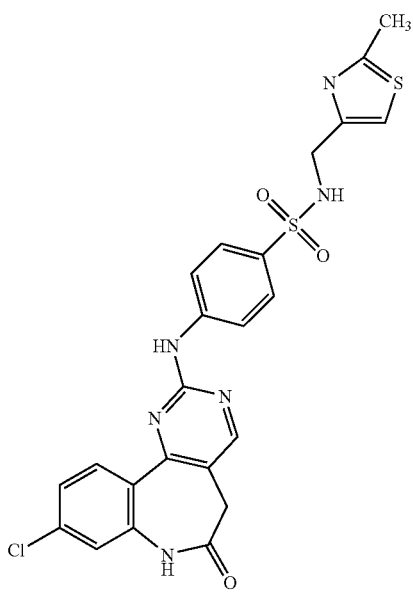
I-1068
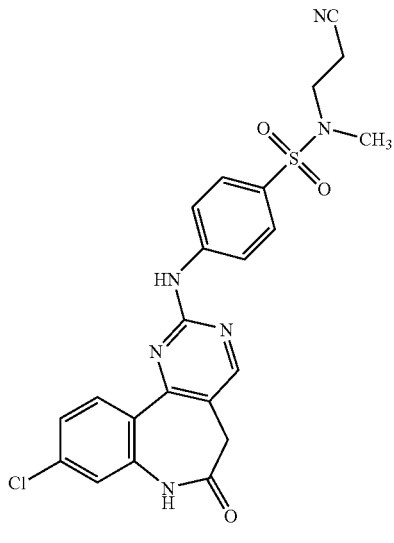
I-1070
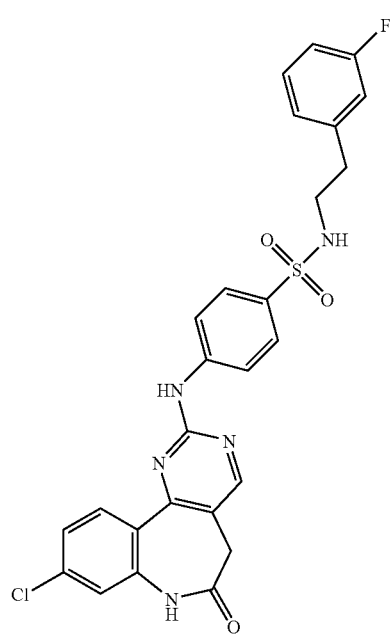
I-1069
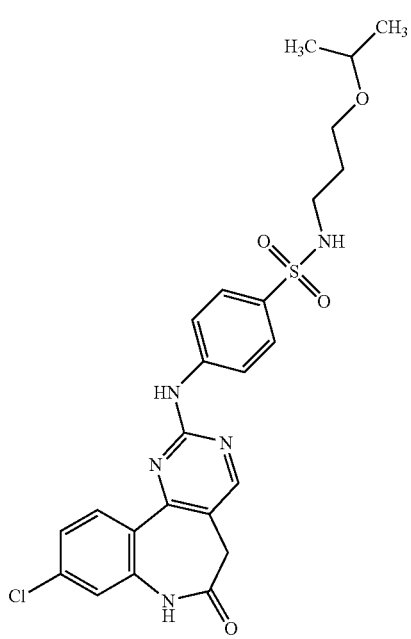
I-1071

403
-continued
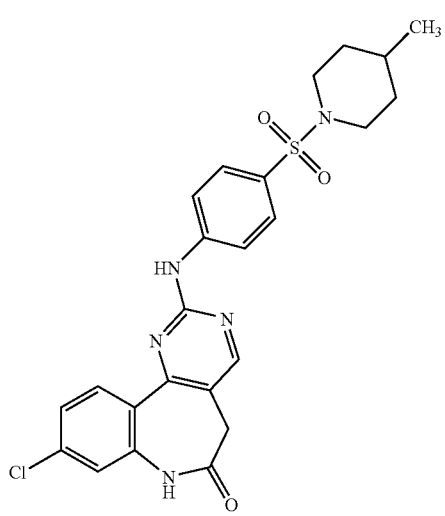
I-1072
I-1073
404
-continued
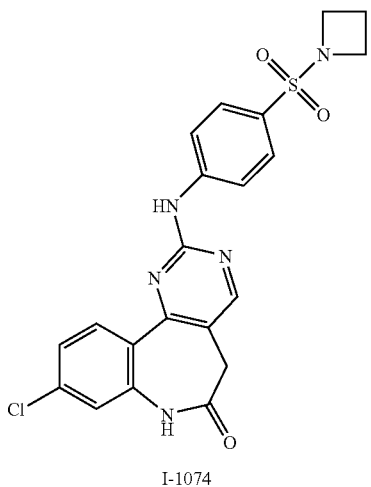
I-1074
I-1075

-continued
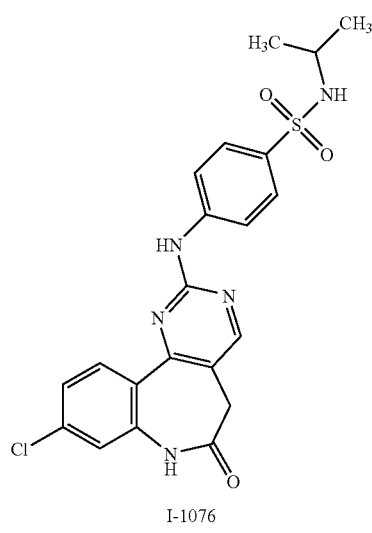
I-1076
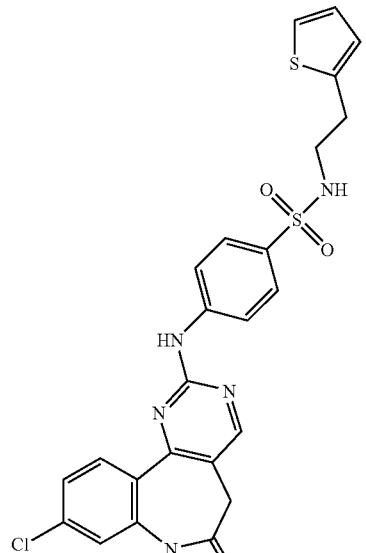
I-1078
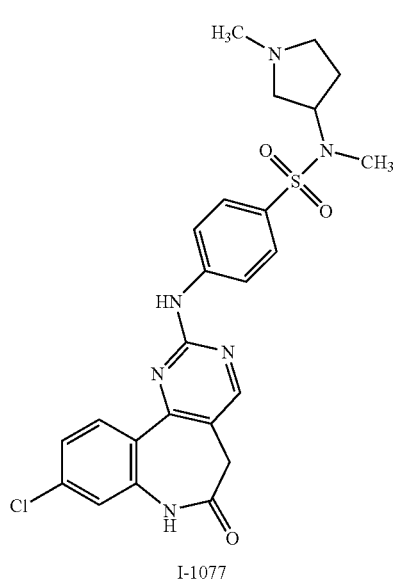
I-1077
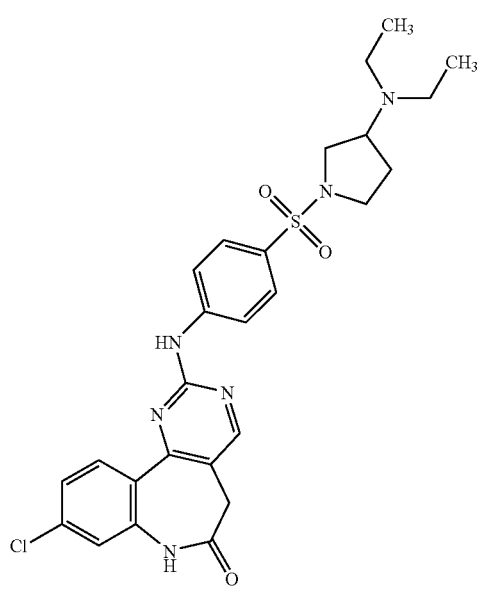
I-1079

-continued
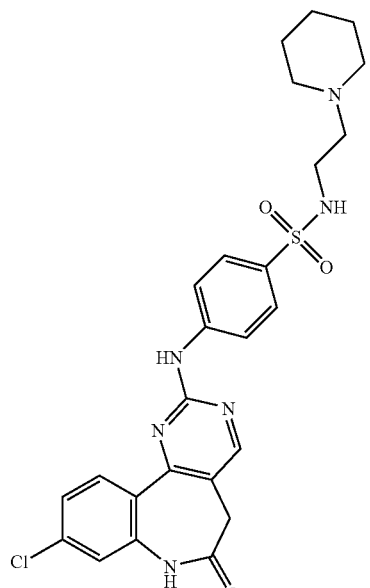
I-1080
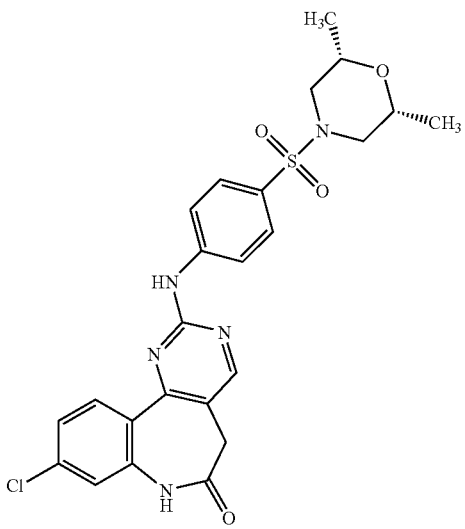
I-1082
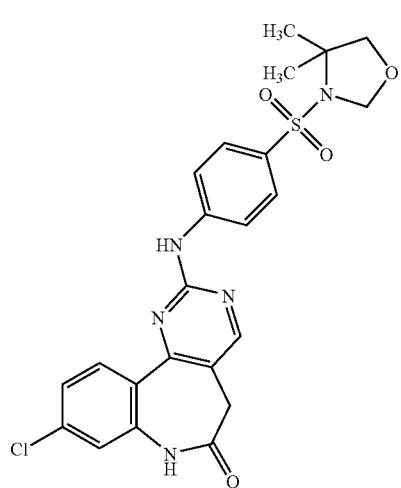
I-1081
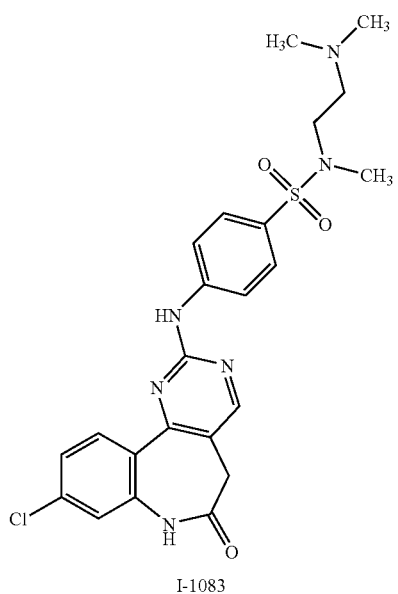
I-1083

-continued
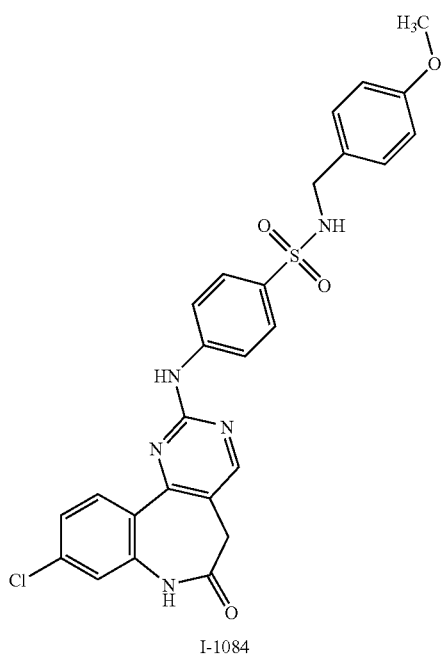
I-1084
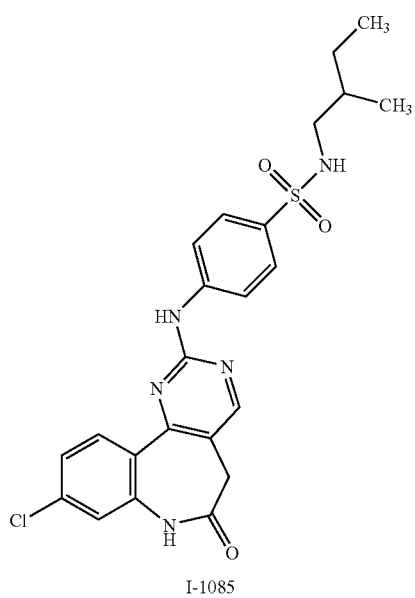
I-1085
-continued
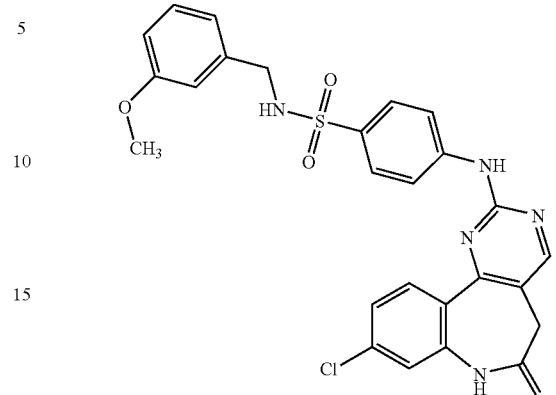
I-1086
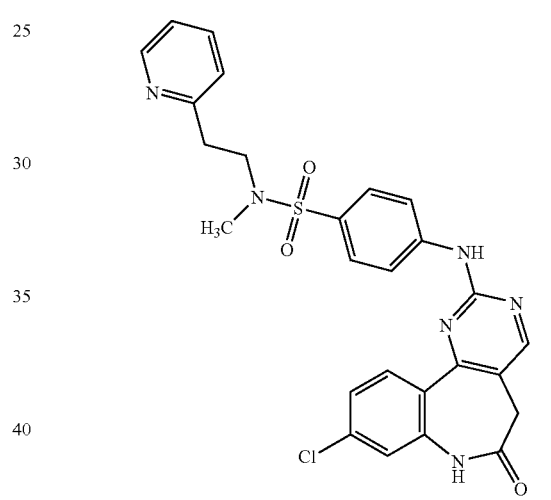
I-1087
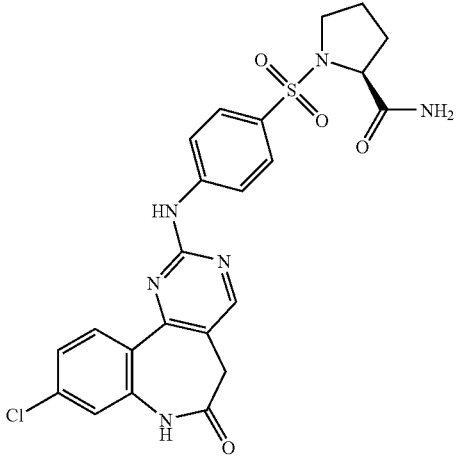
I-1088

-continued
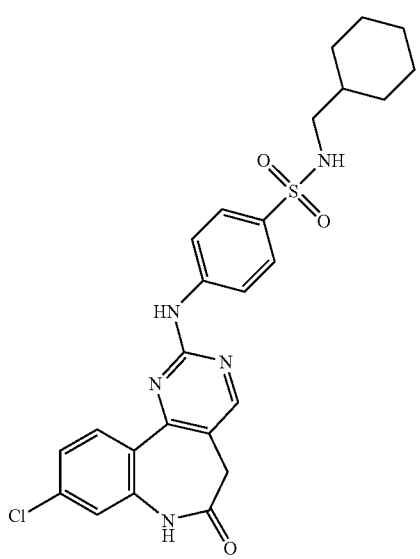
I-1089
-continued
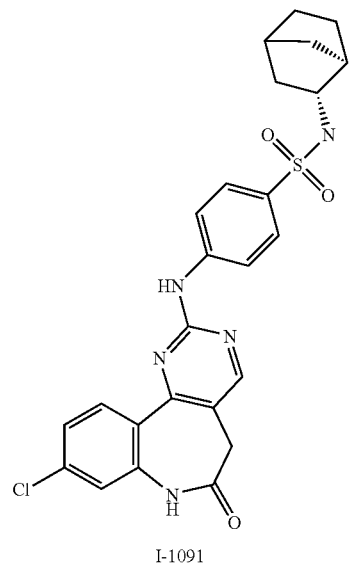
I-1091
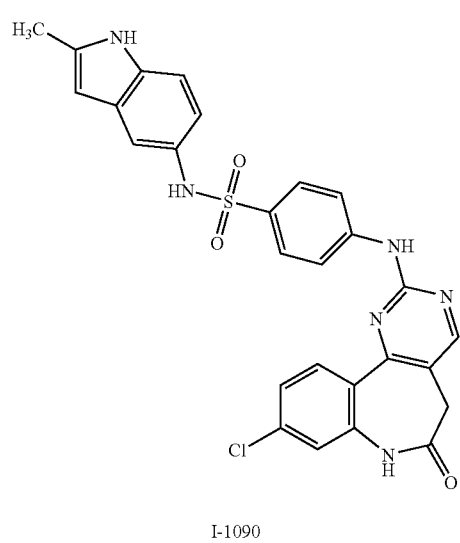
I-1090
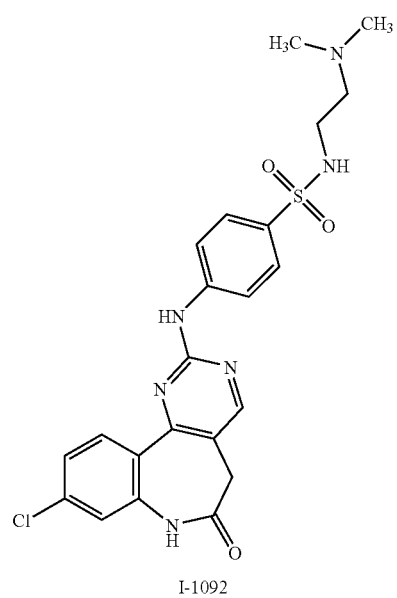
I-1092

-continued
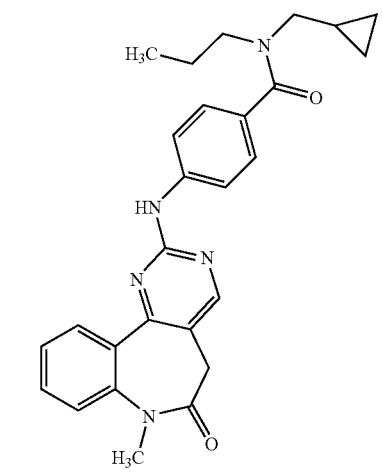
I-1093
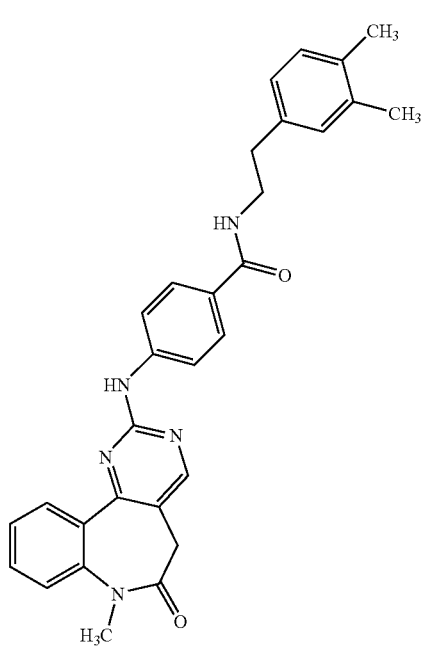
I-1094
-continued
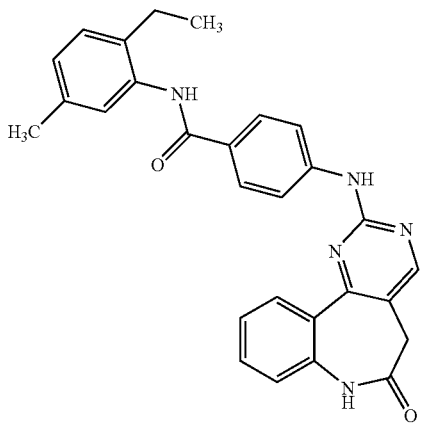
I-1095
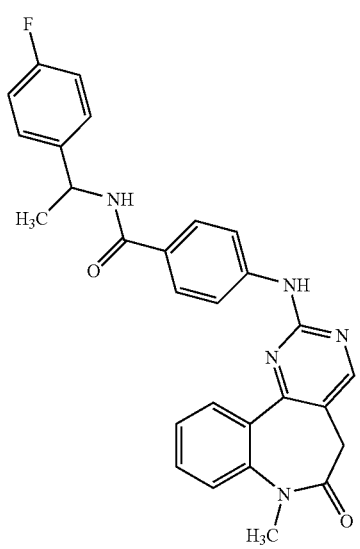
I-1096
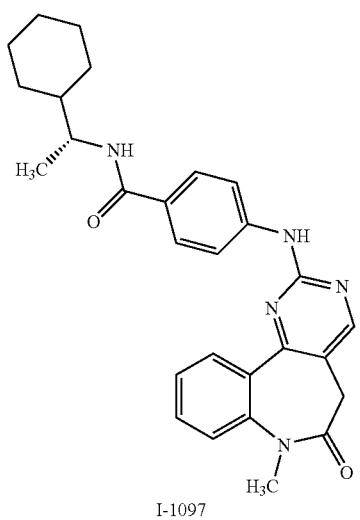
I-1097

-continued
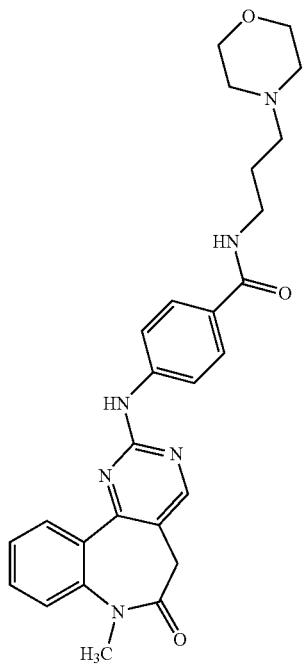
I-1098
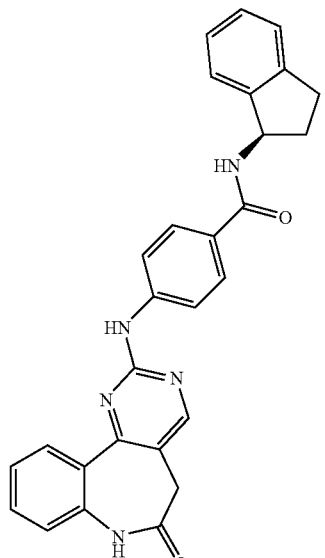
I-1099
-continued
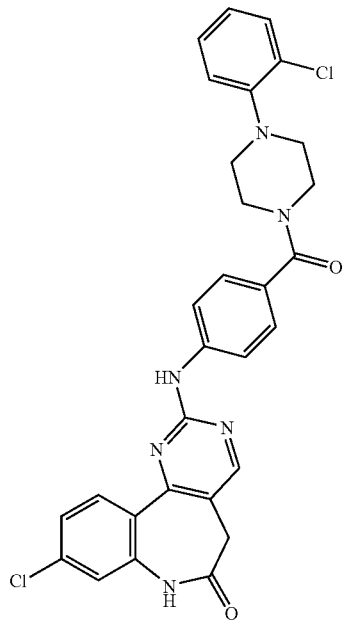
I-1100
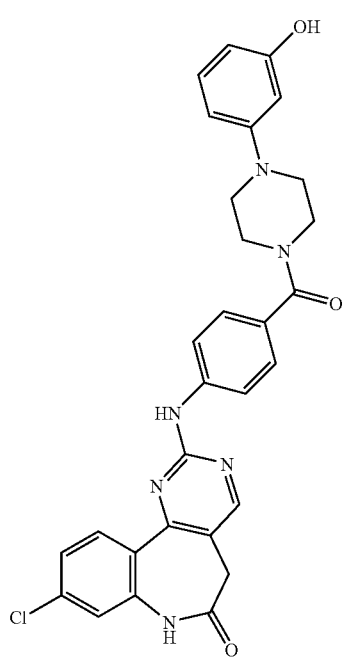
I-1101

-continued
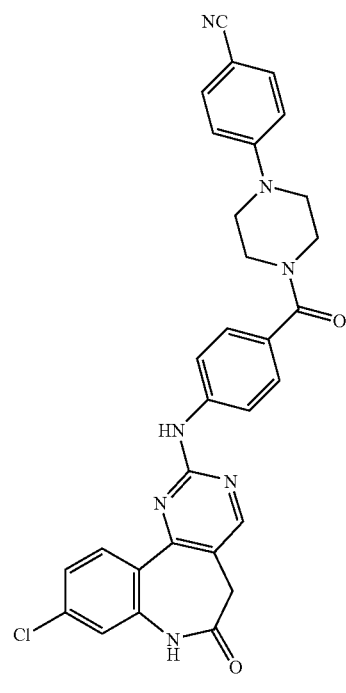
I-1102
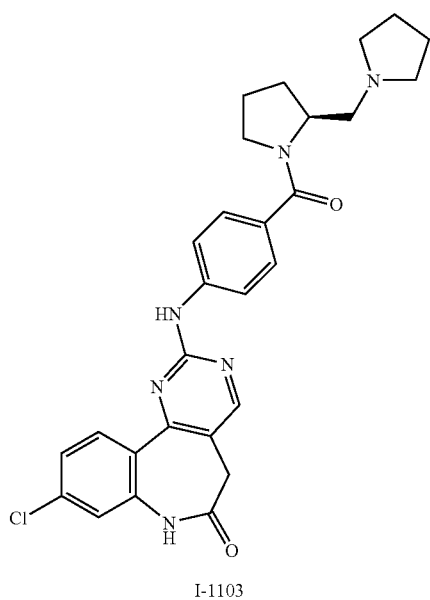
I-1103
-continued
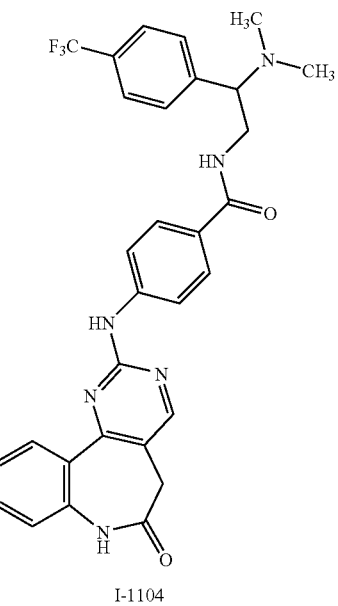
I-1104
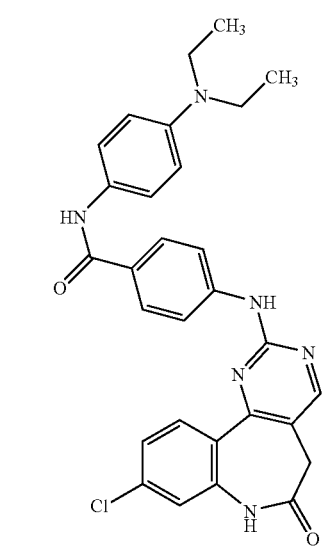
I-1105

-continued
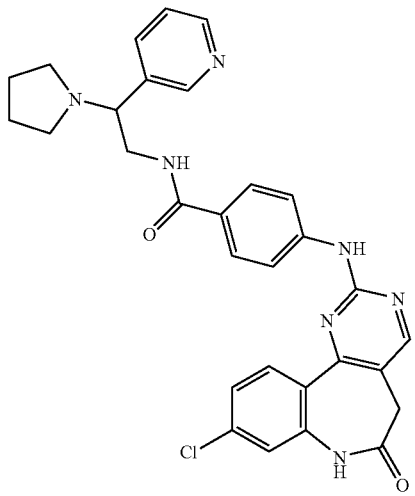
I-1106
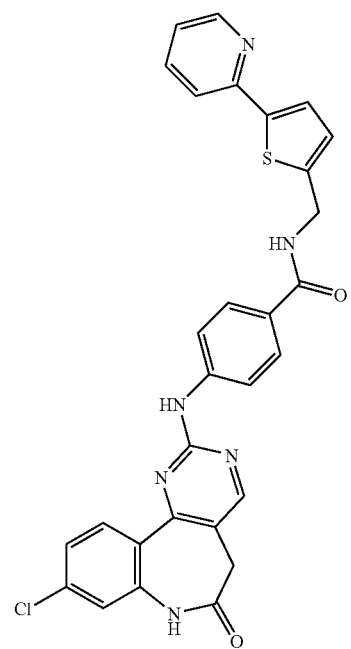
I-1107
-continued
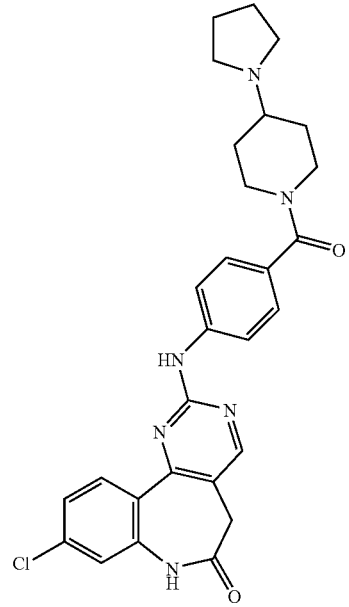
I-1108
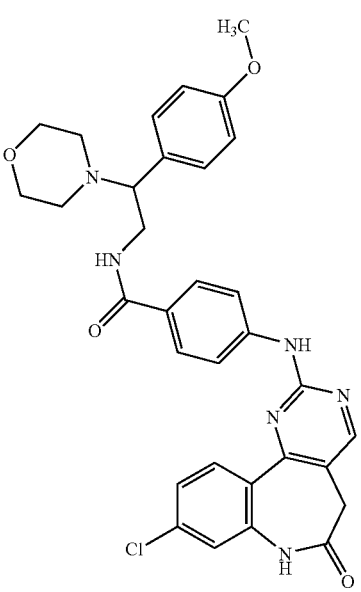
I-1109

-continued
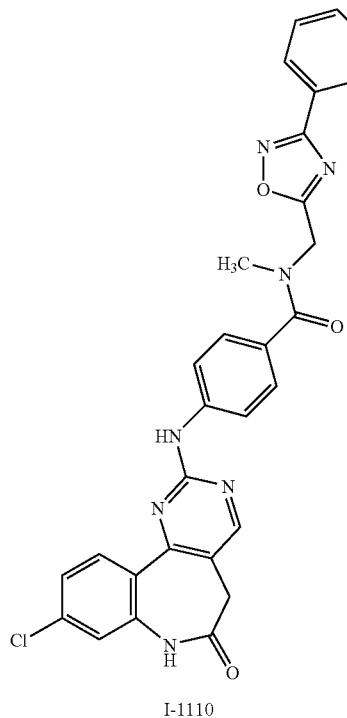
I-1110
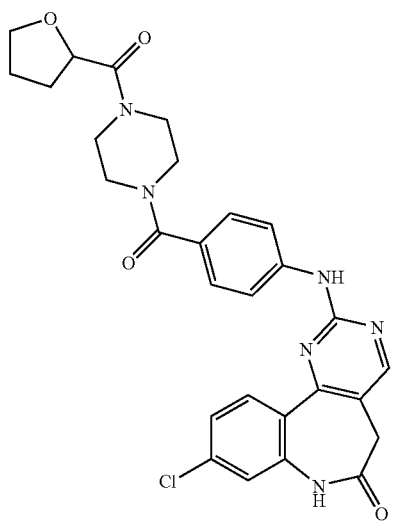
I-1111
-continued
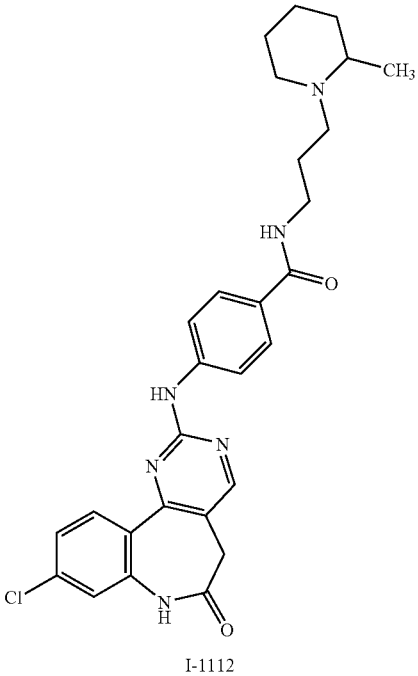
I-1112
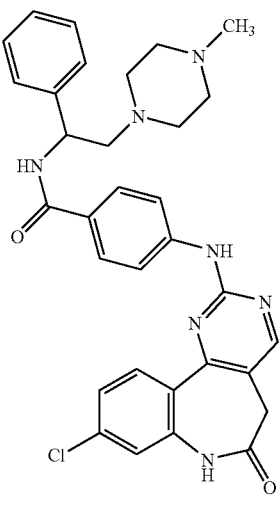
I-1113

-continued
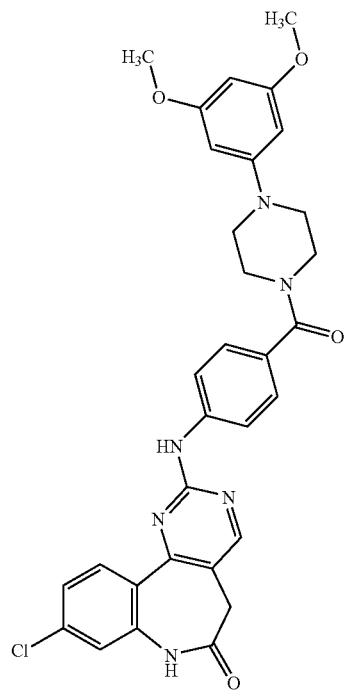
I-1114
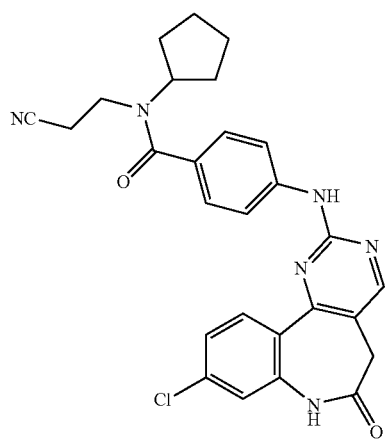
I-1115
-continued
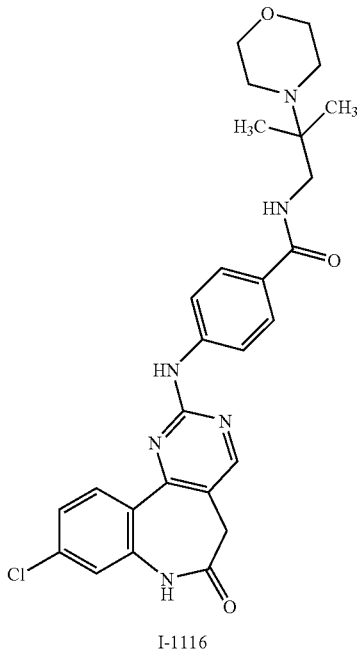
I-1116
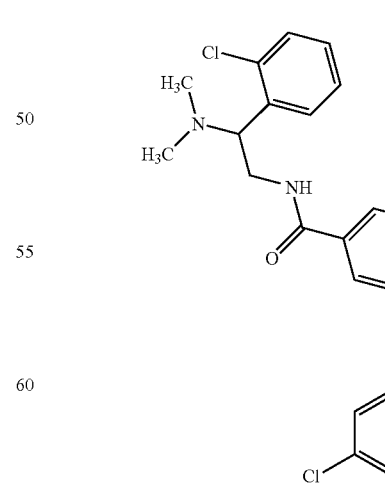
I-1117

-continued
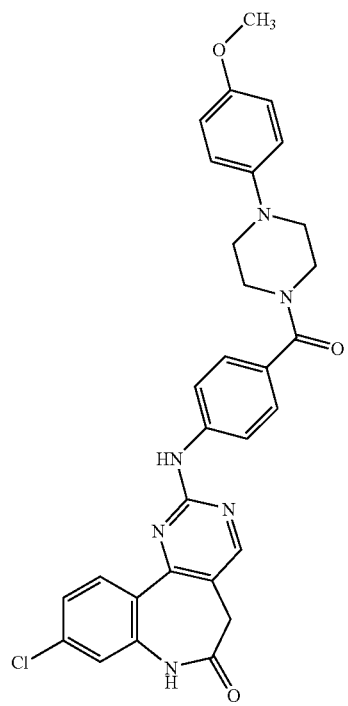
I-1118
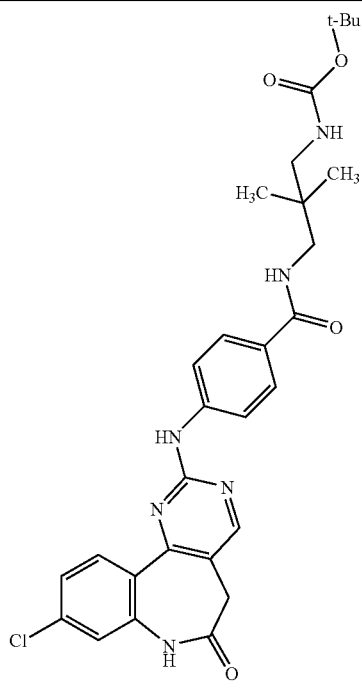
I-1120
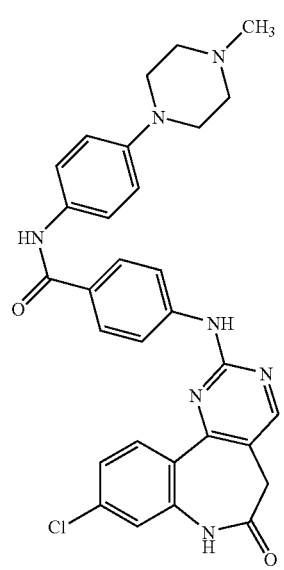
I-1119
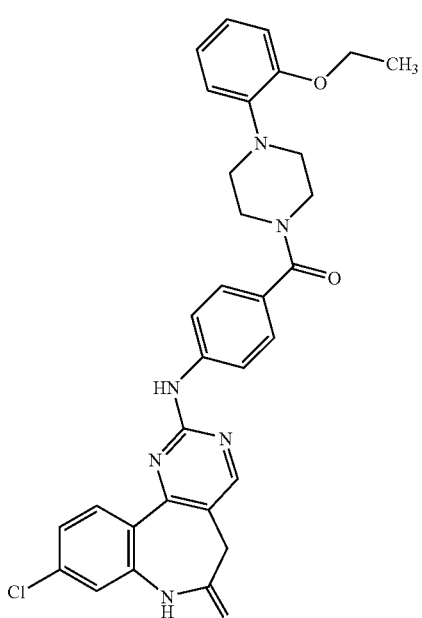
I-1121

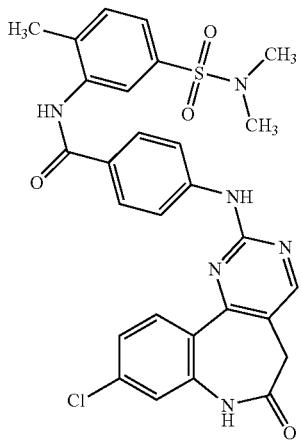
I-1122
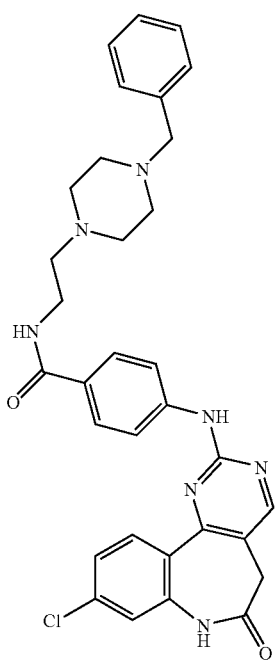
I-1123
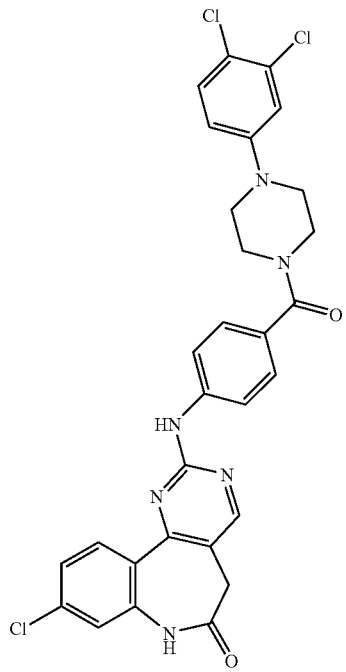
I-1124
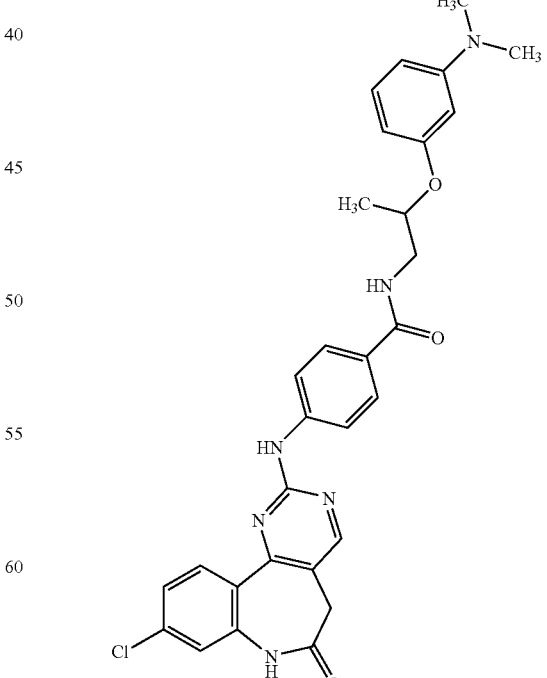
I-1125

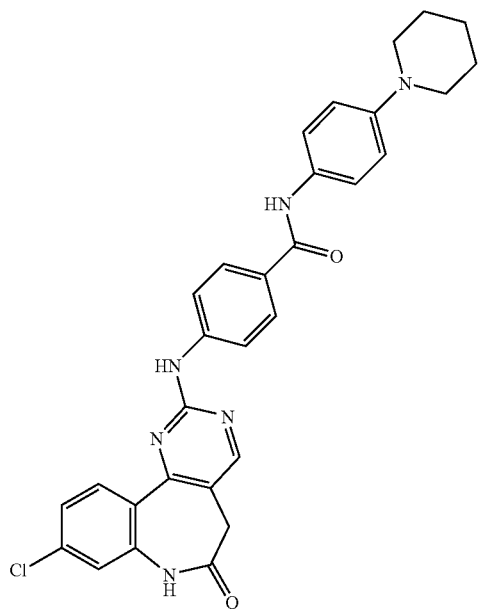
I-1126
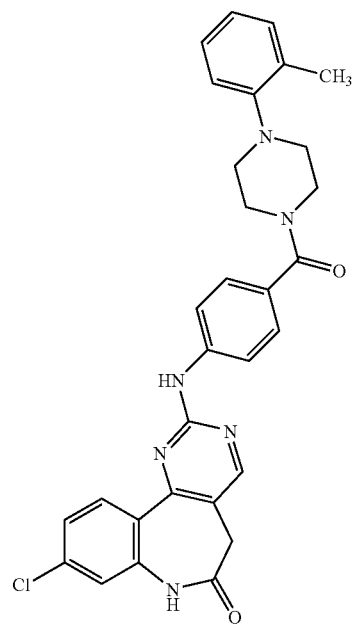
I-1128
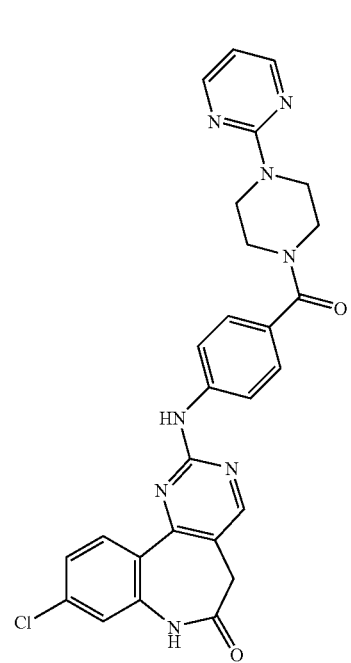
I-1127
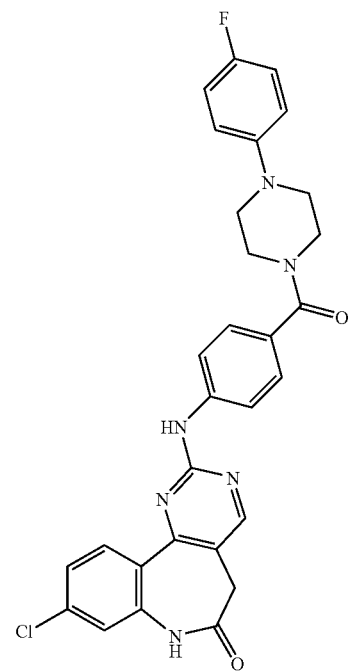
I-1129

-continued
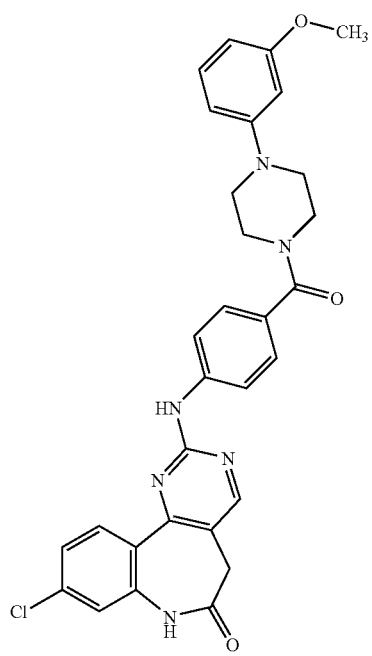
I-1130
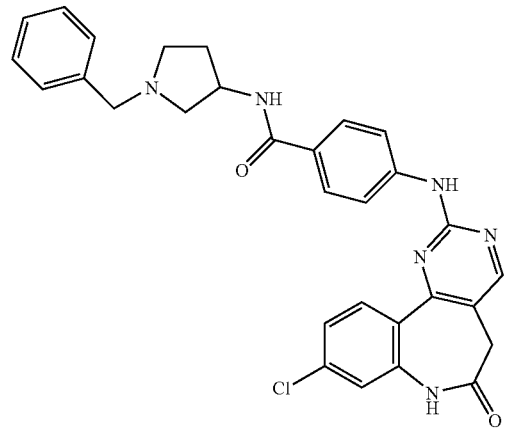
I-1132
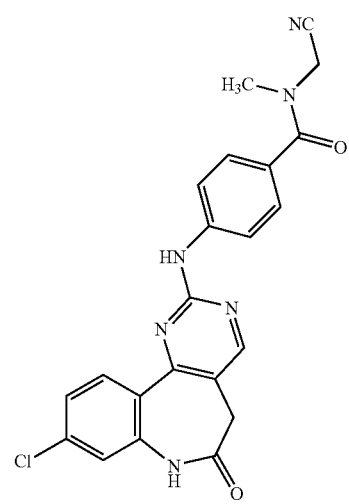
I-1131
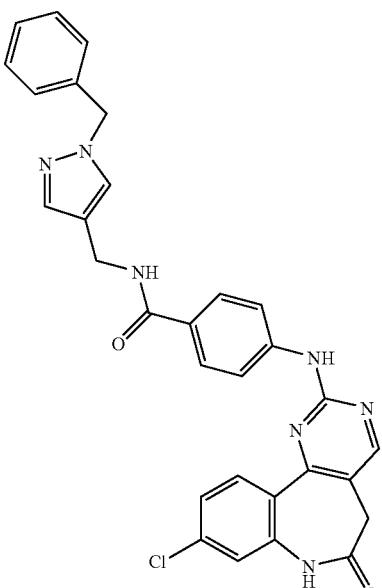
I-1133

-continued
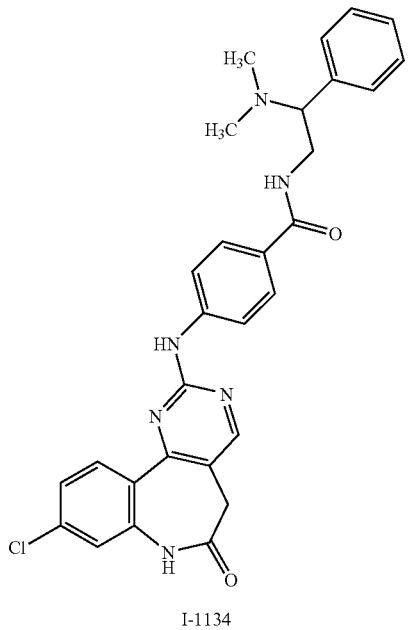
I-1134
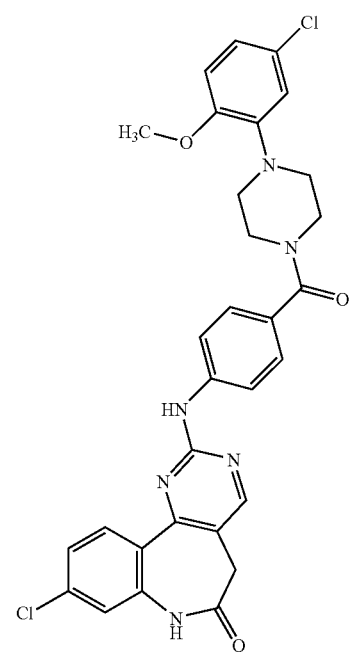
I-1135
-continued
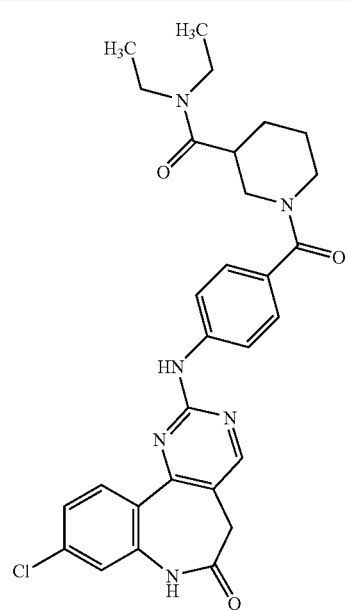
I-1136
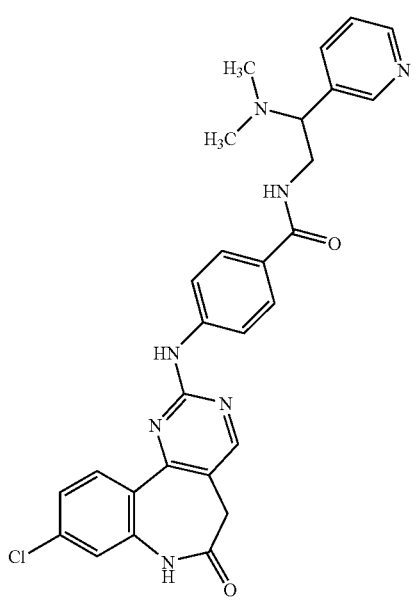
I-1137

-continued
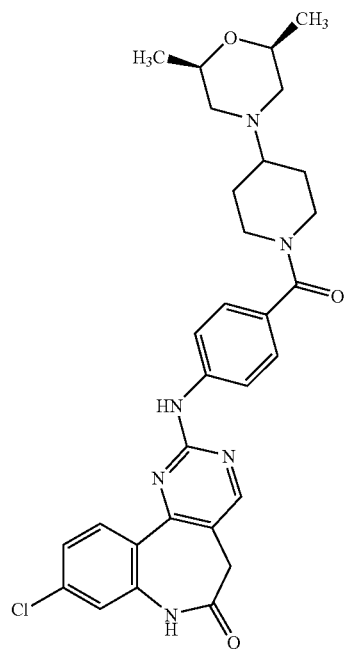
I-1138
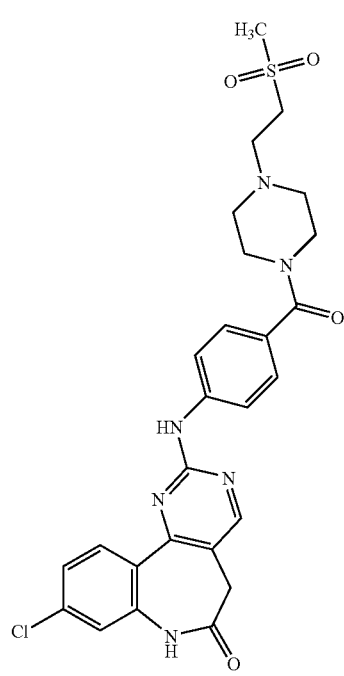
I-1139
-continued
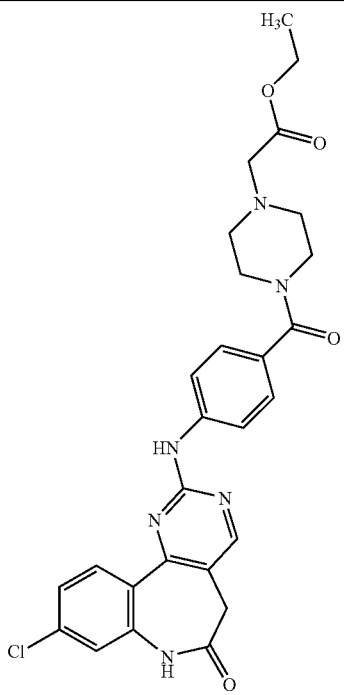
I-1140
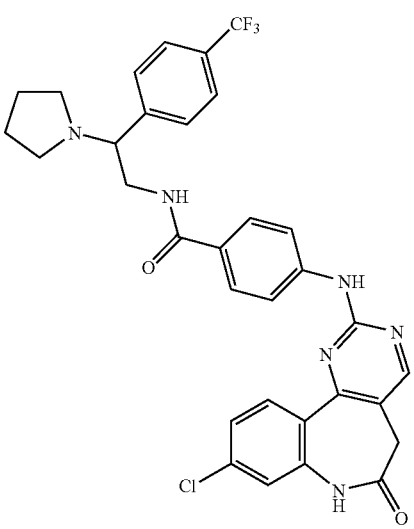
I-1141

-continued
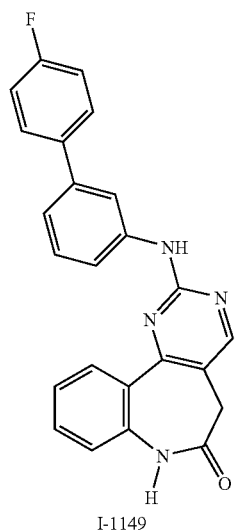
I-1149
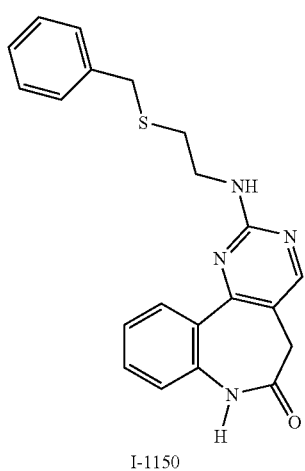
I-1150
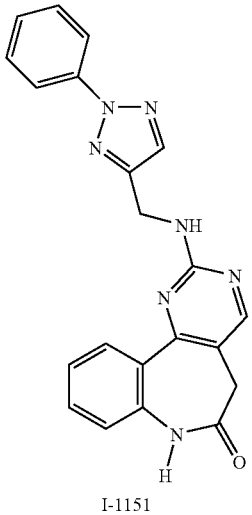
I-1151
-continued
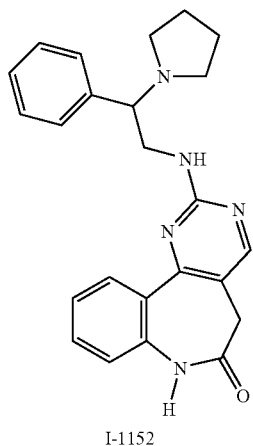
I-1152
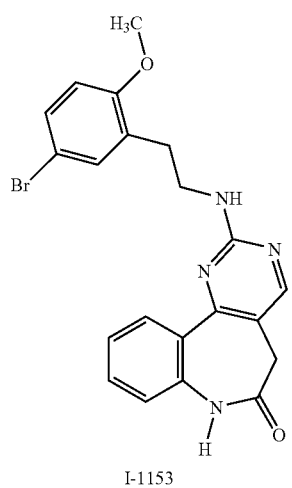
I-1153
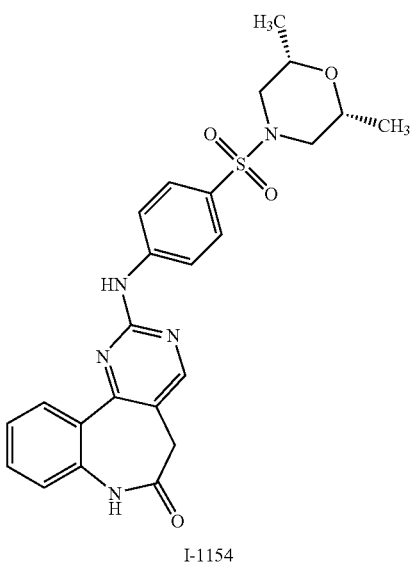
I-1154

-continued
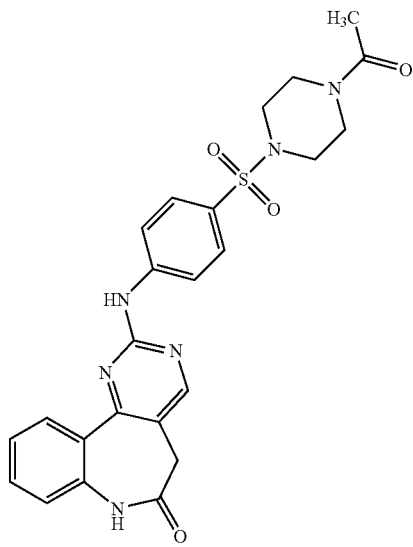
I-1155
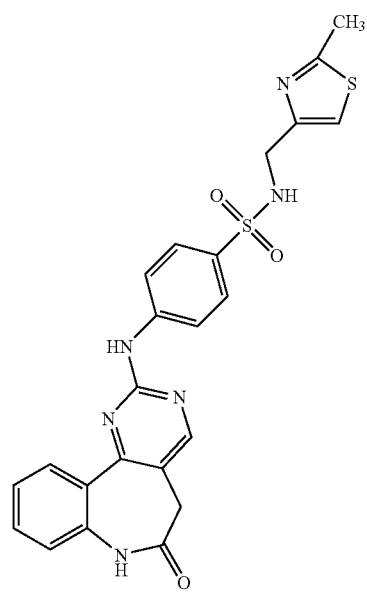
I-1156
-continued
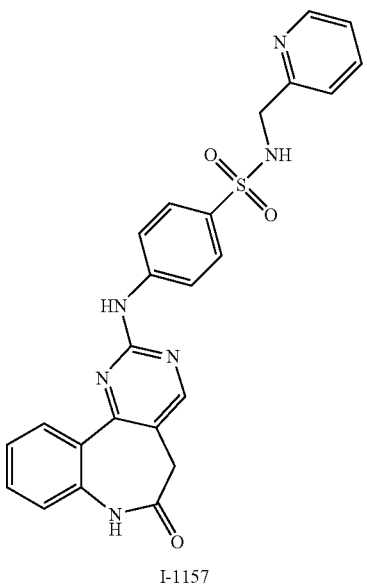
I-1157
I-1158

-continued
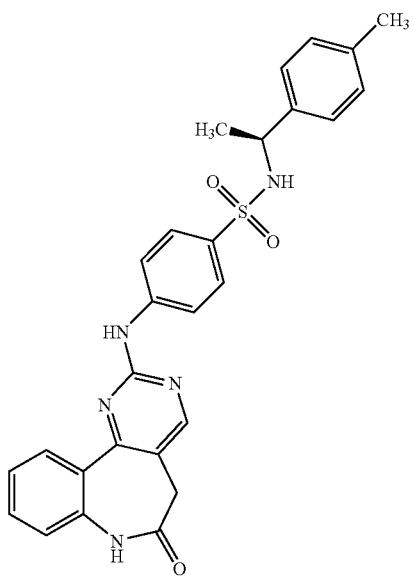
I-1159
-continued
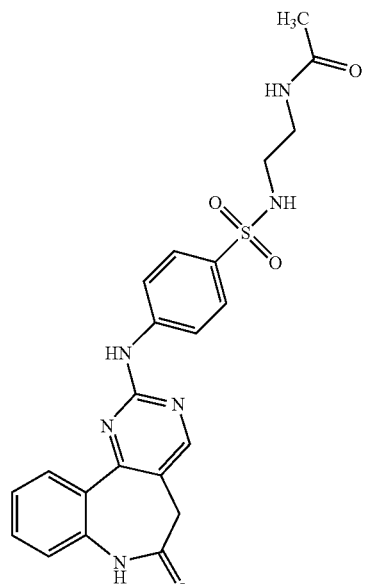
I-1161
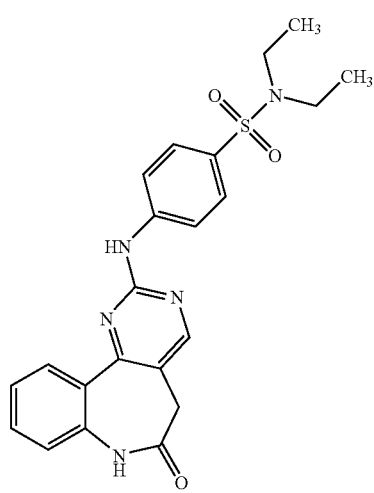
I-1160
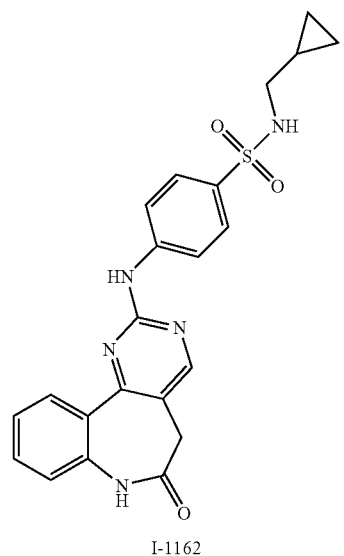
I-1162

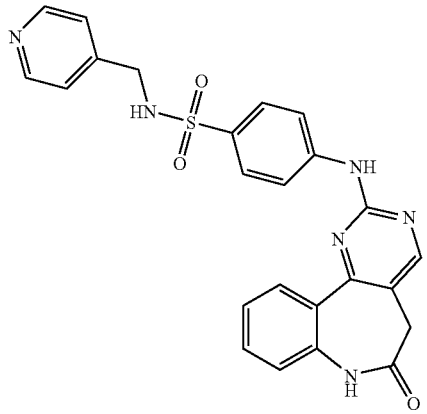
I-1163
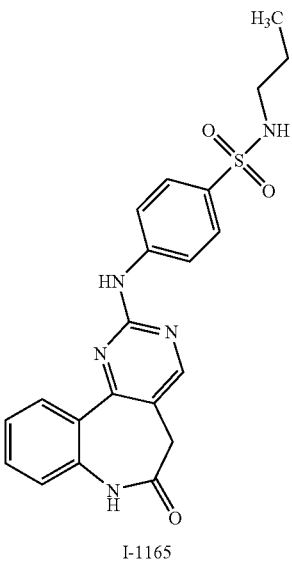
I-1165
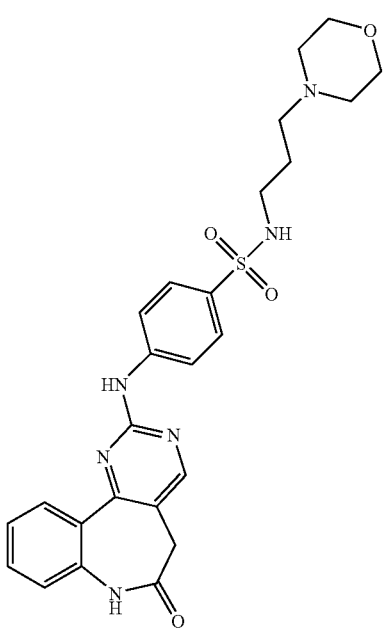
I-1164
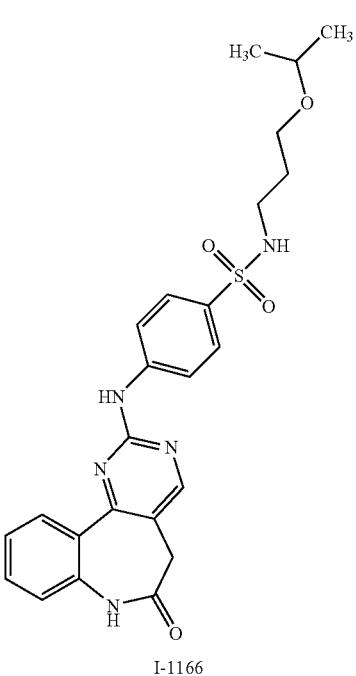
I-1166

-continued
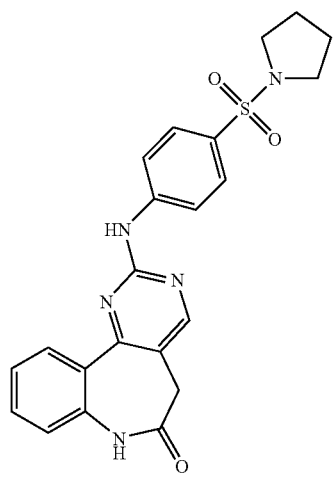
I-1167
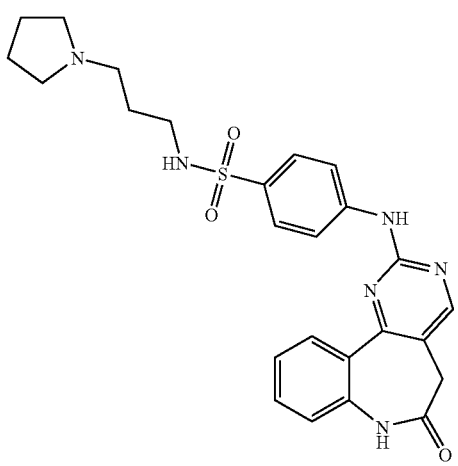
I-1168
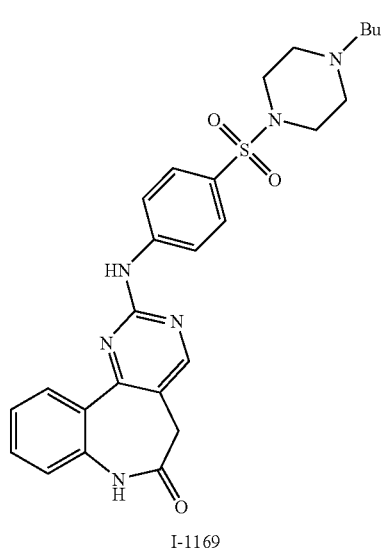
I-1169
-continued
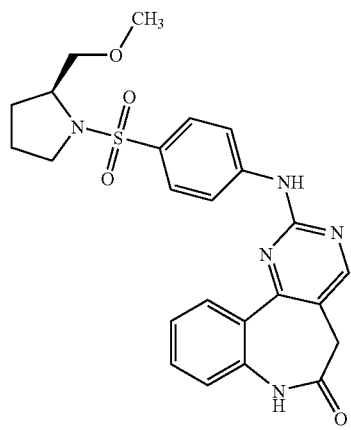
I-1170
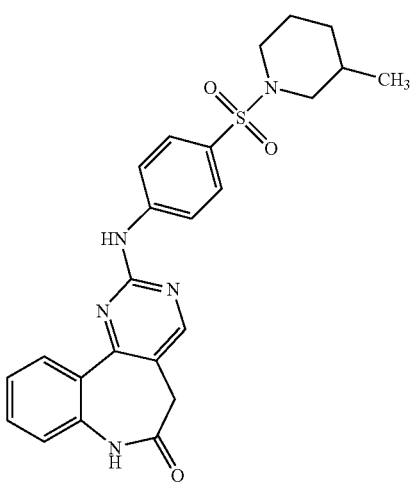
I-1171
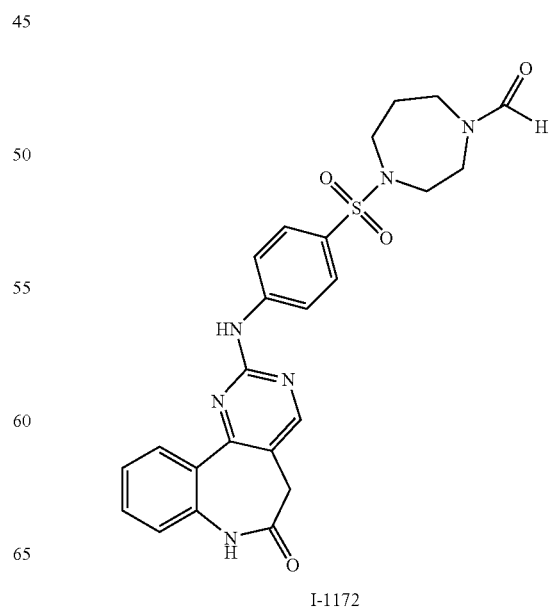
I-1172

-continued
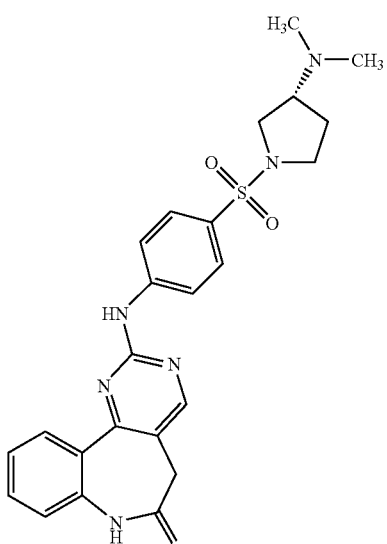
I-1173
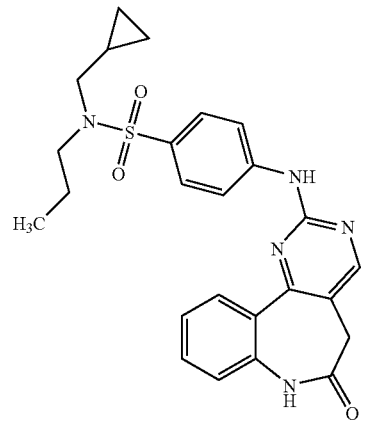
I-1175
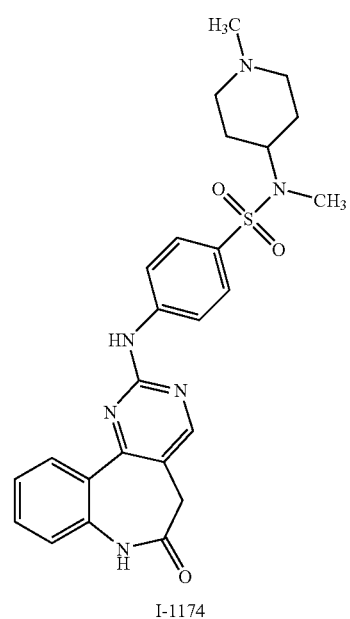
I-1174
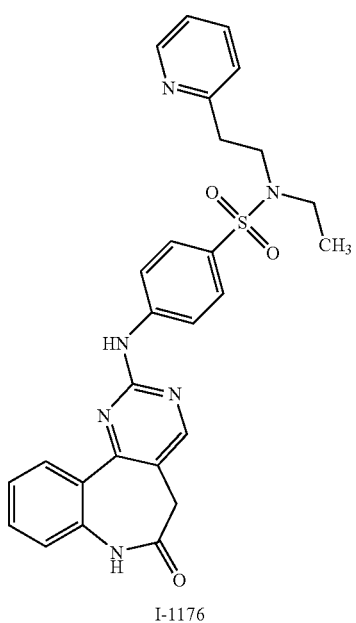
I-1176

-continued
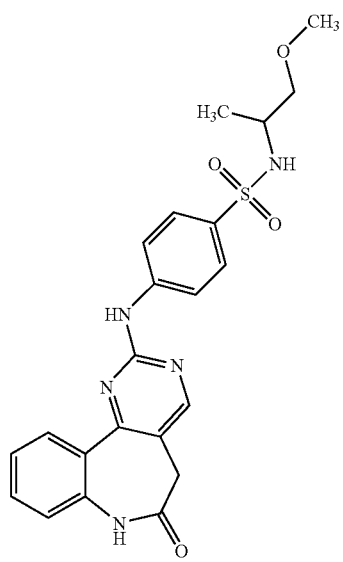
I-1177
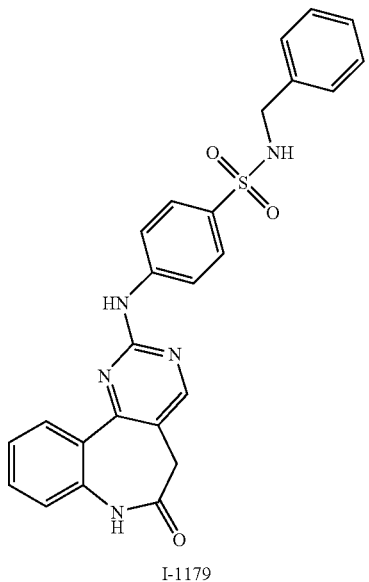
I-1179
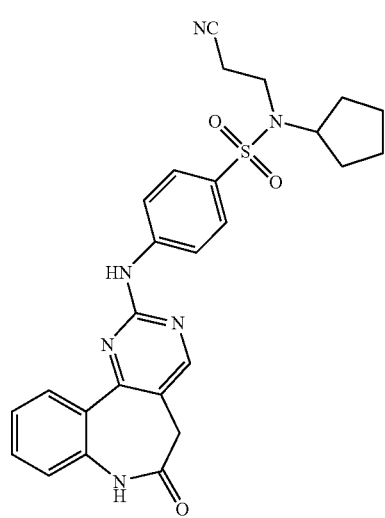
I-1178
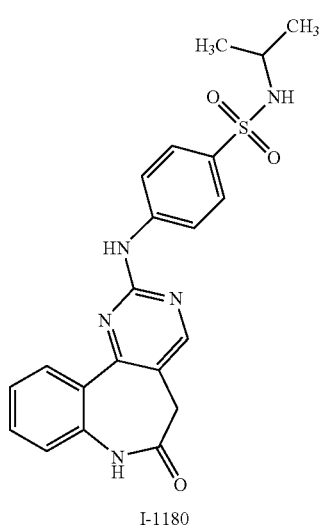
I-1180

-continued
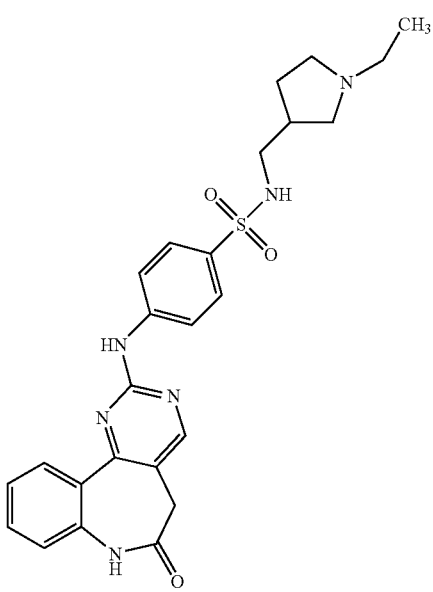
I-1181
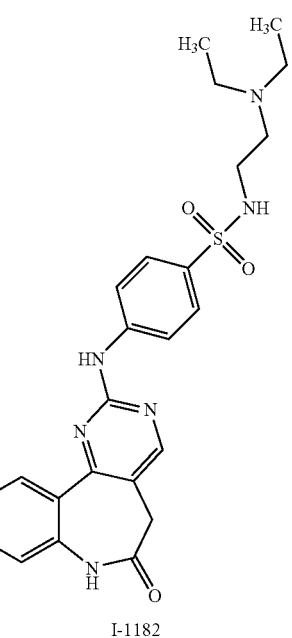
I-1182
-continued
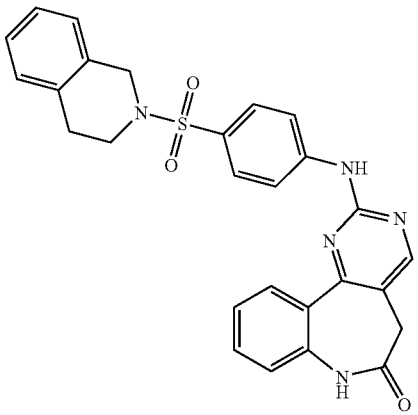
I-1183
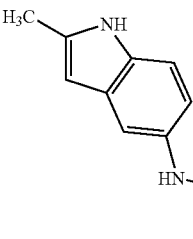
I-1184
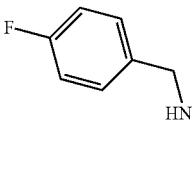
I-1185

| 453 | 454 |
|---|---|
| -continued | -continued |
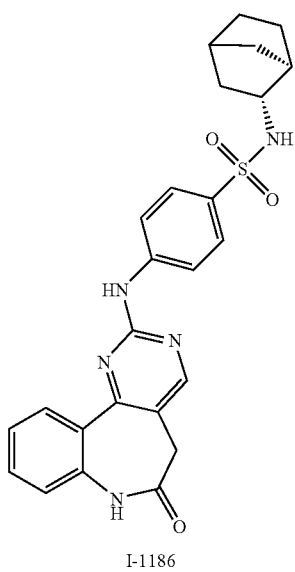
I-1186
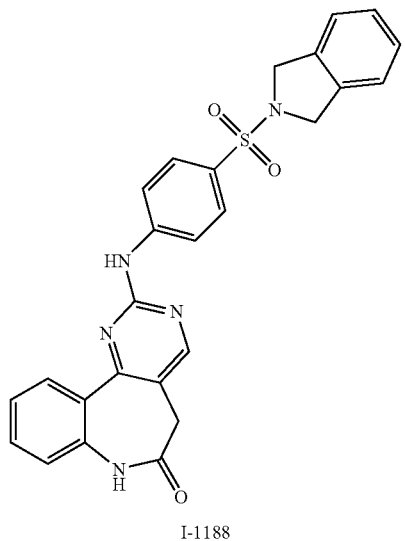
I-1188
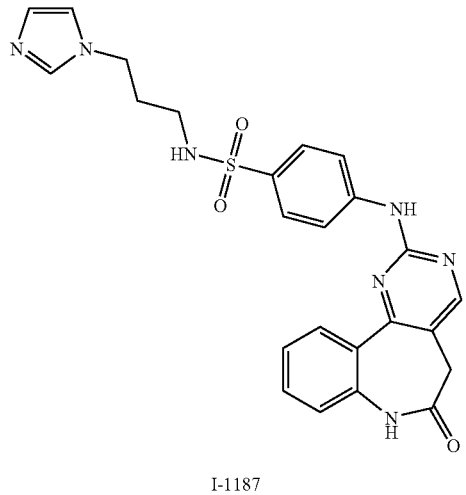
I-1187
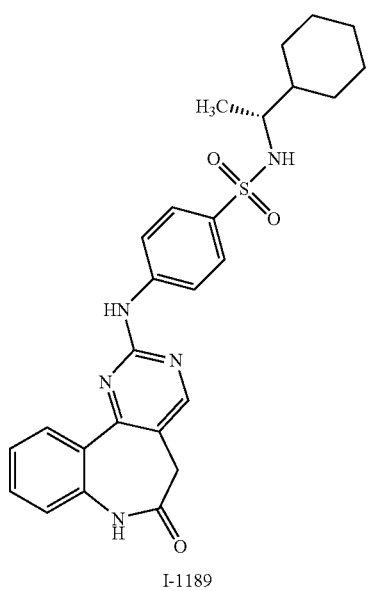
I-1189

-continued
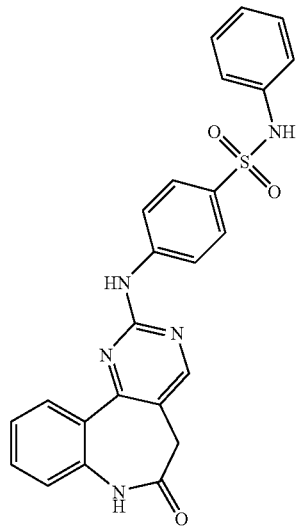
I-1190
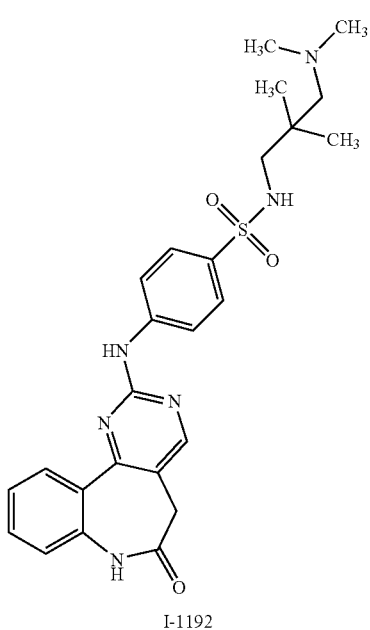
I-1192
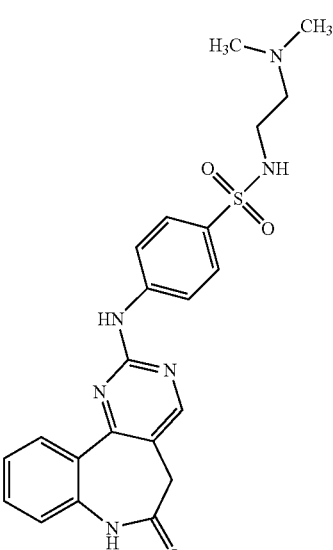
I-1191
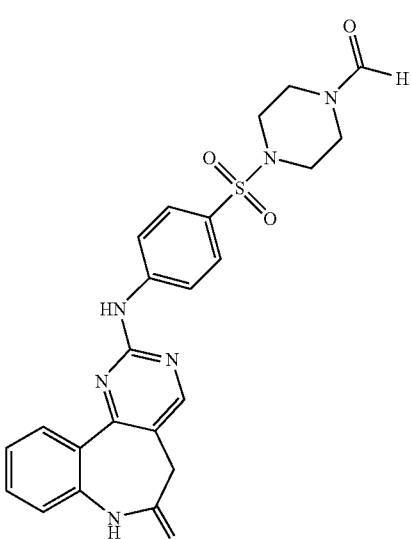
I-1193

-continued
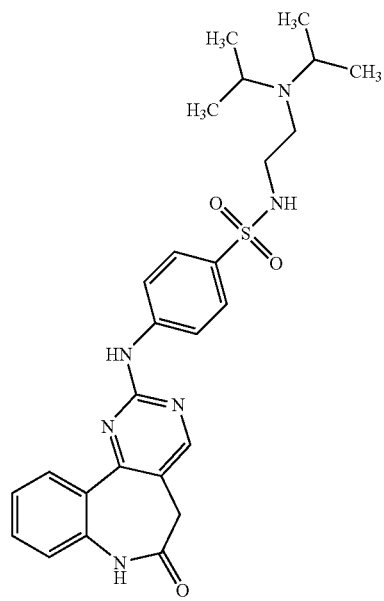
I-1194
-continued
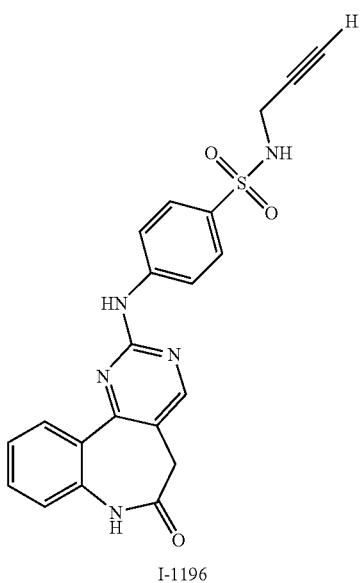
I-1196
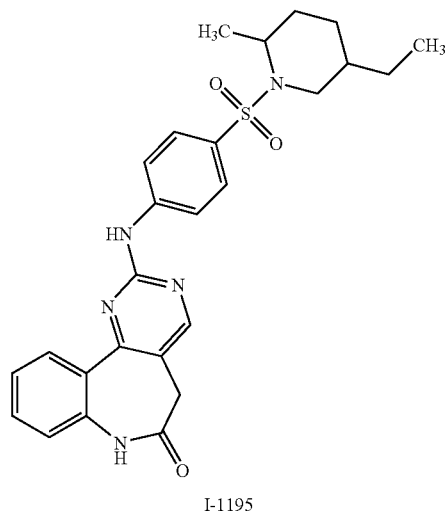
I-1195
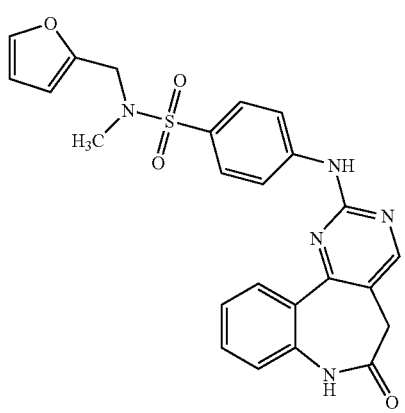
I-1197

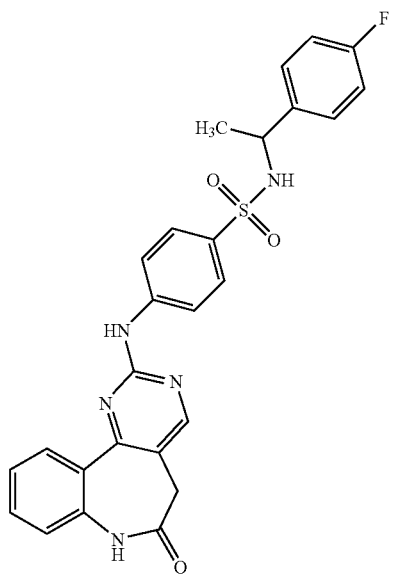
I-1198
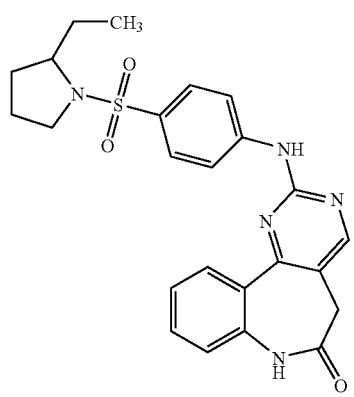
I-1200
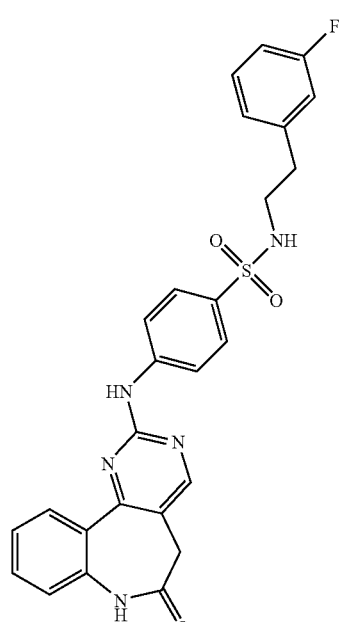
I-1199
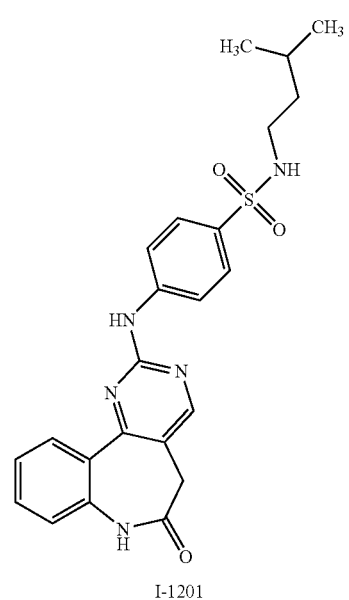
I-1201

-continued
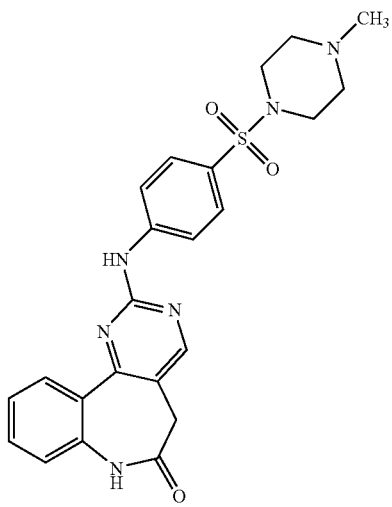
I-1202
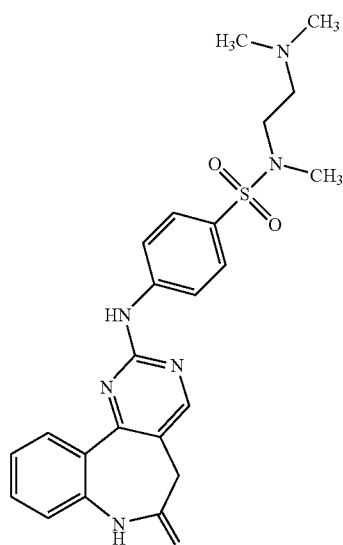
I-1204
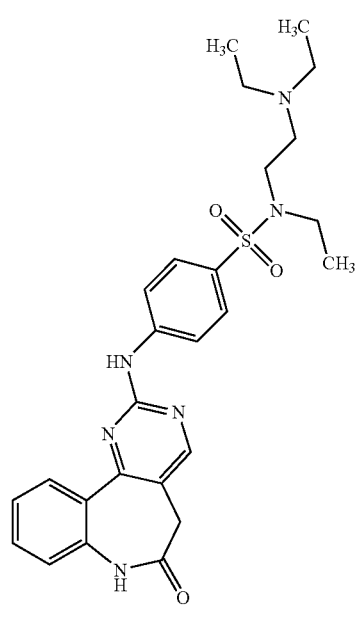
I-1203
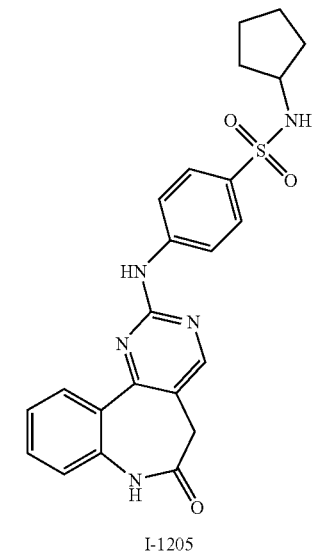
I-1205

-continued
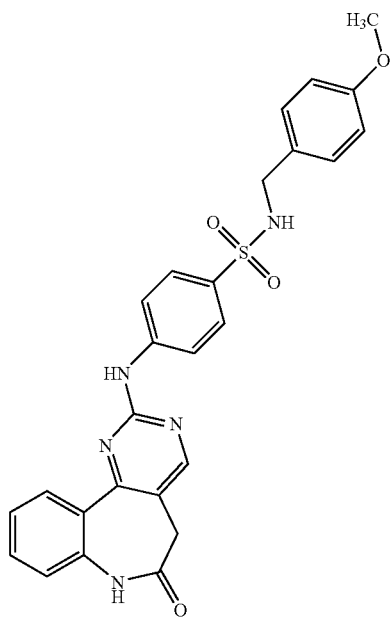
I-1206
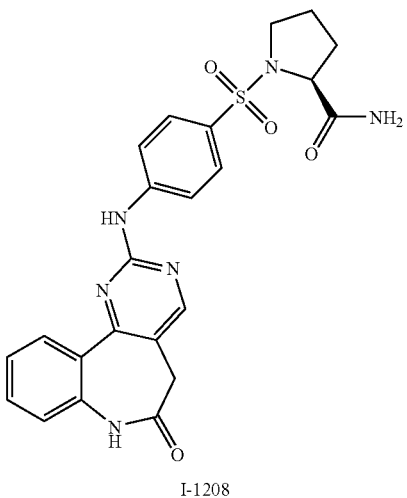
I-1208
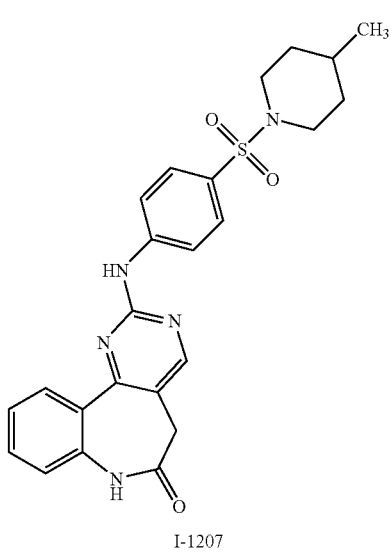
I-1207
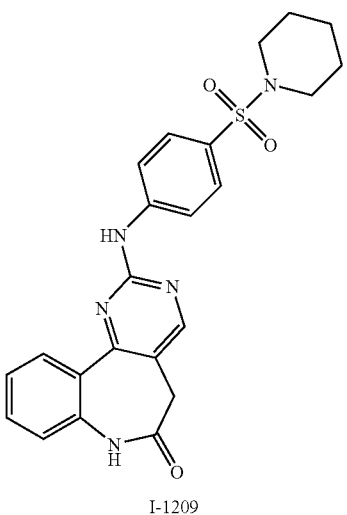
I-1209

-continued
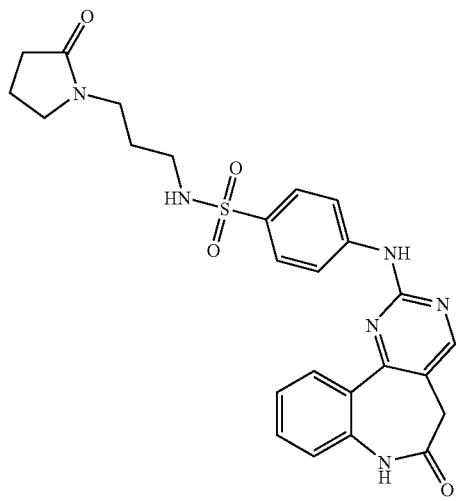
I-1210
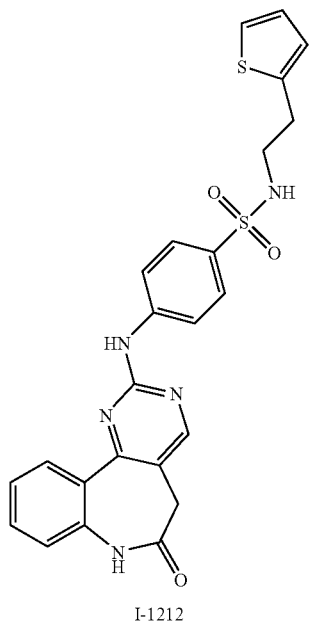
I-1212
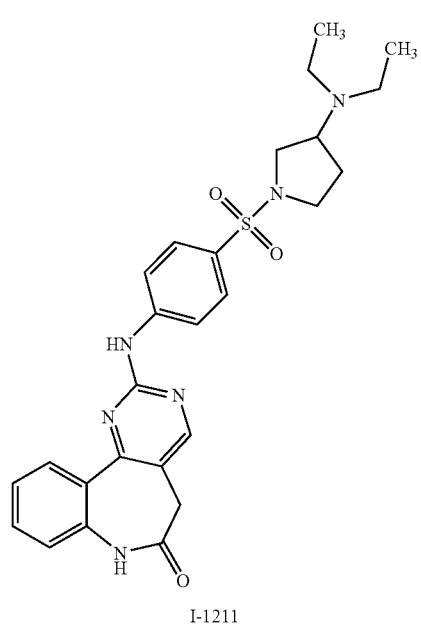
I-1211
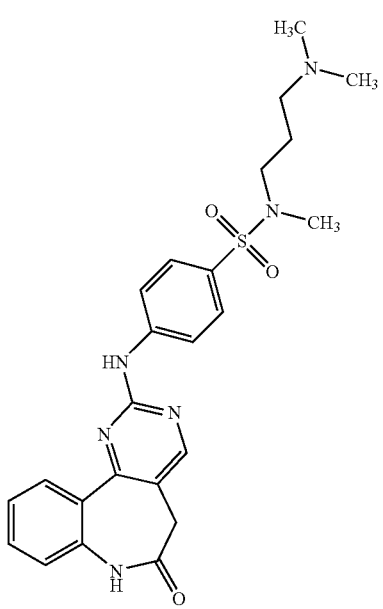
I-1213

467
-continued
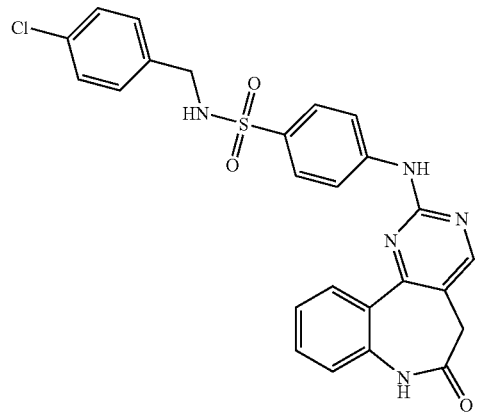
I-1214
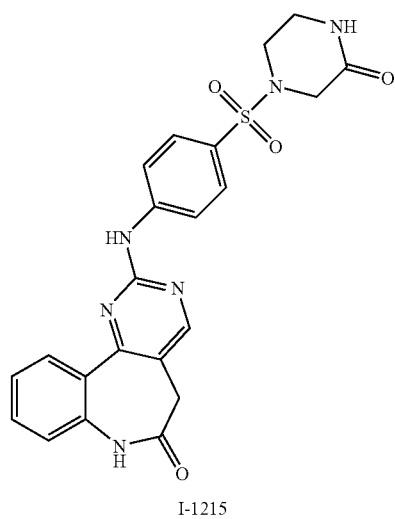
I-1215
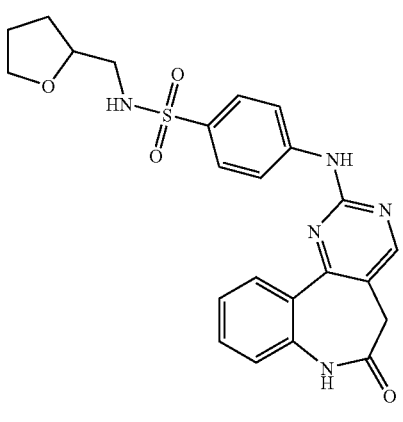
I-1216
468
-continued
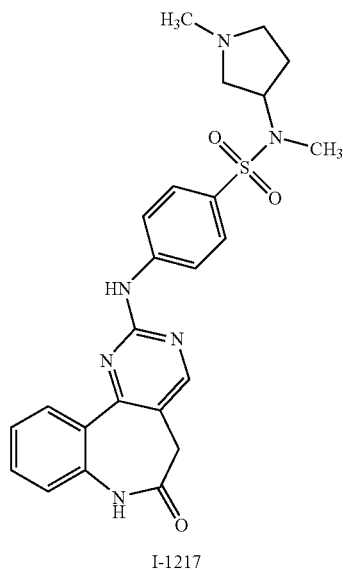
I-1217
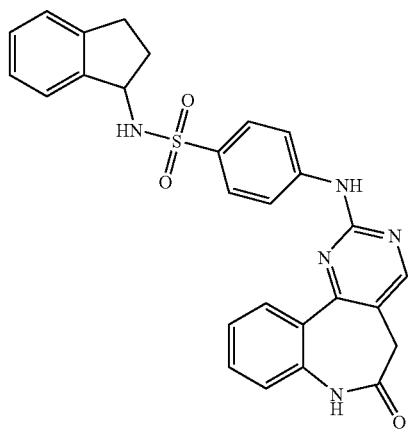
I-1218
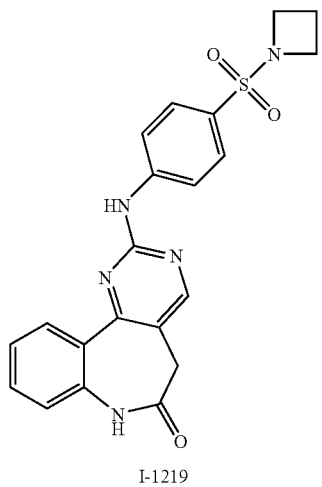
I-1219

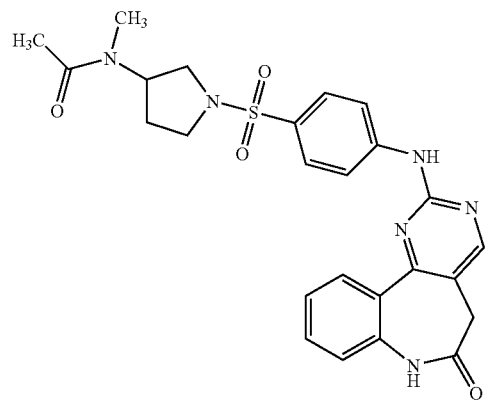
I-1220
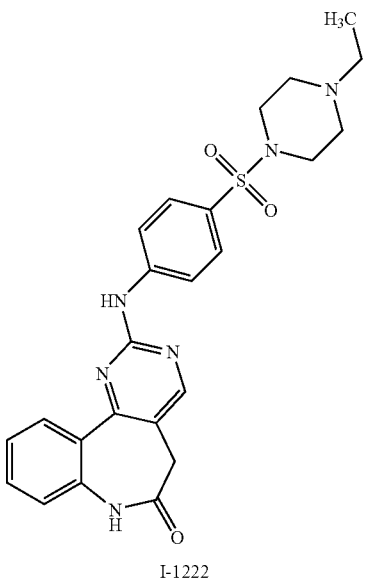
I-1222
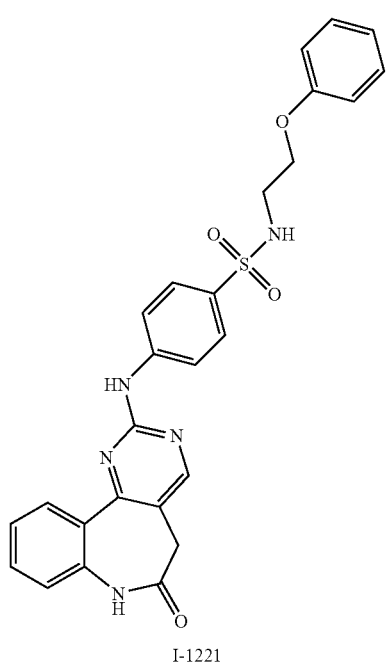
I-1221
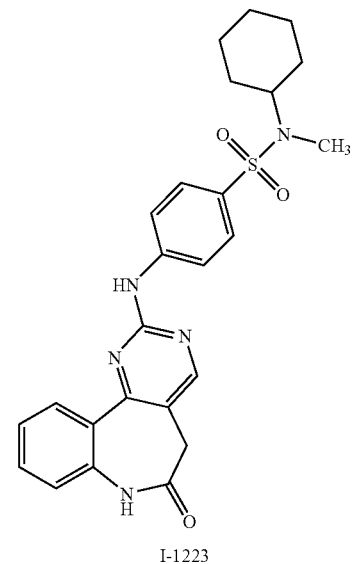
I-1223

-continued
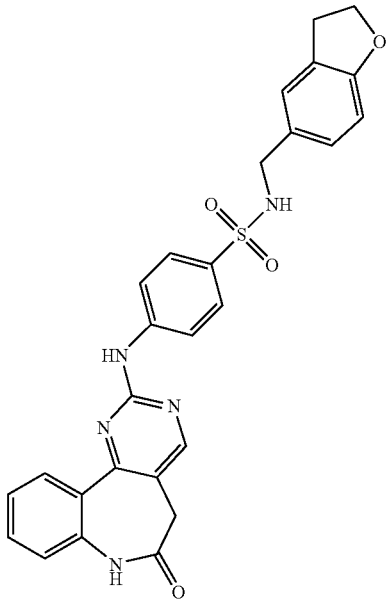
I-1224
-continued
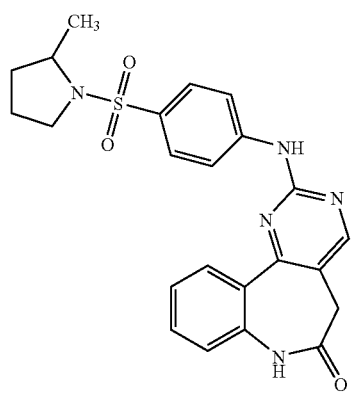
I-1226
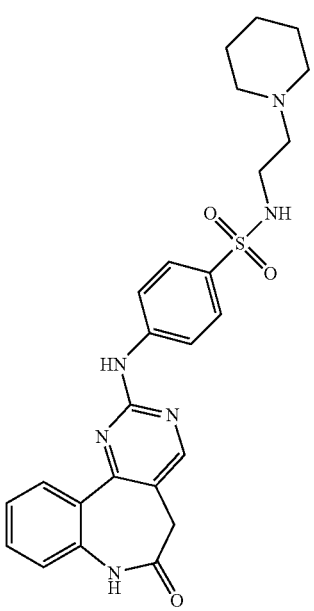
I-1225
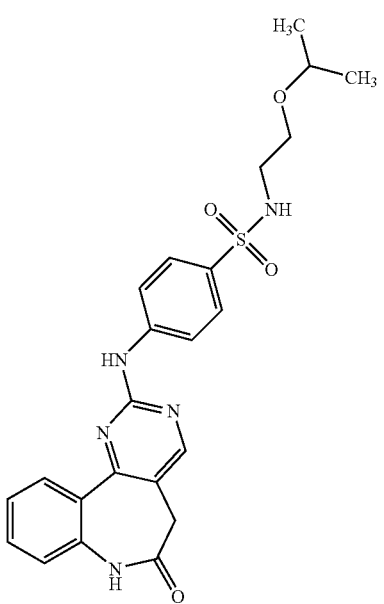
I-1227

-continued
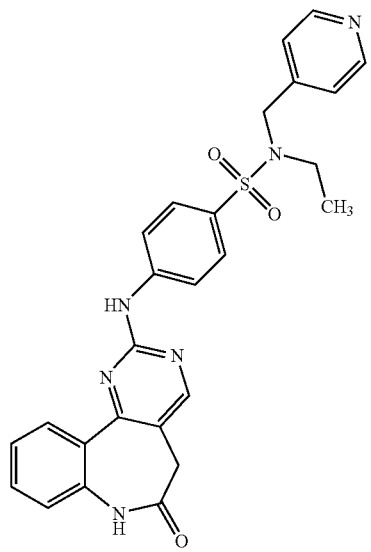
I-1228
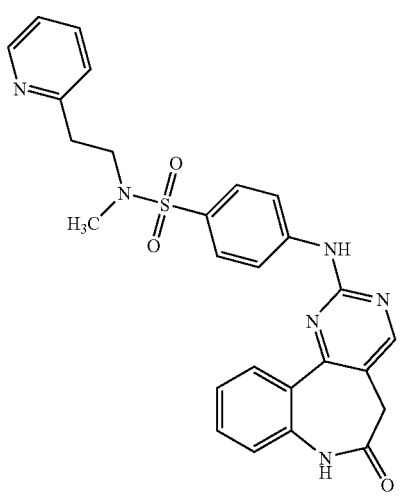
I-1229
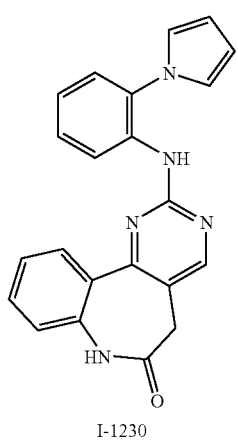
I-1230
-continued
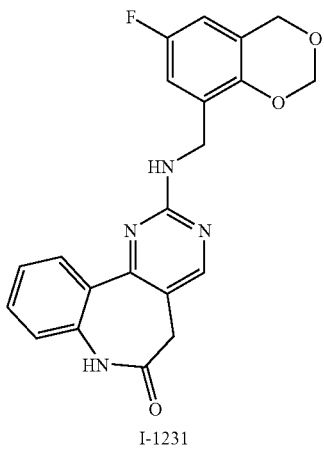
I-1231
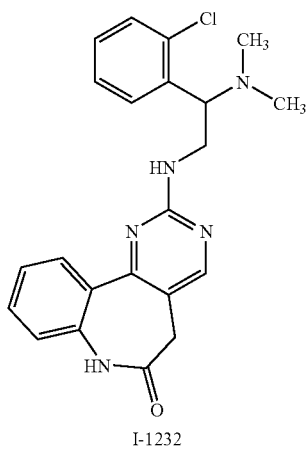
I-1232
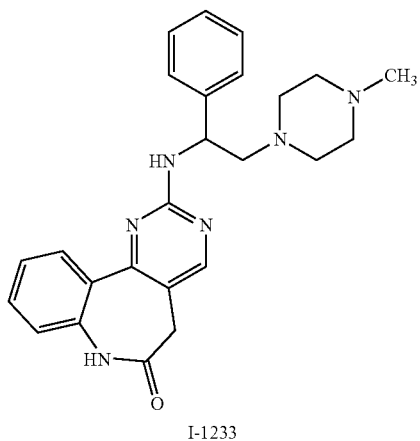
I-1233

-continued
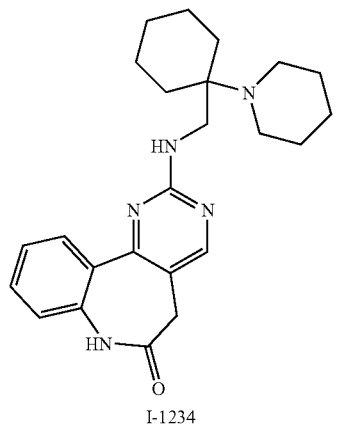
I-1234
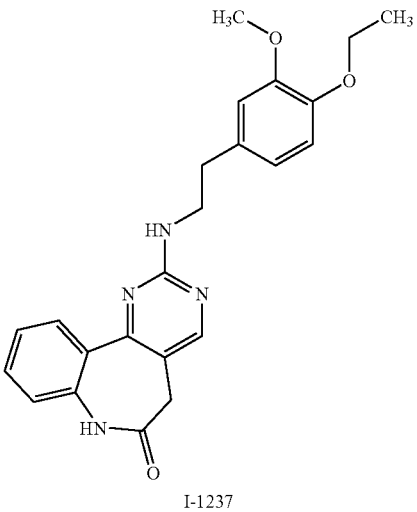
I-1237
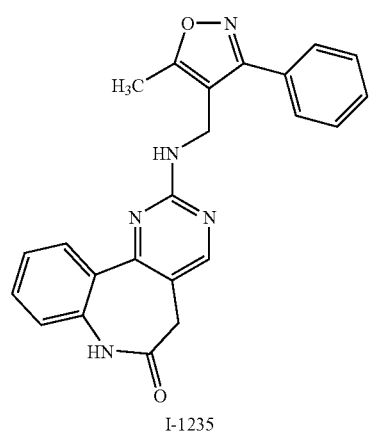
I-1235
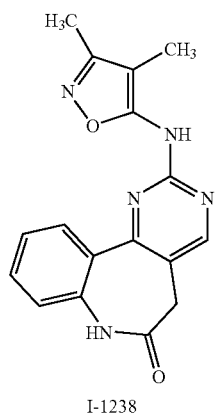
I-1238
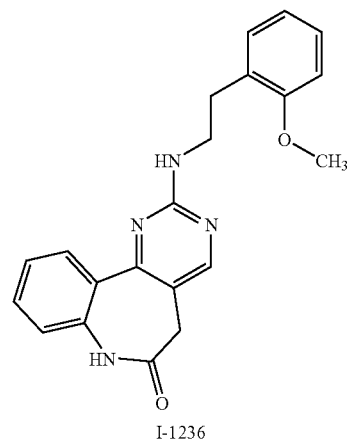
I-1236
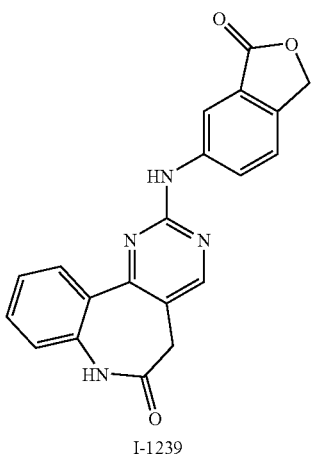
I-1239

-continued
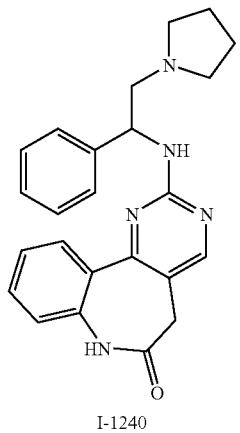
I-1240
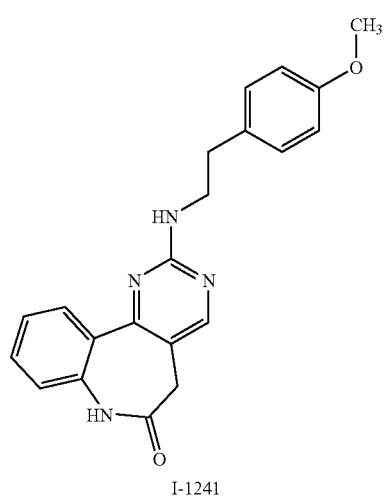
I-1241
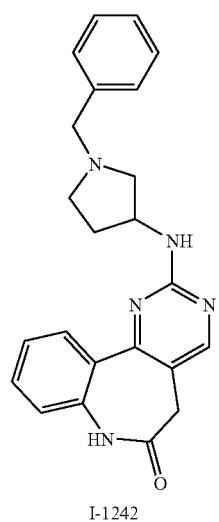
I-1242
-continued
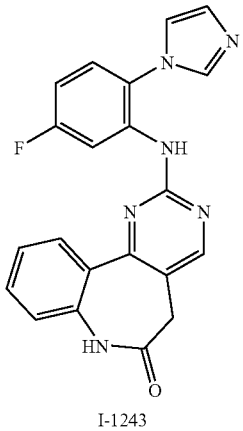
I-1243
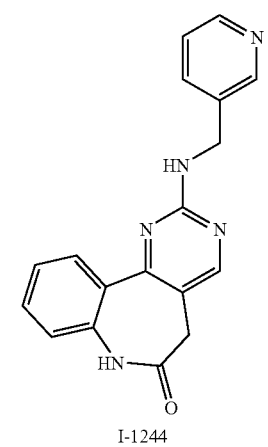
I-1244
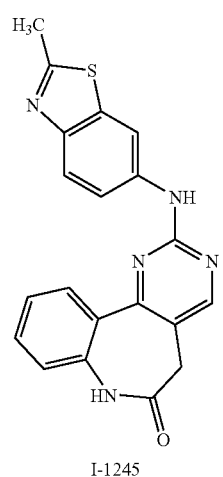
I-1245

-continued
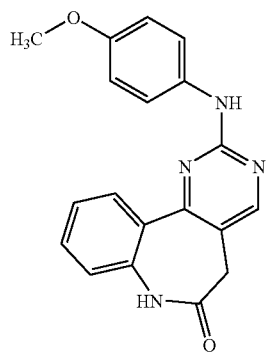
I-1246
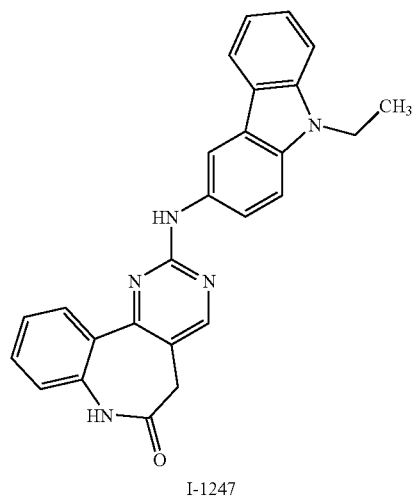
I-1247
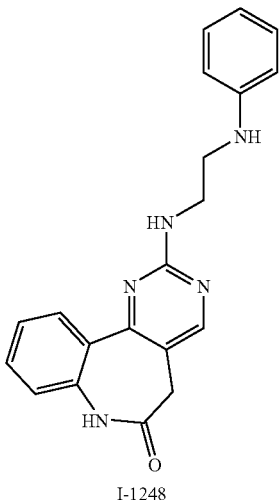
I-1248
-continued
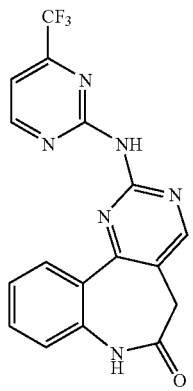
I-1249
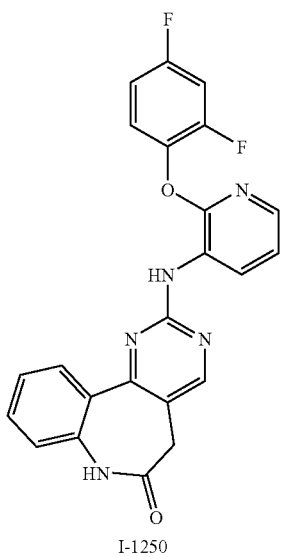
I-1250
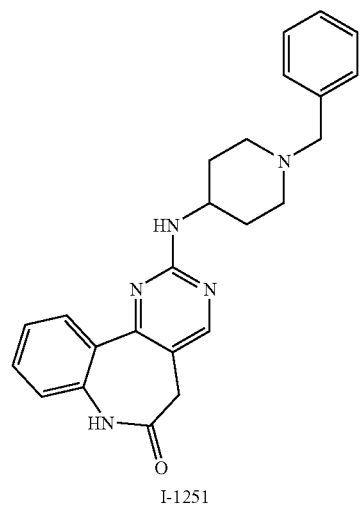
I-1251

-continued
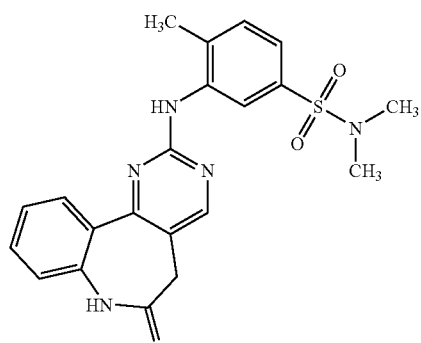
I-1252
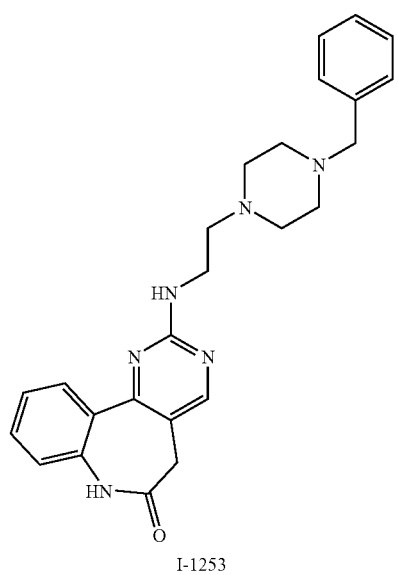
I-1253
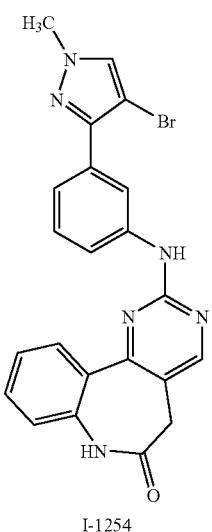
I-1254
-continued
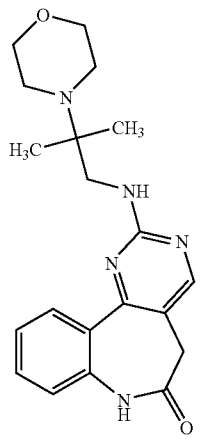
I-1255
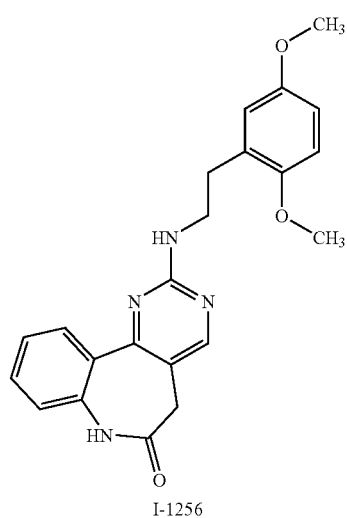
I-1256
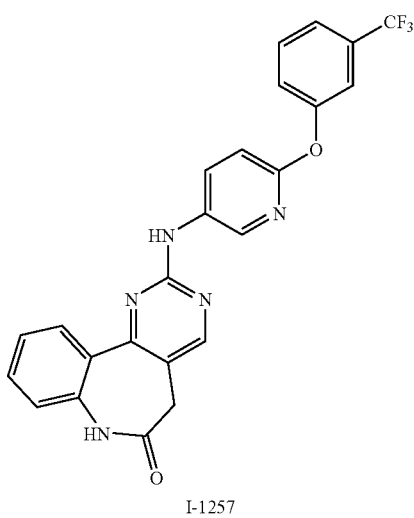
I-1257

-continued
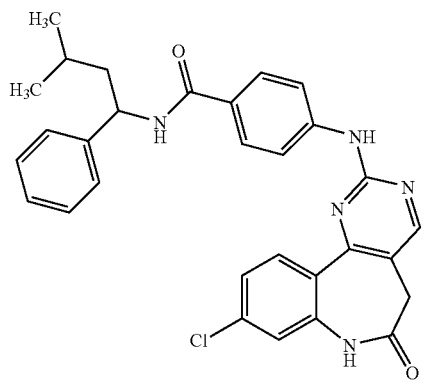
I-1258
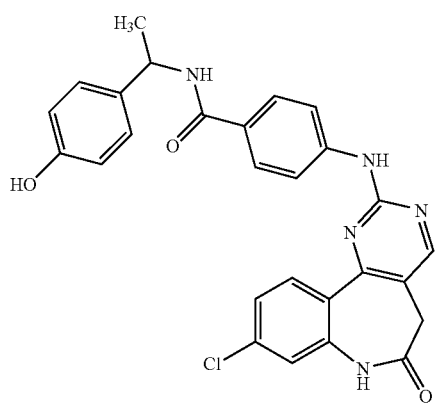
I-1259
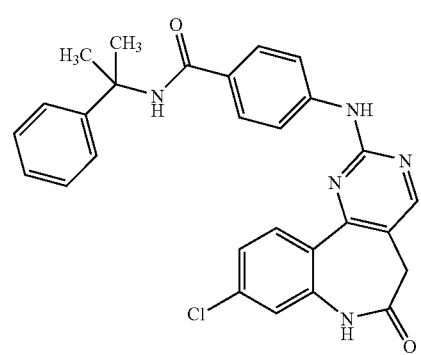
I-1260
-continued
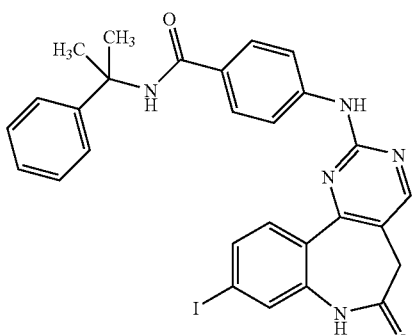
I-1261
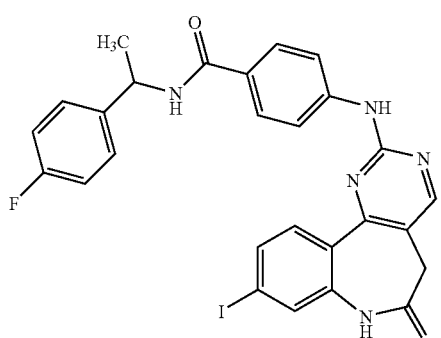
I-1262
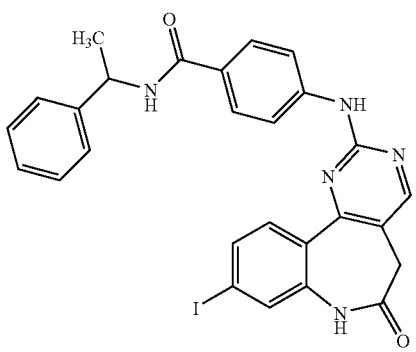
I-1263

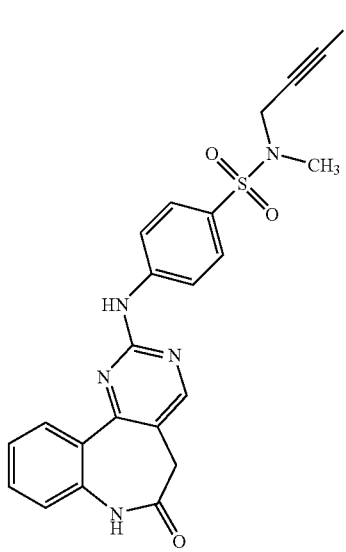
I-1264
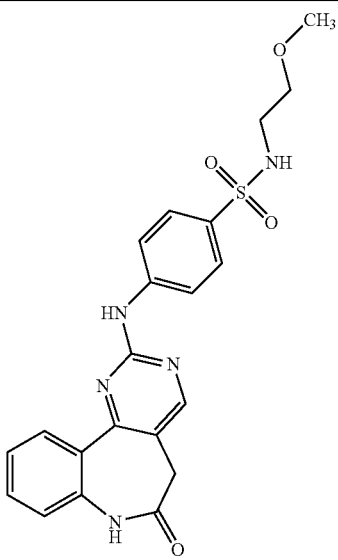
I-1266
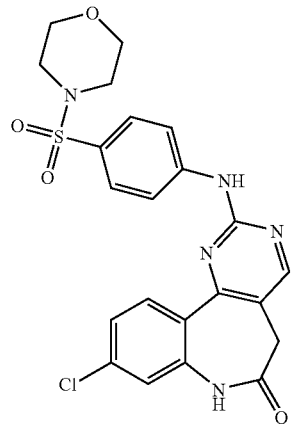
I-1265
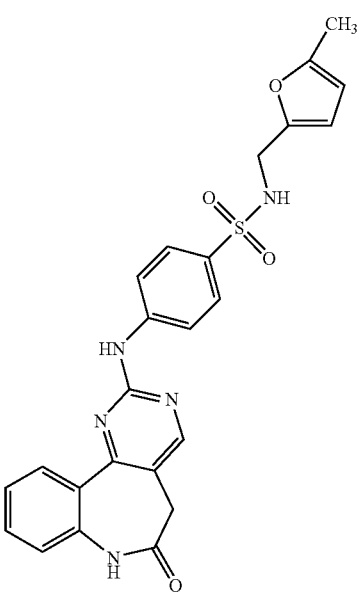
I-1267

| 487 | 488 |
|---|---|
| -continued | -continued |
| 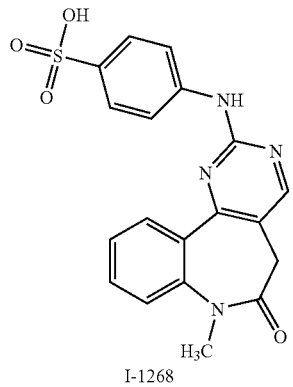<br>I-1268 | 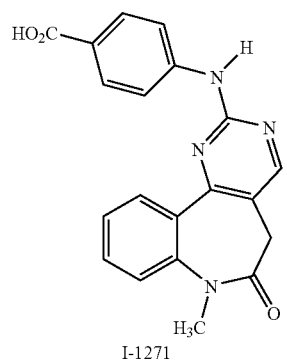<br>I-1271 |
| 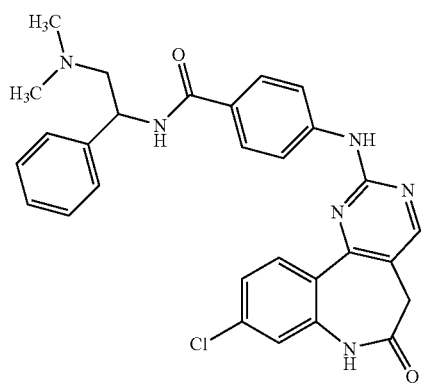<br>I-1269 | 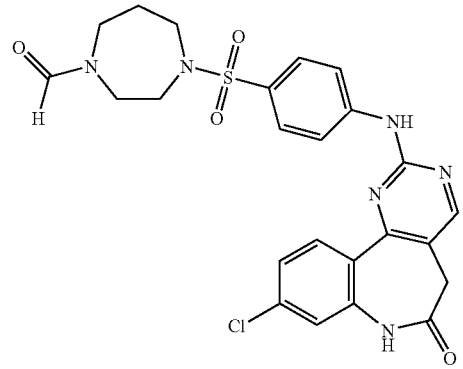<br>I-1272 |
| 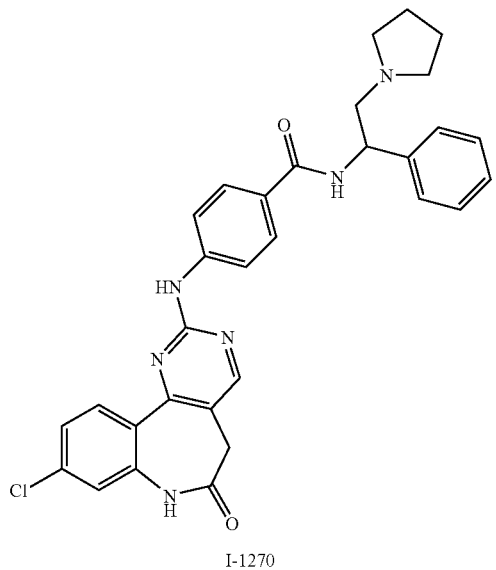<br>I-1270 | 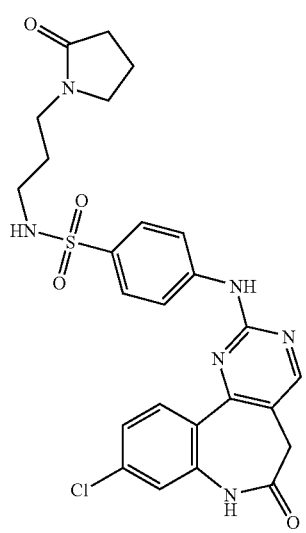<br>I-1273 |

489
-continued
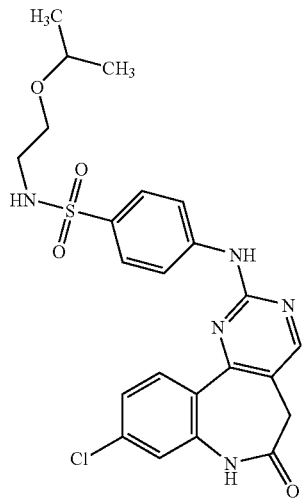
I-1274
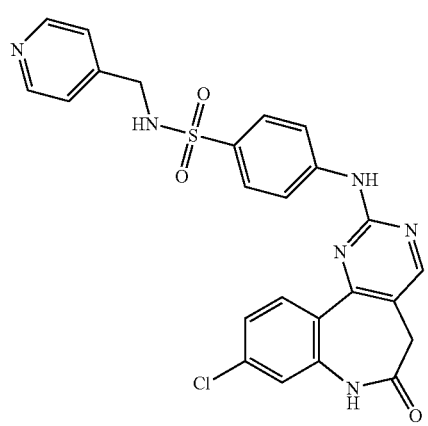
I-1275
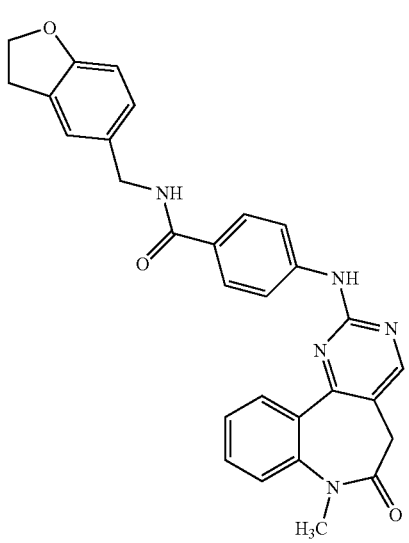
I-1276
490
-continued
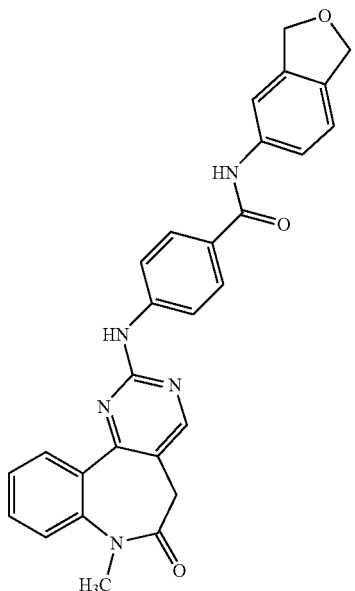
I-1277
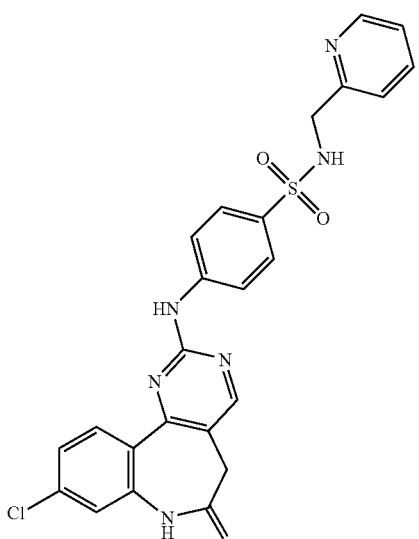
I-1278

-continued

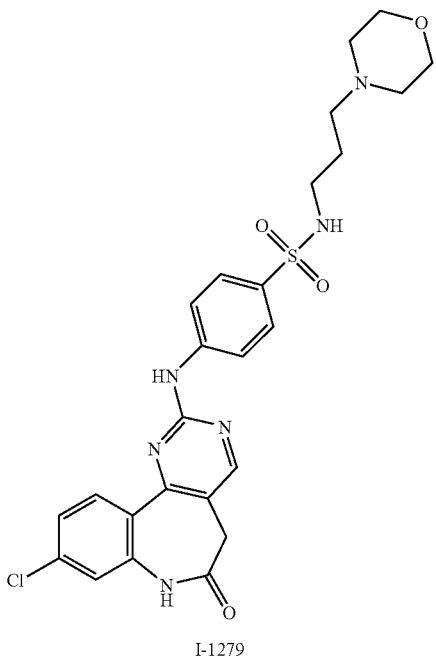

I-1279

The compounds in Table 1 above also may be identified by the following chemical names:

Chemical Name

I-1 2-(3,4-Dimethoxy-phenylamino)-5,7-dihydro-1,3,7,8-tetraaza-dibenzo[a,c]cyclohepten-6-one
I-2 9-Chloro-2-(3,4-dimethoxy-phenylamino)-5H,7H-benzo[b]pyrimido[4,5-d]azepin-6-one
I-3 4-(9-Chloro-6-oxo-6,7-dihydro-5H-benzo[b]pyrimido[4,5-d]azepin-2-ylamino)-benzoic acid
I-4 4-(9-Chloro-6-oxo-6,7-dihydro-5H-benzo[b]pyrimido[4,5-d]azepin-2-ylamino)-benzoic acid methyl ester
I-5 4-(10-Fluoro-6-oxo-6,7-dihydro-5H-benzo[b]pyrimido[4,5-d]azepin-2-ylamino)-benzoic acid
I-6 4-(7-Benzyl-9-chloro-6-oxo-6,7-dihydro-5H-benzo[b]pyrimido[4,5-d]azepin-2-ylamino)-benzoic acid
I-7 4-(9-Chloro-7-methyl-6-oxo-6,7-dihydro-5H-benzo[b]pyrimido[4,5-d]azepin-2-ylamino)-benzoic acid
I-8 4-(10-Methoxy-6-oxo-6,7-dihydro-5H-benzo[b]pyrimido[4,5-d]azepin-2-ylamino)-benzoic acid
I-9 4-(9-Methyl-6-oxo-6,7-dihydro-5H-benzo[b]pyrimido[4,5-d]azepin-2-ylamino)-benzoic acid
I-10 4-(9-Chloro-6-oxo-7-phenyl-6,7-dihydro-5H-benzo[b]pyrimido[4,5-d]azepin-2-ylamino)-benzoic acid
I-11 9-Chloro-2-(4-chloro-phenylamino)-5H,7H-benzo[b]pyrimido[4,5-d]azepin-6-one
I-12 9-Chloro-2-(2-chloro-phenylamino)-5H,7H-benzo[b]pyrimido[4,5-d]azepin-6-one
I-13 9-Chloro-2-(3-chloro-phenylamino)-5H,7H-benzo[b]pyrimido[4,5-d]azepin-6-one
I-14 9-Chloro-2-(4-methoxy-phenylamino)-5H,7H-benzo[b]pyrimido[4,5-d]azepin-6-one
I-15 9-Chloro-2-(3-methoxy-phenylamino)-5H,7H-benzo[b]pyrimido[4,5-d]azepin-6-one
I-16 9-Chloro-2-(2-methoxy-phenylamino)-5H,7H-benzo[b]pyrimido[4,5-d]azepin-6-one
I-17 9-Chloro-2-(3,4-dimethoxy-benzylamino)-5H,7H-benzo[b]pyrimido[4,5-d]azepin-6-one
I-18 10-Bromo-2-(3,4-dimethoxy-phenylamino)-5H,7H-benzo[b]pyrimido[4,5-d]azepin-6-one
I-19 4-(9-Chloro-6-oxo-6,7-dihydro-5H-benzo[b]pyrimido[4,5-d]azepin-2-ylamino)-butyric acid
I-20 9-Chloro-2-methylamino-5H,7H-benzo[b]pyrimido[4,5-d]azepin-6-one
I-21 N'-(9-Chloro-6-oxo-6,7-dihydro-5H-benzo[b]pyrimido[4,5-d]azepin-2-yl)-N,N-dimethyl-guanidine
I-22 9-Chloro-2-dimethylamino-5H,7H-benzo[b]pyrimido[4,5-d]azepin-6-one
I-23 2-Amino-9-chloro-5H,7H-benzo[b]pyrimido[4,5-d]azepin-6-one
I-24 10-Chloro-2-(3,4-dimethoxy-phenylamino)-5H,7H-benzo[b]pyrimido[4,5-d]azepin-6-one
I-25 4-(10-Bromo-6-oxo-6,7-dihydro-5H-benzo[b]pyrimido[4,5-d]azepin-2-ylamino)-benzoic acid
I-26 2-(3,4-Dimethoxy-phenylamino)-10-iodo-5H,7H-benzo[b]pyrimido[4,5-d]azepin-6-one
I-27 2-(3,4-Dimethoxy-phenylamino)-5H,7H-benzo[b]pyrimido[4,5-d]azepin-6-one
I-28 9-Chloro-2-(2,3-dihydro-benzo[1,4]dioxin-6-ylamino)-5H,7H-benzo[b]pyrimido[4,5-d]azepin-6-one
I-29 9-Chloro-2-(3,4-dimethyl-phenylamino)-5H,7H-benzo[b]pyrimido[4,5-d]azepin-6-one
I-30 2-(3,4-Dimethoxy-phenylamino)-9-iodo-5H,7H-benzo[b]pyrimido[4,5-d]azepin-6-one
I-31 2-(3,4-Dimethoxy-phenylamino)-10-(3-pyrrolidin-1-yl-prop-1-ynyl)-5H,7H-benzo[b]pyrimido[4,5-d]azepin-6-one
I-32 2-(3,4-Dimethoxy-phenylamino)-9-(3-pyrrolidin-1-yl-prop-1-ynyl)-5H,7H-benzo[b]pyrimido[4,5-d]azepin-6-one
I-33 2-(3,4-Dimethoxy-phenylamino)-9-ethynyl-5H,7H-benzo[b]pyrimido[4,5-d]azepin-6-one
I-34 2-(Benzo[1,3]dioxol-5-ylamino)-9-chloro-5H,7H-benzo[b]pyrimido[4,5-d]azepin-6-one
I-35 9-Chloro-2-(3,5-dimethyl-phenylamino)-5H,7H-benzo[b]pyrimido[4,5-d]azepin-6-one
I-36 9-Chloro-2-(4-iodo-phenylamino)-5H,7H-benzo[b]pyrimido[4,5-d]azepin-6-one
I-37 2-(3,4-Dimethoxy-phenylamino)-9-ethyl-5H,7H-benzo[b]pyrimido[4,5-d]azepin-6-one
I-38 9-(3-Amino-prop-1-ynyl)-2-(3,4-dimethoxy-phenylamino)-5H,7H-benzo[b]pyrimido[4,5-d]azepin-6-one
I-39 {3-[2-(3,4-Dimethoxy-phenylamino)-6-oxo-6,7-dihydro-5H-benzo[b]pyrimido[4,5-d]azepin-9-yl]-prop-2-ynyl}-carbamic acid tert-butyl ester
I-40 7-(3-Amino-propyl)-9-chloro-2-(3,4-dimethoxy-phenylamino)-5H,7H-benzo[b]pyrimido[4,5-d]azepin-6-one
I-41 {3-[2-(3,4-Dimethoxy-phenylamino)-6-oxo-6,7-dihydro-5H-benzo[b]pyrimido[4,5-d]azepin-9-yl]-propyl}-carbamic acid tert-butyl ester
I-42 2-(3,4-Dimethoxy-phenylamino)-9-methyl-5H,7H-benzo[b]pyrimido[4,5-d]azepin-6-one
I-43 2-(3,4-Dimethoxy-phenylamino)-6-oxo-6,7-dihydro-5H-benzo[b]pyrimido[4,5-d]azepine-10-carboxylic acid
I-44 2-Amino-10-bromo-5H,7H-benzo[b]pyrimido[4,5-d]azepin-6-one
I-45 9-Chloro-2-(4-ethynyl-phenylamino)-5H,7H-benzo[b]pyrimido[4,5-d]azepin-6-one
I-46 2-[4-(3-Amino-prop-1-ynyl)-phenylamino]-9-chloro-5H,7H-benzo[b]pyrimido[4,5-d]azepin-6-one
I-47 9-Chloro-2-[4-(3-pyrrolidin-1-yl-prop-1-ynyl)-phenylamino]-5H,7H-benzo[b]pyrimido[4,5-d]azepin-6-one I-48 2-(3,4-Dimethoxy-phenylamino)-6-oxo-6,7-dihydro-5H-benzo[b]pyrimido[4,5-d]azepine-10-carboxylic acid (2-pyridin-4-yl-ethyl)-amide I-49 2-(3,4-Dimethoxy-phenylamino)-9-(3-pyrrolidin-1-yl-propyl)-5H,7H-benzo[b]pyrimido[4,5-d]azepin-6-one I-50 9-(3-Amino-propyl)-2-(3,4-dimethoxy-phenylamino)-5H,7H-benzo[b]pyrimido[4,5-d]azepin-6-one I-51 2-Amino-10-iodo-5H,7H-benzo[b]pyrimido[4,5-d]azepin-6-one I-52 2-(3,4-Dimethoxy-phenylamino)-9-(3-hydroxy-prop-1-ynyl)-5H,7H-benzo[b]pyrimido[4,5-d]azepin-6-one I-53 2-(3,4-Dimethoxy-phenylamino)-6-oxo-6,7-dihydro-5H-benzo[b]pyrimido[4,5-d]azepine-9-carboxylic acid I-54 9-Chloro-2-[4-(3-hydroxy-prop-1-ynyl)-phenylamino]-5H,7H-benzo[b]pyrimido[4,5-d]azepin-6-one I-55 9-Chloro-2-(3,5-dimethoxy-phenylamino)-5H,7H-benzo[b]pyrimido[4,5-d]azepin-6-one I-56 2-(3,4-Dimethoxy-phenylamino)-10-(3-pyrrolidin-1-yl-propyl)-5H,7H-benzo[b]pyrimido[4,5-d]azepin-6-one I-57 2-[4-(3-Amino-propyl)-phenylamino]-9-chloro-5H,7H-benzo[b]pyrimido[4,5-d]azepin-6-one I-58 9-Chloro-2-(3-iodo-phenylamino)-5H,7H-benzo[b]pyrimido[4,5-d]azepin-6-one I-59 10-(3-Amino-prop-1-ynyl)-2-(3,4-dimethoxy-phenylamino)-5H,7H-benzo[b]pyrimido[4,5-d]azepin-6-one I-60 10-(3-Amino-propyl)-2-(3,4-dimethoxy-phenylamino)-5H,7H-benzo[b]pyrimido[4,5-d]azepin-6-one I-61 9-Chloro-2-phenylamino-5H,7H-benzo[b]pyrimido[4,5-d]azepin-6-one I-62 N-(2-Amino-ethyl)-3-(9-chloro-6-oxo-6,7-dihydro-5H-benzo[b]pyrimido[4,5-d]azepin-2-ylamino)-benzamide I-63 N-(3-Amino-propyl)-3-(9-chloro-6-oxo-6,7-dihydro-5H-benzo[b]pyrimido[4,5-d]azepin-2-ylamino)-benzamide I-64 N-(4-Amino-butyl)-3-(9-chloro-6-oxo-6,7-dihydro-5H-benzo[b]pyrimido[4,5-d]azepin-2-ylamino)-benzamide I-65 9-Chloro-2-(3-hydroxy-4-methoxy-phenylamino)-5H,7H-benzo[b]pyrimido[4,5-d]azepin-6-one I-66 9-Chloro-2-[4-(3-pyrrolidin-1-yl-propyl)-phenylamino]-5H,7H-benzo[b]pyrimido[4,5-d]azepin-6-one I-67 2-[3-(3-Amino-prop-1-ynyl)-phenylamino]-9-chloro-5H,7H-benzo[b]pyrimido[4,5-d]azepin-6-one I-68 4-(9-Chloro-5,7-dimethyl-6-oxo-6,7-dihydro-5H-benzo[b]pyrimido[4,5-d]azepin-2-ylamino)-benzoic acid I-69 4-(9-Chloro-5-methyl-6-oxo-6,7-dihydro-5H-benzo[b]pyrimido[4,5-d]azepin-2-ylamino)-benzoic acid I-70 2-(3,4-Dimethoxy-phenylamino)-6-oxo-6,7-dihydro-5H-benzo[b]pyrimido[4,5-d]azepine-9-carboxylic acid amide I-71 2-(3,4-Dimethoxy-phenylamino)-6-oxo-6,7-dihydro-5H-benzo[b]pyrimido[4,5-d]azepine-9-carboxylic acid (2-amino-ethyl)-amide I-72 2-(3,4-Dimethoxy-phenylamino)-6-oxo-6,7-dihydro-5H-benzo[b]pyrimido[4,5-d]azepine-9-carboxylic acid (3-amino-propyl)-amide I-73 2-(3,4-Dimethoxy-phenylamino)-6-oxo-6,7-dihydro-5H-benzo[b]pyrimido[4,5-d]azepine-9-carboxylic acid (4-amino-butyl)-amide I-74 10-(4-Amino-piperidine-1-carbonyl)-2-(3,4-dimethoxy-phenylamino)-5H,7H-benzo[b]pyrimido[4,5-d]azepin-6-one I-75 2-(3,4-Dimethoxy-phenylamino)-6-oxo-6,7-dihydro-5H-benzo[b]pyrimido[4,5-d]azepine-10-carboxylic acid (2-pyrrolidin-1-yl-ethyl)-amide I-76 2-(3,4-Dimethoxy-phenylamino)-6-oxo-6,7-dihydro-5H-benzo[b]pyrimido[4,5-d]azepine-10-carboxylic acid (3-amino-propyl)-amide I-77 2-(3,4-Dimethoxy-phenylamino)-6-oxo-6,7-dihydro-5H-benzo[b]pyrimido[4,5-d]azepine-10-carboxylic acid (3-pyrrolidin-1-yl-propyl)-amide I-78 [3-(9-Chloro-6-oxo-6,7-dihydro-5H-benzo[b]pyrimido[4,5-d]azepin-2-ylamino)-phenyl]-acetonitrile I-79 9-Chloro-2-(3-hydroxymethyl-phenylamino)-5H,7H-benzo[b]pyrimido[4,5-d]azepin-6-one I-80 9-Chloro-2-[3-(2-hydroxy-ethyl)-phenylamino]-5H,7H-benzo[b]pyrimido[4,5-d]azepin-6-one I-81 2-(3,4-Dimethoxy-phenylamino)-9-(3-hydroxy-propyl)-5H,7H-benzo[b]pyrimido[4,5-d]azepin-6-one I-82 2-(3,4-Dimethoxy-phenylamino)-9-propyl-5H,7H-benzo[b]pyrimido[4,5-d]azepin-6-one I-83 N-(10-Iodo-6-oxo-6,7-dihydro-5H-benzo[b]pyrimido[4,5-d]azepin-2-yl)-benzamide I-84 2-Amino-6-oxo-6,7-dihydro-5H-benzo[b]pyrimido[4,5-d]azepine-10-carboxylic acid I-85 10-Bromo-2-(methyl-phenyl-amino)-5H,7H-benzo[b]pyrimido[4,5-d]azepin-6-one I-86 2-[3-(2-Amino-ethyl)-phenylamino]-9-chloro-5H,7H-benzo[b]pyrimido[4,5-d]azepin-6-one I-87 2-(3,4-Dimethoxy-phenylamino)-9-(3-methylamino-propyl)-5H,7H-benzo[b]pyrimido[4,5-d]azepin-6-one I-88 2-(3,4-Dimethoxy-phenylamino)-9-(3-dimethylamino-propyl)-5H,7H-benzo[b]pyrimido[4,5-d]azepin-6-one I-89 9-Chloro-2-[3-(3-pyrrolidin-1-yl-prop-1-ynyl)-phenylamino]-5H,7H-benzo[b]pyrimido[4,5-d]azepin-6-one I-90 3-(9-Chloro-6-oxo-6,7-dihydro-5H-benzo[b]pyrimido[4,5-d]azepin-2-ylamino)-benzonitrile I-91 2-(3,4-Dimethoxy-phenylamino)-9-(3-dimethylamino-prop-1-ynyl)-5H,7H-benzo[b]pyrimido[4,5-d]azepin-6-one I-92 2-(3,4-Dimethoxy-phenylamino)-6-oxo-6,7-dihydro-5H-benzo[b]pyrimido[4,5-d]azepine-9-carbonitrile I-93 3-(9-Chloro-6-oxo-6,7-dihydro-5H-benzo[b]pyrimido[4,5-d]azepin-2-ylamino)-N-(3-dimethylamino-propyl)-N-methyl-benzamide I-94 4-[9-Chloro-7-(2-fluoro-phenyl)-6-oxo-6,7-dihydro-5H-benzo[b]pyrimido[4,5-d]azepin-2-ylamino]-benzoic acid I-95 4-[9-Chloro-7-(2-fluoro-phenyl)-6-oxo-6,7-dihydro-5H-benzo[b]pyrimido[4,5-d]azepin-2-ylamino]-N-methyl-N-(1-methyl-pyrrolidin-3-yl)-benzamide I-96 9-Chloro-7-(2,6-difluoro-phenyl)-2-[4-(4-methyl-piperazine-1-carbonyl)-phenylamino]-5H,7H-benzo[b]pyrimido[4,5-d]azepin-6-one I-97 4-[9-Chloro-7-(2-fluoro-phenyl)-6-oxo-6,7-dihydro-5H-benzo[b]pyrimido[4,5-d]azepin-2-ylamino]-benzenesulfonic acid I-98 9-Chloro-2-(3,4-dimethoxy-phenylamino)-7-(2-fluoro-phenyl)-5,7-dihydro-3,4,7-triaza-dibenzo[a,c]cyclohepten-6-one I-99 9-Chloro-2-(3,4-dimethoxy-phenylamino)-7-(2-fluoro-phenyl)-5,7-dihydro-1,3,4,7-tetraaza-dibenzo[a,c]cyclohepten-6-one I-100 N-(3-An-No-propyl)-6-(9-chloro-6-oxo-6,7-dihydro-5H-benzo[b]pyrimido[4,5-d]azepin-2-ylamino)-Nicotinamide I-101 9-Chloro-2-[6-(3-pyrrolidin-1-yl-prop-1-ynyl)-pyridin-2-ylamino]-5H,7H-benzo[b]pyrimido[4,5-d]azepin-6-one I-102 2-(Benzofuran-6-ylamino)-9-chloro-5H,7H-benzo[b]pyrimido[4,5-d]azepin-6-one I-103 9-Chloro-2-(5-methyl-pyrazin-2-ylamino)-5H,7H-benzo[b]pyrimido[4,5-d]azepin-6-one I-104 2-(4-Furan-3-yl-phenylamino)-9-(3-pyrrolidin-1-yl-propyl)-5H,7H-benzo[b]pyrimido[4,5-d]azepin-6-one I-105 2-(3-Aminomethyl-phenylamino)-10-(3-dimethylamino-propyl)-5H,7H-benzo[b]pyrimido[4,5-d]azepin-6-one I-106 9-(3-Dimethylamino-propyl)-2-(3-hydroxymethyl-phenylamino)-5H,7H-benzo[b]pyrimido[4,5-d]azepin-6-one I-107 9-Chloro-2-(pyridin-2-ylamino)-5H,7H-benzo[b]pyrimido[4,5-d]azepin-6-one I-108 9-Chloro-2-(pyridin-3-ylamino)-5H,7H-benzo[b]pyrimido[4,5-d]azepin-6-one I-109 9-Chloro-2-(pyridin-4-ylamino)-5H,7H-benzo[b]pyrimido[4,5-d]azepin-6-one I-110 10-(3-Dimethylamino-propyl)-2-(pyridin-4-ylamino)-5H,7H-benzo[b]pyrimido[4,5-d]azepin-6-one I-111 2-(Pyridin-3-ylamino)-9-(3-pyrrolidin-1-yl-propyl)-5H,7H-benzo[b]pyrimido[4,5-d]azepin-6-one I-112 5-Amino-9-chloro-2-(3,4-dimethoxy-phenylamino)-5H,7H-benzo[b]pyrimido[4,5-d]azepin-6-one I-113 10-(3-Diethylamino-propyl)-2-(4-methoxy-phenylamino)-5H,7H-benzo[b]pyrimido[4,5-d]azepin-6-one I-114 2-(3,4-Dimethoxy-phenylamino)-9-(3-piperidin-1-yl-propyl)-5H,7H-benzo[b]pyrimido[4,5-d]azepin-6-one I-115 9-(3-Diethylamino-propyl)-2-(3,4-dimethoxy-phenylamino)-5H,7H-benzo[b]pyrimido[4,5-d]azepin-6-one I-116 2-(4-Methoxy-phenylamino)-10-(3-piperidin-1-yl-propyl)-5H,7H-benzo[b]pyrimido[4,5-d]azepin-6-one I-117 2-(3,4-Dimethoxy-phenylamino)-9-(3-morpholin-4-yl-propyl)-5H,7H-benzo[b]pyrimido[4,5-d]azepin-6-one I-118 2-(4-Methoxy-phenylamino)-10-(3-morpholin-4-yl-propyl)-5H,7H-benzo[b]pyrimido[4,5-d]azepin-6-one I-119 9-Chloro-2-[2-(3,5-difluoro-phenyl)-ethylamino]-5H,7H-benzo[b]pyrimido[4,5-d]azepin-6-one I-120 9-Chloro-2-(4-trifluoromethoxy-phenylamino)-5H,7H-benzo[b]pyrimido[4,5-d]azepin-6-one I-121 9-Chloro-2-(3-trifluoromethyl-benzylamino)-5H,7H-benzo[b]pyrimido[4,5-d]azepin-6-one I-122 2-(3-Methoxy-4-methyl-phenylamino)-9-trifluoromethyl-5H,7H-benzo[b]pyrimido[4,5-d]azepin-6-one I-123 2-(3,4-Dimethoxy-phenylamino)-9-(1H-imidazol-2-yl)-5H,7H-benzo[b]pyrimido[4,5-d]azepin-6-one I-124 9-Chloro-2-[4-(1H-imidazol-2-yl)-phenylamino]-5H,7H-benzo[b]pyrimido[4,5-d]azepin-6-one I-125 2-[4-(1H-Pyrazol-4-yl)-phenylamino]-9-(3-pyrrolidin-1-yl-propyl)-5H,7H-benzo[b]pyrimido[4,5-d]azepin-6-one I-126 10-(1H-Imidazol-2-yl)-2-(4-methoxy-phenylamino)-5H,7H-benzo[b]pyrimido[4,5-d]azepin-6-one I-127 9-Chloro-2-[3-(1H-imidazol-2-yl)-phenylamino]-5H,7H-benzo[b]pyrimido[4,5-d]azepin-6-one I-128 2-[3-(1H-Imidazol-2-yl)-phenylamino]-9-(3-pyrrolidin-1-yl-propyl)-5H,7H-benzo[b]pyrimido[4,5-d]azepin-6-one I-129 2-[3-(3-Dimethylamino-propyl)-phenylamino]-9-thiophen-3-yl-5H,7H-benzo[b]pyrimido[4,5-d]azepin-6-one I-130 9-Amino-2-(3,4-dimethoxy-phenylamino)-5H,7H-benzo[b]pyrimido[4,5-d]azepin-6-one I-131 9-(3-Pyrrolidin-1-yl-propyl)-2-(3-thiophen-2-yl-phenylamino)-5H,7H-benzo[b]pyrimido[4,5-d]azepin-6-one I-132 2-(3,4-Dimethoxy-phenylamino)-9-dimethylamino-5H,7H-benzo[b]pyrimido[4,5-d]azepin-6-one I-133 2-[3-(3-Diethylamino-propyl)-phenylamino]-9-methoxy-5H,7H-benzo[b]pyrimido[4,5-d]azepin-6-one I-134 2-[3-(3-Dimethylamino-propyl)-phenylamino]-9-(1H-imidazol-2-yl)-5H,7H-benzo[b]pyrimido[4,5-d]azepin-6-one I-135 2-(4-Methoxy-phenylamino)-10-(3-pyrrolidin-1-yl-propyl)-5H,7H-benzo[b]pyrimido[4,5-d]azepin-6-one I-136 2-(4-Methoxy-phenylamino)-10-(3-pyrrolidin-1-yl-prop-1-ynyl)-5H,7H-benzo[b]pyrimido[4,5-d]azepin-6-one I-137 7-(3-Amino-propyl)-9-chloro-2-(3,4-dimethoxy-phenylamino)-5H,7H-benzo[b]pyrimido[4,5-d]azepin-6-one I-138 9-Aminomethyl-2-(3,4-dimethoxy-phenylamino)-5H,7H-benzo[b]-pyrimido[4,5-d]azepin-6-one I-139 2-[3-(3-Amino-propyl)-phenylamino]-9-chloro-5H,7H-benzo[b]pyrimido-[4,5-d]azepin-6-one I-140 2-(3-Aminomethyl-phenylamino)-9-chloro-5H,7H-benzo[b]pyrimido[4,5-d]-azepin-6-one I-141 N-(8-Chloro-2-oxo-4-vinyl-2,3-dihydro-1H-benzo[b]azepin-5-yl)-N'-(3-nitro-phenyl)-acetamidine I-142 2-[(4-methoxyphenyl)amino]-10-(3-pyrrolidin-1-yl-prop-1-yn-1-yl)-5,7-dihydro-6H-pyrimido[5,4-d][1]benzazepin-6-one I-143 2-[(4-methoxyphenyl)amino]-10-(3-pyrrolidin-1-yl-propyl)-5,7-dihydro-6H-pyrimido[5,4-d][1]benzazepin-6-one I-144 2-[(3-aminophenyl)amino]-9-chloro-5,7-dihydro-6H-pyrimido[5,4-d][1]benzazepin-6-one I-145 9-chloro-2-{[3-(3-hydroxypropyl)phenyl]amino}-5,7-dihydro-6H-pyrimido[5,4-d][1]benzazepin-6-one I-146 (2E)-3-{2-[(3,4-dimethoxyphenyl)amino]-6-oxo-6,7-dihydro-5H-pyrimido[5,4-d][1]benzazepin-9-yl}acrylamide I-147 tert-butyl 4-({9-chloro-2-[(3,4-dimethoxyphenyl)amino]-6-oxo-5,6-dihydro-7H-pyrimido[5,4-d][1]benzazepin-7-yl}methyl)piperidine-1-carboxylate I-148 2-(2-{2-[(3,4-dimethoxyphenyl)amino]-6-oxo-5,6-dihydro-7H-pyrimido[5,4-d][1]benzazepin-7-yl}ethyl)-1H-isoindole-1,3(2H)-dione I-149 9-chloro-2-[(3,4-dimethoxyphenyl)amino]-7-(piperidin-4-ylmethyl)-5,7-dihydro-6H-pyrimido[5,4-d][1]benzazepin-6-one I-150 2-[(4-methoxyphenyl)amino]-9-(3-pyrrolidin-1-yl-prop-1-yn-1-yl)-5,7-dihydro-6H-pyrimido[5,4-d][1]benzazepin-6-one I-151 2-[(3-methoxyphenyl)amino]-9-(3-pyrrolidin-1-yl-prop-1-yn-1-yl)-5,7-dihydro-6H-pyrimido[5,4-d][1]benzazepin-6-one I-152 2-[(4-chlorophenyl)amino]-9-(3-pyrrolidin-1-ylprop-1-yn-1-yl)-5,7-dihydro-6H-pyrimido[5,4-d][1]benzazepin-6-one I-153 2-[(3-chlorophenyl)amino]-9-(3-pyrrolidin-1-ylprop-1-yn-1-yl)-5,7-dihydro-6H-pyrimido[5,4-d][1]benzazepin-6-one I-154 2-[(3,4-dimethylphenyl)amino]-9-(3-pyrrolidin-1-yl-prop-1-yn-1-yl)-5,7-dihydro-6H-pyrimido[5,4-d][1]benzazepin-6-one I-155 9-chloro-2-({3-[3-(dimethylamino)propyl]phenyl}amino)-5,7-dihydro-6H-pyrimido[5,4-d][1]benzazepin-6-one I-157 9-chloro-2-({3-[3-(diethylamino)propyl]phenyl}amino)-5,7-dihydro-6H-pyrimido[5,4-d][1]benzazepin-6-one I-157 9-chloro-2-{[3-(3-morpholin-4-ylpropyl)phenyl]amino}-5,7-dihydro-6H-pyrimido[5,4-d][1]benzazepin-6-one I-158 9-chloro-2-{[3-(3-piperidin-1-ylpropyl)phenyl]amino}-5,7-dihydro-6H-pyrimido[5,4-d][1]benzazepin-6-one I-159 9-chloro-2-{[3-(3-pyrrolidin-1-ylpropyl)phenyl]amino}-5,7-dihydro-6H-pyrimido[5,4-d]d[1]benzazepin-6-one I-160 10-bromo-2-[(3-methoxyphenyl)amino]-5,7-dihydro-6H-pyrimido[5,4-d][1]benzazepin-6-one I-161 10-bromo-2-[(3,5-dimethoxyphenyl)amino]-5,7-dihydro-6H-pyrimido[5,4-d][1]benzazepin-6-one I-162 9-chloro-2-{[2-(4-methoxyphenyl)ethyl]amino}-5,7-dihydro-6H-pyrimido[5,4-d][1]benzazepin-6-one I-163 9-chloro-2-[(4-methyl-1,3-thiazol-2-yl)amino]-5,7-dihydro-6H-pyrimido[5,4-d][1]benzazepin-6-one I-164 2-[(3-methoxyphenyl)amino]-10-(3-pyrrolidin-1-yl-prop-1-yn-1-yl)-5,7-dihydro-6H-pyrimido[5,4-d][1]benzazepin-6-one I-165 2-[(3,4-dimethoxyphenyl)amino]-9-fluoro-5,7-dihydro-6H-pyrimido[5,4-d][1]benzazepin-6-one I-166 2-[(3-methoxyphenyl)amino]-10-(3-pyrrolidin-1-yl-propyl)-5,7-dihydro-6H-pyrimido[5,4-d][1]benzazepin-6-one I-167 2-[(3,5-dimethoxyphenyl)amino]-10-(3-pyrrolidin-1-ylprop-1-yn-1-yl)-5,7-dihydro-6H-pyrimido[5,4-d][1]benzazepin-6-one I-168 2-[(3,5-dimethoxyphenyl)amino]-10-(3-pyrrolidin-1-ylpropyl)-5,7-dihydro-6H-pyrimido[5,4-d][1]benzazepin-6-one I-169 9-chloro-2-({3-[4-(dimethylamino)but-1-yn-1-yl]phenyl}amino)-5,7-dihydro-6H-pyrimido[5,4-d][1]benzazepin-6-one I-170 9-chloro-2-({3-[4-(dimethylamino)butyl]phenyl}amino)-5,7-dihydro-6H-pyrimido[5,4-d][1]benzazepin-6-one I-171 3-{[6-oxo-10-(3-pyrrolidin-1-ylprop-1-yn-1-yl)-6,7-dihydro-5H-pyrimido[5,4-d][1]benzazepin-2-yl]amino}benzoic acid I-172 9-chloro-7-[2-(diethylamino)ethyl]-2-[(3,4-dimethoxyphenyl)amino]-5,7-dihydro-6H-pyrimido[5,4-d][1]benzazepin-6-one I-173 9-chloro-2-[(3,4-dimethoxyphenyl)amino]-7-(2-morpholin-4-ylethyl)-5,7-dihydro-6H-pyrimido[5,4-d][1]benzazepin-6-one I-174 9-chloro-2-[(3,4-dimethoxyphenyl)amino]-7-[2-(1-methylpyrrolidin-2-yl)ethyl]-5,7-dihydro-6H-pyrimido[5,4-d][1]benzazepin-6-one I-175 9-chloro-2-[(6-chloro-1,3-benzothiazol-2-yl)amino]-5,7-dihydro-6H-pyrimido[5,4-d][1]benzazepin-6-one I-176 3-{[6-oxo-10-(3-pyrrolidin-1-ylpropyl)-6,7-dihydro-5H-pyrimido[5,4-d][1]benzazepin-2-yl]amino}benzoic acid I-177 2-anilino-10-iodo-5,7-dihydro-6H-pyrimido[5,4-d][1]benzazepin-6-one I-178 2-(1,3-benzodioxol-5-ylamino)-10-iodo-5,7-dihydro-6H-pyrimido[5,4-d][1]benzazepin-6-one I-179 9-chloro-2-[(6-methoxypyridin-3-yl)amino]-5,7-dihydro-6H-pyrimido[5,4-d][1]benzazepin-6-one I-180 9-chloro-2-[(5-ethyl-1,3,4-thiadiazol-2-yl)amino]-5,7-dihydro-6H-pyrimido[5,4-d][1]benzazepin-6-one I-181 2-{[4-(4-bromophenyl)-1,3-thiazol-2-yl]amino}-9-chloro-5,7-dihydro-6H-pyrimido[5,4-d][1]benzazepin-6-one I-182 9-chloro-2-{[5-(trifluoromethyl)-1,3,4-thiadiazol-2-yl]amino}-5,7-dihydro-6H-pyrimido[5,4-d][1]benzazepin-6-one I-183 9-(3-pyrrolidin-1-ylprop-1-yn-1-yl)-2-{[4-(2-thienyl)phenyl]amino}-5,7-dihydro-6H-pyrimido[5,4-d][1]benzazepin-6-one I-184 2-anilino-10-(3-pyrrolidin-1-ylprop-1-yn-1-yl)-5,7-dihydro-6H-pyrimido[5,4-d][1]benzazepin-6-one I-185 2-(1,3-benzodioxol-5-ylamino)-10-(3-pyrrolidin-1-yl-prop-1-yn-1-yl)-5,7-dihydro-6H-pyrimido[5,4-d][1]benzazepin-6-one I-186 9-(3-pyrrolidin-1-ylpropyl)-2-{[4-(2-thienyl)phenyl]amino}-5,7-dihydro-6H-pyrimido[5,4-d][1]benzazepin-6-one I-187 9-chloro-2-{[4-(trifluoromethoxy)phenyl]amino}-5,7-dihydro-6H-pyrimido[5,4-d][1]benzazepin-6-one I-188 9-chloro-2-[(4-morpholin-4-ylphenyl)amino]-5,7-dihydro-6H-pyrimido[5,4-d][1]benzazepin-6-one I-189 9-chloro-2-{[4-(dimethylamino)phenyl]amino}-5,7-dihydro-6H-pyrimido[5,4-d][1]benzazepin-6-one I-190 9-chloro-2-[(1-methyl-3-phenyl-1H-pyrazol-5-yl)amino]-5,7-dihydro-6H-pyrimido[5,4-d][1]benzazepin-6-one I-191 9-chloro-2-{[4-(4-methylpiperazin-1-yl)phenyl]amino}-5,7-dihydro-6H-pyrimido[5,4-d][1]benzazepin-6-one I-192 9-chloro-2-[(5-methyl-1,3-thiazol-2-yl)amino]-5,7-dihydro-6H-pyrimido[5,4-d][1]benzazepin-6-one I-193 9-chloro-2-(1,3-dihydro-2-benzofuran-5-ylamino)-5,7-dihydro-6H-pyrimido[5,4-d][1]benzazepin-6-one I-194 3-{3-[(10-iodo-6-oxo-6,7-dihydro-5H-pyrimido[5,4-d][1]benzazepin-2-yl)amino]phenyl}propanoic acid I-195 2-[(3-aminophenyl)amino]-10-(3-pyrrolidin-1-ylpropyl)-5,7-dihydro-6H-pyrimido[5,4-d][1]benzazepin-6-one I-196 2-[(4-aminophenyl)amino]-10-(3-pyrrolidin-1-ylpropyl)-5,7-dihydro-6H-pyrimido[5,4-d][1]benzazepin-6-one I-197 9-chloro-2-(pyridin-2-ylamino)-5,7-dihydro-6H-pyrimido[5,4-d][1]benzazepin-6-one I-198 2-[(3,4-dimethoxyphenyl)amino]-5,7-dihydro-6H-pyrimido[4,5-d]thieno[3,2-b]azepin-6-one I-199 2-[(4-methoxyphenyl)amino]-5,7-dihydro-6H-pyrimido[4,5-d]thieno[3,2-b]azepin-6-one I-200 2-[(4-methylphenyl)amino]-5,7-dihydro-6H-pyrimido[4,5-d]thieno[3,2-b]azepin-6-one I-201 2-amino-9-[(4-methoxyphenyl)amino]-5,7-dihydro-6H-pyrimido[5,4-d][1]benzazepin-6-one I-202 2-[(3,4-dichlorophenyl)amino]-5,7-dihydro-6H-pyrimido[4,5-d]thieno[3,2-b]azepin-6-one I-203 2-amino-9-(1,3-benzodioxol-5-ylamino)-5,7-dihydro-6H-pyrimido[5,4-d][1]benzazepin-6-one I-204 2-[(4-chlorophenyl)amino]-5,7-dihydro-6H-pyrimido[4,5-d]thieno[3,2-b]azepin-6-one I-205 2-amino-9-[(4-methylphenyl)amino]-5,7-dihydro-6H-pyrimido[5,4-d][1]benzazepin-6-one I-206 2-amino-9-[(3-fluorophenyl)amino]-5,7-dihydro-6H-pyrimido[5,4-d][1]benzazepin-6-one I-207 2-{[4-(trifluoromethyl)phenyl]amino}-5,7-dihydro-6H-pyrimido[4,5-d]thieno[3,2-b]azepin-6-one I-208 2-[(3-fluorophenyl)amino]-5,7-dihydro-6H-pyrimido[4,5-d]thieno[3,2-b]azepin-6-one I-209 4-[(6-oxo-6,7-dihydro-5H-pyrimido[4,5-d]thieno[3,2-b]azepin-2-yl)amino]benzoic acid I-210 2-amino-5,7-dihydro-6H-pyrimido[4,5-d]thieno[3,2-b]azepin-6-one I-211 2-anilino-5,7-dihydro-6H-pyrimido[4,5-d]thieno[3,2-b]azepin-6-one I-212 2-[(4-iodophenyl)amino]-10-(3-pyrrolidin-1-ylpropyl)-5,7-dihydro-6H-pyrimido[5,4-d][1]benzazepin-6-one I-213 2-amino-7-[3-(dimethylamino)propyl]-5,7-dihydro-6H-pyrimido[5,4-d][1]benzazepin-6-one I-214 2-amino-7-(2-methoxyethyl)-5,7-dihydro-6H-pyrimido[5,4-d][1]benzazepin-6-one I-215 methyl 3-(2-amino-6-oxo-5,6-dihydro-7H-pyrimido[5,4-d][1]benzazepin-7-yl)propanoate I-216 2-amino-7-[3-(1H-pyrrol-1-yl)propyl]-5,7-dihydro-6H-pyrimido[5,4-d][1]benzazepin-6-one I-217 2-amino-7-[2-(1-methylpyrrolidin-2-yl)ethyl]-5,7-dihydro-6H-pyrimido[5,4-d][1]benzazepin-6-one I-218 2-amino-7-(2-morpholin-4-ylethyl)-5,7-dihydro-6H-pyrimido[5,4-d][1]benzazepin-6-one I-219 2-anilino-10-(3-pyrrolidin-1-ylpropyl)-5,7-dihydro-6H-pyrimido[5,4-d][1]benzazepin-6-one I-220 2-(1,3-benzodioxol-5-ylamino)-10-(3-pyrrolidin-1-ylpropyl)-5,7-dihydro-6H-pyrimido[5,4-d][1]benzazepin-6-one I-221 2-[(3,4-dimethoxyphenyl)amino]-9-[5-(pyrrolidin-1-ylmethyl)-2-thienyl]-5,7-dihydro-6H-pyrimido[5,4-d][1]benzazepin-6-one I-222 2-[(4-chlorophenyl)amino]-10-(3-pyrrolidin-1-ylpropyl)-5,7-dihydro-6H-pyrimido[5,4-d][1]benzazepin-6-one I-223 2-[(3-iodophenyl)amino]-10-(3-pyrrolidin-1-ylpropyl)-5,7-dihydro-6H-pyrimido[5,4-d][1]benzazepin-6-one I-224 tert-butyl 4-({2-[(3,4-dimethoxyphenyl)amino]-6-oxo-6,7-dihydro-5H-pyrimido[5,4-d][1]benzazepin-9-yl}carbonyl)piperazine-1-carboxylate I-225 2-amino-9-[(3-methoxyphenyl)amino]-5,7-dihydro-6H-pyrimido[5,4-d][1]benzazepin-6-one I-226 2-{[3-(hydroxymethyl)phenyl]amino}-10-(3-pyrrolidin-1-ylpropyl)-5,7-dihydro-6H-pyrimido[5,4-d][1]benzazepin-6-one I-227 2-[(3,4-dimethoxyphenyl)amino]-6-oxo-N-(2-pyrrolidin-1-ylethyl)-6,7-dihydro-5H-pyrimido[5,4-d][1]benzazepine-9-carboxamide I-228 2-[(3,4-dimethoxyphenyl)amino]-9-(piperazin-1-ylcarbonyl)-5,7-dihydro-6H-pyrimido[5,4-d][1]benzazepin-6-one I-229 tert-butyl 4-[({2-[(3,4-dimethoxyphenyl)amino]-6-oxo-6,7-dihydro-5H-pyrimido[5,4-d][1]benzazepin-9-yl}carbonyl)amino]piperidine-1-carboxylate I-230 2-amino-7-benzyl-5,7-dihydro-6H-pyrimido[5,4-d][1]benzazepin-6-one I-231 2-amino-5,7-dihydro-6H-pyrimido[5,4-d][1]benzazepin-6-one I-232 2-[(3,5-dimethoxyphenyl)amino]-9-iodo-5,7-dihydro-6H-pyrimido[5,4-d][1]benzazepin-6-one I-233 2-amino-7-[3-(diethylamino)propyl]-5,7-dihydro-6H-pyrimido[5,4-d][1]benzazepin-6-one I-234 tert-butyl 4-[(2-amino-6-oxo-5,6-dihydro-7H-pyrimido[5,4-d][1]benzazepin-7-yl)methyl]piperidine-1-carboxylate I-235 9-chloro-2-{[2-(3-fluorophenyl)ethyl]amino}-5,7-dihydro-6H-pyrimido[5,4-d][1]benzazepin-6-one I-236 9-chloro-2-{[2-(1H-imidazol-5-yl)ethyl]amino}-5,7-dihydro-6H-pyrimido[5,4-d][1]benzazepin-6-one I-237 9-chloro-2-{[2-(4-Nitrophenyl)ethyl]amino}-5,7-dihydro-6H-pyrimido[5,4-d][1]benzazepin-6-one I-238 2-{[2-(4-bromophenyl)ethyl]amino}-9-chloro-5,7-dihydro-6H-pyrimido[5,4-d][1]benzazepin-6-one I-239 2-[(3-aminophenyl)amino]-10-ethyl-5,7-dihydro-6H-pyrimido[5,4-d][1]benzazepin-6-one I-240 2-amino-9-{[4-(dimethylamino)phenyl]amino}-5,7-dihydro-6H-pyrimido[5,4-d][1]benzazepin-6-one I-241 2-[(3,4-dimethoxyphenyl)amino]-6-oxo-N-(3-pyrrolidin-1-ylpropyl)-6,7-dihydro-5H-pyrimido[5,4-d][1]benzazepine-9-carboxamide I-242 tert-butyl {trans-4-[({2-[(3,4-dimethoxyphenyl)amino]-6-oxo-6,7-dihydro-5H-pyrimido[5,4-d][1]benzazepin-9-yl}carbonyl)amino]cyclohexyl}carbamate I-243 2-[(4-ethynylphenyl)amino]-10-(3-pyrrolidin-1-ylpropyl)-5,7-dihydro-6H-pyrimido[5,4-d][1]benzazepin-6-one I-244 2-[(3,4-dimethoxyphenyl)amino]-6-oxo-N-piperidin-4-yl-6,7-dihydro-5H-pyrimido[5,4-d][1]benzazepine-9-carboxamide I-245 N-(trans-4-aminocyclohexyl)-2-[(3,4-dimethoxyphenyl)amino]-6-oxo-6,7-dihydro-5H-pyrimido[5,4-d][1]benzazepine-9-carboxamide I-246 2-amino-7-(4-fluorobenzyl)-5,7-dihydro-6H-pyrimido[5,4-d][1]benzazepin-6-one I-247 2-[(3,4-dimethoxyphenyl)amino]-9-(2-pyrrolidin-1-ylethyl)-5,7-dihydro-6H-pyrimido[5,4-d][1]benzazepin-6-one I-248 2-amino-7-(3-fluorobenzyl)-5,7-dihydro-6H-pyrimido[5,4-d][1]benzazepin-6-one I-249 2-amino-7-(4-methoxybenzyl)-5,7-dihydro-6H-pyrimido[5,4-d][1]benzazepin-6-one I-250 2-[(3-ethynylphenyl)amino]-10-(3-pyrrolidin-1-ylpropyl)-5,7-dihydro-6H-pyrimido[5,4-d][1]benzazepin-6-one I-251 2-amino-7-(4-methylbenzyl)-5,7-dihydro-6H-pyrimido[5,4-d][1]benzazepin-6-one I-252 2-amino-7-(4-chlorobenzyl)-5,7-dihydro-6H-pyrimido[5,4-d][1]benzazepin-6-one I-253 2-amino-7-(3,4-dichlorobenzyl)-5,7-dihydro-6H-pyrimido[5,4-d][1]benzazepin-6-one I-254 2-[(3,4-dimethoxyphenyl)amino]-5H-pyrimido[4,5-d]thieno[3,4-b]azepin-6(7H)-one I-255 2-amino-9-anilino-5,7-dihydro-6H-pyrimido[5,4-d][1]benzazepin-6-one I-256 2-[(4-methoxyphenyl)amino]-5H-pyrimido[4,5-d]thieno[3,4-b]azepin-6(7H)-one I-257 2-amino-9-{[4-(trifluoromethyl)phenyl]amino}-5,7-dihydro-6H-pyrimido[5,4-d][1]benzazepin-6-one I-258 2-[(4-methylphenyl)amino]-5H-pyrimido[4,5-d]thieno[3,4-b]azepin-6(7H)-one I-259 2-[(3,4-dichlorophenyl)amino]-5H-pyrimido[4,5-d]thieno[3,4-b]azepin-6(7H)-one I-260 2-[(4-chlorophenyl)amino]-5H-pyrimido[4,5-d]thieno[3,4-b]azepin-6(7H)-one I-261 2-{[4-(trifluoromethyl)phenyl]amino}-5H-pyrimido[4,5-d]thieno[3,4-b]azepin-6(7H)-one I-262 2-[(3-fluorophenyl)amino]-5H-pyrimido[4,5-d]thieno[3,4-b]azepin-6(7H)-one I-263 4-[(6-oxo-6,7-dihydro-5H-pyrimido[4,5-d]thieno[3,4-b]azepin-2-yl)amino]benzoic acid I-264 2-amino-5H-pyrimido[4,5-d]thieno[3,4-b]azepin-6(7H)-one I-265 2-anilino-5H-pyrimido[4,5-d]thieno[3,4-b]azepin-6(7H)-one I-266 9-chloro-2-{[3-(trifluoromethoxy)phenyl]amino}-5,7-dihydro-6H-pyrimido[5,4-d][1]benzazepin-6-one I-267 9-chloro-2-[(5-chloropyridin-2-yl)amino]-5,7-dihydro-6H-pyrimido[5,4-d][1]benzazepin-6-one I-268 9-chloro-2-[(4-Nitrophenyl)amino]-5,7-dihydro-6H-pyrimido[5,4-d][1]benzazepin-6-one I-269 9-chloro-2-(pyrimidin-4-ylamino)-5,7-dihydro-6H-pyrimido[5,4-d][1]benzazepin-6-one I-270 9-chloro-2-(cyclopropylamino)-5,7-dihydro-6H-pyrimido[5,4-d][1]benzazepin-6-one I-271 9-chloro-2-{[1-(hydroxymethyl)-2-methylpropyl]amino}-5,7-dihydro-6H-pyrimido[5,4-d][1]benzazepin-6-one I-272 9-chloro-2-({4-[(3-methylpiperazin-1-yl)carbonyl]phenyl}amino)-5,7-dihydro-6H-pyrimido[5,4-d][1]benzazepin-6-one I-273 9-chloro-2-({4-[(3,5-dimethylpiperazin-1-yl)carbonyl]phenyl}amino)-5,7-dihydro-6H-pyrimido[5,4-d][1]benzazepin-6-one I-274 9-chloro-2-[(4-{[3-(methylamino)pyrrolidin-1-yl]carbonyl}phenyl)amino]-5,7-dihydro-6H-pyrimido[5,4-d][1]benzazepin-6-one I-275 2-[(3,4-dimethoxyphenyl)amino]-7-methyl-10-(3-pyrrolidin-1-ylpropyl)-5,7-dihydro-6H-pyrimido[5,4-d][1]benzazepin-6-one I-276 2-[(3,4-dimethoxyphenyl)amino]-5,7-dihydro-6H-[1]benzofuro[3,2-b]pyrimido[4,5-d]azepin-6-one I-277 2-[(4-methoxyphenyl)amino]-5,7-dihydro-6H-[1]benzofuro[3,2-b]pyrimido[4,5-d]azepin-6-one I-278 2-[(4-methylphenyl)amino]-5,7-dihydro-6H-[1]benzofuro[3,2-b]pyrimido[4,5-d]azepin-6-one I-279 2-[(3,4-dichlorophenyl)amino]-5,7-dihydro-6H-[1]benzofuro[3,2-b]pyrimido[4,5-d]azepin-6-one I-280 2-[(4-chlorophenyl)amino]-5,7-dihydro-6H-[1]benzofuro[3,2-b]pyrimido[4,5-d]azepin-6-one I-281 2-{[4-(trifluoromethyl)phenyl]amino}-5,7-dihydro-6H-[1]benzofuro[3,2-b]pyrimido[4,5-d]azepin-6-one I-282 4-[(6-oxo-6,7-dihydro-5H-[1]benzofuro[3,2-b]pyrimido[4,5-d]azepin-2-yl)amino]benzoic acid I-283 2-amino-5,7-dihydro-6H-[1]benzofuro[3,2-b]pyrimido[4,5-d]azepin-6-one I-284 2-{[3-(3-piperidin-1-ylpropyl)phenyl]amino}-10-(3-pyrrolidin-1-ylpropyl)-5,7-dihydro-6H-pyrimido[5,4-d][1]benzazepin-6-one I-285 2-amino-7-[4-(1H-pyrazol-1-yl)benzyl]-5,7-dihydro-6H-pyrimido[5,4-d][1]benzazepin-6-one I-286 2-amino-7-[4-(1H-1,2,4-triazol-1-yl)benzyl]-5,7-dihydro-6H-pyrimido[5,4-d][1]benzazepin-6-one I-287 2-amino-7-[(1-methyl-1H-1,2,3-benzotriazol-6-yl)methyl]-5,7-dihydro-6H-pyrimido[5,4-d][1]benzazepin-6-one I-288 2-amino-7-[2-(diethylamino)ethyl]-5,7-dihydro-6H-pyrimido[5,4-d][1]benzazepin-6-one I-289 methyl 4-(2-amino-6-oxo-5,6-dihydro-7H-pyrimido[5,4-d][1]benzazepin-7-yl)butanoate I-290 2-amino-7-(3-methoxypropyl)-5,7-dihydro-6H-pyrimido[5,4-d][I]benzazepin-6-one I-291 2-amino-7-(piperidin-4-ylmethyl)-5,7-dihydro-6H-pyrimido[5,4-d][1]benzazepin-6-one I-292 5-amino-2-[(3,4-dimethoxyphenyl)amino]-5,7-dihydro-6H-pyrimido[5,4-d][1]benzazepin-6-one I-293 2-[(3-fluorophenyl)amino]-5,7-dihydro-6H-[1]benzofuro[3,2-b]pyrimido[4,5-d]azepin-6-one I-294 2-anilino-5,7-dihydro-6H-[1]benzofuro[3,2-b]pyrimido[4,5-d]azepin-6-one I-295 N-(6-oxo-6,7-dihydro-5H-pyrimido[5,4-d][1]benzazepin-2-yl)benzamide I-296 2-methoxy-N-(6-oxo-6,7-dihydro-5H-pyrimido[5,4-d][1]benzazepin-2-yl)benzamide I-297 4-chloro-N-(6-oxo-6,7-dihydro-5H-pyrimido[5,4-d][1]benzazepin-2-yl)benzamide I-298 3,4-dichloro-N-(6-oxo-6,7-dihydro-5H-pyrimido[5,4-d][1]benzazepin-2-yl)benzamide I-299 3,4-dimethoxy-N-(6-oxo-6,7-dihydro-5H-pyrimido[5,4-d][1]benzazepin-2-yl)benzamide I-300 2-({4-[(4-methylpiperazin-1-yl)carbonyl]phenyl}amino)-5,7-dihydro-6H-pyrimido[4,5-d]thieno[3,2-b]azepin-6-one I-301 N-[2-(dimethylamino)ethyl]-4-[(6-oxo-6,7-dihydro-5H-pyrimido[4,5-d]thieno[3,2-b]azepin-2-yl)amino]benzamide I-302 tert-butyl (1-{4-[(6-oxo-6,7-dihydro-5H-pyrimido[4,5-d]thieno[3,2-b]azepin-2-yl)amino]benzoyl}pyrrolidin-3-yl)carbamate I-303 2-[(4-{[3-(dimethylamino)pyrrolidin-1-yl]carbonyl}phenyl)amino]-5,7-dihydro-6H-pyrimido[4,5-d]thieno[3,2-b]azepin-6-one I-304 2-({4-[(3-methylpiperazin-1-yl)carbonyl]phenyl}amino)-5,7-dihydro-6H-pyrimido[4,5-d]thieno[3,2-b]azepin-6-one I-305 2-[(2-methoxyphenyl)amino]-5,7-dihydro-6H-pyrimido[4,5-d]thieno[3,2-b]azepin-6-one I-306 2-[(2-fluorophenyl)amino]-5,7-dihydro-6H-pyrimido[4,5-d]thieno[3,2-b]azepin-6-one I-307 2-[(2-methylphenyl)amino]-5,7-dihydro-6H-pyrimido[4,5-d]thieno[3,2-b]azepin-6-one I-308 2-[(2-methoxyphenyl)amino]-5H-pyrimido[4,5-d]thieno[3,4-b]azepin-6(7H)-one I-309 2-[(2-fluorophenyl)amino]-5H-pyrimido[4,5-d]thieno[3,4-b]azepin-6(7H)-one I-310 2-[(2-methylphenyl)amino]-5H-pyrimido[4,5-d]thieno[3,4-b]azepin-6(7H)-one I-311 2-[(2-methoxyphenyl)amino]-5,7-dihydro-6H-[1]benzofuro[3,2-b]pyrimido[4,5-d]azepin-6-one I-312 2-[(2-fluorophenyl)amino]-5,7-dihydro-6H-[1]benzofuro[3,2-b]pyrimido[4,5-d]azepin-6-one I-313 2-[(2-methylphenyl)amino]-5,7-dihydro-6H-[1]benzofuro[3,2-b]pyrimido[4,5-d]azepin-6-one I-314 2-({4-[(3-aminopyrrolidin-1-yl)carbonyl]phenyl}amino)-5,7-dihydro-6H-pyrimido[4,5-d]thieno[3,2-b]azepin-6-one I-315 9-chloro-2-{[4-(1H-imidazol-1-yl)phenyl]amino}-5,7-dihydro-6H-pyrimido[5,4-d][1]benzazepin-6-one I-316 9-chloro-2-{[3-(4-methylpiperazin-1-yl)phenyl]amino}-5,7-dihydro-6H-pyrimido[5,4-d][1]benzazepin-6-one I-317 9-chloro-2-{[4-(4-ethylpiperazin-1-yl)phenyl]amino}-5,7-dihydro-6H-pyrimido[5,4-d][1]benzazepin-6-one I-318 9-chloro-2-{[4-(1-methylpiperidin-4-yl)phenyl]amino}-5,7-dihydro-6H-pyrimido[5,4-d][1]benzazepin-6-one I-319 2-[(2-aminophenyl)amino]-10-(3-pyrrolidin-1-ylpropyl)-5,7-dihydro-6H-pyrimido[5,4-d][1]benzazepin-6-one I-320 2-({4-[(4-methylpiperazin-1-yl)carbonyl]phenyl}amino)-5H-pyrimido[4,5-d]thieno[3,4-b]azepin-6(7H)-one I-321 2-({4-[(3-methylpiperazin-1-yl)carbonyl]phenyl}amino)-5H-pyrimido[4,5-d]thieno[3,4-b]azepin-6(7H)-one I-322 N-[2-(dimethylamino)ethyl]-4-[(6-oxo-6,7-dihydro-5H-pyrimido[4,5-d]thieno[3,4-b]azepin-2-yl)amino]benzamide I-323 2-[(4-{[3-(dimethylamino)pyrrolidin-1-yl]carbonyl}phenyl)amino]-5H-pyrimido[4,5-d]thieno[3,4-b]azepin-6(7H)-one I-324 4-methyl-N-(6-oxo-6,7-dihydro-5H-pyrimido[5,4-d][1]benzazepin-2-yl)benzamide I-325 2-({4-[(3-aminopyrrolidin-1-yl)carbonyl]phenyl}amino)-5H-pyrimido[4,5-d]thieno[3,4-b]azepin-6(7H)-one I-326 2-[(3,4-dimethoxyphenyl)amino]-8-methyl-5,7-dihydro-6H-pyrimido[5,4-d][1]benzazepin-6-one I-327 8-methyl-2-{[3-(4-methylpiperazin-1-yl)phenyl]amino}-5,7-dihydro-6H-pyrimido[5,4-d][1]benzazepin-6-one I-328 4-[(6-oxo-6,7-dihydro-5H-pyrimido[5,4-d][1]benzazepin-2-yl)amino]benzoic acid
I-329 9-chloro-2-[(3-methylbutyl)amino]-5,7-dihydro-6H-pyrimido[5,4-d][1]benzazepin-6-one
I-330 9-chloro-2-(propylamino)-5,7-dihydro-6H-pyrimido[5,4-d][1]benzazepin-6-one
I-331 9-chloro-7-methyl-2-[(4-{[3-(methylamino)pyrrolidin-1-yl]carbonyl}phenyl)amino]-5,7-dihydro-6H-pyrimido[5,4-d][1]benzazepin-6-one
I-332 9-chloro-2-{[2-(2-thienyl)ethyl]amino}-5,7-dihydro-6H-pyrimido[5,4-d][1]benzazepin-6-one
I-333 methyl (2R)-2-[(9-chloro-6-oxo-6,7-dihydro-5H-pyrimido[5,4-d][1]benzazepin-2-yl)amino]propanoate
I-334 9-chloro-2-{[2-(5-chloro-1H-indol-3-yl)ethyl]amino}-5,7-dihydro-6H-pyrimido[5,4-d][1]benzazepin-6-one
I-335 2-{[(2-bromo-3-thienyl)methyl]amino}-9-chloro-5,7-dihydro-6H-pyrimido[5,4-d][1]benzazepin-6-one
I-336 9-chloro-2-[(2-thienylmethyl)amino]-5,7-dihydro-6H-pyrimido[5,4-d][1]benzazepin-6-one
I-337 3-{2-[(9-chloro-6-oxo-6,7-dihydro-5H-pyrimido[5,4-d][1]benzazepin-2-yl)amino]ethyl}-2-methyl-1H-indole-5-carbonitrile
I-338 9-chloro-2-[(2,3-dihydro-1,4-benzodioxin-6-ylmethyl)amino]-5,7-dihydro-6H-pyrimido[5,4-d][1]benzazepin-6-one
I-339 2-[(1,3-benzodioxol-5-ylmethyl)amino]-9-chloro-5,7-dihydro-6H-pyrimido[5,4-d][1]benzazepin-6-one
I-340 9-chloro-2-[(3-methoxybenzyl)amino]-5,7-dihydro-6H-pyrimido[5,4-d][1]benzazepin-6-one
I-341 9-chloro-2-[[3-(1H-imidazol-1-yl)propyl]amino]-5,7-dihydro-6H-pyrimido[5,4-d][1]benzazepin-6-one
I-342 9-chloro-2-{[2-(2-methyl-1H-indol-3-yl)ethyl]amino}-5,7-dihydro-6H-pyrimido[5,4-d][1]benzazepin-6-one
I-343 9-chloro-2-[(2,3-dihydro-1-benzofuran-5-ylmethyl)amino]-5,7-dihydro-6H-pyrimido[5,4-d][1]benzazepin-6-one
I-344 9-chloro-2-{[2-(3,4-dimethoxyphenyl)ethyl]amino}-5,7-dihydro-6H-pyrimido[5,4-d][1]benzazepin-6-one
I-345 9-chloro-2-{[(2-methyl-1,3-thiazol-4-yl)methyl]amino}-5,7-dihydro-6H-pyrimido[5,4-d][1]benzazepin-6-one
I-346 9-chloro-2-[(2-pyridin-2-ylethyl)amino]-5,7-dihydro-6H-pyrimido[5,4-d][1]benzazepin-6-one
I-347 9-chloro-2-{[(5-methyl-2-furyl)methyl]amino}-5,7-dihydro-6H-pyrimido[5,4-d][1]benzazepin-6-one
I-348 9-chloro-2-[(3-furylmethyl)amino]-5,7-dihydro-6H-pyrimido[5,4-d][1]benzazepin-6-one
I-349 9-chloro-2-{[2-(5-methoxy-1H-indol-3-yl)ethyl]amino}-5,7-dihydro-6H-pyrimido[5,4-d][1]benzazepin-6-one
I-350 9-chloro-2-[(2-phenylethyl)amino]-5,7-dihydro-6H-pyrimido[5,4-d][1]benzazepin-6-one
I-351 9-chloro-2-{[2-(4-fluorophenyl)ethyl]amino}-5,7-dihydro-6H-pyrimido[5,4-d][1]benzazepin-6-one
I-352 9-chloro-2-{[2-(4-methylphenyl)ethyl]amino}-5,7-dihydro-6H-pyrimido[5,4-d][1]benzazepin-6-one
I-353 ethyl (2S)-2-[(9-chloro-6-oxo-6,7-dihydro-5H-pyrimido[5,4-d][1]benzazepin-2-yl)amino]propanoate
I-354 9-chloro-2-{[(5-pyridin-2-yl-2-thienyl)methyl]amino}-5,7-dihydro-6H-pyrimido[5,4-d][1]benzazepin-6-one
I-355 9-chloro-2-({3-[methyl(phenyl)amino]propyl}amino)-5,7-dihydro-6H-pyrimido[5,4-d][1]benzazepin-6-one
I-356 9-chloro-2-{[2-(2,4-dimethylphenyl)ethyl]amino}-5,7-dihydro-6H-pyrimido[5,4-d][1]benzazepin-6-one
I-357 2-(benzylamino)-9-chloro-5,7-dihydro-6H-pyrimido[5,4-d][1]benzazepin-6-one
I-358 9-chloro-2-{[2-(1H-indol-3-yl)ethyl]amino}-5,7-dihydro-6H-pyrimido[5,4-d][1]benzazepin-6-one
I-359 9-chloro-2-{[2-(3,5-dimethyl-1H-pyrazol-4-yl)ethyl]amino}-5,7-dihydro-6H-pyrimido[5,4-d][1]benzazepin-6-one
I-360 methyl (2R)-2-[(9-chloro-6-oxo-6,7-dihydro-5H-pyrimido[5,4-d][1]benzazepin-2-yl)amino]-3-phenylpropanoate
I-361 9-chloro-2-{[2-(3-methoxyphenyl)ethyl]amino}-5,7-dihydro-6H-pyrimido[5,4-d][1]benzazepin-6-one
I-362 9-chloro-2-{[2-(2,4-dichlorophenyl)ethyl]amino}-5,7-dihydro-6H-pyrimido[5,4-d][1]benzazepin-6-one
I-363 9-chloro-2-[(2-furylmethyl)amino]-5,7-dihydro-6H-pyrimido[5,4-d][1]benzazepin-6-one
I-364 4-[(6-oxo-6,7-dihydro-5H-pyrido[3,4-b]pyrimido[4,5-d]azepin-2-yl)amino]benzoic acid
I-365 2-[(3,4-dimethoxyphenyl)amino]-5,7-dihydro-6H-pyrido[3,4-b]pyrimido[4,5-d]azepin-6-one
I-366 2-[(4-methylphenyl)amino]-5,7-dihydro-6H-pyrido[3,4-b]pyrimido[4,5-d]azepin-6-one
I-367 2-[(3,4-dichlorophenyl)amino]-5,7-dihydro-6H-pyrido[3,4-b]pyrimido[4,5-d]azepin-6-one
I-368 2-[(2-methylphenyl)amino]-5,7-dihydro-6H-pyrido[3,4-b]pyrimido[4,5-d]azepin-6-one
I-369 2-anilino-5,7-dihydro-6H-pyrido[3,4-b]pyrimido[4,5-d]azepin-6-one
I-370 9-chloro-7-ethyl-2-[(4-{[3-(methylamino)pyrrolidin-1-yl]carbonyl}phenyl)amino]-5,7-dihydro-6H-pyrimido[5,4-d][1]benzazepin-6-one
I-371 9-chloro-7-isopropyl-2-[(4-{[3-(methylamino)pyrrolidin-1-yl]carbonyl}phenyl)amino]-5,7-dihydro-6H-pyrimido[5,4-d][1]benzazepin-6-one
I-372 N-(3-isopropoxypropyl)-4-[(6-oxo-6,7-dihydro-5H-pyrimido[5,4-d][1]benzazepin-2-yl)amino]benzamide
I-373 N-isopropyl-4-[(6-oxo-6,7-dihydro-5H-pyrimido[5,4-d][1]benzazepin-2-yl)amino]benzamide
I-374 N-(4-fluorobenzyl)-4-[(6-oxo-6,7-dihydro-5H-pyrimido[5,4-d][1]benzazepin-2-yl)amino]benzamide
I-375 2-{[4-(pyrrolidin-1-ylcarbonyl)phenyl]amino}-5,7-dihydro-6H-pyrimido[5,4-d][1]benzazepin-6-one
I-376 4-[(6-oxo-6,7-dihydro-5H-pyrimido[5,4-d][1]benzazepin-2-yl)amino]-N-(tetrahydrofuran-2-ylmethyl)benzamide
I-377 2-{[4-(morpholin-4-ylcarbonyl)phenyl]amino}-5,7-dihydro-6H-pyrimido[5,4-d][1]benzazepin-6-one
I-378 N,N-diethyl-4-[(6-oxo-6,7-dihydro-5H-pyrimido[5,4-d][1]benzazepin-2-yl)amino]benzamide
I-379 2-({4-[(4-methylpiperidin-1-yl)carbonyl]phenyl}amino)-5,7-dihydro-6H-pyrimido[5,4-d][1]benzazepin-6-one
I-380 N-isobutyl-4-[(6-oxo-6,7-dihydro-5H-pyrimido[5,4-d][1]benzazepin-2-yl)amino]benzamide
I-381 N-(3,5-dimethylisoxazol-4-yl)-4-[(6-oxo-6,7-dihydro-5H-pyrimido[5,4-d][1]benzazepin-2-yl)amino]benzamide
I-382 N-[(1R)-1-cyclohexylethyl]-4-[(6-oxo-6,7-dihydro-5H-pyrimido[5,4-d][1]benzazepin-2-yl)amino]benzamide
I-383 N-(1-ethynylcyclohexyl)-4-[(6-oxo-6,7-dihydro-5H-pyrimido[5,4-d][1]benzazepin-2-yl)amino]benzamide
I-384 2-({4-[(4-acetylpiperazin-1-yl)carbonyl]phenyl}amino)-5,7-dihydro-6H-pyrimido[5,4-d][1]benzazepin-6-one I-385 4-[(6-oxo-6,7-dihydro-5H-pyrimido[5,4-d][1]benzazepin-2-yl)amino]-N-(2-thienylmethyl)benzamide I-386 N-[2-(1-methylpyrrolidin-2-yl)ethyl]-4-[(6-oxo-6,7-dihydro-5H-pyrimido[5,4-d][1]benzazepin-2-yl)amino]benzamide I-387 4-[(6-oxo-6,7-dihydro-5H-pyrimido[5,4-d][1]benzazepin-2-yl)amino]-N-(tetrahydro-2H-pyran-4-ylmethyl)benzamide I-388 N-(2-furylmethyl)-N-methyl-4-[(6-oxo-6,7-dihydro-5H-pyrimido[5,4-d][1]benzazepin-2-yl)amino]benzamide I-389 4-[(6-oxo-6,7-dihydro-5H-pyrimido[5,4-d][1]benzazepin-2-yl)amino]-N-[2-(2-thienyl)ethyl]benzamide I-390 2-[(4-{[(3R)-3-(dimethylamino)pyrrolidin-1-yl]carbonyl}phenyl)amino]-5,7-dihydro-6H-pyrimido[5,4-d][1]benzazepin-6-one I-391 N-[(5-methyl-2-furyl)methyl]-4-[(6-oxo-6,7-dihydro-5H-pyrimido[5,4-d][1]benzazepin-2-yl)amino]benzamide I-392 4-[(6-oxo-6,7-dihydro-5H-pyrimido[5,4-d][1]benzazepin-2-yl)amino]-N-pyridin-3-ylbenzamide I-393 N-cyclopentyl-4-[(6-oxo-6,7-dihydro-5H-pyrimido[5,4-d][1]benzazepin-2-yl)amino]benzamide I-394 4-[(6-oxo-6,7-dihydro-5H-pyrimido[5,4-d][1]benzazepin-2-yl)amino]-N-(3-propoxypropyl)benzamide I-395 4-[(6-oxo-6,7-dihydro-5H-pyrimido[5,4-d][1]benzazepin-2-yl)amino]-N-(2-phenylethyl)benzamide I-396 N-[(1R,2R,4S)-bicyclo[2.2.1]hept-2-yl]-4-[(6-oxo-6,7-dihydro-5H-pyrimido[5,4-d][1]benzazepin-2-yl)amino]benzamide I-397 4-[(6-oxo-6,7-dihydro-5H-pyrimido[5,4-d][1]benzazepin-2-yl)amino]-N-(1,3,5-trimethyl-1H-pyrazol-4-yl)benzamide I-398 N-(4-methoxyphenyl)-4-[(6-oxo-6,7-dihydro-5H-pyrimido[5,4-d][1]benzazepin-2-yl)amino]benzamide I-399 2-({4-[(4-ethylpiperazin-1-yl)carbonyl]phenyl}amino)-5,7-dihydro-6H-pyrimido[5,4-d][1]benzazepin-6-one I-400 N-(2-methoxy-1-methylethyl)-4-[(6-oxo-6,7-dihydro-5H-pyrimido[5,4-d][1]benzazepin-2-yl)amino]benzamide I-401 4-[(6-oxo-6,7-dihydro-5H-pyrimido[5,4-d][1]benzazepin-2-yl)amino]-N-(2-pyridin-2-ylethyl)benzamide I-402 N-[(1-ethylpyrrolidin-3-yl)methyl]-4-[(6-oxo-6,7-dihydro-5H-pyrimido[5,4-d][1]benzazepin-2-yl)amino]benzamide I-403 2-({4-[(3-oxopiperazin-1-yl)carbonyl]phenyl}amino)-5,7-dihydro-6H-pyrimido[5,4-d][1]benzazepin-6-one I-404 4-{[(6-oxo-6,7-dihydro-5H-pyrimido[5,4-d][1]benzazepin-2-yl)amino]benzoyl}-1,4-diazepane-1-carbaldehyde I-405 N-(cyclohexylmethyl)-4-[(6-oxo-6,7-dihydro-5H-pyrimido[5,4-d][1]benzazepin-2-yl)amino]benzamide I-406 N-(3-furylmethyl)-4-[(6-oxo-6,7-dihydro-5H-pyrimido[5,4-d][1]benzazepin-2-yl)amino]benzamide I-407 2-({4-[(2-ethylpyrrolidin-1-yl)carbonyl]phenyl}amino)-5,7-dihydro-6H-pyrimido[5,4-d][1]benzazepin-6-one I-408 N-(3-methylbutyl)-4-[(6-oxo-6,7-dihydro-5H-pyrimido[5,4-d][1]benzazepin-2-yl)amino]benzamide I-409 N-(2-cyanoethyl)-N-cyclopropyl-4-[(6-oxo-6,7-dihydro-5H-pyrimido[5,4-d][1]benzazepin-2-yl)amino]benzamide I-410 N-(cyclopropylmethyl)-4-[(6-oxo-6,7-dihydro-5H-pyrimido[5,4-d][1]benzazepin-2-yl)amino]benzamide I-411 2-[(4-{[(2S)-2-(methoxymethyl)pyrrolidin-1-yl]carbonyl}phenyl)amino]-5,7-dihydro-6H-pyrimido[5,4-d][1]benzazepin-6-one I-412 2-({4-[(4-methylpiperazin-1-yl)carbonyl]phenyl}amino)-5,7-dihydro-6H-pyrimido[5,4-d][1]benzazepin-6-one I-413 N-cyclohexyl-N-methyl-4-[(6-oxo-6,7-dihydro-5H-pyrimido[5,4-d][1]benzazepin-2-yl)amino]benzamide I-414 N-(2-cyanoethyl)-N-methyl-4-[(6-oxo-6,7-dihydro-5H-pyrimido[5,4-d][1]benzazepin-2-yl)amino]benzamide I-415 2-{[4-(1,3-dihydro-2H-isoindol-2-ylcarbonyl)phenyl]amino}-5,7-dihydro-6H-pyrimido[5,4-d][1]benzazepin-6-one I-416 N-[3-(1H-imidazol-1-yl)propyl]-4-[(6-oxo-6,7-dihydro-5H-pyrimido[5,4-d][1]benzazepin-2-yl)amino]benzamide I-417 N-methyl-4-[(6-oxo-6,7-dihydro-5H-pyrimido[5,4-d][1]benzazepin-2-yl)amino]-N-prop-2-yn-1-ylbenzamide I-418 N-[2-(dimethylamino)ethyl]-N-ethyl-4-[(6-oxo-6,7-dihydro-5H-pyrimido[5,4-d][1]benzazepin-2-yl)amino]benzamide I-419 N-[2-(acetylamino)ethyl]-4-[(6-oxo-6,7-dihydro-5H-pyrimido[5,4-d][1]benzazepin-2-yl)amino]benzamide I-420 N-(2-methoxyethyl)-4-[(6-oxo-6,7-dihydro-5H-pyrimido[5,4-d][1]benzazepin-2-yl)amino]benzamide I-421 4-[(6-oxo-6,7-dihydro-5H-pyrimido[5,4-d][1]benzazepin-2-yl)amino]-N-(2-piperidin-1-ylethyl)benzamide I-422 N-cyclohexyl-4-[(6-oxo-6,7-dihydro-5H-pyrimido[5,4-d][1]benzazepin-2-yl)amino]benzamide I-423 N-[2-(dimethylamino)ethyl]-4-[(6-oxo-6,7-dihydro-5H-pyrimido[5,4-d][1]benzazepin-2-yl)amino]benzamide I-424 4-[(6-oxo-6,7-dihydro-5H-pyrimido[5,4-d][1]benzazepin-2-yl)amino]-N-(pyridin-2-ylmethyl)benzamide I-425 N-[2-(diethylamino)ethyl]-4-[(6-oxo-6,7-dihydro-5H-pyrimido[5,4-d][1]benzazepin-2-yl)amino]benzamide I-426 N-methyl-N-(1-methylpiperidin-4-yl)-4-[(6-oxo-6,7-dihydro-5H-pyrimido[5,4-d][1]benzazepin-2-yl)amino]benzamide I-427 N-[2-(dimethylamino)ethyl]-N-methyl-4-[(6-oxo-6,7-dihydro-5H-pyrimido[5,4-d][1]benzazepin-2-yl)amino]benzamide I-428 N-methyl-N-(1-methylpyrrolidin-3-yl)-4-[(6-oxo-6,7-dihydro-5H-pyrimido[5,4-d][1]benzazepin-2-yl)amino]benzamide I-429 2-{[4-(piperidin-1-ylcarbonyl)phenyl]amino}-5,7-dihydro-6H-pyrimido[5,4-d][1]benzazepin-6-one I-430 N-[(2-methyl-1,3-thiazol-4-yl)methyl]-4-[(6-oxo-6,7-dihydro-5H-pyrimido[5,4-d][1]benzazepin-2-yl)amino]benzamide I-431 4-[(6-oxo-6,7-dihydro-5H-pyrimido[5,4-d][1]benzazepin-2-yl)amino]-N-(3-pyrrolidin-1-ylpropyl)benzamide I-432 2-{[4-(azetidin-1-ylcarbonyl)phenyl]amino}-5,7-dihydro-6H-pyrimido[5,4-d][1]benzazepin-6-one I-433 4-[(6-oxo-6,7-dihydro-5H-pyrimido[5,4-d][1]benzazepin-2-yl)amino]-N-(pyridin-4-ylmethyl)benzamide I-434 N-(2-isopropoxyethyl)-4-[(6-oxo-6,7-dihydro-5H-pyrimido[5,4-d][1]benzazepin-2-yl)amino]benzamide I-435 2-({4-[(2-isobutylpyrrolidin-1-yl)carbonyl]phenyl}amino)-5,7-dihydro-6H-pyrimido[5,4-d][1]benzazepin-6-one I-436 N-(4,6-dimethylpyridin-2-yl)-4-[(6-oxo-6,7-dihydro-5H-pyrimido[5,4-d][1]benzazepin-2-yl)amino]benzamide I-437 N-(2-morpholin-4-ylethyl)-4-[(6-oxo-6,7-dihydro-5H-pyrimido[5,4-d][1]benzazepin-2-yl)amino]benzamide I-438 2-({4-[(5-ethyl-2-methylpiperidin-1-yl)carbonyl]phenyl}amino)-5,7-dihydro-6H-pyrimido[5,4-d][1]benzazepin-6-one I-439 4-[(9-chloro-6-oxo-6,7-dihydro-5H-pyrimido[5,4-d][1]benzazepin-2-yl)amino]-N-methyl-N-(1-methylpyrrolidin-3-yl)benzamide I-440 4-[(9-chloro-6-oxo-6,7-dihydro-5H-pyrimido[5,4-d][1]benzazepin-2-yl)amino]-N-(2,2-dimethylpropyl)benzamide I-441 4-[(9-chloro-6-oxo-6,7-dihydro-5H-pyrimido[5,4-d][1]benzazepin-2-yl)amino]-N-(2-ethoxyethyl)benzamide I-442 4-[(9-chloro-6-oxo-6,7-dihydro-5H-pyrimido[5,4-d][1]benzazepin-2-yl)amino]-N-[2-(diethylamino)ethyl]benzamide I-443 4-[(9-chloro-6-oxo-6,7-dihydro-5H-pyrimido[5,4-d][1]benzazepin-2-yl)amino]-N-cyclohexylbenzamide I-444 2-{[4-(azetidin-1-ylcarbonyl)phenyl]amino}-9-chloro-5,7-dihydro-6H-pyrimido[5,4-d][1]benzazepin-6-one I-445 4-[(9-chloro-6-oxo-6,7-dihydro-5H-pyrimido[5,4-d][1]benzazepin-2-yl)amino]-N-(1H-imidazol-2-ylmethyl)benzamide I-446 9-chloro-2-({4-[(3,5-dimethylpiperidin-1-yl)carbonyl]phenyl}amino)-5,7-dihydro-6H-pyrimido[5,4-d][1]benzazepin-6-one I-447 4-[(9-chloro-6-oxo-6,7-dihydro-5H-pyrimido[5,4-d][1]benzazepin-2-yl)amino]-N-cyclopropylbenzamide I-448 9-chloro-2-{[4-(piperidin-1-ylcarbonyl)phenyl]amino}-5,7-dihydro-6H-pyrimido[5,4-d][1]benzazepin-6-one I-449 4-[(9-chloro-6-oxo-6,7-dihydro-5H-pyrimido[5,4-d][1]benzazepin-2-yl)amino]-N-(tetrahydrofuran-2-ylmethyl)benzamide I-450 9-chloro-2-({4-[(3-methoxypiperidin-1-yl)carbonyl]phenyl}amino)-5,7-dihydro-6H-pyrimido[5,4-d][1]benzazepin-6-one I-451 4-[(9-chloro-6-oxo-6,7-dihydro-5H-pyrimido[5,4-d][1]benzazepin-2-yl)amino]-N-[(4-methyl-1H-imidazol-2-yl)methyl]benzamide I-452 4-[(9-chloro-6-oxo-6,7-dihydro-5H-pyrimido[5,4-d][1]benzazepin-2-yl)amino]-N-propylbenzamide I-453 4-[(9-chloro-6-oxo-6,7-dihydro-5H-pyrimido[5,4-d][1]benzazepin-2-yl)amino]-N-(1-methylbutyl)benzamide I-454 N-butyl-4-[(9-chloro-6-oxo-6,7-dihydro-5H-pyrimido[5,4-d][1]benzazepin-2-yl)amino]benzamide I-455 9-chloro-2-{[4-(pyrrolidin-1-ylcarbonyl)phenyl]amino}-5,7-dihydro-6H-pyrimido[5,4-d][1]benzazepin-6-one I-456 4-[(9-chloro-6-oxo-6,7-dihydro-5H-pyrimido[5,4-d][1]benzazepin-2-yl)amino]-N-pyridin-4-ylbenzamide I-457 4-[(9-chloro-6-oxo-6,7-dihydro-5H-pyrimido[5,4-d][1]benzazepin-2-yl)amino]-N-[2-(dimethylamino)ethyl]-N-methylbenzamide I-458 N-[2-(acetylamino)ethyl]-4-[(9-chloro-6-oxo-6,7-dihydro-5H-pyrimido[5,4-d][1]benzazepin-2-yl)amino]benzamide I-459 4-[(9-chloro-6-oxo-6,7-dihydro-5H-pyrimido[5,4-d][1]benzazepin-2-yl)amino]-N-(1,3-dioxolan-2-ylmethyl)-N-methylbenzamide I-460 4-[(9-chloro-6-oxo-6,7-dihydro-5H-pyrimido[5,4-d][1]benzazepin-2-yl)amino]-N-(tetrahydro-2H-pyran-4-ylmethyl)benzamide I-461 4-[(9-chloro-6-oxo-6,7-dihydro-5H-pyrimido[5,4-d][1]benzazepin-2-yl)amino]-N-(4-methylcyclohexyl)benzamide I-462 4-[(9-chloro-6-oxo-6,7-dihydro-5H-pyrimido[5,4-d][1]benzazepin-2-yl)amino]-N-cyclohexyl-N-methylbenzamide I-463 4-[(9-chloro-6-oxo-6,7-dihydro-5H-pyrimido[5,4-d][1]benzazepin-2-yl)amino]-N-(2-isopropoxyethyl)benzamide I-464 4-[(9-chloro-6-oxo-6,7-dihydro-5H-pyrimido[5,4-d][1]benzazepin-2-yl)amino]-N-(pyrimidin-4-ylmethyl)benzamide I-465 4-[(9-chloro-6-oxo-6,7-dihydro-5H-pyrimido[5,4-d][1]benzazepin-2-yl)amino]-N-(2-pyridin-2-ylethyl)benzamide I-466 4-[(9-chloro-6-oxo-6,7-dihydro-5H-pyrimido[5,4-d][1]benzazepin-2-yl)amino]-N-(2-cyanoethyl)-N-cyclopropylbenzamide I-467 4-[(9-chloro-6-oxo-6,7-dihydro-5H-pyrimido[5,4-d][1]benzazepin-2-yl)amino]-N-(3,3-dimethylbutyl)benzamide I-468 4-[(9-chloro-6-oxo-6,7-dihydro-5H-pyrimido[5,4-d][1]benzazepin-2-yl)amino]-N-(2-furylmethyl)-N-methylbenzamide I-469 4-[(9-chloro-6-oxo-6,7-dihydro-5H-pyrimido[5,4-d][1]benzazepin-2-yl)amino]-N-cyclopentylbenzamide I-470 4-[(9-chloro-6-oxo-6,7-dihydro-5H-pyrimido[5,4-d][1]benzazepin-2-yl)amino]-N-(4-methylbenzyl)benzamide I-471 4-[(9-chloro-6-oxo-6,7-dihydro-5H-pyrimido[5,4-d][1]benzazepin-2-yl)amino]-N-isobutylbenzamide I-472 9-chloro-2-[(4-{[(2R,6S)-2,6-dimethylmorpholin-4-yl]carbonyl}phenyl)amino]-5,7-dihydro-6H-pyrimido[5,4-d][1]benzazepin-6-one I-473 N-[(1R,2R,4S)-bicyclo[2.2.1]hept-2-yl]-4-[(9-chloro-6-oxo-6,7-dihydro-5H-pyrimido[5,4-d][1]benzazepin-2-yl)amino]benzamide I-474 4-[(9-chloro-6-oxo-6,7-dihydro-5H-pyrimido[5,4-d][1]benzazepin-2-yl)amino]-N-(3-isopropoxypropyl)benzamide I-475 4-[(9-chloro-6-oxo-6,7-dihydro-5H-pyrimido[5,4-d][1]benzazepin-2-yl)amino]-N-(1,3-dioxolan-2-ylmethyl)benzamide I-476 4-[(9-chloro-6-oxo-6,7-dihydro-5H-pyrimido[5,4-d][1]benzazepin-2-yl)amino]-N-(4-methyl-1,3-oxazol-2-yl)benzamide I-477 4-[(9-chloro-6-oxo-6,7-dihydro-5H-pyrimido[5,4-d][1]benzazepin-2-yl)amino]-N-(1H-imidazol-2-ylmethyl)-N-methylbenzamide I-478 4-[(9-chloro-6-oxo-6,7-dihydro-5H-pyrimido[5,4-d][1]benzazepin-2-yl)amino]-N-(3-methylbutyl)benzamide I-479 4-[(9-chloro-6-oxo-6,7-dihydro-5H-pyrimido[5,4-d][1]benzazepin-2-yl)amino]-N-(2-methylbenzyl)benzamide I-480 4-[(9-chloro-6-oxo-6,7-dihydro-5H-pyrimido[5,4-d][1]benzazepin-2-yl)amino]-N-(pyridin-2-ylmethyl)benzamide I-481 4-[(9-chloro-6-oxo-6,7-dihydro-5H-pyrimido[5,4-d][1]benzazepin-2-yl)amino]-N-isopropylbenzamide I-482 9-chloro-2-({4-[(2-ethylpyrrolidin-1-yl)carbonyl]phenyl}amino)-5,7-dihydro-6H-pyrimido[5,4-d][1]benzazepin-6-one I-483 N-benzyl-4-[(9-chloro-6-oxo-6,7-dihydro-5H-pyrimido[5,4-d][1]benzazepin-2-yl)amino]benzamide I-484 4-[(9-chloro-6-oxo-6,7-dihydro-5H-pyrimido[5,4-d][1]benzazepin-2-yl)amino]-N-[2-(dimethylamino)-1-methylethyl]benzamide I-485 4-[(9-chloro-6-oxo-6,7-dihydro-5H-pyrimido[5,4-d][1]benzazepin-2-yl)amino]-N,N-diethylbenzamide I-486 4-[(9-chloro-6-oxo-6,7-dihydro-5H-pyrimido[5,4-d][1]benzazepin-2-yl)amino]-N-(1,3-dimethyl-1H-pyrazol-5-yl)benzamide I-487 4-[(9-chloro-6-oxo-6,7-dihydro-5H-pyrimido[5,4-d][1]benzazepin-2-yl)amino]-N-(3-methoxyphenyl)benzamide I-488 4-[(9-chloro-6-oxo-6,7-dihydro-5H-pyrimido[5,4-d][1]benzazepin-2-yl)amino]-N-(3-thienylmethyl)benzamide I-489 4-[(9-chloro-6-oxo-6,7-dihydro-5H-pyrimido[5,4-d][1]benzazepin-2-yl)amino]-N-(1-phenylethyl)benzamide I-490 9-chloro-2-({4-[(4-methylpiperidin-1-yl)carbonyl]phenyl}amino)-5,7-dihydro-6H-pyrimido[5,4-d][1]benzazepin-6-one I-491 4-[(9-chloro-6-oxo-6,7-dihydro-5H-pyrimido[5,4-d][1]benzazepin-2-yl)amino]-N-[1-(methoxymethyl)propyl]benzamide I-492 9-chloro-2-({4-[(2-methylpyrrolidin-1-yl)carbonyl]phenyl}amino)-5,7-dihydro-6H-pyrimido[5,4-d][1]benzazepin-6-one I-493 4-[(9-chloro-6-oxo-6,7-dihydro-5H-pyrimido[5,4-d][1]benzazepin-2-yl)amino]-N-(2-methoxy-1-methylethyl)benzamide I-494 4-[(9-chloro-6-oxo-6,7-dihydro-5H-pyrimido[5,4-d][1]benzazepin-2-yl)amino]-N-methyl-N-prop-2-yn-1-ylbenzamide I-495 9-chloro-2-({4-[(4-methylpiperazin-1-yl)carbonyl]phenyl}amino)-5,7-dihydro-6H-pyrimido[5,4-d][1]benzazepin-6-one I-496 4-[(9-chloro-6-oxo-6,7-dihydro-5H-pyrimido[5,4-d][1]benzazepin-2-yl)amino]-N-(3,5-dimethylisoxazol-4-yl)benzamide I-497 9-chloro-2-({4-[(4-ethylpiperazin-1-yl)carbonyl]phenyl}amino)-5,7-dihydro-6H-pyrimido[5,4-d][1]benzazepin-6-one I-498 4-[(9-chloro-6-oxo-6,7-dihydro-5H-pyrimido[5,4-d][1]benzazepin-2-yl)amino]-N-[3-(dimethylamino)propyl]-N-methylbenzamide I-499 9-chloro-2-({4-[(3,4-dimethylpiperazin-1-yl)carbonyl]phenyl}amino)-5,7-dihydro-6H-pyrimido[5,4-d][1]benzazepin-6-one I-500 4-[(9-chloro-6-oxo-6,7-dihydro-5H-pyrimido[5,4-d][1]benzazepin-2-yl)amino]-N-pyridin-3-ylbenzamide I-501 9-chloro-2-[(4-{[(2S)-2-(methoxymethyl)pyrrolidin-1-yl]carbonyl}phenyl)amino]-5,7-dihydro-6H-pyrimido[5,4-d][1]benzazepin-6-one I-502 4-[(9-chloro-6-oxo-6,7-dihydro-5H-pyrimido[5,4-d][1]benzazepin-2-yl)amino]-N-(cyclopropylmethyl)benzamide I-503 4-[(9-chloro-6-oxo-6,7-dihydro-5H-pyrimido[5,4-d][1]benzazepin-2-yl)amino]-N-isopropyl-N-methylbenzamide I-504 4-[(9-chloro-6-oxo-6,7-dihydro-5H-pyrimido[5,4-d][1]benzazepin-2-yl)amino]-N-(3-methoxypropyl)benzamide I-505 4-[(9-chloro-6-oxo-6,7-dihydro-5H-pyrimido[5,4-d][1]benzazepin-2-yl)amino]-N-(3-ethoxypropyl)benzamide I-506 4-[(9-chloro-6-oxo-6,7-dihydro-5H-pyrimido[5,4-d][1]benzazepin-2-yl)amino]-N-(2-cyanoethyl)-N-methylbenzamide I-507 4-[(9-chloro-6-oxo-6,7-dihydro-5H-pyrimido[5,4-d][1]benzazepin-2-yl)amino]-N-(2-methoxyethyl)benzamide I-508 4-[(9-chloro-6-oxo-6,7-dihydro-5H-pyrimido[5,4-d][1]benzazepin-2-yl)amino]-N-1H-indol-5-ylbenzamide I-509 N-1,3-benzodioxol-5-yl-4-[(9-chloro-6-oxo-6,7-dihydro-5H-pyrimido[5,4-d][1]benzazepin-2-yl)amino]benzamide I-510 4-[(9-chloro-6-oxo-6,7-dihydro-5H-pyrimido[5,4-d][1]benzazepin-2-yl)amino]-N-methyl-N-[(5-methyl-1H-pyrazol-3-yl)methyl]benzamide I-511 4-[(9-chloro-6-oxo-6,7-dihydro-5H-pyrimido[5,4-d][1]benzazepin-2-yl)amino]-N-(3-isobutoxypropyl)benzamide I-512 4-[(9-chloro-6-oxo-6,7-dihydro-5H-pyrimido[5,4-d][1]benzazepin-2-yl)amino]-N-[(1R)-1-cyclohexylethyl]benzamide I-513 4-[(9-chloro-6-oxo-6,7-dihydro-5H-pyrimido[5,4-d][1]benzazepin-2-yl)amino]-N-[1-(4-methyl-1,3-thiazol-2-yl)ethyl]benzamide I-514 4-[(9-chloro-6-oxo-6,7-dihydro-5H-pyrimido[5,4-d][1]benzazepin-2-yl)amino]-N-[2-(methylsulfonyl)ethyl]benzamide I-515 4-[(9-chloro-6-oxo-6,7-dihydro-5H-pyrimido[5,4-d][1]benzazepin-2-yl)amino]-N-methyl-N-(3-thienylmethyl)benzamide I-516 9-chloro-2-({4-[(5-fluoro-2,3-dihydro-1H-indol-1-yl)carbonyl]phenyl}amino)-5,7-dihydro-6H-pyrimido[5,4-d][1]benzazepin-6-one I-517 2-({4-[(4-acetylpiperazin-1-yl)carbonyl]phenyl}amino)-9-chloro-5,7-dihydro-6H-pyrimido[5,4-d][1]benzazepin-6-one I-518 4-[(9-chloro-6-oxo-6,7-dihydro-5H-pyrimido[5,4-d][1]benzazepin-2-yl)amino]-N-(3-fluoro-4-methoxyphenyl)benzamide I-519 4-[(9-chloro-6-oxo-6,7-dihydro-5H-pyrimido[5,4-d][1]benzazepin-2-yl)amino]-N-(2,5-difluorobenzyl)benzamide I-520 4-[(9-chloro-6-oxo-6,7-dihydro-5H-pyrimido[5,4-d][1]benzazepin-2-yl)amino]-N-[(1-ethylpyrrolidin-3-yl)methyl]benzamide I-521 4-[(9-chloro-6-oxo-6,7-dihydro-5H-pyrimido[5,4-d][1]benzazepin-2-yl)amino]-N-[1-(2-methyl-1,3-thiazol-4-yl)ethyl]benzamide I-522 4-[(9-chloro-6-oxo-6,7-dihydro-5H-pyrimido[5,4-d][1]benzazepin-2-yl)amino]-N-(2,3-dihydro-1-benzofuran-5-ylmethyl)benzamide I-523 4-[(9-chloro-6-oxo-6,7-dihydro-5H-pyrimido[5,4-d][1]benzazepin-2-yl)amino]-N-[3-(2-oxopyrrolidin-1-yl)propyl]benzamide I-524 4-[(9-chloro-6-oxo-6,7-dihydro-5H-pyrimido[5,4-d][1]benzazepin-2-yl)amino]-N-[2-(5-methyl-4H-1,2,4-triazol-3-yl)ethyl]benzamide I-525 4-[(9-chloro-6-oxo-6,7-dihydro-5H-pyrimido[5,4-d][1]benzazepin-2-yl)amino]-N-[(1S)-1-(4-methylphenyl)ethyl]benzamide I-526 4-[(9-chloro-6-oxo-6,7-dihydro-5H-pyrimido[5,4-d][1]benzazepin-2-yl)amino]-N-(1,3,5-trimethyl-1H-pyrazol-4-yl)benzamide I-527 4-[(9-chloro-6-oxo-6,7-dihydro-5H-pyrimido[5,4-d][1]benzazepin-2-yl)amino]-N-(2-methoxy-5-methylphenyl)benzamide I-528 9-chloro-2-[(4-{[2-(2-furyl)pyrrolidin-1-yl]carbonyl}phenyl)amino]-5,7-dihydro-6H-pyrimido[5,4-d][1]benzazepin-6-one I-529 9-chloro-2-({4-[(3-pyridin-3-ylpyrrolidin-1-yl)carbonyl]phenyl}amino)-5,7-dihydro-6H-pyrimido[5,4-d][1]benzazepin-6-one I-530 4-[(9-chloro-6-oxo-6,7-dihydro-5H-pyrimido[5,4-d][1]benzazepin-2-yl)amino]-N-[2-(1-methylpyrrolidin-2-yl)ethyl]benzamide I-531 4-[(9-chloro-6-oxo-6,7-dihydro-5H-pyrimido[5,4-d][1]benzazepin-2-yl)amino]-N-[3-(1H-imidazol-1-yl)propyl]benzamide I-532 4-[(9-chloro-6-oxo-6,7-dihydro-5H-pyrimido[5,4-d][1]benzazepin-2-yl)amino]-N-methyl-N-(1-methylpiperidin-4-yl)benzamide I-533 N-1-azabicyclo[2.2.2]oct-3-yl-4-[(9-chloro-6-oxo-6,7-dihydro-5H-pyrimido[5,4-d][1]benzazepin-2-yl)amino]benzamide I-534 4-[(9-chloro-6-oxo-6,7-dihydro-5H-pyrimido[5,4-d][1]benzazepin-2-yl)amino]-N-[3-(dimethylamino)phenyl]benzamide I-535 4-[(9-chloro-6-oxo-6,7-dihydro-5H-pyrimido[5,4-d][1]benzazepin-2-yl)amino]-N-methyl-N-(tetrahydro-2H-pyran-4-ylmethyl)benzamide I-536 4-[(9-chloro-6-oxo-6,7-dihydro-5H-pyrimido[5,4-d][1]benzazepin-2-yl)amino]-N-(4-methoxy-2-methylphenyl)benzamide I-537 4-[(9-chloro-6-oxo-6,7-dihydro-5H-pyrimido[5,4-d][1]benzazepin-2-yl)amino]-N-(2-piperidin-1-ylethyl)benzamide I-538 9-chloro-2-({4-[(4-propylpiperazin-1-yl)carbonyl]phenyl}amino)-5,7-dihydro-6H-pyrimido[5,4-d][1]benzazepin-6-one I-539 4-[(9-chloro-6-oxo-6,7-dihydro-5H-pyrimido[5,4-d][1]benzazepin-2-yl)amino]-N-[1-(5-methyl-4H-1,2,4-triazol-3-yl)ethyl]benzamide I-540 9-chloro-2-[(4-{[3-(methylsulfonyl)pyrrolidin-1-yl]carbonyl}phenyl)amino]-5,7-dihydro-6H-pyrimido[5,4-d][1]benzazepin-6-one I-541 4-[(9-chloro-6-oxo-6,7-dihydro-5H-pyrimido[5,4-d][1]benzazepin-2-yl)amino]-N-[2-(3-fluorophenyl)ethyl]benzamide I-542 4-[(9-chloro-6-oxo-6,7-dihydro-5H-pyrimido[5,4-d][1]benzazepin-2-yl)amino]-N-[2-(diisopropylamino)ethyl]benzamide I-543 9-chloro-2-[(4-{[3-(diethylamino)pyrrolidin-1-yl]carbonyl}phenyl)amino]-5,7-dihydro-6H-pyrimido[5,4-d][1]benzazepin-6-one I-544 4-[(9-chloro-6-oxo-6,7-dihydro-5H-pyrimido[5,4-d][1]benzazepin-2-yl)amino]-N-(2-methoxybenzyl)benzamide I-545 4-[(9-chloro-6-oxo-6,7-dihydro-5H-pyrimido[5,4-d][1]benzazepin-2-yl)amino]-N-(3-methoxybenzyl)benzamide I-546 4-[(9-chloro-6-oxo-6,7-dihydro-5H-pyrimido[5,4-d][1]benzazepin-2-yl)amino]-N-[4-(dimethylamino)phenyl]benzamide I-547 4-[(9-chloro-6-oxo-6,7-dihydro-5H-pyrimido[5,4-d][1]benzazepin-2-yl)amino]-N-[2-(2-thienyl)ethyl]benzamide I-548 4-[(9-chloro-6-oxo-6,7-dihydro-5H-pyrimido[5,4-d][1]benzazepin-2-yl)amino]-N-[(2-methyl-1,3-thiazol-4-yl)methyl]benzamide I-549 4-[(9-chloro-6-oxo-6,7-dihydro-5H-pyrimido[5,4-d][1]benzazepin-2-yl)amino]-N-[(3,5-dimethyl-1H-pyrazol-4-yl)methyl]benzamide I-550 4-[(9-chloro-6-oxo-6,7-dihydro-5H-pyrimido[5,4-d][1]benzazepin-2-yl)amino]-N-(2,2-diethoxyethyl)benzamide I-551 4-[(9-chloro-6-oxo-6,7-dihydro-5H-pyrimido[5,4-d][1]benzazepin-2-yl)amino]-N-(2-morpholin-4-ylethyl)benzamide I-552 4-[(9-chloro-6-oxo-6,7-dihydro-5H-pyrimido[5,4-d][1]benzazepin-2-yl)amino]-N-methyl-N-[(4-methyl-1H-imidazol-2-yl)methyl]benzamide I-553 4-[(9-chloro-6-oxo-6,7-dihydro-5H-pyrimido[5,4-d][1]benzazepin-2-yl)amino]-N-(5-ethyl-1,3,4-thiadiazol-2-yl)benzamide I-554 4-[(9-chloro-6-oxo-6,7-dihydro-5H-pyrimido[5,4-d][1]benzazepin-2-yl)amino]-N-(1-ethynylcyclohexyl)benzamide I-555 4-[(9-chloro-6-oxo-6,7-dihydro-5H-pyrimido[5,4-d][1]benzazepin-2-yl)amino]-N-(4-methoxyphenyl)benzamide I-556 4-[(9-chloro-6-oxo-6,7-dihydro-5H-pyrimido[5,4-d][1]benzazepin-2-yl)amino]-N-methyl-N-[(3-methylisoxazol-5-yl)methyl]benzamide I-557 4-[(9-chloro-6-oxo-6,7-dihydro-5H-pyrimido[5,4-d][1]benzazepin-2-yl)amino]-N-[2-(3,5-dimethyl-1H-pyrazol-1-yl)ethyl]benzamide I-558 2-({4-[(3-acetylpiperidin-1-yl)carbonyl]phenyl}amino)-9-chloro-5,7-dihydro-6H-pyrimido[5,4-d][1]benzazepin-6-one I-559 4-[(9-chloro-6-oxo-6,7-dihydro-5H-pyrimido[5,4-d][1]benzazepin-2-yl)amino]-N-(2-oxo-2-phenylethyl)benzamide I-560 4-[(9-chloro-6-oxo-6,7-dihydro-5H-pyrimido[5,4-d][1]benzazepin-2-yl)amino]-N,N-dimethylbenzamide I-561 4-[(9-chloro-6-oxo-6,7-dihydro-5H-pyrimido[5,4-d][1]benzazepin-2-yl)amino]-N-[2-(diethylamino)ethyl]-N-methylbenzamide I-562 4-[(9-chloro-6-oxo-6,7-dihydro-5H-pyrimido[5,4-d][1]benzazepin-2-yl)amino]-N-(3-morpholin-4-ylpropyl)benzamide I-563 4-[(9-chloro-6-oxo-6,7-dihydro-5H-pyrimido[5,4-d][1]benzazepin-2-yl)amino]-N-[(1S)-2-phenylcyclopropyl]benzamide I-564 9-chloro-2-({4-[(2-isobutylpyrrolidin-1-yl)carbonyl]phenyl}amino)-5,7-dihydro-6H-pyrimido[5,4-d][1]benzazepin-6-one I-565 9-chloro-2-({4-[(5-ethyl-2-methylpiperidin-1-yl)carbonyl]phenyl}amino)-5,7-dihydro-6H-pyrimido[5,4-d][1]benzazepin-6-one I-566 4-[(9-chloro-6-oxo-6,7-dihydro-5H-pyrimido[5,4-d][1]benzazepin-2-yl)amino]-N-(6-methoxypyridin-3-yl)benzamide I-567 4-[(9-chloro-6-oxo-6,7-dihydro-5H-pyrimido[5,4-d][1]benzazepin-2-yl)amino]-N-[3-(dimethylamino)-2,2-dimethylpropyl]benzamide I-568 4-[(9-chloro-6-oxo-6,7-dihydro-5H-pyrimido[5,4-d][1]benzazepin-2-yl)amino]-N-(3-pyrrolidin-1-ylpropyl)benzamide I-569 4-[(9-chloro-6-oxo-6,7-dihydro-5H-pyrimido[5,4-d][1]benzazepin-2-yl)amino]-N-[1-(4-fluorophenyl)ethyl]benzamide I-570 9-chloro-2-[(4-morpholin-4-ylbenzyl)amino]-5,7-dihydro-6H-pyrimido[5,4-d][1]benzazepin-6-one I-571 N-isopropyl-N-methyl-4-[(6-oxo-6,7-dihydro-5H-pyrimido[5,4-d][1]benzazepin-2-yl)amino]benzamide I-572 2-({4-[(2-methylaziridin-1-yl)carbonyl]phenyl}amino)-5,7-dihydro-6H-pyrimido[5,4-d][1]benzazepin-6-one I-573 2-({4-[(2-methylpyrrolidin-1-yl)carbonyl]phenyl}amino)-5,7-dihydro-6H-pyrimido[5,4-d][1]benzazepin-6-one I-574 4-[(6-oxo-6,7-dihydro-5H-pyrimido[5,4-d][1]benzazepin-2-yl)amino]-N-phenylbenzamide I-575 9-chloro-2-{[2-(1-methylpyrrolidin-2-yl)ethyl]amino}-5,7-dihydro-6H-pyrimido[5,4-d][1]benzazepin-6-one I-576 2-({4-[(2-pyridin-4-ylpyrrolidin-1-yl)carbonyl]phenyl}amino)-5,7-dihydro-6H-pyrimido[5,4-d][1]benzazepin-6-one I-577 4-[(6-oxo-6,7-dihydro-5H-pyrimido[5,4-d][1]benzazepin-2-yl)amino]-N-[3-(2-oxopyrrolidin-1-yl)propyl]benzamide I-578 N-(3-isobutoxypropyl)-4-[(6-oxo-6,7-dihydro-5H-pyrimido[5,4-d][1]benzazepin-2-yl)amino]benzamide I-579 N-(2-fluorobenzyl)-4-[(6-oxo-6,7-dihydro-5H-pyrimido[5,4-d][1]benzazepin-2-yl)amino]benzamide I-580 N-[(1S)-1-(4-methylphenyl)ethyl]-4-[(6-oxo-6,7-dihydro-5H-pyrimido[5,4-d][1]benzazepin-2-yl)amino]benzamide I-581 N-(2-fluorophenyl)-4-[(6-oxo-6,7-dihydro-5H-pyrimido[5,4-d][1]benzazepin-2-yl)amino]benzamide I-582 2-{[4-(2,3-dihydro-1H-indol-1-ylcarbonyl)phenyl]amino}-5,7-dihydro-6H-pyrimido[5,4-d][1]benzazepin-6-one I-583 N-1,3-benzodioxol-5-yl-4-[(6-oxo-6,7-dihydro-5H-pyrimido[5,4-d][1]benzazepin-2-yl)amino]benzamide I-584 2-({4-[(3-methylpiperidin-1-yl)carbonyl]phenyl}amino)-5,7-dihydro-6H-pyrimido[5,4-d][1]benzazepin-6-one I-585 N-(1,3-dihydro-2-benzofuran-5-yl)-4-[(6-oxo-6,7-dihydro-5H-pyrimido[5,4-d][1]benzazepin-2-yl)amino]benzamide I-586 N-(4-methoxybenzyl)-4-[(6-oxo-6,7-dihydro-5H-pyrimido[5,4-d][1]benzazepin-2-yl)amino]benzamide I-587 N-[2-(diethylamino)ethyl]-N-methyl-4-[(6-oxo-6,7-dihydro-5H-pyrimido[5,4-d][1]benzazepin-2-yl)amino]benzamide I-588 N-(3-morpholin-4-ylpropyl)-4-[(6-oxo-6,7-dihydro-5H-pyrimido[5,4-d][1]benzazepin-2-yl)amino]benzamide I-589 N-[3-(dimethylamino)propyl]-N-methyl-4-[(6-oxo-6,7-dihydro-5H-pyrimido[5,4-d][1]benzazepin-2-yl)amino]benzamide I-590 2-{[4-(3,4-dihydroisoquinolin-2(1H)-ylcarbonyl)phenyl]amino}-5,7-dihydro-6H-pyrimido[5,4-d][1]benzazepin-6-one I-591 N-(2,4-dimethylbenzyl)-4-[(6-oxo-6,7-dihydro-5H-pyrimido[5,4-d][1]benzazepin-2-yl)amino]benzamide I-592 N-[3-(dimethylamino)-2,2-dimethylpropyl]-4-[(6-oxo-6,7-dihydro-5H-pyrimido[5,4-d][1]benzazepin-2-yl)amino]benzamide I-593 4-[(6-oxo-6,7-dihydro-5H-pyrimido[5,4-d][1]benzazepin-2-yl)amino]-N-pyridin-4-ylbenzamide I-594 4-[(6-oxo-6,7-dihydro-5H-pyrimido[5,4-d][1]benzazepin-2-yl)amino]-N-(2-phenoxyethyl)benzamide I-595 2-({4-[(2-pyridin-2-ylpyrrolidin-1-yl)carbonyl]phenyl}amino)-5,7-dihydro-6H-pyrimido[5,4-d][1]benzazepin-6-one I-596 N-(2-cyanoethyl)-N-cyclopentyl-4-[(6-oxo-6,7-dihydro-5H-pyrimido[5,4-d][1]benzazepin-2-yl)amino]benzamide I-597 N-methyl-N-(1-{4-[(6-oxo-6,7-dihydro-5H-pyrimido[5,4-d][1]benzazepin-2-yl)amino]benzoyl}pyrrolidin-3-yl)acetamide I-598 N-[2-(3,4-dimethylphenyl)ethyl]-4-[(6-oxo-6,7-dihydro-5H-pyrimido[5,4-d][1]benzazepin-2-yl)amino]benzamide I-599 N-(2,5-difluorobenzyl)-4-[(6-oxo-6,7-dihydro-5H-pyrimido[5,4-d][1]benzazepin-2-yl)amino]benzamide I-600 N-1H-indol-5-yl-4-[(6-oxo-6,7-dihydro-5H-pyrimido[5,4-d][1]benzazepin-2-yl)amino]benzamide I-601 N-(4-methyl-1,3-thiazol-2-yl)-4-[(6-oxo-6,7-dihydro-5H-pyrimido[5,4-d][1]benzazepin-2-yl)amino]benzamide I-602 2-[(4-{[3-(diethylamino)pyrrolidin-1-yl]carbonyl}phenyl)amino]-5,7-dihydro-6H-pyrimido[5,4-d][1]benzazepin-6-one I-603 N-(5-cyclopropyl-1,3,4-thiadiazol-2-yl)-4-[(6-oxo-6,7-dihydro-5H-pyrimido[5,4-d][1]benzazepin-2-yl)amino]benzamide I-604 2-({4-[(5-fluoro-2,3-dihydro-1H-indol-1-yl)carbonyl]phenyl}amino)-5,7-dihydro-6H-pyrimido[5,4-d][1]benzazepin-6-one I-605 N-(2-methyl-1H-indol-5-yl)-4-[(6-oxo-6,7-dihydro-5H-pyrimido[5,4-d][1]benzazepin-2-yl)amino]benzamide I-606 4-[(6-oxo-6,7-dihydro-5H-pyrimido[5,4-d][1]benzazepin-2-yl)amino]-N-(2-phenylpropyl)benzamide I-607 N-(3-methoxyphenyl)-4-[(6-oxo-6,7-dihydro-5H-pyrimido[5,4-d][1]benzazepin-2-yl)amino]benzamide I-608 N-ethyl-4-[(6-oxo-6,7-dihydro-5H-pyrimido[5,4-d][1]benzazepin-2-yl)amino]-N-(pyridin-4-ylmethyl)benzamide I-609 N-(3-methoxybenzyl)-4-[(6-oxo-6,7-dihydro-5H-pyrimido[5,4-d][1]benzazepin-2-yl)amino]benzamide I-610 N-[1-(4-fluorophenyl)ethyl]-4-[(6-oxo-6,7-dihydro-5H-pyrimido[5,4-d][1]benzazepin-2-yl)amino]benzamide I-611 2-({4-[(3-pyridin-3-ylpyrrolidin-1-yl)carbonyl]phenyl}amino)-5,7-dihydro-6H-pyrimido[5,4-d][1]benzazepin-6-one I-612 2-({4-[(4-butylpiperazin-1-yl)carbonyl]phenyl}amino)-5,7-dihydro-6H-pyrimido[5,4-d][1]benzazepin-6-one I-613 N-[4-(dimethylamino)phenyl]-4-[(6-oxo-6,7-dihydro-5H-pyrimido[5,4-d][1]benzazepin-2-yl)amino]benzamide I-614 4-[(6-oxo-6,7-dihydro-5H-pyrimido[5,4-d][1]benzazepin-2-yl)amino]-N-quinolin-3-ylbenzamide I-615 N-(4-fluorobenzyl)-N-methyl-4-[(6-oxo-6,7-dihydro-5H-pyrimido[5,4-d][1]benzazepin-2-yl)amino]benzamide I-616 N-(cyclopropylmethyl)-4-[(6-oxo-6,7-dihydro-5H-pyrimido[5,4-d][1]benzazepin-2-yl)amino]-N-propylbenzamide I-617 2-[(4-{[3-(methylsulfonyl)pyrrolidin-1-yl]carbonyl}phenyl)amino]-5,7-dihydro-6H-pyrimido[5,4-d][1]benzazepin-6-one I-618 N-[2-(diisopropylamino)ethyl]-4-[(6-oxo-6,7-dihydro-5H-pyrimido[5,4-d][1]benzazepin-2-yl)amino]benzamide I-619 N-methyl-4-[(6-oxo-6,7-dihydro-5H-pyrimido[5,4-d][1]benzazepin-2-yl)amino]-N-(2-pyridin-2-ylethyl)benzamide I-620 N-ethyl-4-[(6-oxo-6,7-dihydro-5H-pyrimido[5,4-d][1]benzazepin-2-yl)amino]-N-(2-pyridin-2-ylethyl)benzamide I-621 N-[2-(diethylamino)ethyl]-N-ethyl-4-[(6-oxo-6,7-dihydro-5H-pyrimido[5,4-d][1]benzazepin-2-yl)amino]benzamide I-622 N-(5-methyl-1,3-thiazol-2-yl)-4-[(6-oxo-6,7-dihydro-5H-pyrimido[5,4-d][1]benzazepin-2-yl)amino]benzamide I-623 N-(4-chlorobenzyl)-4-[(6-oxo-6,7-dihydro-5H-pyrimido[5,4-d][1]benzazepin-2-yl)amino]benzamide I-624 4-[(6-oxo-6,7-dihydro-5H-pyrimido[5,4-d][1]benzazepin-2-yl)amino]-N-(4-pyrrolidin-1-ylbutyl)benzamide
I-625 2-{[2-(2-fluorophenyl)ethyl]amino}-5,7-dihydro-6H-pyrimido[5,4-d][1]benzazepin-6-one
I-626 2-{[2-(trifluoromethyl)benzyl]amino}-5,7-dihydro-6H-pyrimido[5,4-d][1]benzazepin-6-one
I-627 2-{[(1S)-1-(3-methoxyphenyl)ethyl]amino}-5,7-dihydro-6H-pyrimido[5,4-d][1]benzazepin-6-one
I-628 2-[(2-fluoro-5-methylphenyl)amino]-5,7-dihydro-6H-pyrimido[5,4-d][1]benzazepin-6-one
I-629 2-[(2-methoxy-1-methylethyl)amino]-5,7-dihydro-6H-pyrimido[5,4-d][1]benzazepin-6-one
I-630 2-[(6-chloropyridin-3-yl)amino]-5,7-dihydro-6H-pyrimido[5,4-d][1]benzazepin-6-one
I-631 2-(cyclohexylamino)-5,7-dihydro-6H-pyrimido[5,4-d][1]benzazepin-6-one
I-632 2-[(2-phenylpropyl)amino]-5,7-dihydro-6H-pyrimido[5,4-d][1]benzazepin-6-one
I-633 2-[(4-methylpyridin-2-yl)amino]-5,7-dihydro-6H-pyrimido[5,4-d][1]benzazepin-6-one
I-634 2-[(2,6-dimethoxypyridin-3-yl)amino]-5,7-dihydro-6H-pyrimido[5,4-d][1]benzazepin-6-one
I-635 2-(cyclobutylamino)-5,7-dihydro-6H-pyrimido[5,4-d][1]benzazepin-6-one
I-636 2-[(3-isopropoxypropyl)amino]-5,7-dihydro-6H-pyrimido[5,4-d][1]benzazepin-6-one
I-637 2-{[4-(trifluoromethyl)phenyl]amino}-5,7-dihydro-6H-pyrimido[5,4-d][1]benzazepin-6-one
I-638 2-[(4-morpholin-4-ylphenyl)amino]-5,7-dihydro-6H-pyrimido[5,4-d][1]benzazepin-6-one
I-639 2-(2,3-dihydro-1,4-benzodioxin-6-ylamino)-5,7-dihydro-6H-pyrimido[5,4-d][1]benzazepin-6-one
I-640 2-{[3-(trifluoromethyl)benzyl]amino}-5,7-dihydro-6H-pyrimido[5,4-d][1]benzazepin-6-one
I-641 2-[(3-pyrrolidin-1-ylpropyl)amino]-5,7-dihydro-6H-pyrimido[5,4-d][1]benzazepin-6-one
I-642 2-[(2-isopropoxyethyl)amino]-5,7-dihydro-6H-pyrimido[5,4-d][1]benzazepin-6-one
I-643 2-{[(1S,2R)-2-hydroxy-1-methyl-2-phenylethyl]amino}-5,7-dihydro-6H-pyrimido[5,4-d][1]benzazepin-6-one
I-644 2-{[(1S)-1-phenylethyl]amino}-5,7-dihydro-6H-pyrimido[5,4-d][1]benzazepin-6-one
I-645 2-[(2,4-difluorophenyl)amino]-5,7-dihydro-6H-pyrimido[5,4-d][1]benzazepin-6-one
I-646 2-[(3-methylbutyl)amino]-5,7-dihydro-6H-pyrimido[5,4-d][1]benzazepin-6-one
I-647 2-[(3-bromo-5-methylpyridin-2-yl)amino]-5,7-dihydro-6H-pyrimido[5,4-d][1]benzazepin-6-one
I-648 2-[(6-methoxypyridin-3-yl)amino]-5,7-dihydro-6H-pyrimido[5,4-d][1]benzazepin-6-one
I-649 2-[(3,5-dimethoxyphenyl)amino]-5,7-dihydro-6H-pyrimido[5,4-d][1]benzazepin-6-one
I-650 2-(1,3-benzodioxol-5-ylamino)-5,7-dihydro-6H-pyrimido[5,4-d][1]benzazepin-6-one
I-651 2-[(trans-4-hydroxycyclohexyl)amino]-5,7-dihydro-6H-pyrimido[5,4-d][1]benzazepin-6-one
I-652 2-{[1-(4-chlorobenzyl)-2-hydroxyethyl]amino}-5,7-dihydro-6H-pyrimido[5,4-d][1]benzazepin-6-one
I-653 2-(pyrimidin-2-ylamino)-5,7-dihydro-6H-pyrimido[5,4-d][1]benzazepin-6-one
I-654 2-[(4-methoxy-2-methylphenyl)amino]-5,7-dihydro-6H-pyrimido[5,4-d][1]benzazepin-6-one
I-655 2-[(3-chloro-4-fluorophenyl)amino]-5,7-dihydro-6H-pyrimido[5,4-d][1]benzazepin-6-one
I-656 2-{[3-(2-oxopyrrolidin-1-yl)propyl]amino}-5,7-dihydro-6H-pyrimido[5,4-d][1]benzazepin-6-one
I-657 2-{[3-(2-methylpiperidin-1-yl)propyl]amino}-5,7-dihydro-6H-pyrimido[5,4-d][1]benzazepin-6-one
I-658 2-{[2-(difluoromethoxy)phenyl]amino}-5,7-dihydro-6H-pyrimido[5,4-d][1]benzazepin-6-one
I-659 2-{[3-fluoro-5-(trifluoromethyl)benzyl]amino}-5,7-dihydro-6H-pyrimido[5,4-d][1]benzazepin-6-one
I-660 2-[(5-chloropyridin-2-yl)amino]-5,7-dihydro-6H-pyrimido[5,4-d][1]benzazepin-6-one
I-661 ethyl 4-[(6-oxo-6,7-dihydro-5H-pyrimido[5,4-d][1]benzazepin-2-yl)amino]piperidine-1-carboxylate
I-662 2-{[2-(trifluoromethyl)phenyl]amino}-5,7-dihydro-6H-pyrimido[5,4-d][1]benzazepin-6-one
I-663 44-[(9-chloro-6-oxo-6,7-dihydro-5H-pyrimido[5,4-d][1]benzazepin-2-yl)amino]-N-[2-(3,5-dimethyl-1H-pyrazol-4-yl)ethyl]benzamide
I-664 9-chloro-2-{[4-(morpholin-4-ylcarbonyl)phenyl]amino}-5,7-dihydro-6H-pyrimido[5,4-d][1]benzazepin-6-one
I-665 9-chloro-2-{[4-(3,4-dihydroisoquinolin-2(1H)-ylcarbonyl)phenyl]amino}-5,7-dihydro-6H-pyrimido[5,4-d][1]benzazepin-6-one
I-666 4-[(9-chloro-6-oxo-6,7-dihydro-5H-pyrimido[5,4-d][1]benzazepin-2-yl)amino]-N-[2-(1,3-dioxolan-2-yl)ethyl]benzamide
I-667 4-[(9-chloro-6-oxo-6,7-dihydro-5H-pyrimido[5,4-d][1]benzazepin-2-yl)amino]-N-methyl-N-phenylbenzamide
I-668 4-[(9-chloro-6-oxo-6,7-dihydro-5H-pyrimido[5,4-d][1]benzazepin-2-yl)amino]-N-(1,3-dihydro-2-benzofuran-5-yl)benzamide
I-669 4-[(9-chloro-6-oxo-6,7-dihydro-5H-pyrimido[5,4-d][1]benzazepin-2-yl)amino]-N-[1-(hydroxymethyl)-2-methylpropyl]benzamide
I-670 4-[(9-chloro-6-oxo-6,7-dihydro-5H-pyrimido[5,4-d][1]benzazepin-2-yl)amino]-N-[2-(dimethylamino)ethyl]benzamide
I-671 N-(3-acetylphenyl)-4-[(9-chloro-6-oxo-6,7-dihydro-5H-pyrimido[5,4-d][1]benzazepin-2-yl)amino]benzamide
I-672 4-[(9-chloro-6-oxo-6,7-dihydro-5H-pyrimido[5,4-d][1]benzazepin-2-yl)amino]-N-(2,2-dimethoxyethyl)-N-methylbenzamide
I-673 44-[(9-chloro-6-oxo-6,7-dihydro-5H-pyrimido[5,4-d][1]benzazepin-2-yl)amino]-N-cyclobutylbenzamide
I-674 4-[(9-chloro-6-oxo-6,7-dihydro-5H-pyrimido[5,4-d][1]benzazepin-2-yl)amino]-N-(6-methylpyridin-2-yl)benzamide
I-675 4-[(9-chloro-6-oxo-6,7-dihydro-5H-pyrimido[5,4-d][1]benzazepin-2-yl)amino]-N-(2-fluorobenzyl)benzamide
I-676 4-[(9-chloro-6-oxo-6,7-dihydro-5H-pyrimido[5,4-d][1]benzazepin-2-yl)amino]-N-methylbenzamide
I-677 4-[(9-chloro-6-oxo-6,7-dihydro-5H-pyrimido[5,4-d][1]benzazepin-2-yl)amino]-N-methyl-N-(2-thienylmethyl)benzamide
I-678 4-[(9-chloro-6-oxo-6,7-dihydro-5H-pyrimido[5,4-d][1]benzazepin-2-yl)amino]-N-(4,5-dihydro-1,3-thiazol-2-yl)benzamide
I-679 4-[(9-chloro-6-oxo-6,7-dihydro-5H-pyrimido[5,4-d][1]benzazepin-2-yl)amino]-N-[(1R)-2,3-dihydro-1H-inden-1-yl]benzamide
I-680 4-[(9-chloro-6-oxo-6,7-dihydro-5H-pyrimido[5,4-d][1]benzazepin-2-yl)amino]-N-[cyano(phenyl)methyl]benzamide
I-681 4-[(9-chloro-6-oxo-6,7-dihydro-5H-pyrimido[5,4-d][1]benzazepin-2-yl)amino]-N-(2,3-dimethylcyclohexyl)benzamide I-682 4-[(9-chloro-6-oxo-6,7-dihydro-5H-pyrimido[5,4-d][1]benzazepin-2-yl)amino]-N-(4-fluoro-2-methylphenyl)benzamide I-683 2-[(3-methoxypropyl)amino]-5,7-dihydro-6H-pyrimido[5,4-d][1]benzazepin-6-one I-684 2-[(2-phenylethyl)amino]-5,7-dihydro-6H-pyrimido[5,4-d][1]benzazepin-6-one I-685 2-{[2-(diethylamino)ethyl]amino}-5,7-dihydro-6H-pyrimido[5,4-d][1]benzazepin-6-one I-686 2-[(2-methoxyphenyl)amino]-5,7-dihydro-6H-pyrimido[5,4-d][1]benzazepin-6-one I-687 2-[(2-methoxybenzyl)amino]-5,7-dihydro-6H-pyrimido[5,4-d][1]benzazepin-6-one I-688 2-({3-[methyl(phenyl)amino]propyl}amino)-5,7-dihydro-6H-pyrimido[5,4-d][1]benzazepin-6-one I-689 2-[(2-phenoxyethyl)amino]-5,7-dihydro-6H-pyrimido[5,4-d][1]benzazepin-6-one I-690 2-[(2,2-dimethylpropyl)amino]-5,7-dihydro-6H-pyrimido[5,4-d][1]benzazepin-6-one I-691 2-[(tetrahydrofuran-2-ylmethyl)amino]-5,7-dihydro-6H-pyrimido[5,4-d][1]benzazepin-6-one I-692 2-(cyclopentylamino)-5,7-dihydro-6H-pyrimido[5,4-d][1]benzazepin-6-one I-693 2-(propylamino)-5,7-dihydro-6H-pyrimido[5,4-d][1]benzazepin-6-one I-694 2-(prop-2-yn-1-ylamino)-5,7-dihydro-6H-pyrimido[5,4-d][1]benzazepin-6-one I-695 2-[(3,3-dimethylbutyl)amino]-5,7-dihydro-6H-pyrimido[5,4-d][1]benzazepin-6-one I-696 2-[(1,3,5-trimethyl-1H-pyrazol-4-yl)amino]-5,7-dihydro-6H-pyrimido[5,4-d][1]benzazepin-6-one I-697 2-{[2-(3,4-dimethylphenyl)ethyl]amino}-5,7-dihydro-6H-pyrimido[5,4-d][1]benzazepin-6-one I-698 2-[(3-morpholin-4-ylpropyl)amino]-5,7-dihydro-6H-pyrimido[5,4-d][1]benzazepin-6-one I-699 2-[(2-ethoxyethyl)amino]-5,7-dihydro-6H-pyrimido[5,4-d][1]benzazepin-6-one I-700 2-[(2-piperidin-1-ylethyl)amino]-5,7-dihydro-6H-pyrimido[5,4-d][1]benzazepin-6-one I-701 2-[(pyridin-2-ylmethyl)amino]-5,7-dihydro-6H-pyrimido[5,4-d][1]benzazepin-6-one I-702 2-[(2-fluorobenzyl)amino]-5,7-dihydro-6H-pyrimido[5,4-d][1]benzazepin-6-one I-703 2-[(4-chloro-2-fluorophenyl)amino]-5,7-dihydro-6H-pyrimido[5,4-d][1]benzazepin-6-one I-704 2-(isopropylamino)-5,7-dihydro-6H-pyrimido[5,4-d][1]benzazepin-6-one I-705 2-[(cyclohexylmethyl)amino]-5,7-dihydro-6H-pyrimido[5,4-d][1]benzazepin-6-one I-706 2-[(1H-benzimidazol-2-ylmethyl)amino]-5,7-dihydro-6H-pyrimido[5,4-d][1]benzazepin-6-one I-707 2-{[1-(4-methyl-1,3-thiazol-2-yl)ethyl]amino}-5,7-dihydro-6H-pyrimido[5,4-d][1]benzazepin-6-one I-708 2-{[1-(methoxymethyl)propyl]amino}-5,7-dihydro-6H-pyrimido[5,4-d][1]benzazepin-6-one I-709 2-{[(2-bromo-3-thienyl)methyl]amino}-5,7-dihydro-6H-pyrimido[5,4-d][1]benzazepin-6-one I-710 2-{[3-(trifluoromethoxy)phenyl]amino}-5,7-dihydro-6H-pyrimido[5,4-d][1]benzazepin-6-one I-711 2-{[2-(4-fluorophenyl)ethyl]amino}-5,7-dihydro-6H-pyrimido[5,4-d][1]benzazepin-6-one I-712 2-{[2-(methylsulfonyl)ethyl]amino}-5,7-dihydro-6H-pyrimido[5,4-d][1]benzazepin-6-one I-713 2-{[(3-methyl-2-thienyl)methyl]amino}-5,7-dihydro-6H-pyrimido[5,4-d][1]benzazepin-6-one I-714 2-{[2-(2,4-dichlorophenyl)ethyl]amino}-5,7-dihydro-6H-pyrimido[5,4-d][1]benzazepin-6-one I-715 2-[(2,5-difluorobenzyl)amino]-5,7-dihydro-6H-pyrimido[5,4-d][1]benzazepin-6-one I-716 2-{[4-(methylsulfanyl)phenyl}amino]-5,7-dihydro-6H-pyrimido[5,4-d][1]benzazepin-6-one I-717 2-(1H-indol-5-ylamino)-5,7-dihydro-6H-pyrimido[5,4-d][1]benzazepin-6-one I-718 2-[(3-fluoro-4-methoxyphenyl)amino]-5,7-dihydro-6H-pyrimido[5,4-d][1]benzazepin-6-one I-719 2-{[2-(2,5-dimethylphenyl)ethyl]amino}-5,7-dihydro-6H-pyrimido[5,4-d][1]benzazepin-6-one I-720 2-{[2-(5-chloro-1H-indol-3-yl)ethyl]amino}-5,7-dihydro-6H-pyrimido[5,4-d][1]benzazepin-6-one I-721 2-[(1R)-2,3-dihydro-1H-inden-1-ylamino]-5,7-dihydro-6H-pyrimido[5,4-d][1]benzazepin-6-one I-722 2-{[(1R)-1-cyclohexylethyl]amino}-5,7-dihydro-6H-pyrimido[5,4-d][1]benzazepin-6-one I-723 2-[(cyclopropylmethyl)amino]-5,7-dihydro-6H-pyrimiddo[5,4-d][1]benzazepin-6-one I-724 2-{[(1-ethylpyrrolidin-3-yl)methyl]amino}-5,7-dihydro-6H-pyrimido[5,4-d][1]benzazepin-6-one I-725 2-{[2-(5-chloro-1H-benzimidazol-2-yl)ethyl]amino}-5,7-dihydro-6H-pyrimido[5,4-d][1]benzazepin-6-one I-726 2-{[2-(4-aminophenyl)ethyl]amino}-5,7-dihydro-6H-pyrimido[5,4-d][1]benzazepin-6-one I-727 2-[(4-fluorobenzyl)amino]-5,7-dihydro-6H-pyrimido[5,4-d][1]benzazepin-6-one I-728 2-{[2-(2-thienyl)ethyl]amino}-5,7-dihydro-6H-pyrimido[5,4-d][1]benzazepin-6-one I-729 2-[(1-methylbutyl)amino]-5,7-dihydro-6H-pyrimido[5,4-d][ ]benzazepin-6-one I-730 2-{[2-(3-fluorophenyl)ethyl]amino}-5,7-dihydro-6H-pyrimido[5,4-d][1]benzazepin-6-one I-731 2-{[(5-chloro-1-benzothien-3-yl)methyl]amino}-5,7-dihydro-6H-pyrimido[5,4-d][1]benzazepin-6-one I-732 2-{[2-(3,5-dimethyl-1H-pyrazol-4-yl)ethyl]amino}-5,7-dihydro-6H-pyrimido[5,4-d][1]benzazepin-6-one I-733 2-{[2-(diisopropylamino)ethyl]amino}-5,7-dihydro-6H-pyrimido[5,4-d][1]benzazepin-6-one I-734 2-{[2-(2,4-dimethylphenyl)ethyl]amino}-5,7-dihydro-6H-pyrimido[5,4-d][1]benzazepin-6-one I-735 2-{[2-(3,4-dimethoxyphenyl)ethyl]amino}-5,7-dihydro-6H-pyrimido[5,4-d][1]benzazepin-6-one I-736 2-[(3-methoxybenzyl)amino]-5,7-dihydro-6H-pyrimido[5,4-d][1]benzazepin-6-one I-737 2-[(2-methylcyclohexyl)amino]-5,7-dihydro-6H-pyrimido[5,4-d][1]benzazepin-6-one I-738 2-methyl-3-{2-[(6-oxo-6,7-dihydro-5H-pyrimido[5,4-d][1]benzazepin-2-yl)amino]ethyl}-1H-indole-5-carbonitrile I-739 2-{[2-(5-methoxy-1H-indol-3-yl)ethyl]amino}-5,7-dihydro-6H-pyrimido[5,4-d][1]benzazepin-6-one I-740 2-[(1,3-benzodioxol-5-ylmethyl)amino]-5,7-dihydro-6H-pyrimido[5,4-d][1]benzazepin-6-one I-741 2-(quinolin-3-ylamino)-5,7-dihydro-6H-pyrimido[5,4-d][1]benzazepin-6-one I-742 2-{[3-(1H-imidazol-1-yl)propyl]amino}-5,7-dihydro-6H-pyrimido[5,4-d][1]benzazepin-6-one I-743 2-(benzylamino)-5,7-dihydro-6H-pyrimido[5,4-d][1]benzazepin-6-one I-744 2-{[(1S)-2-phenylcyclopropyl]amino}-5,7-dihydro-6H-pyrimido[5,4-d][1]benzazepin-6-one I-745 2-(ethylamino)-5,7-dihydro-6H-pyrimido[5,4-d][1]benzazepin-6-one I-746 2-[(4-methylcyclohexyl)amino]-5,7-dihydro-6H-pyrimido[5,4-d][1]benzazepin-6-one I-747 2-{[3-(dimethylamino)-2,2-dimethylpropyl]amino}-5,7-dihydro-6H-pyrimido[5,4-d][1]benzazepin-6-one I-748 2-[(2-chloro-4-methylphenyl)amino]-5,7-dihydro-6H-pyrimido[5,4-d][1]benzazepin-6-one I-749 2-{[3-(dimethylamino)phenyl]amino}-5,7-dihydro-6H-pyrimido[5,4-d][1]benzazepin-6-one I-750 2-{[2-(4-methylphenyl)ethyl]amino}-5,7-dihydro-6H-pyrimido[5,4-d][1]benzazepin-6-one I-751 2-{[(5-methyl-2-furyl)methyl]amino}-5,7-dihydro-6H-pyrimido[5,4-d][1]benzazepin-6-one I-752 2-[(2-furylmethyl)amino]-5,7-dihydro-6H-pyrimido[5,4-d][1]benzazepin-6-one I-753 2-{[2-(dimethylamino)-1-methylethyl]amino}-5,7-dihydro-6H-pyrimido[5,4-d][1]benzazepin-6-one I-754 2-(1,3-dihydro-2-benzofuran-5-ylamino)-5,7-dihydro-6H-pyrimido[5,4-d][1]benzazepin-6-one I-755 N-cyclohexyl-4-[(7-methyl-6-oxo-6,7-dihydro-5H-pyrimido[5,4-d][1]benzazepin-2-yl)amino]benzamide I-756 N-[2-(dimethylamino)ethyl]-4-[(7-methyl-6-oxo-6,7-dihydro-5H-pyrimido[5,4-d][1]benzazepin-2-yl)amino]benzamide I-757 N-methyl-4-[(7-methyl-6-oxo-6,7-dihydro-5H-pyrimido[5,4-d][1]benzazepin-2-yl)amino]-N-(2-pyridin-2-ylethyl)benzamide I-758 N-isopropyl-4-[(7-methyl-6-oxo-6,7-dihydro-5H-pyrimido[5,4-d][1]benzazepin-2-yl)amino]benzamide I-759 N-[2-(dimethylamino)ethyl]-N-ethyl-4-[(7-methyl-6-oxo-6,7-dihydro-5H-pyrimido[5,4-d][1]benzazepin-2-yl)amino]benzamide I-760 4-[(7-methyl-6-oxo-6,7-dihydro-5H-pyrimido[5,4-d][1]benzazepin-2-yl)amino]-N-quinolin-2-ylbenzamide I-761 N-(3-isopropoxypropyl)-4-[(7-methyl-6-oxo-6,7-dihydro-5H-pyrimido[5,4-d][1]benzazepin-2-yl)amino]benzamide I-762 2-({4-[(4-acetylpiperazin-1-yl)carbonyl]phenyl}amino)-7-methyl-5,7-dihydro-6H-pyrimido[5,4-d][1]benzazepin-6-one I-763 4-[(7-methyl-6-oxo-6,7-dihydro-5H-pyrimido[5,4-d][1]benzazepin-2-yl)amino]-N-(2-piperidin-1-ylethyl)benzamide I-764 N-(1-ethynylcyclohexyl)-4-[(7-methyl-6-oxo-6,7-dihydro-5H-pyrimido[5,4-d][1]benzazepin-2-yl)amino]benzamide I-765 N-(4-methoxybenzyl)-4-[(7-methyl-6-oxo-6,7-dihydro-5H-pyrimido[5,4-d][1]benzazepin-2-yl)amino]benzamide I-766 4-[(7-methyl-6-oxo-6,7-dihydro-5H-pyrimido[5,4-d][1]benzazepin-2-yl)amino]-N-(2-phenylethyl)benzamide I-767 N-cyclohexyl-N-methyl-4-[(7-methyl-6-oxo-6,7-dihydro-5H-pyrimido[5,4-d][1]benzazepin-2-yl)amino]benzamide I-768 4-[(7-methyl-6-oxo-6,7-dihydro-5H-pyrimido[5,4-d][1]benzazepin-2-yl)amino]-N-(4-methyl-1,3-thiazol-2-yl)benzamide I-769 7-methyl-2-({4-[(4-methylpiperidin-1-yl)carbonyl]phenyl}amino)-5,7-dihydro-6H-pyrimido[5,4-d][1]benzazepin-6-one I-770 N-1H-indol-5-yl-4-[(7-methyl-6-oxo-6,7-dihydro-5H-pyrimido[5,4-d][1]benzazepin-2-yl)amino]benzamide I-771 N-(2-isopropoxyethyl)-4-[(7-methyl-6-oxo-6,7-dihydro-5H-pyrimido[5,4-d][1]benzazepin-2-yl)amino]benzamide I-772 N-(cyclopropylmethyl)-4-[(7-methyl-6-oxo-6,7-dihydro-5H-pyrimido[5,4-d][1]benzazepin-2-yl)amino]benzamide I-773 4-[(7-methyl-6-oxo-6,7-dihydro-5H-pyrimido[5,4-d][1]benzazepin-2-yl)amino]-N-(1,3,5-trimethyl-1H-pyrazol-4-yl)benzamide I-774 N-[4-(dimethylamino)phenyl]-4-[(7-methyl-6-oxo-6,7-dihydro-5H-pyrimido[5,4-d][1]benzazepin-2-yl)amino]benzamide I-775 2-[(4-{[3-(diethylamino)pyrrolidin-1-yl]carbonyl}phenyl)amino]-7-methyl-5,7-dihydro-6H-pyrimido[5,4-d][1]benzazepin-6-one I-776 2-[(4-{[(2S)-2-(methoxymethyl)pyrrolidin-1-yl]carbonyl}phenyl)amino]-7-methyl-5,7-dihydro-6H-pyrimido[5,4-d][1]benzazepin-6-one I-777 N-[2-(diethylamino)ethyl]-N-ethyl-4-[(7-methyl-6-oxo-6,7-dihydro-5H-pyrimido[5,4-d][1]benzazepin-2-yl)amino]benzamide I-778 N-(3,5-dimethylisoxazol-4-yl)-4-[(7-methyl-6-oxo-6,7-dihydro-5H-pyrimido[5,4-d][1]benzazepin-2-yl)amino]benzamide I-779 N-(2-fluorobenzyl)-4-[(7-methyl-6-oxo-6,7-dihydro-5H-pyrimido[5,4-d][1]benzazepin-2-yl)amino]benzamide I-780 2-[(4-{[(3R)-3-(dimethylamino)pyrrolidin-1-yl]carbonyl}phenyl)amino]-7-methyl-5,7-dihydro-6H-pyrimido[5,4-d][1]benzazepin-6-one I-781 2-({4-[(4-butylpiperazin-1-yl)carbonyl]phenyl}amino)-7-methyl-5,7-dihydro-6H-pyrimido[5,4-d][1]benzazepin-6-one I-782 4-[(7-methyl-6-oxo-6,7-dihydro-5H-pyrimido[5,4-d][1]benzazepin-2-yl)amino]-N-(pyridin-4-ylmethyl)benzamide I-783 4-[(7-methyl-6-oxo-6,7-dihydro-5H-pyrimido[5,4-d][1]benzazepin-2-yl)amino]-N-pyridin-4-ylbenzamide I-784 N-(2-methoxy-1-methylethyl)-4-[(7-methyl-6-oxo-6,7-dihydro-5H-pyrimido[5,4-d][1]benzazepin-2-yl)amino]benzamide I-785 2-{[4-(2,3-dihydro-1H-indol-1-ylcarbonyl)phenyl]amino}-7-methyl-5,7-dihydro-6H-pyrimido[5,4-d][1]benzazepin-6-one I-786 4-[(7-methyl-6-oxo-6,7-dihydro-5H-pyrimido[5,4-d][1]benzazepin-2-yl)amino]-N-[(1S)-1-(4-methylphenyl)ethyl]benzamide I-787 N-(2,4-dimethylbenzyl)-4-[(7-methyl-6-oxo-6,7-dihydro-5H-pyrimido[5,4-d][1]benzazepin-2-yl)amino]benzamide I-788 4-{4-[(7-methyl-6-oxo-6,7-dihydro-5H-pyrimido[5,4-d][1]benzazepin-2-yl)amino]benzoyl}-1,4-diazepane-1-carbaldehyde I-789 N-[(1R)-2,3-dihydro-1H-inden-1-yl]-4-[(7-methyl-6-oxo-6,7-dihydro-5H-pyrimido[5,4-d][1]benzazepin-2-yl)amino]benzamide I-790 N-ethyl-4-[(7-methyl-6-oxo-6,7-dihydro-5H-pyrimido[5,4-d][1]benzazepin-2-yl)amino]-N-(pyridin-4-ylmethyl)benzamide I-791 N-[2-(acetylamino)ethyl]-4-[(7-methyl-6-oxo-6,7-dihydro-5H-pyrimido[5,4-d][1]benzazepin-2-yl)amino]benzamide I-792 7-methyl-2-{[4-(morpholin-4-ylcarbonyl)phenyl]amino}-5,7-dihydro-6H-pyrimido[5,4-d][1]benzazepin-6-one I-793 N-(4-methoxyphenyl)-4-[(7-methyl-6-oxo-6,7-dihydro-5H-pyrimido[5,4-d][1]benzazepin-2-yl)amino]benzamide I-794 N-[(1-ethylpyrrolidin-3-yl)methyl]-4-[(7-methyl-6-oxo-6,7-dihydro-5H-pyrimido[5,4-d][1]benzazepin-2-yl)amino]benzamide I-795 N-[(5-methyl-2-furyl)methyl]-4-[(7-methyl-6-oxo-6,7-dihydro-5H-pyrimido[5,4-d][1]benzazepin-2-yl)amino]benzamide I-796 7-methyl-2-({4-[(3-oxopiperazin-1-yl)carbonyl]phenyl}amino)-5,7-dihydro-6H-pyrimido[5,4-d][1]benzazepin-6-one I-797 N-cyclopentyl-4-[(7-methyl-6-oxo-6,7-dihydro-5H-pyrimido[5,4-d][1]benzazepin-2-yl)amino]benzamide I-798 4-[(7-methyl-6-oxo-6,7-dihydro-5H-pyrimido[5,4-d][1]benzazepin-2-yl)amino]-N-[2-(2-thienyl)ethyl]benzamide I-799 N-[(1R,2R,4S)-bicyclo[2.2.1]hept-2-yl]-4-[(7-methyl-6-oxo-6,7-dihydro-5H-pyrimido[5,4-d][1]benzazepin-2-yl)amino]benzamide I-800 2-{[4-(3,4-dihydroisoquinolin-2(H)-ylcarbonyl)phenyl]amino}-7-methyl-5,7-dihydro-6H-pyrimido[5,4-d][1]benzazepin-6-one I-801 N-methyl-N-(1-{4-[(7-methyl-6-oxo-6,7-dihydro-5H-pyrimido[5,4-d][1]benzazepin-2-yl)amino]benzoyl}pyrrolidin-3-yl)acetamide I-802 N-(3-methylbutyl)-4-[(7-methyl-6-oxo-6,7-dihydro-5H-pyrimido[5,4-d][1]benzazepin-2-yl)amino]benzamide I-803 N-(2-cyanoethyl)-N-cyclopropyl-4-[(7-methyl-6-oxo-6,7-dihydro-5H-pyrimido[5,4-d][1]benzazepin-2-yl)amino]benzamide I-804 N,N-diethyl-4-[(7-methyl-6-oxo-6,7-dihydro-5H-pyrimido[5,4-d][1]benzazepin-2-yl)amino]benzamide I-805 N-[3-(1H-imidazol-1-yl)propyl]-4-[(7-methyl-6-oxo-6,7-dihydro-5H-pyrimido[5,4-d][1]benzazepin-2-yl)amino]benzamide I-806 N-[3-(dimethylamino)-2,2-dimethylpropyl]-4-[(7-methyl-6-oxo-6,7-dihydro-5H-pyrimido[5,4-d][1]benzazepin-2-yl)amino]benzamide I-807 N-ethyl-4-[(7-methyl-6-oxo-6,7-dihydro-5H-pyrimido[5,4-d][1]benzazepin-2-yl)amino]-N-(2-pyridin-2-ylethyl)benzamide I-808 7-methyl-2-{[4-(pyrrolidin-1-ylcarbonyl)phenyl]amino}-5,7-dihydro-6H-pyrimido[5,4-d][1]benzazepin-6-one I-809 N-(4-fluorobenzyl)-4-[(7-methyl-6-oxo-6,7-dihydro-5H-pyrimido[5,4-d][1]benzazepin-2-yl)amino]benzamide I-810 2-({4-[(2-isobutylpyrrolidin-1-yl)carbonyl]phenyl}amino)-7-methyl-5,7-dihydro-6H-pyrimido[5,4-d][1]benzazepin-6-one I-811 7-methyl-2-({4-[(4-methylpiperazin-1-yl)carbonyl]phenyl}amino)-5,7-dihydro-6H-pyrimido[5,4-d][1]benzazepin-6-one I-812 4-[(7-methyl-6-oxo-6,7-dihydro-5H-pyrimido[5,4-d][1]benzazepin-2-yl)amino]-N-(tetrahydrofuran-2-ylmethyl)benzamide I-813 N-(2-methyl-1H-indol-5-yl)-4-[(7-methyl-6-oxo-6,7-dihydro-5H-pyrimido[5,4-d][1]benzazepin-2-yl)amino]benzamide I-814 N-(2-furylmethyl)-N-methyl-4-[(7-methyl-6-oxo-6,7-dihydro-5H-pyrimido[5,4-d][1]benzazepin-2-yl)amino]benzamide I-815 N-(cyclohexylmethyl)-4-[(7-methyl-6-oxo-6,7-dihydro-5H-pyrimido[5,4-d][1]benzazepin-2-yl)amino]benzamide I-816 4-[(7-methyl-6-oxo-6,7-dihydro-5H-pyrimido[5,4-d][1]benzazepin-2-yl)amino]-N-(2-phenoxyethyl)benzamide I-817 2-({4-[(5-ethyl-2-methylpiperidin-1-yl)carbonyl]phenyl}amino)-7-methyl-5,7-dihydro-6H-pyrimido[5,4-d][1]benzazepin-6-one I-818 N-(2-methoxyethyl)-4-[(7-methyl-6-oxo-6,7-dihydro-5H-pyrimido[5,4-d][1]benzazepin-2-yl)amino]benzamide I-819 N-(2-cyanoethyl)-N-methyl-4-[(7-methyl-6-oxo-6,7-dihydro-5H-pyrimido[5,4-d][1]benzazepin-2-yl)amino]benzamide I-820 N-(3-isobutoxypropyl)-4-[(7-methyl-6-oxo-6,7-dihydro-5H-pyrimido[5,4-d][1]benzazepin-2-yl)amino]benzamide I-821 2-{[4-(1,3-dihydro-2H-isoindol-2-ylcarbonyl)phenyl]amino}-7-methyl-5,7-dihydro-6H-pyrimido[5,4-d][1]benzazepin-6-one I-822 4-[(7-methyl-6-oxo-6,7-dihydro-5H-pyrimido[5,4-d][1]benzazepin-2-yl)amino]-N-(3-propoxypropyl)benzamide I-823 44-[(7-methyl-6-oxo-6,7-dihydro-5H-pyrimido[5,4-d][1]benzazepin-2-yl)amino]-N-[4-(methylsulfanyl)phenyl]benzamide I-824 4-[(7-methyl-6-oxo-6,7-dihydro-5H-pyrimido[5,4-d][1]benzazepin-2-yl)amino]-N-pyridin-3-ylbenzamide I-825 2-({4-[(5-fluoro-2,3-dihydro-1H-indol-1-yl)carbonyl]phenyl}amino)-7-methyl-5,7-dihydro-6H-pyrimido[5,4-d][1]benzazepin-6-one I-826 2-({4-[(2-ethylpyrrolidin-1-yl)carbonyl]phenyl}amino)-7-methyl-5,7-dihydro-6H-pyrimido[5,4-d][1]benzazepin-6-one I-827 N-[2-(diisopropylamino)ethyl]-4-[(7-methyl-6-oxo-6,7-dihydro-5H-pyrimido[5,4-d][1]benzazepin-2-yl)amino]benzamide I-828 N-(2-cyanoethyl)-N-cyclopentyl-4-[(7-methyl-6-oxo-6,7-dihydro-5H-pyrimido[5,4-d][1]benzazepin-2-yl)amino]benzamide I-829 4-[(7-methyl-6-oxo-6,7-dihydro-5H-pyrimido[5,4-d][1]benzazepin-2-yl)amino]-N-[3-(2-oxopyrrolidin-1-yl)propyl]benzamide I-830 7-methyl-2-({4-[(3-methylpiperidin-1-yl)carbonyl]phenyl}amino)-5,7-dihydro-6H-pyrimido[5,4-d][1]benzazepin-6-one I-831 7-methyl-2-{[4-(piperidin-1-ylcarbonyl)phenyl]amino}-5,7-dihydro-6H-pyrimido[5,4-d][1]benzazepin-6-one I-832 N-(4-chlorobenzyl)-4-[(7-methyl-6-oxo-6,7-dihydro-5H-pyrimido[5,4-d][1]benzazepin-2-yl)amino]benzamide I-833 N-(2,5-difluorobenzyl)-4-[(7-methyl-6-oxo-6,7-dihydro-5H-pyrimido[5,4-d][1]benzazepin-2-yl)amino]benzamide I-834 4-[(9-chloro-6-oxo-6,7-dihydro-5H-pyrimido[5,4-d][1]benzazepin-2-yl)amino]-N-[(1,3,5-trimethyl-1H-pyrazol-4-yl)methyl]benzamide I-835 2-({4-[(4-butylpiperazin-1-yl)carbonyl]phenyl}amino)-9-chloro-5,7-dihydro-6H-pyrimido[5,4-d][1]benzazepin-6-one I-836 4-[(9-chloro-6-oxo-6,7-dihydro-5H-pyrimido[5,4-d][1]benzazepin-2-yl)amino]-N-ethyl-N-(2-pyridin-2-ylethyl)benzamide I-837 4-{4-[(9-chloro-6-oxo-6,7-dihydro-5H-pyrimido[5,4-d][1]benzazepin-2-yl)amino]benzoyl}-1,4-diazepane-1-carbaldehyde I-838 4-[(9-chloro-6-oxo-6,7-dihydro-5H-pyrimido[5,4-d][1]benzazepin-2-yl)amino]-N-(4-fluoro-3-methylphenyl)benzamide I-839 9-chloro-2-{[4-(1,4-dioxa-8-azaspiro[4.5]dec-8-ylcarbonyl)phenyl]amino}-5,7-dihydro-6H-pyrimido[5,4-d][1]benzazepin-6-one I-840 N-(1-{4-[(9-chloro-6-oxo-6,7-dihydro-5H-pyrimido[5,4-d][1]benzazepin-2-yl)amino]benzoyl}pyrrolidin-3-yl)-N-methylacetamide I-841 N-(2-chloro-4-methylphenyl)-4-[(9-chloro-6-oxo-6,7-dihydro-5H-pyrimido[5,4-d][1]benzazepin-2-yl)amino]benzamide I-842 4-[(9-chloro-6-oxo-6,7-dihydro-5H-pyrimido[5,4-d][1]benzazepin-2-yl)amino]-N-(2-methyl-1H-benzimidazol-6-yl)benzamide I-843 4-[(9-chloro-6-oxo-6,7-dihydro-5H-pyrimido[5,4-d][1]benzazepin-2-yl)amino]-N-(3-ethoxyphenyl)benzamide I-844 N-butyl-4-[(9-chloro-6-oxo-6,7-dihydro-5H-pyrimido[5,4-d][1]benzazepin-2-yl)amino]-N-(2-cyanoethyl)benzamide I-845 4-[(9-chloro-6-oxo-6,7-dihydro-5H-pyrimido[5,4-d][1]benzazepin-2-yl)amino]-N-(4-fluorobenzyl)benzamide I-846 4-[(9-chloro-6-oxo-6,7-dihydro-5H-pyrimido[5,4-d][1]benzazepin-2-yl)amino]-N-(2-chloropyridin-4-yl)benzamide I-847 N-(1H-benzimidazol-2-ylmethyl)-4-[(9-chloro-6-oxo-6,7-dihydro-5H-pyrimido[5,4-d][1]benzazepin-2-yl)amino]benzamide I-848 4-[(9-chloro-6-oxo-6,7-dihydro-5H-pyrimido[5,4-d][1]benzazepin-2-yl)amino]-N-(4-ethylbenzyl)-N-methylbenzamide I-849 4-[(9-chloro-6-oxo-6,7-dihydro-5H-pyrimido[5,4-d][1]benzazepin-2-yl)amino]-N-(2-phenoxyethyl)benzamide I-850 4-[(9-chloro-6-oxo-6,7-dihydro-5H-pyrimido[5,4-d][1]benzazepin-2-yl)amino]-N-(2-ethoxyphenyl)benzamide I-851 4-[(9-chloro-6-oxo-6,7-dihydro-5H-pyrimido[5,4-d][1]benzazepin-2-yl)amino]-N-(cyclopropylmethyl)-N-propylbenzamide I-852 4-[(9-chloro-6-oxo-6,7-dihydro-5H-pyrimido[5,4-d][1]benzazepin-2-yl)amino]-N-[2-(dimethylamino)ethyl]-N-ethylbenzamide I-853 9-chloro-2-({4-[(6-methyl-3,4-dihydroquinolin-1(2H)-yl)carbonyl]phenyl}amino)-5,7-dihydro-6H-pyrimido[5,4-d][1]benzazepin-6-one I-854 4-[(9-chloro-6-oxo-6,7-dihydro-5H-pyrimido[5,4-d][1]benzazepin-2-yl)amino]-N-isoquinolin-1-ylbenzamide I-855 9-chloro-2-({4-[(2-pyridin-4-ylpyrrolidin-1-yl)carbonyl]phenyl}amino)-5,7-dihydro-6H-pyrimido[5,4-d][1]benzazepin-6-one I-856 9-chloro-2-({4-[(2-ethylpiperidin-1-yl)carbonyl]phenyl}amino)-5,7-dihydro-6H-pyrimido[5,4-d][1]benzazepin-6-one I-857 4-[(9-chloro-6-oxo-6,7-dihydro-5H-pyrimido[5,4-d][1]benzazepin-2-yl)amino]-N-(4-fluorobenzyl)-N-methylbenzamide I-858 4-[(9-chloro-6-oxo-6,7-dihydro-5H-pyrimido[5,4-d][1]benzazepin-2-yl)amino]-N-phenylbenzamide I-859 4-[(9-chloro-6-oxo-6,7-dihydro-5H-pyrimido[5,4-d][1]benzazepin-2-yl)amino]-N-(4-chlorophenyl)-N-methylbenzamide I-860 4-[(9-chloro-6-oxo-6,7-dihydro-5H-pyrimido[5,4-d][1]benzazepin-2-yl)amino]-N-(2,4-difluorophenyl)-N-methylbenzamide I-861 4-[(9-chloro-6-oxo-6,7-dihydro-5H-pyrimido[5,4-d][1]benzazepin-2-yl)amino]-N-(2-methoxyphenyl)benzamide I-862 4-[(9-chloro-6-oxo-6,7-dihydro-5H-pyrimido[5,4-d][1]benzazepin-2-yl)amino]-N-(3-ethyl-6-methylpyridin-2-yl)benzamide I-863 4-[(9-chloro-6-oxo-6,7-dihydro-5H-pyrimido[5,4-d][1]benzazepin-2-yl)amino]-N-(4-chlorophenyl)benzamide I-864 4-[(9-chloro-6-oxo-6,7-dihydro-5H-pyrimido[5,4-d][1]benzazepin-2-yl)amino]-N-methyl-N-(2-pyridin-2-ylethyl)benzamide I-865 4-[(9-chloro-6-oxo-6,7-dihydro-5H-pyrimido[5,4-d][1]benzazepin-2-yl)amino]-N-(3-phenylpropyl)benzamide I-866 4-[(9-chloro-6-oxo-6,7-dihydro-5H-pyrimido[5,4-d][1]benzazepin-2-yl)amino]-N-[2-(2,5-dimethylphenyl)ethyl]benzamide I-867 4-[(9-chloro-6-oxo-6,7-dihydro-5H-pyrimido[5,4-d][1]benzazepin-2-yl)amino]-N-(1-phenylpropyl)benzamide I-868 9-chloro-2-[(4-{[2-(2-methoxyethyl)piperidin-1-yl]carbonyl}phenyl)amino]-5,7-dihydro-6H-pyrimido[5,4-d][1]benzazepin-6-one I-869 4-[(9-chloro-6-oxo-6,7-dihydro-5H-pyrimido[5,4-d][1]benzazepin-2-yl)amino]-N-[2-(4-fluorophenyl)ethyl]benzamide I-870 4-[(9-chloro-6-oxo-6,7-dihydro-5H-pyrimido[5,4-d][1]benzazepin-2-yl)amino]-N-(2-fluoro-5-methylphenyl)benzamide I-871 4-[(9-chloro-6-oxo-6,7-dihydro-5H-pyrimido[5,4-d][1]benzazepin-2-yl)amino]-N-(3,3,5-trimethylcyclohexyl)benzamide I-872 4-[(9-chloro-6-oxo-6,7-dihydro-5H-pyrimido[5,4-d][1]benzazepin-2-yl)amino]-N-methyl-N-[(2-methyl-1,3-thiazol-4-yl)methyl]benzamide I-873 4-[(9-chloro-6-oxo-6,7-dihydro-5H-pyrimido[5,4-d][1]benzazepin-2-yl)amino]-N-(4-methoxybenzyl)benzamide I-874 4-[(9-chloro-6-oxo-6,7-dihydro-5H-pyrimido[5,4-d][1]benzazepin-2-yl)amino]-N-(2-phenylpropyl)benzamide I-875 9-chloro-2-({4-[(2-pyridin-3-ylpyrrolidin-1-yl)carbonyl]phenyl}amino)-5,7-dihydro-6H-pyrimido[5,4-d][1]benzazepin-6-one I-876 4-[(9-chloro-6-oxo-6,7-dihydro-5H-pyrimido[5,4-d][1]benzazepin-2-yl)amino]-N-cyclohexyl-N-ethylbenzamide I-877 4-[(9-chloro-6-oxo-6,7-dihydro-5H-pyrimido[5,4-d][1]benzazepin-2-yl)amino]-N-(1,2,3,4-tetrahydronaphthalen-1-yl)benzamide I-878 N-(4-chlorobenzyl)-4-[(9-chloro-6-oxo-6,7-dihydro-5H-pyrimido[5,4-d][1]benzazepin-2-yl)amino]benzamide I-879 4-[(9-chloro-6-oxo-6,7-dihydro-5H-pyrimido[5,4-d][1]benzazepin-2-yl)amino]-N-(4-pyrrolidin-1-ylbutyl)benzamide I-880 4-[(9-chloro-6-oxo-6,7-dihydro-5H-pyrimido[5,4-d][1]benzazepin-2-yl)amino]-N-(3-furylmethyl)benzamide I-881 9-chloro-2-({4-[(2-pyridin-2-ylpyrrolidin-1-yl)carbonyl]phenyl}amino)-5,7-dihydro-6H-pyrimido[5,4-d][1]benzazepin-6-one I-882 4-[(9-chloro-6-oxo-6,7-dihydro-5H-pyrimido[5,4-d][1]benzazepin-2-yl)amino]-N-(6-chloropyridin-3-yl)benzamide I-883 4-[(9-chloro-6-oxo-6,7-dihydro-5H-pyrimido[5,4-d][1]benzazepin-2-yl)amino]-N-[2-(3,4-dimethylphenyl)ethyl]benzamide I-884 4-[(9-chloro-6-oxo-6,7-dihydro-5H-pyrimido[5,4-d][1]benzazepin-2-yl)amino]-N-[2-(2-fluorophenyl)ethyl]benzamide I-885 4-[(9-chloro-6-oxo-6,7-dihydro-5H-pyrimido[5,4-d][1]benzazepin-2-yl)amino]-N-(4-isopropylphenyl)benzamide I-886 4-[(9-chloro-6-oxo-6,7-dihydro-5H-pyrimido[5,4-d][1]benzazepin-2-yl)amino]-N-cyclooctylbenzamide I-887 4-[(9-chloro-6-oxo-6,7-dihydro-5H-pyrimido[5,4-d][1]benzazepin-2-yl)amino]-N-[2-(1,3-dioxolan-2-yl)ethyl]-N-methylbenzamide I-888 9-chloro-2-({4-[(2-methyl-2,3-dihydro-1H-indol-1-yl)carbonyl]phenyl}amino)-5,7-dihydro-6H-pyrimido[5,4-d][1]benzazepin-6-one I-889 4-[(9-chloro-6-oxo-6,7-dihydro-5H-pyrimido[5,4-d][1]benzazepin-2-yl)amino]-N-methyl-N-[1-(2-thienyl)ethyl]benzamide I-890 4-[(9-chloro-6-oxo-6,7-dihydro-5H-pyrimido[5,4-d][1]benzazepin-2-yl)amino]-N-(4-methylpyridin-2-yl)benzamide I-891 4-[(9-chloro-6-oxo-6,7-dihydro-5H-pyrimido[5,4-d][1]benzazepin-2-yl)amino]-N-methyl-N-(4-methylbenzyl)benzamide I-892 2-{[4-(6-azabicyclo[3.2.1]oct-6-ylcarbonyl)phenyl]amino}-9-chloro-5,7-dihydro-6H-pyrimido[5,4-d][1]benzazepin-6-one I-893 7-methyl-2-{[4-(morpholin-4-ylsulfonyl)phenyl]amino}-5,7-dihydro-6H-pyrimido[5,4-d][1]benzazepin-6-one I-894 N-cyclopentyl-4-[(7-methyl-6-oxo-6,7-dihydro-5H-pyrimido[5,4-d][1]benzazepin-2-yl)amino]benzenesulfonamide I-895 4-[(7-methyl-6-oxo-6,7-dihydro-5H-pyrimido[5,4-d][1]benzazepin-2-yl)amino]-N-[(2R)-2-phenylpropyl]benzamide I-896 2-[(4-{[(2R,6S)-2,6-dimethylmorpholin-4-yl]carbonyl}phenyl)amino]-7-methyl-5,7-dihydro-6H-pyrimido[5,4-d][1]benzazepin-6-one I-897 2-({4-[(4-ethylpiperazin-1-yl)carbonyl]phenyl}amino)-7-methyl-5,7-dihydro-6H-pyrimido[5,4-d][1]benzazepin-6-one I-898 N-{2-[(6-oxo-6,7-dihydro-5H-pyrimido[5,4-d][1]benzazepin-2-yl)amino]ethyl}acetamide I-899 2-{[2-(4-ethylphenyl)ethyl]amino}-5,7-dihydro-6H-pyrimido[5,4-d][1]benzazepin-6-one I-900 2-({[(2S)-1-ethylpyrrolidin-2-yl]methyl}amino)-5,7-dihydro-6H-pyrimido[5,4-d][1]benzazepin-6-one I-901 2-{[2-(3-chlorophenyl)ethyl]amino}-5,7-dihydro-6H-pyrimido[5,4-d][1]benzazepin-6-one I-902 2-[(2-pyridin-2-ylethyl)amino]-5,7-dihydro-6H-pyrimido[5,4-d][1]benzazepin-6-one I-903 2-{[2-(4-chlorophenyl)ethyl]amino}-5,7-dihydro-6H-pyrimido[5,4-d][1]benzazepin-6-one I-904 2-{[2-(3-methoxyphenyl)ethyl]amino}-5,7-dihydro-6H-pyrimido[5,4-d][1]benzazepin-6-one I-905 2-{[2-(4-methoxyphenoxy)ethyl]amino}-5,7-dihydro-6H-pyrimido[5,4-d][1]benzazepin-6-one I-906 2-(2,1,3-benzoxadiazol-4-ylamino)-5,7-dihydro-6H-pyrimido[5,4-d][1]benzazepin-6-one I-907 2-{[2-(4-phenoxyphenyl)ethyl]amino}-5,7-dihydro-6H-pyrimido[5,4-d][1]benzazepin-6-one I-908 2-{[2-(2-phenoxyphenyl)ethyl]amino}-5,7-dihydro-6H-pyrimido[5,4-d][1]benzazepin-6-one I-909 2-{[2-(3-ethoxyphenyl)ethyl]amino}-5,7-dihydro-6H-pyrimido[5,4-d][1]benzazepin-6-one I-910 2-(quinolin-6-ylamino)-5,7-dihydro-6H-pyrimido[5,4-d][1]benzazepin-6-one I-911 2-[(3-isobutoxypropyl)amino]-5,7-dihydro-6H-pyrimido[5,4-d][1]benzazepin-6-one I-912 2-[(2-cyclohex-1-en-1-ylethyl)amino]-5,7-dihydro-6H-pyrimido[5,4-d][1]benzazepin-6-one I-913 2-{[2-(3,5-dimethoxyphenyl)ethyl]amino}-5,7-dihydro-6H-pyrimido[5,4-d][1]benzazepin-6-one I-914 2-{[2-(3-ethoxy-4-methoxyphenyl)ethyl]amino}-5,7-dihydro-6H-pyrimido[5,4-d][1]benzazepin-6-one I-915 2-[(3-ethoxypropyl)amino]-5,7-dihydro-6H-pyrimido[5,4-d][1]benzazepin-6-one I-916 2-{[2-(2,6-dichlorophenyl)ethyl]amino}-5,7-dihydro-6H-pyrimido[5,4-d][1]benzazepin-6-one I-917 2-{[2-(3,5-dimethyl-1H-pyrazol-1-yl)ethyl]amino}-5,7-dihydro-6H-pyrimido[5,4-d][1]benzazepin-6-one I-918 2-{[2-(3-bromo-4-methoxyphenyl)ethyl]amino}-5,7-dihydro-6H-pyrimido[5,4-d][1]benzazepin-6-one I-919 2-{[2-(1-methylpyrrolidin-2-yl)ethyl]amino}-5,7-dihydro-6H-pyrimido[5,4-d][1]benzazepin-6-one I-920 2-{[2-(2-chlorophenyl)ethyl]amino}-5,7-dihydro-6H-pyrimido[5,4-d][1]benzazepin-6-one I-921 2-{[3-(cyclohexylamino)propyl]amino}-5,7-dihydro-6H-pyrimido[5,4-d][1]benzazepin-6-one I-922 2-[(3-phenylpropyl)amino]-5,7-dihydro-6H-pyrimido[5,4-d][1]benzazepin-6-one I-923 2-({2-pyrrolidin-1-yl-2-[4-(trifluoromethyl)phenyl]ethyl}amino)-5,7-dihydro-6H-pyrimido[5,4-d][1]benzazepin-6-one I-924 2-{[2-(4-bromophenyl)ethyl]amino}-5,7-dihydro-6H-pyrimido[5,4-d][1]benzazepin-6-one I-925 2-{[1-(hydroxymethyl)-2-methylpropyl]amino}-5,7-dihydro-6H-pyrimido[5,4-d][1]benzazepin-6-one I-926 2-{[2-(4-ethoxyphenyl)ethyl]amino}-5,7-dihydro-6H-pyrimido[5,4-d][1]benzazepin-6-one I-927 2-{[2-(pyridin-3-yloxy)propyl]amino}-5,7-dihydro-6H-pyrimido[5,4-d][1]benzazepin-6-one I-928 2-({2-(dimethylamino)-2-[4-(trifluoromethyl)phenyl]ethyl}amino)-5,7-dihydro-6H-pyrimido[5,4-d][1]benzazepin-6-one I-929 2-({[5-methyl-2-(trifluoromethyl)-3-furyl]methyl}amino)-5,7-dihydro-6H-pyrimido[5,4-d][1]benzazepin-6-one I-930 2-[(4-pyrrolidin-1-ylbutyl)amino]-5,7-dihydro-6H-pyrimido[5,4-d][1]benzazepin-6-one I-931 2-({2-[3-(dimethylamino)phenoxy]propyl}amino)-5,7-dihydro-6H-pyrimido[5,4-d][1]benzazepin-6-one I-932 2-{[4-(diethylamino)phenyl]amino}-5,7-dihydro-6H-pyrimido[5,4-d][1]benzazepin-6-one I-933 2-{[2,4-dimethoxy-5-(trifluoromethyl)phenyl]amino}-5,7-dihydro-6H-pyrimido[5,4-d][1]benzazepin-6-one I-934 2-{[2-(2-fluorophenoxy)pyridin-3-yl]amino}-5,7-dihydro-6H-pyrimido[5,4-d][1]benzazepin-6-one I-935 2-[(tetrahydro-2H-pyran-4-ylmethyl)amino]-5,7-dihydro-6H-pyrimido[5,4-d][1]benzazepin-6-one I-936 2-[(4-piperidin-1-ylphenyl)amino]-5,7-dihydro-6H-pyrimido[5,4-d][1]benzazepin-6-one I-937 2-[(2-pyrrolidin-1-ylethyl)amino]-5,7-dihydro-6H-pyrimido[5,4-d][1]benzazepin-6-one I-938 N,N-dimethyl-4-[(6-oxo-6,7-dihydro-5H-pyrimido[5,4-d][1]benzazepin-2-yl)amino]benzamide I-939 2-[(2-anilinophenyl)amino]-5,7-dihydro-6H-pyrimido[5,4-d][1]benzazepin-6-one I-940 2-({2-[ethyl(3-methylphenyl)amino]ethyl}amino)-5,7-dihydro-6H-pyrimido[5,4-d][1]benzazepin-6-one I-941 2-{[4-(1,3-oxazol-5-yl)phenyl]amino}-5,7-dihydro-6H-pyrimido[5,4-d][1]benzazepin-6-one I-942 2-[(pyridin-4-ylmethyl)amino]-5,7-dihydro-6H-pyrimido[5,4-d][1]benzazepin-6-one I-943 2-{[2-(2,3-dimethylphenoxy)pyridin-3-yl]amino}-5,7-dihydro-6H-pyrimido[5,4-d][1]benzazepin-6-one I-944 2-{[4-(4-methylpiperazin-1-yl)phenyl]amino}-5,7-dihydro-6H-pyrimido[5,4-d][1]benzazepin-6-one I-945 2-{[3-methoxy-5-(trifluoromethyl)phenyl]amino}-5,7-dihydro-6H-pyrimido[5,4-d][1]benzazepin-6-one I-946 (2S)-1-({4-[(7-methyl-6-oxo-6,7-dihydro-5H-pyrimido[5,4-d][1]benzazepin-2-yl)amino]phenyl}sulfonyl)pyrrolidine-2-carboxamide I-947 N-[3-(dimethylamino)propyl]-N-methyl-4-[(7-methyl-6-oxo-6,7-dihydro-5H-pyrimido[5,4-d][1]benzazepin-2-yl)amino]benzenesulfonamide I-948 4-[(7-methyl-6-oxo-6,7-dihydro-5H-pyrimido[5,4-d][1]benzazepin-2-yl)amino]-N-prop-2-yn-1-ylbenzenesulfonamide I-949 4-[(7-methyl-6-oxo-6,7-dihydro-5H-pyrimido[5,4-d][1]benzazepin-2-yl)amino]-N-(3-morpholin-4-ylpropyl)benzenesulfonamide I-950 N-(2-cyanoethyl)-N-cyclopentyl-4-[(7-methyl-6-oxo-6,7-dihydro-5H-pyrimido[5,4-d][1]benzazepin-2-yl)amino]benzenesulfonamide I-951 4-[(7-methyl-6-oxo-6,7-dihydro-5H-pyrimido[5,4-d][1]benzazepin-2-yl)amino]-N-(2-phenylethyl)benzenesulfonamide I-952 N-(4-fluorobenzyl)-4-[(7-methyl-6-oxo-6,7-dihydro-5H-pyrimido[5,4-d][1]benzazepin-2-yl)amino]benzenesulfonamide I-953 2-({4-[(2-ethylpyrrolidin-1-yl)sulfonyl]phenyl}amino)-7-methyl-5,7-dihydro-6H-pyrimido[5,4-d][1]benzazepin-6-one I-954 2-[(4-{[(3R)-3-(dimethylamino)pyrrolidin-1-yl]sulfonyl}phenyl)amino]-7-methyl-5,7-dihydro-6H-pyrimido[5,4-d][1]benzazepin-6-one I-955 N-[2-(3,4-dimethylphenyl)ethyl]-4-[(7-methyl-6-oxo-6,7-dihydro-5H-pyrimido[5,4-d][1]benzazepin-2-yl)amino]benzenesulfonamide I-956 7-methyl-2-({4-[(3-methylpiperidin-1-yl)sulfonyl]phenyl}amino)-5,7-dihydro-6H-pyrimido[5,4-d][1]benzazepin-6-one I-957 N-(3-methylbutyl)-4-[(7-methyl-6-oxo-6,7-dihydro-5H-pyrimido[5,4-d][1]benzazepin-2-yl)amino]benzenesulfonamide I-958 N-(3-isopropoxypropyl)-4-[(7-methyl-6-oxo-6,7-dihydro-5H-pyrimido[5,4-d][1]benzazepin-2-yl)amino]benzenesulfonamide I-959 N-methyl-4-[(7-methyl-6-oxo-6,7-dihydro-5H-pyrimido[5,4-d][1]benzazepin-2-yl)amino]-N-(1-methylpyrrolidin-3-yl)benzenesulfonamide I-960 N-[1-(methoxymethyl)propyl]-4-[(7-methyl-6-oxo-6,7-dihydro-5H-pyrimido[5,4-d][1]benzazepin-2-yl)amino]benzenesulfonamide I-961 4-[(7-methyl-6-oxo-6,7-dihydro-5H-pyrimido[5,4-d][1]benzazepin-2-yl)amino]-N-(pyridin-4-ylmethyl)benzenesulfonamide I-962 N-[2-(diethylamino)ethyl]-4-[(7-methyl-6-oxo-6,7-dihydro-5H-pyrimido[5,4-d][1]benzazepin-2-yl)amino]benzenesulfonamide I-963 N-methyl-4-[(7-methyl-6-oxo-6,7-dihydro-5H-pyrimido[5,4-d][1]benzazepin-2-yl)amino]-N-prop-2-yn-1-ylbenzenesulfonamide I-964 N-cyclohexyl-N-methyl-4-[(7-methyl-6-oxo-6,7-dihydro-5H-pyrimido[5,4-d][1]benzazepin-2-yl)amino]benzenesulfonamide I-965 4-[(7-methyl-6-oxo-6,7-dihydro-5H-pyrimido[5,4-d][1]benzazepin-2-yl)amino]-N-phenylbenzenesulfonamide I-966 7-methyl-2-({4-[(2-methylpyrrolidin-1-yl)sulfonyl]phenyl}amino)-5,7-dihydro-6H-pyrimido[5,4-d][1]benzazepin-6-one I-967 N-[2-(dimethylamino)ethyl]-N-methyl-4-[(7-methyl-6-oxo-6,7-dihydro-5H-pyrimido[5,4-d][1]benzazepin-2-yl)amino]benzenesulfonamide I-968 4-[(7-methyl-6-oxo-6,7-dihydro-5H-pyrimido[5,4-d][1]benzazepin-2-yl)amino]-N-(tetrahydrofuran-2-ylmethyl)benzenesulfonamide I-969 N-methyl-4-[(7-methyl-6-oxo-6,7-dihydro-5H-pyrimido[5,4-d][1]benzazepin-2-yl)amino]-N-(1-methylpiperidin-4-yl)benzenesulfonamide I-970 N-cyclohexyl-4-[(7-methyl-6-oxo-6,7-dihydro-5H-pyrimido[5,4-d][1]benzazepin-2-yl)amino]benzenesulfonamide I-971 N-benzyl-4-[(7-methyl-6-oxo-6,7-dihydro-5H-pyrimido[5,4-d][1]benzazepin-2-yl)amino]benzenesulfonamide I-972 4-[(9-chloro-6-oxo-6,7-dihydro-5H-pyrimido[5,4-d][1]benzazepin-2-yl)amino]-N-[(1-ethylpyrrolidin-3-yl)methyl]benzenesulfonamide I-973 N-[2-(diisopropylamino)ethyl]-4-[(7-methyl-6-oxo-6,7-dihydro-5H-pyrimido[5,4-d][1]benzazepin-2-yl)amino]benzenesulfonamide I-974 9-chloro-2-({4-[(2-methylpyrrolidin-1-yl)sulfonyl]phenyl}amino)-5,7-dihydro-6H-pyrimido[5,4-d][1]benzazepin-6-one I-975 N,N-diethyl-4-[(7-methyl-6-oxo-6,7-dihydro-5H-pyrimido[5,4-d][1]benzazepin-2-yl)amino]benzenesulfonamide I-976 4-[(9-chloro-6-oxo-6,7-dihydro-5H-pyrimido[5,4-d][1]benzazepin-2-yl)amino]-N-(2-phenylethyl)benzenesulfonamide I-977 N-methyl-4-[(7-methyl-6-oxo-6,7-dihydro-5H-pyrimido[5,4-d][1]benzazepin-2-yl)amino]-N-(2-pyridin-2-ylethyl)benzenesulfonamide I-978 9-chloro-2-[(4-{[(2S)-2-(methoxymethyl)pyrrolidin-1-yl]sulfonyl}phenyl)amino]-5,7-dihydro-6H-pyrimido[5,4-d][1]benzazepin-6-one I-979 N-(2-methoxy-1-methylethyl)-4-[(7-methyl-6-oxo-6,7-dihydro-5H-pyrimido[5,4-d][1]benzazepin-2-yl)amino]benzenesulfonamide I-980 4-({4-[(9-chloro-6-oxo-6,7-dihydro-5H-pyrimido[5,4-d][1]benzazepin-2-yl)amino]phenyl}sulfonyl)piperazine-1-carbaldehyde I-981 N-{2-[({4-[(7-methyl-6-oxo-6,7-dihydro-5H-pyrimido[5,4-d][1]benzazepin-2-yl)amino]phenyl}sulfonyl)amino]ethyl}acetamide I-982 4-[(9-chloro-6-oxo-6,7-dihydro-5H-pyrimido[5,4-d][1]benzazepin-2-yl)amino]-N-(2-furylmethyl)-N-methylbenzenesulfonamide I-983 N-ethyl-4-[(7-methyl-6-oxo-6,7-dihydro-5H-pyrimido[5,4-d][1]benzazepin-2-yl)amino]-N-(2-pyridin-2-ylethyl)benzenesulfonamide I-984 2-({4-[(4-butylpiperazin-1-yl)sulfonyl]phenyl}amino)-9-chloro-5,7-dihydro-6H-pyrimido[5,4-d][1]benzazepin-6-one I-985 N-(1-ethynylcyclohexyl)-4-[(7-methyl-6-oxo-6,7-dihydro-5H-pyrimido[5,4-d][1]benzazepin-2-yl)amino]benzenesulfonamide I-986 4-[(9-chloro-6-oxo-6,7-dihydro-5H-pyrimido[5,4-d][1]benzazepin-2-yl)amino]-N-(3-methylbutyl)benzenesulfonamide I-987 4-({4-[(7-methyl-6-oxo-6,7-dihydro-5H-pyrimido[5,4-d][1]benzazepin-2-yl)amino]phenyl}sulfonyl)piperazine-1-carbaldehyde I-988 4-[(9-chloro-6-oxo-6,7-dihydro-5H-pyrimido[5,4-d][1]benzazepin-2-yl)amino]-N-[3-(1H-imidazol-1-yl)propyl]benzenesulfonamide I-989 4-({4-[(7-methyl-6-oxo-6,7-dihydro-5H-pyrimido[5,4-d][1]benzazepin-2-yl)amino]phenyl}sulfonyl)-1,4-diazepane-1-carbaldehyde I-990 9-chloro-2-({4-[(5-fluoro-2,3-dihydro-1H-indol-1-yl)sulfonyl]phenyl}amino)-5,7-dihydro-6H-pyrimido[5,4-d][1]benzazepin-6-one I-991 2-{[4-(2,3-dihydro-1H-indol-1-ylsulfonyl)phenyl]amino}-7-methyl-5,7-dihydro-6H-pyrimido[5,4-d][1]benzazepin-6-one I-992 9-chloro-2-{[4-(piperidin-1-ylsulfonyl)phenyl}amino]-5,7-dihydro-6H-pyrimido[5,4-d][1]benzazepin-6-one I-993 7-methyl-2-({4-[(3-oxopiperazin-1-yl)sulfonyl]phenyl}amino)-5,7-dihydro-6H-pyrimido[5,4-d][1]benzazepin-6-one I-994 4-[(9-chloro-6-oxo-6,7-dihydro-5H-pyrimido[5,4-d][1]benzazepin-2-yl)amino]-N-methyl-N-(1-methylpiperidin-4-yl)benzenesulfonamide I-995 N-benzyl-4-[(9-chloro-6-oxo-6,7-dihydro-5H-pyrimido[5,4-d][1]benzazepin-2-yl)amino]benzenesulfonamide I-996 2-[(4-{[(2S)-2-(methoxymethyl)pyrrolidin-1-yl]sulfonyl}phenyl)amino]-7-methyl-5,7-dihydro-6H-pyrimido[5,4-d][1]benzazepin-6-one I-997 4-[(9-chloro-6-oxo-6,7-dihydro-5H-pyrimido[5,4-d][1]benzazepin-2-yl)amino]-N-[1-(methoxymethyl)propyl]benzenesulfonamide I-998 7-methyl-2-({4-[(4-methylpiperazin-1-yl)sulfonyl]phenyl}amino)-5,7-dihydro-6H-pyrimido[5,4-d][1]benzazepin-6-one I-999 4-[(9-chloro-6-oxo-6,7-dihydro-5H-pyrimido[5,4-d][1]benzazepin-2-yl)amino]-N-phenylbenzenesulfonamide I-1000 N-[2-(3-fluorophenyl)ethyl]-4-[(7-methyl-6-oxo-6,7-dihydro-5H-pyrimido[5,4-d][1]benzazepin-2-yl)amino]benzenesulfonamide I-1001 4-[(9-chloro-6-oxo-6,7-dihydro-5H-pyrimido[5,4-d][1]benzazepin-2-yl)amino]-N-propylbenzenesulfonamide I-1002 N-[(1-ethylpyrrolidin-3-yl)methyl]-4-[(7-methyl-6-oxo-6,7-dihydro-5H-pyrimido[5,4-d][1]benzazepin-2-yl)amino]benzenesulfonamide I-1003 4-[(9-chloro-6-oxo-6,7-dihydro-5H-pyrimido[5,4-d][1]benzazepin-2-yl)amino]-N,N-diethylbenzenesulfonamide I-1004 4-[(7-methyl-6-oxo-6,7-dihydro-5H-pyrimido[5,4-d][1]benzazepin-2-yl)amino]-N-[(2-methyl-1,3-thiazol-4-yl)methyl]benzenesulfonamide I-1005 N-{2-[({4-[(9-chloro-6-oxo-6,7-dihydro-5H-pyrimido[5,4-d][1]benzazepin-2-yl)amino]phenyl}sulfonyl)amino]ethyl}acetamide I-1006 2-({4-[(5-ethyl-2-methylpiperidin-1-yl)sulfonyl]phenyl}amino)-7-methyl-5,7-dihydro-6H-pyrimido[5,4-d][1]benzazepin-6-one I-1007 4-[(9-chloro-6-oxo-6,7-dihydro-5H-pyrimido[5,4-d][1]benzazepin-2-yl)amino]-N-[4-(dimethylamino)phenyl]benzenesulfonamide I-1008 4-[(7-methyl-6-oxo-6,7-dihydro-5H-pyrimido[5,4-d][1]benzazepin-2-yl)amino]-N-[(1S)-1-(4-methylphenyl)ethyl]benzenesulfonamide I-1009 9-chloro-2-({4-[(4-ethylpiperazin-1-yl)sulfonyl]phenyl}amino)-5,7-dihydro-6H-pyrimido[5,4-d][1]benzazepin-6-one I-1010 N-[1-(4-fluorophenyl)ethyl]-4-[(7-methyl-6-oxo-6,7-dihydro-5H-pyrimido[5,4-d][1]benzazepin-2-yl)amino]benzenesulfonamide I-1011 9-chloro-2-{[4-(pyrrolidin-1-ylsulfonyl)phenyl]amino}-5,7-dihydro-6H-pyrimido[5,4-d][1]benzazepin-6-one I-1012 4-[(7-methyl-6-oxo-6,7-dihydro-5H-pyrimido[5,4-d][1]benzazepin-2-yl)amino]-N-(2-phenoxyethyl)benzenesulfonamide I-1013 4-[(9-chloro-6-oxo-6,7-dihydro-5H-pyrimido[5,4-d][1]benzazepin-2-yl)amino]-N-methyl-N-prop-2-yn-1-ylbenzenesulfonamide I-1014 4-[(7-methyl-6-oxo-6,7-dihydro-5H-pyrimido[5,4-d][1]benzazepin-2-yl)amino]-N-(3-pyrrolidin-1-ylpropyl)benzenesulfonamide I-1015 4-[(9-chloro-6-oxo-6,7-dihydro-5H-pyrimido[5,4-d][1]benzazepin-2-yl)amino]-N-ethyl-N-(2-pyridin-2-ylethyl)benzenesulfonamide I-1016 N-(cyclopropylmethyl)-4-[(7-methyl-6-oxo-6,7-dihydro-5H-pyrimido[5,4-d][1]benzazepin-2-yl)amino]-N-propylbenzenesulfonamide I-1017 4-[(9-chloro-6-oxo-6,7-dihydro-5H-pyrimido[5,4-d][1]benzazepin-2-yl)amino]-N-(cyclopropylmethyl)-N-propylbenzenesulfonamide I-1018 4-[(7-methyl-6-oxo-6,7-dihydro-5H-pyrimido[5,4-d][1]benzazepin-2-yl)amino]-N-(pyridin-2-ylmethyl)benzenesulfonamide I-1019 4-[(9-chloro-6-oxo-6,7-dihydro-5H-pyrimido[5,4-d][1]benzazepin-2-yl)amino]-N-[2-(dimethylamino)-1-methylethyl]benzenesulfonamide I-1020 7-methyl-2-({4-[(4-methylpiperidin-1-yl)sulfonyl]phenyl}amino)-5,7-dihydro-6H-pyrimido[5,4-d][1]benzazepin-6-one I-1021 4-[(9-chloro-6-oxo-6,7-dihydro-5H-pyrimido[5,4-d][1]benzazepin-2-yl)amino]-N-1H-indol-5-ylbenzenesulfonamide I-1022 4-[(7-methyl-6-oxo-6,7-dihydro-5H-pyrimido[5,4-d][1]benzazepin-2-yl)amino]-N-(2-piperidin-1-ylethyl)benzenesulfonamide I-1023 4-[(9-chloro-6-oxo-6,7-dihydro-5H-pyrimido[5,4-d][1]benzazepin-2-yl)amino]-N-cyclohexylbenzenesulfonamide I-1024 2-[(4-{[3-(diethylamino)pyrrolidin-1-yl]sulfonyl}phenyl)amino]-7-methyl-5,7-dihydro-6H-pyrimido[5,4-d][1]benzazepin-6-one I-1025 9-chloro-2-[(4-{[(3R)-3-(dimethylamino)pyrrolidin-1-yl]sulfonyl}phenyl)amino]-5,7-dihydro-6H-pyrimido[5,4-d][1]benzazepin-6-one I-1026 N-(2-methoxyethyl)-4-[(7-methyl-6-oxo-6,7-dihydro-5H-pyrimido[5,4-d][1]benzazepin-2-yl)amino]benzenesulfonamide I-1027 4-[(9-chloro-6-oxo-6,7-dihydro-5H-pyrimido[5,4-d][1]benzazepin-2-yl)amino]-N-[(1S)-1-(4-methylphenyl)ethyl]benzenesulfonamide I-1028 2-{[4-(3,4-dihydroisoquinolin-2(1H)-ylsulfonyl)phenyl]amino}-7-methyl-5,7-dihydro-6H-pyrimido[5,4-d][1]benzazepin-6-one I-1029 4-[(9-chloro-6-oxo-6,7-dihydro-5H-pyrimido[5,4-d][1]benzazepin-2-yl)amino]-N-(4-fluorobenzyl)benzenesulfonamide I-1030 N-(cyclopropylmethyl)-4-[(7-methyl-6-oxo-6,7-dihydro-5H-pyrimido[5,4-d][1]benzazepin-2-yl)amino]benzenesulfonamide I-1031 9-chloro-2-{[4-(1,3-dihydro-2H-isoindol-2-ylsulfonyl)phenyl]amino}-5,7-dihydro-6H-pyrimido[5,4-d][1]benzazepin-6-one I-1032 N-(2-cyanoethyl)-N-cyclopropyl-4-[(7-methyl-6-oxo-6,7-dihydro-5H-pyrimido[5,4-d][1]benzazepin-2-yl)amino]benzenesulfonamide I-1033 4-[(9-chloro-6-oxo-6,7-dihydro-5H-pyrimido[5,4-d][1]benzazepin-2-yl)amino]-N-prop-2-yn-1-ylbenzenesulfonamide I-1034 4-[(7-methyl-6-oxo-6,7-dihydro-5H-pyrimido[5,4-d][1]benzazepin-2-yl)amino]-N-[3-(2-oxopyrrolidin-1-yl)propyl]benzenesulfonamide I-1035 4-[(9-chloro-6-oxo-6,7-dihydro-5H-pyrimido[5,4-d][1]benzazepin-2-yl)amino]-N-(2-methoxy-1-methylethyl)benzenesulfonamide I-1036 2-({4-[(4-butylpiperazin-1-yl)sulfonyl]phenyl}amino)-7-methyl-5,7-dihydro-6H-pyrimido[5,4-d][1]benzazepin-6-one I-1037 N-[1-({4-[(9-chloro-6-oxo-6,7-dihydro-5H-pyrimido[5,4-d][1]benzazepin-2-yl)amino]phenyl}sulfonyl)pyrrolidin-3-yl]-N-methylacetamide I-1038 2-({4-[(4-ethylpiperazin-1-yl)sulfonyl]phenyl}amino)-7-methyl-5,7-dihydro-6H-pyrimido[5,4-d][1]benzazepin-6-one I-1039 4-[(9-chloro-6-oxo-6,7-dihydro-5H-pyrimido[5,4-d][1]benzazepin-2-yl)amino]-N-[2-(diisopropylamino)ethyl]benzenesulfonamide I-1040 N-[3-(1H-imidazol-1-yl)propyl]-4-[(7-methyl-6-oxo-6,7-dihydro-5H-pyrimido[5,4-d][1]benzazepin-2-yl)amino]benzenesulfonamide I-1041 4-[(9-chloro-6-oxo-6,7-dihydro-5H-pyrimido[5,4-d][1]benzazepin-2-yl)amino]-N-[(1R)-2,3-dihydro-1H-inden-1-yl]benzenesulfonamide I-1042 N-(cyclohexylmethyl)-4-[(7-methyl-6-oxo-6,7-dihydro-5H-pyrimido[5,4-d][1]benzazepin-2-yl)amino]benzenesulfonamide I-1043 9-chloro-2-({4-[(4-methylpiperazin-1-yl)sulfonyl]phenyl}amino)-5,7-dihydro-6H-pyrimido[5,4-d][1]benzazepin-6-one I-1044 N-[(5-methyl-2-furyl)methyl]-4-[(7-methyl-6-oxo-6,7-dihydro-5H-pyrimido[5,4-d][1]benzazepin-2-yl)amino]benzenesulfonamide I-1045 4-[(9-chloro-6-oxo-6,7-dihydro-5H-pyrimido[5,4-d][1]benzazepin-2-yl)amino]-N-(cyclopropylmethyl)benzenesulfonamide I-1046 2-[(4-{[(2R,6S)-2,6-dimethylmorpholin-4-yl]sulfonyl}phenyl)amino]-7-methyl-5,7-dihydro-6H-pyrimido[5,4-d][1]benzazepin-6-one I-1047 9-chloro-2-({4-[(3-methylpiperidin-1-yl)sulfonyl]phenyl}amino)-5,7-dihydro-6H-pyrimido[5,4-d][1]benzazepin-6-one I-1048 N-[2-(dimethylamino)-1-methylethyl]-4-[(7-methyl-6-oxo-6,7-dihydro-5H-pyrimido[5,4-d][1]benzazepin-2-yl)amino]benzenesulfonamide I-1049 4-[(9-chloro-6-oxo-6,7-dihydro-5H-pyrimido[5,4-d][1]benzazepin-2-yl)amino]-N-cyclopentylbenzenesulfonamide I-1050 N-isopropyl-4-[(7-methyl-6-oxo-6,7-dihydro-5H-pyrimido[5,4-d][1]benzazepin-2-yl)amino]benzenesulfonamide I-1051 4-[(9-chloro-6-oxo-6,7-dihydro-5H-pyrimido[5,4-d][1]benzazepin-2-yl)amino]-N-[2-(diethylamino)ethyl]-N-ethylbenzenesulfonamide I-1052 N-(2-isopropoxyethyl)-4-[(7-methyl-6-oxo-6,7-dihydro-5H-pyrimido[5,4-d][1]benzazepin-2-yl)amino]benzenesulfonamide I-1053 N-(4-chlorobenzyl)-4-[(9-chloro-6-oxo-6,7-dihydro-5H-pyrimido[5,4-d][1]benzazepin-2-yl)amino]benzenesulfonamide I-1054 2-{[4-(azetidin-1-ylsulfonyl)phenyl]amino}-7-methyl-5,7-dihydro-6H-pyrimido[5,4-d][1]benzazepin-6-one I-1055 4-[(9-chloro-6-oxo-6,7-dihydro-5H-pyrimido[5,4-d][1]benzazepin-2-yl)amino]-N-(3-pyrrolidin-1-ylpropyl)benzenesulfonamide I-1056 N-[(1R)-1-cyclohexylethyl]-4-[(7-methyl-6-oxo-6,7-dihydro-5H-pyrimido[5,4-d][1]benzazepin-2-yl)amino]benzenesulfonamide I-1057 4-[(9-chloro-6-oxo-6,7-dihydro-5H-pyrimido[5,4-d][1]benzazepin-2-yl)amino]-N-[3-(dimethylamino)-2,2-dimethylpropyl]benzenesulfonamide I-1058 N-(2-cyanoethyl)-N-methyl-4-[(7-methyl-6-oxo-6,7-dihydro-5H-pyrimido[5,4-d][1]benzazepin-2-yl)amino]benzenesulfonamide I-1059 4-[(9-chloro-6-oxo-6,7-dihydro-5H-pyrimido[5,4-d][1]benzazepin-2-yl)amino]-N-[(5-methyl-2-furyl)methyl]benzenesulfonamide I-1060 7-methyl-2-{[4-(pyrrolidin-1-ylsulfonyl)phenyl]amino}-5,7-dihydro-6H-pyrimido[5,4-d][1]benzazepin-6-one I-1061 4-[(9-chloro-6-oxo-6,7-dihydro-5H-pyrimido[5,4-d][1]benzazepin-2-yl)amino]-N-[2-(diethylamino)ethyl]benzenesulfonamide I-1062 2-{[4-(1,3-dihydro-2H-isoindol-2-ylsulfonyl)phenyl]amino}-7-methyl-5,7-dihydro-6H-pyrimido[5,4-d][1]benzazepin-6-one I-1063 4-[(9-chloro-6-oxo-6,7-dihydro-5H-pyrimido[5,4-d][1]benzazepin-2-yl)amino]-N-[2-(3,4-dimethylphenyl)ethyl]benzenesulfonamide I-1064 4-[(9-chloro-6-oxo-6,7-dihydro-5H-pyrimido[5,4-d][1]benzazepin-2-yl)amino]-N-(2-cyanoethyl)-N-cyclopentylbenzenesulfonamide I-1065 4-[(9-chloro-6-oxo-6,7-dihydro-5H-pyrimido[5,4-d][1]benzazepin-2-yl)amino]-N-(1-ethynylcyclohexyl)benzenesulfonamide I-1066 4-[(9-chloro-6-oxo-6,7-dihydro-5H-pyrimido[5,4-d][1]benzazepin-2-yl)amino]-N-ethyl-N-(pyridin-4-ylmethyl)benzenesulfonamide I-1067 4-[(9-chloro-6-oxo-6,7-dihydro-5H-pyrimido[5,4-d][1]benzazepin-2-yl)amino]-N-(2,3-dihydro-1-benzofuran-5-ylmethyl)benzenesulfonamide I-1068 4-[(9-chloro-6-oxo-6,7-dihydro-5H-pyrimido[5,4-d][1]benzazepin-2-yl)amino]-N-[(2-methyl-1,3-thiazol-4-yl)methyl]benzenesulfonamide I-1069 4-[(9-chloro-6-oxo-6,7-dihydro-5H-pyrimido[5,4-d][1]benzazepin-2-yl)amino]-N-[2-(3-fluorophenyl)ethyl]benzenesulfonamide I-1070 4-[(9-chloro-6-oxo-6,7-dihydro-5H-pyrimido[5,4-d][1]benzazepin-2-yl)amino]-N-(2-cyanoethyl)-N-methylbenzenesulfonamide I-1071 4-[(9-chloro-6-oxo-6,7-dihydro-5H-pyrimido[5,4-d][1]benzazepin-2-yl)amino]-N-(3-isopropoxypropyl)benzenesulfonamide I-1072 9-chloro-2-({4-[(4-methylpiperidin-1-yl)sulfonyl]phenyl}amino)-5,7-dihydro-6H-pyrimido[5,4-d][1]benzazepin-6-one I-1073 4-[(9-chloro-6-oxo-6,7-dihydro-5H-pyrimido[5,4-d][1]benzazepin-2-yl)amino]-N-(2-cyanoethyl)-N-cyclopropylbenzenesulfonamide I-1074 2-{[4-(azetidin-1-ylsulfonyl)phenyl]amino}-9-chloro-5,7-dihydro-6H-pyrimido[5,4-d][1]benzazepin-6-one I-1075 4-[(9-chloro-6-oxo-6,7-dihydro-5H-pyrimido[5,4-d][1]benzazepin-2-yl)amino]-N-[1-(4-fluorophenyl)ethyl]benzenesulfonamide I-1076 4-[(9-chloro-6-oxo-6,7-dihydro-5H-pyrimido[5,4-d][1]benzazepin-2-yl)amino]-N-isopropylbenzenesulfonamide I-1077 4-[(9-chloro-6-oxo-6,7-dihydro-5H-pyrimido[5,4-d][1]benzazepin-2-yl)amino]-N-methyl-N-(1-methylpyrrolidin-3-yl)benzenesulfonamide I-1078 4-[(9-chloro-6-oxo-6,7-dihydro-5H-pyrimido[5,4-d][1]benzazepin-2-yl)amino]-N-[2-(2-thienyl)ethyl]benzenesulfonamide I-1079 9-chloro-2-[(4-{[3-(diethylamino)pyrrolidin-1-yl]sulfonyl}phenyl)amino]-5,7-dihydro-6H-pyrimido[5,4-d][1]benzazepin-6-one I-1080 4-[(9-chloro-6-oxo-6,7-dihydro-5H-pyrimido[5,4-d][1]benzazepin-2-yl)amino]-N-(2-piperidin-1-ylethyl)benzenesulfonamide I-1081 9-chloro-2-({4-[(4,4-dimethyl-1,3-oxazolidin-3-yl)sulfonyl]phenyl}amino)-5,7-dihydro-6H-pyrimido[5,4-d][1]benzazepin-6-one I-1082 9-chloro-2-[(4-{[(2R,6S)-2,6-dimethylmorpholin-4-yl]sulfonyl}phenyl)amino]-5,7-dihydro-6H-pyrimido[5,4-d][1]benzazepin-6-one I-1083 4-[(9-chloro-6-oxo-6,7-dihydro-5H-pyrimido[5,4-d][1]benzazepin-2-yl)amino]-N-[2-(dimethylamino)ethyl]-N-methylbenzenesulfonamide I-1084 4-[(9-chloro-6-oxo-6,7-dihydro-5H-pyrimido[5,4-d][1]benzazepin-2-yl)amino]-N-(4-methoxybenzyl)benzenesulfonamide I-1085 4-[(9-chloro-6-oxo-6,7-dihydro-5H-pyrimido[5,4-d][1]benzazepin-2-yl)amino]-N-(2-methylbutyl)benzenesulfonamide I-1086 4-[(9-chloro-6-oxo-6,7-dihydro-5H-pyrimido[5,4-d][1]benzazepin-2-yl)amino]-N-(3-methoxybenzyl)benzenesulfonamide I-1087 4-[(9-chloro-6-oxo-6,7-dihydro-5H-pyrimido[5,4-d][1]benzazepin-2-yl)amino]-N-methyl-N-(2-pyridin-2-ylethyl)benzenesulfonamide I-1088 (2S)-1-({4-[(9-chloro-6-oxo-6,7-dihydro-5H-pyrimido[5,4-d][1]benzazepin-2-yl)amino]phenyl}sulfonyl)pyrrolidine-2-carboxamide I-1089 4-[(9-chloro-6-oxo-6,7-dihydro-5H-pyrimido[5,4-d][1]benzazepin-2-yl)amino]-N-(cyclohexylmethyl)benzenesulfonamide I-1090 4-[(9-chloro-6-oxo-6,7-dihydro-5H-pyrimido[5,4-d][1]benzazepin-2-yl)amino]-N-(2-methyl-1H-indol-5-yl)benzenesulfonamide I-1091 N-[(1R,2R,4S)-bicyclo[2.2.1]hept-2-yl]-4-[(9-chloro-6-oxo-6,7-dihydro-5H-pyrimido[5,4-d][1]benzazepin-2-yl)amino]benzenesulfonamide I-1092 4-[(9-chloro-6-oxo-6,7-dihydro-5H-pyrimido[5,4-d][1]benzazepin-2-yl)amino]-N-[2-(dimethylamino)ethyl]benzenesulfonamide I-1093 N-(cyclopropylmethyl)-4-[(7-methyl-6-oxo-6,7-dihydro-5H-pyrimido[5,4-d][1]benzazepin-2-yl)amino]-N-propylbenzamide I-1094 N-[2-(3,4-dimethylphenyl)ethyl]-4-[(7-methyl-6-oxo-6,7-dihydro-5H-pyrimido[5,4-d][1]benzazepin-2-yl)amino]benzamide I-1095 N-(3-ethyl-6-methylpyridin-2-yl)-4-[(6-oxo-6,7-dihydro-5H-pyrimido[5,4-d][1]benzazepin-2-yl)amino]benzamide I-1096 N-[1-(4-fluorophenyl)ethyl]-4-[(7-methyl-6-oxo-6,7-dihydro-5H-pyrimido[5,4-d][1]benzazepin-2-yl)amino]benzamide I-1097 N-[(1R)-1-cyclohexylethyl]-4-[(7-methyl-6-oxo-6,7-dihydro-5H-pyrimido[5,4-d][1]benzazepin-2-yl)amino]benzamide I-1098 4-[(7-methyl-6-oxo-6,7-dihydro-5H-pyrimido[5,4-d][1]benzazepin-2-yl)amino]-N-(3-morpholin-4-ylpropyl)benzamide I-1099 N-[(1R)-2,3-dihydro-1H-inden-1-yl]-4-[(6-oxo-6,7-dihydro-5H-pyrimido[5,4-d][1]benzazepin-2-yl)amino]benzamide I-1100 9-chloro-2-[(4-{[4-(2-chlorophenyl)piperazin-1-yl]carbonyl}phenyl)amino]-5,7-dihydro-6H-pyrimido[5,4-d][1]benzazepin-6-one I-1101 9-chloro-2-[(4-{[4-(3-hydroxyphenyl)piperazin-1-yl]carbonyl}phenyl)amino]-5,7-dihydro-6H-pyrimido[5,4-d][1]benzazepin-6-one I-1102 4-(4-{4-[(9-chloro-6-oxo-6,7-dihydro-5H-pyrimido[5,4-d][1]benzazepin-2-yl)amino]benzoyl}piperazin-1-yl)benzonitrile I-1103 9-chloro-2-[(4-{[(2S)-2-(pyrrolidin-1-ylmethyl)pyrrolidin-1-yl]carbonyl}phenyl)amino]-5,7-dihydro-6H-pyrimido[5,4-d][1]benzazepin-6-one I-1104 4-[(9-chloro-6-oxo-6,7-dihydro-5H-pyrimido[5,4-d][1]benzazepin-2-yl)amino]-N-{2-(dimethylamino)-2-[4-(trifluoromethyl)phenyl]ethyl}benzamide I-1105 4-[(9-chloro-6-oxo-6,7-dihydro-5H-pyrimido[5,4-d][1]benzazepin-2-yl)amino]-N-[4-(diethylamino)phenyl]benzamide I-1106 4-[(9-chloro-6-oxo-6,7-dihydro-5H-pyrimido[5,4-d][1]benzazepin-2-yl)amino]-N-(2-pyridin-3-yl-2-pyrrolidin-1-ylethyl)benzamide I-1107 4-[(9-chloro-6-oxo-6,7-dihydro-5H-pyrimido[5,4-d][1]benzazepin-2-yl)amino]-N-[(5-pyridin-2-yl-2-thienyl)methyl]benzamide I-1108 9-chloro-2-({4-[(4-pyrrolidin-1-ylpiperidin-1-yl)carbonyl]phenyl}amino)-5,7-dihydro-6H-pyrimido[5,4-d][1]benzazepin-6-one I-1109 4-[(9-chloro-6-oxo-6,7-dihydro-5H-pyrimido[5,4-d][1]benzazepin-2-yl)amino]-N-[2-(4-methoxyphenyl)-2-morpholin-4-ylethyl]benzamide I-1110 4-[(9-chloro-6-oxo-6,7-dihydro-5H-pyrimido[5,4-d][1]benzazepin-2-yl)amino]-N-methyl-N-[(3-phenyl-1,2,4-oxadiazol-5-yl)methyl]benzamide I-1111 9-chloro-2-[(4-{[4-(tetrahydrofuran-2-ylcarbonyl)piperazin-1-yl]carbonyl}phenyl)amino]-5,7-dihydro-6H-pyrimido[5,4-d][1]benzazepin-6-one I-1112 4-[(9-chloro-6-oxo-6,7-dihydro-5H-pyrimido[5,4-d][1]benzazepin-2-yl)amino]-N-[3-(2-methylpiperidin-1-yl)propyl]benzamide I-1113 4-[(9-chloro-6-oxo-6,7-dihydro-5H-pyrimido[5,4-d][1]benzazepin-2-yl)amino]-N-[2-(4-methylpiperazin-1-yl)-1-phenylethyl]benzamide I-1114 9-chloro-2-[(4-{[4-(3,5-dimethoxyphenyl)piperazin-1-yl]carbonyl}phenyl)amino]-5,7-dihydro-6H-pyrimido[5,4-d][1]benzazepin-6-one I-1115 4-[(9-chloro-6-oxo-6,7-dihydro-5H-pyrimido[5,4-d][1]benzazepin-2-yl)amino]-N-(2-cyanoethyl)-N-cyclopentylbenzamide I-1116 4-[(9-chloro-6-oxo-6,7-dihydro-5H-pyrimido[5,4-d][1]benzazepin-2-yl)amino]-N-(2-methyl-2-morpholin-4-ylpropyl)benzamide I-1117 4-[(9-chloro-6-oxo-6,7-dihydro-5H-pyrimido[5,4-d][1]benzazepin-2-yl)amino]-N-[2-(2-chlorophenyl)-2-(dimethylamino)ethyl]benzamide I-1118 9-chloro-2-[(4-{[4-(4-methoxyphenyl)piperazin-1-yl]carbonyl}phenyl)amino]-5,7-dihydro-6H-pyrimido[5,4-d][1]benzazepin-6-one I-1119 4-[(9-chloro-6-oxo-6,7-dihydro-5H-pyrimido[5,4-d][1]benzazepin-2-yl)amino]-N-[4-(4-methylpiperazin-1-yl)phenyl]benzamide I-1120 tert-butyl [3-({4-[(9-chloro-6-oxo-6,7-dihydro-5H-pyrimido[5,4-d][1]benzazepin-2-yl)amino]benzoyl}amino)-2,2-dimethylpropyl]carbamate I-1121 9-chloro-2-[(4-{[4-(2-ethoxyphenyl)piperazin-1-yl]carbonyl}phenyl)amino]-5,7-dihydro-6H-pyrimido[5,4-d][1]benzazepin-6-one I-1122 4-[(9-chloro-6-oxo-6,7-dihydro-5H-pyrimido[5,4-d][1]benzazepin-2-yl)amino]-N-{5-[(dimethylamino)sulfonyl]-2-methylphenyl}benzamide I-1123 N-[2-(4-benzylpiperazin-1-yl)ethyl]-4-[(9-chloro-6-oxo-6,7-dihydro-5H-pyrimido[5,4-d][1]benzazepin-2-yl)amino]benzamide I-1124 9-chloro-2-[(4-{[4-(3,4-dichlorophenyl)piperazin-1-yl]carbonyl}phenyl)amino]-5,7-dihydro-6H-pyrimido[5,4-d][1]benzazepin-6-one I-1125 4-[(9-chloro-6-oxo-6,7-dihydro-5H-pyrimido[5,4-d][1]benzazepin-2-yl)amino]-N-{2-[3-(dimethylamino)phenoxy]propyl}benzamide I-1126 4-[(9-chloro-6-oxo-6,7-dihydro-5H-pyrimido[5,4-d][1]benzazepin-2-yl)amino]-N-(4-piperidin-1-ylphenyl)benzamide I-1127 9-chloro-2-({4-[(4-pyrimidin-2-ylpiperazin-1-yl)carbonyl]phenyl}amino)-5,7-dihydro-6H-pyrimido[5,4-d][1]benzazepin-6-one I-1128 9-chloro-2-[(4-{[4-(2-methylphenyl)piperazin-1-yl]carbonyl}phenyl)amino]-5,7-dihydro-6H-pyrimido[5,4-d][1]benzazepin-6-one I-1129 9-chloro-2-[(4-{[4-(4-fluorophenyl)piperazin-1-yl]carbonyl}phenyl)amino]-5,7-dihydro-6H-pyrimido[5,4-d][1]benzazepin-6-one I-1130 9-chloro-2-[(4-{[4-(3-methoxyphenyl)piperazin-1-yl]carbonyl}phenyl)amino]-5,7-dihydro-6H-pyrimido[5,4-d][1]benzazepin-6-one I-1131 4-[(9-chloro-6-oxo-6,7-dihydro-5H-pyrimido[5,4-d][1]benzazepin-2-yl)amino]-N-(cyanomethyl)-N-methylbenzamide I-1132 N-(1-benzylpyrrolidin-3-yl)-4-[(9-chloro-6-oxo-6,7-dihydro-5H-pyrimido[5,4-d][1]benzazepin-2-yl)amino]benzamide I-1133 N-[(1-benzyl-1H-pyrazol-4-yl)methyl]-4-[(9-chloro-6-oxo-6,7-dihydro-5H-pyrimido[5,4-d][1]benzazepin-2-yl)amino]benzamide I-1134 4-[(9-chloro-6-oxo-6,7-dihydro-5H-pyrimido[5,4-d][1]benzazepin-2-yl)amino]-N-[2-(dimethylamino)-2-phenylethyl]benzamide I-1135 9-chloro-2-[(4-{[4-(5-chloro-2-methoxyphenyl)piperazin-1-yl]carbonyl}phenyl)amino]-5,7-dihydro-6H-pyrimido[5,4-d][1]benzazepin-6-one I-1136 1-{4-[(9-chloro-6-oxo-6,7-dihydro-5H-pyrimido[5,4-d][1]benzazepin-2-yl)amino]benzoyl}-N,N-diethylpiperidine-3-carboxamide I-1137 4-[(9-chloro-6-oxo-6,7-dihydro-5H-pyrimido[5,4-d][1]benzazepin-2-yl)amino]-N-[2-(dimethylamino)-2-pyridin-3-ylethyl]benzamide I-1138 9-chloro-2-{[4-({4-[(2R,6S)-2,6-dimethylmorpholin-4-yl]piperidin-1-yl}carbonyl)phenyl]amino}-5,7-dihydro-6H-pyrimido[5,4-d][1]benzazepin-6-one I-1139 9-chloro-2-{[4-({4-[2-(methylsulfonyl)ethyl]piperazin-1-yl}carbonyl)phenyl]amino}-5,7-dihydro-6H-pyrimido[5,4-d][1]benzazepin-6-one I-1140 ethyl (4-{4-[(9-chloro-6-oxo-6,7-dihydro-5H-pyrimido[5,4-d][1]benzazepin-2-yl)amino]benzoyl}piperazin-1-yl)acetate I-1141 4-[(9-chloro-6-oxo-6,7-dihydro-5H-pyrimido[5,4-d][1]benzazepin-2-yl)amino]-N-{2-pyrrolidin-1-yl-2-[4-(trifluoromethyl)phenyl]ethyl}benzamide I-1142 4-[(9-chloro-6-oxo-6,7-dihydro-5H-pyrimido[5,4-d][1]benzazepin-2-yl)amino]-N-(pyridin-4-ylmethyl)benzamide I-1143 4-[(9-chloro-6-oxo-6,7-dihydro-5H-pyrimido[5,4-d][1]benzazepin-2-yl)amino]-N-[2-(dimethylamino)-2-(4-methoxyphenyl)ethyl]benzamide I-1144 2-{[4-(1H-pyrazol-1-yl)phenyl]amino}-5,7-dihydro-6H-pyrimido[5,4-d][1]benzazepin-6-one I-1145 2-(1H-indazol-5-ylamino)-5,7-dihydro-6H-pyrimido[5,4-d][1]benzazepin-6-one I-1146 2-({4-[ethyl(2-hydroxyethyl)amino]-2-methylphenyl}amino)-5,7-dihydro-6H-pyrimido[5,4-d][1]benzazepin-6-one I-1147 2-{[2-(phenylsulfonyl)ethyl]amino}-5,7-dihydro-6H-pyrimido[5,4-d][1]benzazepin-6-one I-1148 2-{[(1-pyrimidin-2-ylpiperidin-3-yl)methyl]amino}-5,7-dihydro-6H-pyrimido[5,4-d][1]benzazepin-6-one I-1149 2-[(4'-fluorobiphenyl-3-yl)amino]-5,7-dihydro-6H-pyrimido[5,4-d][1]benzazepin-6-one I-1150 2-{[2-(benzylsulfanyl)ethyl]amino}-5,7-dihydro-6H-pyrimido[5,4-d][1]benzazepin-6-one I-1151 2-{[(2-phenyl-2H-1,2,3-triazol-4-yl)methyl]amino}-5,7-dihydro-6H-pyrimido[5,4-d][1]benzazepin-6-one I-1152 2-[(2-phenyl-2-pyrrolidin-1-ylethyl)amino]-5,7-dihydro-6H-pyrimido[5,4-d][1]benzazepin-6-one I-1153 2-{[2-(5-bromo-2-methoxyphenyl)ethyl]amino}-5,7-dihydro-6H-pyrimido[5,4-d][1]benzazepin-6-one I-1154 2-[(4-{[(2R,6S)-2,6-dimethylmorpholin-4-yl]sulfonyl}phenyl)amino]-5,7-dihydro-6H-pyrimido[5,4-d][1]benzazepin-6-one I-1155 2-({4-[(4-acetylpiperazin-1-yl)sulfonyl]phenyl}amino)-5,7-dihydro-6H-pyrimido[5,4-d][1]benzazepin-6-one I-1156 N-[(2-methyl-1,3-thiazol-4-yl)methyl]-4-[(6-oxo-6,7-dihydro-5H-pyrimido[5,4-d][1]benzazepin-2-yl)amino]benzenesulfonamide I-1157 4-[(6-oxo-6,7-dihydro-5H-pyrimido[5,4-d][1]benzazepin-2-yl)amino]-N-(pyridin-2-ylmethyl)benzenesulfonamide I-1158 N-[2-(dimethylamino)-1-methylethyl]-4-[(6-oxo-6,7-dihydro-5H-pyrimido[5,4-d][1]benzazepin-2-yl)amino]benzenesulfonamide I-1159 N-[(1S)-1-(4-methylphenyl)ethyl]-4-[(6-oxo-6,7-dihydro-5H-pyrimido[5,4-d][1]benzazepin-2-yl)amino]benzenesulfonamide I-1160 N,N-diethyl-4-[(6-oxo-6,7-dihydro-5H-pyrimido[5,4-d][1]benzazepin-2-yl)amino]benzenesulfonamide I-1161 N-{2-[({4-[(6-oxo-6,7-dihydro-5H-pyrimido[5,4-d][1]benzazepin-2-yl)amino]phenyl}sulfonyl)amino]ethyl}acetamide I-1162 N-(cyclopropylmethyl)-4-[(6-oxo-6,7-dihydro-5H-pyrimido[5,4-d][1]benzazepin-2-yl)amino]benzenesulfonamide I-1163 4-[(6-oxo-6,7-dihydro-5H-pyrimido[5,4-d][1]benzazepin-2-yl)amino]-N-(pyridin-4-ylmethyl)benzenesulfonamide I-1164 N-(3-morpholin-4-ylpropyl)-4-[(6-oxo-6,7-dihydro-5H-pyrimido[5,4-d][1]benzazepin-2-yl)amino]benzenesulfonamide I-1165 4-[(6-oxo-6,7-dihydro-5H-pyrimido[5,4-d][1]benzazepin-2-yl)amino]-N-propylbenzenesulfonamide I-1166 N-(3-isopropoxypropyl)-4-[(6-oxo-6,7-dihydro-5H-pyrimido[5,4-d][1]benzazepin-2-yl)amino]benzenesulfonamide I-1167 2-{[4-(pyrrolidin-1-ylsulfonyl)phenyl]amino}-5,7-dihydro-6H-pyrimido[5,4-d][1]benzazepin-6-one I-1168 4-[(6-oxo-6,7-dihydro-5H-pyrimido[5,4-d][1]benzazepin-2-yl)amino]-N-(3-pyrrolidin-1-ylpropyl)benzenesulfonamide I-1169 2-({4-[(4-butylpiperazin-1-yl)sulfonyl]phenyl}amino)-5,7-dihydro-6H-pyrimido[5,4-d][1]benzazepin-6-one I-1170 2-[(4-{[(2S)-2-(methoxymethyl)pyrrolidin-1-yl]sulfonyl}phenyl)amino]-5,7-dihydro-6H-pyrimido[5,4-d][1]benzazepin-6-one I-1171 2-({4-[(3-methylpiperidin-1-yl)sulfonyl]phenyl}amino)-5,7-dihydro-6H-pyrimido[5,4-d][1]benzazepin-6-one I-1172 4-({4-[(6-oxo-6,7-dihydro-5H-pyrimido[5,4-d][1]benzazepin-2-yl)amino]phenyl}sulfonyl)-1,4-diazepane-1-carbaldehyde I-1173 2-[(4-{[(3R)-3-(dimethylamino)pyrrolidin-1-yl]sulfonyl}phenyl)amino]-5,7-dihydro-6H-pyrimido[5,4-d][1]benzazepin-6-one I-1174 N-methyl-N-(1-methylpiperidin-4-yl)-4-[(6-oxo-6,7-dihydro-5H-pyrimido[5,4-d][1]benzazepin-2-yl)amino]benzenesulfonamide I-1175 N-(cyclopropylmethyl)-4-[(6-oxo-6,7-dihydro-5H-pyrimido[5,4-d][1]benzazepin-2-yl)amino]-N-propylbenzenesulfonamide I-1176 N-ethyl-4-[(6-oxo-6,7-dihydro-5H-pyrimido[5,4-d][1]benzazepin-2-yl)amino]-N-(2-pyridin-2-ylethyl)benzenesulfonamide I-1177 N-(2-methoxy-1-methylethyl)-4-[(6-oxo-6,7-dihydro-5H-pyrimido[5,4-d][1]benzazepin-2-yl)amino]benzenesulfonamide I-1178 N-(2-cyanoethyl)-N-cyclopentyl-4-[(6-oxo-6,7-dihydro-5H-pyrimido[5,4-d][1]benzazepin-2-yl)amino]benzenesulfonamide I-1179 N-benzyl-4-[(6-oxo-6,7-dihydro-5H-pyrimido[5,4-d][1]benzazepin-2-yl)amino]benzenesulfonamide I-1180 N-isopropyl-4-[(6-oxo-6,7-dihydro-5H-pyrimido[5,4-d][1]benzazepin-2-yl)amino]benzenesulfonamide I-1181 N-[(1-ethylpyrrolidin-3-yl)methyl]-4-[(6-oxo-6,7-dihydro-5H-pyrimido[5,4-d][1]benzazepin-2-yl)amino]benzenesulfonamide I-1182 N-[2-(diethylamino)ethyl]-4-[(6-oxo-6,7-dihydro-5H-pyrimido[5,4-d][1]benzazepin-2-yl)amino]benzenesulfonamide I-1183 2-{[4-(3,4-dihydroisoquinolin-2(1H)-ylsulfonyl)phenyl]amino}-5,7-dihydro-6H-pyrimido[5,4-d][1]benzazepin-6-one I-1184 N-(2-methyl-1H-indol-5-yl)-4-[(6-oxo-6,7-dihydro-5H-pyrimido[5,4-d][1]benzazepin-2-yl)amino]benzenesulfonamide I-1185 N-(4-fluorobenzyl)-4-[(6-oxo-6,7-dihydro-5H-pyrimido[5,4-d][1]benzazepin-2-yl)amino]benzenesulfonamide I-1186 N-[(1R,2R,4S)-bicyclo[2.2.1]hept-2-yl]-4-[(6-oxo-6,7-dihydro-5H-pyrimido[5,4-d][1]benzazepin-2-yl)amino]benzenesulfonamide I-1187 N-[3-(1H-imidazol-1-yl)propyl]-4-[(6-oxo-6,7-dihydro-5H-pyrimido[5,4-d][1]benzazepin-2-yl)amino]benzenesulfonamide I-1188 2-{[4-(1,3-dihydro-2H-isoindol-2-ylsulfonyl)phenyl]amino}-5,7-dihydro-6H-pyrimido[5,4-d][1]benzazepin-6-one I-1189 N-[(1R)-1-cyclohexylethyl]-4-[(6-oxo-6,7-dihydro-5H-pyrimido[5,4-d][1]benzazepin-2-yl)amino]benzenesulfonamide I-1190 4-[(6-oxo-6,7-dihydro-5H-pyrimido[5,4-d][1]benzazepin-2-yl)amino]-N-phenylbenzenesulfonamide I-1191 N-[2-(dimethylamino)ethyl]-4-[(6-oxo-6,7-dihydro-5H-pyrimido[5,4-d][1]benzazepin-2-yl)amino]benzenesulfonamide I-1192 N-[3-(dimethylamino)-2,2-dimethylpropyl]-4-[(6-oxo-6,7-dihydro-5H-pyrimido[5,4-d][1]benzazepin-2-yl)amino]benzenesulfonamide I-1193 4-({4-[(6-oxo-6,7-dihydro-5H-pyrimido[5,4-d][1]benzazepin-2-yl)amino]phenyl}sulfonyl)piperazine-1-carbaldehyde I-1194 N-[2-(diisopropylamino)ethyl]-4-[(6-oxo-6,7-dihydro-5H-pyrimido[5,4-d][1]benzazepin-2-yl)amino]benzenesulfonamide I-1195 2-({4-[(5-ethyl-2-methylpiperidin-1-yl)sulfonyl]phenyl}amino)-5,7-dihydro-6H-pyrimido[5,4-d][1]benzazepin-6-one I-1196 4-[(6-oxo-6,7-dihydro-5H-pyrimido[5,4-d][1]benzazepin-2-yl)amino]-N-prop-2-yn-1-ylbenzenesulfonamide I-1197 N-(2-furylmethyl)-N-methyl-4-[(6-oxo-6,7-dihydro-5H-pyrimido[5,4-d][1]benzazepin-2-yl)amino]benzenesulfonamide I-1198 N-[1-(4-fluorophenyl)ethyl]-4-[(6-oxo-6,7-dihydro-5H-pyrimido[5,4-d][1]benzazepin-2-yl)amino]benzenesulfonamide I-1199 N-[2-(3-fluorophenyl)ethyl]-4-[(6-oxo-6,7-dihydro-5H-pyrimido[5,4-d][1]benzazepin-2-yl)amino]benzenesulfonamide I-1200 2-({4-[(2-ethylpyrrolidin-1-yl)sulfonyl]phenyl}amino)-5,7-dihydro-6H-pyrimido[5,4-d][1]benzazepin-6-one I-1201 N-(3-methylbutyl)-4-[(6-oxo-6,7-dihydro-5H-pyrimido[5,4-d][1]benzazepin-2-yl)amino]benzenesulfonamide I-1202 1222-({4-[(4-methylpiperazin-1-yl)sulfonyl]phenyl}amino)-5,7-dihydro-6H-pyrimido[5,4-d][1]benzazepin-6-one I-1203 N-[2-(diethylamino)ethyl]-N-ethyl-4-[(6-oxo-6,7-dihydro-5H-pyrimido[5,4-d][1]benzazepin-2-yl)amino]benzenesulfonamide I-1204 N-[2-(dimethylamino)ethyl]-N-methyl-4-[(6-oxo-6,7-dihydro-5H-pyrimido[5,4-d][1]benzazepin-2-yl)amino]benzenesulfonamide I-1205 N-cyclopentyl-4-[(6-oxo-6,7-dihydro-5H-pyrimido[5,4-d][1]benzazepin-2-yl)amino]benzenesulfonamide I-1206 N-(4-methoxybenzyl)-4-[(6-oxo-6,7-dihydro-5H-pyrimido[5,4-d][1]benzazepin-2-yl)amino]benzenesulfonamide I-1207 2-({4-[(4-methylpiperidin-1-yl)sulfonyl]phenyl}amino)-5,7-dihydro-6H-pyrimido[5,4-d][1]benzazepin-6-one I-1208 (2S)-1-({4-[(6-oxo-6,7-dihydro-5H-pyrimido[5,4-d][1]benzazepin-2-yl)amino]phenyl}sulfonyl)pyrrolidine-2-carboxamide I-1209 2-{[4-(piperidin-1-ylsulfonyl)phenyl]amino}-5,7-dihydro-6H-pyrimido[5,4-d][1]benzazepin-6-one I-1210 4-[(6-oxo-6,7-dihydro-5H-pyrimido[5,4-d][1]benzazepin-2-yl)amino]-N-[3-(2-oxopyrrolidin-1-yl)propyl]benzenesulfonamide I-1211 2-[(4-{[3-(diethylamino)pyrrolidin-1-yl]sulfonyl}phenyl)amino]-5,7-dihydro-6H-pyrimido[5,4-d][1]benzazepin-6-one I-1212 4-[(6-oxo-6,7-dihydro-5H-pyrimido[5,4-d][1]benzazepin-2-yl)amino]-N-[2-(2-thienyl)ethyl]benzenesulfonamide I-1213 N-[3-(dimethylamino)propyl]-N-methyl-4-[(6-oxo-6,7-dihydro-5H-pyrimido[5,4-d][1]benzazepin-2-yl)amino]benzenesulfonamide I-1214 N-(4-chlorobenzyl)-4-[(6-oxo-6,7-dihydro-5H-pyrimido[5,4-d][1]benzazepin-2-yl)amino]benzenesulfonamide I-1215 2-({4-[(3-oxopiperazin-1-yl)sulfonyl]phenyl}amino)-5,7-dihydro-6H-pyrimido[5,4-d][1]benzazepin-6-one I-1216 4-[(6-oxo-6,7-dihydro-5H-pyrimido[5,4-d][1]benzazepin-2-yl)amino]-N-(tetrahydrofuran-2-ylmethyl)benzenesulfonamide I-1217 N-methyl-N-(1-methylpyrrolidin-3-yl)-4-[(6-oxo-6,7-dihydro-5H-pyrimido[5,4-d][1]benzazepin-2-yl)amino]benzenesulfonamide I-1218 N-[(1R)-2,3-dihydro-1H-inden-1-yl]-4-[(6-oxo-6,7-dihydro-5H-pyrimido[5,4-d][1]benzazepin-2-yl)amino]benzenesulfonamide I-1219 2-{[4-(azetidin-1-ylsulfonyl)phenyl]amino}-5,7-dihydro-6H-pyrimido[5,4-d][1]benzazepin-6-one I-1220 N-methyl-N-[1-({4-[(6-oxo-6,7-dihydro-5H-pyrimido[5,4-d][1]benzazepin-2-yl)amino]phenyl}sulfonyl)pyrrolidin-3-yl]acetamide I-1221 4-[(6-oxo-6,7-dihydro-5H-pyrimido[5,4-d][1]benzazepin-2-yl)amino]-N-(2-phenoxyethyl)benzenesulfonamide I-1222 2-({4-[(4-ethylpiperazin-1-yl)sulfonyl]phenyl}amino)-5,7-dihydro-6H-pyrimido[5,4-d][1]benzazepin-6-one I-1223 N-cyclohexyl-N-methyl-4-[(6-oxo-6,7-dihydro-5H-pyrimido[5,4-d][1]benzazepin-2-yl)amino]benzenesulfonamide I-1224 N-(2,3-dihydro-1-benzofuran-5-ylmethyl)-4-[(6-oxo-6,7-dihydro-5H-pyrimido[5,4-d][1]benzazepin-2-yl)amino]benzenesulfonamide I-1225 4-[(6-oxo-6,7-dihydro-5H-pyrimido[5,4-d][1]benzazepin-2-yl)amino]-N-(2-piperidin-1-ylethyl)benzenesulfonamide I-1226 2-({4-[(2-methylpyrrolidin-1-yl)sulfonyl]phenyl}amino)-5,7-dihydro-6H-pyrimido[5,4-d][1]benzazepin-6-one I-1227 N-(2-isopropoxyethyl)-4-[(6-oxo-6,7-dihydro-5H-pyrimido[5,4-d][1]benzazepin-2-yl)amino]benzenesulfonamide I-1228 N-ethyl-4-[(6-oxo-6,7-dihydro-5H-pyrimido[5,4-d][1]benzazepin-2-yl)amino]-N-(pyridin-4-ylmethyl)benzenesulfonamide I-1229 N-methyl-4-[(6-oxo-6,7-dihydro-5H-pyrimido[5,4-d][1]benzazepin-2-yl)amino]-N-(2-pyridin-2-ylethyl)benzenesulfonamide I-1230 2-{[2-(1H-pyrrol-1-yl)phenyl]amino}-5,7-dihydro-6H-pyrimido[5,4-d][1]benzazepin-6-one I-1231 2-{[(6-fluoro-4H-1,3-benzodioxin-8-yl)methyl]amino}-5,7-dihydro-6H-pyrimido[5,4-d][1]benzazepin-6-one I-1232 2-{[2-(2-chlorophenyl)-2-(dimethylamino)ethyl]amino}-5,7-dihydro-6H-pyrimido[5,4-d][1]benzazepin-6-one I-1233 2-{[2-(4-methylpiperazin-1-yl)-1-phenylethyl]amino}-5,7-dihydro-6H-pyrimido[5,4-d][1]benzazepin-6-one I-1234 2-{[(1-piperidin-1-ylcyclohexyl)methyl]amino}-5,7-dihydro-6H-pyrimido[5,4-d][1]benzazepin-6-one I-1235 2-{[(5-methyl-3-phenylisoxazol-4-yl)methyl]amino}-5,7-dihydro-6H-pyrimido[5,4-d][1]benzazepin-6-one I-1236 2-{[2-(2-methoxyphenyl)ethyl]amino}-5,7-dihydro-6H-pyrimido[5,4-d][1]benzazepin-6-one I-1237 2-{[2-(4-ethoxy-3-methoxyphenyl)ethyl]amino}-5,7-dihydro-6H-pyrimido[5,4-d][1]benzazepin-6-one I-1238 2-[(3,4-dimethylisoxazol-5-yl)amino]-5,7-dihydro-6H-pyrimido[5,4-d][1]benzazepin-6-one I-1239 2-[(3-oxo-1,3-dihydro-2-benzofuran-5-yl)amino]-5,7-dihydro-6H-pyrimido[5,4-d][1]benzazepin-6-one I-1240 2-[(1-phenyl-2-pyrrolidin-1-ylethyl)amino]-5,7-dihydro-6H-pyrimido[5,4-d][1]benzazepin-6-one I-1241 2-{[2-(4-methoxyphenyl)ethyl]amino}-5,7-dihydro-6H-pyrimido[5,4-d][1]benzazepin-6-one I-1242 2-[(1-benzylpyrrolidin-3-yl)amino]-5,7-dihydro-6H-pyrimido[5,4-d][1]benzazepin-6-one I-1243 2-{[5-fluoro-2-(1H-imidazol-1-yl)phenyl]amino}-5,7-dihydro-6H-pyrimido[5,4-d][1]benzazepin-6-one I-1244 2-[(pyridin-3-ylmethyl)amino]-5,7-dihydro-6H-pyrimido[5,4-d][1]benzazepin-6-one I-1245 2-[(2-methyl-1,3-benzothiazol-6-yl)amino]-5,7-dihydro-6H-pyrimido[5,4-d][1]benzazepin-6-one I-1246 2-[(4-methoxyphenyl)amino]-5,7-dihydro-6H-pyrimido[5,4-d][1]benzazepin-6-one I-1247 2-[(9-ethyl-9H-carbazol-3-yl)amino]-5,7-dihydro-6H-pyrimido[5,4-d][1]benzazepin-6-one I-1248 2-[(2-anilinoethyl)amino]-5,7-dihydro-6H-pyrimido[5,4-d][1]benzazepin-6-one I-1249 2-{[4-(trifluoromethyl)pyridin-2-yl]amino}-5,7-dihydro-6H-pyrimido[5,4-d][1]benzazepin-6-one I-1250 2-{[2-(2,4-difluorophenoxy)pyridin-3-yl]amino}-5,7-dihydro-6H-pyrimido[5,4-d][1]benzazepin-6-one I-1251 2-[(1-benzylpiperidin-4-yl)amino]-5,7-dihydro-6H-pyrimido[5,4-d][1]benzazepin-6-one I-1252 N,N,4-trimethyl-3-[(6-oxo-6,7-dihydro-5H-pyrimido[5,4-d][1]benzazepin-2-yl)amino]benzenesulfonamide I-1253 2-{[2-(4-benzylpiperazin-1-yl)ethyl]amino}-5,7-dihydro-6H-pyrimido[5,4-d][1]benzazepin-6-one I-1254 2-{[3-(4-bromo-1-methyl-1H-pyrazol-3-yl)phenyl]amino}-5,7-dihydro-6H-pyrimido[5,4-d][1]benzazepin-6-one I-1255 2-[(2-methyl-2-morpholin-4-ylpropyl)amino]-5,7-dihydro-6H-pyrimido[5,4-d][1]benzazepin-6-one I-1256 2-{[2-(2,5-dimethoxyphenyl)ethyl]amino}-5,7-dihydro-6H-pyrimido[5,4-d][1]benzazepin-6-one I-1257 2-({6-[3-(trifluoromethyl)phenoxy]pyridin-3-yl}amino)-5,7-dihydro-6H-pyrimido[5,4-d][1]benzazepin-6-one I-1258 4-[(9-chloro-6-oxo-6,7-dihydro-5H-pyrimido[5,4-d][1]benzazepin-2-yl)amino]-N-(3-methyl-1-phenylbutyl)benzamide I-1259 4-[(9-chloro-6-oxo-6,7-dihydro-5H-pyrimido[5,4-d][1]benzazepin-2-yl)amino]-N-[1-(4-hydroxyphenyl)ethyl]benzamide I-1260 4-[(9-chloro-6-oxo-6,7-dihydro-5H-pyrimido[5,4-d][1]benzazepin-2-yl)amino]-N-(1-methyl-1-phenylethyl)benzamide I-1261 4-[(9-iodo-6-oxo-6,7-dihydro-5H-pyrimido[5,4-d][1]benzazepin-2-yl)amino]-N-(1-methyl-1-phenylethyl)benzamide I-1262 N-[1-(4-fluorophenyl)ethyl]-4-[(9-iodo-6-oxo-6,7-dihydro-5H-pyrimido[5,4-d][1]benzazepin-2-yl)amino]benzamide I-1263 4-[(9-iodo-6-oxo-6,7-dihydro-5H-pyrimido[5,4-d][1]benzazepin-2-yl)amino]-N-(1-phenylethyl)benzamide I-1264 N-methyl-4-[(6-oxo-6,7-dihydro-5H-pyrimido[5,4-d][1]benzazepin-2-yl)amino]-N-prop-2-yn-1-ylbenzenesulfonamide I-1265 9-chloro-2-{[4-(morpholin-4-ylsulfonyl)phenyl]amino}-5,7-dihydro-6H-pyrimido[5,4-d][1]benzazepin-6-one I-1266 N-(2-methoxyethyl)-4-[(6-oxo-6,7-dihydro-5H-pyrimido[5,4-d][1]benzazepin-2-yl)amino]benzenesulfonamide I-1267 N-[(5-methyl-2-furyl)methyl]-4-[(6-oxo-6,7-dihydro-5H-pyrimido[5,4-d][1]benzazepin-2-yl)amino]benzenesulfonamide I-1268 4-[(7-methyl-6-oxo-6,7-dihydro-5H-pyrimido[5,4-d][1]benzazepin-2-yl)amino]benzenesulfonic acid I-1269 4-[(9-chloro-6-oxo-6,7-dihydro-5H-pyrimido[5,4-d][1]benzazepin-2-yl)amino]-N-[2-(dimethylamino)-1-phenylethyl]benzamide I-1270 4-[(9-chloro-6-oxo-6,7-dihydro-5H-pyrimido[5,4-d][1]benzazepin-2-yl)amino]-N-(1-phenyl-2-pyrrolidin-1-ylethyl)benzamide General Synthetic Methodology The compounds of the present invention can be prepared by methods known to one of ordinary skill in the art and/or by reference to the schemes shown below and the synthetic examples that follow. Exemplary synthetic rqutes are set forth in Schemes 1-12 below, and in the Examples.

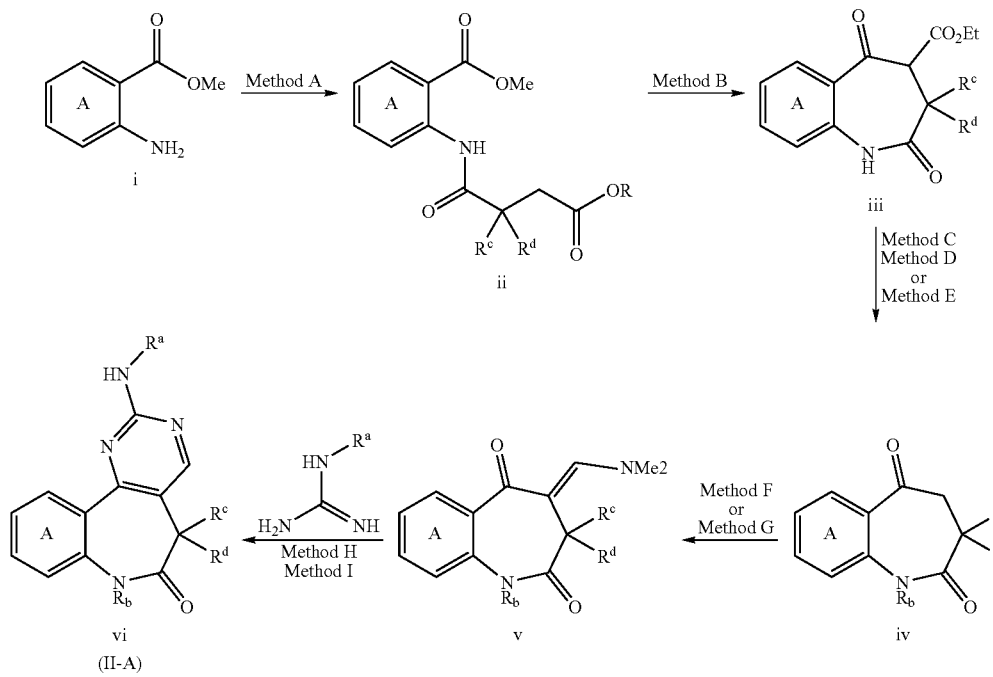

Scheme 1: General route for the synthesis of N-Substituted 2-Amino-5H,7H-benzo[b]pyrimido[4,5-d]azepin-6-ones (Formula II-A)

I-1271 4-[(7-methyl-6-oxo-6,7-dihydro-5H-pyrimido[5,4-d][1]benzazepin-2-yl)amino]benzoic acid I-1272 4-({4-[(9-chloro-6-oxo-6,7-dihydro-5H-pyrimido[5,4-d][1]benzazepin-2-yl)amino]phenyl}sulfonyl)-1,4-diazepane-1-carbaldehyde I-1273 4-[(9-chloro-6-oxo-6,7-dihydro-5H-pyrimido[5,4-d][1]benzazepin-2-yl)amino]-N-[3-(2-oxopyrrolidin-1-yl)propyl]benzenesulfonamide I-1274 4-[(9-chloro-6-oxo-6,7-dihydro-5H-pyrimido[5,4-d][1]benzazepin-2-yl)amino]-N-(2-isopropoxyethyl)benzenesulfonamide I-1275 4-[(9-chloro-6-oxo-6,7-dihydro-5H-pyrimido[5,4-d][1]benzazepin-2-yl)amino]-N-(pyridin-4-ylmethyl)benzenesulfonamide I-1276 N-(2,3-dihydro-1-benzofuran-5-ylmethyl)-4-[(7-methyl-6-oxo-6,7-dihydro-5H-pyrimido[5,4-d][1]benzazepin-2-yl)amino]benzamide I-1277 N-(1,3-dihydro-2-benzofuran-5-yl)-4-[(7-methyl-6-oxo-6,7-dihydro-5H-pyrimido[5,4-d][1]benzazepin-2-yl)amino]benzamide I-1278 4-[(9-chloro-6-oxo-6,7-dihydro-5H-pyrimido[5,4-d][1]benzazepin-2-yl)amino]-N-(pyridin-2-ylmethyl)benzenesulfonamide I-1279 4-[(9-chloro-6-oxo-6,7-dihydro-5H-pyrimido[5,4-d][1]benzazepin-2-yl)amino]-N-(3-morpholin-4-ylpropyl)benzenesulfonamide Scheme 1 above shows a general route for preparing compounds of formula (II-A). Those of ordinary skill in the art will recognize that compounds of formula (I) wherein Ring A is other than phenyl can be prepared by the same general route, beginning with appropriate starting materials analogous to i.

Methods for the synthesis of substituted amino benzoic acid methyl esters such as formula i are known. As shown in Scheme 1, conversion of i to the acylated amino benzoic acid methyl ester of formula ii can be accomplished by coupling with the appropriately substituted acyl chloride. Compound iii can be prepared from ii by cyclization with a suitable base, such as KOt-Bu. Decarboxylation of iii to provide iv can be effected by microwave irradiation in DMF/H$_2$O, according to Method C. Alternatively, iii can be converted to iv by heating in DMSO/H$_2$O with NaCl (Method D) or without NaCl (Method E). Those skilled in the art will appreciate that the lactam nitrogen of formula iv can be alkylated using a suitable base, such as Cs$_2$CO$_3$, and an alkyl halide as described in Method W. Alternatively, iv can be arylated using aryl halides through a CuI-mediated process.

Treatment of iv with N,N-dimethylformamide dimethyl acetal in refluxing THF affords v, according to Method F. Alternatively, the reaction may be performed by treatment of iv with N,N-dimethylformamide dimethyl acetal in DMF followed by microwave irradiation, according to Method G.

Enamine v is converted to the pyrimido compound vi by treatment with an aryl or alkyl guanidine. The reaction may be performed in the presence of a mild base in ethanol or DMF utilizing heat or microwave irradiation, according to Method H and Method I.

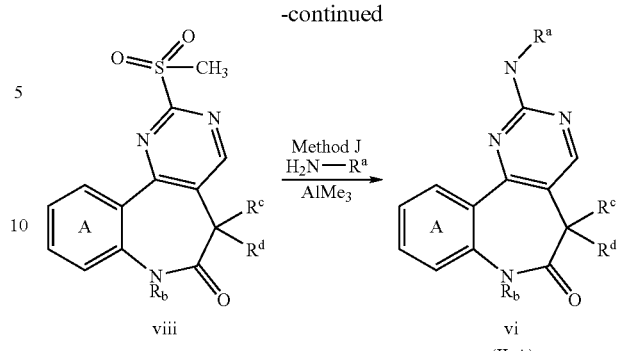

Scheme 2: Alternate route for the synthesis of N-Substituted 2-Amino-5H,7H-benzo[b]pyrimido[4,5-d]azepin-6-ones (Formula II-A)

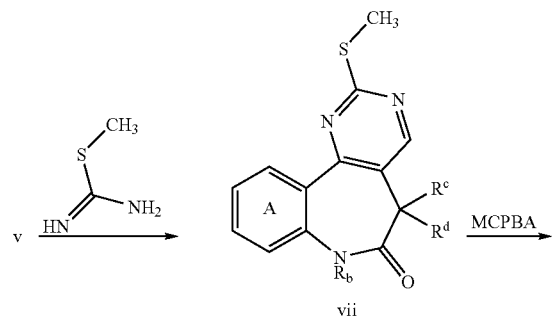

As an alternative procedure to using guanidines to provide compounds of formula (II-A), a leaving group, such as a sulfone, can be directly displaced by alkyl and aryl amines. As shown in Scheme 2, treatment of v with 2-methylisothiourea using Method I, provides compounds of formula vii. Treatment of vii with an oxidizing agent, such as MCPBA, provides the sulfone viii. Compounds of formula viii can then be reacted with substituted amines or anilines in the presence of AlMe₃ to provide compounds of formula vi (Method J). The conversion of compounds viii to vi (formula (I)) is amenable to solution phase library synthesis.

Scheme 3: Substitution at Ring A of N-Substituted 2-Amino-5H,7H-benzo[b]pyrimido[4,5-d]azepin-6-ones (Formula II-A)

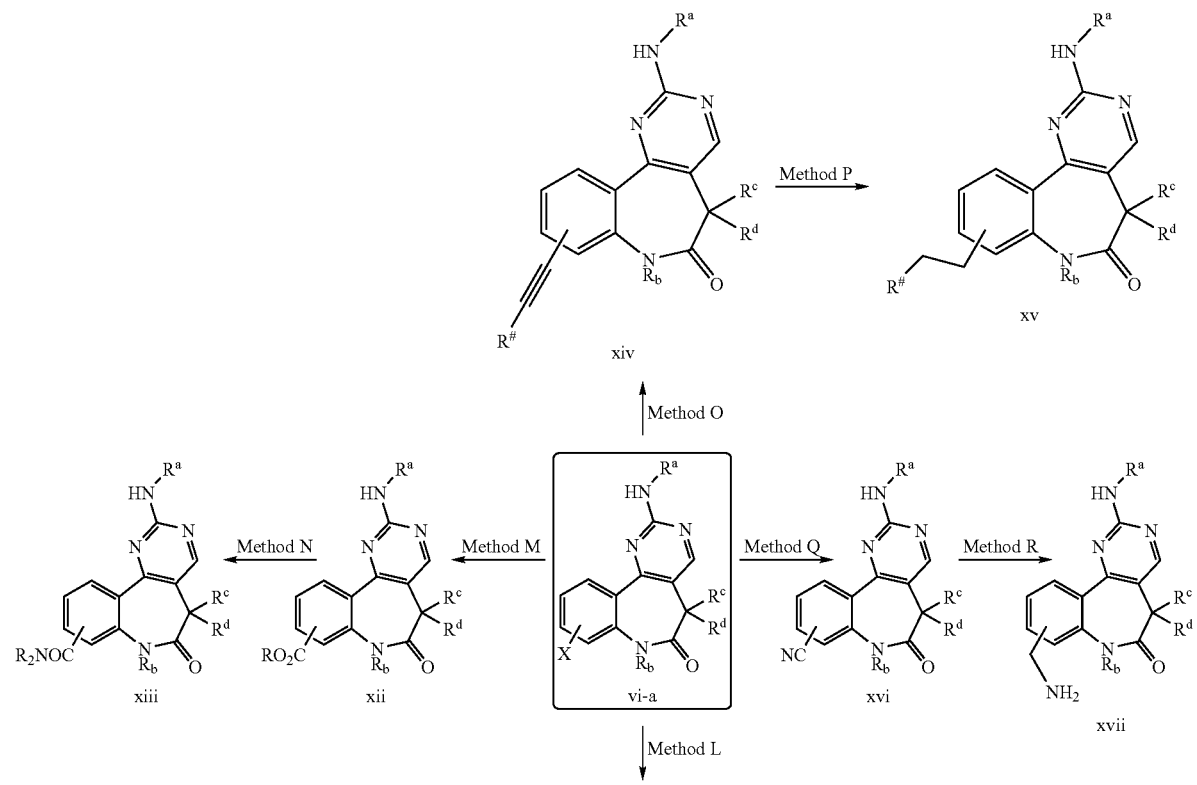

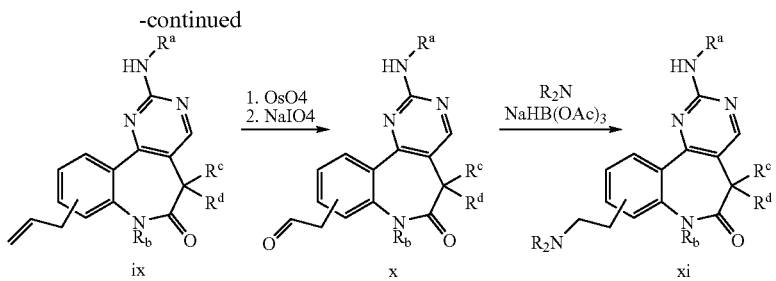

Compounds of formula vi where Ring A is substituted with a halogen, such as iodine, can be converted to a variety of compounds exemplified through formulae ix-xvii in Scheme 3. Thus, Stille coupling of vi-a with an allyl halide according to Method L provides compounds of formula ix, which can be converted to the aldehyde x through standard oxidation/ cleavage conditions. Substituted amines of formula xi are obtained from x through reductive amination. Those skilled in the art will appreciate that the aldehyde x can be oxidized using a suitable reagent to provide the acid, which can be further elaborated to provide alternate substitutions, such as esters or amides. Aldehyde x can also be reduced using a suitable reagent to provide the alcohol, which can be further elaborated to provide alternate substitutions, such as ethers or nitrites.

Alternatively, compounds of formula vi-a can be converted to xii through a palladium-mediated process outlined in Method M. The xii acid can be further elaborated to the amides xiii according to Method N using a standard coupling reagent, such as TBTU, and the desired amine. Those skilled in the art will appreciate that the acid xii can be converted to the ester and/or reduced using a suitable reagent to provide the alcohol, which can be further elaborated to provide alternate substitutions, such as ethers or nitrites. The alcohol could then be oxidized to the aldehyde, which could undergo reductive amination with a variety of substituted amines.

Compounds of formula vi-a readily undergo Sonogashira reactions with substituted acetylenes according to Method O to provide compounds of formula xiv. When treated with a suitable reducing agent, such as Pd/C according to Method I, compounds xiv are converted to compounds of formula xv. One skilled in the art will recognize that R# can represent a variety of groups, including H and substituted alkyls, such as —CH$_2$N(R$^+$)$_2$, and —CH$_2$OH. The compounds xiv and xv, derived from reaction of vi with propargyl alcohol, can be oxidized using a suitable reagent to the acid, which can be further elaborated to amides or esters. Alternatively, the alcohol can be oxidized using a suitable reagent to the aldehyde, which can undergo reductive amination to provide substituted amines.

Lastly, compounds of formula vi can be converted to the cyano-substituted compound xvi according to Method O. Using a suitable reducing agent, such as Raney nickel according to Method R, compounds of formula xvii are prepared from xvi.

Scheme 4: Guanidine Synthesis

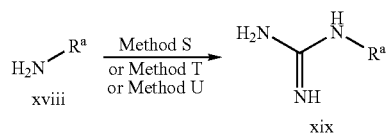

The guanidines used for the preparation of compounds of formula xix are either commercially available, or they can be prepared through the literature methods described in Scheme 4 (Methods S or T or U).

Scheme 5: Substitution at Ring B of N-Substituted 2-Amino-5H,7H-benzo[b]pyrimido[4,5-d]azepin-6-ones (Formula II-A)

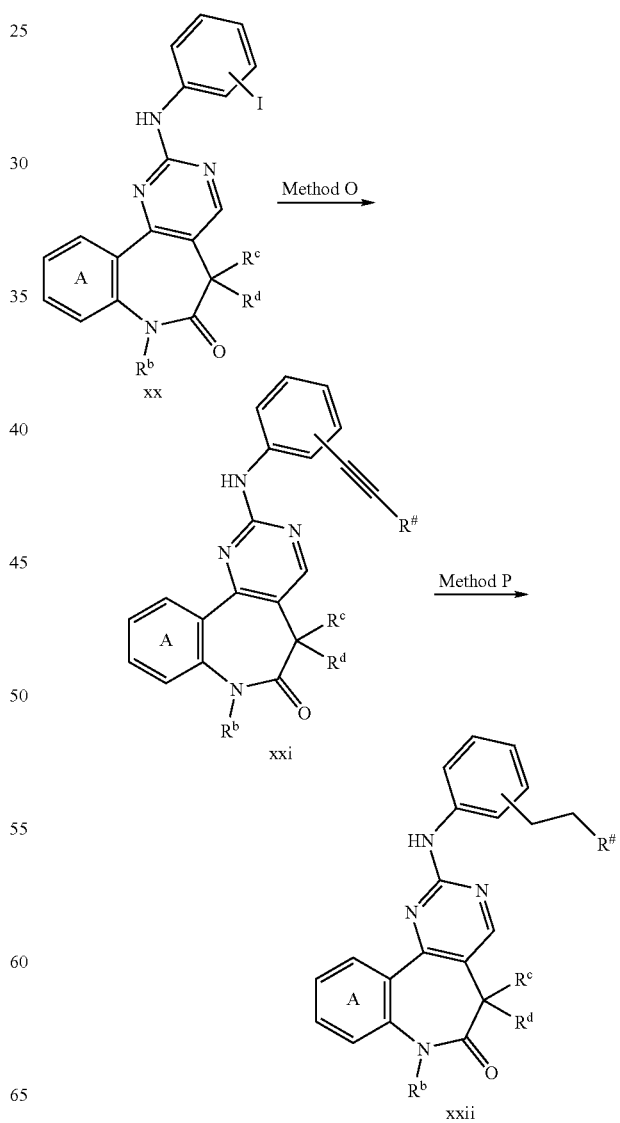

Compounds of formula xx (Scheme 5) can be prepared from v using guanidines xix wherein $R^a$ is an aryl iodide. In methods analogous to those described above for Scheme 3, a Sonogashira reaction with substituted acetylenes provides compounds of formula xxi. Using a suitable reducing agent, such as Pd/C, converts xxi to the saturated compounds xxii. One skilled in the art will recognize that R# can represent a variety of groups, including H and substituted alkyls, such as —$CH_2N(R^+)_2$, and —$CH_2OH$. The compounds xxi and xxii, derived from reaction of xx with propargyl alcohol, can be oxidized using a suitable reagent to the acid, which can be further elaborated to amides or esters. Alternatively, the alcohol can be oxidized using a suitable reagent to the aldehyde, which can undergo reductive amination to provide substituted amines.

Compounds of formula xxiii (Scheme 6) can be prepared from v according to the method depicted in Scheme 1, using guanidines xix, where $R^a$ is a phenyl group substituted with the appropriate alcohol. From the alcohols xxiii, aldehydes xxiv can be prepared using a suitable oxidizing agent, such as Dess-Martin periodinane. Compounds of formula xxiv can be further elaborated to amines such as xxv through reductive amination a suitable reducing agent, such as $NaHB(OAc)_3$. Additionally, alcohols xxiii can be converted to cyano compounds such as xxvi, which can be further elaborated to the amines xxvii using a suitable reducing agent, such as Raney nickel, as outlined in Method R.

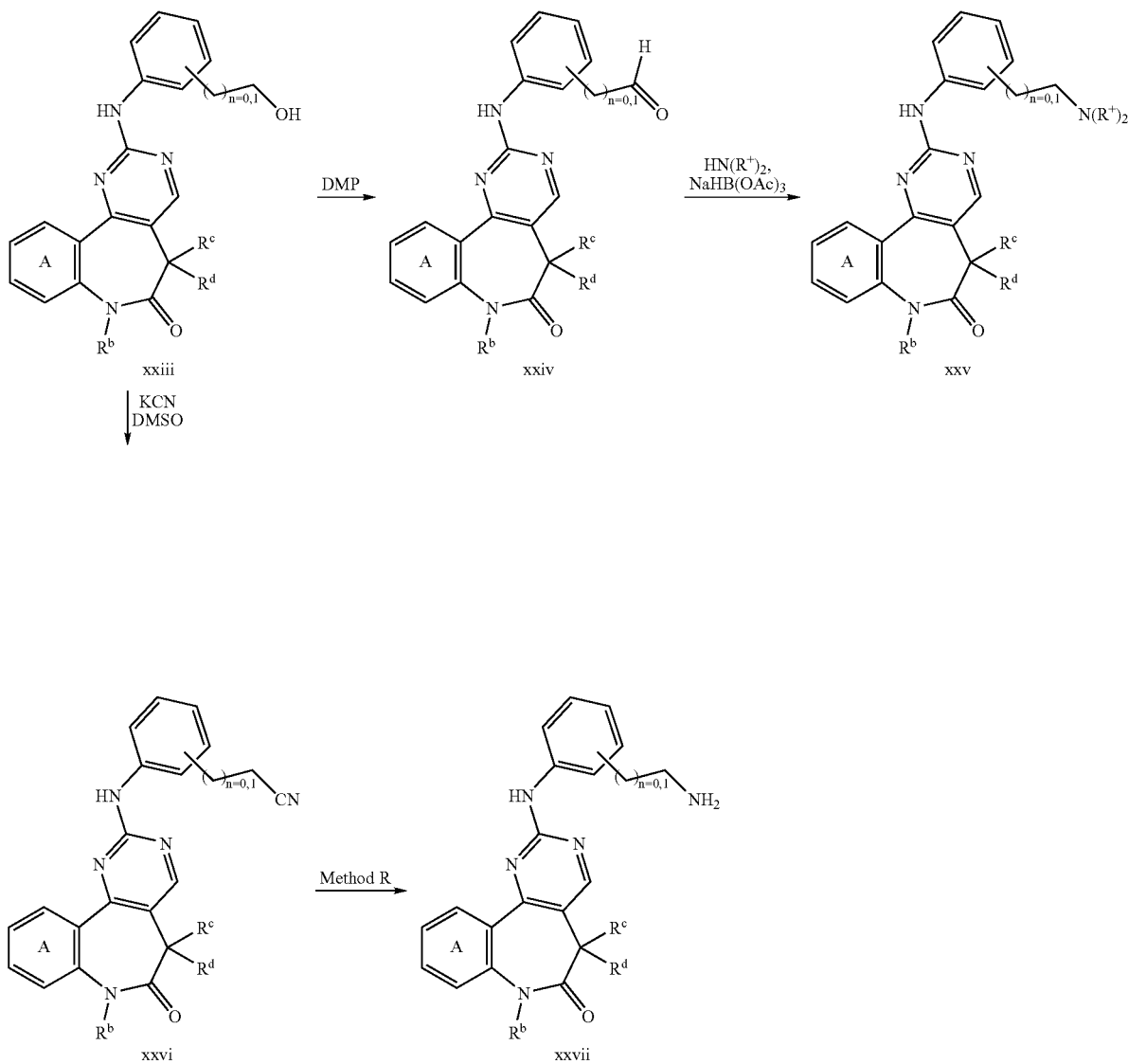

Scheme 6: 1 and 2-Carbon Linked Substitution at Ring B of N-Substituted 2-Amino-5H,7H-benzo[b]pyrimido[4,5-d]azepin-6-ones (Formula II-A)

Scheme 7: Amide Substitution at the B ring of N-Substituted 2-Amino-5H,7H-benzo[b]pyrimido[4,5-d]azepin-6-ones

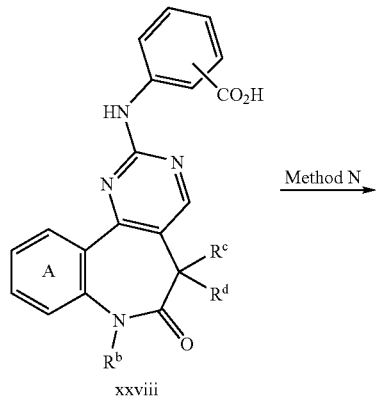

xxviii

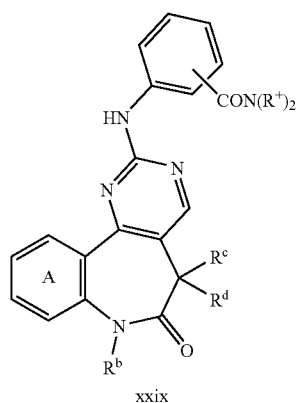

xxix

Compounds of formula xxviii (Scheme 7) can be prepared from v according to methods depicted in Scheme 1, using guanidines xix, where $R^a$ is a phenyl group substituted with the appropriate carboxylic acid. The acids can be further elaborated to the amides xxix according to Method N using a standard coupling reagent, such as TBTU, and the desired amine.

Scheme 8: Conversion of N-Substituted 2-Amino-5H,7H-benzo[b]pyrimido[4,5-d]azepin-6-ones (Formula II-A) to N-Substituted 2-Amino-5H,7H-benzo[b]pyrimido[4,5-d]azepine-6-thiones (Formula II-D)

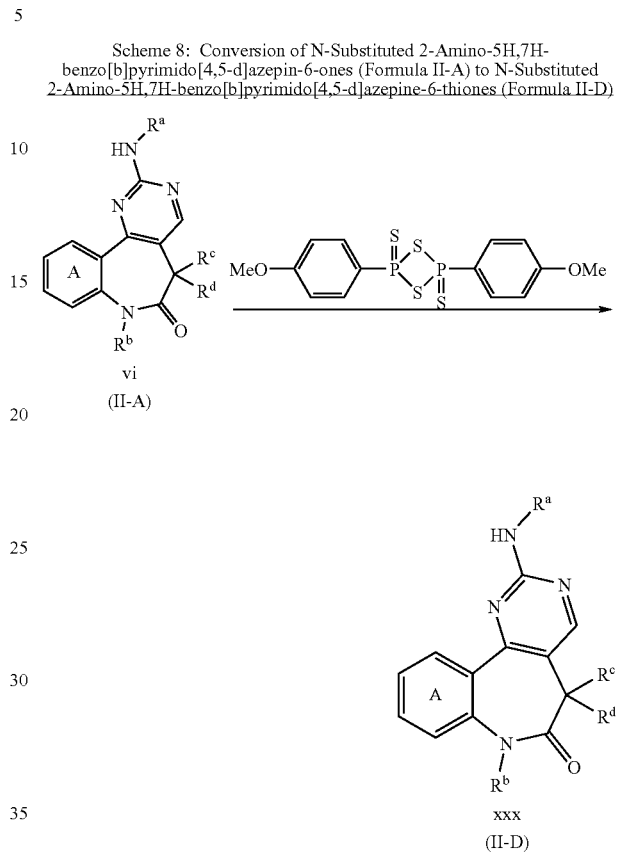

vi
(II-A)

xxx
(II-D)

Thioamides of formula xxx (corresponding to Formula (II-D)) can be prepared from vi according to Scheme 8 using a suitable reagent, such as Lawesson's Reagent. Similarly, the thioamides of Formulae (II-E) and (II-F) can be prepared from compounds of Formulae (II-B) and (II-C).

Scheme 9: Alternate Synthesis of N-Substituted 2-Amino-5H,7H-benzo[b]pyrimido[4,5-d]azepin-6-ones and Generation of N-Substituted 2-Amino-5,7-dihydro-1,3,4,7-tetraaza-dibenzo[a,c]cyclohepten-6-ones (Formula II-B)

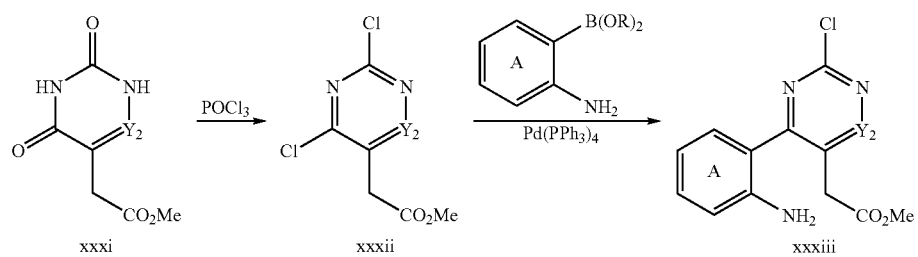

xxxi  xxxii  xxxiii

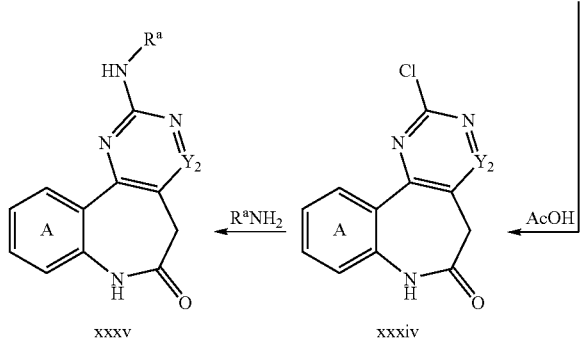

As outlined in Scheme 9, compounds of formula xxxv can be prepared from xxxi using a 4-step sequence. Compound xxxi is converted to xxxii using a suitable chlorinating agent, such as $POCl_3$. The dichloro pyrimidine is then coupled with the appropriately substituted aniline using a palladium-catalyzed procedure to provide xxxiii. The ester xxxiii can be hydrolyzed and coupled to the aniline using a suitable reagent, such as AcOH, to provide the lactam xxxiv. Finally, chloro pyrimidine xxxiv can be displaced with the appropriately substituted amine or aniline to provide compounds of formula xxxv.

Scheme 10: Synthesis of N-Substituted 2-Amino-5,7-dihydro-3,4,7-triaza-dibenzo[a,c]cyclohepten-6-ones (Formula (II-C))

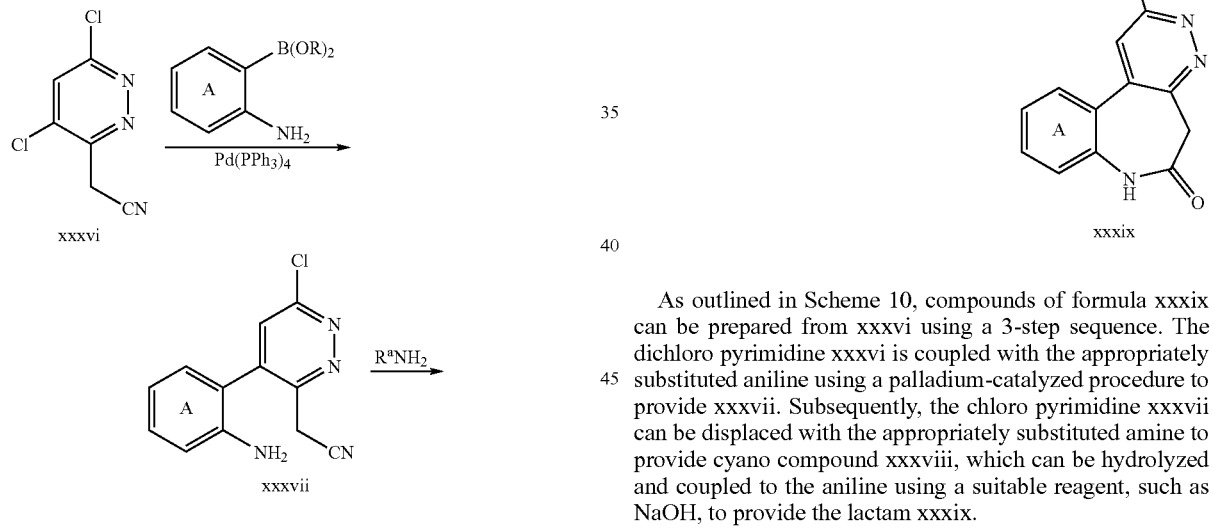

As outlined in Scheme 10, compounds of formula xxxix can be prepared from xxxvi using a 3-step sequence. The dichloro pyrimidine xxxvi is coupled with the appropriately substituted aniline using a palladium-catalyzed procedure to provide xxxvii. Subsequently, the chloro pyrimidine xxxvii can be displaced with the appropriately substituted amine to provide cyano compound xxxviii, which can be hydrolyzed and coupled to the aniline using a suitable reagent, such as NaOH, to provide the lactam xxxix.

Scheme 11: Synthesis of N-Substituted 2-Amino-4-substituted-5H,7H-benzo[b]pyrimido[4,5-d]azepin-6-ones (Formula II-A)

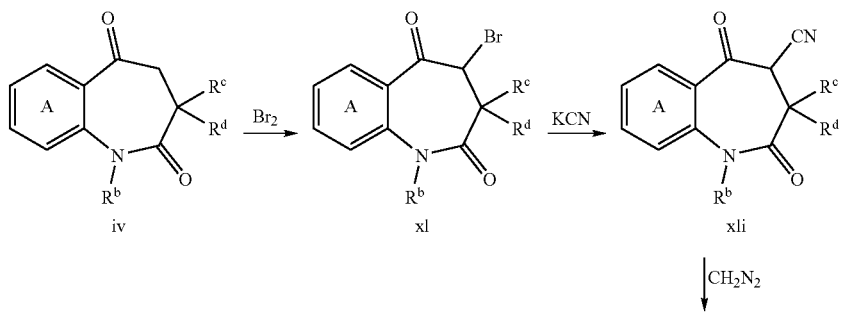

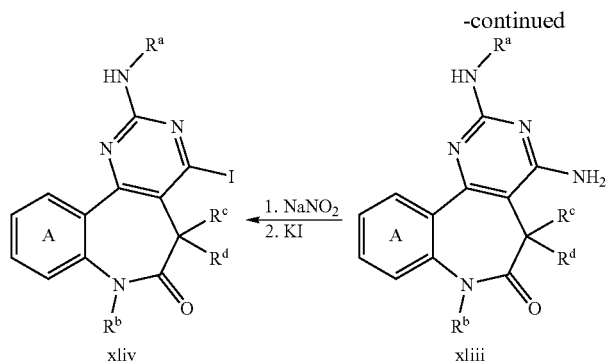

-continued

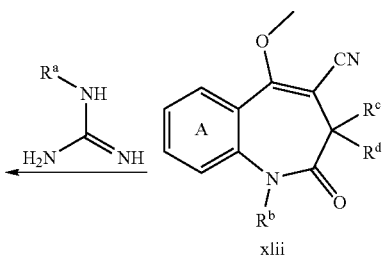

Preparation of compounds of formula (II-B), wherein $Y^2$ is $CR^e$, is achieved as shown in Scheme 11. The keto-intermediate iv undergoes α-bromination followed by conversion to the nitrile xli. Subsequent treatment with an appropriate methylating agent, such as diazomethane; provides enol ether xlii, which when condensed with substituted guanidines results in the 4-amino-substituted compound xliii. One skilled in the art will recognize that compounds of formula xliii can be further elaborated to the substituted amines or amides. Compound xliii can also be converted to the iodide xliv. Those skilled in the art will appreciate that the iodide xliv can undergo a variety of transformations, including the Sonogashira reactions mentioned above, as well as other palladium couplings.

Scheme 12: Synthesis of N-Substituted 2-Amino-4-substituted-5H,7H-benzo[b]pyrimido[4,5-d]azepin-6-ones (Formula II-A)

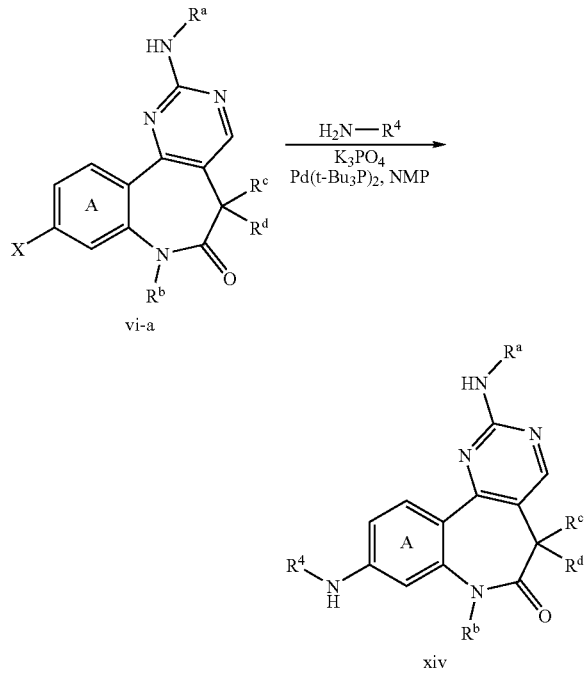

As outlined in Scheme 12, compounds of formula xlv can be prepared from compound vi-a by palladium-mediated coupling with an amine.

Uses, Formulation, and Administration

As discussed above, the present invention provides compounds that are inhibitors of protein kinases. The compounds can be assayed in vitro or in vivo for their ability to bind to and/or inhibit a protein kinase. In vitro assays include assays to determine inhibition of the ability of the kinase to phosphorylate a substrate protein or peptide. Alternate in vitro assays quantitate the ability of the compound to bind to the kinase. Inhibitor binding may be measured by radiolabelling the inhibitor prior to binding, isolating the inhibitor/kinase complex and determining the amount of radiolabel bound. Alternatively, inhibitor binding may be determined by running a competition experiment in which new inhibitors are incubated with the kinase bound to a known radioligand. The compounds also can be assayed for their ability to affect cellular or physiological functions mediated by protein kinase activity. Assays for each of these activities are described in the Examples and/or are known in the art. Non-limiting examples of protein kinases that are inhibited by the compounds of the invention include Chk-1, Aurora kinase, PLK, Chk-2, LCK, CDK1, CDK2E, PKA. In some embodiments, the compound of formula (I) inhibits a protein kinase selected from the group consisting of Chk-1, Aurora kinase, and PLK.

In another aspect, therefore, the invention provides a method for inhibiting protein kinase activity in a cell, comprising contacting a cell in which inhibition of a protein kinase is desired with a compound of formula (I). In some embodiments, the compound of formula (I) interacts with and reduces the activity of more than one protein kinase enzyme in the cell. By way of example, when assayed against Chk-1, Aurora kinase, and PLK, some compounds of formula (I) show inhibition of all three enzymes.

In some embodiments, the compound of formula (I) is selective, i.e., the concentration of the compound that is required for inhibition of one or several protein kinase enzymes is lower, preferably at least 2-fold, 5-fold, 10-fold, or 50-fold lower, than the concentration of the compound required for inhibition of other protein kinase enzymes. In some such embodiments, the compound of formula (I) inhibits one or two of Chk-1, Aurora kinase, and PLK at a concentration that is lower than that required for inhibition of the other enzyme(s).

In some embodiments, the compound of formula (I) inhibits one or more protein kinase enzymes involved in cell cycle regulation or cell division. The invention thus provides a method for inhibiting cell proliferation, comprising contacting a cell in which such inhibition is desired with a compound of formula (I). The phrase "inhibiting cell proliferation" is used to denote the ability of a compound of formula (I) to inhibit cell number or cell growth in contacted cells as compared to cells not contacted with the inhibitor. An assessment of cell proliferation can be made by counting cells using a cell counter or by an assay of cell viability, e.g., an MTT or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with the inhibitor is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, a kinase inhibitor that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising a compound of formula (I) as defined above, or a pharmaceutically acceptable salt thereof, and a pharmaceutically acceptable carrier.

If pharmaceutically acceptable salts of the compounds of the invention are utilized in these compositions, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy,* 20*th Ed.*, ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-Naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bio-availability modifiers and combinations of these.

Pharmaceutical formulations may be prepared as liquid suspensions or solutions using a liquid, such as, but not limited to, an oil, water, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The pharmaceutical compositions of the invention preferably are formulated for administration to a patient having, or at risk of developing or experiencing a recurrence of, a protein kinase-mediated disorder. The term "patient", as used herein, means an animal, preferably a mammal, more preferably a human. Preferred pharmaceutical compositions of the invention are those formulated for oral, intravenous, or subcutaneous administration. However, any of the above dosage forms containing a therapeutically effective amount of a compound of the invention are well within the bounds of routine experimentation and therefore, well within the scope of the instant invention. In some embodiments, the pharmaceutical composition of the invention may further comprise another therapeutic agent. In some embodiments, such other therapeutic agent is one that is normally administered to patients with the disease or condition being treated.

By "therapeutically effective amount" is meant an amount sufficient to cause a detectable decrease in protein kinase activity or the severity of a protein kinase-mediated disorder. The amount of protein kinase inhibitor needed will depend on the effectiveness of the inhibitor for the given cell type and the length of time required to treat the disorder. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. The amount of additional therapeutic agent present in a composition of this invention typically will be no more than the amount that would normally be administered in a composition comprising that therapeutic agent as the only active agent. Preferably, the amount of additional therapeutic agent will range from about 50% to about 100% of the amount normally present in a composition comprising that agent as the only therapeutically active agent.

In another aspect, the invention provides a method for treating a patient having, or at risk of developing or experiencing a recurrence of, a protein kinase-mediated disorder. As used herein, the term "protein kinase-mediated disorder" includes any disorder, disease or condition which is caused or characterized by an increase in kinase expression or activity, or which requires kinase activity. The term "protein kinase-mediated disorder" also includes any disorder, disease or condition in which inhibition of protein kinase activity is beneficial. In some embodiments, the protein kinase-mediated disorder is one in which inhibition of Chk-1, Aurora kinase, or PLK activity is beneficial.

The protein kinase inhibitors of the invention can be used to achieve a beneficial therapeutic or prophylactic effect, for example, in subjects with a proliferative disorder. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed protein kinase inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed protein kinase inhibitors include acute myeloid leukemia (A ML); chronic myelogenous leukemia (C ML), including accelerated C ML and C ML blast phase (C ML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

The compounds of formula (I) are particularly useful in the treatment of cancers or cell types in which protein kinase activity is upregulated. The compounds of the invention are especially useful in the treatment of cancers or cell types in which Chk-1, Aurora, or PLK activity is upregulated, including, in particular, rapidly proliferating cells. Chk-1 also is upregulated in drug-resistant cells (Shyjan et al., U.S. Pat. No. 6,723,498 (2004)), as well as retinoblastomas such as Rb negative or inactivated cells (Gottifredi et al., *Mol. Cell. Biol.*, 21:1066 (2001)), or cells in which the $ARF^{p14/p19}$ locus has been inactivated or misregulated. The disclosed Chk-1 inhibitors also are particularly useful in the treatment of cancers or cell types in which another checkpoint pathway has been mutated or abrogated, including, without limitation, cancers or cell types in which p53 or the p53 pathway has been inactivated or abrogated.

In some embodiments, the compound or composition of the invention is used to treat a patient having or at risk of developing or experiencing a recurrence in a cancer selected from the group consisting of colorectal cancer, ovarian cancer, breast cancer, gastric cancer, prostate cancer, and pancreatic cancer. In certain embodiments, the cancer is selected from the group consisting of breast cancer, colorectal cancer, and pancreatic cancer.

In some embodiments, the protein kinase inhibitor of the invention is administered in conjunction with another therapeutic agent. The other therapeutic agent may inhibit the same or a different protein kinase, or may operate by a different mechanism. In some embodiments, the other therapeutic agent is one that is normally administered to patients with the disease or condition being treated. The protein kinase inhibitor of the invention may be administered with the other therapeutic agent in a single dosage form or as a separate dosage form. When administered as a separate dosage form, the other therapeutic agent may be administered prior to, at the same time as, or following administration of the protein kinase inhibitor of the invention.

In some embodiments, a protein kinase inhibitor of formula (I) is administered in conjunction with an anticancer agent. As used herein, the term "anticancer agent" refers to any agent that is administered to a subject with cancer for purposes of treating the cancer. Nonlimiting examples anticancer agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In some embodiments, a compound of formula (I) that inhibits Chk-1 is used in combination with radiation therapy or a chemotherapeutic agent that acts by causing damage to the genetic material of cells (collectively referred to herein as "DNA damaging agents"). In some embodiments, the combination of a Chk-1 inhibitor of formula (I) with a DNA damaging agent is used to treat a subject with a multi-drug resistant cancer. A cancer is resistant to a drug when it resumes a normal rate of tumor growth while undergoing treatment with the drug after the tumor had initially responded to the drug. A tumor "responds to a drug" when it exhibits a decrease in tumor mass or a decrease in the rate of tumor growth. The term "multi-drug resistant cancer" refers to cancer that is resistant to two or more drugs, often as many as five or more.

When used in combination with a DNA damaging agent, an "effective amount" of a Chk-1 inhibitor is the quantity of the inhibitor at which a greater response is achieved when the Chk-1 inhibitor is co-administered with the DNA damaging anti-cancer drug and/or radiation therapy than is achieved when the DNA damaging anti-cancer drug and/or radiation therapy is administered alone.

In order that this invention be more fully understood, the following preparative and testing examples are set forth. These examples illustrate how to make or test specific compounds, and are not to be construed as limiting the scope of the invention in any way.

EXAMPLES

Definitions

AcOH acetic acid
ATP adenosine triphosphate
BINAP 2,2'-bis(diphenylphosphino)-1,1'-binaphthyl
Boc tert-butoxycarbonyl
BSA bovine serum albumin
DMAP 4-dimethylaminopyridine
DMF dimethylformamide
DMF-DMA dimethylformamide dimethylacetal
DMSO dimethylsulfoxide
DTT dithiothreitol
EDTA ethylenediaminetetraacetic acid
EtOAc ethyl acetate
EtOH ethanol
MCPBA meta-chloroperbenzoic acid
MeOH methanol
MTT methylthiazoletetrazolium
WST (4-[3-(4-iodophenyl)-2-(4-Nitrophenyl)-2H-5-tetrazolio]-1,3-benzene disulfonate sodium salt)
PKA cAMP-dependent protein kinase
tBu tert-butyl
THF tetrahydrofuran
TBTU O-(benzotriazol-1-yl)-N,N,N',N'-tetramethyluronium tetrafluoroborate
h hours
min minutes
m/z mass to charge
MS mass spectrum
RP LC-MS reverse phase liquid chromatography-mass spectrometry
HRMS high resolution mass spectrum Compounds I-1 to I-93 and I-135 to I-1279 in Table 1 were prepared by methods generally analogous to those described in Schemes 1-12 above and Examples 1-24 below. Mass spectra matched calculated values.

HRMS data were collected on a Sciex Ostar time of flight mass spectrometer coupled to an Agilent HPLC. Experimentally determined (M+H)$^+$ were within 10 ppm error of calculated (M+H)$^+$.

LCMS conditions: spectra were run on a Phenominex Luna 5 μm C18 50×4.6 mm column on a Hewlett-Packard HP1100 at 2.5 mL/min for a 3 minute run using the following gradients:

Method Formic Acid (FA): Acetonitrile containing zero to 100 percent 0.1% formic acid in water.
Method Ammonium Acetate (AA): Acetonitrile containing zero to 100 percent 10 mM ammonium acetate in water.

Example 1

Representative Synthesis of Compounds of Formula i (See Scheme 1)

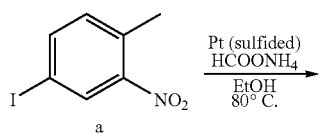

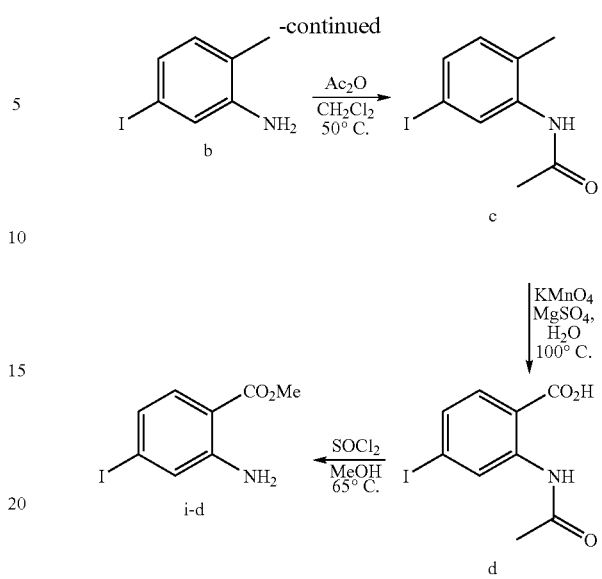

5-Iodo-2-methyl-phenylamine (b)

To a solution of 4-iodo-1-methyl-2-nitro-benzene (25.0 g, 107 mmol) in 300 mL of ethanol was added sulfided platinum (3.00 g) and ammonium formate (20.3 g, 321 mmol). The mixture was heated to reflux for 12 h and then cooled to 22° C., filtered through Celite® and concentrated in vacuo. The resulting residue was diluted with H$_2$O (300 mL) and extracted with 3×200 mL CH$_2$Cl$_2$. The organic fractions were combined, washed with brine, dried over Na$_2$SO$_4$ and concentrated in vacuo to give b (21.1 g, 95%): MS m/z=234 (M+H).

N-(5-Iodo-2-methyl-phenyl)-acetamide (c)

A solution of 5-iodo-2-methyl-phenylamine (20.4 g, 87.6 mmol) in 200 mL of dry CH$_2$Cl$_2$ was cooled to 0° C. and acetic anhydride (16.5 mL, 175 mmol) was added dropwise. The mixture was heated to 50° C. for 2 h and then cooled to 22° C. The resulting white precipitate was filtered to give c (18.4 g, 76%): MS m/z=276 (M+H).

2-Acetylamino-4-iodo-benzoic acid (d)

To a suspension of N-(5-iodo-2-methyl-phenyl)-acetamide (18.9 g, 68.9 mmol) in 200 mL H$_2$O was added magnesium sulfate (10.8 g, 89.7 mmol). The mixture was heated to 100° C., and potassium permanganate (32.7 g, 206 mmol) was added. After 1 h, an additional portion of potassium permanganate (10.9 g, 68.9 mmol) was added. Again after 1 h, a final portion of potassium permanganate (10.9 g, 68.9 mmol) was added and the reaction was stirred 12 h. The mixture was then cooled to 22° C. and filtered through a pad of Celite®. The filtrate was acidified with 1 N HCl, and the resulting white precipitate was filtered to give d (14.8 g, 70%): MS m/z=304 (M−H).

2-Amino-4-iodo-benzoic acid methyl ester (i-b)

To 2-acetylamino-4-iodo-benzoic acid (13.8 g, 45.3 mmol) in 200 mL of dry methanol was added SOCl$_2$ (32.7 mL, 453 mmol) dropwise at 0° C. The reaction mixture was then heated at 65° C. for 2 h. The reaction was then cooled to 0° C., an additional portion of SOCl$_2$ (10 mL, 137 mmol) was added, and the reaction was heated at 65° C. for 2 h. The reaction was then cooled to 0° C., a final portion of SOCl$_2$ (10 mL, 137 mmol) was added, and the reaction was heated at 65°

C. for 48 h. The reaction was then cooled to 22° C. and concentrated in vacuo The resulting residue was diluted with H$_2$O and extracted with 3×150 mL CH$_2$Cl$_2$. The combined organic fractions were washed with brine and dried over Na$_2$SO$_4$ to give i-b (11.7 g, 93%): MS m/z=278 (M+H).

Methyl 2-amino-5-methoxybenzoate (i-e)

Hydrogen chloride gas was bubbled through a solution of 2-amino-5-methoxybenzoic acid (5.0 g, 30 mmol) in MeOH (200 mL) for 30 minutes. The solution was heated at 60° C. overnight. The reaction was cooled and the solvent removed in vacuo. The residue was dissolved in water, basified with 5M NaOH and extracted twice with ether. The ether extracts were washed with 5M NaOH and water, dried (MgSO$_4$), filtered and concentrated in vacuo to give i-e (4.25 g, 78%): MS m/z=182 (M+H).

Methyl 2-amino-5-fluorobenzoate (i-f)

In a manner similar to that described above for methyl 2-amino-5-methoxybenzoate, 7.82 g of 2-amino-5-fluorobenzoic acid was converted to i-f (40%): MS m/z=170 (M+H).

Methyl 2-amino-4-methylbenzoate (i-g)

In a manner similar to that described above for methyl 2-amino-5-methoxybenzoate, 1.90 g of 2-amino-4-methylbenzoic acid was converted to i-g (94%): MS m/z=166 (M+H).

Esters i-a, i-c, i-d, i-i, i-j, and i-k are commercially available. Ester i-h was not prepared; ii-h was prepared as described below.

Example 2

Method A for the Synthesis of Compounds of Formula ii (See Scheme 1)

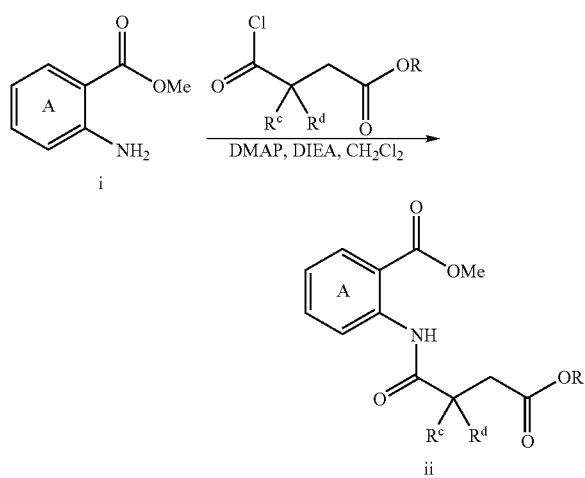

2-(3-Ethoxycarbonyl-propionylamino)-5-iodo-benzoic acid methyl ester (ii-a)

To methyl 2-amino-5-iodobenzoate (i-a) (15 g, 54 mmol) was added 200 mL of CH$_2$Cl$_2$, followed by DIEA (9.4 mL, 54 mmol) and a catalytic amount of DMAP. Ethyl 4-chloro-4-oxobutanoate ($R^c=R^d=H$) (8.5 mL, 60 mmol) was added, and the reaction mixture was allowed to stir at room temperature overnight. The reaction mixture was then poured into 250 mL H$_2$O, and the organic layer was washed with brine, dried over MgSO$_4$, filtered, and concentrated in vacuo to afford ii-a (22 g, 99%) as a pale yellow solid: MS m/z=406 (M+H).

2-(3-Ethoxycarbonyl-propionylamino)-4-iodo-benzoic acid methyl ester (ii-b)

In a manner similar to that described for method A, 2-amino-4-iodobenzoic acid methyl ester (i-b) was converted to ii-b (99%): MS m/z=406 (M+H).

2-(3-Ethoxycarbonyl-propionylamino)-benzoic acid methyl ester (ii-c)

In a manner similar to that described for method A, 2-amino-benzoic acid methyl ester (i-c) was converted to ii-c (93%): MS m/z=280 (M+H).

5-Chloro-2-(3-ethoxycarbonyl-propionylamino)-benzoic acid methyl ester (ii-d)

In a manner similar to that described in method A, 2-amino-5-chloro-benzoic acid methyl ester (i-d) was converted to ii-d (90%): MS m/z=314 (M+H).

Methyl 2-(4-ethoxy-4-oxobutanamido)-5-methoxybenzoate (ii-e)

In a manner similar to that described for method A, methyl 2-amino-5-methoxybenzoate (i-e) was converted to ii-e (93%): MS m/z=310 (M+H).

Methyl 2-(4-ethoxy-4-oxobutanamido)-5-fluorobenzoate (ii-f)

In a manner similar to that described for method A, methyl 2-amino-5-fluorobenzoate (i-f) was converted to ii-f (95%): MS m/z=298 (M+H).

Methyl 2-(4-ethoxy-4-oxobutanamido)-4-methylbenzoate (ii-g)

In a manner similar to that described for method A, methyl 2-amino-4-methylbenzoate (i-g) was converted to ii-g (97%): MS m/z=294 (M+H).

2-(4-Methoxy-4-oxobutanamido)nicotinic acid (ii-h-1)

In a manner similar to method A, 2-aminonicotinic acid was converted to ii-h-1 (46%).

Methyl 2-(4-methoxy-4-oxobutanamido)nicotinate (ii-h)

2-(4-Methoxy-4-oxobutanamido)nicotinic acid (ii-h-1) (1.28 g, 4.8 mmol) was dissolved in an equimolar mixture of CH$_2$Cl$_2$ and methanol (20 mL) and cooled to 0° C. TMS diazomethane (2M solution in diethyl ether; 5.2 mL, 10.6 mmol) was added dropwise. The mixture was stirred for 1 h and warmed to 23° C. Volatiles were removed under reduced pressure to provide ii-h as a pale yellow solid (1.37 g, 100%) MS m/z=267 (M+1).

4-Chloro-2-(3-methoxycarbonyl-2(R)-methyl-propionylamino)-benzoic acid methyl ester (ii-i)

(R)-(+)-2-Methylsuccinic acid 4-methyl ester (1 g, 6.8 mmol) was dissolved in CH$_2$Cl$_2$ (40 mL). Oxalyl chloride [2M in CH$_2$Cl$_2$ (3.7 mL, 7.4 mmol)] was then added followed by a few drops of DMF (0.1 mL). The mixture was stirred at 22° C. for 3 h, after which it was concentrated under reduced pressure. The resulting residue was then suspended in CH$_2$Cl$_2$ (10 mL) and added slowly to a stirring solution of methyl 2-amino-4-chlorobenzoate (i-i) (1.26 g, 6.8 mmol) in triethylamine (3.76 mL, 27.2 mmol) in CH$_2$Cl$_2$ (40 mL). The reaction mixture was allowed to stir at 22° C. for 1 h. The mixture was then partitioned between CH$_2$Cl$_2$ (50 mL) and H$_2$O (50 mL). The aqueous layer was extracted with CH$_2$Cl$_2$ (3×50 mL) and the combined organic layers were washed with brine, dried over MgSO$_4$, filtered and concentrated to dryness. The resulting orange residue was purified by column chromatography, eluting with 20% ethyl acetate in hexane to give ii-i as a clear oil (1.8 g, 85% yield): MS m/z=314 (M+H).

4-Chloro-2-(3-ethoxycarbonyl-propionylamino)-benzoic acid methyl ester (ii-j)

In a manner similar to that described in method A, 2-amino-5-chloro-benzoic acid methyl ester (i-j) was converted to ii-j (90%): MS m/z=314 (M+H).

5-Bromo-2-(3-ethoxycarbonyl-propionylamino)-benzoic acid methyl ester (ii-k)

In a manner similar to that described for method A, 2-amino-5-bromo-benzoic acid methyl ester (i-k) was converted to ii-k (100%): MS m/z=358 (M+H), 360 (M+2H).

Example 3

Method B for the Synthesis of Compounds of Formula iii (See Scheme 1)

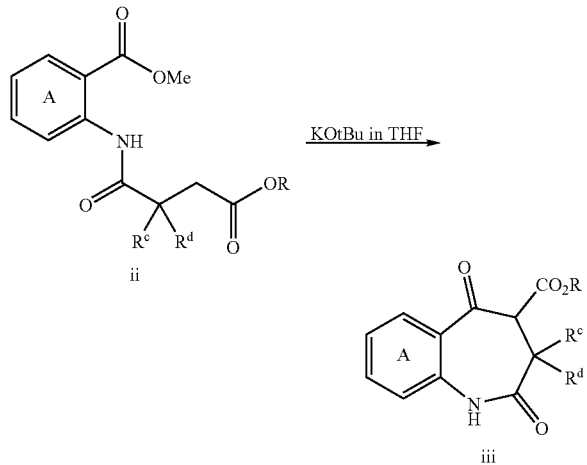

7-Iodo-2,5-dioxo-2,3,4,5-tetrahydro-1H-benzo[b]azepine-4-carboxylic acid ethyl ester (iii-a)

To a solution of methyl 2-(4-ethoxy-4-oxobutanamido)-5-iodobenzoate (ii-a) (22.0 g, 54 mmol) in 125 mL of THF was added a 1 M solution of KOt-Bu in THF (119 mL, 119 mmol). The reaction was complete after 2.5 h at 22° C. H$_2$O (250 mL) and 1N HCl (60 mL) were added to the solution, and the resulting precipitate was filtered, washed with 2×50 mL Et$_2$O, and dried in vacuo to give iii-a (16.1 g, 83%) as a whitish/gray solid as a mixture of ethyl and methyl esters: MS m/z=374 (M+H) and 360 (M+H).

8-Iodo-2,5-dioxo-2,3,4,5-tetrahydro-1H-benzo[b]azepine-4-carboxylic acid ethyl ester (iii-b)

In a manner similar to that described for method B, 2-(3-ethoxycarbonyl-propionylamino)-4-iodo-benzoic acid methyl ester (ii-b) was converted to iii-b (89% yield mixture methyl and ethyl esters): MS m/z=374 (M+H) and 360 (M+H).

2,5-Dioxo-2,3,4,5-tetrahydro-1H-benzo[b]azepine-4-carboxylic acid ethyl ester (iii-c)

In a manner similar to that described in method B, 2-(3-ethoxycarbonyl-propionylamino)-benzoic acid methyl ester (ii-c) was converted to iii-c (87%): MS m/z 248 (M+H).

7-Chloro-2,5-dioxo-2,3,4,5-tetrahydro-1H-benzo[b]azepine-4-carboxylic acid ethyl ester (iii-d)

In a manner similar to that described in method B, 5-chloro-2-(3-ethoxycarbonyl-propionylamino)-benzoic acid methyl ester (ii-d) was converted to iii-d (84%): MS m/z=282 (M+H).

7-Methoxy-2,5-dioxo-2,3,4,5-tetrahydro-1H-benzo[b]azepine-4-carboxylic acid, mixture of methyl and ethyl esters (iii-e)

In a manner similar to that described for method B, methyl 2-(4-ethoxy-4-oxobutanamido)-5-methoxybenzoate (ii-e) was converted to iii-e (59%, recrystallized from EtOH): MS m/z=264 and 278 (M+H).

7-Fluoro-2,5-dioxo-2,3,4,5-tetrahydro-1H-benzo[b]azepine-4-carboxylic acid, mixture of methyl and ethyl esters (iii-f)

In a manner similar to that described for method B, methyl 2-(4-ethoxy-4-oxobutanamido)-5-fluorobenzoate (ii-f) was converted to iii-f (57%, recrystallized from EtOH): MS m/z=252 and 266 (M+H).

8-Methyl-2,5-dioxo-2,3,4,5-tetrahydro-1H-benzo[b]azepine-4-carboxylic acid, mixture of methyl and ethyl esters (iii-g)

In a manner similar to that described for method B, methyl 2-(4-ethoxy-4-oxobutanamido)-4-methylbenzoate (ii-g) was converted to iii-g (49%, recrystallized from EtOH): MS m/z=248 and 262 (M+H).

Methyl 5,8-dioxo-6,7,8,9-tetrahydro-5H-pyrido[2,3-b]azepine-6-carboxylate (iii-h)

In a manner similar to method B, methyl 2-(4-methoxy-4-oxobutanamido)-Nicotinate (ii-h) was converted to iii-h (47%): MS m/z=235 (M+H).

8-Chloro-3-methyl-2,5-dioxo-2,3,4,5-tetrahydro-1H-benzo[b]azepine-4-carboxylic acid methyl ester (iii-i)

In a manner similar to that described for method B, 4-chloro-2-(3-methoxycarbonyl-2-methyl-propionylamino)-benzoic acid methyl ester (ii-i) was converted to iii-i (78%): MS m/z=282 (M+H).

8-Chloro-2,5-dioxo-2,3,4,5-tetrahydro-1H-benzo[b]azepine-4-carboxylic acid methyl ester (iii-j)

In a manner similar to that described for method B, 4-chloro-2-(3-ethoxycarbonyl-propionylamino)-benzoic acid methyl ester (ii-j) was converted to iii-j (81%): MS m/z=268 (M+H).

7-Bromo-2,5-dioxo-2,3,4,5-tetrahydro-1H-benzo[b]azepine-4-carboxylic acid ethyl ester (iii-k)

In a manner similar to that described for method B, 5-bromo-2-(3-ethoxycarbonyl-propionylamino)-benzoic acid methyl ester (ii-k) was converted to iii-k (60% yield mixture methyl and ethyl esters): MS m/z=312 (M+H), 314 (M+2H) and 326 (M+H), 328 (M+2H).

Example 4

Method C for the Synthesis of Compounds of Formula iv (See Scheme 1)

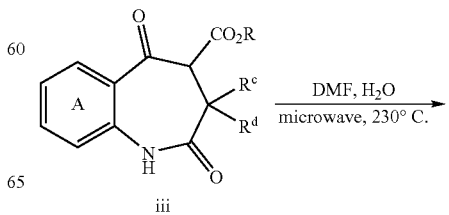

-continued

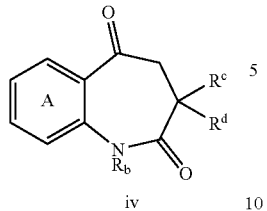

iv

8-Chloro-3-methyl-3,4-dihydro-1H-benzo[b]azepine-2,5-dione (iv-i)

To a solution of 8-chloro-3-methyl-2,5-dioxo-2,3,4,5-tetrahydro-1H-benzo[b]azepine-4-carboxylic acid methyl ester (iii-i) (0.2 g, 0.7 mmol) in DMF (2 mL) was added $H_2O$ (0.3 mL) and the reaction mixture heated to 230° C. in a microwave reactor for 5 minutes. $H_2O$ (20 mL) was added to the reaction mixture and the resulting precipitate was filtered and washed with $H_2O$. The solid was dried under reduced pressure at 40° C. for 16 h to afford iv-i (0.12 g, 77%) as a white solid: MS m/z=224 (M+H).

8-Iodo-3,4-dihydro-1H-benzo[b]azepine-2,5-dione (iv-b)

In a manner similar to that described for method C, 8-iodo-2,5-dioxo-2,3,4,5-tetrahydro-1H-benzo[b]azepine-4-carboxylic acid ethyl ester (iii-b) was converted to iv-b (69%): MS m/z=300 (M−H).

3,4-Dihydro-1H-benzo[b]azepine-2,5-dione (iv-c)

In a manner similar to that described for method C, 2,5-dioxo-2,3,4,5-tetrahydro-1H-benzo[b]azepine-4-carboxylic acid ethyl ester (iii-c) was converted to iv-c (48%): MS m/z=174 (M−H).

7-Chloro-3,4-dihydro-1H-benzo[b]azepine-2,5-dione (iv-d)

In a manner similar to that described for method C, 7-chloro-2,5-dioxo-2,3,4,5-tetrahydro-1H-benzo[b]azepine-4-carboxylic acid ethyl ester (iii-d) was converted to iv-d (29%): MS m/z=208 (M−H).

8-Chloro-3,4-dihydro-1H-benzo[b]azepine-2,5-dione (iv-j)

In a manner similar to that described for method C, 8-chloro-2,5-dioxo-2,3,4,5-tetrahydro-1H-benzo[b]azepine-4-carboxylic acid methyl ester (iii-j) was converted to iv-j (80%): MS m/z=210 (M+H).

7-Bromo-3,4-dihydro-1H-benzo[b]azepine-2,5-dione (iv-k)

In a manner similar to that described for method C, 7-bromo-2,5-dioxo-2,3,4,5-tetrahydro-1H-benzo[b]azepine-4-carboxylic acid ethyl ester (iii-k) was converted to iv-k (89%): MS m/z=254 (M+H), 256 (M+2H).

Example 5

Method D for the Synthesis of Compounds of Formula iv (See Scheme 1)

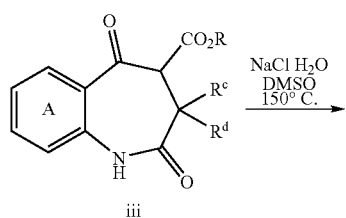

-continued

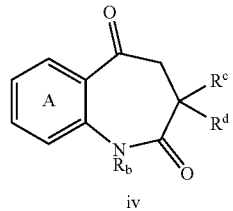

iv

7-Iodo-3,4-dihydro-1H-benzo[b]azepine-2,5-dione (iv-a)

To a solution of ethyl 7-iodo-2,5-dioxo-2,3,4,5-tetrahydro-1H-benzo[b]azepine-4-carboxylate (iii-a) (4.84 g, 13.2 mmol) in dimethyl sulfoxide (66 mL) was added a solution of NaCl (81 mg, 15.9 mmol) in $H_2O$ (475 μL, 26.4 mmol). The reaction mixture was heated to 150° C. for 2 h, and subsequently cooled to 0° C. for 30 min. $H_2O$ (120 mL) was added and the solution was allowed to stir for an additional 1.5 h at 0° C. The resulting precipitate was filtered to provide iv-a (3.2 g, 81%) as a purple/brown solid: MS m/z=302 (M+H).

6,7-Dihydro-9H-pyrido[2,3-b]azepine-5,8-dione (iv-h)

In a manner similar to method D, methyl-5,8-dioxo-6,7,8,9-tetrahydro-5H-pyrido[2,3-b]azepine-6-carboxylate (iii-h) was converted to iv-h (50%): MS m/z=177 (M+H).

Example 6

Method E for the Synthesis of Compounds of Formula iv (See Scheme 1)

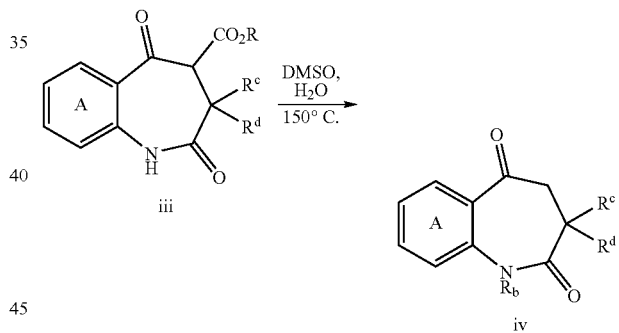

8-Methyl-3,4-dihydro-1H-benzo[b]azepine-2,5-dione (iv-g)

To a solution of iii-g (mixture of methyl and ethyl esters) (1.32 g, 5.19 mmol) in DMSO (50 mL) was added $H_2O$ (2.4 mL) and the resulting solution was heated to 150° C. for 1 h. An additional portion of $H_2O$ (2.4 mL) was added and the solution heated at 150° C. for 1 h. A third portion of $H_2O$ (2.4 mL) was added and the solution heated at 150° C. for 2 h. The reaction mixture was cooled to room temperature and diluted with $H_2O$ (50 mL). The solution was extracted with $CH_2Cl_2$ (3×50 mL) and the combined organics were washed with $H_2O$ (2×50 mL). The organics were dried ($MgSO_4$), filtered and evaporated in vacuo to give the crude product, which was recrystallized from ethanol to give pure iv-g (641 mg, 65%) as a white powder.

7-Methoxy-3,4-dihydro-1H-benzo[b]azepine-2,5-dione (iv-e)

In a manner similar to that described for Method E, iii-e was converted to iv-e (76%, recrystallized from EtOH): MS m/z=206 (M+H).

7-Fluoro-3,4-dihydro-1H-benzo[b]azepine-2,5-dione (iv-f)

In a manner similar to that described for Method E, iii-f was converted to iv-f (62%, recrystallized from EtOH): MS m/z=194 (M+H).

Example 7

Method F for the Synthesis of Compounds of Formula v (See Scheme 1)

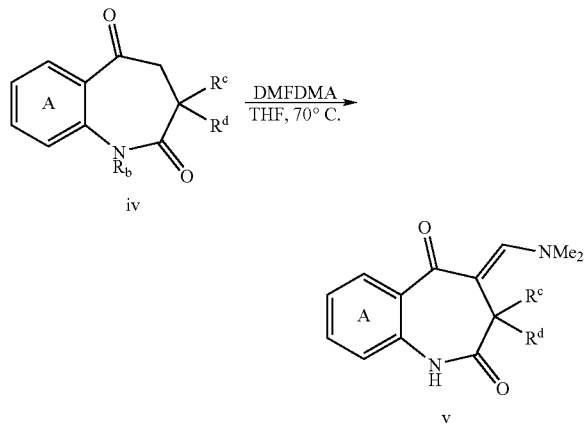

4-Dimethylaminomethylene-7-iodo-3,4-dihydro-1H-benzo[b]azepine-2,5-dione (v-a)

To a solution of 7-iodo-3,4-dihydro-1H-benzo[b]azepine-2,5-dione (iv-a) (1.67 g, 5.54 mmol) in THF (15 mL) was added dimethylformamide dimethylacetal (4.0 mL, 27.7 mmol) and the reaction mixture heated to 70° C. for 1 h. The reaction mixture was cooled to 22° C., treated with Et$_2$O (50 mL), and the resulting precipitate filtered and dried in vacuo to give v-a (1.64 g, 83%) as a brown powder: MS m/z=357 (M+H).

4-Dimethylaminomethylene-8-iodo-3,4-dihydro-1H-benzo[b]azepine-2,5-dione (v-b)

In a manner similar to that described for method F, 8-iodo-3,4-dihydro-1H-benzo[b]azepine-2,5-dione (iv-b) was converted to v-b (66%): MS m/z=357 (M+H).

4-Dimethylaminomethylene-7-methoxy-3,4-dihydro-1H-benzo[b]azepine-2,5-dione (v-e)

To a flask containing iv-e (1.9 g) was added DMF-DMA (15 mL) and the mixture was heated to 110° C. for 1 h. The mixture was cooled to 0° C., filtered, washed with ether and dried to give v-e (2.2 g, 91%): MS m/z=261 (M+H).

4-Dimethylaminomethylene-7-fluoro-3,4-dihydro-1H-benzo[b]azepine-2,5-dione (v-f)

In a manner similar to that described above for 4-dimethylamino-methylene-7-methoxy-3,4-dihydro-1H-benzo[b]azepine-2,5-dione, 7-fluoro-3,4-dihydro-1H-benzo[b]azepine-2,5-dione (iv-f) was converted to v-f (85%): MS m/z=249 (M+H).

4-Dimethylaminomethylene-8-methyl-3,4-dihydro-1H-benzo[b]azepine-2,5-dione (v-g)

In a manner similar to that described above for 4-dimethylamino-methylene-7-methoxy-3,4-dihydro-1H-benzo[b] azepine-2,5-dione, 7-fluoro-3,4-dihydro-1H-benzo[b]azepine-2,5-dione, 0.64 g of 8-methyl-3,4-dihydro-1H-benzo[b]azepine-2,5-dione was converted to v-g (87%): MS m/z=245 (M+H).

(Z)-6-Dimethylaminomethylene-6,7-dihydro-9H-pyrido[2,3-b]azepine-5,8-dione (v-h)

In a manner similar to method F (CH$_2$Cl$_2$ used in place of THF), 6,7-dihydro-9H-pyrido[2,3-b]azepine-5,8-dione (iv-h) was converted to v-h (100%): MS m/z=232 (M+H).

7-Bromo-4-dimethylaminomethylene-3,4-dihydro-1H-benzo[b]azepine-2,5-dione (v-k)

In a manner similar to that described for method F, 7-bromo-3,4-dihydro-1H-benzo[b]azepine-2,5-dione (iv-k) was converted to v-k (63%): MS m/z=309 (M+H), 311 (M+2H).

8-Chloro-1-phenyl-3,4-dihydro-1H-benzo[b]azepine-2,5-dione (v-l-1)

8-Chloro-3,4-dihydro-1H-benzo[b]azepine-2,5-dione (iv-j) (500 mg, 2.4 mmol) was combined with K$_2$CO$_3$ (660 mg, 4.8 mmol) under an atmosphere of argon. Phenylbromide (370 mg, 2.4 mmol) and N,N'-Dimethyl-ethane-1,2-diamine (21 mg, 0.24 mmol, 10 mol %) were added, followed by 10 mL of toluene. The mixture was degassed with an argon sparge for 10 min. CuI (23 mg, 0.12 mmol, 5 mol %) was added and the reaction was heated to 110° C. for 48 h. The mixture was filtered and volatiles removed in vacuo. Chromatographic purification provided the desired product containinated with 10% 8-chloro-3,4-dihydro-1H-benzo[b]azepine-2,5-dione (172 mg, 34%) MS m/z=286 (M+1).

8-Chloro-4-dimethylaminometylene-1-phenyl-3,4-dihydro-1H-benzo[b]azepine-2,5-dione (v-l)

In a manner similar to method F (toluene used in place of THF) 8-chloro-1-phenyl-3,4-dihydro-1H-benzo[b]azepine-2,5-dione (v-l-1) was converted to v-l: MS m/z=341 (M+H).

Example 8

Method G for the Synthesis of Compounds of Formula v (See Scheme 1)

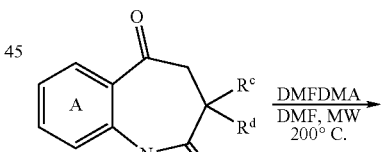

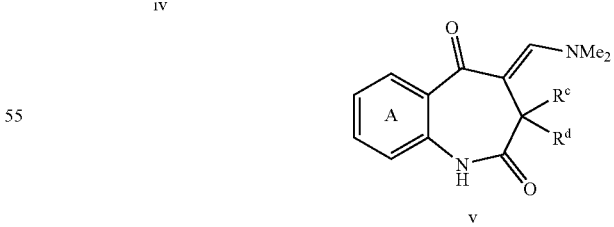

8-Chloro-4-dimethylaminomethylene-3,4-dihydro-1H-benzo[b]azepine-2,5-dione (v-j)

To a solution of iv-j (0.15 g, 0.72 mmol) in DMF (5 mL) was added dimethylformamide dimethylacetal (0.11 mL, 0.79 mmol) and the reaction mixture heated at 200° C. for 100 s in the microwave. The reaction mixture was cooled to 22°

C., treated with Et$_2$O (5 mL), and the resulting precipitate filtered and dried in vacuo to give v-j (0.062 g, 33%) as a brown powder: MS m/z=265 (M+H).

4-Dimethylaminomethylene-3,4-dihydro-1H-benzo[b]azepine-2,5-dione (v-c)

In a manner similar to that described for method G, 3,4-dihydro-1H-benzo[b]azepine-2,5-dione (iv-c) was converted to v-c (95%): MS m/z=231 (M+H).

7-Chloro-4-dimethylaminomethylene-3,4-dihydro-1H-benzo[b]azepine-2,5-dione (v-d)

In a manner similar to that described for method G, 7-chloro-3,4-dihydro-1H-benzo[b]azepine-2,5-dione (iv-d) was converted to v-d (24%): MS m/z=265 (M+H).

8-Chloro-4-dimethylaminomethylene-3-methyl-3,4-dihydro-1H-benzo[b]azepine-2,5-dione (v-i)

In a manner similar to that described for method G, 8-chloro-3-methyl-3,4-dihydro-1H-benzo[b]azepine-2,5-dione (iv-i) was converted to v-i (100%): MS m/z=279 (M+H).

8-Chloro-4-dimethylaminomethylene-1-methyl-3,4-dihydro-1H-benzo[b]azepine-2,5-dione (v-m)

In a manner similar to that described for method G, 8-chloro-1-methyl-3,4-dihydro-1H-benzo[b]azepine-2,5-dione (v-m-1, prepared by Method W, as described below) was converted to v-m (100% yield): MS m/z=279 (M+H).

1-Benzyl-8-chloro-4-dimethylaminomethylene-3,4-dihydro-1H-benzo[b]azepine-2,5-dione (v-N)

In a manner similar to that described for method G, 1-benzyl-8-chloro-3,4-dihydro-1H-benzo[b]azepine-2,5-dione (v-N-1, prepared by Method W, as described below) was converted to v-N (100%): MS m/z=355 (M+H).

8-Chloro-4-dimethylaminomethylene-1,3-dimethyl-3,4-dihydro-1H-benzo[b]azepine-2,5-dione (v-o)

In a manner similar to that described for method G, 8-chloro-1,3-dimethyl-3,4-dihydro-1H-benzo[b]azepine-2,5-dione (prepared from iv-i in a manner similar to that described for Method W below) was converted to v-o (100% yield): MS m/z=293 (M+H).

Example 9

Method W for Lactam Alkylation

8-Chloro-1-methyl-3,4-dihydro-1H-benzo[b]azepine-2,5-dione (v-m-1)

8-Chloro-3,4-dihydro-1H-benzo[b]azepine-2,5-dione (iv-j) (0.2 g, 1 mmol) was dissolved in a mixture of THF (10 mL) and DMF (2 mL). Cesium carbonate (0.98 g, 3 mmol) and methyl iodide (0.069 mL, 1.1 mmol) were added and the reaction mixture was stirred at room temperature for 3 h. The mixture was concentrated under reduced pressure and dichloromethane (10 mL) was added. The inorganic precipitate was filtered and the filtrate was concentrated under reduced pressure to give a viscous residue. This residue was purified utilizing column chromatography, eluting with 50% ethyl acetate/hexane to afford the title compound as a white solid (0.1 g, 45%): MS m/z=224 (M+H).

1-Benzyl-8-chloro-3,4-dihydro-1H-benzo[b]azepine-2,5-dione (v-N-1)

In a manner similar to that described for Method W, 8-chloro-3,4-dihydro-1H-benzo[b]azepine-2,5-dione and benzyl bromide were converted to the title compound (38%): MS m/z=300 (M+H).

Example 10

Method H for the Synthesis of Compounds of Formula vi (See Scheme 1)

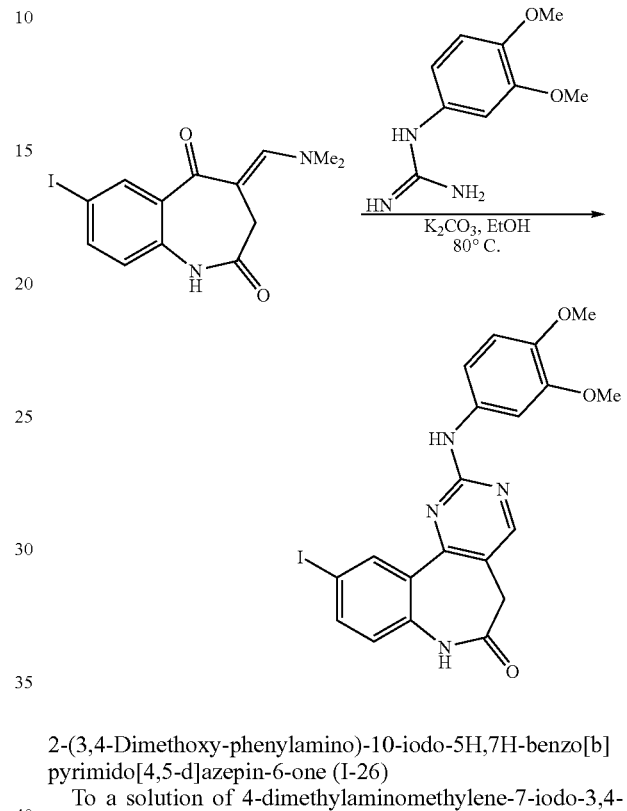

2-(3,4-Dimethoxy-phenylamino)-10-iodo-5H,7H-benzo[b]pyrimido[4,5-d]azepin-6-one (I-26)

To a solution of 4-dimethylaminomethylene-7-iodo-3,4-dihydro-1H-benzo[b]azepine-2,5-dione (v-a) (1.64 g, 4.6 mmol) in 50 mL EtOH was added K$_2$CO$_3$ (1.82 g, 11.04 mmol) and 1-(3,4-dimethoxyphenyl)guanidine (1.31 g, 5.06 mmol), and the reaction was heated to 80° C. for 12 h. The reaction was then cooled to 22° C., diluted with H$_2$O, and treated with 1 M HCl to pH 3. The resulting solid was filtered and washed with H$_2$O, followed by EtOH and Et$_2$O. The crude product was dried in vacuo to give I-26 (1.8 g, 81%): HRMS Calcd. for C$_{20}$H$_{17}$IN$_4$O$_3$: 489.0423, Found 489.0431.

Example 11

Method I for the Synthesis of Compounds of Formula vi (See Scheme 1)

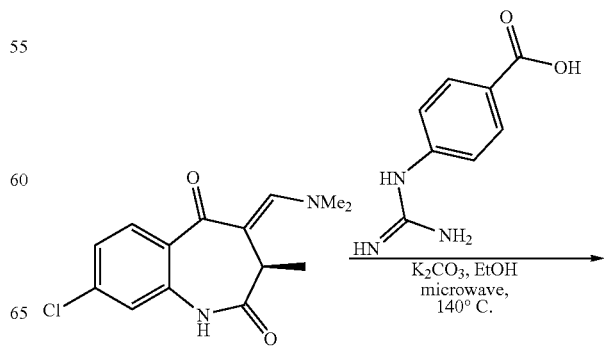

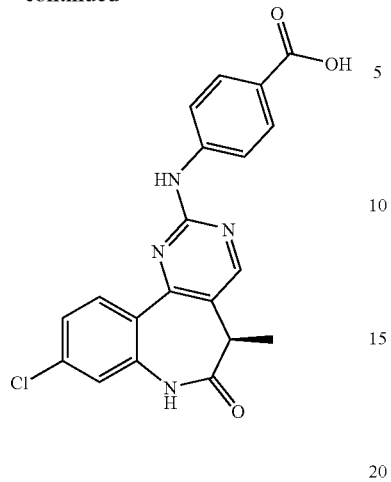

4-(9-Chloro-5-methyl-6-oxo-6,7-dihydro-5H-benzo[b]pyrimido[4,5-d]azepin-2-ylamino)-benzoic acid (I-69)

8-Chloro-4-dimethylamino-methylene-3-methyl-3,4-dihydro-1H-benzo[b]azepine-2,5-dione (v-i) (0.125 g, 0.45 mmol) was dissolved in ethanol (5 mL), then 4-guanidinebenzoic acid hydrochloride (0.116 g, 0.54 mmol) and potassium carbonate (0.153 g, 1.08 mmol) were added. The mixture was heated to 140° C. in a microwave reactor for 10 minutes, after which it was poured into water (10 mL). Using 1M aqueous HCl, the mixture was acidified to pH 4. The solid was filtered and washed with water and diethyl ether, then dried under reduced pressure at 40° C. for 16 h to give I-69 (5% yield) after purification by C-18 RP LC-MS chromatography: HRMS Calcd. for $C_{20}H_{15}ClN_4O_3$: 395.0910, Found 395.0938.

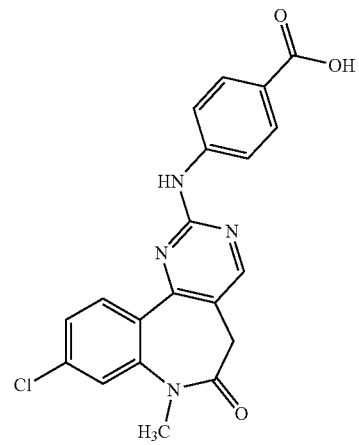

4-(9-Chloro-7-methyl-6-oxo-6,7-dihydro-5H-benzo[b]pyrimido[4,5-d]azepin-2-ylamino)-benzoic acid (I-7)

In a manner similar to that described for method I, 8-chloro-4-dimethylaminomethylene-1-methyl-3,4-dihydro-1H-benzo[b]azepine-2,5-dione (v-m) and 4-guanidinobenzoic acid were converted to I-7 (30%): HRMS Calcd. for $C_{20}H_{15}ClN_4O_3$: 395.0910, Found 395.0923.

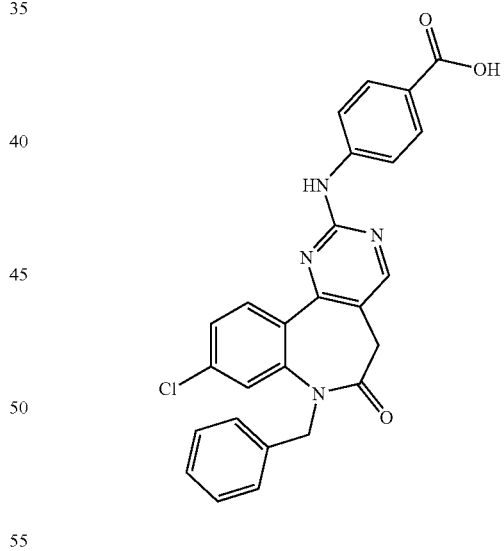

4-(9-Chloro-6-oxo-6,7-dihydro-5H-benzo[b]pyrimido[4,5]azepin-2-ylamino)-benzoic acid methyl ester (I-4)

In a manner similar to that described for Method I, (N-methyl-pyrrolidinone and NaHCO$_3$ used in place of EtOH and K$_2$CO$_3$), 8-chloro-4-dimethylaminomethylene-3,4-dihydro-1H-benzo[b]azepine-2,5-dione (v-j) and methyl 4-guanidinobenzoate hydrochloride were converted to I-4 (59%): HRMS Calcd. for $C_{20}H_{15}ClN_4O_3$: 395.0910, Found 395.0917

4-(7-Benzyl-9-chloro-6-oxo-6,7-dihydro-5H-benzo[b]pyrimido[4,5-d]azepin-2-ylamino)-benzoic acid (I-6)

In a manner similar to that described for method I, 1-benzyl-8-chloro-4-dimethylaminomethylene-3,4-dihydro-1H-benzo[b]azepine-2,5-dione (v-N) and 4-guanidinobenzoic acid were converted to I-6 (26%): MS m/z=471 (M+H) HRMS Calcd. for $C_{26}H_{19}ClN_4O_3$: 471.1223, Found 471.1310.

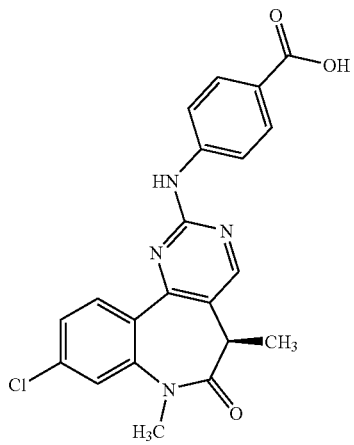

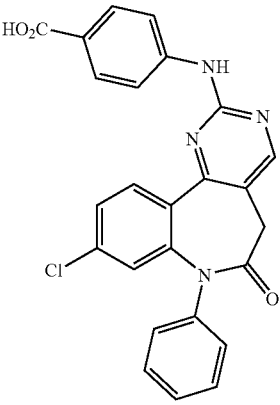

4-(9-Chloro-5,7-dimethyl-6-oxo-6,7-dihydro-5H-benzo[b]pyrimido[4,5-d]azepin-2-ylamino)-benzoic acid (I-68)

In a manner similar to that described for method I, 8-chloro-4-dimethylaminomethylene-1,3-dimethyl-3,4-dihydro-1H-benzo[b]azepine-2,5-dione (v-o) and 4-guanidinobenzoic acid were converted to I-68 (6%) after purification by C-18 RP LC-MS chromatography: HRMS Calcd. for $C_{21}H_{17}ClN_4O_3$: 409.1067, Found 409.1052.

4-(9-Chloro-6-oxo-7-phenyl-6,7-dihydro-5H-benzo[b]pyrimido[4,5-d]azepin-2-ylamino)-benzoic acid (I-10)

In a manner similar to method I (DMF and NaHCO$_3$ were used in place of EtOH and KCO$_3$), 8-chloro-4-dimethylaminomethylene-1-phenyl-3,4-dihydro-1H-benzo[b]azepine-2,5-dione (v-i) and 4-guanidinobenzoic acid were converted to I-10 (61%): HRMS Calcd. for $C_{25}H_{17}ClN_4O_3$: 457.1067, Found 457.1076.

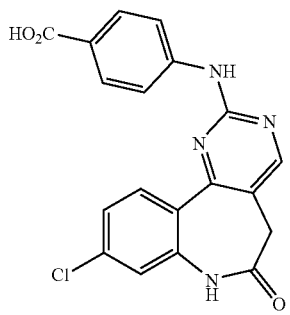

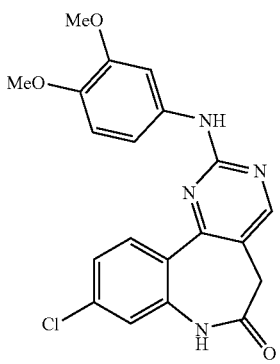

4-(9-Chloro-6-oxo-6,7-dihydro-5H-benzo[b]pyrimido[4,5-d]azepin-2-ylamino)-benzoic acid (I-3)

In a manner similar to method I (DMF and NaHCO$_3$ were used in place of EtOH and K$_2$CO$_3$), 8-chloro-4-dimethylaminomethylene-3,4-dihydro-1H-benzo[b]azepine-2,5-dione (v-j) and 4-guanidinobenzoic acid were converted to I-3 (68%): HRMS Calcd. for $C_{19}H_{13}ClN_4O_3$: 381.0754, Found 381.0721.

9-Chloro-2-(3,4-dimethoxy-phenylamino)-5H,7H-benzo[b]pyrimido[4,5-d]azepin-6-one In a manner similar to method I (DMF and NaHCO$_3$ were used in place of EtOH and K$_2$CO$_3$), 8-chloro-4-dimethylaminomethylene-3,4-dihydro-1H-benzo[b]-azepine-2,5-dione (v-j) and 1-(3,4-dimethoxyphenyl)guanidine were converted to I-2 (87%): HRMS Calcd. for $C_{20}H_{17}ClN_4O_3$: 397.1067, Found 397.109.

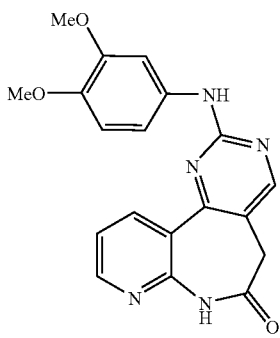

2-(3,4-Dimethoxy-phenylamino)-5,7-dihydro-1,3,7,8-tetraaza-dibenzo[a,c]cyclohepten-6-one (I-1)

In a manner similar to method H (NaHCO$_3$ used in place of K$_2$CO$_3$) (Z)-6-dimethylaminomethylene-6,7-dihydro-9H-pyrido[2,3-b]azepine-5,8-dione (v-h) and 1-(3,4-dimethoxyphenyl)guanidine were converted to I-1 (85%): MS R$_f$=1.3 min. m/z 364 (M+H).

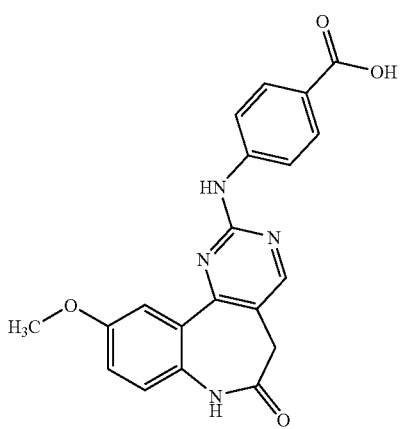

4-(10-Methoxy-6-oxo-6,7-dihydro-5H-benzo[b]pyrimido[4,5-d]azepin-2-ylamino)-benzoic acid (I-8)

In a manner similar to that described for Method H, 4-dimethylamino-methylene-7-methoxy-3,4-dihydro-1H-benzo[b]azepine-2,5-dione (v-e) and 4-guanidinobenzoic acid were converted to I-8 (48%): HRMS Calcd. for C$_{20}$H$_{16}$N$_4$O$_4$: 377.1249, Found 377.1231.

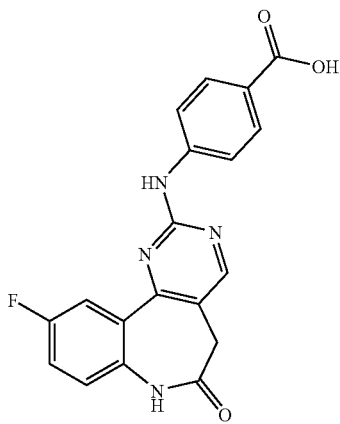

4-(10-Fluoro-6-oxo-6,7-dihydro-5H-benzo[b]pyrimido[4,5-d]azepin-2-ylamino)-benzoic acid (I-5)

In a manner similar to that described for Method H, 4-dimethylaminomethylene-7-fluoro-3,4-dihydro-1H-benzo[b]azepine-2,5-dione (v-f) and 4-guanidinobenzoic acid were converted to I-5 (98%): HRMS Calcd. for C$_{19}$H$_{13}$FN$_4$O$_3$: 365.1049, Found 365.1069.

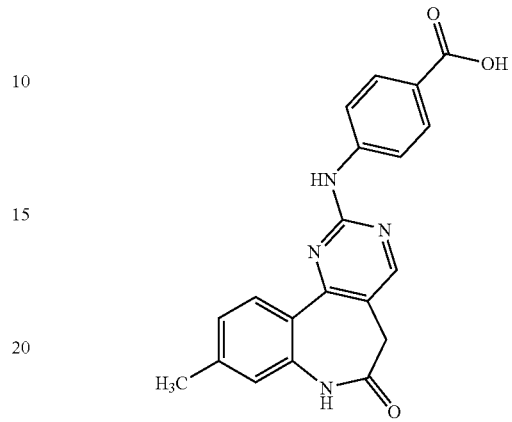

4-(9-Methyl-6-oxo-6,7-dihydro-5H-benzo[b]pyrimido[4,5-d]azepin-2-ylamino)-benzoic acid (I-9)

In a manner similar to that described for Method H, 4-dimethylamino-methylene-8-methyl-3,4-dihydro-1H-benzo[b]azepine-2,5-dione (v-g) and 4-guanidinobenzoic acid were converted to I-9 (36%): HRMS Calcd. for C$_{20}$H$_{16}$N$_4$O$_3$: 361.1300, Found 361.1306.

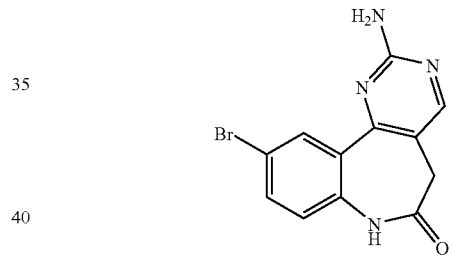

2-Amino-10-bromo-5H,7H-benzo[b]pyrimido[4,5-d]azepin-6-one (I-44)

In a manner similar to that described in method H, 7-bromo-4-dimethylaminomethylene-3,4-dihydro-1H-benzo[b]azepine-2,5-dione (v-k) and guanidine were converted to I-44 (79%): HRMS Calcd. for C$_{12}$H$_9$BrN$_4$O: 305.0037, Found 305.0042.

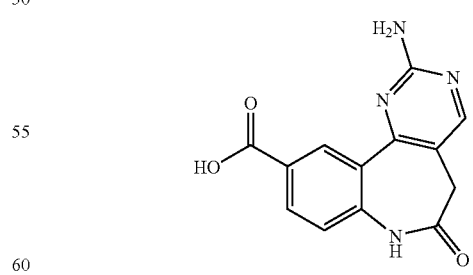

2-Amino-6-oxo-6,7-dihydro-5H-benzo[b]pyrimido[4,5-d]azepine-10-carboxylic acid (I-84)

In a manner similar to Method M, 2-amino-10-bromo-5H,7H-benzo[b]pyrimido[4,5-d]azepin-6-one (I-44) was converted to I-84 (97%) after purification by C-18 RP LC-MS chromatography. MS (FA) R$_f$=0.99 min, m/z=271 (M+H).

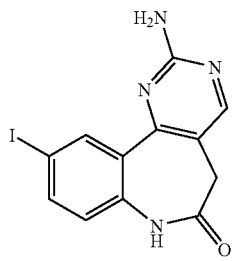

2-Amino-10-iodo-5H,7H-benzo[b]pyrimido[4,5-d]azepin-6-one (I-51)

In a manner similar to that described in method H, 7-iodo-4-dimethylaminomethylene-3,4-dihydro-1H-benzo[b]azepine-2,5-dione (v-a) and guanidine were converted to I-51 (79%): HRMS Calcd. for $C_{12}H_9N_4O$: 352.9899, Found 352.9900.

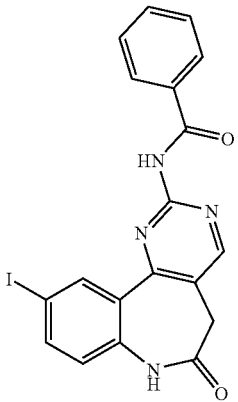

N-(10-Iodo-6-oxo-6,7-dihydro-5H-benzo[b]pyrimido[4,5-d]azepin-2-yl)-benzamide (I-83)

2-Amino-10-iodo-5H,7H-benzo[b]pyrimido[4,5-d]azepin-6-one (I-51) (69.7 mg, 0.20 mmol) was dissolved in pyridine (800 μL) and benzoyl chloride (23 mL, 0.20 mmol). The mixture was stirred at 110° C. for 1 h, then cooled to 22° C. Et$_2$O was added and the product was filtered from the solution to give I-83 (37%): MS (FA) R$_t$=1.49 min, m/z=457 (M+H).

Example 12

Method M for the Synthesis of Compounds of Formula xii (See Scheme 3)

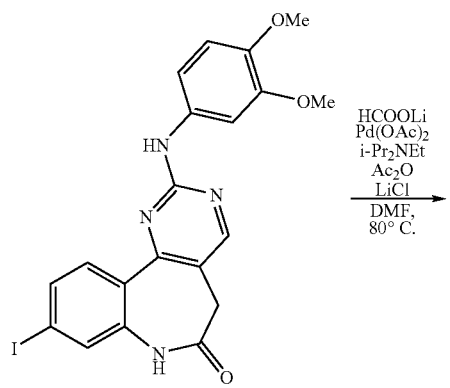

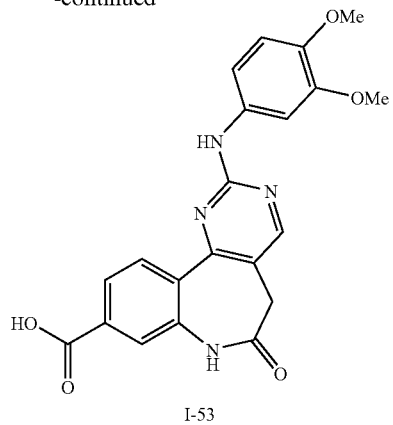

2-(3,4-Dimethoxy-phenylamino)-6-oxo-6,7-dihydro-5H-benzo[b]pyrimido[4,5-d]azepine-9-carboxylic acid (I-53)

To a solution of 2-(3,4-dimethoxy-phenylamino)-9-iodo-5H,7H-benzo[b]pyrimido[4,5-d]azepin-6-one (I-30) (0.60 g, 1.20 mmol) in dry DMF (8 mL) was added Ac$_2$O (0.23 mL, 2.44 mmol), HCOOLi (0.19 g, 3.66 mmol), LiCl (0.155 g, 3.66 mmol), and Pd(OAc)$_2$ (0.01 g, 0.06 mmol). Lastly, i-Pr$_2$NEt (0.42 mL, 2.44 mmol) was added and the mixture heated for 16 h at 80° C. in a sealed tube. The reaction mixture was then diluted with CH$_2$Cl$_2$ (30 mL), and the organic layer was washed with H$_2$O (3×30 mL), dried over MgSO$_4$, filtered and concentrated in vacuo to give crude product as a yellow solid. The solid was treated with EtOAc and sonicated to provide a white solid which was collected by filtration to provide I-53 (0.33 g, 71%): HRMS Calcd. for $C_{21}H_{18}N_4O_5$: 407.1355, Found 407.1364.

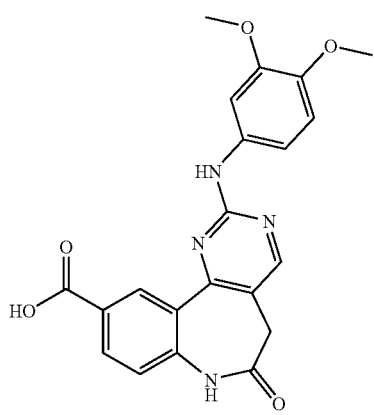

2-(3,4-Dimethoxy-phenylamino)-6-oxo-6,7-dihydro-5H-benzo[b]pyrimido[4,5-d]azepine-10-carboxylic acid (I-43)

In a manner similar to Method M, 2-(3,4-dimethoxy-phenylamino)-10-iodo-5H,7H-benzo[b]pyrimido[4,5-d]azepin-6-one (I-26) was converted to I-43 (100%):

HRMS Calcd. for $C_{21}H_{18}N_4O_5$: 407.1355, Found 407.1357.

Example 13

Method N for the Synthesis of Compounds of Formula xiii and xxix (See Schemes 3 and 7)

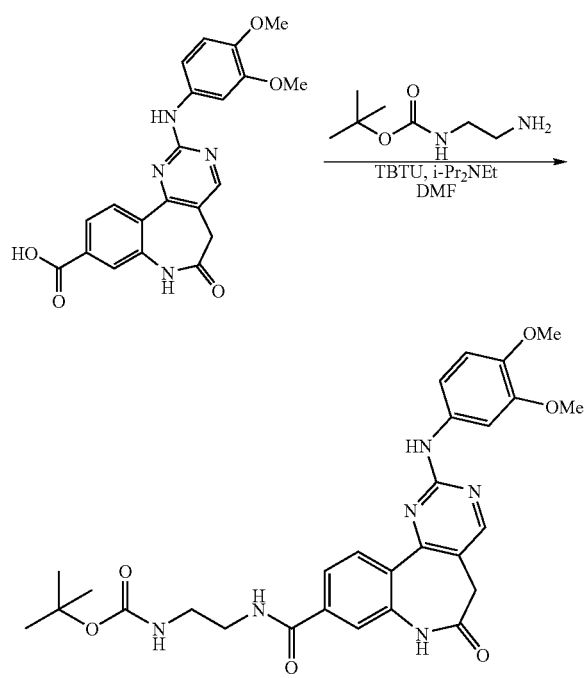

(2-{[2-(3,4-Dimethoxy-phenylamino)-6-oxo-6,7-dihydro-5H-benzo[b]pyrimido[4,5-d]azepine-9-carbonyl]-amino}-ethyl)-carbamic acid tert-butyl ester (I-71-a)

To a solution of 2-(3,4-dimethoxy-phenylamino)-6-oxo-6,7-dihydro-5H-benzo[b]pyrimido[4,5-d]azepine-9-carboxylic acid (I-53) (75 mg, 0.18 mmol) in DMF (5 mL) was added N,N-diisopropylethylamine (0.10 mL, 0.55 mmol), TBTU (65 mg, 0.20 mmol), and tert-butyl 2-aminoethylcarbamate (35.5 mg, 0.22 mmol). The reaction stirred at 22° C. overnight. The reaction mixture was diluted with H$_2$O, and the precipitate that formed was filtered, washed with H$_2$O and dried to give I-71-a [MS m/z=549 (M+H)] which was carried on crude to the deprotection.

Example 14

Method K for Boc-Deprotections

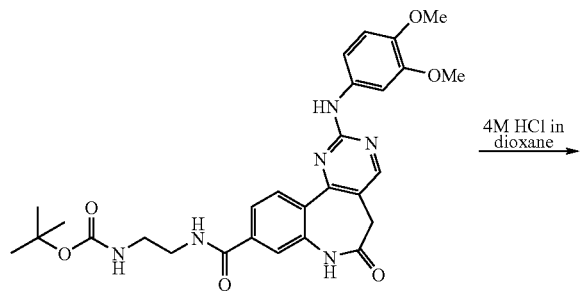

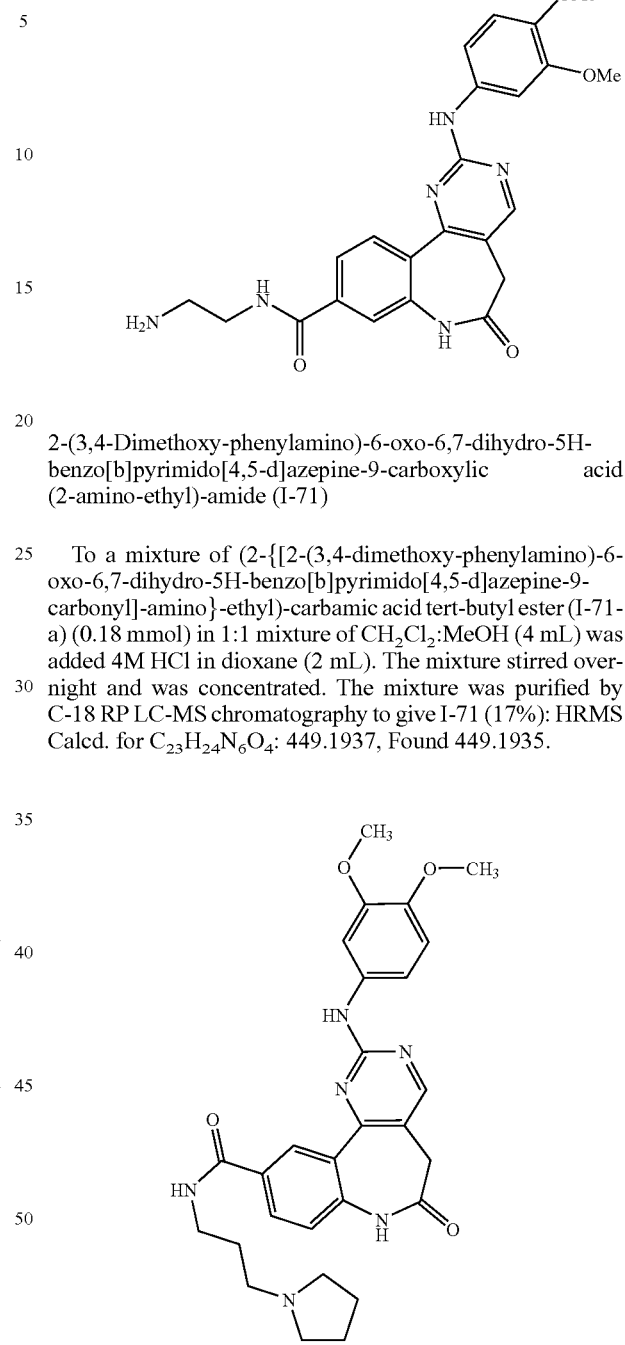

2-(3,4-Dimethoxy-phenylamino)-6-oxo-6,7-dihydro-5H-benzo[b]pyrimido[4,5-d]azepine-9-carboxylic acid (2-amino-ethyl)-amide (I-71)

To a mixture of (2-{[2-(3,4-dimethoxy-phenylamino)-6-oxo-6,7-dihydro-5H-benzo[b]pyrimido[4,5-d]azepine-9-carbonyl]-amino}-ethyl)-carbamic acid tert-butyl ester (I-71-a) (0.18 mmol) in 1:1 mixture of CH$_2$Cl$_2$:MeOH (4 mL) was added 4M HCl in dioxane (2 mL). The mixture stirred overnight and was concentrated. The mixture was purified by C-18 RP LC-MS chromatography to give I-71 (17%): HRMS Calcd. for C$_{23}$H$_{24}$N$_6$O$_4$: 449.1937, Found 449.1935.

2-(3,4-Dimethoxy-phenylamino)-6-oxo-6,7-dihydro-5H-benzo[b]pyrimido[4,5-d]azepine-10-carboxylic acid (3-pyrrolidin-1-yl-propyl)-amide (I-77)

In a manner similar to that described in Method N, 2-(3,4-dimethoxy-phenylamino)-6-oxo-6,7-dihydro-5H-benzo[b]pyrimido[4,5-d]azepine-10-carboxylic acid (I-43) and 3-(pyrrolidin-1-yl)propan-1-amine were converted to I-77 (6%) after purification by C-18 RP LC-MS chromatography. HRMS Calcd. for C$_{28}$H$_{32}$N$_6$O$_4$: 517.2563, Found 517.2552.

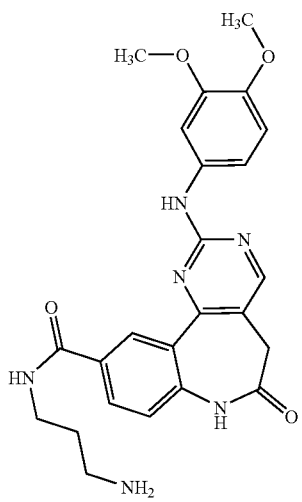

2-(3,4-Dimethoxy-phenylamino)-6-oxo-6,7-dihydro-5H-benzo[b]pyrimido[4,5-d]azepine-10-carboxylic acid (3-amino-propyl)-amide (I-76)

In a manner similar to that described in Method N, 2-(3,4-dimethoxy-phenylamino)-6-oxo-6,7-dihydro-5H-benzo[b]pyrimido[4,5-d]azepine-10-carboxylic acid (I-43) and 3-amino-propyl-carbamic acid tert-butyl ester were converted to (3-{[2-(3,4-dimethoxy-phenylamino)-6-oxo-6,7-dihydro-5H-benzo[b]pyrimido[4,5-d]azepine-10-carbonyl]-amino}-propyl)-carbamic acid tert-butyl ester, which was subsequently deprotected (Method K) and purified by C-18 RP LC-MS chromatography to give I-76 (14%): HRMS Calcd. for $C_{24}H_{26}N_6O_4$: 463.2093, Found 463.2085.

after purification by C-18 RP LC-MS chromatography. HRMS Calcd. for $C_{27}H_{30}N_6O_4$: 503.2406, Found 503.2399.

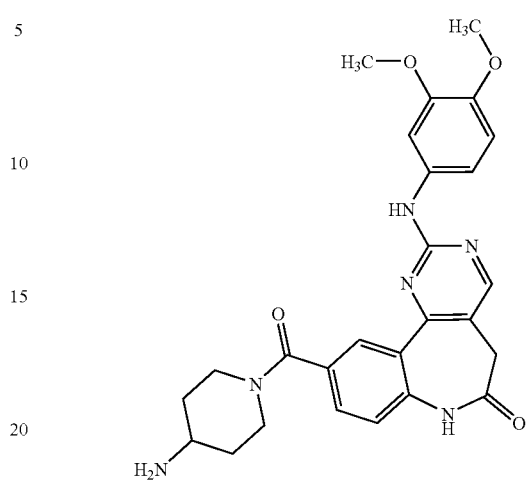

10-(4-Amino-piperidine-1-carbonyl)-2-(3,4-dimethoxy-phenylamino)-5H,7H-benzo[b]pyrimido[4,5-d]azepin-6-one (I-74)

In a manner similar to that described for Method N, 2-(3,4-dimethoxy-phenylamino)-6-oxo-6,7-dihydro-5H-benzo[b]pyrimido[4,5-d]azepine-10-carboxylic acid (I-43) and piperidin-4-yl-carbamic acid tert-butyl ester were converted to {1-[2-(3,4-dimethoxy-phenylamino)-6-oxo-6,7-dihydro-5H-benzo[b]pyrimido[4,5-d]azepine-10-carbonyl]-piperidin-4-yl}-carbamic acid tert-butyl ester, which was subsequently deprotected according to Method K. Purification by C-18 RP LC-MS chromatography afforded I-74 (19%): HRMS Calcd. for $C_{26}H_{28}N_6O_4$: 489.2250, Found 489.2253.

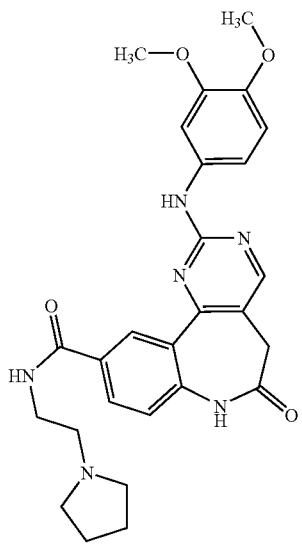

2-(3,4-Dimethoxy-phenylamino)-6-oxo-6,7-dihydro-5H-benzo[b]pyrimido[4,5-d]azepine-10-carboxylic acid (2-pyrrolidin-1-yl-ethyl)-amide (I-75)

In a manner similar to that described for Method N, 2-(3,4-dimethoxy-phenylamino)-6-oxo-6,7-dihydro-5H-benzo[b]pyrimido[4,5-d]azepine-10-carboxylic acid (I-43) and 2-(pyrrolidin-1-yl)ethanamine were converted to I-75 (6%)

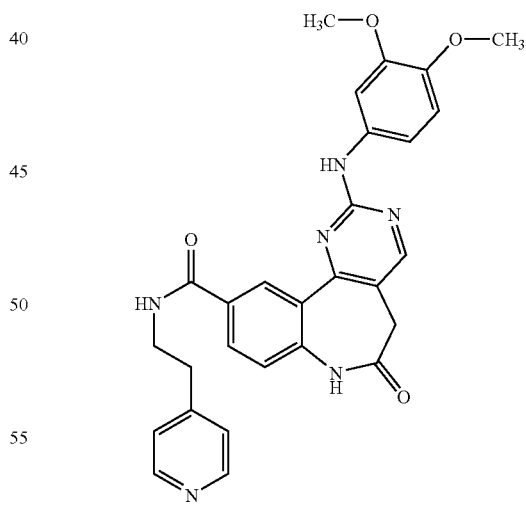

2-(3,4-Dimethoxy-phenylamino)-6-oxo-6,7-dihydro-5H-benzo[b]pyrimido[4,5-d]azepine-10-carboxylic acid (2-pyridin-4-yl-ethyl)-amide (I-48)

In a manner similar to that described for Method N, 2-(3,4-dimethoxy-phenylamino)-6-oxo-6,7-dihydro-5H-benzo[b]pyrimido[4,5-d]azepine-10-carboxylic acid (I-43) and 2-(pyridin-4-yl)ethanamine were converted I-48 (6%): HRMS Calcd. for $C_{28}H_{26}N_6O_4$: 551.2093, Found 511.2098.

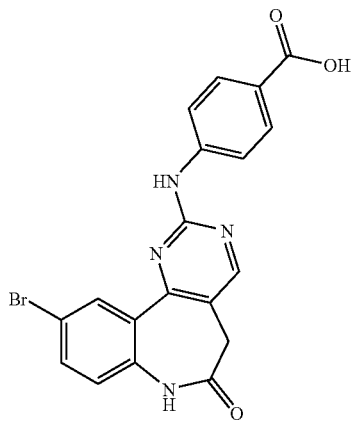

4-(10-Bromo-6-oxo-6,7-dihydro-5H-benzo[b]pyrimido[4,5-d]azepin-2-ylamino)-benzoic acid (I-25)

In a manner similar to method I, 7-bromo-4-dimethylaminomethylene-3,4-dihydro-1H-benzo[b]azepine-2,5-dione (v-k) and 4-guanidinobenzoic acid were converted to I-25 (22%): HRMS Calcd. for $C_{19}H_{13}BrN_4O_3$: 425.0249, Found 425.0269.

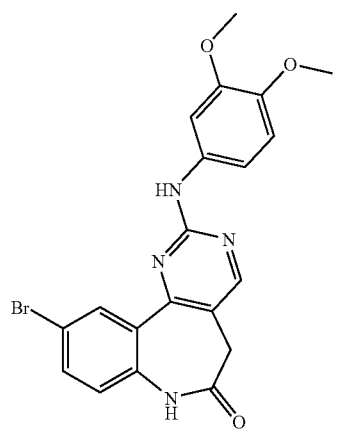

10-Bromo-2-(3,4-dimethoxy-phenylamino)-5H,7H-benzo[b]pyrimido[4,5-d]azepin-6-one (I-18)

In a manner similar to method I (NaHCO$_3$ used instead of K$_2$CO$_3$), 7-bromo-4-dimethylaminomethylene-3,4-dihydro-1H-benzo[b]azepine-2,5-dione (v-k) and 1-(3,4-dimethoxyphenyl)-guanidine were converted to I-18 (74%): HRMS Calcd. for $C_{20}H_{17}BrN_4O_3$: 441.0562, Found 441.0548.

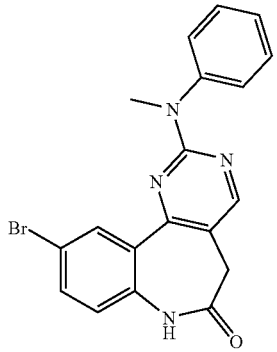

10-Bromo-2-(methyl-phenyl-amino)-5H,7H-benzo[b]pyrimido[4,5-d]azepin-6-one (I-85)

A mixture of 10-bromo-2-methanesulfinyl-5H,7H-benzo[b]pyrimido[4,5-d]azepin-6-one (100 mg) was stirred with N-methyl aniline (1 mL) and refluxed overnight at 150° C. Water was added and the product was extracted with methylene chloride, dried over MgSO$_4$, filtered and concentrated. Purification by C-18 RP LC-MS chromatography afforded I-85 (10%): MS m/z=395 (M+H).

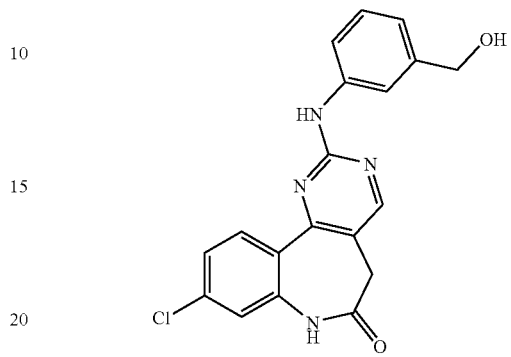

9-Chloro-2-(3-hydroxymethyl-phenylamino)-5H,7H-benzo[b]pyrimido[4,5-d]-azepine-6-one (I-79)

In a manner similar to method I, 8-chloro-4-((dimethylamino)methylene)-3,4-dihydro-1H-benzo[b]azepine-2,5-dione (v-j) and 1-(3-(hydroxymethyl)phenyl)-guanidine were converted to I-79 (51%): HRMS Calcd. for $C_{19}H_{15}ClN_4O_2$: 367.0961, Found 367.0973.

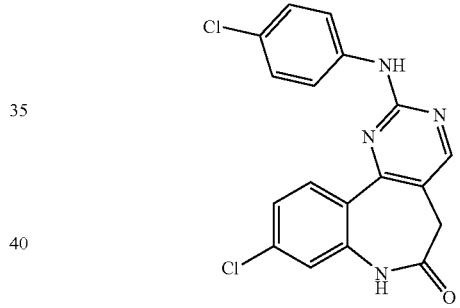

9-Chloro-2-(4-chloro-phenylamino)-5H,7H-benzo[b]pyrimido[4,5-d]azepin-6-one (I-11)

In a manner similar to that described for method I, 8-chloro-4-dimethylaminomethylene-3,4-dihydro-1H-benzo[b]azepine-2,5-dione (v-j) and 1-(4-chlorophenyl)guanidine were converted to I-11 (23%): HRMS Calcd. for $C_{18}H_{12}Cl_2N_4O$: 371.0466, Found 371.0471.

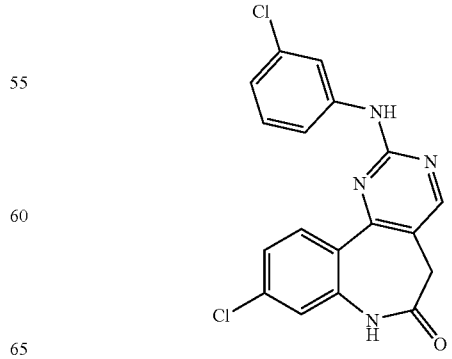

9-Chloro-2-(3-chloro-phenylamino)-5H,7H-benzo[b]pyrimido[4,5-d]azepin-6-one (I-13)

In a manner similar to that described for method I, 8-chloro-4-dimethylaminomethylene-3,4-dihydro-1H-benzo[b]azepine-2,5-dione (v-j) and 1-(3-chlorophenyl)guanidine were converted to I-13 (26%): HRMS Calcd. for $C_{18}H_{12}Cl_2N_4O$: 371.0466, Found 371.0489.

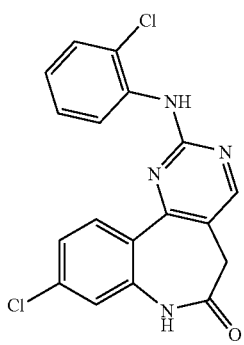

9-Chloro-2-(2-chloro-phenylamino)-5H,7H-benzo[b]pyrimido[4,5-d]azepin-6-one (I-12)

In a manner similar to that described for method I, 8-chloro-4-dimethylaminomethylene-3,4-dihydro-1H-benzo[b]azepine-2,5-dione (v-j) and 1-(2-chlorophenyl)guanidine were converted to I-12 (26%): HRMS Calcd. for $C_{18}H_{12}Cl_2N_4O$: 371.0466, Found 371.0467.

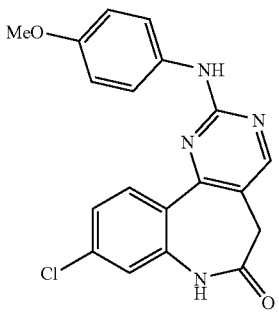

9-Chloro-2-(4-methoxy-phenylamino)-5H,7H-benzo[b]pyrimido[4,5-d]azepin-6-one (I-14)

In a manner similar to that described for method I, 8-chloro-4-dimethylaminomethylene-3,4-dihydro-1H-benzo[b]azepine-2,5-dione (v-j) and 1-(4-methoxyphenyl)guanidine were converted to I-14 (39%): HRMS Calcd. for $C_{19}H_{15}ClN_4O_2$: 367.0960, Found 367.0975.

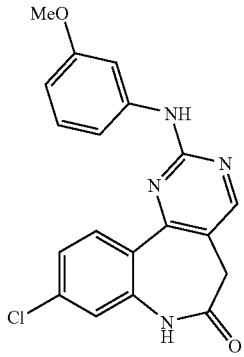

9-Chloro-2-(3-methoxy-phenylamino)-5H,7H-benzo[b]pyrimido[4,5-d]azepin-6-one (I-15)

In a manner similar to that described for method I, 8-chloro-4-dimethylaminomethylene-3,4-dihydro-1H-benzo[b]azepine-2,5-dione (v-j) and 1-(3-methoxyphenyl)guanidine were converted to I-15 (25%): HRMS Calcd. for $C_{19}H_{15}ClN_4O_2$: 367.0961, Found 367.0961.

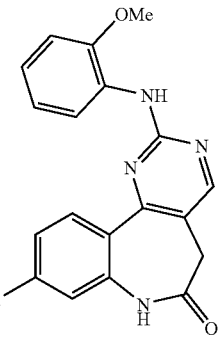

9-Chloro-2-(2-methoxy-phenylamino)-5H,7H-benzo[b]pyrimido[4,5-d]azepin-6-one (I-16)

In a manner similar to that described for method I, 8-chloro-4-dimethylaminomethylene-3,4-dihydro-1H-benzo[b]azepine-2,5-dione (v-j) and 1-(2-methoxyphenyl)guanidine were converted to I-16 (39%): HRMS Calcd. for $C_{19}H_{15}ClN_4O_2$: 367.0961, Found 367.0947.

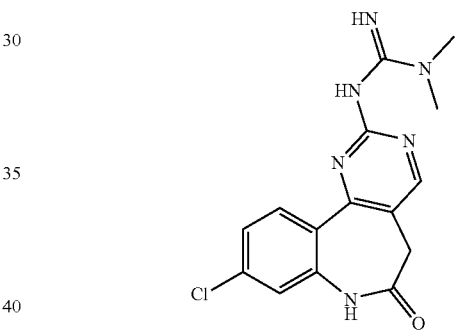

N'-(9-Chloro-6-oxo-6,7-dihydro-5H-benzo[b]pyrimido[4,5-d]azepin-2-yl)-N,N-dimethyl-guanidine (I-21)

In a manner similar to that described for method I, 8-chloro-4-dimethylaminomethylene-3,4-dihydro-1H-benzo[b]azepine-2,5-dione (v-j) and 1,1-dimethylbiguanidine hydrochloride were converted to I-21 (9%): HRMS Calcd. for $C_{15}H_{15}ClN_6O$: 331.1074, Found 331.1063.

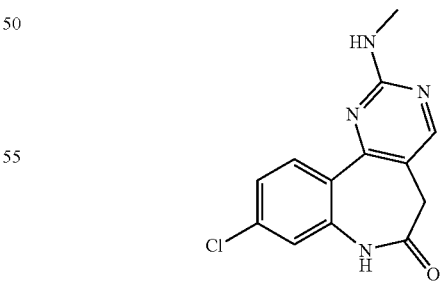

9-Chloro-2-methylamino-5H,7H-benzo[b]pyrimido[4,5-d]azepin-6-one (I-20)

In a manner similar to that described for method I, 8-chloro-4-dimethylaminomethylene-3,4-dihydro-1H-benzo[b]azepine-2,5-dione (v-j) and N-methylguanidine hydrochloride were converted to I-20 (32%): HRMS Calcd. for $C_{13}H_{11}ClN_4O$: 275.0699, Found 275.0708.

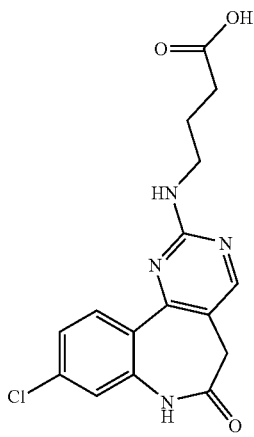

4-(9-Chloro-6-oxo-6,7-dihydro-5H-benzo[b]pyrimido[4,5-d]azepin-2-ylamino)-butyric acid (I-19)

In a manner similar to that described for method I, 8-chloro-4-dimethylaminomethylene-3,4-dihydro-1H-benzo[b]azepine-2,5-dione (v-j) and 4-guanidino butyric acid were converted to I-19 (6%): HRMS Calcd. for $C_{16}H_{15}ClN_4O_3$: 347.091, Found 347.092.

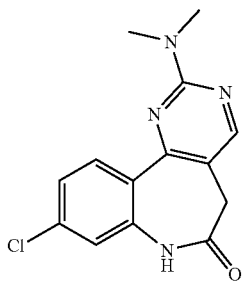

9-Chloro-2-dimethylamino-5H,7H-benzo[b]pyrimido[4,5-d]azepin-6-one (I-22)

In a manner similar to that described for method I, 8-chloro-4-dimethylaminomethylene-3,4-dihydro-1H-benzo[b]azepine-2,5-dione (v-j) and 1,1-dimethylguanidine sulfate were converted to I-22 (42%): HRMS Calcd. for $C_{14}H_{13}ClN_4O$: 289.0856, Found 289.0843.

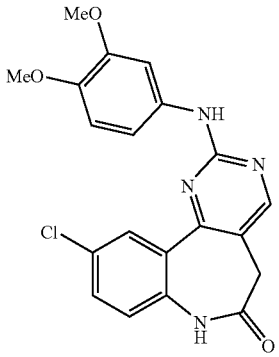

10-Chloro-2-(3,4-dimethoxy-phenylamino)-5H,7H-benzo[b]pyrimido[4,5-d]azepin-6-one (I-24)

In a manner similar to that described for method I, 7-chloro-4-dimethylaminomethylene-3,4-dihydro-1H-benzo[b]azepine-2,5-dione (v-d) and N-(3,4-dimethoxyphenyl)guanidine nitrate were converted to I-24 (67%): HRMS Calcd. for $C_{20}H_{17}ClN_4O_3$: 397.1067, Found 397.1059.

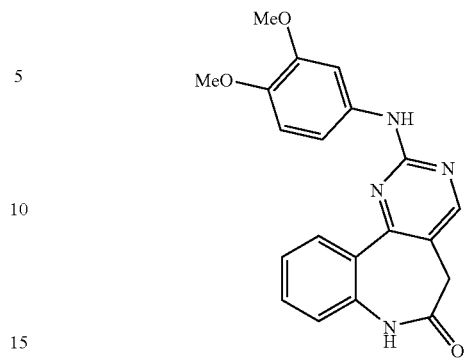

2-(3,4-Dimethoxy-phenylamino)-5H,7H-benzo[b]pyrimido[4,5-d]azepin-6-one (I-27)

In a manner similar to that described for method I, 4-dimethylaminomethylene-3,4-dihydro-1H-benzo[b]azepine-2,5-dione (v-c) and N-(3,4-dimethoxyphenyl)guanidine nitrate were converted to I-27 (58%): HRMS Calcd. for $C_{20}H_{18}N_4O_3$: 363.1457, Found 363.1441.

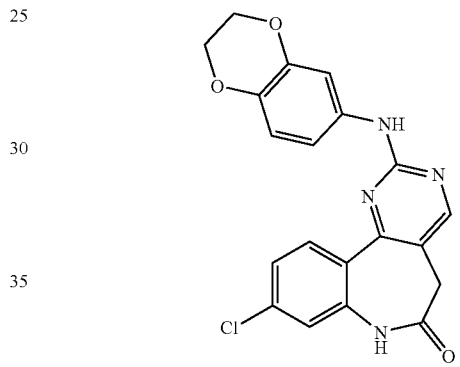

9-Chloro-2-(2,3-dihydro-benzo[1,4]dioxin-6-ylamino)-5H, 7H-benzo[b]pyrimido[4,5-d]azepin-6-one (I-28)

In a manner similar to that described for method I, 8-chloro-4-dimethylaminomethylene-3,4-dihydro-1H-benzo[b]azepine-2,5-dione (v-j) and N-(2,3-dihydro-benzo[1,4]dioxin-6-yl)-guanidine nitrate were converted to I-28 (71%): HRMS Calcd. for $C_{20}H_{15}ClN_4O_3$: 395.091, Found 395.0912.

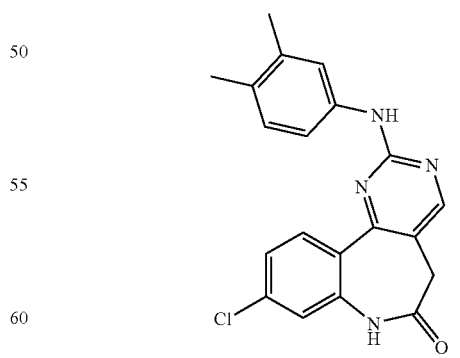

9-Chloro-2-(3,4-dimethyl-phenylamino)-5H,7H-benzo[b]pyrimido[4,5-d]azepin-6-one (I-29)

In a manner similar to that described for method I, 8-chloro-4-dimethylaminomethylene-3,4-dihydro-1H-benzo[b]azepine-2,5-dione (v-j) and N-(3,4-dimethyl-phe-

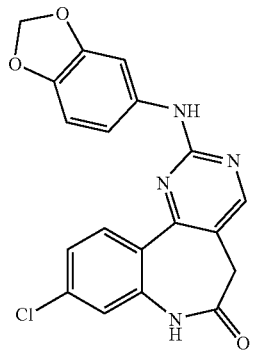

2-(Benzo[1,3]dioxol-5-ylamino)-9-chloro-5H,7H-benzo[b]pyrimido[4,5-d]azepin-6-one (I-34)

In a manner similar to that described for method I, 8-chloro-4-dimethylaminomethylene-3,4-dihydro-1H-benzo[b]azepine-2,5-dione (v-j) and N-benzo[1,3]dioxol-5-yl-guanidine nitrate were converted to I-34 (32%): HRMS Calcd. for $C_{19}H_{13}ClN_4O_3$: 381.0754, Found 381.0759.

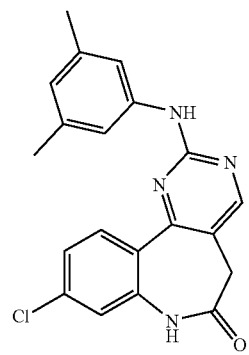

9-Chloro-2-(3,5-dimethyl-phenylamino)-5H,7H-benzo[b]pyrimido[4,5-d]azepin-6-one (I-35)

In a manner similar to that described for method I, 8-chloro-4-dimethylaminomethylene-3,4-dihydro-1H-benzo[b]azepine-2,5-dione (v-j) and N-(3,5-dimethyl-phenyl)-guanidine nitrate were converted to I-35 (71%): HRMS Calcd. for $C_{20}H_{17}ClN_4O$: 365.1169, Found 365.1190.

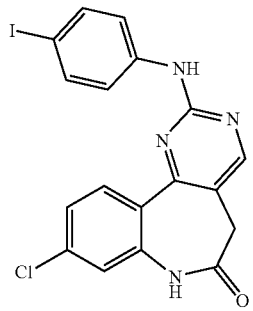

9-Chloro-2-(4-iodo-phenylamino)-5H,7H-benzo[b]pyrimido[4,5-d]azepin-6-one (I-36)

In a manner similar to that described for method I, 8-chloro-4-dimethylaminomethylene-3,4-dihydro-1H-benzo[b]azepine-2,5-dione (v-j) and N-(4-iodo-phenyl)-guanidine nitrate were converted to I-36 (62%): HRMS Calcd. for $C_{18}H_{12}ClIN_4O$: 462.9822, Found 462.9818.

Example 15

Method O for the Synthesis of Compounds of Formula xiv and xxi (See Schemes 3 and 5)

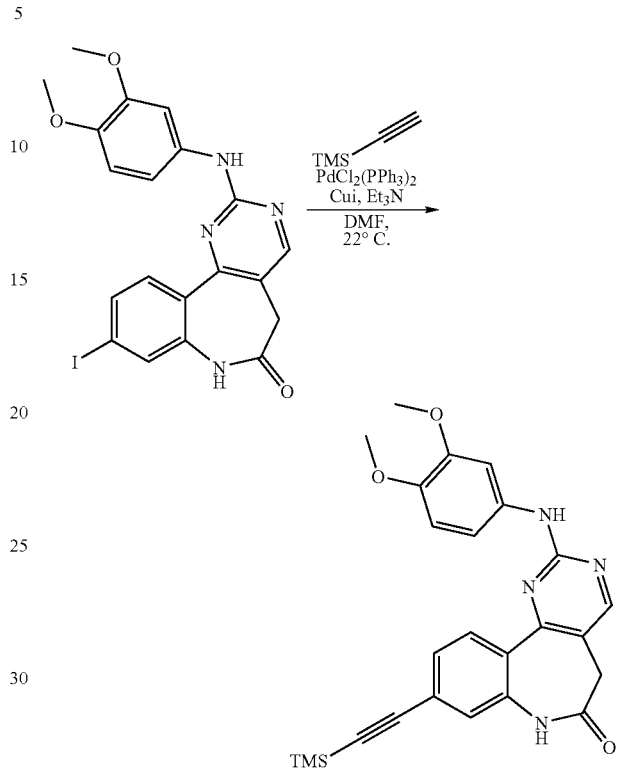

2-(3,4-Dimethoxy-phenylamino)-9-trimethylsilanylethynyl-5H,7H-benzo[b]-pyrimido[4,5-d]azepin-6-one (I-33-a)

To a solution of 2-(3,4-dimethoxy-phenylamino)-9-iodo-5H,7H-benzo[b]pyrimido[4,5-d]azepin-6-one (I-30) (300 mg, 0.614 mmol) in 4 mL DMF at 22° C. was added dichlorobis(triphenylphosphine)palladium (15 mg, 0.02 mmol), copper iodide (9 mg, 0.05 mmol), and triethylamine (0.34 mL, 2.45 mmol). The solution was degassed with argon, and stirred at 22° C. for 1 h. (Trimethylsilyl)acetylene (120 mg, 1.22 mmol) was added and the solution was stirred at 22° C. for 2 h. Water was added to the reaction mixture, and the resulting precipitate was filtered and purified by silica gel chromatography (ISCO, elution with 30-100% ethyl acetate in hexanes) to give I-33-a (180 mg, 64%): MS m/z=459 (M+H).

Example 16

Method for Ethynyl Trimethylsilane Deprotection

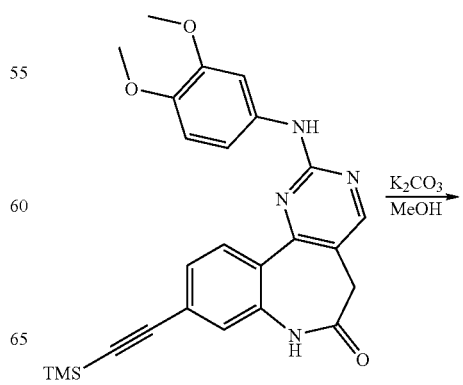

-continued

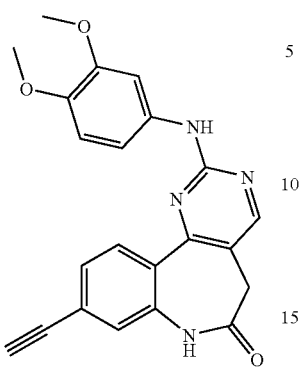

2-(3,4-Dimethoxy-phenylamino)-9-ethynyl-5H,7H-benzo[b]pyrimido[4,5-d]azepin-6-one (I-33)

To a solution of 2-(3,4-dimethoxy-phenylamino)-9-trimethylsilanyl-ethynyl-5H,7H-benzo[b]pyrimido[4,5-d]azepin-6-one (I-33-a) (180 mg, 0.39 mmol) in methanol (4 mL) was added potassium carbonate (217 mg, 1.57 mmol). The reaction stirred at 22° C. overnight. The mixture was then concentrated in vacuo, redissolved in water (100 mL) and extracted with methylene chloride (3×100 mL). The organic fractions were combined, washed with brine, dried over $Na_2SO_4$ and concentrated in vacuo to give I-33 (50 mg, 99%): HRMS Calcd. for $C_{22}H_{18}N_4O_3$: 387.1457, Found 387.1451.

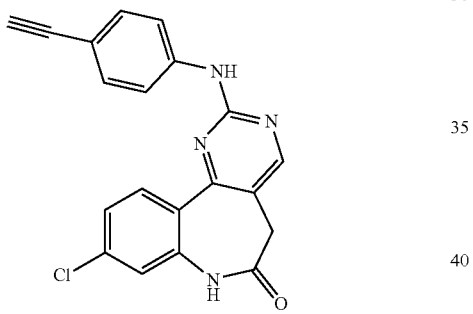

9-Chloro-2-(4-ethynyl-phenylamino)-5H,7H-benzo[b]pyrimido[4,5-d]azepin-6-one (I-45)

In a manner similar to that described for Method O, 9-chloro-2-(4-iodo-phenylamino)-5H,7H-benzo[b]pyrimido[4,5-d]azepin-6-one (I-36) and ethynyltrimethylsilane were converted to 9-chloro-2-(4-trimethylsilanylethynyl-phenylamino)-5H,7H-benzo[b]pyrimido[4,5-d]azepin-6-one, which was deprotected in a manner similar to I-33 to give I-45 (38%): HRMS Calcd. for $C_{20}H_{13}ClN_4O$: 361.0856, Found 361.0848.

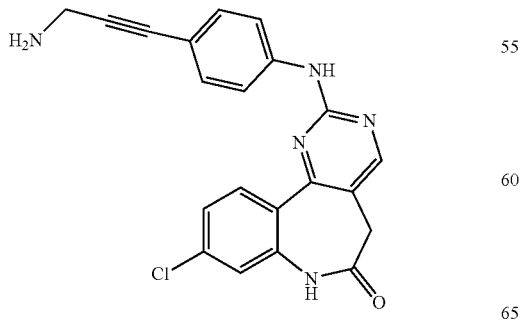

2-[4-(3-Amino-prop-1-ynyl)-phenylamino]-9-chloro-5H,7H-benzo[b]pyrimido[4,5-d]azepin-6-one (HCl salt) (I-46)

In a manner similar to that described for Method O, 9-chloro-2-(4-iodo-phenylamino)-5H,7H-benzo[b]pyrimido[4,5-d]azepin-6-one (I-36) and tert-butyl prop-2-ynylcarbamate were converted to {3-[4-(9-chloro-6-oxo-6,7-dihydro-5H-benzo[b]pyrimido[4,5-d]azepin-2-ylamino)-phenyl]-prop-2-ynyl}-carbamic acid tert-butyl ester, which was deprotected according to Method K to give I-46 (29%): HRMS Calcd. for $C_{21}H_{16}ClN_5O$: 390.1121, Found 390.1120.

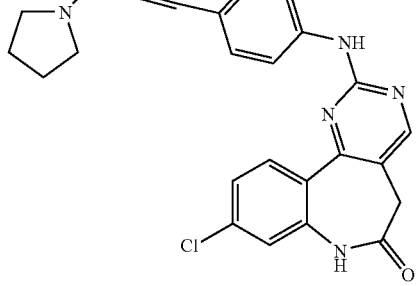

9-Chloro-2-[4-(3-pyrrolidin-1-yl-prop-1-ynyl)-phenylamino]-5H,7H-benzo[b]-pyrimido[4,5-d]azepin-6-one (I-47)

In a manner similar to that described for Method O, 9-chloro-2-(4-iodo-phenylamino)-5H,7H-benzo[b]pyrimido[4,5-d]azepin-6-one (I-36) and 1-(prop-2-ynyl)pyrrolidine were converted to I-47 (52%): HRMS Calcd. for $C_{25}H_{22}ClN_5O$: 444.1591, Found 444.1589.

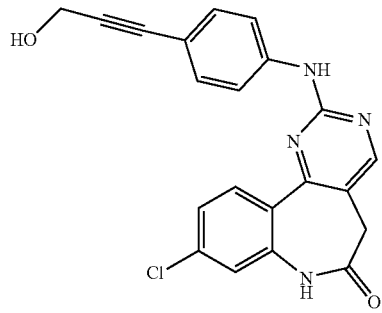

9-Chloro-2-[4-(3-hydroxy-prop-1-ynyl)-phenylamino]-5H,7H-benzo[b]pyrimido[4,5-d]azepin-6-one (I-54)

In a manner similar to that described for Method O, 9-chloro-2-(4-iodo-phenylamino)-5H,7H-benzo[b]pyrimido[4,5-d]azepin-6-one (I-36) and prop-2-yn-1-ol were converted to I-54 (86%): HRMS Calcd. for $C_{21}H_{15}ClN_4O_2$: 391.0961, Found 391.0960.

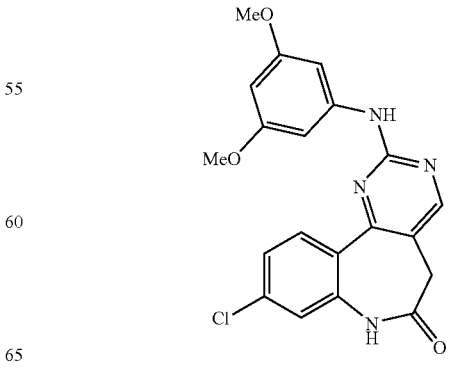

9-Chloro-2-(3,5-dimethoxy-phenylamino)-5H,7H-benzo[b]pyrimido[4,5-d]azepin-6-one (I-55)

In a manner similar to that described for method I, 8-chloro-4-dimethylaminomethylene-3,4-dihydro-1H-benzo[b]azepine-2,5-dione (v-j) and N-(3,5-dimethoxy-phenyl)-guanidine nitrate were converted to I-55 (62%): HRMS Calcd. for $C_{20}H_{17}ClN_4O_3$: 397.1067, Found 397.1056.

Example: 17

Method P for the Synthesis of Compounds of Formula xv and xxii (See Schemes 3 and 5)

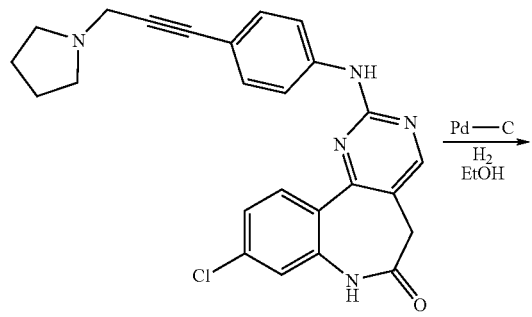

9-Chloro-2-[4-(3-pyrrolidin-1-yl-propyl)-phenylamino]-5H,7H-benzo[b]pyrimido[4,5-d]-azepin-6-one (I-66)

To a solution of 9-chloro-2-[4-(3-pyrrolidin-1-yl-prop-1-ynyl)-phenylamino]-5H,7H benzo[b]pyrimido[4,5-d]azepin-6-one (I-47) (0.082 g, 0.19 mmol) in EtOH (5 mL) was added Pd/C (10% wt, ~50% $H_2O$, 0.01 g) and the mixture was placed under $H_2$ (1 atm) and stirred for 12 h at 22° C. The reaction mixture was filtered through Celite® and the filtrate concentrated in vacuo to give crude product as a yellow oil. Purification by C-18 RP LC-MS chromatography afforded I-66 (0.046 g, 56%):

HRMS Calcd. for $C_{25}H_{26}ClN_5O$: 448.1904, Found 448.1907.

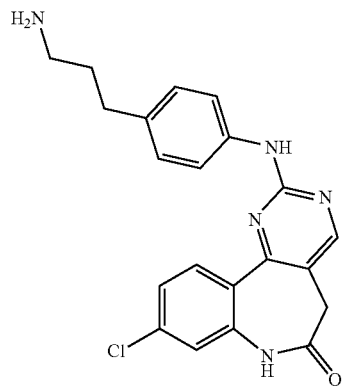

2-[4-(3-Amino-propyl)-phenylamino]-9-chloro-5H,7H-benzo[b]pyrimido[4,5-d]azepin-6-one (I-57)

In a manner similar to that described for Method P, 2-[4-(3-amino-prop-1-ynyl)-phenylamino]-9-chloro-5H,7H-benzo[b]pyrimido[4,5-d]azepin-6-one (I-46) was converted to I-57 (24%): HRMS Calcd. for $C_{21}H_{20}ClN_5O$: 394.1434, Found 394.1448.

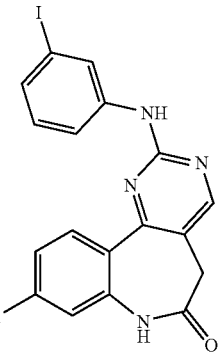

9-Chloro-2-(3-iodo-phenylamino)-5H,7H-benzo[b]pyrimido[4,5-d]azepin-6-one (I-58)

In a manner similar to that described for method I, 8-chloro-4-dimethylaminomethylene-3,4-dihydro-1H-benzo[b]azepine-2,5-dione (v-j) and N-(3-iodo-phenyl)-guanidine nitrate were converted to I-58 (50%): HRMS Calcd. for $C_{18}H_{12}ClIN_4O$: 462.9822, Found 462.9838.

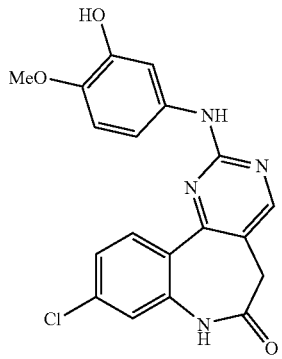

9-Chloro-2-(3-hydroxy-4-methoxy-phenylamino)-5H,7H-benzo[b]pyrimido[4,5-d]azepin-6-one (I-65)

In a manner similar to that described for method I, 8-chloro-4-dimethylaminomethylene-3,4-dihydro-1H-benzo[b]azepine-2,5-dione (v-j) and N-(3-hydroxy-4-methoxy-phenyl)-guanidine nitrate were converted to I-65 (69%): HRMS Calcd. for $C_{19}H_{15}ClN_4O_3$: 383.091, Found 383.0913.

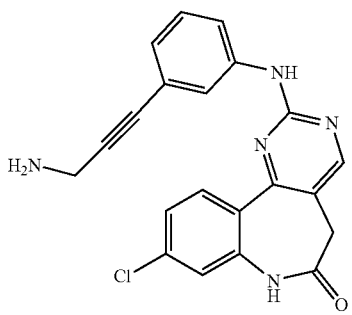

2-[3-(3-Amino-prop-1-ynyl)-phenylamino]-9-chloro-5H,7H-benzo[b]pyrimido[4,5-d]azepin-6-one (I-67)

In a manner similar to that described for Method O, 9-chloro-2-(3-iodo-phenylamino)-5H,7H-benzo[b]pyrimido[4,5-d]azepin-6-one (I-58) and tert-butyl prop-2-ynylcarbamate was converted to {3-[3-(9-chloro-6-oxo-6,7-dihydro- 5H-benzo[b]pyrimido[4,5-d]azepin-2-ylamino)-phenyl]-prop-2-ynyl}-carbamic acid tert-butyl ester, which was subsequently deprotected according to Method K to give I-67 (62%): HRMS Calcd. for $C_{21}H_{16}ClN_5O$: 390.1121, Found 390.1117.

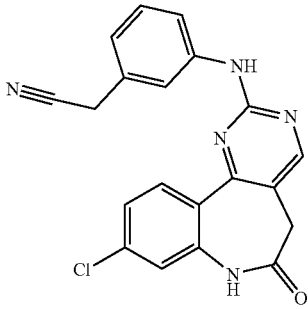

[3-(9-Chloro-6-oxo-6,7-dihydro-5H-benzo[b]pyrimido[4,5-d]azepin-2-ylamino)-phenyl]-acetonitrile (I-78)

In a manner similar to that described for method I, 8-chloro-4-dimethylaminomethylene-3,4-dihydro-1H-benzo[b]azepine-2,5-dione (v-j) and N-(3-cyanomethyl-phenyl)-guanidine nitrate were converted to I-78 (6%): HRMS Calcd. for $C_{20}H_{14}ClN_5O$: 376.0965, Found 376.0994.

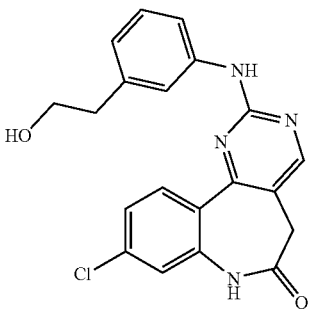

9-Chloro-2-[3-(2-hydroxy-ethyl)-phenylamino]-5H,7H-benzo[b]pyrimido[4,5-d]azepin-6-one (I-80)

In a manner similar to that described for method I, 8-chloro-4-dimethylaminomethylene-3,4-dihydro-1H-benzo[b]azepine-2,5-dione (v-j) and N-[3-(2-hydroxy-ethyl)-phenyl]-guanidine nitrate were converted to I-80 (65%): HRMS Calcd. for $C_{20}H_{17}ClN_4O_2$: 381.1118, Found 381.1126.

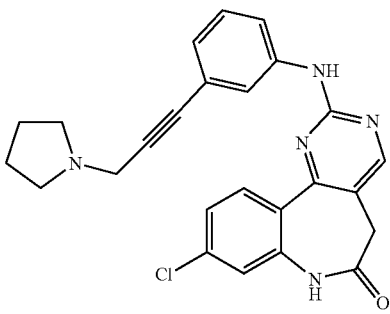

9-Chloro-2-[3-(3-pyrrolidin-1-yl-prop-1-ynyl)-phenylamino]-5H,7H-benzo[b]-pyrimido[4,5-d]azepin-6-one (I-89)

In a manner similar to that described for Method O, 9-chloro-2-(3-iodo-phenylamino)-5H,7H-benzo[b]pyrimido[4,5-d]azepin-6-one (v-j) and 1-(prop-2-ynyl)pyrrolidine were converted to I-89 (46%): MS (AA) $R_f$=1.32 min, m/z=444 (M+H).

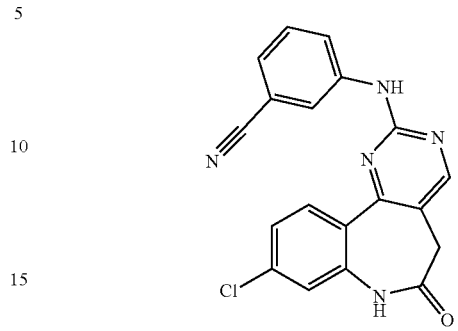

3-(9-Chloro-6-oxo-6,7-dihydro-5H-benzo[b]pyrimido[4,5-d]azepin-2-ylamino)-benzonitrile (I-90)

In a manner similar to that described for method I, 8-chloro-4-dimethylaminomethylene-3,4-dihydro-1H-benzo[b]azepine-2,5-dione (v-j) and N-(3-cyano-phenyl)-guanidine nitrate were converted to I-90 (58%): MS (AA) $R_f$=1.79 min, m/z=362 (M+H).

Example 18

Method R for the Reduction of Nitriles

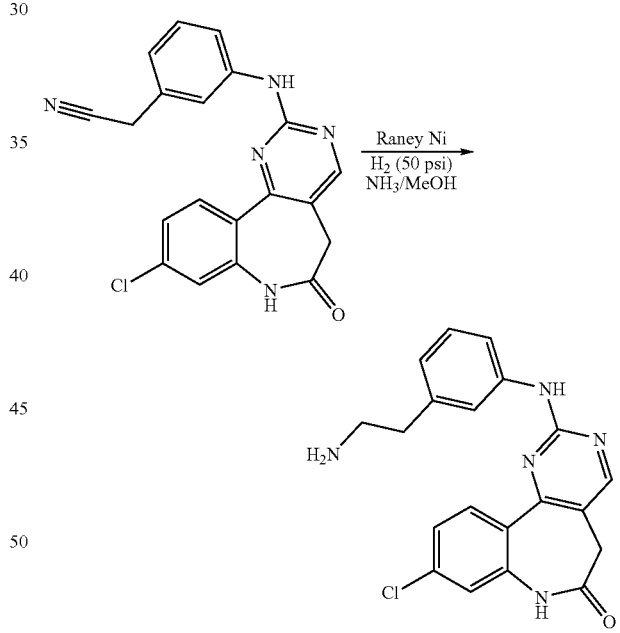

2-[3-(2-Amino-ethyl)-phenylamino]-9-chloro-5H,7H-benzo[b]pyrimido[4,5-d]azepin-6-one (I-86)

To a solution of [3-(9-chloro-6-oxo-6,7-dihydro-5H-benzo[b]pyrimido[4,5-d]azepin-2-ylamino)-phenyl]-acetonitrile (I-78) (0.131 g, 0.349 mmol) in saturated $NH_3$ in MeOH solution (50 mL) was added a catalytic amount of Raney 2800 Ni in $H_2O$ and the mixture was placed under $H_2$ (50 psi) and stirred for 12 h at 22° C. The reaction mixture was filtered through Celite® and the filtrate concentrated in vacuo to give crude product as a yellow oil. Purification by C-18 RP LC-MS chromatography afforded I-86 (0.019 g, 14%): MS (AA) $R_f$=1.25 min, m/z=380 (M+H).

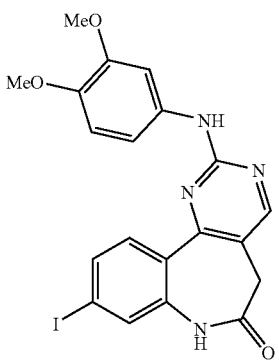

2-(3,4-Dimethoxy-phenylamino)-9-iodo-5H,7H-benzo[b]pyrimido[4,5-d]azepin-6-one (I-30)

In a manner similar to that described for method H, 4-dimethylaminomethylene-8-iodo-3,4-dihydro-1H-benzo[b]azepine-2,5-dione (v-b) was converted to I-30 (84%): HRMS Calcd. for $C_{20}H_{17}IN_4O_3$: 489.0423, Found 489.0443.

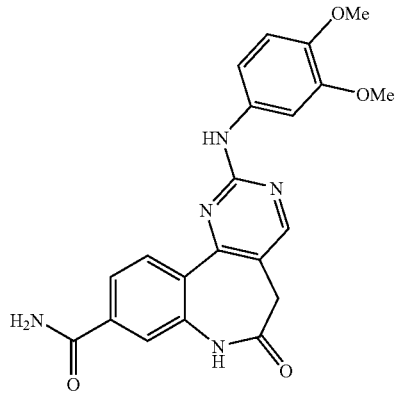

2-(3,4-Dimethoxy-phenylamino)-6-oxo-6,7-dihydro-5H-benzo[b]pyrimido[4,5-d]azepine-9-carboxylic acid amide (I-70)

In a manner similar to that described for Method N, 2-(3,4-dimethoxy-phenylamino)-6-oxo-6,7-dihydro-5H-benzo[b]pyrimido[4,5-d]azepine-9-carboxylic acid (I-53) and NH$_3$ gas were converted to 2-(3,4-dimethoxy-phenylamino)-6-oxo-6,7-dihydro-5H-benzo[b]pyrimido[4,5-d]azepine-9-carboxylic acid amide. The mixture was purified by C-18 RP LC-MS chromatography to afford pure I-70 (6%): HRMS Calcd. for $C_{21}H_{19}N_5O_4$: 406.1515, Found 406.1519.

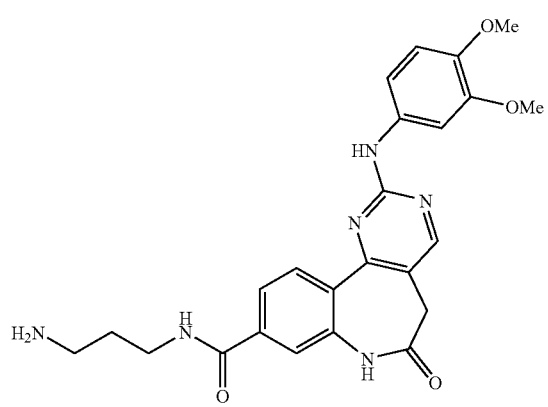

2-(3,4-Dimethoxy-phenylamino)-6-oxo-6,7-dihydro-5H-benzo[b]pyrimido[4,5-d]azepine-9-carboxylic acid (3-amino-propyl)-amide (I-72)

In a manner similar to that described for Method N, 2-(3,4-dimethoxy-phenylamino)-6-oxo-6,7-dihydro-5H-benzo[b]pyrimido[4,5-d]azepine-9-carboxylic acid (I-53) and tert-butyl 4-aminopropylcarbamate were converted to (2-{[2-(3,4-dimethoxy-phenylamino)-6-oxo-6,7-dihydro-5H-benzo[b]pyrimido[4,5-d]azepine-9-carbonyl]-amino}-ethyl)-carbamic acid tert-butyl ester, which was subsequently deprotected (Method K) to give I-72 (30%): HRMS Calcd. for $C_{24}H_{26}N_6O_4$: 463.2093, Found 463.2078.

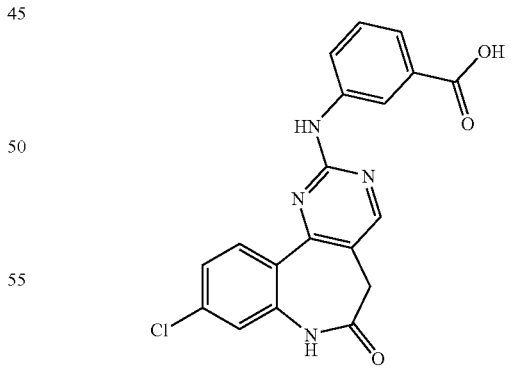

2-(3,4-Dimethoxy-phenylamino)-6-oxo-6,7-dihydro-5H-benzo[b]pyrimido[4,5-d]azepine-9-carboxylic acid (4-amino-butyl)-amide (I-73)

In a manner similar to that described Method N, 2-(3,4-dimethoxy-phenylamino)-6-oxo-6,7-dihydro-5H-benzo[b]pyrimido[4,5-d]azepine-9-carboxylic acid (I-53) and tert-butyl 4-aminobutylcarbamate were converted to (2-{[2-(3,4-dimethoxy-phenylamino)-6-oxo-6,7-dihydro-5H-benzo[b]pyrimido[4,5-d]azepine-9-carbonyl]-amino}-ethyl)-carbamic acid tert-butyl ester, which was subsequently deprotected (Method K) to give I-73 (25%): HRMS Calcd. for $C_{25}H_{28}N_6O_4$: 477.2250, Found 477.2250.

3-(9-Chloro-6-oxo-6,7-dihydro-5H-benzo[b]pyrimido[4,5-d]azepin-2-ylamino)-benzoic acid (I-62-a)

In a manner similar to method I, 8-chloro-4-((dimethylamino)methylene)-3,4-dihydro-1H-benzo[b]azepine-2,5-dione (v-j) and 3-guanidino-benzoic acid were converted to I-62-a (72%): MS m/z=381 (M+H).

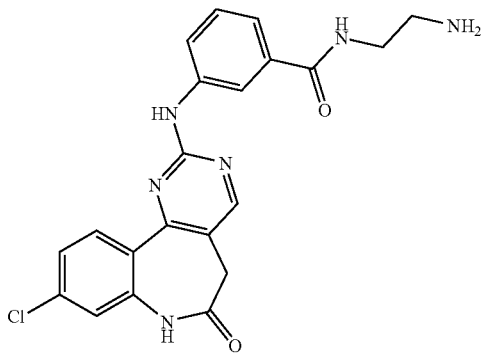

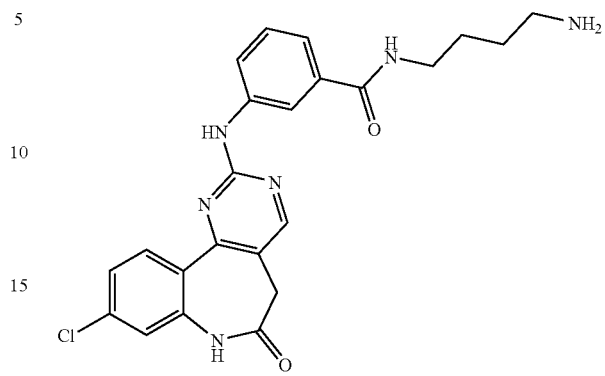

N-(2-Amino-ethyl)-3-(9-chloro-6-oxo-6,7-dihydro-5H-benzo[b]pyrimido[4,5-d]azepin-2-ylamino)-benzamide (I-62)

In a manner similar to Method N, 3-(9-chloro-6-oxo-6,7-dihydro-5H-benzo[b]pyrimido[4,5-d]azepin-2-ylamino)-benzoic acid (I-62-a) and tert-butyl 4-aminoethylcarbamate were converted to {3-[3-(9-chloro-6-oxo-6,7-dihydro-H-benzo[b]pyrimido[4,5-d]azepin-2-ylamino)-benzoylamino]-ethyl}-carbamic acid tert-butyl ester. Subsequent deprotection (Method K) and purification by C-18 RP LC-MS chromatography afforded I-62 (13%): HRMS Calcd. for $C_{21}H_{19}ClN_6O_2$: 423.1336, Found 423.1346.

N-(4-Amino-butyl)-3-(9-chloro-6-oxo-6,7-dihydro-5H-benzo[b]pyrimido[4,5-d]azepin-2-ylamino)-benzamide (I-64)

In a manner similar to Method N, 3-(9-chloro-6-oxo-6,7-dihydro-5H-benzo[b]pyrimido[4,5-d]azepin-2-ylamino)-benzoic acid (I-62-a) and tert-butyl 4-aminobutylcarbamate were converted to {4-[3-(9-chloro-6-oxo-6,7-dihydro-5H-benzo[b]pyrimido[4,5-d]azepin-2-ylamino)-benzoylamino]-butyl}-carbamic acid tert-butyl ester. Subsequent deprotection (Method K) and purification by C-18 RP LC-MS chromatography afforded I-64 (10%): HRMS Calcd. for $C_{23}H_{23}ClN_6O_2$: 451.1649, Found 451.1668.

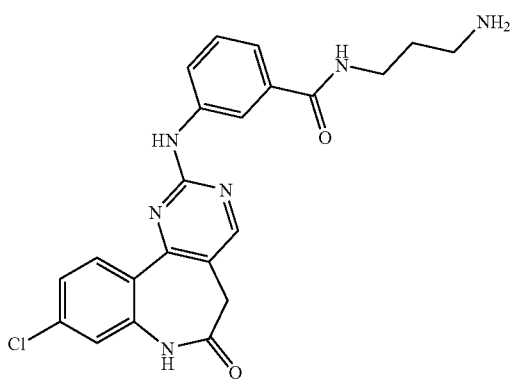

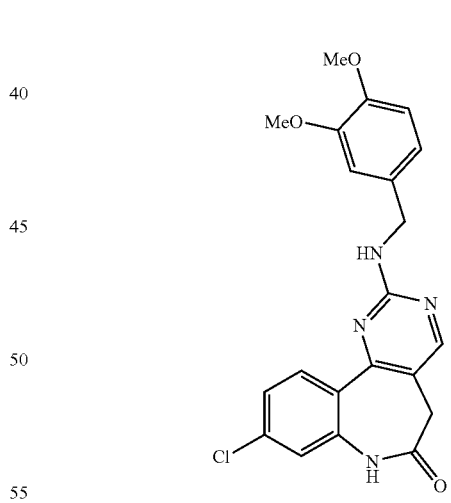

N-(3-Amino-propyl)-3-(9-chloro-6-oxo-6,7-dihydro-5H-benzo[b]pyrimido[4,5-d]azepin-2-ylamino)-benzamide (I-63)

In a manner similar to Method N, 3-(9-chloro-6-oxo-6,7-dihydro-5H-benzo[b]pyrimido[4,5-d]azepin-2-ylamino)-benzoic acid (I-62-a) and tert-butyl 4-aminopropylcarbamate were converted to {3-[3-(9-chloro-6-oxo-6,7-dihydro-H-benzo[b]pyrimido[4,5-d]azepin-2-ylamino)-benzoylamino]-propyl}-carbamic acid tert-butyl ester. Subsequent deprotection (Method K) and purification by C-18 RP LC-MS chromatography afforded I-63 (16%): HRMS Calcd. for $C_{22}H_{21}ClN_6O_2$: 437.1492, Found 437.1480

9-Chloro-2-(3,4-dimethoxybenzyl)-5H,7H-benzo[b]pyrimido[4,5-d]azepin-6-one (I-17)

In a manner similar to method I, 8-chloro-4-((dimethylamino)methylene)-3,4-dihydro-1H-benzo[b]azepine-2,5-dione (v-j) and 1-(3,4-dimethoxybenzyl)guanidine were converted to I-17 (41%): HRMS Calcd. for $C_{21}H_{19}ClN_4O_3$: 411.1223, Found 411.1241.

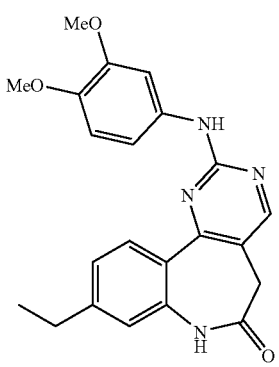

2-(3,4-Dimethoxy-phenylamino)-9-ethyl-5H,7H-benzo[b]pyrimido[4,5-d]azepin-6-one (I-37)

In a manner similar to that described for Method P, 2-(3,4-dimethoxy-phenylamino)-9-ethynyl-5H,7H-benzo[b]pyrimido[4,5-d]azepin-6-one (I-33) was converted to I-37 (23%): HRMS Calcd. for $C_{22}H_{22}N_4O_3$: 391.1770, Found 391.1796.

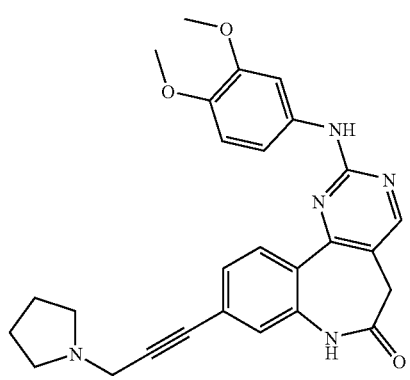

2-(3,4-Dimethoxy-phenylamino)-9-(3-pyrrolidin-1-yl-prop-1-ynyl)-5H,7H benzo[b]pyrimido[4,5-d]azepin-6-one (I-32)

In a manner similar to that described above for Method O, 2-(3,4-dimethoxy-phenylamino)-9-iodo-5H,7H-benzo[b]pyrimido[4,5-d]azepin-6-one (I-30) and 1-(prop-2-ynyl)pyrrolidine were converted to I-32 (42%): HRMS Calcd. for $C_{27}H_{27}N_5O_3$: 470.2192, Found 470.2192.

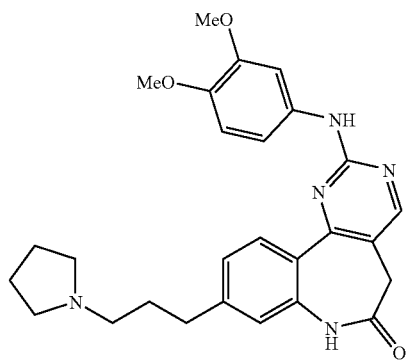

2-(3,4-Dimethoxy-phenylamino)-9-(3-pyrrolidin-1-yl-propyl)-5H,7H-benzo[b]-pyrimido[4,5-d]azepin-6-one (HCl) (I-49)

In a manner similar to that described above for Method P, 2-(3,4-dimethoxy-phenylamino)-9-(3-pyrrolidin-1-yl-prop-1-ynyl)-5H,7H-benzo[b]pyrimido[4,5-d]azepin-6-one (I-32) was converted to 2-(3,4-dimethoxy-phenylamino)-9-(3-pyrrolidin-1-yl-propyl)-5H,7H-benzo[b]pyrimido[4,5-d]azepin-6-one, which was then converted to the HCl salt as described in Method K to give I-49 (9%): HRMS Calcd. for $C_{27}H_{31}N_5O_3$: 474.2505, Found 474.2491.

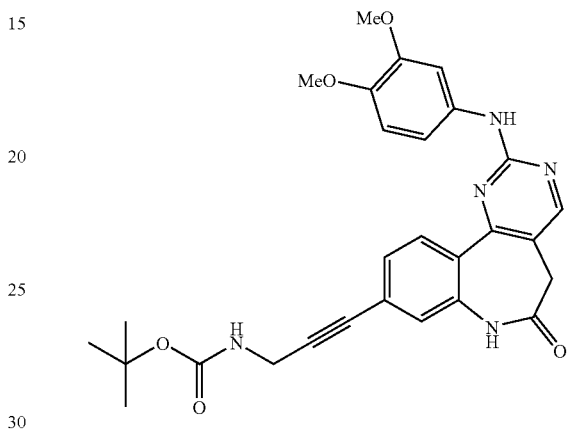

{3-[2-(3,4-Dimethoxy-phenylamino)-6-oxo-6,7-dihydro-5H-benzo[b]pyrimido[4,5-d]azepin-9-yl]-prop-2-ynyl}-carbamic acid tert-butyl ester (I-39)

In a manner similar to that described for Method O, 2-(3,4-dimethoxy-phenylamino)-9-iodo-5H,7H-benzo[b]pyrimido[4,5-d]azepin-6-one (I-30) and tert-butyl prop-2-ynyl-carbamate were converted to I-39 (31%): HRMS Calcd. for $C_{28}H_{29}N_5O_5$: 516.2246, Found 516.2244.

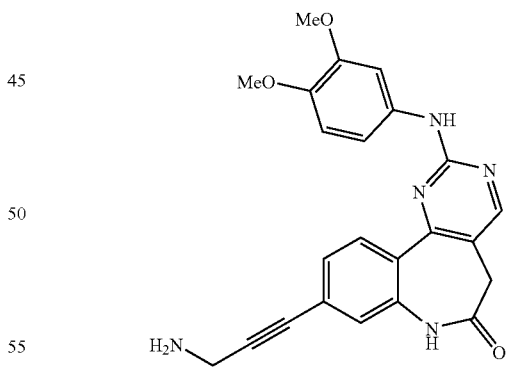

9-(3-Amino-prop-1-ynyl)-2-(3,4-dimethoxy-phenylamino)-5H,7H-benzo[b]pyrimido[4,5-d]azepin-6-one (HCl) (I-38)

In a manner similar to that described for Method K, {3-[2-(3,4-dimethoxy-phenylamino)-6-oxo-6,7-dihydro-5H-benzo[b]pyrimido[4,5-d]azepin-9-yl]-prop-2-ynyl}-carbamic acid tert-butyl ester (I-39) was converted to the HCl salt of I-38 (30%): HRMS Calcd. for $C_{23}H_{21}N_5O_3$: 416.1720, Found 416.1722.

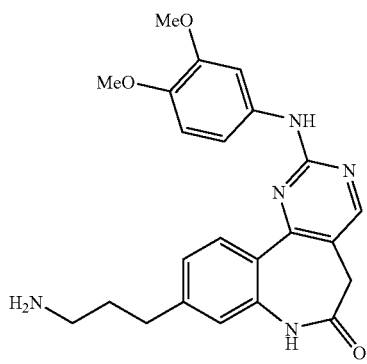

9-(3-Amino-propyl)-2-(3,4-dimethoxy-phenylamino)-5H, 7H-benzo[b]pyrimido[4,5-d]azepin-6-one (I-50)

In a manner similar to that described for Method P, {3-[2-(3,4-dimethoxy-phenylamino)-6-oxo-6,7-dihydro-5H-benzo[b]pyrimido[4,5-d]azepin-9-yl]-prop-2-ynyl}-carbamic acid tert-butyl ester (I-39) was converted to {3-[2-(3,4-dimethoxy-phenylamino)-6-oxo-6,7-dihydro-5H-benzo[b]pyrimido[4,5-d]azepin-9-yl]-propyl}-carbamic acid tert-butyl ester (I-41: HRMS Calcd. for $C_{28}H_{33}N_5O_5$: 520.2559, found 520.2551), which was subsequently deprotected (Method K) to give I-50 (80%) HRMS Calcd. for $C_{23}H_{25}N_5O_3$: 420.2035, Found 420.2045.

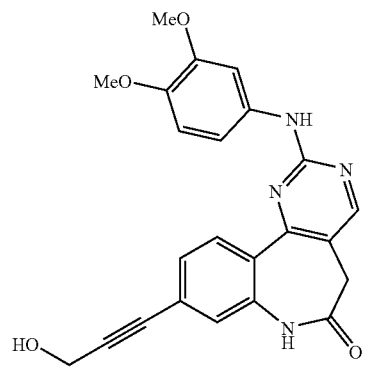

2-(3,4-Dimethoxy-phenylamino)-9-(3-hydroxy-prop-1-ynyl)-5H,7H-benzo[b]pyrimido[4,5-d]azepin-6-one (I-52)

In a manner similar to that described for Method O, 2-(3,4-dimethoxy-phenylamino)-9-iodo-5H,7H-benzo[b]pyrimido[4,5-d]azepin-6-one (I-30) and prop-2-yn-1-ol were converted to I-52 (38%): HRMS Calcd. for $C_{23}H_{20}N_4O_4$: 417.1562, Found 417.1551.

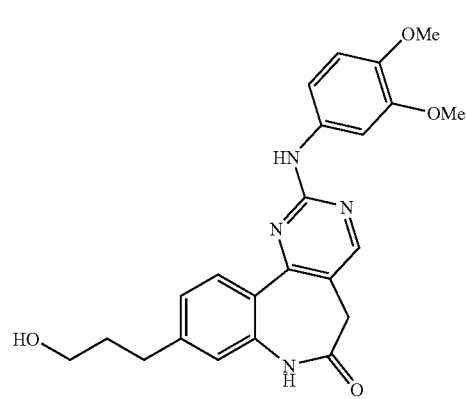

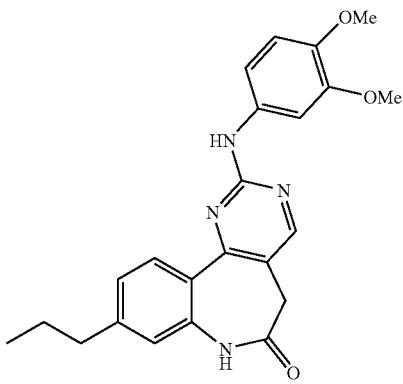

2-(3,4-Dimethoxy-phenylamino)-9-(3-hydroxy-propyl)-5H,7H-benzo[b]pyrimido[4,5-d]azepin-6-one (I-81) and 2-(3,4-Dimethoxy-phenylamino)-9-propyl-5H,7H-benzo[b]pyrimido[4,5-d]azepin-6-one (I-82)

In a manner similar to that described for Method P (50 psi $H_2$), 2-(3,4-dimethoxy-phenylamino)-9-(3-hydroxy-prop-1-ynyl)-5H,7H-benzo[b]pyrimido[4,5-d]azepin-6-one (I-52) was converted to I-81 (8% yield): HRMS Calcd. for $C_{23}H_{24}N_4O_4$: 421.1875, Found 421.1881 and I-82 (8% yield) HRMS Calcd. for $C_{23}H_{24}N_4O_3$: 405.1926, Found 405.1930. The two compounds were separated by column chromatography in 0%-10% MeOH/$CH_2Cl_2$.

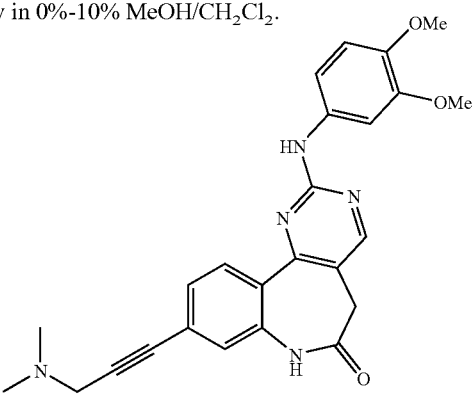

2-(3,4-Dimethoxy-phenylamino)-9-(3-dimethylamino-prop-1-ynyl)-5H,7H-benzo[b]pyrimido[4,5-d]azepin-6-one (I-91)

In a manner similar to that described for Method O, 2-(3,4-dimethoxy-phenylamino)-9-iodo-5H,7H-benzo[b]pyrimido[4,5-d]azepin-6-one (I-30) and N,N-dimethylprop-2-yn-1-amine were converted to 2-(3,4-dimethoxy-phenylamino)-9-(3-dimethylamino-prop-1-ynyl)-5H,7H-benzo[b]pyrimido[4,5-d]azepin-6-one, which was purified by C-18 RP LC-MS chromatography to afford pure I-91 (16%): MS (FA) R=0.98 min, m/z=444 (M+H).

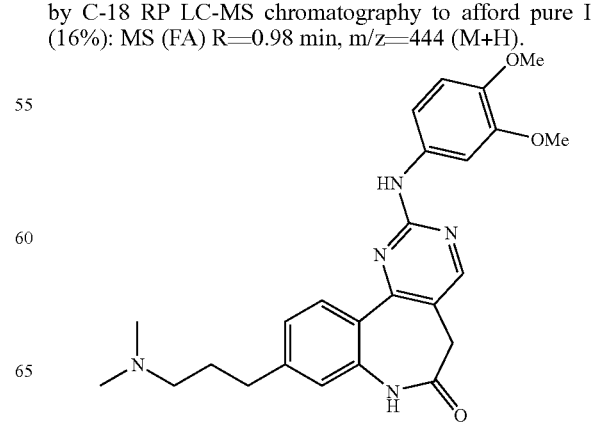

2-(3,4-Dimethoxy-phenylamino)-9-(3-dimethylamino-propyl)-5H,7H-benzo[b]pyrimido[4,5-d]azepin-6-one (I-88)

In a manner similar to that described for Method P, 2-(3,4-dimethoxy-phenylamino)-9-(3-dimethylamino-prop-1-ynyl)-5H,7H-benzo[b]pyrimido[4,5-d]azepin-6-one (I-91) was converted to I-88 (72%): MS $R_f$=1.01 min, m/z=448 (M+H).

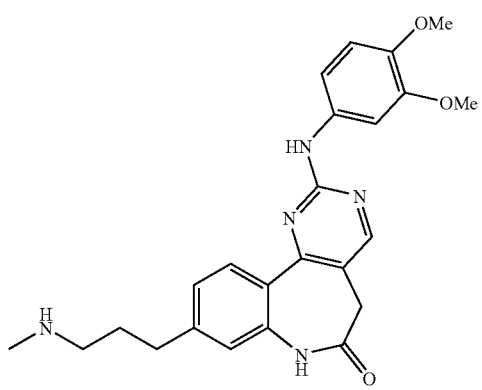

2-(3,4-Dimethoxy-phenylamino)-9-(3-methylamino-propyl)-5H,7H-benzo[b]pyrimido[4,5-d]azepin-6-one (HCl) (I-87)

In a manner similar to that described for Method O, 2-(3,4-dimethoxy-phenylamino)-9-iodo-5H,7H-benzo[b]pyrimido[4,5-d]azepin-6-one (I-30) and N-methylprop-2-yn-1-amine were converted to 2-(3,4-dimethoxy-phenylamino)-9-(3-methylamino-prop-1-ynyl)-5H,7H-benzo[b]pyrimido[4,5-d]azepin-6-one. The crude product (unstable) was carried on in a similar manner to that described for Method P to give I-87, which was converted to the HCl salt (40%): MS $R_f$=0.98 min, m/z=434 (M+H).

Example 19

Method O for the Preparation of Compounds of Formula xvi

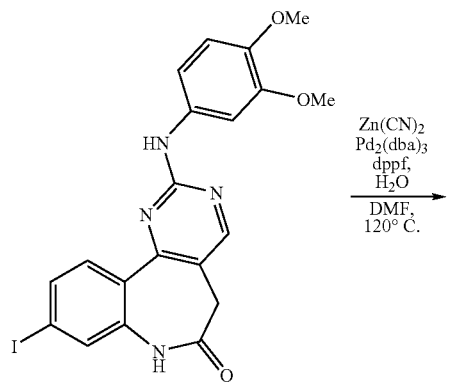

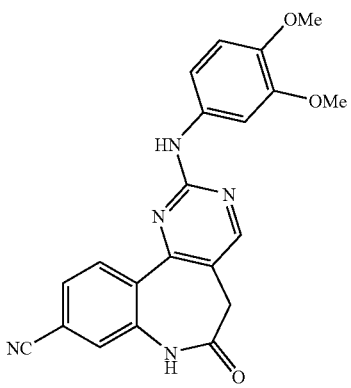

2-(3,4-Dimethoxy-phenylamino)-6-oxo-6,7-dihydro-5H-benzo[b]pyrimido[4,5-d]azepine-9-carbonitrile (I-92)

To a solution of 2-(3,4-dimethoxy-phenylamino)-9-iodo-5H,7H-benzo[b]pyrimido[4,5-d]azepin-6-one (I-30) (100 mg, 0.210 mmol) in 4 mL anhydrous DMF at room temperature was added zinc cyanide (14 mg, 0.120 mmol), tris(dibenzylideneacetone)dipalladium (9.5 mg, 0.01 mmol), 1,1'-bis(diphenyl-phosphino)ferrocene (14.0 mg, 0.02 mmol) and a drop of H$_2$O. The solution was degassed with argon then stirred at 1° C. for 16 h. The solution was allowed to cool to 22° C., then diluted with EtOAc and saturated aqueous sodium bicarbonate. The organic layer was then washed with H$_2$O and brine, dried over Na$_2$SO$_4$, and concentrated in vacuo. The product was recrystallized in methanol and CH$_2$Cl$_2$ to give I-92 (92%): MS $R_f$=2.49 min, m/z=388 (M+H).

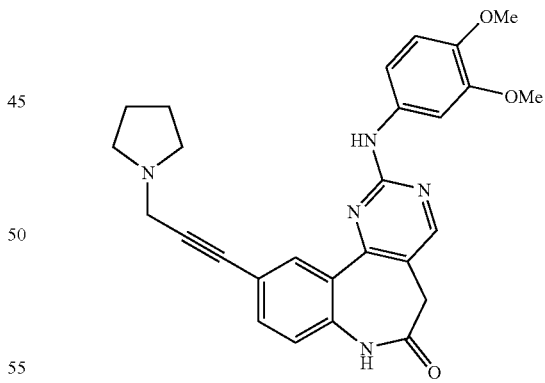

2-(3,4-Dimethoxy-phenylamino)-10-(3-pyrrolidin-1-yl-prop-1-ynyl)-5H,7H-benzo[b]pyrimido[4,5-d]azepin-6-one (I-31)

In a manner similar to Method O, 2-(3,4-dimethoxy-phenylamino)-10-iodo-5H,7H-benzo[b]pyrimido[4,5-d]azepin-6-one (I-26) and 1-(prop-2-ynyl)pyrrolidine were converted to I-31 (29%): HRMS Calcd. for C$_{27}$H$_{27}$N$_5$O$_3$: 470.2192, Found 470.2185.

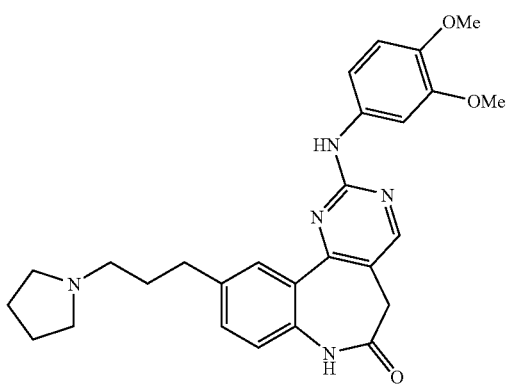

2-(3,4-Dimethoxy-phenylamino)-10-(3-pyrrolidin-1-yl-propyl)-5H,7H-benzo[b]pyrimido[4,5-d]azepin-6-one (I-56)

In a manner similar to Method P, 2-(3,4-dimethoxy-phenylamino)-10-(3-pyrrolidin-1-yl-prop-1-ynyl)-5H,7H-benzo[b]pyrimido[4,5-d]azepin-6-one (I-31) was converted to I-56 (42%): HRMS Calcd. for $C_{27}H_{31}N_5O_3$: 474.2505, Found 474.2498.

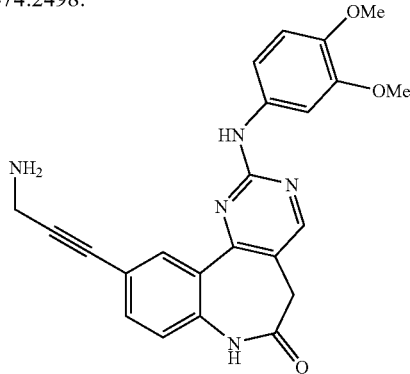

10-(3-Amino-prop-1-ynyl)-2-(3,4-dimethoxy-phenylamino)-5H,7H-benzo[b]-pyrimido[4,5-d]azepin-6-one (HCl) (I-59)

In a manner similar to Method O, 2-(3,4-dimethoxy-phenylamino)-10-iodo-5H,7H-benzo[b]pyrimido[4,5-d]azepin-6-one (I-26) and tert-butyl prop-2-ynylcarbamate were converted to {3-[2-(3,4-dimethoxy-phenylamino)-6-oxo-6,7-dihydro-5H-benzo[b]pyrimido[4,5-d]azepin-10-yl]-prop-2-ynyl}-carbamic acid tert-butyl ester. Subsequent deprotection (Method K) and purification by C-18 RP LC-MS chromatography afforded the HCl salt of I-59 (24%): HRMS Calcd. for $C_{23}H_{21}N_5O_3$: 416.1722, Found 416.1725.

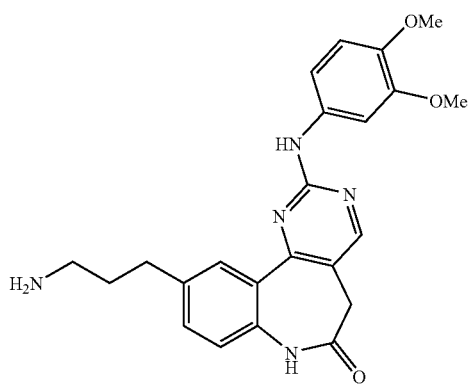

10-(3-Amino-propyl)-2-(3,4-dimethoxy-phenylamino)-5H,7H-benzo[b]pyrimido[4,5-d]azepin-6-one (I-60)

In a manner similar to Method P, 10-(3-amino-prop-1-ynyl)-2-(3,4-dimethoxy-phenylamino)-5H,7H-benzo[b]pyrimido[4,5-d]azepin-6-one (I-59) was converted to I-60 (41%): HRMS Calcd. for $C_{23}H_{25}N_5O_3$: 420.2035, Found 420.2043.

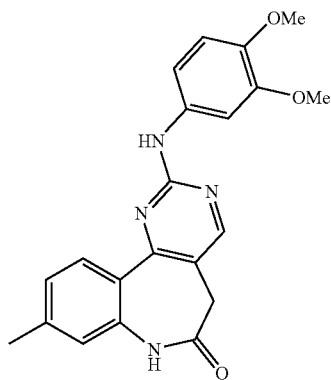

2-(3,4-Dimethoxy-phenylamino)-9-methyl-5H,7H-benzo[b]pyrimido[4,5-d]azepin-6-one (I-42)

In a manner similar to method I, 4-((dimethylamino)methylene)-8-methyl-3,4-dihydro-1H-benzo[b]azepine-2,5-dione (v-g) and 1-(3,4-dimethoxyphenyl)guanidine were converted to I-42 (57%): HRMS Calcd. for $C_{21}H_{20}N_4O_3$: 377.1613, Found 377.1613.

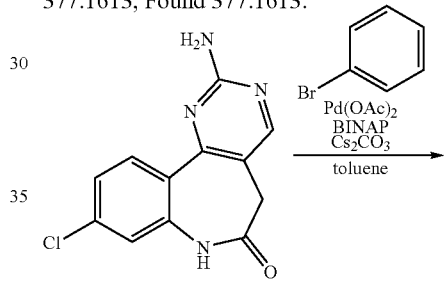

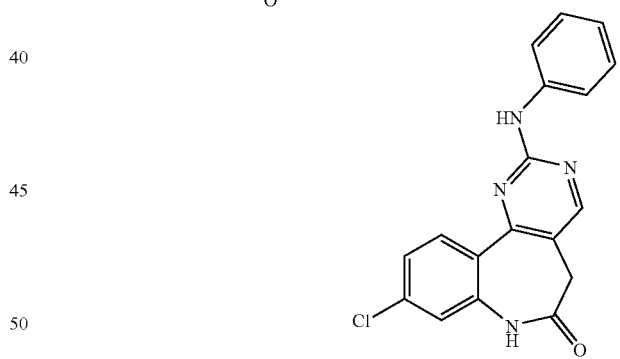

9-Chloro-2-phenylamino-5H,7H-benzo[b]pyrimido[4,5-d]azepin-6-one (I-61)

To a solution of 2-amino-9-chloro-5H,7H-benzo[b]pyrimido[4,5-d]azepin-6-one (I-23) (148 mg, 0.568 mmol), 1-bromobenzene (0.072 mL, 0.681 mmol), Cs$_2$CO$_3$ (333 mg, 1.02 mmol), and BINAP (53 mg, 0.085 mmol) in 4 mL toluene was added Pd(OAc)$_2$ (12.8 mg, 0.057 mmol), and the reaction was stirred at 100° C. for 12 h. The reaction mixture was then treated with H$_2$O and extracted with CH$_2$Cl$_2$ (2×30 mL). The organic fractions were combined, filtered, dried over MgSO$_4$ and concentrated in vacuo to give an orange oil which was purified by C-18 RP LC-MS chromatography to afford I-61 (0.9%): HRMS Calcd. for $C_{18}H_{13}ClN_4O$: 337.0856, Found 337.0853.

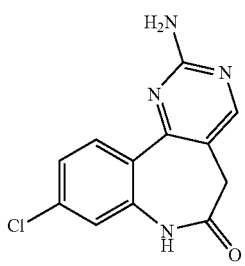

2-Amino-9-chloro-5H,7H-benzo[b]pyrimido[4,5-d]azepin-6-one (I-23)

In a manner similar to that described for method I (NaHCO$_3$ used instead of K$_2$CO$_3$), guanidine hydrochloride and 8-chloro-4-((dimethylamino)methylene)-3,4-dihydro-1H-benzo[b]azepine-2,5-dione (v-j) were converted to I-23 (72%): HRMS Calcd. for C$_{12}$H$_9$ClN$_4$O: 261.0543, Found 261.0543.

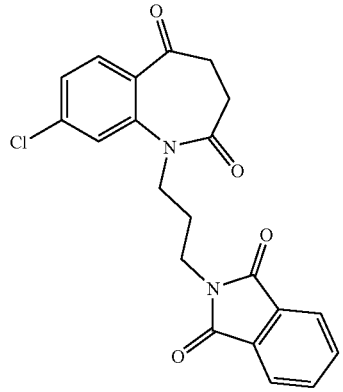

8-Chloro-1-(3-(1,3-dioxoisoindolin-2-yl)propyl)-3,4-dihydro-1H-benzo[b]azepine-2,5-dione (I-40-a)

To a stirring solution of 8-chloro-3,4-dihydro-1H-benzo[b]azepine-2,5-dione (iv-j) (1.2 g, 5.7 mmol) in DMF (75 mL) was added cesium carbonate (5.63 g, 17.3 mmol) and 2-(3-bromopropyl)isoindoline-1,3-dione (1.7 g, 6.34 mmol). The solution was stirred at room temperature for 12 h and then sodium iodide (100 mg) was added. The reaction was stirred at room temperature for 72 h. The solution was then diluted with dichloromethane and washed with water. The organics were dried over magnesium sulfate and concentrated. Column chromatography (1:1 ethyl acetate/hexanes) yielded I-40-a which was carried on crude: MS m/z=397 (M+H).

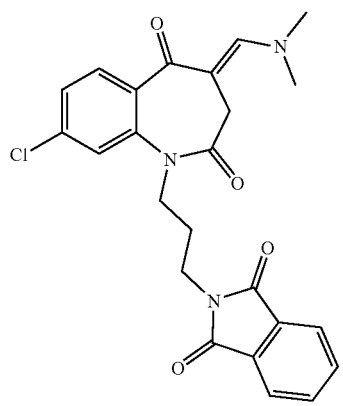

8-Chloro-4-((dimethylamino)methylene)-1-(3-(1,3-dioxoisoindolin-2-yl)propyl)-3,4-dihydro-1H-benzo[b]azepine-2,5-dione (I-40-b)

In a manner similar to that described for method G, 8-chloro-1-(3-(1,3-dioxoisoindolin-2-yl)propyl)-3,4-dihydro-1H-benzo[b]azepine-2,5-dione (I-40-a) and DMF-DMA were converted to I-40-b and carried on crude: MS m/z=452 (M+H).

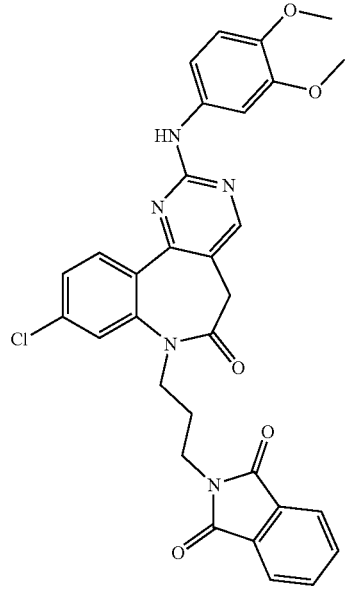

2-{3-[9-Chloro-2-(3,4-dimethoxy-phenylamino)-6-oxo-5,6-dihydro benzo[b]pyrimido[4,5-d]azepin-7-yl]-propyl}-isoindole-1,3-dione (I-40-c)

In a manner similar to that described for method I (NaHCO$_3$ used instead of K$_2$CO$_3$), 1-(3,4-dimethoxyphenyl)guanidine and 8-chloro-4-((dimethylamino)-methylene)-1-(3-(1,3-dioxoisoindolin-2-yl)propyl)-3,4-dihydro-1H-benzo[b]azepine-2,5-dione (I-40-b) were converted to I-40-c and carried on crude: MS m/z=584 (M+H).

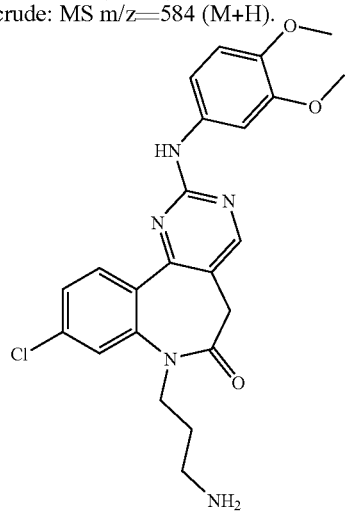

7-(3-Amino-propyl)-9-chloro-2-(3,4-dimethoxy-phenylamino)-5H,7H-benzo[b]pyrimido[4,5-d]azepin-6-one (I-40)

To a stirring solution of 2-{3-[9-chloro-2-(3,4-dimethoxyphenylamino)-6-oxo-5,6-dihydrobenzo[b]pyrimido[4,5-d]azepin-7-yl]-propyl}-isoindole-1,3-dione (I-40-c) (51 mg, 0.09 mmol) in ethanol (1.5 mL) was added methylamine (40% by wt in H$_2$O, 0.5 mL). After stirring for 2.5 h at room temperature, the solution was diluted with dichloromethane and washed with water. The organics were dried over magnesium sulfate and concentrated. Preparative HPLC gave I-40: MS R$_t$=1.32 min. m/z=454 (M+H).

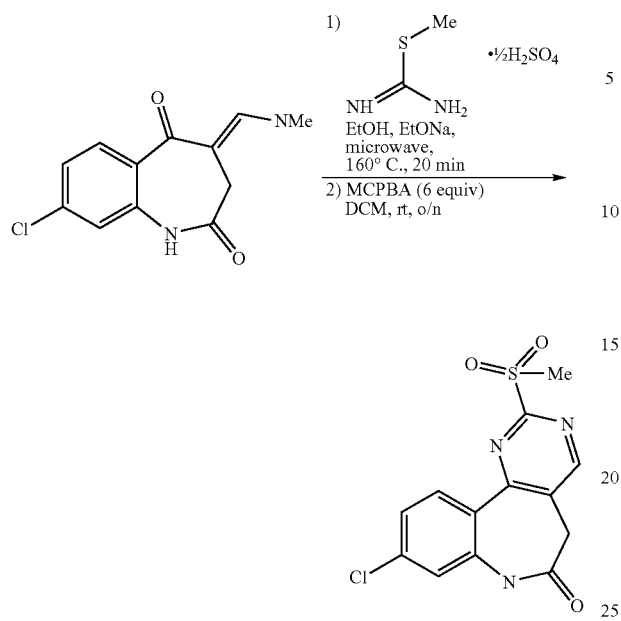

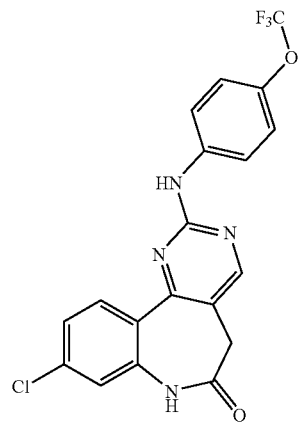

9-Chloro-2-(4-trifluoromethoxy-phenylamino)-5H,7H-benzo[b]pyrimido[4,5-d]azepin-6-one 9-Chloro-2-methanesulfonyl-5H,7H-benzo[b]pyrimido[4,5-d]azepin-6-one (I-14-a)

Sodium ethoxide (340 mL, 1.05 mmol) and S-methyl-isothiourea-hemisulfate (146 mg, 1.05 mmol) was suspended in absolute EtOH (3 mL). The suspension was stirred for 1 h, then the Na$_2$SO$_4$ was removed by filtration. The filtrate was then added to enamine v-j (253 mg, 0.956 mmol) in absolute EtOH (1 mL). The reaction mixture was microwaved at 160° C. for 20 min. EtOH was removed and the remaining solid was treated with water. The resulting precipitate was filtered, washed with water and ether, and dried to give 243 mg of the crude sulfide (87% crude).

To a suspension of crude sulfide (96 mg, 0.33 mmol) in anhydrous CH$_2$Cl$_2$ (6.5 mL) was added MCPBA (342 mg, 1.98 mmol). After the reaction was stirred at 22° C. for 12 h, the reaction mixture was washed with 1N NaOH (0.35 mL) and water (15 mL). The aqueous layer was extracted with CH$_2$Cl$_2$ and then EtOAc. The combined organic layers were dried (MgSO$_4$), concentrated and chromatographed to give 63 mg of pale yellow solid I-14-a (51% over two steps). MS 324/326 (M+H).

In a glovebox, to a vial containing 4-(trifluoromethoxy)aniline (531 mg, 3 mmol) in THF (0.8 mL) and toluene (2.4 mL), was slowly added 2M solution of AlMe$_3$ in toluene (1.5 mL, 3 mmol). The solution was stirred at 50° C. for 2 h. The resulting solution was then added to a vial containing sulfone viii (97 mg, 0.3 mmol). The reaction mixture was stirred at 60° C. overnight, and then concentrated. A fine suspension of KF (192 mg, 3.3 mmol) in DCM (1.6 mL) was added to the dried residue in the vial, followed by H$_2$O (0.05 mL). The suspension was sonicated for 20 min, and then a spatula-full of Celite® was added to the vial, followed by another 20 min of sonication. The suspension was filtered and washed with EtOAc and MeOH, and the filtrate was evaporated. To the resulting residue was added DCM (10 mL) and DMF (5 mL), PL-CHO resin (Polymer Laboratories, Inc., Amherst, Mass.) (2.4 g, 7.2 mmol), and 1M AcOH in DCM (0.72 mL, 0.72 mmol). The resin mixture was shaken at rt overnight. The resin was filtered off and the filtrate was concentrated. The resulting mixture was purified by C-18 RP LC-MS chromatography to provide 9-Chloro-2-(4-trifluoro-methoxyphenylamino)-5H,7H-benzo[b]pyrimido[4,5-d]azepin-6-one (25.5%): $^1$H NMR (300 MHz, acetone-d6): δ 8.53 (s, 1H), 8.18 (d, J=9.0 Hz, 1H), 8.05 (d, J=9.0 Hz, 1H), 8.03-8.06 (m, 1H), 7.38-7.41 (m, 2H), 7.28-7.31 (m, 2H), 3.49 (s, 2H), 2.84 (br. s, 1H); MS m/z=421 (M+H).

Example 20

Method J for the Preparation of Compounds of Formula vi

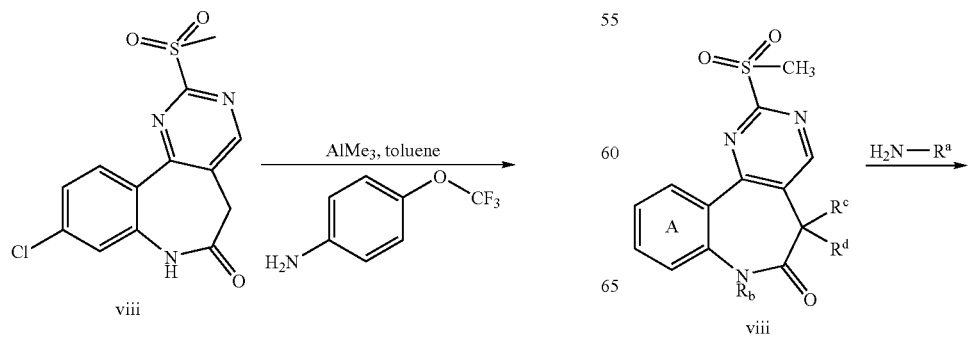

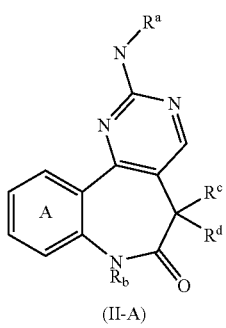

(II-A)

Example 21

Method J for the Preparation of Compounds of Formula vi—Library Synthesis

To each vial containing sulfone viii (48 mg, 0.15 mmol), was added 0.2M solution of an amine in THF/toluene (1:1) (0.3-0.6 mmol). For insoluble amines, DMF (0.2 mL to 1.6 mL) was added; and for amine salts, Hunig's base was added to neutralize the amine. Hunig's base (0.15 mL) was added to the solution. The solutions were shaken at 70° C. overnight. The reaction mixtures were concentrated, and the residues were dissolved in DCM (1.0 mL) and DMF (1.0 mL). PL-CHO resins (Polymer Laboratories, Inc., Amherst, Mass.) (400 mg, 1.2 mmol), and 1M AcOH in DCM (0.12 mL, 0.12 mmol) were added to the solution. The resin mixtures were shaken at rt overnight. The resins were filtered off and the filtrates were concentrated. Each resulting residue was purified by reverse phase HPLC using an Agilent HPLC equipped with a SunFire™ column (Waters Corporation), Method Formic Acid.

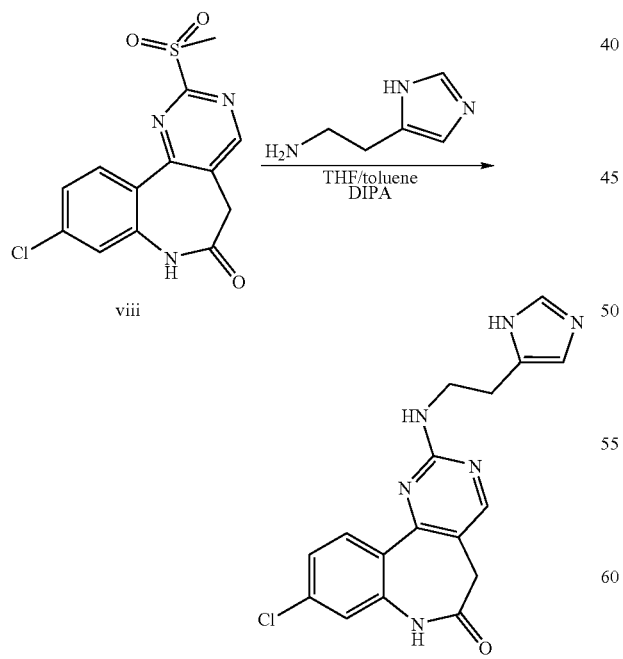

9-Chloro-2-{[2-(1H-imidazol-5-yl)ethyl]amino}-5,7-dihydro-6H-pyrimido[5,4-d][1]benzazepin-6-one (I-236)

To a vial containing sulfone viii (48 mg, 0.15 mmol), was added 0.2M solution of 2-(4-imidazolyl)ethylamine in THF/toluene (1:1) (0.15-0.30 mL, 0.3-0.6 mmol). Hunig's base (0.15 mL) was added to the solution. The solution was shaken at 70° C. overnight. The reaction mixture was concentrated, and the residue was dissolved in DCM (1.0 mL) and DMF (1.0 mL). PL-CHO resins (400 mg, 1.2 mmol), and 1M AcOH in DCM (0.12 mL, 0.12 mmol) were added to the solution. The resin mixture was shaken at room temperature overnight. The resins were filtered off and the filtrate was concentrated. The resulting residue was purified by RP-HPLC using an Agilent HPLC equipped with a SunFire™ column (Waters Corporation), Method Formic Acid, to give compound I-236 (47.0%): $^1$H NMR (300 MHz, CD$_3$OD): δ 8.29-7.98 (m, 4H), 7.28-7.06 (m, 4H), 3.68 (br. t., 2H), 3.28 (s, 2H), 2.93 (br. t, 2H); MS m/z=355 (M+H).

Example 22

Method S for Guanidine Synthesis

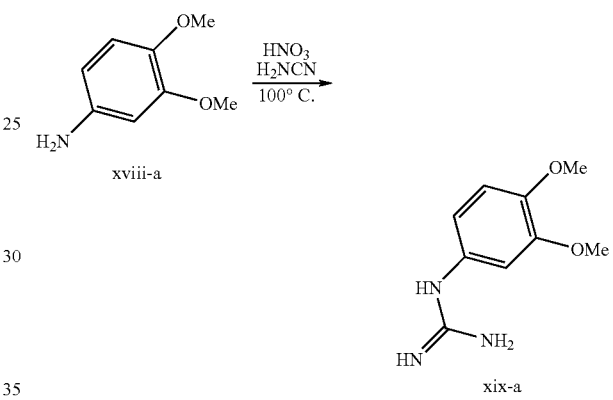

1-(3,4-Dimethoxyphenyl)guanidine (HNO$_3$ salt) (xix-a)

To a vigorously stirred solution of 3,4-dimethoxyaniline (15.3 g, 0.1 mol) in EtOH (60 mL) at 0° C. was added nitric acid (69%, 9.0 mL, 0.1 mol) dropwise. A solution of cyanamide (4.6 g, 0.1 mol) in H$_2$O (8.5 mL) was added and the solution was heated at reflux for 3 h. The mixture was then diluted with EtOH (50 mL), cooled to 4° C. The resulting golden needles were collected and dried in vacuo to provide xix-a as the nitric acid salt (14.7 g, 57%): MS m/z=196 (M+H).

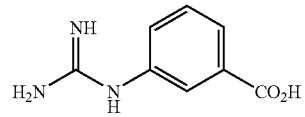

3-Guanidino-benzoic acid (HNO$_3$ salt)(xix-b)

In a manner similar to that described for method S, 3-amino-benzoic acid was converted to xix-b (78%): MS m/z=178 (M−H).

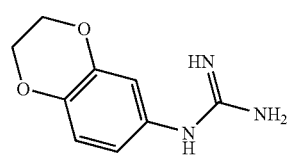

N-(2,3-Dihydro-benzo[1,4]dioxin-6-yl)-guanidine (HNO$_3$ salt) (xix-c)

In a manner similar to that described in method S, 2,3-dihydro-benzo[1,4]dioxin-6-ylamine was converted to xix-c (23%): MS m/z=194 (M−H).

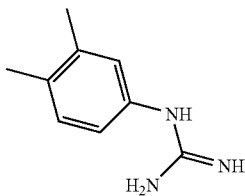

N-(3,4-Dimethyl-phenyl)-guanidine (HNO, salt) (xix-d)

In a manner similar to that described in method S, 3,4-dimethyl-phenylamine was converted to xix-d (31%): MS m/z=164 (M−H).

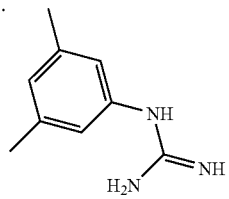

N-(3,5-Dimethyl-phenyl)-guanidine (HNO, salt) (xix-e)

In a manner similar to that described in method S, 3,5-dimethyl-phenylamine was converted to xix-e (20%): MS m/z=164 (M−H).

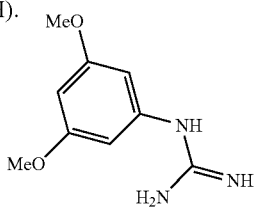

N-(3,5-Dimethoxy-phenyl)-guanidine (HNO, salt) (xix-f)

In a manner similar to that described in method S, 3,5-dimethoxy-phenylamine was converted to xix-f (39%): MS m/z=196 (M−H).

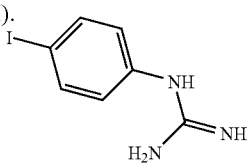

N-(4-Iodo-phenyl)-guanidine (HNO$_3$ salt) (xix-g)

In a manner similar to that described in method S, 4-iodo-phenylamine was converted to xix-g (99%): MS m/z=262 (M−H).

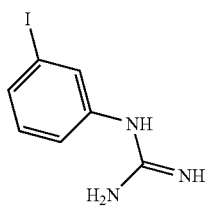

N-(3-Iodo-phenyl)-guanidine (HNO salt) (xix-h)

In a manner similar to that described in method S, 3-iodo-phenylamine was converted to xix-h (42%): MS m/z=262 (M−H).

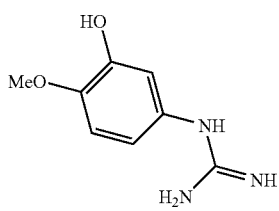

N-(3-Hydroxy-4-methoxy-phenyl)-guanidine (HNO, salt) (xix-i)

In a manner similar to that described in method S, 5-amino-2-methoxy-phenol was converted to xix-i (27%): MS m/z=182 (M−H).

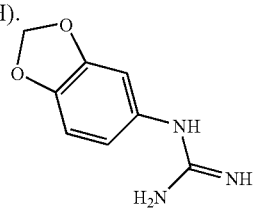

N-Benzo[1,3]dioxol-5-yl-guanidine (HNO$_3$ salt) (xix-j)

In a manner similar to that described in method S, benzo[1,3]dioxol-5-ylamine was converted to xix-j (59%): MS m/z=180 (M−H).

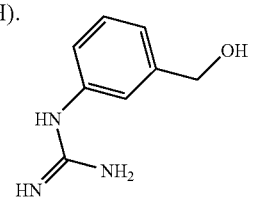

1-(3-(Hydroxymethyl)phenyl)guanidine (HNO$_3$ salt) (xix-k)

In a manner similar to that described for method S, (3-aminophenyl)-methanol was converted to xix-k: MS m/z=166 (M−H).

Example 23

Method V for Nitro-Group Reduction

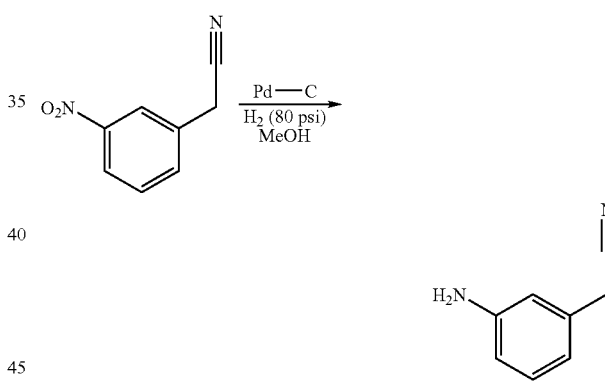

(3-Amino-phenyl)-acetonitrile (xix-l-1)

To a solution of 3-Nitro-phenyl-acetonitrile (3.20 g, 19.7 mmol) in MeOH (50 mL) was added Pd/C (10% wt, ~50% H$_2$O, 0.32 g) and the mixture was placed under H$_2$ (80 psi) and stirred for 2 days at 22° C. The reaction mixture was filtered through Celite® and the filtrate concentrated in vacuo to give crude product as a yellow oil. The residue was purified by silica gel chromatography (ISCO, elution with 0-10% ethyl acetate in hexanes) to give xix-l-1 (1.15 g, 44%): MS m/z=133 (M−H).

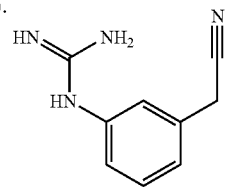

N-(3-Cyanomethyl-phenyl)-guanidine (HNO, salt) (xix-l)

In a manner similar to that described in method S, 3-amino-phenyl-acetonitrile was converted to xix-l (81%): MS m/z=175 (M−H).

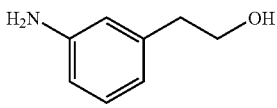

2-(3-Amino-phenyl)-ethanol (xix-m-1)

In a manner similar to that described for method V, 2-(3-Nitrophenyl)-ethanol was converted to xix-m-1 (89%): MS m/z=138 (M−H).

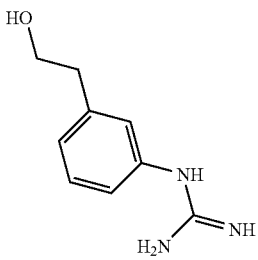

N-[3-(2-Hydroxy-ethyl)-phenyl]-guanidine (HNO$_3$ salt) (xix-m)

In a manner similar to that described in method S, 2-(3-amino-phenyl)-ethanol was converted to xix-m: MS m/z=180 (M−H).

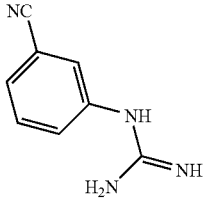

N-(3-Cyano-phenyl)-guanidine (HNO$_3$ salt) (xix-N)

In a manner similar to that described in method S, 3-aminobenzonitrile was converted to xix-N (42%): MS m/z=161 (M−H).

Example 24

Method T for Guanidine Synthesis

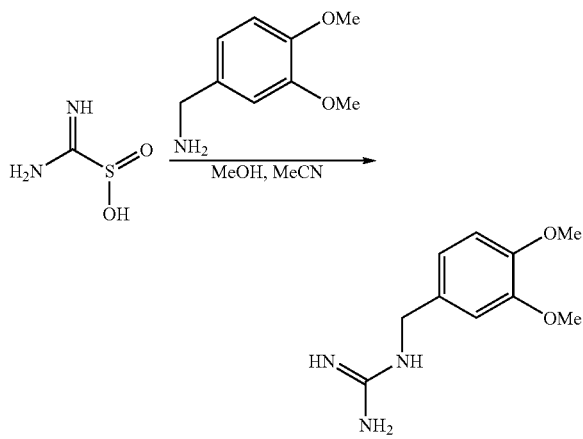

1-(3,4-Dimethoxybenzyl)guanidine (H$_2$SO$_3$ salt) (xix-o)

Formamidinesulfinic acid (2.65 g, 24.5 mmol) was dissolved in acetic acid (8.3 mL) and cooled to 10° C. Peracetic acid (5.7 mL, 27 mmol) was slowly added to the cooled solution. After addition was complete, the reaction was warmed slowly to 22° C. and stirred for 3 h. The solid was filtered and washed with ethanol (200 proof) then dried in vacuo to give an unstable intermediate 2.44 g (80%). The intermediate was dissolved in mixture of CH$_3$CN (5 mL) and MeOH (10 mL). Then (3,4-dimethoxy-phenyl)methanamine (1.27 mL, 8.39 mmol) was added slowly and stirred at 22° C. The reaction was stirred for 12 h and then concentrated in vacuo to give xix-o (2.44 g, 99%).

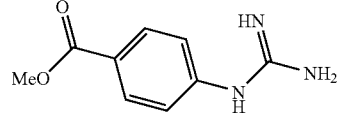

4-Guanidino-benzoic acid methyl ester (HCl salt) (xix-p)

4-guanidine-benzoic acid (1.12 g) was dissolved in anhydrous methanol (25 mL) and HCl in diethyl ether was added (1M; 800 μL). The mixture was heated in a sealed tube for 16 hours. Solvents were removed under reduced pressure to provide xix-p as a white solid (1.17 g, 99%).

Example 25

Method U for Guanidine Synthesis

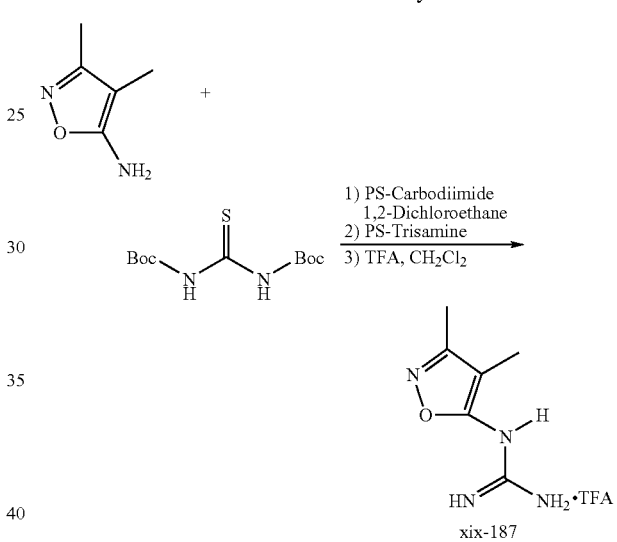

N-(3,4-dimethylisoxazol-5-yl)guanidine (trifluoroacetic acid salt) (xix-187)

To PS-carbodiimide resin (Argonaut Technologies) (1.069 g, 1.71 mmol, 1.6 mmol/g) placed in a 20 mL vial was added anhydrous 1,2-dichloroethane (6.0 mL), N,N'-bis(tert-butoxycarbonyl)thiourea (235 mg, 0.85 mmol) in anhydrous 1,2-dichloroethane (2.0 mL), and 5-amino-3,4-dimethylisoxazole (63.9 mg, 0.57 mmol) solution or dispersion in anhydrous 1,2-dichloroethane (1.0 mL). The reaction mixture was shaken at 50° C. until the reaction completed, typically for 36 hours. The reaction mixture was brought to room temperature and PS-trisamine (317 mg, 1.14 mmol, 3.6 mmol/g) was added. The reaction mixture was shaken at room temperature for 24 hours. The resin was removed by filtration and washed with 1,2-dichloroethane (3.0 mL) and methanol (3.0 mL). The combined organic layers were dried in a Genevac at 40° C. The resultant crude reaction mixture was mixed with TFA in dichloromethane (25% vol., 5.0 mL) and shaken at room temperature for 6 hours followed by evaporation in Genevac 40° C. to give crude xxix-187 (152 mg, 99%).: MS m/z=155 (M+H).

Guanidines xix listed in Table 2 were prepared in a manner similar to Example 25, utilizing method U.

TABLE 2
Guanidines
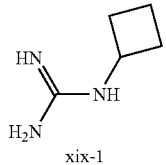
xix-1
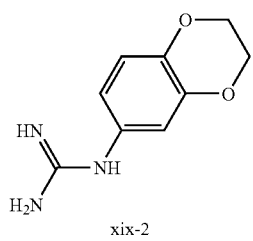
xix-2
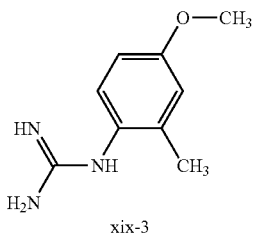
xix-3
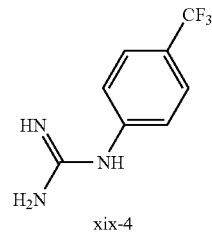
xix-4
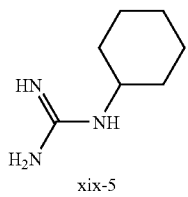
xix-5
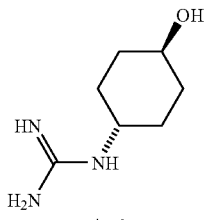
xix-6
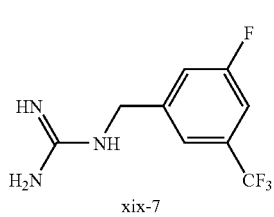
xix-7
TABLE 2-continued
Guanidines
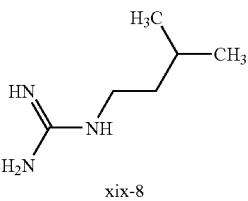
xix-8
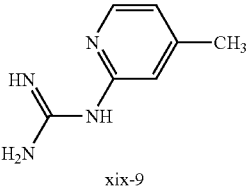
xix-9
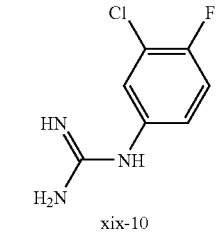
xix-10
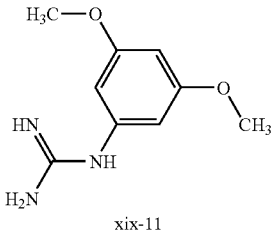
xix-11
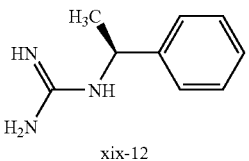
xix-12
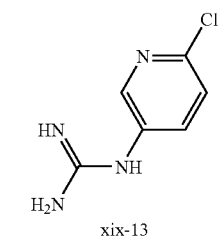
xix-13
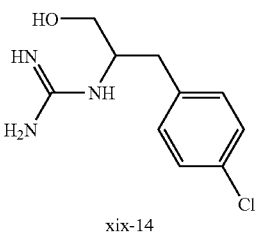
xix-14

TABLE 2-continued
Guanidines
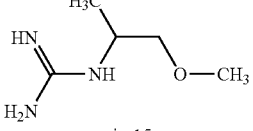
xix-15
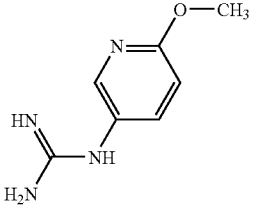
xix-16
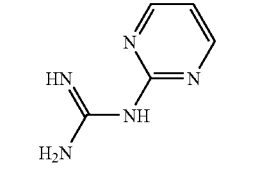
xix-17
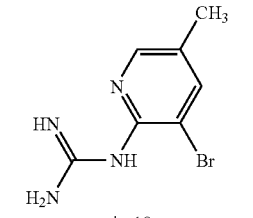
xix-18
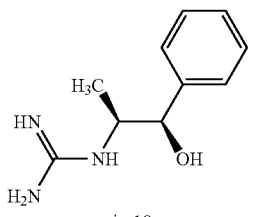
xix-19
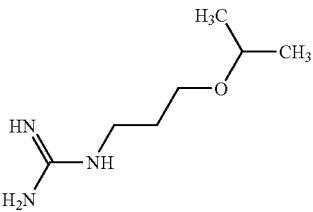
xix-20
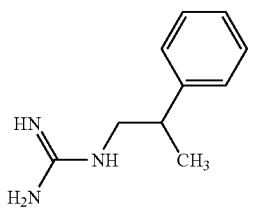
xix-21
TABLE 2-continued
Guanidines
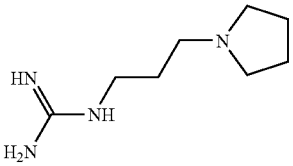
xix-22
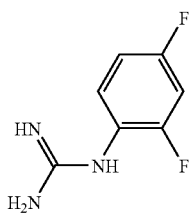
xix-23
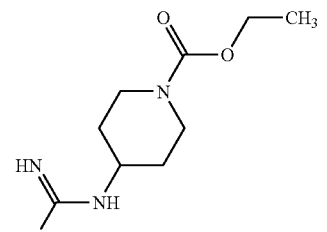
xix-24
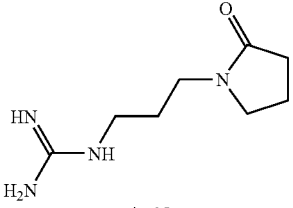
xix-25
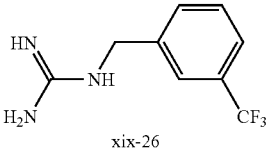
xix-26
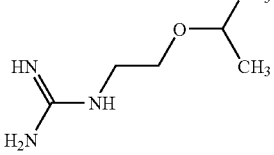
xix-27
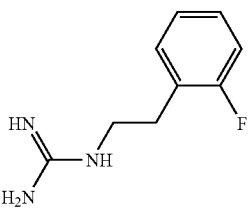
xix-28

TABLE 2-continued
Guanidines
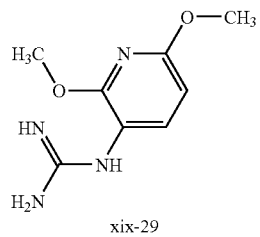
xix-29
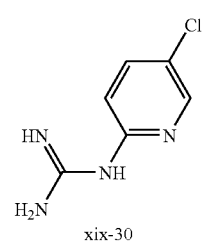
xix-30
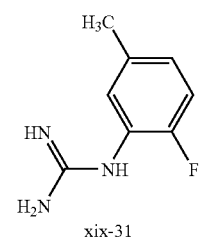
xix-31
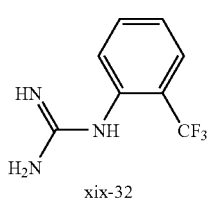
xix-32
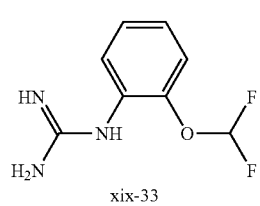
xix-33
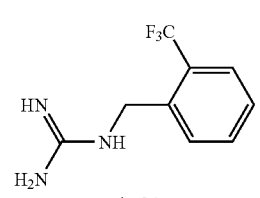
xix-34
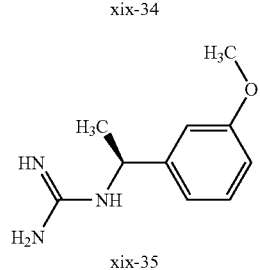
xix-35
TABLE 2-continued
Guanidines
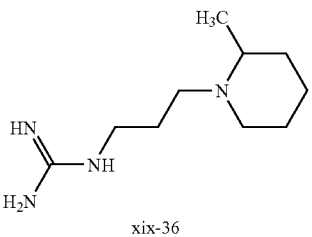
xix-36
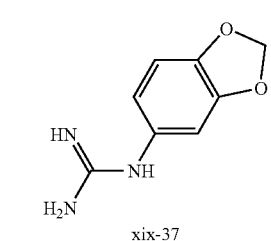
xix-37
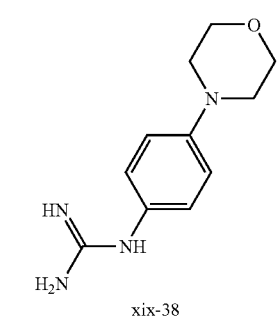
xix-38
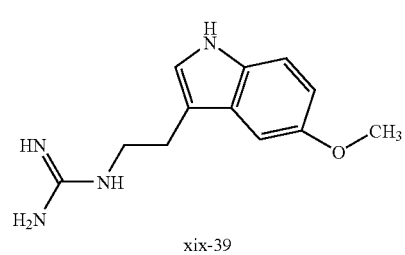
xix-39
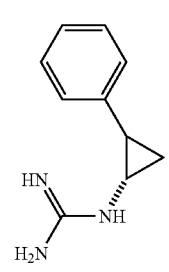
xix-40
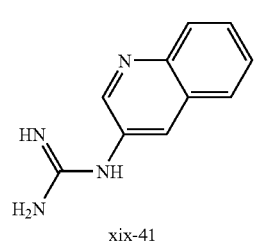
xix-41

TABLE 2-continued
Guanidines
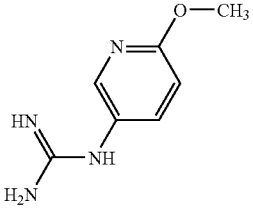
xix-42
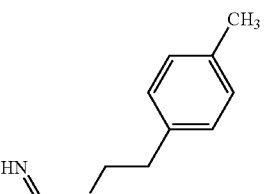
xix-43
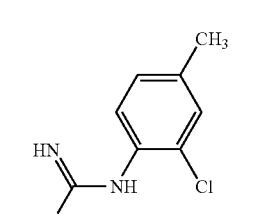
xix-44
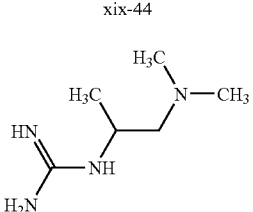
xix-45
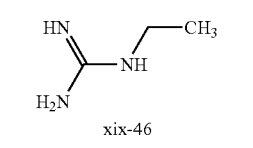
xix-46
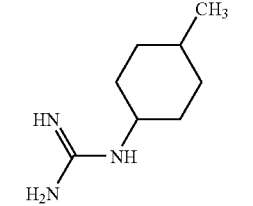
xix-47
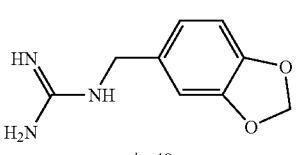
xix-48
TABLE 2-continued
Guanidines
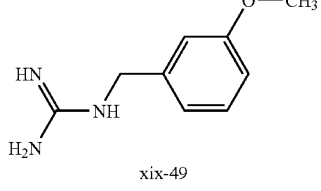
xix-49
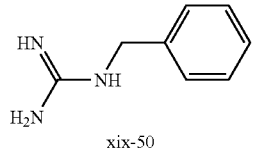
xix-50
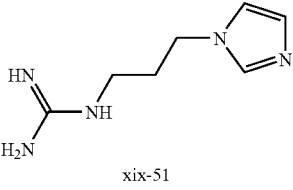
xix-51
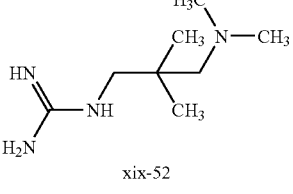
xix-52
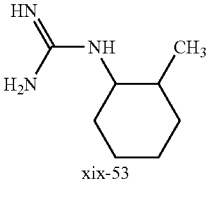
xix-53
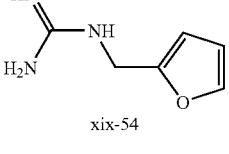
xix-54
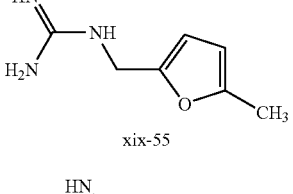
xix-55
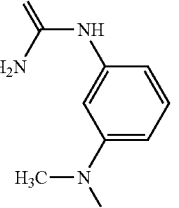
xix-56

TABLE 2-continued
Guanidines
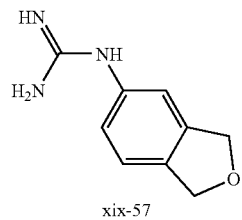
xix-57
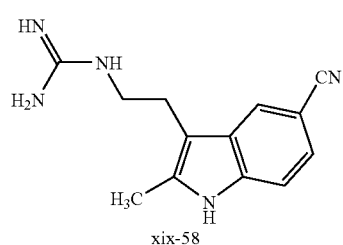
xix-58
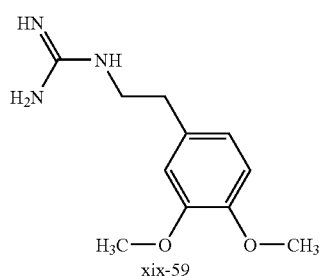
xix-59
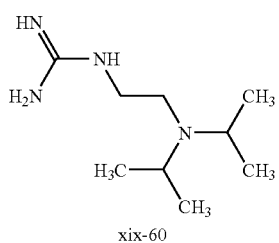
xix-60
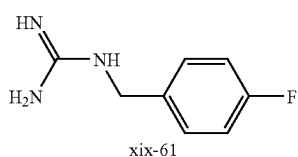
xix-61
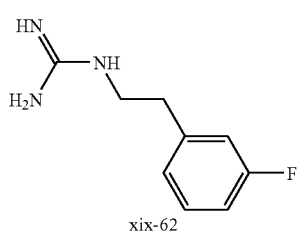
xix-62
TABLE 2-continued
Guanidines
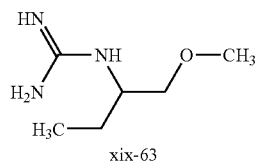
xix-63
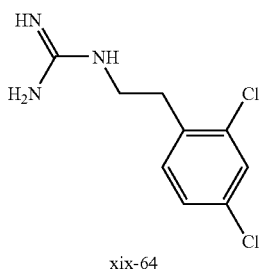
xix-64
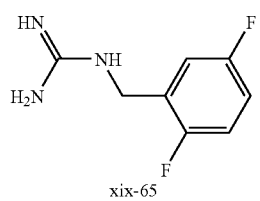
xix-65
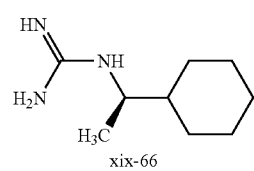
xix-66
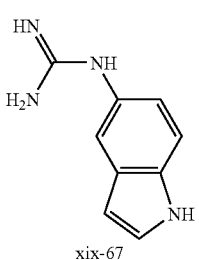
xix-67
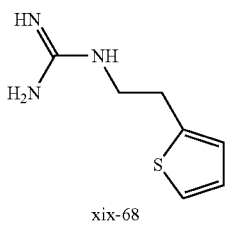
xix-68

TABLE 2-continued
Guanidines
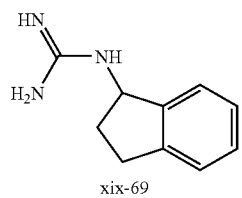
xix-69
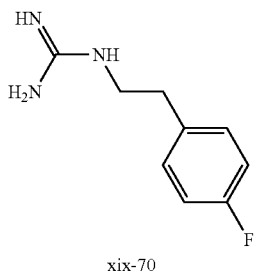
xix-70
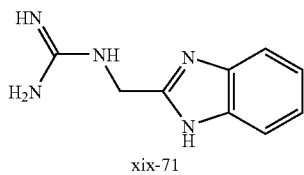
xix-71
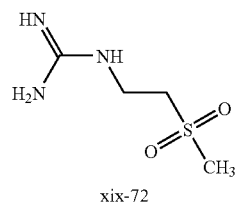
xix-72
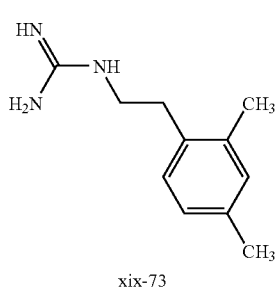
xix-73
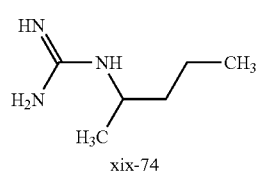
xix-74
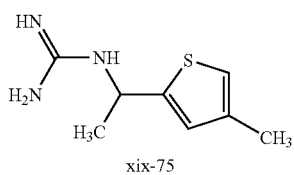
xix-75
TABLE 2-continued
Guanidines
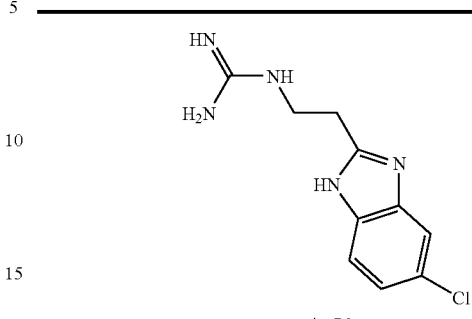
xix-76
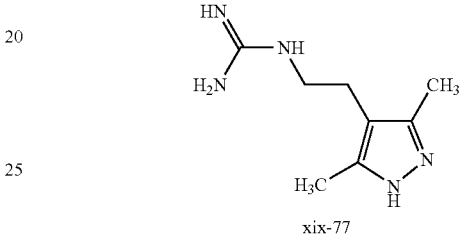
xix-77
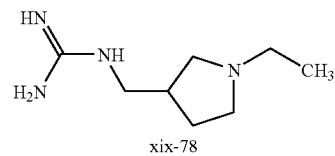
xix-78
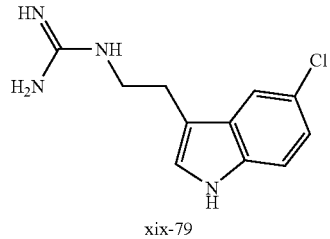
xix-79
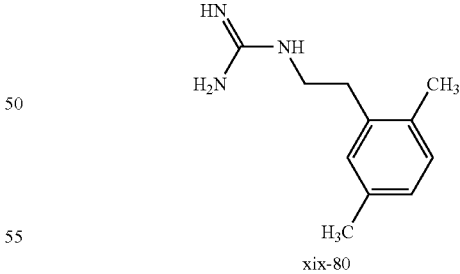
xix-80
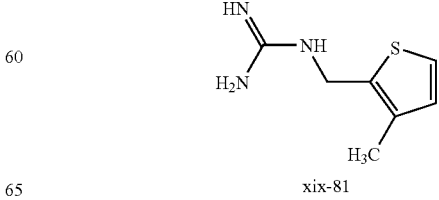
xix-81

TABLE 2-continued
Guanidines
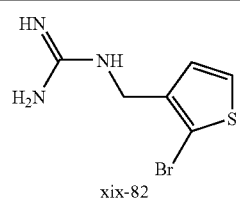
xix-82
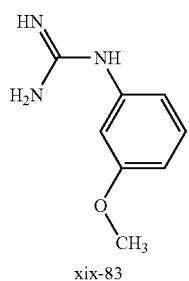
xix-83
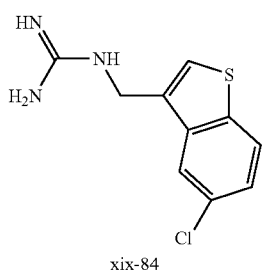
xix-84
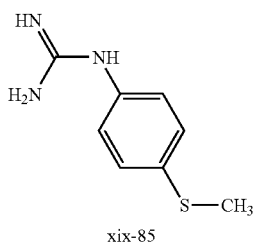
xix-85
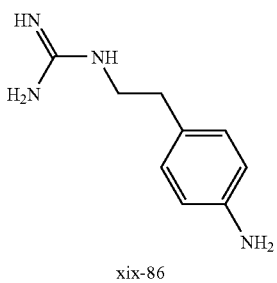
xix-86
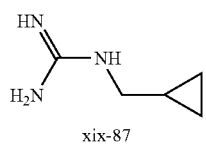
xix-87
TABLE 2-continued
Guanidines
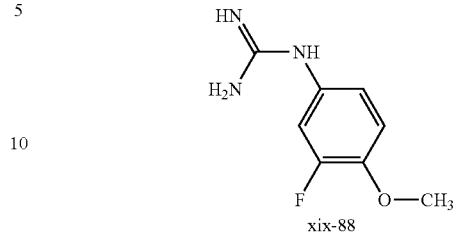
xix-88
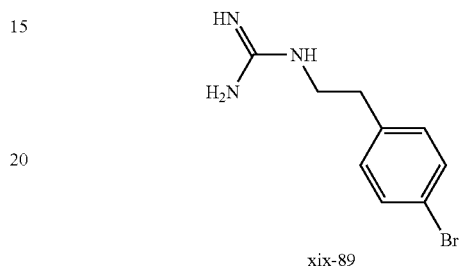
xix-89
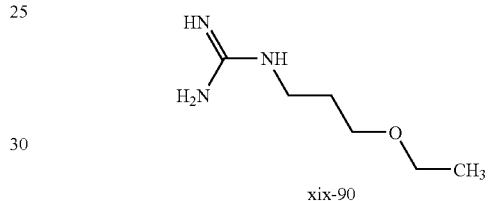
xix-90
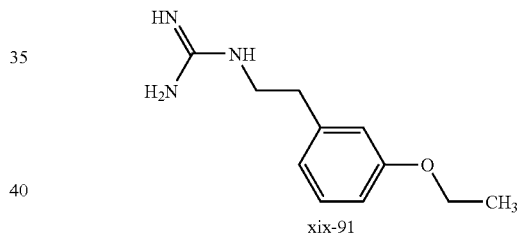
xix-91
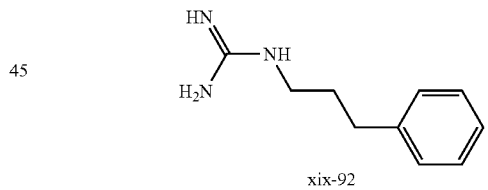
xix-92
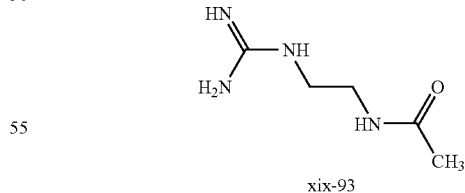
xix-93
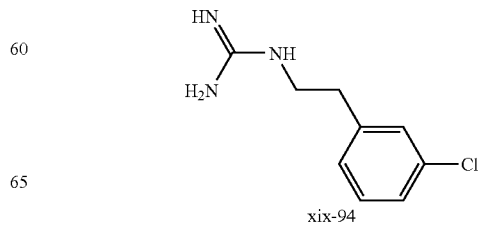
xix-94

TABLE 2-continued
Guanidines
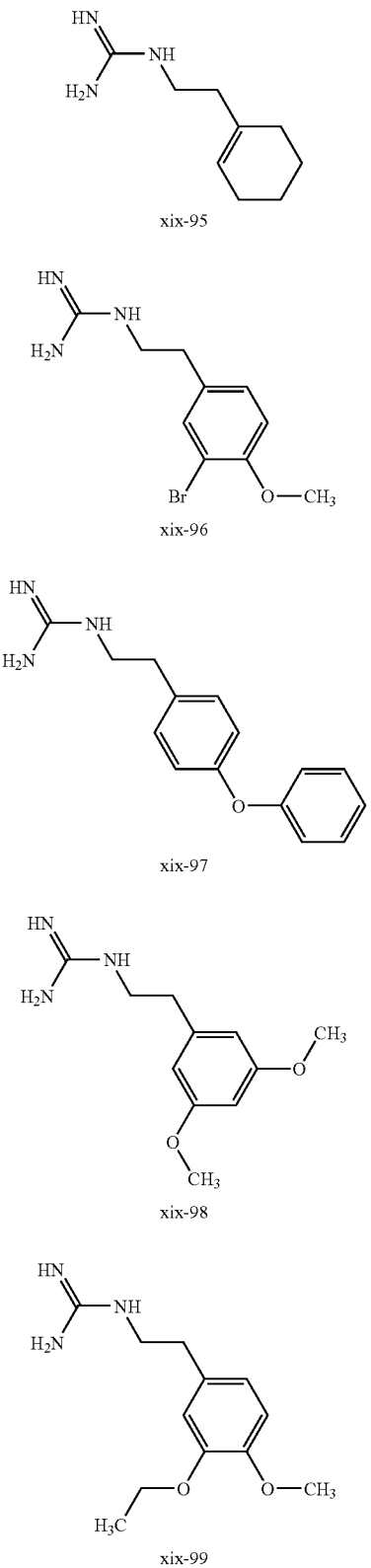
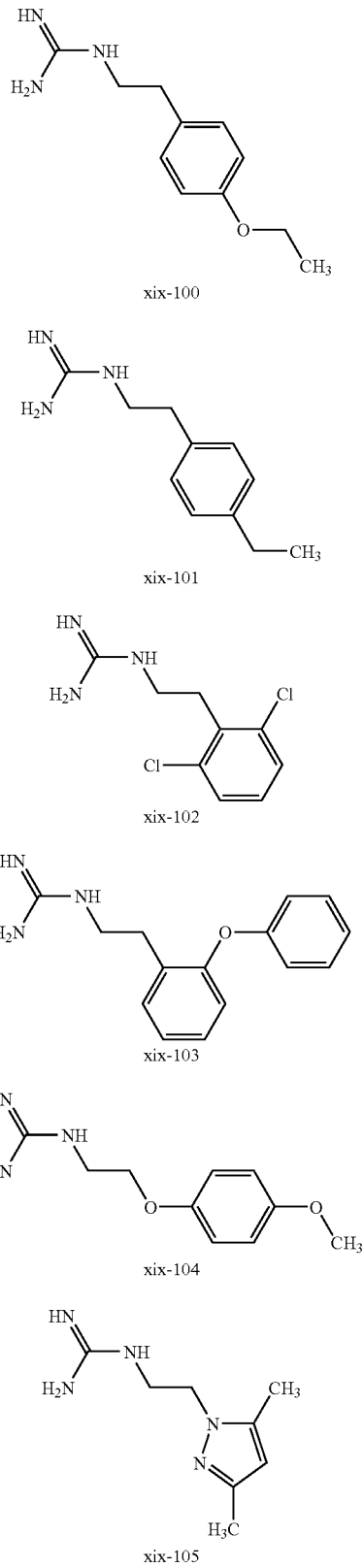

TABLE 2-continued
Guanidines
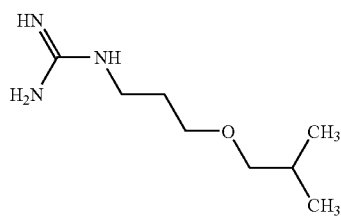
xix-106
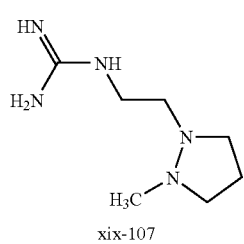
xix-107
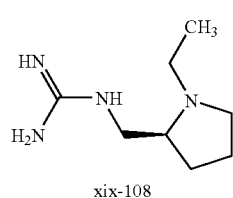
xix-108
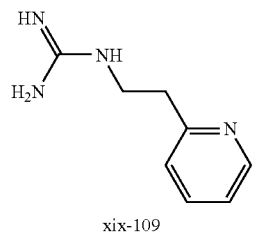
xix-109
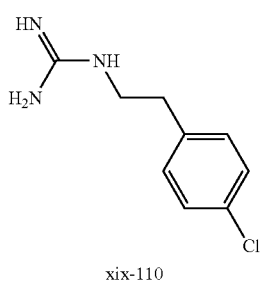
xix-110
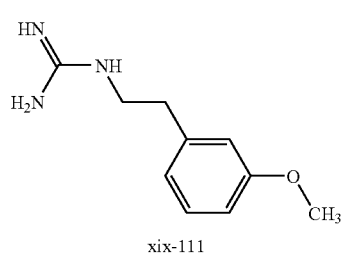
xix-111
TABLE 2-continued
Guanidines
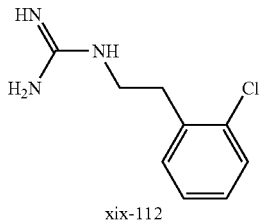
xix-112
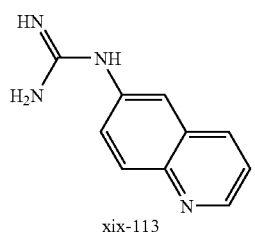
xix-113
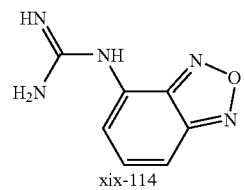
xix-114
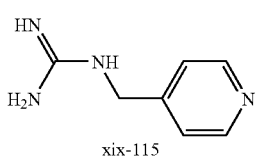
xix-115
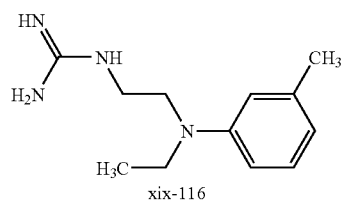
xix-116
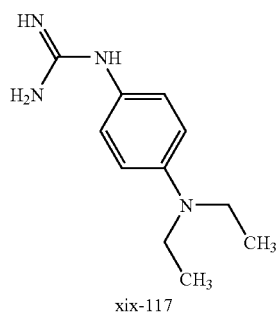
xix-117
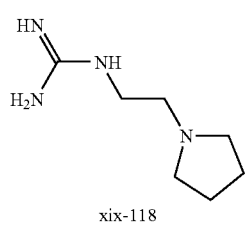
xix-118

TABLE 2-continued
Guanidines
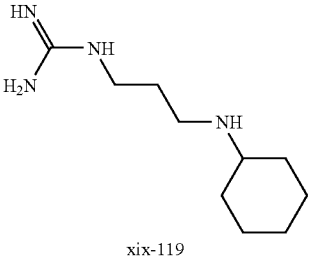
xix-119
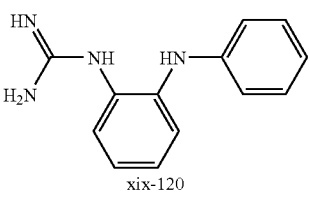
xix-120
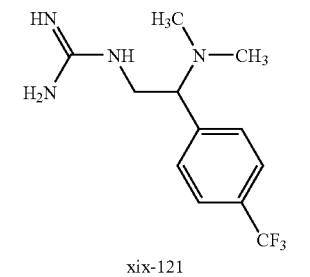
xix-121
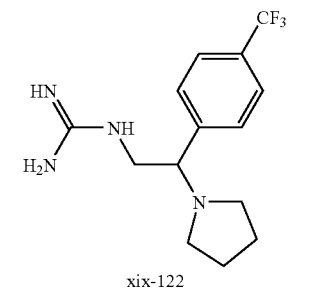
xix-122
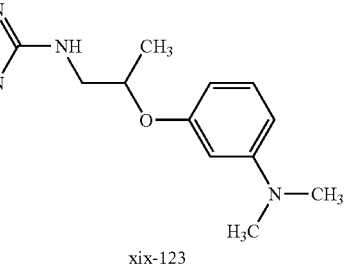
xix-123
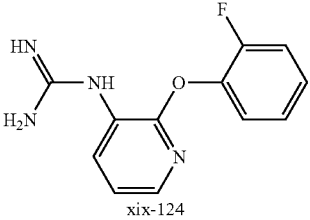
xix-124
TABLE 2-continued
Guanidines
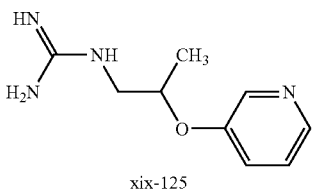
xix-125
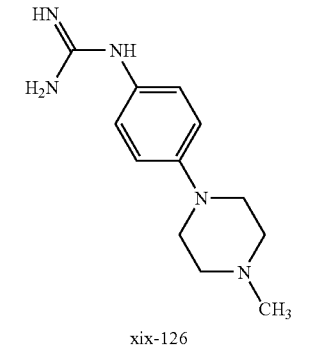
xix-126
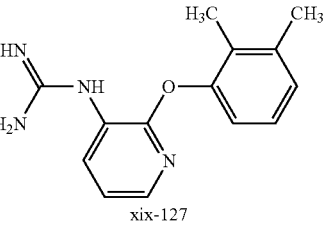
xix-127
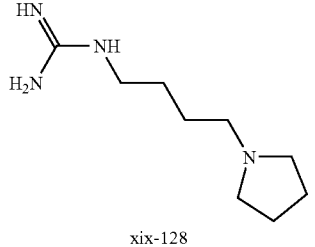
xix-128
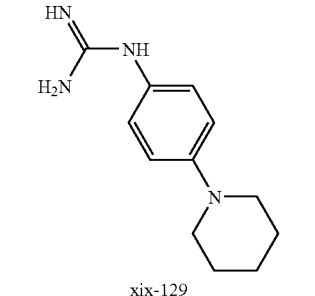
xix-129
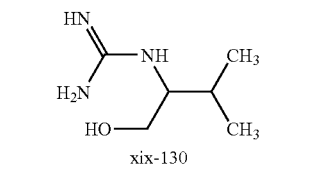
xix-130

TABLE 2-continued
Guanidines
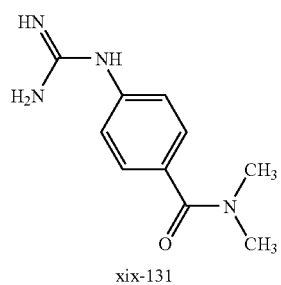
xix-131
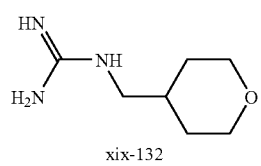
xix-132
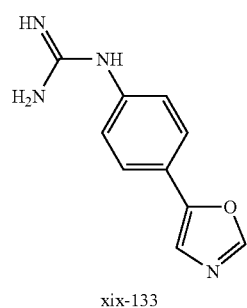
xix-133
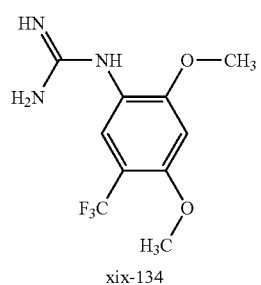
xix-134
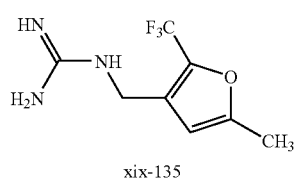
xix-135
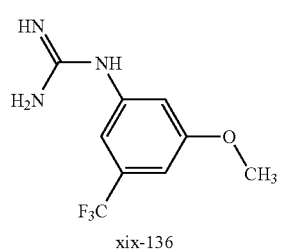
xix-136
TABLE 2-continued
Guanidines
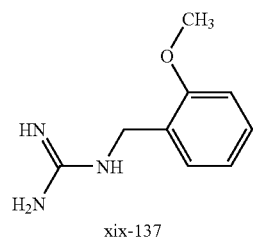
xix-137
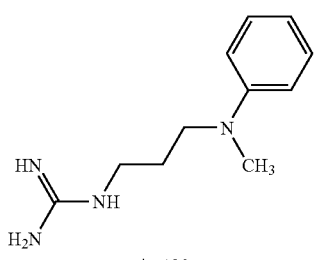
xix-138
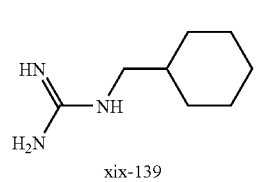
xix-139
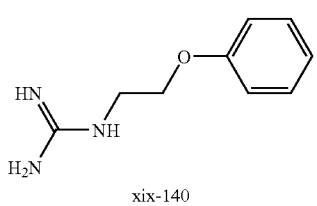
xix-140
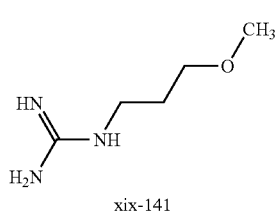
xix-141
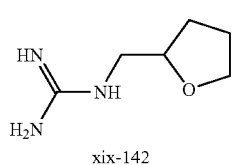
xix-142
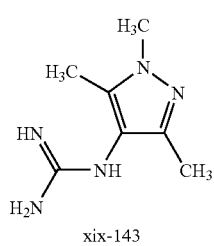
xix-143

TABLE 2-continued
Guanidines
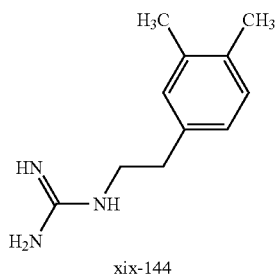
xix-144
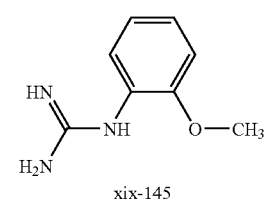
xix-145
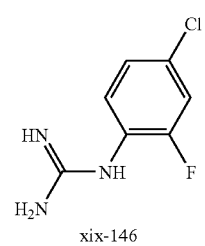
xix-146
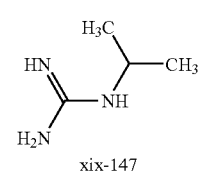
xix-147
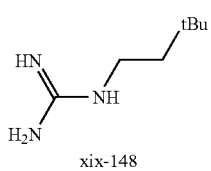
xix-148
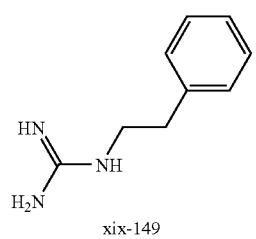
xix-149
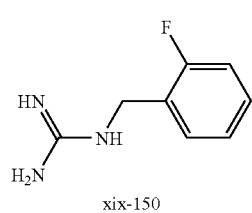
xix-150
TABLE 2-continued
Guanidines
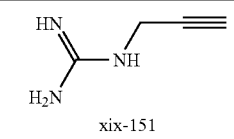
xix-151
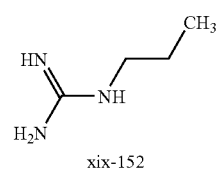
xix-152
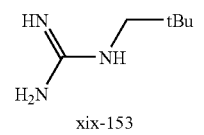
xix-153
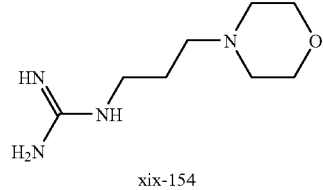
xix-154
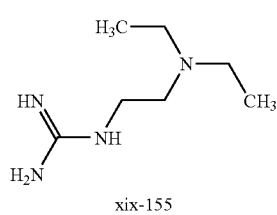
xix-155
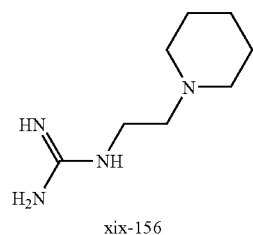
xix-156
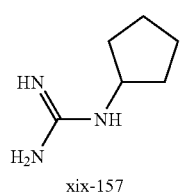
xix-157
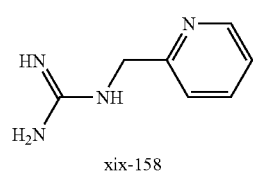
xix-158

TABLE 2-continued
Guanidines
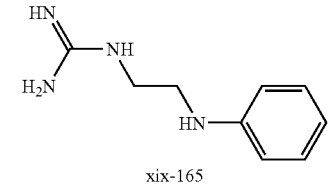
xix-159
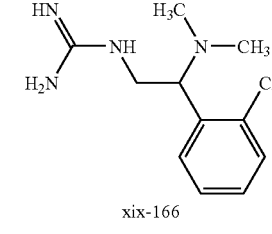
xix-160
xix-161
xix-162
xix-163
xix-164
TABLE 2-continued
Guanidines
xix-165
xix-166
xix-167
xix-168
xix-169
xix-170

TABLE 2-continued
Guanidines
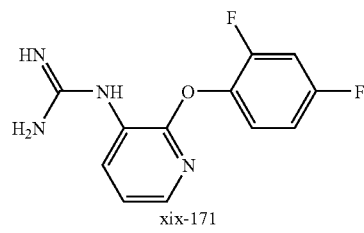
xix-171
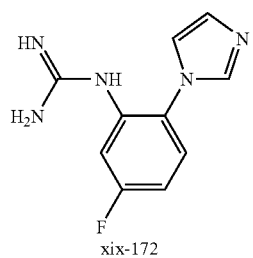
xix-172
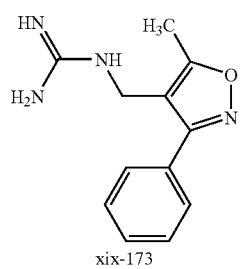
xix-173
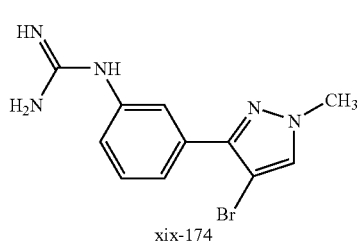
xix-174
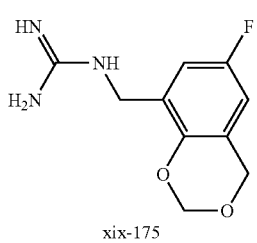
xix-175
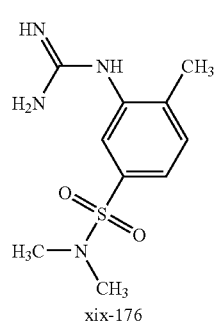
xix-176
TABLE 2-continued
Guanidines
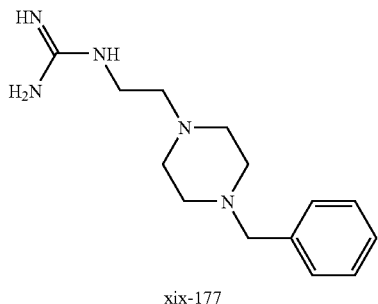
xix-177
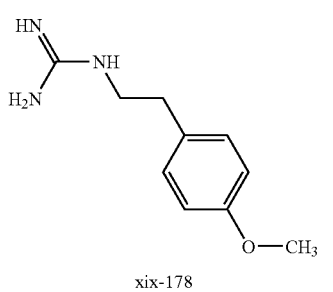
xix-178
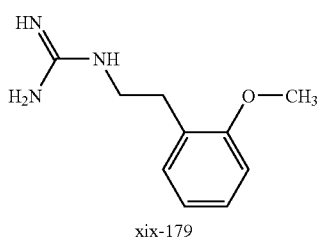
xix-179
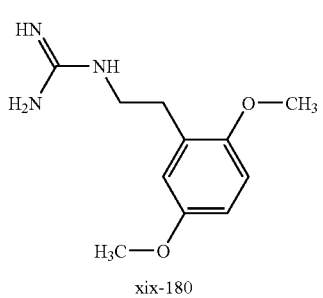
xix-180
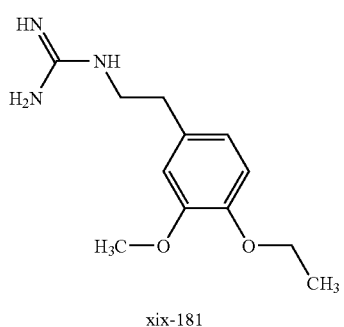
xix-181

TABLE 2-continued
Guanidines
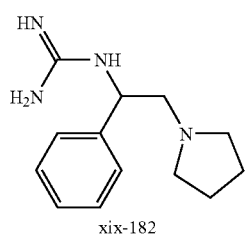
xix-182
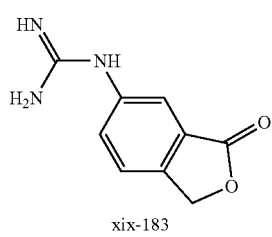
xix-183
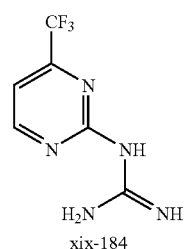
xix-184
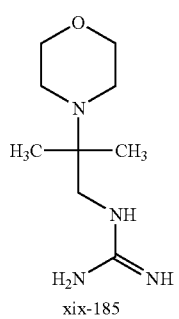
xix-185
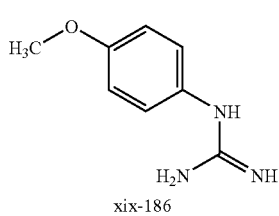
xix-186
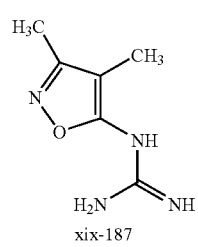
xix-187
TABLE 2-continued
Guanidines
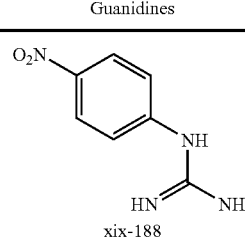
xix-188
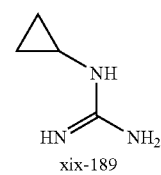
xix-189
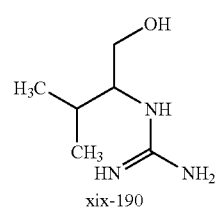
xix-190
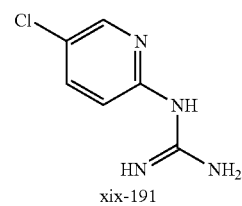
xix-191
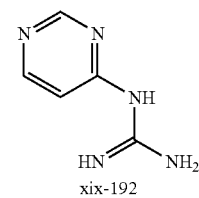
xix-192
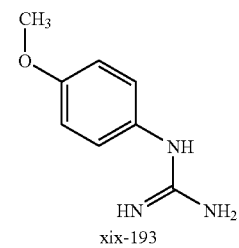
xix-193
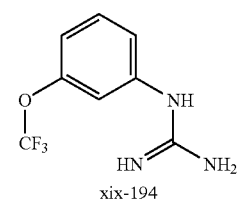
xix-194
Guanidines xix listed in Table 3 were prepared in a manner similar to Method S.

TABLE 3
Guanidines
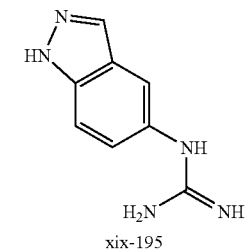
xix-195
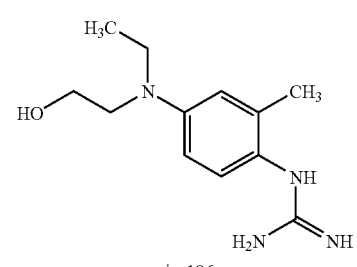
xix-196
xix-197
xix-198
xix-199
TABLE 3-continued
Guanidines
xix-200
xix-201
xix-202
xix-203
xix-204

653
Example 26
Method X for the Synthesis of Sulfonamides

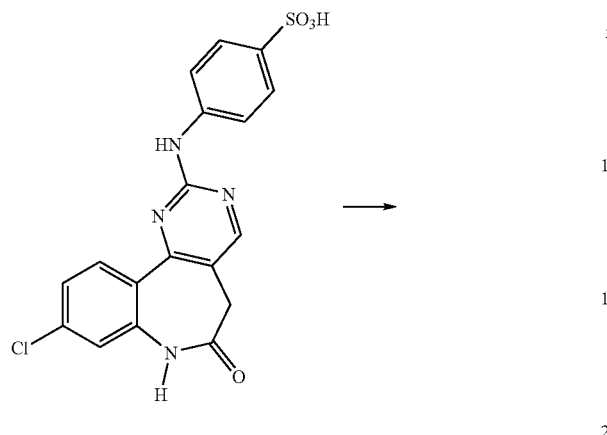

654
Example 27
Method Y for Solid Phase Amide Coupling

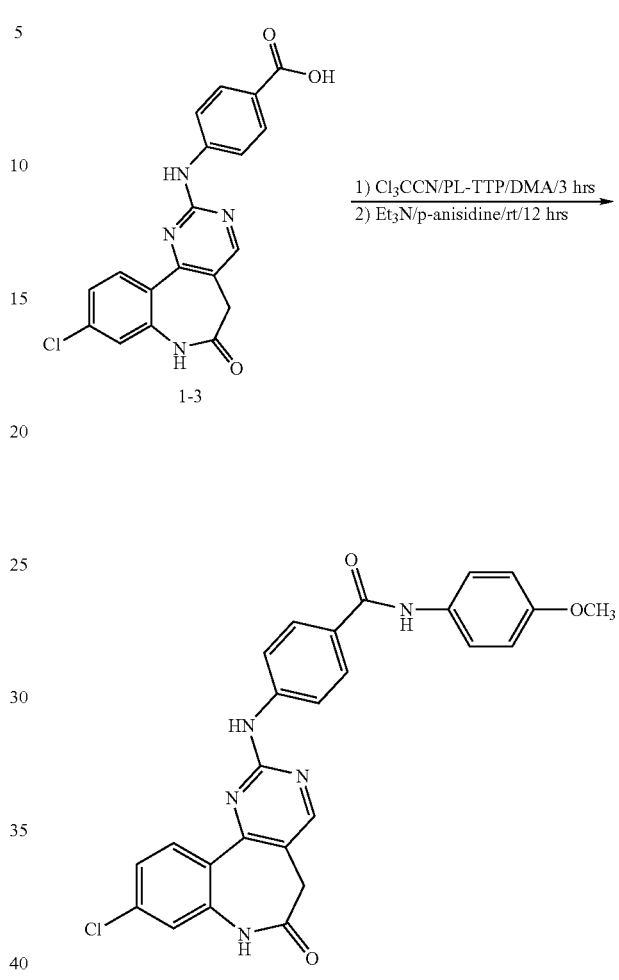

4-[(9-chloro-6-oxo-6,7-dihydro-5H-pyrimido[5,4-d][1]benzazepin-2-yl)amino]-N-(3-morpholin-4-ylpropyl)benzenesulfonamide (I-1279).

To a well in a sealed reaction block containing PL-TPP resins (1.5 mmol/g, 200 mg per well, 0.3 mmol per well), was added a mixture of sulfonic acid (29 mg, 0.07 mmol) and trichloroacetonitrile (40 mg, 0.28 mmol) in DMA (2.5 mL). The reaction block was shaken at rt for 1 h. To the reaction mixture was added Et$_3$N (0.07 mL), followed by N-aminopropylmorpholine (14 mg, 0.10 mmol) in DMA (0.3 mL). (When low-boiling amines were used in this Method, 0.35 mmol of the amine were added.) The reaction block was shaken at rt for overnight. The resins were then filtered off, and were washed with DMF (2×1.5 mL). The filtrate was concentrated in vacuo. The residue was purified by RP-HPLC using an Agilent HPLC equipped with a SunFire™ column (Waters Corporation), Method Formic Acid, or equipped with a Symmetry® column (Waters Corporation), Method Ammonium Acetate, to give compound I-1279 (15.6%): $^1$H NMR (300 MHz, CD$_3$OD): δ 8.44 (s, 1H), 8.12 (d, J=8.4 Hz, 1H), 7.98-7.94 (m, 2H), 7.75-7.71 (m, 2H), 7.35 (dd, J=2.1, 8.5 Hz, 1H), 7.23 (d, J=2.1 Hz, 1H), 3.78 (br. t., 4H), 3.42 (s, 2H), 3.05-3.00 (br. m., 6H), 2.93 (t, J=6.3 Hz, 2H), 1.88-1.78 (m, 2H); MS m/z=543 (M+H).

4-[(9-Chloro-6-oxo-6,7-dihydro-5H-pyrimido[5,4-d][1]benzazepin-2-yl)amino]-N-(4-methoxyphenyl)benzamide (I-555)

To a pre swelled PL-TPP resin [200 mg, 0.3 mmol, (Polymer labs, 1.5 mmol/gram loading)] in DMA (1.0 mL) was added a mixture of 4-(9-Chloro-6-oxo-6,7-dihydro-5H-benzo[b]pyrimido[4,5-d]azepin-2-ylamino)-benzoic acid (I-3) (25 mg 0.066 mmol), DMA (1.5 mL) and trichloroacetonitrile (0.53 mmol). After agitating for three hours at room temperature, triethylamine (46 μL, 0.33 mmol) was added, followed by p-anisidine (8.1 mg, 0.066 mmol). The reaction mixture was stirred at 22° C. overnight. The reaction mixture was filtered and the resin was washed with DMF, DMA, and MeOH (1×1 mL). The combined organic layers were concentrated and the crude product was purified by RP-HPLC using an Agilent HPLC equipped with a SunFire™ column (Waters Corporation), Method Formic Acid, to give I-555 (22 mg, 69%). $^1$H NMR (DMSO): δ 10.38 (s, 1H), 10.32 (s, 1H), 9.93 (s, 1H), 8.59 (s, 1H), 8.10(d, J=8.9 Hz, 1H), 7.92 (s, 1H), 7.64 (d, J=9.3 Hz, 1H), 7.42 (d, J=8.1 Hz, 1H), 7.29 (s, 1H), 6.89 9d, J=8.5 Hz, 1H), 3.73 (s, 2H), 3.43 (s, 1H), 3.32 (s, 3H); MS R$_f$=2.70 min (m/z) 466 (M+1),

Example 28

Method for Pd-Mediated Amine Coupling

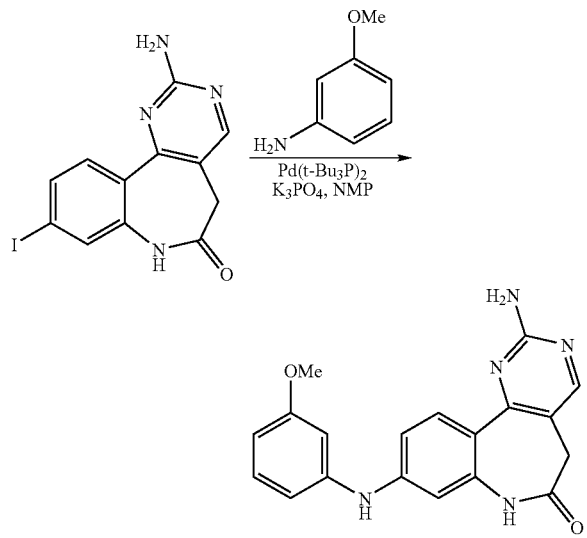

2-Amino-9-(3-methoxy-phenylamino)-5H,7H-benzo[b]pyrimido[4,5-d]azepin-6-one (I-225)

2-Amino-9-iodo-5H,7H-benzo[b]pyrimido[4,5-d]azepin-6-one (200 mg, 0.568 mmol, 1.0 equiv), anhydrous $K_3PO_4$ powder (241 mg, 1.14 mmol, 2.0 equiv) and palladium bis-tri-t-butyl phosphine (58 mg, 0.1136 mmol, 20 mol %) were combined in a sealable vial with a magnetic stir bar under a nitrogen atmosphere (glove box). 3-Methoxyaniline (209 mg, 1.70 mmol, 3.0 equiv) was added, followed by 6 mL of anhydrqus N-methylpyrrolidinone. The vial was sealed with a silicone lined crimp cap and removed from the glove box. The vial was sonicated for 2 minutes and then heated to 90° C. (oil bath temperature) for 18 hours. The dark brown solution was diluted with 50 mL of water and the brown solids were collected by filtration and washed with water and then diethyl ether. Purification by silica gel chromatography (10% methanol, 85% dichloromethane, 5% formic acid) afforded an orange powder, which was recrystallized from methanol and diethyl ether to yield 120 mg (61%) of 2-amino-9-(3-methoxy-phenylamino)-5H,7H-benzo[b]pyrimido[4,5-d]azepin-6-one (I-225) as a yellow-orange powder.

Example 29

Expression and Purification of Protein Kinase Enzymes

Aurora A Enzyme Expression and Purification

Recombinant mouse Aurora A with an amino-terminus hexahistidine tag (His-Aurora A) was expressed using a standard baculovirus vector and insect cell expression system (Bac-to-Bac®, Invitrogen).

Soluble, recombinant mouse Aurora A was purified from insect cells using Ni—NTA agarose (Oiagen) as described by the manufacturer and further purified over an S75 size exclusion column (Amersham Pharmacia Biotech).

Aurora B Enzyme Expression and Purification

Recombinant mouse Aurora B with an amino-terminus hexahistidine tag (His-Aurora B) was expressed using a standard baculovirus vector and insect cell expression system (Bac-to-Bac®, Invitrogen).

Soluble, recombinant mouse Aurora B was purified from insect cells using Ni—NTA agarose (Oiagen) as described by the manufacturer.

Chk-1 Enzyme Expression and Purification:

Recombinant human Chk-1 was expressed as a fusion protein with glutathione S-transferase at the amino-terminus (GST-Chk1) using standard baculovirus vectors and (Bac-to-Bac®) insect cell expression system purchased from GIBCO-Invitrogen. Recombinant protein expressed in insect cells was purified using glutathione sepharose (Amersham Biotech) using standard procedures described by the manufacturer.

PLK1 Enzyme Expression and Purification:

Recombinant human PLK1 was expressed in *E. coli* as an N-terminal Smt fusion protein using a proprietary vector (pSGX4) by Structural Genomics (SGX). The fusion partner was removed through cleavage with Ulp1 after an initial purification using a Ni2+ affinity column.

Example 30

Protein Kinase Enzyme Assays

Aurora A DELFIA® Kinase Assay

The mouse Aurora A enzymatic reaction totaled 25 μL and contained 25 mM Tris-HCl (pH 8.5), 2.5 mM $MgCl_2$, 0.05% Surfact-AMPS-20, 5 mM Sodium Fluoride, 5 mM DTT, 1 mM ATP, 3 μM peptide substrate (Biotin-β-Ala-OTRRK-STGGKAPR—$NH_2$), and 20 nM recombinant murine Aurora A enzyme. The enzymatic reaction mixture, with and without Aurora inhibitors, was incubated for 10 minutes at room temperature before termination with 100 μL of stop buffer (1% BSA, 0.05% Surfact-AMPS-20, and 100 mM EDTA). A total of 100 μL of the enzyme reaction mixture was transferred to wells of a Neutravidin-coated 96-well plate (Pierce) and incubated at room temperature for 30 minutes. The wells were washed with wash buffer (25 mM Tris, 150 mM sodium chloride, and 0.1% Tween 20) and incubated for 1 hour with 100 μL of antibody reaction mixture containing 1% BSA, 0.05% Surfact-AMPS-20, anti-phospho-PKA rabbit polyclonal antibody (1:2000, New England Biolabs), and europium labeled anti-rabbit IgG (1:2000, Perkin Elmer). The wells were washed and then the bound europium was liberated using 100 μL of Enhancement Solution (Perkin Elmer). quantification of europium was done using a Wallac™ EnVision (Perkin Elmer).

Compounds of the invention were shown to inhibit Aurora A using the assay method described above. For example, compounds I-1 to I-93 provided the following test results: I-1 to I-10, I-14 to I-15, I-18, I-24 to I-28, I-30, I-32 to I-33, I-37 to I-42, I-46, to I-47, I-49 to I-50, I-52 to I-57, I-59 to I-60, I-62 to I-67, I-70 to I-73, I-78 to I-79, I-81 to I-82, I-86 to I-89, and I-91 were shown to have $IC_{50}$ values in this assay of less than or equal to 5.0 μM, and compounds I-2, 1-3, I-7, 1-9, I-10, I-27, I-30, I-32, I-33, I-37, I-38, I-42, I-47, I-49, I-50, I-53, I-57, I-62, I-64, I-66, I-67, I-70, I-71 to I-73, I-82, I-86 to I-89, and I-91 were shown to have $IC_{50}$ values in this assay of less than or equal to 0.5 μM.

Aurora B DELFIA® Kinase Assay

The mouse Aurora B enzymatic reaction totaling 25 μL contained 25 mM Tris-HCl (pH 8.5), 2.5 mM $MgCl_2$, 0.025% Surfact-AMPS-20 (Pierce), 1% Glycerol, 1 mM DTT, 1 mM ATP, 3 μM peptide substrate (Biotin-β-Ala-OTRRKSTG-GKAPR—$NH_2$), and 20 nM recombinant murine Aurora B enzyme. The enzymatic reaction mixture, with or without Aurora inhibitors, was incubated for 3 hours at room temperature before termination with 100 μL of stop buffer (1% BSA, 0.05% Surfact-AMPS-20, and 100 mM EDTA). A total of 100 μL of the enzyme reaction mixture was transferred to wells of a Neutravidin-coated 96-well plate (Pierce) and incubated at room temperature for 30 minutes. The wells were washed with wash buffer (25 mM Tris, 150 mM sodium chloride, and 0.1% Tween 20) and incubated for 1 hour with 100 μL of antibody reaction mix containing 1% BSA, 0.05% Surfact-AMPS-20, anti-phospho-PKA rabbit polyclonal antibody (1:2000, New England Biolabs), and europium labeled anti-rabbit IgG (1:2000, Perkin Elmer). The wells were washed and then the bound europium was liberated using 100 μL of Enhancement Solution (Perkin Elmer). quantification of europium was done using a Wallac™ EnVision (Perkin Elmer).

Chk-1 DELFIA® kinase assay:

Assays (25 μL) utilized 1.94 nM GST-Chk-1 containing 10 mM Tris, pH 7.5, 0.1% BSA (TBS), 50 mM NaCl$_2$, 0.01% Surfact-Amps® 20, 1 μM peptide substrate (Biotin-GLYR-SPSMPEN-amide), 2 mM DTT, 4% DMSO, 50 or 600 μM ATP (depending on potency), 10 mM MgCl$_2$ and were reacted for 90 minutes at room temperature. Reactions were terminated with 120 μL of Stop buffer containing 1% BSA (TBS), 100 mM EDTA, pH 8.0, 0.05% Surfact-Amps® 20. Stopped reactions (100 μL) were transferred to 96 well neutravidin plates (Pierce) to capture the biotin-peptide substrate during a 45 minute room temperature incubation. Wells were washed and reacted with 100 μL Perkin-Elmer Wallac™ Assay Buffer containing 22 ng/mL anti-phospho-Ser216-Cdc25c rabbit polyclonal antibody from Cell Signaling Technology (Beverly, Mass.) and 405 ng/mL europium labeled anti-rabbit-IgG for 1 hour at room temperature. Wells were washed and europium released from the bound antibody by addition of Enhancement Solution (100 μL) (Perkin-Elmer Wallac) and detected using a Wallac Victor2™ and standard manufacturer settings.

Compounds of the invention were shown to inhibit Chk-1 using the assay method described above. For example, compounds I-1 to I-93 provided the following test results: compounds I-1 to I-3, I-5, I-6, I-9, I-14, I-15, I-18, I-24, I-26, I-27, I-30 to I-33, I-37 to I-42, I-46, I-47, I-49, I-50, I-52 to I-54, I-56, I-57, I-59 to I-67, I-69 to I-73, I-76, I-78, I-79, I-81, I-82, and I-86 to I-92 were shown to have IC$_{50}$ values in this assay of less than or equal to 5 μM, and compounds I-1 to I-3, 1-9, 1-18, I-24, I-27, I-30, I-32, I-33, I-37, I-38, I-41, I-42, I-46, I-47, I-49, I-50, I-52, I-53, I-56, I-57, I-60, I-62 to I-67, I-70 to I-73, I-77 to I-79, I-81, I-82, I-86 to I-89, I-91, and I-92 were shown to have IC$_{50}$ values in this assay of less than or equal to 0.5 μM.

PLK1 Flash Plate Assay

The human PLK1 enzymatic reaction totaling 30 μL contained 50 mM Tris-HCl (pH 8.0), 10 mM MgCl$_2$, 0.02% BSA, 10% glycerol, 1 mM DTT, 100 mM NaCl, 3.3% DMSO, 8 μM ATP, 0.2 μCi [γ-$^{33}$P]-ATP, 4 μM peptide substrate (Biotin-AHXLDETGHLDSSGLOEVHLA-CONH$_2$) and 10 nM recombinant human PLK1[2-369]T210D. The enzymatic reaction mixture, with or without PLK inhibitors, was incubated for 2.5 hours at 30° C. before termination with 20 μL of 150 mM EDTA. 25 μL of the stopped enzyme reaction mixture was transferred to a 384-well streptavidin coated Image FlashPlate® (Perkin Elmer) and incubated at room temperature for 3 hours. The Image Flash Plate® wells were washed 3 times with 0.02% Tween-20 and then read on the Perkin Elmer Viewlux™.

Compounds of the invention were shown to inhibit PLK using the assay described above. For example, compounds I-1 to I-93 provided the following test results: compounds I-2,1-3, I-5, I-7 to I-9, I-11 to I-18, I-24 to I-30, I-32 to I-38, I-41, I-42, I-45 to I-47, I-49, I-50, I-52 to I-56, I-65 to I-73, I-78 to I-82, and I-86 to I-89 were shown to have an IC$_{50}$ of less than or equal to 5 μM in this assay, and compounds I-2, I-3, I-5,1-7, I-9, I-11 to I-15, I-18, I-24, I-27 to I-30, I-33 to I-37, I-42, I-45 to I-47, I-49, I-50, I-54 to I-56, I-65 to I-67, I-69, I-70, I-78, I-79, I-81, I-82, and I-86 to I-89 were shown to have an IC$_{50}$ of less than or equal to 0.5 μM in this assay.

Example 31

Cellular Assay

Aurora Phosphorylation Assays

Inhibition of Aurora A or Aurora B activity in whole cell systems can be assessed by determination of decreased phosphorylation of Aurora substrates. For example, determining decreased phosphorylation of histone H3 on Serine 10, an Aurora B substrate can be used to measure inhibition of Aurora B activity in a whole cell system. Alternatively, any known Aurora B substrate can be used in similar assay methods to assess inhibition of Aurora B activity. Similarly, Aurora A inhibition can be determined using analogous methods and known Aurora A substrates for detection.

In a specific example, HeLa cells were seeded in a 96-well cell culture plate (10×10$^3$ cells/well) and incubated overnight at 37° C. Cells were incubated with Aurora inhibitors for 1 hour at 37° C., fixed with 4% paraformaldehyde for 10 minutes and then permeabilized with 0.5% TritonX-100 in PBS. Cells were incubated with mouse anti-pH is H3 (1:120, Cell Signaling Technologies) and rabbit anti-mitotic marker (1:120, Millennium Pharmaceuticals Inc.) antibodies for 1 hour at room temperature. After washing with PBS the cells were stained with anti-rabbit IgG Alexa 488 (1:180, Molecular Probes) and anti-mouse IgG Alexa 594 (1:180) for 1 hour at room temperature. DNA was then stained with Hoechst solution (2 μg/mL). The percentage of pH is H3 and anti-mitotic positive cells were quantified using Discovery I and MetaMorph (Universal Imaging Corp.). Aurora B inhibition was determined by calculating the decrease of pH is H3 positive cells.

Anti-proliferation Assays

HCT-116 (1000) or other tumor cells in 100 μl of appropriate cell culture medium (McCoy's 5A for HCT-116, Invitrogen) supplemented with 10% fetal bovine serum (Invitrogen) was seeded in wells of a 96-well cell culture plate and incubated overnight at 37 C. Test compounds were added to the wells and the plates were incubated for 96 hours at 37° C. MTT or WST reagent (10 μl, Roche) was added to each well and incubated for 4 hours at 37° C. as described by the manufacturer. For MTT the metabolized dye was solublized overnight according to manufacturer's instructions (Roche). The optical density for each well was read at 595 nm (primary) and 690 nm (reference) for the MTT and 450 nm for the WST using a spectrophotometer (Molecular Devices). For the MTT the reference optical density values were subtracted from the values of the primary wavelength. Percent inhibition was calculated using the values from a DMSO control set to 100%.

Anti-proliferation Assay—Combination of Test Compound and DNA Damaging Agent

HT29, HCT116 (5000 cells/well) or other cells were seeded (75 μL) to 96 well clear bottom plates at densities which provide linear growth curves for 72 hours. Cells were cultured under sterile conditions in appropriate media; for HT29 and HCT116, this media was McCoy's 5A containing 10% Fetal Bovine Serum (FBS). Following the initial seeding of cells they were incubated at 37° C., 5% $CO_2$ from 17 to 24 hours at which time the appropriate DNA damaging agents (camptothecins, 5-fluorouracil, doxorubicin, and etoposide) were added at increasing concentrations to a point which is capable of causing at least 80% cell killing with in 48 hours. Final volume of all DNA damaging agent and test compound additions was 25 μL and assays contained <1% DMSO final. At the same time as DNA damaging agent addition, the test compound was added at fixed concentrations to each DNA damaging agent titration to observe enhancement of cell killing. In addition, toxicity of each test compound alone was observed. By doing this over a range of test compound concentrations, compounds were identified which maximally enhance (2-30 fold) cell killing by each DNA damaging agent and generated ≦80% cell killing by the compound alone. Cell viability/cell killing under the conditions described above was determined by addition WST reagent (Roche) according to the manufacturer at 47 hours following DNA damage & Chk-1 inhibitor addition and following a 3.5 hour or 2.5 hour incubation at 37 C, 5% $CO_2/OD_{450}$ was measured.

Example 32

In vivo Assays

In vivo Tumor Efficacy Model

HCT-116 ($1 \times 10^6$) or other tumor cells in 100 μL of phosphate buffered saline are aseptically injected into the subcutaneous space in the right dorsal flank of female CD-1 nude mice (age 5-8 weeks, Charles River) using a 23-ga needle. Beginning at day 7 after inoculation tumors are measured twice weekly using a vernier caliper. Tumor volumes are calculated using standard procedures ($0.5 \times (length \times width^2)$). When the tumors reach a volume of approximately 200 mm$^3$ mice are injected i.v. in the tail vein with test compound (100 μL) at various doses and schedules. All control groups receive vehicle alone. Tumor size and body weight are measured twice a week and the study is terminated when the control tumors reach approximately 2000 mm$^3$.

In vivo Tumor Efficacy Model—Combination of Test Compound and DNA Damaging Agent HT29 human colon cancer cells with p53 deficiency are cultured with 10% FBS in McCoy's 3A medium and incubated at 5% $CO_2$. The cells are trypsinized and resuspended in Hanks buffer at $2 \times 10^7$ cells/mL. 100 μL of the cell suspension ($2 \times 10^6$ cells) is aseptically implanted into the subcutaneous space in the right dorsal flank of male NCR nude mice (age 5-8 weeks, Taconic) using a 23-ga needle. Seven days after implantation, the tumors are measured in two dimensions (length and width) with a caliper and the animal body weight is measured with a balance. Tumor volume is calculated with the following formula: tumor volume=$L \times W^2 \times 0.5$. When the average tumor volume reaches about 200 mm$^3$, the individual animals are assigned to different study groups using a random number generation method. The typical study consists of vehicle control, CPT-11 alone (i.v.), Chk-1 inhibitor alone (i.p.), and CPT-11 in combination with Chk-1 inhibitor groups at various doses and schedules. Tumor size and body weight are measured twice a week for four weeks. Once the tumor volume reaches over 10% of the body weight of the animal, or the mouse body weight loss is more than 20%, the mouse is euthanized. Data is collected only from those study groups in which there are five or more animals.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A compound of formula (I):

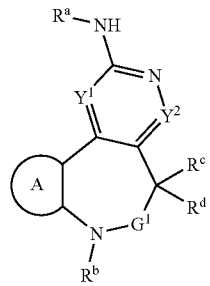

(I)

or a pharmaceutically acceptable salt thereof;
wherein:
Ring A is an optionally substituted 5- or 6-membered aryl or heteroaryl ring;
$G^1$ is C=O, C=S, or S(=O)$_2$;
$Y^1$ is N or CH and $Y^2$ is N or CR$^e$, provided that at least one of $Y^1$ and $Y^2$ is N;
$R^a$ is hydrogen, —C(O)R$^{5a}$, —C(O)N(R$^{4a}$)$_2$, —CO$_2$R$^{6a}$, —SO$_2$R$^{6a}$, —SO$_2$N(R$^{4a}$)$_2$, an optionally substituted $C_{1-10}$ aliphatic, or an optionally substituted aryl, heteroaryl, or heterocyclyl ring;
$R^b$ is hydrogen or an optionally substituted aliphatic, aryl, heteroaryl, or heterocyclyl group;
$R^c$ is hydrogen, fluoro, —OR$^5$, —N(R$^4$)$_2$, or an optionally substituted $C_{1-4}$ aliphatic;
$R^d$ is hydrogen, fluoro, $C_{1-4}$ aliphatic or $C_{1-4}$ fluoroaliphatic; or R$^c$ and R$^d$, taken together with the carbon atom to which they are attached, form an optionally substituted 3- to 6-membered carbocyclic ring;
$R^e$ is hydrogen, halo, —NO$_2$, —CN, —C(R$^5$)=C(R$^5$)$_2$, —C≡C—R$^5$, —C(R$^5$)=C(R$^5$)(R$^{10}$), —C≡C—R$^{10}$, —OR$^5$, —N(R$^4$)$_2$, —NR$^4$C(O)R$^5$, —NR$^4$C(O)N(R$^4$)$_2$, —NR$^4$CO$_2$R$^6$, —CO$_2$R$^5$, —C(O)R$^5$, —C(O)N(R$^4$)$_2$, —N(R$^4$)SO$_2$R$^6$, —N(R$^4$)SO$_2$N(R$^4$)$_2$, or an optionally substituted $C_{1-4}$ aliphatic;
each R$^4$ independently is hydrogen or an optionally substituted aliphatic, aryl, heteroaryl, or heterocyclyl group; or two R$^4$ on the same nitrogen atom, taken together with the nitrogen atom, form an optionally substituted 4- to 8-membered heterocyclyl ring having, in addition to the nitrogen atom, 0-2 ring heteroatoms selected from N, O, and S;

each $R^{4a}$ independently is hydrogen or an optionally substituted aliphatic, aryl, heteroaryl, or heterocyclyl group; or two $R^{4a}$ on the same nitrogen atom, taken together with the nitrogen atom, form an optionally substituted 4- to 8-membered heterocyclyl ring having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^{5a}$ independently is hydrogen or an optionally substituted aliphatic, aryl, heteroaryl, or heterocyclyl group;

each $R^6$ independently is an optionally substituted aliphatic or aryl group;

each $R^{6a}$ independently is an optionally substituted aliphatic or aryl group; and $R^{10}$ is —$CO_2R^5$ or —$C(O)N(R^4)_2$.

2. The compound of claim 1, characterized by one or more of the following features (a)-(e):
(a) $Y^1$ is N;
(b) $Y^2$ is $CR^e$, where $R^e$ is selected from the group consisting of hydrogen, $C_{1-4}$ aliphatic, $C_{1-4}$ fluoroaliphatic, -halo, —$OR^5$, —$N(R^4)_2$, —CN, —$CO_2R^5$, —$C(O)N(R^4)_2$, —$C(R^5)=C(R^5)_2$, —$C(R^5)=C(R^5)(R^{10})$, —C≡C—$R^5$, and —C≡C—$R^{10}$;
(c) $G^1$ is C=O;
(d) $R^c$ is selected from the group consisting of hydrogen, fluoro, —$OR^5$, —$N(R^4)_2$, and $C_{1-4}$aliphatic optionally substituted with one or two groups independently selected from $C_{1-3}$aliphatic, fluoro, —$OR^5$, —$N(R^4)_2$, —$CO_2R^5$, —$C(O)N(R^4)_2$, and optionally substituted 5- or 6-membered aryl or heteroaryl; and
(e) $R^d$ is hydrogen.

3. The compound of claim 1, wherein Ring A is a substituted or unsubstituted 5- or 6-membered aryl or heteroaryl ring selected from the group consisting of furano, thieno, pyrrolo, oxazolo, thiazolo, imidazolo, pyrazolo, isoxazolo, isothiazolo, oxadiazolo, triazolo, thiadiazolo, benzo, pyridino, pyridazino, pyrmidino, pyrazino, and triazine.

4. The compound of claim 3, wherein:
Ring A is substituted with 0-2 $R^h$ and 0-2 $R^{8h}$;
each $R^h$ independently is selected from the group consisting of $C_{1-6}$aliphatic, $C_{1-6}$fluoroaliphatic, halo, —$R^{1b}$, —$R^{2h}$, -$T^4$-$R^{2h}$, -$T^4$-$R^{1h}$, -$V^3$-$T^4$-$R^{1h}$, and -$V^3$-$T^4$-$R^{2h}$, or two adjacent Rh, taken together with the intervening ring atoms, form an optionally substituted fused 4- to 8-membered aromatic or non-aromatic ring having 0-3 ring heteroatoms selected from the group consisting of O, N, and S;
$T^4$ is a $C_{1-6}$alkylene chain optionally substituted with one or two independently selected $R^{3a}$ or $R^{3b}$, wherein the alkylene chain optionally is interrupted by —$C(R^5)=C(R^5)$—, —C≡C—, —O—, —S—, —S(O)—, —S(O)_2—, —$SO_2N(R^4)$—, —$N(R^4)$—, —$N(R^4)C(O)$—, —$NR^4C(O)N(R^4)$—, —$N(R^4)$$C_2$—, —$C(O)N(R^4)$—, —C(O)—, —C(O)—C(O)—, —$CO_2$—, —OC(O)—, —OC(O)O—, —OC(O)N(R^4)$—, —$N(R^4)S_2$—, or —$SO_2N(R^4)$;
$V^3$ is —$C(R^5)=C(R^5)$—, —C≡C—, —O—, —S—, —S(O)—, —S(O)_2—, —$SO_2N(R^4)$—, —$N(R^4)$—, —$N(R^4)C(O)$—, —$NR^4C(O)N(R^4)$—, —$N(R^4)$$CO_2$—, —$C(O)N(R^4)$—, —C(O)—, —C(O)—C(O)—, —$CO_2$—, —OC(O)—, —OC(O)O—, —OC(O)N(R^4)$—, —$C(NR^4)=N$—, —$C(OR^5)=N$—, —$N(R^4)SO_2$—, —$N(R^4)SO_2N(R^4)$—, —P(O)(R^5)$—, —P(O)(OR^5)$—O—, —P(O)—O—, or —P(O)(NR^5)$—N(R^5)$—;

each $R^{1b}$ independently is an optionally substituted aryl, heteroaryl, heterocyclyl, or cycloaliphatic ring;

each $R^{2h}$ independently is —$NO_2$, —CN, —$C(R^5)=C(R^5)_2$, —C≡C—$R^5$, —$C(R^5)=C(R^5)(R^{10})$, —C≡C—$R^{10}$, —$OR^5$, —$SR^6$, —$S(O)R^6$, —$SO_2R^6$, $S_3R^5$, —$SO_2N(R^4)_2$, —$N(R^4)_2$, —$NR^4C(O)R^5$, —$NR^4C(O)N(R^4)_2$, —$NR^4CO_2R^6$, —O—$C_2R^5$, —OC(O)N(R^4)_2$, —O—C(O)R^5$, —$C_2R^5$, —C(O)—C(O)R^5$, —C(O)R^5$, —$C(O)N(R^4)_2$, —$C(O)N(R^4)C(=NR^4)$—$N(R^4)_2$, —$N(R^4)C(=NR^4)$—$N(R^4)$—C(O), —$C(=NR^4)$—$N(R^4)_2$, —$C(=NR^4)$—$OR^5$, —$C(R^6)=N$—$OR^5$, —$N(R^4)C(=NR^4)$—$N(R^4)_2$, —$N(R^4)SO_2R^6$, —$N(R^4)SO_2N(R^4)_2$, —$P(O)(R^5)_2$ or —$P(O)(OR^5)_2$;

each $R^{3a}$ independently is selected from the group consisting of —F, —OH, —$O(C_{1-3}$alkyl), —CN, —$N(R^4)_2$, —$C(O)(C_{1-3}$alkyl), —$CO_2H$, —$C_2(C_{1-3}$alkyl), —$C(O)NH_2$, and —$C(O)NH(C_{1-3}$alkyl);

each $R^{3b}$ independently is a $C_{1-3}$ aliphatic optionally substituted with $R^{3a}$ or $R^7$, or two substituents $R^{3b}$ on the same adjacent carbon atom(s), taken together with the carbon atom(s) to which they are attached, form a 3- to 6-membered carbocyclic ring;

each $R^7$ independently is an optionally substituted aryl or heteroaryl ring; and each $R^{8h}$ independently is selected from the group consisting of $C_{1-4}$ aliphatic, $C_{1-4}$ fluoroaliphatic, -halo, and —$O(C_{1-4}$aliphatic).

5. The compound of claim 4, having formula (II):

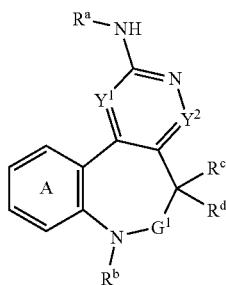

(II)

or a pharmaceutically acceptable salt thereof;

wherein Ring A is substituted with 0-2 $R^h$ and 0-2 $R^{8h}$.

6. The compound of claim 5, wherein Ring A is substituted with 0-2$R^{8h}$ substituents independently selected from the group consisting of $C_{1-4}$ aliphatic, $C_{1-4}$ fluoroaliphatic, -halo, and —$O(C_{1-4}$aliphatic), or two adjacent substituents, taken together with the intervening ring atoms, form a fused dioxolane or dioxane ring.

7. The compound of claim 5, wherein Ring A has the formula A-i, A-ii, or A-iii:

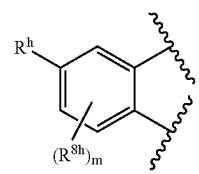

A-i

-continued

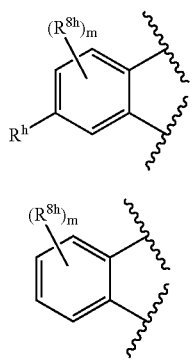

A-ii

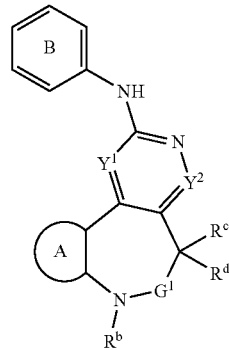

(III)

A-iii wherein m is 0, 1, or 2.

8. The compound of claim 6, wherein $R^h$ is —CN, —$CO_2R^5$, —$C(O)N(R^4)_2$, —$N(R_4)_2$ or —$OR^5$.

9. The compound of claim 6, wherein:
$R^h$ is -$T^4$-$R^{2h}$, -$V^3$-$T^4$-$R^{2h}$, or -Cy-$T^4$-$R^{2h}$;
$V^3$ is —C≡C—, —$C(R^5)$=$C(R^5)$—, or —$C(O)N(R^4)$—;
Cy is a 5- or 6-membered arylene or heteroarylene;
$T^4$ is a $C_{1-4}$ alkylene chain; and
$R^{2b}$ is —$OR^5$, —$N(R^4)_2$, or —$C(O)N(R^4)_2$.

10. The compound of claim 9, wherein $R^b$ is hydrogen.

11. The compound of claim 1, wherein $R^a$ is hydrogen, $C_{1-6}$aliphatic, -$T^{11}$-$R^{1a}$, -$T^{11}$-$R^{21a}$, -$T^{12}$-$R^{22a}$, -$V^1$-$T^{11}$-$R^{1a}$, -$V^1$-$T^{11}$-$R^{21a}$, -$V^1$-$T^{11}$-$R^{22a}$, or —$R^{1a}$;
$V^1$ is —C(O)—, —$C(O)N(R^{4a})$—, —C(O)O—, —$SO_2$—, or —$SO_2N(R^{4a})$—;
$T^{11}$ is a $C_{1-6}$ alkylene chain optionally substituted with one or two independently selected $R^{3a}$ or $R^{3b}$, wherein the alkylene chain optionally is interrupted by —$C(R^5)$=C($R^5$)— or —C≡C—;
$T^{12}$ is a $C_{2-6}$ alkylene chain optionally substituted with one or two independently selected $R^{3a}$ or $R^{3b}$, wherein the alkylene chain optionally is interrupted by —$C(R^5)$=C($R^5$)— or —C≡C—;
each $R^{3a}$ independently is selected from the group consisting of —F, —OH, —O($C_{1-3}$alkyl), —CN, —$N(R^4)_2$, —C(O)($C_{1-3}$alkyl), —$CO_2H$, —$CO_2$($C_{1-3}$alkyl), —$C(O)NH_2$, and —$C(O)NH(C_{1-3}$alkyl);
each $R^{3b}$ independently is a $C_{1-3}$ aliphatic optionally substituted with $R^{3a}$ or $R^7$, or two substituents $R^{3b}$ on the same or adjacent carbon atom(s), taken together with the carbon atom(s) to which they are attached, form a 3- to 6-membered carbocyclic ring;
$R^{21a}$ is —$C(R^{5a})$=$C(R^{5a})_2$, —C≡C—$R^{5a}$, —$S(O)R^{6a}$, —$SO_2R^{6a}$, —$SO_3R^{5a}$, —$SO_2N(R^{4a})_2$, —$CO_2R^{5a}$, —C(O)—C(O)$R^{5a}$, —$C(O)R^{5a}$, —$C(O)N(R^{4a})_2$, —$C(O)N(R^{4a})C(=NR^{4a})$—$N(R^{4a})_2$, —$C(=NR^{4a})$—$N(R^{4a})_2$, —$C(=NR^{4a})$—$OR^{5a}$, —$C(R^{6a})$=N—$OR^{5a}$, —$P(O)(R^{5a})_2$, or —$P(O)(R^{5a}$;
$R^{22a}$ is —$NO_2$, —CN, —$OR^{5a}$, —$SR^{6a}$, —$N(R^{4a})_2$, —$NR^{4a}C(O)R^{5a}$, —$NR^{4a}C(O)N(R^{4a})_2$, —$NR^{4a}CO_2R^{6a}$, —O—$CO_2R^{5a}$, —$OC(O)N(R^{4a})_2$, —O—$C(O)R^{5a}$, —$N(R^{4a})C(=NR^{4a})$—$N(R^{4a})_2$, —$N(R^{4a})C(=NR^{4a})$—$N(R^{4a})$—$C(O)R^5$, —$N(R^{4a})SO_2R^{6a}$, or —$N(R^{4a})SO_2N(R^{4a}$;
each $R^7$ independently is an optionally substituted aryl or heteroaryl ring; and
$R^{1a}$ is an optionally substituted aryl, heteroaryl, heterocyclyl, or cycloaliphatic ring.

12. The compound of claim 11, having formula (III):

or a pharmaceutically acceptable salt thereof;
wherein Ring B is substituted with 0-2 $R^j$ and 0-2 $R^{8j}$,
each $R^j$ independently is selected from the group consisting of $C_{1-6}$aliphatic, $C_{1-6}$ fluoroaliphatic, halo, —$R^{1j}$, —$R^{2j}$, -$T^5$-$R^{2j}$, -$T^5$-$R^{1j}$, -$V^4$-$T^5$-$R^{1j}$, and -$V^4$-$T^5$-$R^{2j}$; or two adjacent $R^j$, taken together with the intervening ring atoms, form an optionally substituted fused 4- to 8-membered aromatic or non-aromatic ring having 0-3 ring heteroatoms selected from the group consisting of O, N, and S;
$T^5$ is a $C_{1-6}$ alkylene chain optionally substituted with one or two independently selected $R^{3a}$ or $R^{3b}$, wherein the alkylene chain optionally is interrupted by —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —$OC(O)O$—, —OC(O)N($R^4$)—, —$N(R^4)SO_2$—, or —$SO_2N(R^4)$;
$V^4$ is —$C(R^5)$=$C(R^5)$—, —C≡C—, —O—, —S—, —S(O)—, —$S(O)_2$—, —$SO_2N(R^4)$—, —$N(R^4)$—, —$N(R^4)C(O)$—, —$OC(O)O$—, —$OC(O)N(R^4)$—, —$C(NR^4)$=N—, —$C(OR^5)$=N—, —$N(R^4)SO_2$—, —$N(R^4)SO_2N(R^4)$—, —$P(O)(R^5)$—, —$P(O)(OR^5)$—O—, —P(O)—O—, or —$P(O)(NR^5)$—$N(R^5)$—;
each $R^{1j}$ independently is an optionally substituted aryl, heteroaryl, heterocyclyl, or cycloaliphatic ring;
each $R^{2j}$ independently is —$NO_2$, —CN, —$C(R^5)$=C($R^5$, —C≡C—$R^5$, R, —$C(R^5)(R^{10})$, —C≡C—$R^{10}$, —$OR^5$, —$SR^6$, —$S(O)R^6$, —$SO_2R^6$, —$SO_3R^5$, —$SO_2N(R^4)_2$, —$N(R^4)_2$, —$NR^4C(O)R^5$, —$NR^4C(O)N(R^4)_2$, —$NR^4CO_2R^6$, —O—$CO_2R^5$, —OC(O)$N(R^4)_2$, —O—$C(O)R^5$, —$CO_2R^5$, —C(O)—C(O)$R^5$, —$C(O)R^5$, —$C(O)N(R^4)_2$, —$C(O)N(R^4)C(=NR^4)$—$N(R^4)_2$, —$N(R^4)C(=NR^4)$—$N(R^4)$—C(O), —$C(=NR^4)$—$N(R^4)_2$, —$C(=NR^4)$—$OR^5$, —$N(R^4)C(=NR^4)$—$N(R^4)_2$, —$N(R^4)SO_2R^6$, —$N(R^4)SO_2N(R_4)_2$, —$P(O)(R^5)_2$, or —$P(O)(OR^5)_2$;
each $R^{3a}$ independently is selected from the group consisting of —F, —OH, —O($C_{1-3}$alkyl), —CN, —$N(R^4)_2$, —C(O)($C_{1-3}$alkyl), —$CO_2H$, —$CO_2$($C_{1-3}$ alkyl), —$C(O)NH_2$, and —$C(O)NH(C_{1-3}$alkyl);
each $R^{3b}$ independently is a $C_{1-3}$aliphatic optionally substituted with $R^{3a}$ or $R^7$, or two substituents $R^{3b}$ on the same or adjacent carbon atom(s), taken together with the carbon atom(s) to which they are attached, form a 3- to 6-membered carbocycic ring;

each R⁷ independently is an optionally substituted aryl or heteroaryl ring; and each $R^{8j}$ independently is selected from the group consisting of $C_{1-4}$aliphatic, $C_{1-4}$fluoroaliphatic, -halo, —CO₂H, —CO₂($C_{1-4}$aliphatic), —OH, and —O($C_{1-4}$ aliphatic).

13. The compound of claim 12, wherein Ring B has the formula B-i, B-ii, or B-iii:

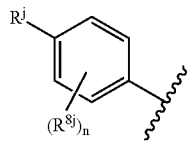

B-i

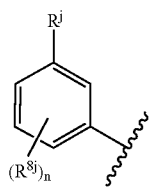

B-ii

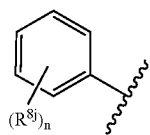

B-iii wherein n is 0, 1, or 2.

14. The compound of claim 13, wherein:
$R^j$ is -T⁵-$R^{2j}$ or -V⁴-T⁵-$R^{2j}$;
V⁴ is —C≡C—, or —C(R⁵)═C(R⁵)—; and
$R^{2j}$ is —OR⁵ or —N(R⁴)₂.

15. The compound of claim 13, wherein $R^j$ is -V⁴-T⁵-$R^{2j}$ or -V⁴-T⁵-$R^{1j}$;
V⁴ is —C(O)N(R⁴)— or —SO₂N(R⁴)—; and
T⁵ is a $C_{2-4}$alkylene chain, optionally substituted with —F or $C_{1-4}$aliphatic.

16. The compound of claim 1, wherein $R^b$ is hydrogen or $C_{1-6}$aliphatic.

17. The compound of claim 1, wherein:
$R^b$ is -T²¹-$R^{1b}$, -T²¹-$R^{21b}$, or -T²²-$R^{22b}$;
$T^{21b}$ is a $C_{1-6}$alkylene chain optionally substituted with one or two R³, wherein the alkylene chain optionally is interrupted by —C(R⁵)═C(R⁵)— or —C≡C—;
T²² is a $C_{2-6}$alkylene chain optionally substituted with one or two R₃, wherein the alkylene chain optionally is interrupted by —C(R₅)═C(R⁵)— or —C≡C—;
$R^{1b}$ is an optionally substituted aryl, heteroaryl, heterocyclyl, or cycloaliphatic ring;
each R³ independently is selected from the group consisting of $C_{1-3}$aliphatic, -fluoro, —OH, and —O($C_{1-3}$alkyl), or two substituents R³ on the same carbon atom, taken together with the carbon atom to which they are attached, form a 3- to 6-membered carbocyclic ring; and
$R^{21b}$ is —C(R⁵)₂, —C≡C—R⁵, —C(R⁵)═C(R⁵)(R¹⁰), —S(O)R⁶, —SO₂R⁶, —SO₃R⁵, —SO₂N(R⁴)₂, —CO₂R⁵, —C(O)—C(O)R⁵, —C(O)R⁵, —C(O)N(R⁴)₂, —C(O)N(R⁴)C(═NR⁴)—N(R⁴)₂, —C(═NR⁴)—N(R⁴)₂, —C(═NR⁴)—OR⁵, —C(R⁶)═N—OR⁵, —P(O)(R⁵)₂, or —P(O)(OR⁵)₂;
$R^{22b}$ is —NO₂, —CN, —OR⁵, —SR⁶, —N(R⁴)₂, —NR⁴C(O)R⁵, —NR4C(O)N(R⁴)₂, —NR⁴CO₂R⁶, —O—CO₂R⁵, —OC(O)N(R⁴), —O—C(O)R⁵, —N(R⁴)C(═NR⁴)—N(R⁴)₂, —N(R⁴)C(═NR⁴)—N(R⁴)—C(O)R⁵, —N(R⁴)SO₂R⁶, or —N(R⁴)SO₂N(R⁴)₂.

18. The compound of claim 1, wherein $R^b$ is an optionally substituted aryl, heteroaryl, or heterocyclyl ring.

19. The compound of claim 18, having formula (IV)

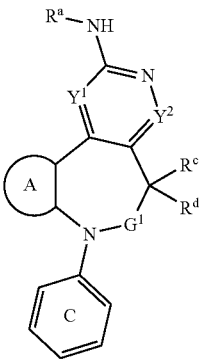

(IV)

or a pharmaceutically acceptable salt thereof;
wherein Ring C is substituted with 0-2 $R^k$ and 0-2 $R^{8k}$;
each $R^k$ independently is selected from the group consisting of $C_{1-6}$aliphatic, $C_{1-6}$fluoroaliphatic, -halo, —$R^{1k}$, —$R^{2k}$, -T⁶-$R^{2k}$, -T⁶-$R^{1k}$, -V⁵T⁶-$R^{1k}$, and -V⁵-T⁶-$R^{2k}$; or two adjacent $R^k$, taken together with the intervening ring atoms, form an optionally substituted fused 4- to 8-membered aromatic or non-aromatic ring having 0-3 ring heteroatoms selected from the group consisting of O, N, and S;
T⁶ is a $C_{1-6}$alkylene chain optionally substituted with one or two independently selected $R^{3a}$ or $R^{3b}$, wherein the ailcylene chain optionally is interrupted by —C(R⁵)═C(R⁵)—, —C≡C—, —O—, —S—, —S(O)—, —S(O)₂—, —SO₂N(R⁴)—, —N(R⁴)—, —N(R⁴)C(O)—, —NR⁴C(O)N(R⁴)—, —N(R⁴)CO₂—, —C(O)N(R⁴)—, —C(0)—, —C(O)—C(O)—, —CO2 OC(O)—, —OC(O)O—, —OC(O)N(R⁴)—, —N(R⁴)SO₂—, or —SO₂N(R⁴);
V⁵ is —C(R⁵)═C(R⁵)—, —C≡C—, —O—, —S—, —S(O)—, —S(O)₂—, —SO₂N(R⁴)—, —N(R⁴)—, —N(R⁴)C(O)—, —NR⁴C(O)N(R⁴)—, —N(R⁴)CO₂—, —C(O)N(R⁴)—, —C(O)—, —C(O)—C(O)—, —CO₂—, —OC(O)—, —OC(O)O—, —OC(O)N(R⁴)—, —C(NR⁴)═N—, —C(OR⁵)═N—, —N(R⁴)SO₂—, —N(R⁴)SO₂N(R⁴)—, —P(O)(R⁵)—, —P(O)(OR⁵)—O—, —P(O)—O—, or —P(O)(NR⁵)—N(R⁵)—;
each $R^{1k}$ independently is an optionally substituted aryl, heteroaryl, heterocyclyl, or cycloaliphatic ring;
each $R^{2k}$ independently is —NO₂, —CN, —C(R⁵)═C(R⁵)₂, —C≡C—R⁵, C(R⁵)═C(R⁵)(R¹⁰), —C≡C—R¹⁰, —OR⁵, —SR⁶, —S(O)R⁶, —SO₂R⁶, —SO₃R⁵, —SO₂N(R⁴)₂, —N(R⁴)₂, —NR⁴C(O)R⁵, —NR⁴C(O)N(R⁴)₂, —NR⁴CO₂R⁶, —O—CO₂R⁵, —OC(O)N(R⁴)₂, —O—C(O)R⁵, —CO₂R⁵, —C(O)—C(O)R⁵, —C(O)R⁵, —C(O)N(R⁴)₂, —C(O)N(R⁴)C(═NR⁴)—N(R⁴)₂, —N(R⁴)C(═NR⁴)—N(R⁴)—C(O), —C(═NR⁴)—N(R⁴)₂, —C(═NR⁴)—OR⁵, —N(R⁴)C(═NR⁴)—N(R⁴)₂, —N(R⁴)SO₂R⁶, —N(R⁴)SO₂N(R⁴)₂, —P(O)(R⁵)₂, or —P(O)(OR⁵)₂;
each $R^{3a}$ independently is selected from the group consisting of —F, —OH, —O($C_{1-3}$alkyl), —CN, —N(R⁴)₂, —C(O)($C_{1-3}$alkyl), —CO₂H, —CO₂($C_{1-3}$alkyl), —C(O)NH₂, and —C(O)NH($C_{1-3}$alkyl);
each $R^{3b}$ independently is a $C_{1-3}$aliphatic optionally substituted with $R^{3a}$ or R⁷, or two substituents $R^{3b}$ on the same or adjacent carbon atom(s), taken together with the carbon atom(s) to which they are attached, form a 3- to 6-membered carbocyclic ring;
each $R^7$ independently is an optionally substituted aryl or heteroaryl ring; and
each $R^{8k}$ independently is selected from the group consisting of $C_{1-4}$aliphatic, $C_{1-4}$fluoroaliphatic, -halo, and —O($C_{1-4}$aliphatic).

20. The compound of claim 19, wherein Ring C is substituted with 0-2 substituents independently selected from the group consisting of $C_{1-4}$aliphatic, $C_{1-4}$fluoroaliphatic, -halo, and —O($C_{1-4}$aliphatic).

21. A compound of formula (V):

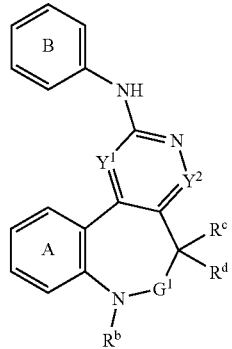

(V)

or a pharmaceutically acceptable salt thereof;
wherein:
Ring A is substituted with 0-2 $R^h$ and 0-2 $R^{8h}$;
Ring B is substituted with 0-2 $R^j$ and 0-2 $R^{8j}$;
$G^1$ is C=O, C=S, or S(=O)$_2$;
$Y^1$ is N or CH;
$Y^2$ is N or C$R^e$;
$R^b$ is hydrogen or an optionally substituted aliphatic, aryl, heteroaryl, or heterocyclyl group;
$R^c$ is hydrogen, fluoro, —OR$^5$, —N(R$^4$)$_2$, or an optionally substituted $C_{1-4}$aliphatic;
$R^d$ is hydrogen, fluoro, or $C_{1-4}$aliphatic; or $R^c$ and $R^d$ taken together with the carbon atom to which they are attached, form an optionally substituted 3- to 6-membered carbocycic ring;
$R^e$ is hydrogen, halo, $C_{1-4}$aliphatic, $C_{1-4}$fluoroaliphatic, —R$^e$, -T$^3$-R$^{1e}$, -T$^3$-R$^{2e}$, -V$^2$-T$^3$-R$^{1e}$, or -V$^2$-T$^3$-R$^{2c}$;
$T^3$ is a $C_{1-4}$alkylene chain optionally substituted with one or two R$^3$;
$V^2$ is —C(R$^5$)=C(R$^5$)— or —C≡C—;
$R^{1e}$ is an optionally substituted aryl, heteroaryl, heterocyclyl, or cycloaliphatic ring;
$R^{2e}$ is —NO$_2$, —CN, —C(R$^5$)=C(R$^5$)$_2$, —C(R$^5$)=C(R$^5$)(R$^{10}$), —C≡C—R$^5$, —C≡C—R$^{10}$, —OR$^5$, —N(R$^4$)$_2$, —NR$^4$C(O)R$^5$, —NR$^4$C(O)N(R$^4$)$_2$, —NR$^4$CO$_2$R$^6$, —CO$_2$R$^5$, —C(O)R$^5$, —C(O)N(R$^4$)$_2$, —N(R$^4$)SO$_2$R$^6$, or —N(R$^4$)SO$_2$N(R$^4$)$_2$;
each $R^h$ independently is selected from the group consisting of $C_{1-6}$aliphatic, $C_{1-6}$fluoroaliphatic, halo, —R$^{1h}$, —R$^{2h}$, -T$^4$-R$^{2h}$, -T$^4$-R$^{1h}$, and -V$^3$-T$^4$-R$^{2h}$, or two adjacent R$^h$, taken together with the intervening ring atoms, form an optionally substituted fused 4- to 8-membered aromatic or non-aromatic ring having 0-3 ring heteroatoms selected from the group consisting of O, N, and S;
$T^4$ is a $C_{1-6}$alkylene chain optionally substituted with one or two independently selected R$^{3a}$ or R$^{3b}$, wherein the alkylene chain optionally is interrupted by —C(R$^5$)=C(R$^5$)—, —C≡C—, —O—, —S—,
—S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)CO$_2$—, or —SO$_2$N(R$^4$);
$V^3$ is —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)CO$_2$—, —C(O)N(R$^4$)—, —C(O)—, —C(O)—C(O)—, —CO$_2$—, —OC(O)—, —OC(O)O—, —OC(O)N(R$^4$)—, —C(NR$^4$)=N—, —C(OR$^5$)=N—, —N(R$^4$)SO$_2$—, —N(R$^4$)SO$_2$N(R$^4$)—, —P(O)(R$^5$)—, —P(O)(OR$^5$)—O—, —P(O)—O—, or —P(O)(NR$^5$)—;
each $R^{1h}$ independently is an optionally substituted aryl, heteroaryl, heterocyclyl, or cycloaliphatic ring;
each $R^{2h}$ independently is —NO$_2$, —CN, —C(R$^5$)=C(R$^5$)$_2$, —C≡C—R$^5$, —C(R$^5$)=C(R$^5$)(R$^{10}$), —C≡C—R$^{10}$, —OR$^5$, —SR$^6$, —S(O)R$^6$, —SO$_2$R$^6$, —SO$_3$R$^5$, —SO$_2$N(R$^4$)$_2$, —N(R$^4$)$_2$, —NR$^4$C(O)R$^5$, —NR$^4$C(O)N(R$^4$)$_2$, —NR$^4$COR$^6$, —O—CO$_2$R$^5$, —OC(O)N(R$^4$)$_2$, —O—C(O)R$^5$, —CO$_2$R$^5$, —C(O)—C(O)R$^5$, —C(O)R$^5$, —C(O)N(R$^4$)$_2$, —C(O)N(R$^4$)C(=NR$^4$)—N(R$^4$)$_2$, —N(R$^4$)C(=NR$^4$)—N(R$^4$)—C(O), —C(=NR$^4$)—N(R$^4$)$_2$, —C(=NR$^4$)—OR$^5$, —C(R$^6$)=N—OR$^5$, —N(R$^4$)C(=NR$^4$)—N(R$^4$)$_2$, —N(R$^4$)SO$_2$R$^6$, —N(R$^4$)SO$_2$N(R$^4$)$_2$, —P(O)(O)R$^5$)$_2$;
each $R^j$ independently is selected from the group consisting of $C_{1-6}$aliphatic, $C_{1-6}$fluoroaliphatic, halo, —R$^{1j}$, —R$^{2j}$, -T$^5$-R$^{2j}$, -T$^5$-R$^{1j}$, -V$^4$-T$^5$-R$^{1j}$, and -V$^4$-T$^5$-R$^{2j}$; or two adjacent R$^j$, taken together with the intervening ring atoms, form an optionally substituted fused 4- to 8-membered aromatic or non-aromatic ring having 0-3 ring heteroatoms selected from the group consisting of O, N, and S;
$T^5$ is a $C_{1-6}$alkylene chain optionally substituted with one or two independently selected R$^{3a}$ or R$^{3b}$, wherein the alkylene chain optioxtally is interrupted by —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)CO2—, —C(O)N(R$^4$)—, —C(O)—, —C(O)—C(O)—, —CO$_2$—, —OC(O)—, —OC(O)O—, —OC(O)N(R$^4$)—, —N(R$^4$)SO$_2$—, or —SO$_2$N(R$^4$);
$V^4$ is —C(R$^5$)=C(R$^5$)—, —C≡C—; —O—, —S—, —S(O)—, —S(O)$_2$—, —SO$_2$N(R$^{4)}$—, —N(R4)—, —N(R$^4$)C(O)—, —OC(O)O—, —OC(O)N(R$^4$)—, —C(NR$^4$)=N—, —C(OR$^5$)=N—, —N(R$^4$)SO$_2$—, —N(R$^4$)SO$_2$N(R$^4$)—, —P(O)(R$^5$)—, —P(O)(OR$^5$)—O—, —P(O)—O—, or —P(O)(NR$^5$)—N(R$^5$)—;
each $R^{1j}$ independently is an optionally substituted aryl, heteroayl, heterocyclyl, or cycloaliphatic ring;
each $R^{2j}$ independently is —NO$_2$, —CN, —C(R$^5$)=C(R$^5$)$_2$, —C≡C—R$^5$, —C(R$^5$)=C(R$^5$)(R$^{10}$), —C≡C—R$^{10}$, —OR$^5$, —SR$^6$, —S(O)R$^6$, —SO$_2$R$^6$, —SO$_3$R$^5$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —O—CO$_2$R$^5$, —OC(O)N(R$^4$)$_2$, —O—C(O)R$^5$, —CO$_2$R$^5$, —C(O)—C(O)R$^5$, —C(O)R$^5$, —C(O)N(R$^4$)$_2$, —C(O)N(R$^4$)C(=NR$^4$)—N(R$^4$)$_2$, —N(R$^4$)—C(=NR$^4$)—N(R$^4$)—C(O), —C(=NR$^4$)—N(R$^4$)$_2$, —C(=NR$^4$)—OR$^5$, —N(R$^4$)C(=NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$;
each $R^3$ independently is selected from the group consisting of $C_{1-3}$aliphatic, —F, —OH, and —O($C_{1-3}$alkyl), or two substituents R$^3$ on the same carbon atom, taken together with the carbon atom to which they are attached, form a 3- to 6-membered carbocyclic ring;

each $R^{3a}$ independently is selected from the group consisting of —F, —OH, —O($C_{1-3}$alkyl), —CN, —N($R^4$)$_2$, —C(O)($C_{1-3}$alkyl), —CO$_2$H, —CO$_2$($C_{1-3}$alkyl), —C(O)NH$_2$, and —C(O)NH($C_{1-3}$alkyl);

each $R^{3b}$ independently is a $C_{1-3}$aliphatic optionally substituted with $R^{3a}$ or $R^7$, or two substituents $R^{3b}$ on the same or adjacent carbon atom(s) taken together with the carbon atom(s) to which they are attached, form a 3- to 6-membered carbocyclic ring; and each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 4- to 8-membered heterocyclyl ring having, in addition to the nitrogen atom, 0-2 ring heteroatoms selected from N, O, and S;

each $R^{4a}$ independently is hydrogen or an optionally substituted aliphatic, aryl, heteroaryl, or heterocyclyl group; or two $R^{4a}$ on the same nitrogen atom, taken together with the nitrogen atom, form an optionally substituted 4- to 8-membered heterocyclyl ring having, in addition to the nitrogen atom, 0-2 ring heteroatonis selected from N, O, and S;

each $R^5$ independently is hydrogen or an optionallysubstituted aliphatic, aryl, heteroaryl, or heterocyclyl group;

each $R^{5a}$ independently is hydrogen or an optiomally substituted aliphatic, aryl, heteroaryl, or heterocyclyl group;

each $R^6$ independently is an optionally substituted aliphatic or aryl group;

each $R^{6a}$ independently is an optionally substituted aliphatic or aryl group;

each $R^7$ independently is an optionally substituted aryl or heteroaryl ring.

each $R^{8h}$ independently is selected from the group consisting of $C_{1-4}$aliphatic, $C_{1-4}$fluoroaliphatic, -halo, and —O($C_{1-4}$aliphatic);

each $R^{8j}$ independently is selected from the group consisting of $C_{1-4}$aliphatic, $C_{1-4}$fluoroaliphatic, -halo, —CO$_2$H, —CO$_2$($C_{1-4}$aliphatic), —OH, and —O($C_{1-4}$aliphatic); and $R^{10}$ is —CO$_{02}$R5 or —C(O)N($R^4$)$_2$.

22. A pharmaceutical composition, comprising a compound according to claim 1 or 21, and a pharmaceutically acceptable carrier.

* * * * *

UNITED STATES PATENT AND TRADEMARK OFFICE
CERTIFICATE OF CORRECTION

PATENT NO. : 7,459,448 B2                                                                         Page 1 of 3
APPLICATION NO. : 11/242413
DATED : December 8, 2008
INVENTOR(S) : Christopher Blackburn et al.

It is certified that error appears in the above-identified patent and that said Letters Patent is hereby corrected as shown below:

Please make the following corrections to the claims:

CLAIMS:

In Claim 4, column 661, line 46, change "-$R^{1b}$," to --$R^{1h}$--;

In Claim 4, column 661, line 48, change "Rh," to --$R^h$--;

In Claim 4, column 661, line 59, change "$C_2$-," to --$CO_2$- --;

In Claim 4, column 661, line 61, change "$N(R^4)S_2$," to --$N(R^4)SO_2$--;

and change "$SO_2 N(R^4$" to --$SO_2 N(R^4)$--;

In Claim 4, column 662, line 5, change "$R^{1b}$," to --$R^{1h}$--;

In Claim 4, column 662, line 8, change "-C=C-$R^5$," to -- -C≡C-$R^5$,--;

In Claim 4, column 662, line 9, change "-C=C-$R^{10}$," to -- -C≡C-$R^{10}$--;

In Claim 4, column 662, line 10, change "-$S_3R^5$," to --$SO_3R^5$-- and change "$SO_2N(R^4$" to --$SO_2N(R^4)$--;

In Claim 4, column 662, line 11, change "$C_2R^5$," to --$CO_2R^5$--;

In Claim 4, column 662, line 12, change "$C_2R^5$," to --$CO_2R^5$--;

In Claim 4, column 662, line 22, change "-$C_2(C_{1-3}$," to -- -$CO_2(C_{1-3}$--;

In Claim 4, column 662, line 27, change "the same adjacent" to --the same or adjacent--.

In Claim 9, column 663, line 27, change "-$R^{1b}$," to --$R^{1h}$--.

In Claim 11, column 663, line 45, change "-C(O)NH($C_{1-3}$alkyl,"

to -- -C(O)NH($C_{1-3}$alkyl)--;

In Claim 11, column 663, line 56, change "-P(O)(O$R^{5a}$," to -- -P(O)(O$R^{5a}$)$_2$,--;

Signed and Sealed this

Thirty-first Day of August, 2010

David J. Kappos
*Director of the United States Patent and Trademark Office*

CERTIFICATE OF CORRECTION (continued)
U.S. Pat. No. 7,459,448 B2

In Claim 11, column 663, line 62, change "-N($R^{4a}$)$SO_2$ N($R^{4a}$" to -- -N($R^{4a}$)$SO_2$ N($R^{4a}$)$_2$--.

In Claim 12, column 664, line 29, change "allcylene" to --alkylene--;

In Claim 12, column 664, line 40, after "-N($R^4$)C(O)-" insert the following -- -$NR^4$C(O)N($R^4$)-, -N($R^4$)$CO_2$-, -C(O)N($R^4$)-, -C(O)-, -C(O)-C(O)-, -$CO_2$-, -OC(O)-,--;

In Claim 12, column 664, line 48, change "($R^5$, -C=C-$R^5$, R, -C($R^5$)($R^{10}$), -C=C-$R^{10}$" to --($R^5$)$_2$, -C≡C-$R^5$, -C($R^5$)=C($R^5$)($R^{10}$), -C≡C-$R^{10}$--;

In Claim 12, column 664, line 58, change "-N($R^4$)$SO_2$N($R_4$)$_2$" to --N($R^4$)$SO_2$N($R^4$)$_2$--;

In Claim 12, column 664, line 67, change "carbocycic," to --carbocyclic--;

In Claim 12, column 665, lines 1 and 2, delete "each $R^7$ independently is an optionally substituted aryl or heteroaryl ring;".

In Claim 17, column 665, line 5, change "-$CO_2$($C_1$ $_4$aliphatic)," to -- -$CO_2$($C_{1-4}$aliphatic),--;

In Claim 17, column 665, line 43, change "$T^{21b}$" to --$T^{21}$--;

In Claim 17, column 665, line 47, change "or two $R_3$" to --or two $R^3$--;

In Claim 17, column 665, line 48, change "-C($R_5$)=C($R^5$)-" to -- -C($R^5$)=C($R^5$)- --;

In Claim 17, column 665, line 57, change "$R^{21b}$ is -C($R^5$)$_2$" to --$R^{21b}$ is -C($R^5$)=C($R^5$)$_2$--;

In Claim 17, column 665, line 58, insert -- -C≡C-$R^{10}$,-- before "-S(O)$R^6$";

In Claim 17, column 665, line 64, change "-NR4C(O)N($R^4$)$_2$," to -- -$NR^4$C(O)N($R^4$)$_2$--;

In Claim 17, column 665, line 65, change "OC(O)N($R^4$)" to --OC(O)N($R^4$)$_2$--.

In Claim 19, column 666, line 24, change "-$V^5T^6$-$R^{1k}$" to -- -$V^5$-$T^6$-$R^{1k}$--;

In Claim 19, column 666, line 32, change "ailcylene" to --alkylene-- and change "intenupted" to --interrupted--;

In Claim 19, column 666, line 33, change "-C=C-" to -- -C≡C- --;

In Claim 19, column 666, line 36, change "-C(0)-" to -- -C(O)- --;

In Claim 19, column 666, line 37, change "-CO2 OC(O)-" to -- $CO_2$-, -OC(O)- --;

In Claim 19, column 666, line 57, change "-N($R^4$)C)(=$NR^4$)-N($R^4$)-C(O)" to -- -N($R^4$)C(=$NR^4$)-N($R^4$)-C(O)--.

In Claim 21, column 667, line 43, change "carbocycic," to --carbocyclic--;

In Claim 21, column 667, line 45, change "$C_{1-4}$fluoroaliphatic, -$R^e$," to --$C_{1-4}$fluoroaliphatic, -$R^{2c}$-- and change "or -$V^2$-$T^3$-$R^{2c}$;" to --or -$V^2$-$T^3$-$R^{2e}$;--;

In Claim 21, column 667, line 51, change "-C($R^5$)= C($R^5)_2$" to -- -C($R^5$)= C($R^5$)$_2$--;

CERTIFICATE OF CORRECTION (continued)
U.S. Pat. No. 7,459,448 B2

In Claim 21, column 667, line 58, insert -- -V$^3$-T$^4$-R$^{1h}$-- after "-T$^4$-R$^{2h}$, -T$^4$-R$^{1h}$,";

In Claim 21, column 668, lines 2 and 3, insert -- -C(O)N(R$^4$)-, -C(O)-, -C(O)-C(O)-, -CO$_2$-, -OC(O)-, -OC(O)O-, -OC(O)N(R$^4$)-, -N(R$^4$)SO$_2$- -- after "-N(R$^4$)CO$_2$-,";

In Claim 21, column 668, line 12, change "P(O)(NR$^5$)-;" to -- -P(O)(NR$^5$)-N(R$^5$)- --;

In Claim 21, column 668, line 26, change "-P(O)(O)(R$^5$)$_2$;" to -- -P(O)(R$^5$)$_2$, or -P(O) (OR$^5$)$_2$;--;

In Claim 21, column 668, line 37, change "optioxally" to --optionally--;

In Claim 21, column 668, line 41, change "-CO2-," to -- -CO$_2$-,--;

In Claim 21, column 668, line 45, change "-SO$_2$N(R$^{4)}$-, -$^{N(R4)}$-,," to -- -SO$_2$N(R$^4$)-, -N(R$^4$)-,--;

In Claim 21, column 668, line 46, insert -- -NR$^4$C(O)N(R$^4$)-, -N(R$^4$)CO$_2$-, -C(O)N(R$^4$)-, -C(O)-, -C(O)-C(O)-, -CO$_2$-, -OC(O)-,-- after "-N(R$^4$)C(O)-,";

In Claim 21, column 668, line 60, please change "-N(R$^4$)-C," to --N(R$^4$)C--;

In Claim 21, column 669, line 19, please change "optionaLly" to --optionally--;

In Claim 21, column 669, line 24, please change "heteroatonis" to --heteroatoms--;

In Claim 21, column 670, line 3, please change "optio mally" to --optionally--;

In Claim 21, column 670, line 20, please change "-CO$_{o2}$R5" to -- -CO$_2$R$^5$--.